US009340817B2

(12) United States Patent
Koeris et al.

(10) Patent No.: US 9,340,817 B2
(45) Date of Patent: May 17, 2016

(54) METHODS OF MAKING RECOMBINANT PHAGE, COMPOSITIONS AND ARTICLES OF MANUFACTURE OF SAME FOR BACTERIAL DETECTION

(71) Applicant: Sample6 Technologies, Inc., Boston, MA (US)

(72) Inventors: Michael Sandor Koeris, Natick, MA (US); Robert Patrick Shivers, Watertown, MA (US); Daniel Robert Brownell, Arlington, MA (US); Jason Wyatt Holder, Swampscott, MA (US); Jayson Linn Bowers, Cambridge, MA (US)

(73) Assignee: Sample6 Technologies, Inc., Cambridge, MA (US)

( * ) Notice: Subject to any disclaimer, the term of this patent is extended or adjusted under 35 U.S.C. 154(b) by 0 days.

(21) Appl. No.: 14/226,889

(22) Filed: Mar. 27, 2014

(65) Prior Publication Data

US 2014/0302487 A1   Oct. 9, 2014

Related U.S. Application Data

(60) Provisional application No. 61/805,917, filed on Mar. 27, 2013.

(51) Int. Cl.
*C12Q 1/04* (2006.01)
*C12N 7/00* (2006.01)

(52) U.S. Cl.
CPC .. *C12Q 1/04* (2013.01); *C12N 7/00* (2013.01); *C12N 2795/00031* (2013.01)

(58) Field of Classification Search
None
See application file for complete search history.

(56) References Cited

U.S. PATENT DOCUMENTS

| | | | |
|---|---|---|---|
| 4,861,709 A | 8/1989 | Ulitzur et al. |
| 4,868,105 A | 9/1989 | Urdea et al. |
| 5,118,801 A | 6/1992 | Lizardi et al. |
| 5,124,246 A | 6/1992 | Urdea et al. |
| 5,130,238 A | 7/1992 | Malek et al. |
| 5,283,174 A | 2/1994 | Arnold et al. |
| 5,312,728 A | 5/1994 | Lizardi et al. |
| 5,399,491 A | 3/1995 | Kacian et al. |
| 5,437,990 A | 8/1995 | Burg et al. |
| 5,480,784 A | 1/1996 | Kacian et al. |
| 5,554,516 A | 9/1996 | Kacian et al. |
| 5,639,604 A | 6/1997 | Arnold et al. |
| 5,925,517 A | 7/1999 | Tyagi et al. |
| 6,033,898 A | 3/2000 | Sarthy et al. |
| 6,361,945 B1 | 3/2002 | Becker et al. |
| 6,534,274 B2 | 3/2003 | Becker et al. |
| 6,835,542 B2 | 12/2004 | Becker et al. |
| 6,849,412 B2 | 2/2005 | Becker et al. |
| 7,374,885 B2 | 5/2008 | Becker et al. |
| 8,178,087 B2 | 5/2012 | Krisch et al. |
| 8,338,144 B2 | 12/2012 | Berry et al. |
| 2004/0137430 A1* | 7/2004 | Anderson et al. ................ 435/5 |
| 2005/0175594 A1 | 8/2005 | Loessner et al. |
| 2006/0046265 A1 | 3/2006 | Becker et al. |
| 2007/0072174 A1 | 3/2007 | Sayler et al. |
| 2008/0241819 A1 | 10/2008 | Smith |
| 2010/0015595 A1 | 1/2010 | Siegel et al. |
| 2010/0075398 A1 | 3/2010 | Mathers et al. |
| 2010/0285460 A1 | 11/2010 | Schofield |
| 2011/0053272 A1 | 3/2011 | Benders et al. |
| 2011/0076672 A1 | 3/2011 | Schofield |
| 2012/0009574 A1 | 1/2012 | Petrauskene et al. |
| 2012/0040441 A1 | 2/2012 | Fujii et al. |
| 2012/0174242 A1 | 7/2012 | Binkowski et al. |
| 2014/0302487 A1 | 10/2014 | Koeris et al. |

FOREIGN PATENT DOCUMENTS

| | | |
|---|---|---|
| EP | 0495960 B1 | 3/1997 |
| WO | WO 88/01302 A1 | 2/1988 |
| WO | WO 95/03430 A1 | 2/1995 |
| WO | WO 95/32304 A1 | 11/1995 |
| WO | WO 88/10315 A1 | 12/1998 |
| WO | WO 2004/041156 A2 | 5/2004 |
| WO | WO 2009/140375 A2 | 11/2009 |
| WO | 2010010192 A1 | 1/2010 |
| WO | 2012061529 A1 | 5/2012 |
| WO | WO 2014/160818 A2 | 10/2014 |

OTHER PUBLICATIONS

Auld et al., PNAS USA, 2010, 107(11):4878-4883.*
GenBank Accession No. AFI79290 (submitted Jan. 23, 2012).*
Dorscht et al., "Comparative genome analysis of Listeria bacteriophages reveals extensive mosaicism, programmed translational frameshifting, and a novel prophage insertion site", J. Bacteriol., Sep. 25, 2009, vol. 191, No. 23, pp. 7206-7215.
Ho et al., "Longitudinal monitoring of Listeria monocytogenes contamination patterns in a farmstead dairy processing facility", J. Dairy Sci., May 1, 2007, vol. 90, No. 5, pp. 2517-2524.
Nightingale et al., "Combined sigB allelic typing and multiplex PCR provide improved discriminatory power and reliability for Listeria monocytogenes molecular serotyping", J. Microbiol. Methods, Aug. 2, 2006, vol. 68, No. 1, pp. 52-59.
International Search Report issued for Application No. PCT/US2014/031931, mailed Sep. 16, 2014.

(Continued)

*Primary Examiner* — Nicole Kinsey White
(74) *Attorney, Agent, or Firm* — Cooley LLP; Ivor Elrifi; Matthew Pavao

(57) ABSTRACT

Methods of detecting target bacteria are provided. In some embodiments the methods comprise exposing the sample to a phage capable of infecting a set of target bacteria and comprising a heterologous nucleic acid sequence encoding a marker. In some embodiments the target bacteria comprise *Listeria*. In some embodiments the target bacteria are all *Listeria*. Recombinant *Listeria* phage comprising a heterologous nucleic acid sequence encoding a marker are also provided as are useful combinations of such phage and articles of manufacture comprising such phage, among other things.

8 Claims, 24 Drawing Sheets

(56) References Cited

OTHER PUBLICATIONS

Almazan F., "Engineering the largest RNA virus genome as an infectious bacterial artificial chromosome," *PNAS*, (2000), vol. 97, No. 10 pp. 5516-5521.

Casjens S et al. "Determining dna packaging stragety by analysis of the termini of the chromosomes in tailed-bacteriophage virions", *Bacteriophages—Methods and protocols*, (2009), vol. 2: molecular and applied aspects, pp. 91-11.

Domi A., "Cloning the vaccinia virus genome as a bacterial artificial chromosome in *Escherichia coli* and recovery of infectious virus in mammalian cells," *PNAS*, (2002), vol. 99, No. 10, pp. 12415-12420.

GenBank Accession No. P08659 (Apr. 24, 1993).

GENEART® High-Order Genetic Assembly System User Manual, Invitrogen (2010).

Gu, Y. et al. "Eliminating the Interference of Oxygen for Sensing Hydrogen Peroxide With the Polyaniline Modified Electrode Sensors", (Dec. 12, 2008), vol. 8, No. 12, pp. 8237-8247.

Hagens S. et al.: "Reporter bacteriophage A511: celB transduces a hyperthermostable glycosidase from Pyrococcus furiosus for rapid and simple detection of viable Listeria cells", *Bacteriophage*, (May 1, 2011), vol. 1, No. 3, pp. 143-151.

Jaschke P., "A fully decompressed synthetic bacteriophage 0X174 genome assembled and archived in yeast," Virology, (2012), vol. 434, pp. 278-284.

Kalantri S. et al. "Bacteriophage-Based Tests for the Detection of *Mycobacterium tuberculosis* in Clinical Specimens: A Systematic Review and Meta-Analysis", *BMC Infectious Disease*, (Jul. 16, 2005), vol. 5, No. 59, p.

Ketner, G. et al. "Efficient manipulation of the human adenovirus genome as an infectious yeast artificial chromosome clone", *Proc. Natl. Acad. Sci. USA*, (Jun. 1994), vol. 91, pp. 6186-6190.

Klumpp J, et al., "The terminally redundant, nonpermuted genome of Listeria bacteriophage A511: a Model for the SPO1-like myoviruses of gram-positive bacteria", *J. Bacteriol.*, (2008), vol. 190, pp. 5753-5765.

Klumpp et al., "Detection of Bacteria with Bioluminescent Reporter Bacteriophage", *Bioluminescence: Fundamentals and Applications in Biotechnology*, (2014), vol. 1, Advances in Biochemical Engineering/Biotechnology 144, pp. 155-171.

Kouprina, N. et al. "TAR cloning: insights into gene function, long-range haplotypes and genome structure and evolution", (2006), *Nature Reviews Genetics*, vol. 7, pp. 805-812.

Liu, D. "Molecular Detection of Human Bacterial Pathogens" CRC Press.2011; Boca Raton, FL; p. 985, right column, third paragraph.

Loessner M. et al.: "Construction of luciferase reporter bacteriophage A511:: luxAB for rapid and sensitive detection of viable Listeria cells", *Applied and Environmental Microbiology*, (Apr. 1, 1996), vol. 62, No. 4, pp. 1133-1140.

Loh J. et al.: "Comparison of firefly luciferase and NanoLuc luciferase for biophotonic labeling of group A *Streptococcus*", *Biotechnology Letters*, (2013), vol. 36, No. 4, pp. 829-834.

Peng L., "Next-Generation DNA Assembly Tools," *Genetic Engineering and Biotechnology News*, (2010), vol. 30, No. 18.

Raymond C., "Linker-Mediated Recombinational Subcloning of Large DNA Fragments Using Yeast," *Genome Research*, (2002), vol. 12, pp. 190-197.

Sauders B.D. et al. "Diversity of *listeria* species in urban and natural environments", *Appl Environ Microbiol.*, (2012), vol. 78, No. 12, pp. 4420-4433.

Sawitzke J., "Recombineering: In Vivo Genetic Engineering in *E. coli, S. enterica*, and Beyond," *Methods in Enzymology*, (2007), vol. 421, pp. 171-199.

Sharan S., "Recombineering: A Homologous Recombination-Based Method of Genetic Engineering," *Nat. Protocol.*, (2010), vol. 4, No. 2, pp. 206-223.

Shaw D. et al. "Use of UV-irradiated bacteriophage T6 to kill extracellular bacteria in tissue culture infectivity assays", *J Immunol Methods.*, (1983), vol. 56, No. 1, pp. 75-83.

Vrancic M., "Mammalian Genome Recombineering: Yeast, Still a Helper Microorganism of Choice?" *Food Technol. Biotechnol.*, (2008), vol. 46, No. 3, pp. 237-251.

Williams S.K. et al. "Molecular ecology of Listeria monocytogenes and other *Listeria* species in small and very small ready-to-eat meat processing plants", *J Food Prot.*, (2011), vol. 47, No. 1, pp. 63-77.

International Search Report and Written Opinion issued for PCT/US2012/057214, mailed Jan. 24, 2013.

International Search Report issued for PCT/US2014/043190, mailed Dec. 31, 2014.

International Search Report and Written Opinion issued for PCT/US2015/029992, mailed Jul. 28, 2015.

\* cited by examiner

FIGURE 1

LP143_cps (SEQ ID NO: 17); A511_cps (SEQ ID NO: 19); LP101_cps (SEQ ID NO: 11); LP124_cps (SEQ ID NO: 13); LP99_cps (SEQ ID NO: 9); LP48_cps (SEQ ID NO: 7); LP125_cps (SEQ ID NO: 15); P100_cps (SEQ ID NO: 21); LP40_cps (SEQ ID NO: 5)

```
LP143_cps    ATGCCAAAAAATAACAAA---GAAGAAGTTAAAGAAGTAAACCTTAATTCAGTACAAGAG  57
A511_cps     ATGCCAAAAAATAACAAA   GAAGAAGTTAAAGAAGTAAACCTTAATTCAGTACAAGAG  57
LP101_cps    ATGCCAAAAAATAACAAAGAAGAAGAAGTTAAAGAAGTAAACCTTAATTCAGTACAAGAG  60
LP124_cps    ATGCCAAAAAATAACAAAGAAGAAGAAGTTAAAGAAGTAAACCTTAATTCAGTACAAGAG  60
LP99_cps     ATGCCAAAAAATAACAAAGAAGAAGAAGTTAAAGAAGTAAACCTTAATTCAGTACAAGAG  60
LP48_cps     ATGCCAAAAAATAACAAAGAAGAAGAAGTTAAAGAAGTAAACCTTAATTCAGTACAAGAG  60
LP125_cps    ATGCCAAAAAATAACAAAGAAGAAGAAGTTAAAGAAGTAAACCTTAATTCAGTACAAGAG  60
P100_cps     ATGCCAAAAAATAACAAAGAAGAAGAAGTTAAAGAAGTAAACCTTAATTCAGTACAAGAG  60
LP40_cps     ATGCCAAAAAATAACAAAGAAGAAGAAGTTAAAGAAGTAAACCTTAATTCAGTACAAGAG  60
             ******************   ***************************************

LP143_cps    GATGCGTTAAAGTCCTTTACGACTGGTTATGGTATCACACCTGATACACAAACAGATGCA  117
A511_cps     GATGCGTTAAAGTCCTTTACGACTGGTTATGGTATCACACCTGATACACAAACAGATGCA  117
LP101_cps    GACGCGTTAAAGTCCTTTACAACTGGTTATGGTATCACACCTGATACACAAACAGATGCA  120
LP124_cps    GACGCGTTAAAGTCCTTTACAACTGGTTATGGTATCACACCTGATACACAAACAGATGCA  120
LP99_cps     GACGCGTTAAAGTCCTTTACAACTGGTTATGGTATCACACCTGATACACAAACAGATGCA  120
LP48_cps     GACGCGTTAAAGTCCTTTACAACTGGTTATGGTATCACACCTGATACACAAACAGATGCA  120
LP125_cps    GACGCGTTAAAGTCCTTTACAACTGGTTATGGTATCACACCTGATACACAAACAGATGCA  120
P100_cps     GACGCGTTAAAGTCCTTTACAACTGGTTATGGTATCACACCTGATACACAAACAGATGCA  120
LP40_cps     GATGCGTTAAAGTCCTTTACAACTGGTTATGGTATCACACCTGATACACAAACAGATGCA  120
             ** ***************** ***************************************

LP143_cps    GGAGCATTAAGACGTGAGTTCCTAGACGACCAAATCTCAATGCTTACTTGGACAGAGAAT  177
A511_cps     GGAGCATTAAGACGTGAGTTCCTAGACGACCAAATCTCAATGCTTACTTGGACAGAGAAT  177
LP101_cps    GGAGCATTAAGACGTGAGTTCCTAGACGACCAAATCTCAATGCTTACTTGGACAGAGAAT  180
LP124_cps    GGAGCATTAAGACGTGAGTTCCTAGACGACCAAATCTCAATGCTTACTTGGACAGAGAAT  180
LP99_cps     GGAGCATTAAGACGTGAGTTCCTAGACGACCAAATCTCAATGCTTACTTGGACAGAGAAT  180
LP48_cps     GGAGCATTAAGACGTGAGTTCCTAGACGACCAAATCTCAATGCTTACTTGGACAGAGAAT  180
LP125_cps    GGAGCATTAAGACGTGAGTTCCTAGACGACCAAATCTCAATGCTTACTTGGACAGAGAAT  180
P100_cps     GGAGCATTAAGACGTGAGTTCCTAGACGACCAAATCTCAATGCTTACTTGGACAGAGAAT  180
LP40_cps     GGGGCACTAAGACGTGAGTTCCTAGACGACCAAATCTCAATGCTTACTTGGACAGAAAAT  180
             ** *** ***************************************************  ***

LP143_cps    GATTTAACATTCTATAAAGACATCGCTAAAAAACCAGCTACATCTACAGTAGCAAAATAC  237
A511_cps     GATTTAACATTCTATAAAGACATCGCTAAAAAACCAGCTACATCTACAGTAGCAAAATAC  237
LP101_cps    GATTTAACATTCTATAAAGACATCGCTAAAAAACCAGCTACATCTACAGTAGCAAAATAC  240
LP124_cps    GATTTAACATTCTATAAAGACATCGCTAAAAAACCAGCTACATCTACAGTAGCAAAATAC  240
LP99_cps     GATTTAACATTCTATAAAGACATCGCTAAAAAACCAGCTACATCTACAGTAGCAAAATAC  240
LP48_cps     GATTTAACATTCTATAAAGACATCGCTAAAAAACCAGCTACATCTACAGTAGCAAAATAC  240
LP125_cps    GATTTAACATTCTATAAAGACATCGCTAAAAAACCAGCTACATCTACAGTAGCAAAATAC  240
P100_cps     GATTTAACATTCTATAAAGACATCGCTAAAAAACCAGCTACATCTACAGTAGCAAAATAC  240
LP40_cps     GATTTAACATTCTACAAAGACATCGCTAAAAAACCAGCTACATCTACAGTAGCAAAATAC  240
             ************** *********************************************

LP143_cps    GATGTATACATGCAACATGGTAAGGTAGGTCATACTAGATTACTCGTGAGATTGGGGTA   297
A511_cps     GATGTATACATGCAACATGGTAAGGTAGGTCATACTAGATTACTCGTGAGATTGGGGTA   297
LP101_cps    GATGTATACATGCAACATGGTAAGGTAGGTCATACTAGATTACTCGTGAGATTGGGGTA   300
LP124_cps    GATGTATACATGCAACATGGTAAGGTAGGTCATACTAGATTACTCGTGAGATTGGGGTA   300
LP99_cps     GATGTATACATGCAACATGGTAAGGTAGGTCATACTAGATTACTCGTGAGATTGGGGTA   300
LP48_cps     GATGTATACATGCAACATGGTAAGGTAGGTCATACTAGATTACTCGTGAGATTGGGGTA   300
LP125_cps    GATGTATACATGCAACATGGTAAGGTAGGTCATACTAGATTACTCGTGAGATTGGGGTA   300
P100_cps     GATGTATACATGCAACATGGTAAGGTAGGTCATACTAGATTACTCGTGAGATTGGGGTA   300
LP40_cps     GATGTATACATGCAACACGGTAAGGTAGGTCATACTAGATTACTCGTGAGATTGGGGTA   300
             ***** *********** ***** ************************************
```

FIGURE 1 (Cont.)

```
LP143_cps   GCACCAGTAAGTGACCCTAACATCCGTCAAAAAACAGTAAATATGAAATTTGCTTCCGAT 357
A511_cps    GCACCAGTAAGTGACCCTAACATCCGTCAAAAAACAGTAAATATGAAATTTGCTTCCGAT 357
LP101_cps   GCACCAGTAAGTGACCCTAACATCCGTCAAAAAACAGTAAACATGAAATTTGCTTCCGAT 360
LP124_cps   GCACCAGTAAGTGACCCTAACATCCGTCAAAAAACAGTAAACATGAAATTTGCTTCCGAT 360
LP99_cps    GCACCAGTAAGTGACCCTAACATCCGTCAAAAAACAGTAAACATGAAATTTGCTTCCGAT 360
LP48_cps    GCACCAGTAAGTGACCCTAACATCCGTCAAAAAACAGTAAACATGAAATTTGCTTCCGAT 360
LP125_cps   GCACCAGTAAGTGACCCTAACATCCGTCAAAAAACAGTAAACATGAAATTTGCTTCCGAT 360
P100_cps    GCACCAGTAAGTGACCCTAACATCCGTCAAAAAACAGTAAATATGAAATTTGCTTCCGAT 360
LP40_cps    GCACCAGTAAGTGACCCTAACATCCGTCAAAAAACAGTAAACATGAAATTTGCTTCTGAT 360
            **********************************************  ************  ***

LP143_cps   ACTAAAAACATCAGTATCGCAGCAGGTCTAGTAAACAACATTCAAGACCCAATGCAAATT 417
A511_cps    ACTAAAAACATCAGTATCGCAGCAGGTCTAGTAAACAACATTCAAGACCCAATGCAAATT 417
LP101_cps   ACTAAAAACATCAGTATCGCAGCAGGTCTAGTAAACAACATTCAAGACCCAATGCAAATT 420
LP124_cps   ACTAAAAACATCAGTATCGCAGCAGGTCTAGTAAACAACATTCAAGACCCAATGCAAATT 420
LP99_cps    ACTAAAAACATCAGTATCGCAGCAGGTCTAGTAAACAACATTCAAGACCCAATGCAAATT 420
LP48_cps    ACTAAAAACATCAGTATCGCAGCAGGTCTAGTAAACAACATTCAAGACCCAATGCAAATT 420
LP125_cps   ACTAAAAACATCAGTATCGCAGCAGGTCTAGTAAACAACATTCAAGACCCAATGCAAATT 420
P100_cps    ACTAAAAACATCAGTATCGCAGCAGGTCTAGTAAACAACATTCAAGACCCAATGCAAATT 420
LP40_cps    ACTAAAAATATTAGTATCGCAGCAGGTCTAGTAAACAACATTCAAGACCCTATGCAAATT 420
            ********  **  ****************************************  *********

LP143_cps   TTGACTGACGATGCTATCGTAAATATTGCTAAAACAATTGAGTGGGCTTCATTCTTTGGA 477
A511_cps    TTGACTGACGATGCTATCGTAAATATTGCTAAAACAATTGAGTGGGCTTCATTCTTTGGA 477
LP101_cps   TTGACTGACGATGCTATCGTAAATATTGCTAAAACAATTGAGTGGGCTTCATTCTTTGGA 480
LP124_cps   TTGACTGACGATGCTATCGTAAATATTGCTAAAACAATTGAGTGGGCTTCATTCTTTGGA 480
LP99_cps    TTGACTGACGATGCTATCGTAAATATTGCTAAAACAATTGAGTGGGCTTCATTCTTTGGA 480
LP48_cps    TTGACTGACGATGCTATCGTAAATATTGCTAAAACAATTGAGTGGGCTTCATTCTTTGGA 480
LP125_cps   TTGACTGACGATGCTATCGTAAATATTGCTAAAACAATTGAGTGGGCTTCATTCTTTGGA 480
P100_cps    TTGACTGACGATGCTATCGTAAATATTGCTAAAACAATTGAGTGGGCTTCATTCTTTGGA 480
LP40_cps    TTGACTGATGATGCTATCGTAAATATCGCTAAAACAATTGAGTGGGCTTCATTCTTTGGA 480
            ********  ****************  ************************************

LP143_cps   GATTCTGACTTATCAGATAGCCCAGAACCACAAGCAGGACTAGAATTTGACGGCTTGGCT 537
A511_cps    GATTCTGACTTATCAGATAGCCCAGAACCACAAGCAGGACTAGAATTTGACGGCTTGGCT 537
LP101_cps   GATTCTGACTTATCAGATAGCCCAGAACCACAAGCAGGACTAGAATTTGACGGCTTGGCT 540
LP124_cps   GATTCTGACTTATCAGATAGCCCAGAACCACAAGCAGGACTAGAATTTGACGGCTTGGCT 540
LP99_cps    GATTCTGACTTATCAGATAGCCCAGAACCACAAGCAGGACTAGAATTTGACGGCTTGGCT 540
LP48_cps    GATTCTGACTTATCAGATAGCCCAGAACCACAAGCAGGACTAGAATTTGACGGCTTGGCT 540
LP125_cps   GATTCTGACTTATCAGATAGCCCAGAACCACAAGCAGGACTAGAATTTGACGGCTTGGCT 540
P100_cps    GATTCTGACTTATCAGATAGCCCAGAACCACAAGCAGGACTAGAATTTGACGGCTTGGCT 540
LP40_cps    GATTCTGACTTATCAGATAGCCCAGAACCACAAGCAGGATTAGAATTTGATGGCTTGGCT 540
            ***************************************  *********  *********

LP143_cps   AAACTTATTAACCAAGATAACGTTCATGATGCTCGTGGAGCTAGCTTGACTGAAAGCTTG 597
A511_cps    AAACTTATTAACCAAGATAACGTTCATGATGCTCGTGGAGCTAGCTTGACTGAAAGCTTG 597
LP101_cps   AAACTTATTAACCAAGATAACGTTCATGATGCTCGTGGAGCTAGCTTGACTGAAAGCTTG 600
LP124_cps   AAACTTATTAACCAAGATAACGTTCATGATGCTCGTGGAGCTAGCTTGACTGAAAGCTTG 600
LP99_cps    AAACTTATTAACCAAGATAACGTTCATGATGCTCGTGGAGCTAGCTTGACTGAAAGCTTG 600
LP48_cps    AAACTTATTAACCAAGATAACGTTCATGATGCTCGTGGAGCTAGCTTGACTGAAAGCTTG 600
LP125_cps   AAACTTATTAACCAAGATAACGTTCATGATGCTCGTGGAGCTAGCTTGACTGAAAGCTTG 600
P100_cps    AAACTTATTAACCAAGATAACGTTCATGATGCTCGTGGAGCTAGCTTGACTGAAAGCTTG 600
LP40_cps    AAACTTATTAACCAAGATAACGTTCATGATGCTCGTGGAGCTAGCTTGACTGAAAGCTTG 600
            ************************************************************
```

FIGURE 1 (Cont.)

```
LP143_cps    TTAAACCAAGCAGCAGTAATGATTAGTAAAGGTTATGGTACACCTACAGATGCTTACATG 657
A511_cps     TTAAACCAAGCAGCAGTAATGATTAGTAAAGGTTATGGTACACCTACAGATGCTTACATG 657
LP101_cps    TTAAACCAAGCAGCAGTAATGATTAGTAAAGGTTATGGTACACCTACAGATGCTTACATG 660
LP124_cps    TTAAACCAAGCAGCAGTAATGATTAGTAAAGGTTATGGTACACCTACAGATGCTTACATG 660
LP99_cps     TTAAACCAAGCAGCAGTAATGATTAGTAAAGGTTATGGTACACCTACAGATGCTTACATG 660
LP48_cps     TTAAACCAAGCAGCAGTAATGATTAGTAAAGGTTATGGTACACCTACAGATGCTTACATG 660
LP125_cps    TTAAACCAAGCAGCAGTAATGATTAGTAAAGGTTATGGTACACCTACAGATGCTTACATG 660
P100_cps     TTAAACCAAGCAGCAGTAATGATTAGTAAAGGTTATGGTACACCTACAGATGCTTACATG 660
LP40_cps     TTAAACCAAGCAGCAGTAATGATTAGTAAAGGTTATGGTACACCTACAGATGCTTACATG 660
             ************************************************************

LP143_cps    CCAGTAGGGGTTCAAGCAGACTTTGTTAACCAACAACTTTCTAAACAAACACAACTTGTT 717
A511_cps     CCAGTAGGGGTTCAAGCAGACTTTGTTAACCAACAACTTTCTAAACAAACACAACTTGTT 717
LP101_cps    CCAGTAGGGGTTCAAGCAGACTTTGTTAACCAACAACTTTCTAAACAAACACAACTTGTT 720
LP124_cps    CCAGTAGGGGTTCAAGCAGACTTTGTTAACCAACAACTTTCTAAACAAACACAACTTGTT 720
LP99_cps     CCAGTAGGGGTTCAAGCAGACTTTGTTAACCAACAACTTTCTAAACAAACACAACTTGTT 720
LP48_cps     CCAGTAGGGGTTCAAGCAGACTTTGTTAACCAACAACTTTCTAAACAAACACAACTTGTT 720
LP125_cps    CCAGTAGGGGTTCAAGCAGACTTTGTTAACCAACAACTTTCTAAACAAACACAACTTGTT 720
P100_cps     CCAGTAGGGGTTCAAGCAGACTTTGTTAACCAACAACTTTCTAAACAAACACAGCTTGTT 720
LP40_cps     CCAGTAGGGGTTCAAGCAGACTTTGTTAACCAACAACTTTCTAAACAAACACAACTTGTT 720
             ***************************************************** ******

LP143_cps    CGCGATAACGGAAACAACGTAAGCGTTGGTTTCAACATCCAAGGTTTCCATTCAGCTCGT 777
A511_cps     CGCGATAACGGAAACAACGTAAGCGTTGGTTTCAACATCCAAGGTTTCCATTCAGCTCGT 777
LP101_cps    CGCGATAACGGAAACAACGTAAGCGTTGGTTTCAACATCCAAGGTTTCCATTCAGCTCGT 780
LP124_cps    CGCGATAACGGAAACAACGTAAGCGTTGGTTTCAACATCCAAGGTTTCCATTCAGCTCGT 780
LP99_cps     CGCGATAACGGAAACAACGTAAGCGTTGGTTTCAACATCCAAGGTTTCCATTCAGCTCGT 780
LP48_cps     CGCGATAACGGAAACAACGTAAGCGTTGGTTTCAACATCCAAGGTTTCCATTCAGCTCGT 780
LP125_cps    CGTGATAACGGAAACAACGTAAGCGTTGGTTTCAACATCCAAGGTTTCCATTCAGCTCGT 780
P100_cps     CGTGATAACGGAAACAACGTAAGCGTTGGTTTCAACATCCAAGGTTTCCATTCAGCTCGT 780
LP40_cps     CGCGATAACGGAAACAACGTAAGCGTTGGTTTCAACATCCAAGGTTTCCATTCAGCTCGT 780
             ** *********************************************************

LP143_cps    GGATTTATCAAACTTCACGGTTCTACAGTAATGGAAAACGAACAAATCTTAGATGAACGT 837
A511_cps     GGATTTATCAAACTTCACGGTTCTACAGTAATGGAAAACGAACAAATCTTAGATGAACGT 837
LP101_cps    GGATTTATCAAACTTCACGGTTCTACAGTAATGGAAAACGAACAAATCTTAGATGAACGT 840
LP124_cps    GGATTTATCAAACTTCACGGTTCTACAGTAATGGAAAACGAACAAATCTTAGATGAACGT 840
LP99_cps     GGATTTATCAAACTTCACGGTTCTACAGTAATGGAAAACGAACAAATCTTAGATGAACGT 840
LP48_cps     GGATTTATCAAACTTCACGGTTCTACAGTAATGGAAAACGAACAAATCTTAGATGAACGT 840
LP125_cps    GGATTTATCAAACTTCACGGTTCTACAGTAATGGAAAACGAACAAATCTTAGATGAACGT 840
P100_cps     GGATTTATCAAACTTCACGGTTCTACAGTAATGGAAAACGAACAAATCTTAGATGAACGT 840
LP40_cps     GGATTTATCAAACTTCACGGTTCTACAGTAATGGAAAACGAACAAATCTTAGATGAACGT 840
             ************************************************************

LP143_cps    ATTCTTGCTTTACCAACAGCTCCACAACCAGCTAAGGTAACTGCAACACAAGAAGCAGGT 897
A511_cps     ATTCTTGCTTTACCAACAGCTCCACAACCAGCTAAGGTAACTGCAACACAAGAAGCAGGT 897
LP101_cps    ATTCTTGCTTTACCAACAGCTCCACAACCAGCTAAGGTAACTGCAACACAAGAAGCAGGT 900
LP124_cps    ATTCTTGCTTTACCAACAGCTCCACAACCAGCTAAGGTAACTGCAACACAAGAAGCAGGT 900
LP99_cps     ATTCTTGCTTTACCAACAGCTCCACAACCAGCTAAGGTAACTGCAACACAAGAAGCAGGT 900
LP48_cps     ATTCTTGCTTTACCAACAGCTCCACAACCAGCTAAGGTAACTGCAACACAAGAAGCAGGT 900
LP125_cps    ATTCTTGCTTTACCAACAGCTCCACAACCAGCTAAGGTAACTGCAACACAAGAAGCAGGT 900
P100_cps     ATTCTTGCTTTACCAACAGCTCCACAACCAGCTAAGGTAACTGCAACACAAGAAGCAGGT 900
LP40_cps     ATTCTTGCTTTACCAACAGCTCCACAACCAGCTAAGGTAACTGCAACACAAGAAGCAGGT 900
             ************************************************************
```

FIGURE 1 (Cont.)

```
LP143_cps    AAAAAAGGACAATTTAGAGCAGAAGATTTAGCAGCACATGAATATAAAGTTGTTGTAAGT 957
A511_cps     AAAAAAGGACAATTTAGAGCAGAAGATTTAGCAGCACATGAATATAAAGTTGTTGTAAGT 957
LP101_cps    AAAAAAGGACAATTTAGAGCAGAAGATTTAGCAGCACATGAATATAAAGTTGTTGTAAGT 960
LP124_cps    AAAAAAGGACAATTTAGAGCAGAAGATTTAGCAGCACATGAATATAAAGTTGTTGTAAGT 960
LP99_cps     AAAAAAGGACAATTTAGAGCAGAAGATTTAGCAGCACATGAATATAAAGTTGTTGTAAGT 960
LP48_cps     AAAAAAGGACAATTTAGAGCAGAAGATTTAGCAGCACATGAATATAAAGTTGTTGTAAGT 960
LP125_cps    AAAAAAGGACAATTTAGAGCAGAAGATTTAGCAGCACATGAATATAAAGTTGTTGTAAGT 960
P100_cps     AAAAAAGGACAATTTAGAGCAGAAGACTTAGCAGCACACGAATACAAAGTTGTTGTAAGT 960
LP40_cps     AAAAAAGGACAATTTAGAGCAGAAGATTTAGCAGCACATGAATATAAAGTTGTTGTAAGT 960
             ************************ ********** ***** ***************

LP143_cps    TCTGACGATGCAGAGTCTATTGCAAGTGAAGTGGCTACAGCTACAGTTACTGCAAAAGAT 1017
A511_cps     TCTGACGATGCAGAGTCTATTGCAAGTGAAGTGGCTACAGCTACAGTTACTGCAAAAGAT 1017
LP101_cps    TCTGACGATGCAGAGTCTATTGCAAGTGAAGTGGCTACAGCTACAGTTACTGCAAAAGAT 1020
LP124_cps    TCTGACGATGCAGAGTCTATTGCAAGTGAAGTGGCTACAGCTACAGTTACTGCAAAAGAT 1020
LP99_cps     TCTGACGATGCAGAGTCTATTGCAAGTGAAGTGGCTACAGCTACAGTTACTGCAAAAGAT 1020
LP48_cps     TCTGACGATGCAGAGTCTATTGCAAGTGAAGTGGCTACAGCTACAGTTACTGCAAAAGAT 1020
LP125_cps    TCTGACGATGCAGAGTCTATTGCAAGTGAAGTGGCTACAGCTACAGTTACTGCAAAAGAT 1020
P100_cps     TCTGACGATGCAGAGTCTATTGCAAGTGAAGTGGCTACAGCTACAGTTACTGCAAAAGAT 1020
LP40_cps     TCTGACGATGCAGAGTCTATTGCAAGTGAAGTGGCTACAGCTACAGTTACTGCAAAAGAT 1020
             ************************************************************

LP143_cps    GACGGCGTTAAACTAGAAATCGAATTAGCTCCAATGTATAGCTCTCGTCCACAATTCGTT 1077
A511_cps     GACGGCGTTAAACTAGAAATCGAATTAGCTCCAATGTATAGCTCTCGTCCACAATTCGTT 1077
LP101_cps    GACGGCGTTAAACTAGAAATCGAATTAGCTCCAATGTATAGCTCTCGTCCACAATTCGTT 1080
LP124_cps    GACGGCGTTAAACTAGAAATCGAATTAGCTCCAATGTATAGCTCTCGTCCACAATTCGTT 1080
LP99_cps     GACGGCGTTAAACTAGAAATCGAATTAGCTCCAATGTATAGCTCTCGTCCACAATTCGTT 1080
LP48_cps     GACGGCGTTAAACTAGAAATCGAATTAGCTCCAATGTATAGCTCTCGTCCACAATTCGTT 1080
LP125_cps    GACGGCGTTAAACTAGAAATCGAATTAGCTCCAATGTATAGCTCTCGTCCACAATTCGTT 1080
P100_cps     GACGGCGTTAAACTAGAAATCGAGTTAGCTCCAATGTACAGCTCCCGTCCACAATTCGTT 1080
LP40_cps     GACGGCGTTAAACTAGAAATCGAATTAGCTCCAATGTATAGCTCTCGTCCACAATTCGTT 1080
             *********************** ************** ***** **************

LP143_cps    TCAATCTATAGAAAAGGTGCAGAAACAGGTTTATTCTACCTAATCGCTCGTGTACCTGCT 1137
A511_cps     TCAATCTATAGAAAAGGTGCAGAAACAGGTTTATTCTACCTAATCGCTCGTGTACCTGCT 1137
LP101_cps    TCAATCTATAGAAAAGGTGCAGAAACAGGTTTATTCTACCTAATCGCTCGTGTACCTGCT 1140
LP124_cps    TCAATCTATAGAAAAGGTGCAGAAACAGGTTTATTCTACCTAATCGCTCGTGTACCTGCT 1140
LP99_cps     TCAATCTATAGAAAAGGTGCAGAAACAGGTTTATTCTACCTAATCGCTCGTGTACCTGCT 1140
LP48_cps     TCAATCTATAGAAAAGGTGCAGAAACAGGTTTATTCTACCTAATCGCTCGTGTACCTGCT 1140
LP125_cps    TCAATCTATAGAAAAGGTGCAGAAACAGGTTTATTCTACCTAATCGCTCGTGTACCTGCT 1140
P100_cps     TCAATCTATAGAAAAGGTGCAGAAACAGGTTTATTCTACCTAATCGCTCGTGTACCTGCT 1140
LP40_cps     TCAATCTATAGAAAAGGTGCAGAAACAGGTTTATTCTACCTAATCGCTCGTGTACCTGCT 1140
             ************************************************************

LP143_cps    AGCAAAGCAGAGAACAACGTAATCACTTTCTACGACTTAAACGACTCTATTCCTGAAACA 1197
A511_cps     AGCAAAGCAGAGAACAACGTAATCACTTTCTACGACTTAAACGACTCTATTCCTGAAACA 1197
LP101_cps    AGCAAAGCAGAGAACAACGTAATCACTTTCTACGACTTAAACGACTCTATTCCTGAAACA 1200
LP124_cps    AGCAAAGCAGAGAACAACGTAATCACTTTCTACGACTTAAACGACTCTATTCCTGAAACA 1200
LP99_cps     AGCAAAGCAGAGAACAACGTAATCACTTTCTACGACTTAAACGACTCTATTCCTGAAACA 1200
LP48_cps     AGCAAAGCAGAGAACAACGTAATCACTTTCTACGACTTAAACGACTCTATTCCTGAAACA 1200
LP125_cps    AGCAAAGCAGAGAACAACGTAATCACTTTCTACGACTTAAACGACTCTATTCCTGAAACA 1200
P100_cps     AGCAAAGCAGAGAACAACGTAATCACTTTCTATGACTTAAACGACTCTATTCCTGAAACA 1200
LP40_cps     AGCAAAGCAGAGAACAACGTAATCACTTTCTACGACTTAAACGACTCTATTCCTGAAACA 1200
             ******************************** ***************************

LP143_cps    GTAGACGTATTCGTTGGTGAAATGTCGGCTAACGTAGTACACTTGTTTGAATTACTACCA 1257
A511_cps     GTAGACGTATTCGTTGGTGAAATGTCGGCTAACGTAGTACACTTGTTTGAATTACTACCA 1257
LP101_cps    GTAGACGTATTCGTTGGTGAAATGTCGGCTAACGTAGTACACTTGTTTGAATTACTACCA 1260
LP124_cps    GTAGACGTATTCGTTGGTGAAATGTCGGCTAACGTAGTACACTTGTTTGAATTACTACCA 1260
LP99_cps     GTAGACGTATTCGTTGGTGAAATGTCGGCTAACGTAGTACACTTGTTTGAATTACTACCA 1260
LP48_cps     GTAGACGTATTCGTTGGTGAAATGTCGGCTAACGTAGTACACTTGTTTGAATTACTACCA 1260
LP125_cps    GTAGACGTATTCGTTGGTGAAATGTCGGCTAACGTAGTACACTTGTTTGAATTACTACCA 1260
P100_cps     GTAGACGTATTCGTTGGTGAAATGTCTGCTAACGTAGTACACTTGTTTGAATTACTACCA 1260
LP40_cps     GTAGACGTATTCGTTGGTGAAATGTCGGCTAACGTAGTACACTTGTTTGAATTACTACCA 1260
             ************************** *********************************
```

FIGURE 1 (Cont.)

```
LP143_cps    ATGATGAGATTACCTCTAGCTCAAATTAACGCATCTGTTACATTTGCAGTTTTATGGTAT 1317
A511_cps     ATGATGAGATTACCTCTAGCTCAAATTAACGCATCTGTTACATTTGCAGTTTTATGGTAT 1317
LP101_cps    ATGATGAGATTACCTCTAGCTCAAATTAACGCATCTGTTACATTTGCAGTTTTATGGTAT 1320
LP124_cps    ATGATGAGATTACCTCTAGCTCAAATTAACGCATCTGTTACATTTGCAGTTTTATGGTAT 1320
LP99_cps     ATGATGAGATTACCTCTAGCTCAAATTAACGCATCTGTTACATTTGCAGTTTTATGGTAT 1320
LP48_cps     ATGATGAGATTACCTCTAGCTCAAATTAACGCATCTGTTACATTTGCAGTTTTATGGTAT 1320
LP125_cps    ATGATGAGATTACCTCTAGCTCAAATTAACGCATCTGTTACATTTGCAGTTTTATGGTAT 1320
P100_cps     ATGATGAGATTACCTCTAGCTCAAATTAACGCATCTGTTACATTTGCAGTTTTATGGTAT 1320
LP40_cps     ATGATGAGATTACCTCTAGCTCAAATTAACGCATCTGTTACATTTGCAGTTTTATGGTAT 1320
             ************************************************************

LP143_cps    GGCGCATTAGCTCTAAGAGCACCTAAGAAATGGGTACGTATTAGAAACGTTAAATATATT 1377
A511_cps     GGCGCATTAGCTCTAAGAGCACCTAAGAAATGGGTACGTATTAGAAACGTTAAATATATT 1377
LP101_cps    GGCGCATTAGCTCTAAGAGCACCTAAGAAATGGGTACGTATTAGAAACGTTAAATATATT 1380
LP124_cps    GGCGCATTAGCTCTAAGAGCACCTAAGAAATGGGTACGTATTAGAAACGTTAAATATATT 1380
LP99_cps     GGCGCATTAGCTCTAAGAGCACCTAAGAAATGGGTACGTATTAGAAACGTTAAATATATT 1380
LP48_cps     GGCGCATTAGCTCTAAGAGCACCTAAGAAATGGGTACGTATTAGAAACGTTAAATATATT 1380
LP125_cps    GGCGCATTAGCTCTAAGAGCACCTAAGAAATGGGTACGTATTAGAAACGTTAAATATATT 1380
P100_cps     GGAGCATTAGCTCTAAGAGCACCTAAGAAATGGGTACGTATTAGAAACGTTAAATATATT 1380
LP40_cps     GGCGCATTAGCTCTAAGAGCACCTAAGAAATGGGTACGTATTAGAAACGTTAAATATATT 1380
             ** *********************************************************

LP143_cps    CCTGTAAAAAACGTTCATAGCAACTAA 1404
A511_cps     CCTGTAAAAAACGTTCATAGCAACTAA 1404
LP101_cps    CCTGTAAAAAACGTTCATAGCAACTAA 1407
LP124_cps    CCTGTAAAAAACGTTCATAGCAACTAA 1407
LP99_cps     CCTGTAAAAAACGTTCATAGCAACTAA 1407
LP48_cps     CCTGTAAAAAACGTTCATAGCAACTAA 1407
LP125_cps    CCTGTAAAAAACGTTCATAGCAACTAA 1407
P100_cps     CCTGTAAAAAACGTTCATAGCAACTAA 1407
LP40_cps     CCTGTAAAAAACGTTCATAGCAACTAA 1407
             ***************************
```

FIGURE 2

LP143_cps (SEQ ID NO: 18); A511_cps (SEQ ID NO: 20); LP40_cps (SEQ ID NO: 6); LP48_cps (SEQ ID NO: 8); LP99_cps (SEQ ID NO: 10); LP101_cps (SEQ ID NO: 12); LP124_cps (SEQ ID NO: 14); P100_cps (SEQ ID NO: 22), LP125_cps (SEQ ID NO: 16)

```
LP143_cps    MPKNNK-EEVKEVNLNSVQEDALKSFTTGYGITPDTQTDAGALRREFLDDQISMLTWTEN  59
A511_cps     MPKNNK EEVKEVNLNSVQEDALKSFTTGYGITPDTQTDAGALRREFLDDQISMLTWTEN  59
LP40_cps     MPKNNKEEEVKEVNLNSVQEDALKSFTTGYGITPDTQTDAGALRREFLDDQISMLTWTEN  60
LP48_cps     MPKNNKEEEVKEVNLNSVQEDALKSFTTGYGITPDTQTDAGALRREFLDDQISMLTWTEN  60
LP99_cps     MPKNNKEEEVKEVNLNSVQEDALKSFTTGYGITPDTQTDAGALRREFLDDQISMLTWTEN  60
LP101_cps    MPKNNKEEEVKEVNLNSVQEDALKSFTTGYGITPDTQTDAGALRREFLDDQISMLTWTEN  60
LP124_cps    MPKNNKEEEVKEVNLNSVQEDALKSFTTGYGITPDTQTDAGALRREFLDDQISMLTWTEN  60
P100_cps     MPKNNKEEEVKEVNLNSVQEDALKSFTTGYGITPDTQTDAGALRREFLDDQISMLTWTEN  60
LP125_cps    MPKNNKEEEVKEVNLNSVQEDALKSFTTGYGITPDTQTDAGALRREFLDDQISMLTWTEN  60
             ****** ****************************************************

LP143_cps    DLTFYKDIAKKPATSTVAKYDVYMQHGKVGHTRFTREIGVAPVSDPNIRQKTVNMKFASD  119
A511_cps     DLTFYKDIAKKPATSTVAKYDVYMQHGKVGHTRFTREIGVAPVSDPNIRQKTVNMKFASD  119
LP40_cps     DLTFYKDIAKKPATSTVAKYDVYMQHGKVGHTRFTREIGVAPVSDPNIRQKTVNMKFASD  120
LP48_cps     DLTFYKDIAKKPATSTVAKYDVYMQHGKVGHTRFTREIGVAPVSDPNIRQKTVNMKFASD  120
LP99_cps     DLTFYKDIAKKPATSTVAKYDVYMQHGKVGHTRFTREIGVAPVSDPNIRQKTVNMKFASD  120
LP101_cps    DLTFYKDIAKKPATSTVAKYDVYMQHGKVGHTRFTREIGVAPVSDPNIRQKTVNMKFASD  120
LP124_cps    DLTFYKDIAKKPATSTVAKYDVYMQHGKVGHTRFTREIGVAPVSDPNIRQKTVNMKFASD  120
P100_cps     DLTFYKDIAKKPATSTVAKYDVYMQHGKVGHTRFTREIGVAPVSDPNIRQKTVNMKFASD  120
LP125_cps    DLTFYKDIAKKPATSTVAKYDVYMQHGKVGHTRFTREIGVAPVSDPNIRQKTVNMKFASD  120
             ************************************************************

LP143_cps    TKNISIAAGLVNNIQDPMQILTDDAIVNIAKTIEWASFFGDSDLSDSPEPQAGLEFDGLA  179
A511_cps     TKNISIAAGLVNNIQDPMQILTDDAIVNIAKTIEWASFFGDSDLSDSPEPQAGLEFDGLA  179
LP40_cps     TKNISIAAGLVNNIQDPMQILTDDAIVNIAKTIEWASFFGDSDLSDSPEPQAGLEFDGLA  180
LP48_cps     TKNISIAAGLVNNIQDPMQILTDDAIVNIAKTIEWASFFGDSDLSDSPEPQAGLEFDGLA  180
LP99_cps     TKNISIAAGLVNNIQDPMQILTDDAIVNIAKTIEWASFFGDSDLSDSPEPQAGLEFDGLA  180
LP101_cps    TKNISIAAGLVNNIQDPMQILTDDAIVNIAKTIEWASFFGDSDLSDSPEPQAGLEFDGLA  180
LP124_cps    TKNISIAAGLVNNIQDPMQILTDDAIVNIAKTIEWASFFGDSDLSDSPEPQAGLEFDGLA  180
P100_cps     TKNISIAAGLVNNIQDPMQILTDDAIVNIAKTIEWASFFGDSDLSDSPEPQAGLEFDGLA  180
LP125_cps    TKNISIAAGLVNNIQDPMQILTDDAIVNIAKTIEWASFFGDSDLSDSPEPQAGLEFDGLA  180
             ************************************************************

LP143_cps    KLINQDNVHDARGASLTESLLNQAAVMISKGYGTPTDAYMPVGVQADFVNQQLSKQTQLV  239
A511_cps     KLINQDNVHDARGASLTESLLNQAAVMISKGYGTPTDAYMPVGVQADFVNQQLSKQTQLV  239
LP40_cps     KLINQDNVHDARGASLTESLLNQAAVMISKGYGTPTDAYMPVGVQADFVNQQLSKQTQLV  240
LP48_cps     KLINQDNVHDARGASLTESLLNQAAVMISKGYGTPTDAYMPVGVQADFVNQQLSKQTQLV  240
LP99_cps     KLINQDNVHDARGASLTESLLNQAAVMISKGYGTPTDAYMPVGVQADFVNQQLSKQTQLV  240
LP101_cps    KLINQDNVHDARGASLTESLLNQAAVMISKGYGTPTDAYMPVGVQADFVNQQLSKQTQLV  240
LP124_cps    KLINQDNVHDARGASLTESLLNQAAVMISKGYGTPTDAYMPVGVQADFVNQQLSKQTQLV  240
P100_cps     KLINQDNVHDARGASLTESLLNQAAVMISKGYGTPTDAYMPVGVQADFVNQQLSKQTQLV  240
LP125_cps    KLINQDNVHDARGASLTESLLNQAAVMISKGYGTPTDAYMPVGVQADFVNQQLSKQTQLV  240
             ************************************************************

LP143_cps    RDNGNNVSVGFNIQGFHSARGFIKLHGSTVMENEQILDERILALPTAPQPAKVTATQEAG  299
A511_cps     RDNGNNVSVGFNIQGFHSARGFIKLHGSTVMENEQILDERILALPTAPQPAKVTATQEAG  299
LP40_cps     RDNGNNVSVGFNIQGFHSARGFIKLHGSTVMENEQILDERILALPTAPQPAKVTATQEAG  300
LP48_cps     RDNGNNVSVGFNIQGFHSARGFIKLHGSTVMENEQILDERILALPTAPQPAKVTATQEAG  300
LP99_cps     RDNGNNVSVGFNIQGFHSARGFIKLHGSTVMENEQILDERILALPTAPQPAKVTATQEAG  300
LP101_cps    RDNGNNVSVGFNIQGFHSARGFIKLHGSTVMENEQILDERILALPTAPQPAKVTATQEAG  300
LP124_cps    RDNGNNVSVGFNIQGFHSARGFIKLHGSTVMENEQILDERILALPTAPQPAKVTATQEAG  300
P100_cps     RDNGNNVSVGFNIQGFHSARGFIKLHGSTVMENEQILDERILALPTAPQPAKVTATQEAG  300
LP125_cps    RDNGNNVSVGFNIQGFHSARGFIKLHGSTVMENEQILDERILALPTAPQPAKVTATQEAG  300
             ************************************************************
```

FIGURE 2 (Cont.)

```
LP143_cps    KKGQFRAEDLAAHEYKVVVSSDDAESIASEVATATVTAKDDGVKLEIELAPMYSSRPQFV 359
A511_cps     KKGQFRAEDLAAHEYKVVVSSDDAESIASEVATATVTAKDDGVKLEIELAPMYSSRPQFV 359
LP40_cps     KKGQFRAEDLAAHEYKVVVSSDDAESIASEVATATVTAKDDGVKLEIELAPMYSSRPQFV 360
LP48_cps     KKGQFRAEDLAAHEYKVVVSSDDAESIASEVATATVTAKDDGVKLEIELAPMYSSRPQFV 360
LP99_cps     KKGQFRAEDLAAHEYKVVVSSDDAESIASEVATATVTAKDDGVKLEIELAPMYSSRPQFV 360
LP101_cps    KKGQFRAEDLAAHEYKVVVSSDDAESIASEVATATVTAKDDGVKLEIELAPMYSSRPQFV 360
LP124_cps    KKGQFRAEDLAAHEYKVVVSSDDAESIASEVATATVTAKDDGVKLEIELAPMYSSRPQFV 360
P100_cps     KKGQFRAEDLAAHEYKVVVSSDDAESIASEVATATVTAKDDGVKLEIELAPMYSSRPQFV 360
LP125_cps    KKGQFRAEDLAAHEYKVVVSSDDAESIASEVATATVTAKDDGVKLEIELAPMYSSRPQFV 360
             ************************************************************

LP143_cps    SIYRKGAETGLFYIIARVPASKAENNVITFYDLNDSIPETVDVFVGEMSANVVHLFELLP 419
A511_cps     SIYRKGAETGLFYIIARVPASKAENNVITFYDLNDSIPETVDVFVGEMSANVVHLFELLP 419
LP40_cps     SIYRKGAETGLFYIIARVPASKAENNVITFYDLNDSIPETVDVFVGEMSANVVHLFELLP 420
LP48_cps     SIYRKGAETGLFYIIARVPASKAENNVITFYDLNDSIPETVDVFVGEMSANVVHLFELLP 420
LP99_cps     SIYRKGAETGLFYIIARVPASKAENNVITFYDLNDSIPETVDVFVGEMSANVVHLFELLP 420
LP101_cps    SIYRKGAETGLFYIIARVPASKAENNVITFYDLNDSIPETVDVFVGEMSANVVHLFELLP 420
LP124_cps    SIYRKGAETGLFYIIARVPASKAENNVITFYDLNDSIPETVDVFVGEMSANVVHLFELLP 420
P100_cps     SIYRKGAETGLFYIIARVPASKAENNVITFYDLNDSIPETVDVFVGEMSANVVHLFELLP 420
LP125_cps    SIYRKGAETGLFYIIARVPASKAENNVITFYDLNDSIPETVDVFVGEMSANVVHLFELLP 420
             ************************************************************

LP143_cps    MMRLPLAQINASVTFAVLWYGALALRAPKKWVRIRNVKYIPVKNVHSN 467
A511_cps     MMRLPLAQINASVTFAVLWYGALALRAPKKWVRIRNVKYIPVKNVHSN 467
LP40_cps     MMRLPLAQINASVTFAVLWYGALALRAPKKWVRIRNVKYIPVKNVHSN 468
LP48_cps     MMRLPLAQINASVTFAVLWYGALALRAPKKWVRIRNVKYIPVKNVHSN 468
LP99_cps     MMRLPLAQINASVTFAVLWYGALALRAPKKWVRIRNVKYIPVKNVHSN 468
LP101_cps    MMRLPLAQINASVTFAVLWYGALALRAPKKWVRIRNVKYIPVKNVHSN 468
LP124_cps    MMRLPLAQINASVTFAVLWYGALALRAPKKWVRIRNVKYIPVKNVHSN 468
P100_cps     MMRLPLAQINASVTFAVLWYGALALRAPKKWVRIRNVKYIPVKNVHSN 468
LP125_cps    MMRLPLAQINASVTFAVLWYGALALRAPKKWVRIRNVKYIPVKNVHSN 468
             ************************************************
```

FIGURE 3

LP48_ffluc (SEQ ID NO: 23); LP125_ffluc (SEQ ID NO: 27); LP143_ffluc (SEQ ID NO: 28); A511_fluc (SEQ ID NO: 29); LP124_ffluc (SEQ ID NO: 26); lp101_ffluc (SEQ ID NO: 25); LP99_ffluc (SEQ ID NO: 24); P100_ffluc (SEQ ID NO: 30)

```
LP48_ffluc     ATGCCAAAAAATAACAAGAAGAAGAAGTTAAAGAAGTAAACCTTAATTCAGTACAAGAG 60
LP125_ffluc    ATGCCAAAAAATAACAAGAAGAAGAAGTTAAAGAAGTAAACCTTAATTCAGTACAAGAG 60
LP143_ffluc    ATGCCAAAAAATAACAAA---GAAGAAGTTAAAGAAGTAAACCTTAATTCAGTACAAGAG 57
A511_ffluc     ATGCCAAAAAATAACAAA---GAAGAAGTTAAAGAAGTAAACCTTAATTCAGTACAAGAG 57
LP124_ffluc    ATGCCAAAAAATAACAAGAAGAAGAAGTTAAAGAAGTAAACCTTAATTCAGTACAAGAG 60
lp101_ffluc    ATGCCAAAAAATAACAAGAAGAAGAAGTTAAAGAAGTAAACCTTAATTCAGTACAAGAG 60
LP99_ffluc     ATGCCAAAAAATAACAAGAAGAAGAAGTTAAAGAAGTAAACCTTAATTCAGTACAAGAG 60
P100_ffluc     ATGCCAAAAAATAACAAGAAGAAGAAGTTAAAGAAGTAAACCTTAATTCAGTACAAGAG 60
               ****************   ****************************************

LP48_ffluc     GACGCGTTAAAGTCCTTTACAACTGGTTATGGTATCACACCTGATACACAAACAGATGCA 120
LP125_ffluc    GACGCGTTAAAGTCCTTTACAACTGGTTATGGTATCACACCTGATACACAAACAGATGCA 120
LP143_ffluc    GATGCGTTAAAGTCCTTTACGACTGGTTATGGTATCACACCTGATACACAAACAGATGCA 117
A511_ffluc     GATGCGTTAAAGTCCTTTACGACTGGTTATGGTATCACACCTGATACACAAACAGATGCA 117
LP124_ffluc    GACGCGTTAAAGTCCTTTACAACTGGTTATGGTATCACACCTGATACACAAACAGATGCA 120
lp101_ffluc    GACGCGTTAAAGTCCTTTACAACTGGTTATGGTATCACACCTGATACACAAACAGATGCA 120
LP99_ffluc     GACGCGTTAAAGTCCTTTACAACTGGTTATGGTATCACACCTGATACACAAACAGATGCA 120
P100_ffluc     GACGCGTTAAAGTCCTTTACAACTGGTTATGGTATCACACCTGATACACAAACAGATGCA 120
               ** ***************** ***************************************

LP48_ffluc     GGAGCATTAAGACGTGAGTTCCTAGACGACCAAATCTCAATGCTTACTTGGACAGAGAAT 180
LP125_ffluc    GGAGCATTAAGACGTGAGTTCCTAGACGACCAAATCTCAATGCTTACTTGGACAGAGAAT 180
LP143_ffluc    GGAGCATTAAGACGTGAGTTCCTAGACGACCAAATCTCAATGCTTACTTGGACAGAGAAT 177
A511_ffluc     GGAGCATTAAGACGTGAGTTCCTAGACGACCAAATCTCAATGCTTACTTGGACAGAGAAT 177
LP124_ffluc    GGAGCATTAAGACGTGAGTTCCTAGACGACCAAATCTCAATGCTTACTTGGACAGAGAAT 180
lp101_ffluc    GGAGCATTAAGACGTGAGTTCCTAGACGACCAAATCTCAATGCTTACTTGGACAGAGAAT 180
LP99_ffluc     GGAGCATTAAGACGTGAGTTCCTAGACGACCAAATCTCAATGCTTACTTGGACAGAGAAT 180
P100_ffluc     GGAGCATTAAGACGTGAGTTCCTAGACGACCAAATCTCAATGCTTACTTGGACAGAGAAT 180
               ************************************************************

LP48_ffluc     GATTTAACATTCTATAAAGACATCGCTAAAAAACCAGCTACATCTACAGTAGCAAAATAC 240
LP125_ffluc    GATTTAACATTCTATAAAGACATCGCTAAAAAACCAGCTACATCTACAGTAGCAAAATAC 240
LP143_ffluc    GATTTAACATTCTATAAAGACATCGCTAAAAAACCAGCTACATCTACAGTAGCAAAATAC 237
A511_ffluc     GATTTAACATTCTATAAAGACATCGCTAAAAAACCAGCTACATCTACAGTAGCAAAATAC 237
LP124_ffluc    GATTTAACATTCTATAAAGACATCGCTAAAAAACCAGCTACATCTACAGTAGCAAAATAC 240
lp101_ffluc    GATTTAACATTCTATAAAGACATCGCTAAAAAACCAGCTACATCTACAGTAGCAAAATAC 240
LP99_ffluc     GATTTAACATTCTATAAAGACATCGCTAAAAAACCAGCTACATCTACAGTAGCAAAATAC 240
P100_ffluc     GATTTAACATTCTATAAAGACATCGCTAAAAAACCAGCTACATCTACAGTAGCAAAATAC 240
               ************************************************************

LP48_ffluc     GATGTATACATGCAACATGGTAAGGTAGGTCATACTAGATTTACTCGTGAGATTGGGGTA 300
LP125_ffluc    GATGTATACATGCAACATGGTAAGGTAGGTCATACTAGATTTACTCGTGAGATTGGGGTA 300
LP143_ffluc    GATGTATACATGCAACATGGTAAGGTAGGTCATACTAGATTTACTCGTGAGATTGGGGTA 297
A511_ffluc     GATGTATACATGCAACATGGTAAGGTAGGTCATACTAGATTTACTCGTGAGATTGGGGTA 297
LP124_ffluc    GATGTATACATGCAACATGGTAAGGTAGGTCATACTAGATTTACTCGTGAGATTGGGGTA 300
lp101_ffluc    GATGTATACATGCAACATGGTAAGGTAGGTCATACTAGATTTACTCGTGAGATTGGGGTA 300
LP99_ffluc     GATGTATACATGCAACATGGTAAGGTAGGTCATACTAGATTTACTCGTGAGATTGGGGTA 300
P100_ffluc     GATGTATACATGCAACATGGTAAGGTAGGTCATACTAGATTTACTCGTGAGATTGGGGTA 300
               ************************************************************

LP48_ffluc     GCACCAGTAAGTGACCCTAACATCCGTCAAAAAACAGTAAACATGAATTTGCTTCCGAT 360
LP125_ffluc    GCACCAGTAAGTGACCCTAACATCCGTCAAAAAACAGTAAACATGAATTTGCTTCCGAT 360
LP143_ffluc    GCACCAGTAAGTGACCCTAACATCCGTCAAAAAACAGTAAATATGAATTTGCTTCCGAT 357
A511_ffluc     GCACCAGTAAGTGACCCTAACATCCGTCAAAAAACAGTAAATATGAATTTGCTTCCGAT 357
LP124_ffluc    GCACCAGTAAGTGACCCTAACATCCGTCAAAAAACAGTAAACATGAATTTGCTTCCGAT 360
lp101_ffluc    GCACCAGTAAGTGACCCTAACATCCGTCAAAAAACAGTAAACATGAATTTGCTTCCGAT 360
LP99_ffluc     GCACCAGTAAGTGACCCTAACATCCGTCAAAAAACAGTAAACATGAATTTGCTTCCGAT 360
P100_ffluc     GCACCAGTAAGTGACCCTAACATCCGTCAAAAAACAGTAAATATGAATTTGCTTCCGAT 360
               ***************************************** *****************
```

FIGURE 3 (Cont.)

```
LP48_ffluc      ACTAAAAACATCAGTATCGCAGCAGGTCTAGTAAACAACATTCAAGACCCAATGCAAATT 420
LP125_ffluc     ACTAAAAACATCAGTATCGCAGCAGGTCTAGTAAACAACATTCAAGACCCAATGCAAATT 420
LP143_ffluc     ACTAAAAACATCAGTATCGCAGCAGGTCTAGTAAACAACATTCAAGACCCAATGCAAATT 417
A511_ffluc      ACTAAAAACATCAGTATCGCAGCAGGTCTAGTAAACAACATTCAAGACCCAATGCAAATT 417
LP124_ffluc     ACTAAAAACATCAGTATCGCAGCAGGTCTAGTAAACAACATTCAAGACCCAATGCAAATT 420
Lp101_ffluc     ACTAAAAACATCAGTATCGCAGCAGGTCTAGTAAACAACATTCAAGACCCAATGCAAATT 420
LP99_ffluc      ACTAAAAACATCAGTATCGCAGCAGGTCTAGTAAACAACATTCAAGACCCAATGCAAATT 420
P100_ffluc      ACTAAAAACATCAGTATCGCAGCAGGTCTAGTAAACAACATTCAAGACCCAATGCAAATT 420
                ************************************************************

LP48_ffluc      TTGACTGACGATGCTATCGTAAATATTGCTAAAACAATTGAGTGGGCTTCATTCTTTGGA 480
LP125_ffluc     TTGACTGACGATGCTATCGTAAATATTGCTAAAACAATTGAGTGGGCTTCATTCTTTGGA 480
LP143_ffluc     TTGACTGACGATGCTATCGTAAATATTGCTAAAACAATTGAGTGGGCTTCATTCTTTGGA 477
A511_ffluc      TTGACTGACGATGCTATCGTAAATATTGCTAAAACAATTGAGTGGGCTTCATTCTTTGGA 477
LP124_ffluc     TTGACTGACGATGCTATCGTAAATATTGCTAAAACAATTGAGTGGGCTTCATTCTTTGGA 480
Lp101_ffluc     TTGACTGACGATGCTATCGTAAATATTGCTAAAACAATTGAGTGGGCTTCATTCTTTGGA 480
LP99_ffluc      TTGACTGACGATGCTATCGTAAATATTGCTAAAACAATTGAGTGGGCTTCATTCTTTGGA 480
P100_ffluc      TTGACTGACGATGCTATCGTAAATATTGCTAAAACAATTGAGTGGGCTTCATTCTTTGGA 480
                ************************************************************

LP48_ffluc      GATTCTGACTTATCAGATAGCCCAGAACCACAAGCAGGACTAGAATTTGACGGCTTGGCT 540
LP125_ffluc     GATTCTGACTTATCAGATAGCCCAGAACCACAAGCAGGACTAGAATTTGACGGCTTGGCT 540
LP143_ffluc     GATTCTGACTTATCAGATAGCCCAGAACCACAAGCAGGACTAGAATTTGACGGCTTGGCT 537
A511_ffluc      GATTCTGACTTATCAGATAGCCCAGAACCACAAGCAGGACTAGAATTTGACGGCTTGGCT 537
LP124_ffluc     GATTCTGACTTATCAGATAGCCCAGAACCACAAGCAGGACTAGAATTTGACGGCTTGGCT 540
Lp101_ffluc     GATTCTGACTTATCAGATAGCCCAGAACCACAAGCAGGACTAGAATTTGACGGCTTGGCT 540
LP99_ffluc      GATTCTGACTTATCAGATAGCCCAGAACCACAAGCAGGACTAGAATTTGACGGCTTGGCT 540
P100_ffluc      GATTCTGACTTATCAGATAGCCCAGAACCACAAGCAGGACTAGAATTTGACGGCTTGGCT 540
                ************************************************************

LP48_ffluc      AAACTTATTAACCAAGATAACGTTCATGATGCTCGTGGAGCTAGCTTGACTGAAAGCTTG 600
LP125_ffluc     AAACTTATTAACCAAGATAACGTTCATGATGCTCGTGGAGCTAGCTTGACTGAAAGCTTG 600
LP143_ffluc     AAACTTATTAACCAAGATAACGTTCATGATGCTCGTGGAGCTAGCTTGACTGAAAGCTTG 597
A511_ffluc      AAACTTATTAACCAAGATAACGTTCATGATGCTCGTGGAGCTAGCTTGACTGAAAGCTTG 597
LP124_ffluc     AAACTTATTAACCAAGATAACGTTCATGATGCTCGTGGAGCTAGCTTGACTGAAAGCTTG 600
Lp101_ffluc     AAACTTATTAACCAAGATAACGTTCATGATGCTCGTGGAGCTAGCTTGACTGAAAGCTTG 600
LP99_ffluc      AAACTTATTAACCAAGATAACGTTCATGATGCTCGTGGAGCTAGCTTGACTGAAAGCTTG 600
P100_ffluc      AAACTTATTAACCAAGATAACGTTCATGATGCTCGTGGAGCTAGCTTGACTGAAAGCTTG 600
                ************************************************************

LP48_ffluc      TTAAACCAAGCAGCAGTAATGATTAGTAAAGGTTATGGTACACCTACAGATGCTTACATG 660
LP125_ffluc     TTAAACCAAGCAGCAGTAATGATTAGTAAAGGTTATGGTACACCTACAGATGCTTACATG 660
LP143_ffluc     TTAAACCAAGCAGCAGTAATGATTAGTAAAGGTTATGGTACACCTACAGATGCTTACATG 657
A511_ffluc      TTAAACCAAGCAGCAGTAATGATTAGTAAAGGTTATGGTACACCTACAGATGCTTACATG 657
LP124_ffluc     TTAAACCAAGCAGCAGTAATGATTAGTAAAGGTTATGGTACACCTACAGATGCTTACATG 660
Lp101_ffluc     TTAAACCAAGCAGCAGTAATGATTAGTAAAGGTTATGGTACACCTACAGATGCTTACATG 660
LP99_ffluc      TTAAACCAAGCAGCAGTAATGATTAGTAAAGGTTATGGTACACCTACAGATGCTTACATG 660
P100_ffluc      TTAAACCAAGCAGCAGTAATGATTAGTAAAGGTTATGGTACACCTACAGATGCTTACATG 660
                ************************************************************

LP48_ffluc      CCAGTAGGGGTTCAAGCAGACTTTGTTAACCAACAACTTCTAAACAAACACAACTTGTT 720
LP125_ffluc     CCAGTAGGGGTTCAAGCAGACTTTGTTAACCAACAACTTCTAAACAAACACAACTTGTT 720
LP143_ffluc     CCAGTAGGGGTTCAAGCAGACTTTGTTAACCAACAACTTCTAAACAAACACAACTTGTT 717
A511_ffluc      CCAGTAGGGGTTCAAGCAGACTTTGTTAACCAACAACTTCTAAACAAACACAACTTGTT 717
LP124_ffluc     CCAGTAGGGGTTCAAGCAGACTTTGTTAACCAACAACTTCTAAACAAACACAACTTGTT 720
Lp101_ffluc     CCAGTAGGGGTTCAAGCAGACTTTGTTAACCAACAACTTCTAAACAAACACAACTTGTT 720
LP99_ffluc      CCAGTAGGGGTTCAAGCAGACTTTGTTAACCAACAACTTCTAAACAAACACAACTTGTT 720
P100_ffluc      CCAGTAGGGGTTCAAGCAGACTTTGTTAACCAACAACTTCTAAACAAACACAGCTTGTT 720
                ***************************************************** *****
```

FIGURE 3 (Cont.)

```
LP48_ffluc    CGCGATAACGGAAACAACGTAAGCGTTGGTTTCAACATCCAAGGTTTCCATTCAGCTCGT 780
LP125_ffluc   CGTGATAACGGAAACAACGTAAGCGTTGGTTTCAACATCCAAGGTTTCCATTCAGCTCGT 780
LP143_ffluc   CGCGATAACGGAAACAACGTAAGCGTTGGTTTCAACATCCAAGGTTTCCATTCAGCTCGT 777
A511_ffluc    CGCGATAACGGAAACAACGTAAGCGTTGGTTTCAACATCCAAGGTTTCCATTCAGCTCGT 777
LP124_ffluc   CGCGATAACGGAAACAACGTAAGCGTTGGTTTCAACATCCAAGGTTTCCATTCAGCTCGT 780
lp101_ffluc   CGCGATAACGGAAACAACGTAAGCGTTGGTTTCAACATCCAAGGTTTCCATTCAGCTCGT 780
LP99_ffluc    CGCGATAACGGAAACAACGTAAGCGTTGGTTTCAACATCCAAGGTTTCCATTCAGCTCGT 780
P100_ffluc    CGTGATAACGGAAACAACGTAAGCGTTGGTTTCAACATCCAAGGTTTCCATTCAGCTCGT 780
              ** *********************************************************

LP48_ffluc    GGATTTATCAAACTTCACGGTTCTACAGTAATGGAAAACGAACAAATCTTAGATGAACGT 840
LP125_ffluc   GGATTTATCAAACTTCACGGTTCTACAGTAATGGAAAACGAACAAATCTTAGATGAACGT 840
LP143_ffluc   GGATTTATCAAACTTCACGGTTCTACAGTAATGGAAAACGAACAAATCTTAGATGAACGT 837
A511_ffluc    GGATTTATCAAACTTCACGGTTCTACAGTAATGGAAAACGAACAAATCTTAGATGAACGT 837
LP124_ffluc   GGATTTATCAAACTTCACGGTTCTACAGTAATGGAAAACGAACAAATCTTAGATGAACGT 840
lp101_ffluc   GGATTTATCAAACTTCACGGTTCTACAGTAATGGAAAACGAACAAATCTTAGATGAACGT 840
LP99_ffluc    GGATTTATCAAACTTCACGGTTCTACAGTAATGGAAAACGAACAAATCTTAGATGAACGT 840
P100_ffluc    GGATTTATCAAACTTCACGGTTCTACAGTAATGGAAAACGAACAAATCTTAGATGAACGT 840
              ************************************************************

LP48_ffluc    ATTCTTGCTTTACCAACAGCTCCACAACCAGCTAAGGTAACTGCAACACAAGAAGCAGGT 900
LP125_ffluc   ATTCTTGCTTTACCAACAGCTCCACAACCAGCTAAGGTAACTGCAACACAAGAAGCAGGT 900
LP143_ffluc   ATTCTTGCTTTACCAACAGCTCCACAACCAGCTAAGGTAACTGCAACACAAGAAGCAGGT 897
A511_ffluc    ATTCTTGCTTTACCAACAGCTCCACAACCAGCTAAGGTAACTGCAACACAAGAAGCAGGT 897
LP124_ffluc   ATTCTTGCTTTACCAACAGCTCCACAACCAGCTAAGGTAACTGCAACACAAGAAGCAGGT 900
lp101_ffluc   ATTCTTGCTTTACCAACAGCTCCACAACCAGCTAAGGTAACTGCAACACAAGAAGCAGGT 900
LP99_ffluc    ATTCTTGCTTTACCAACAGCTCCACAACCAGCTAAGGTAACTGCAACACAAGAAGCAGGT 900
P100_ffluc    ATTCTTGCTTTACCAACAGCTCCACAACCAGCTAAGGTAACTGCAACACAAGAAGCAGGT 900
              ************************************************************

LP48_ffluc    AAAAAAGGACAATTTAGAGCAGAAGATTTAGCAGCACATGAATATAAAGTTGTTGTAAGT 960
LP125_ffluc   AAAAAAGGACAATTTAGAGCAGAAGATTTAGCAGCACATGAATATAAAGTTGTTGTAAGT 960
LP143_ffluc   AAAAAAGGACAATTTAGAGCAGAAGATTTAGCAGCACATGAATATAAAGTTGTTGTAAGT 957
A511_ffluc    AAAAAAGGACAATTTAGAGCAGAAGATTTAGCAGCACATGAATATAAAGTTGTTGTAAGT 957
LP124_ffluc   AAAAAAGGACAATTTAGAGCAGAAGATTTAGCAGCACATGAATATAAAGTTGTTGTAAGT 960
lp101_ffluc   AAAAAAGGACAATTTAGAGCAGAAGATTTAGCAGCACATGAATATAAAGTTGTTGTAAGT 960
LP99_ffluc    AAAAAAGGACAATTTAGAGCAGAAGATTTAGCAGCACATGAATATAAAGTTGTTGTAAGT 960
P100_ffluc    AAAAAAGGACAATTTAGAGCAGAAGACTTAGCAGCACACGAATACAAAGTTGTTGTAAGT 960
              ************************** ********** ***** ***************

LP48_ffluc    TCTGACGATGCAGAGTCTATTGCAAGTGAAGTGGCTACAGCTACAGTTACTGCAAAAGAT 1020
LP125_ffluc   TCTGACGATGCAGAGTCTATTGCAAGTGAAGTGGCTACAGCTACAGTTACTGCAAAAGAT 1020
LP143_ffluc   TCTGACGATGCAGAGTCTATTGCAAGTGAAGTGGCTACAGCTACAGTTACTGCAAAAGAT 1017
A511_ffluc    TCTGACGATGCAGAGTCTATTGCAAGTGAAGTGGCTACAGCTACAGTTACTGCAAAAGAT 1017
LP124_ffluc   TCTGACGATGCAGAGTCTATTGCAAGTGAAGTGGCTACAGCTACAGTTACTGCAAAAGAT 1020
lp101_ffluc   TCTGACGATGCAGAGTCTATTGCAAGTGAAGTGGCTACAGCTACAGTTACTGCAAAAGAT 1020
LP99_ffluc    TCTGACGATGCAGAGTCTATTGCAAGTGAAGTGGCTACAGCTACAGTTACTGCAAAAGAT 1020
P100_ffluc    TCTGACGATGCAGAGTCTATTGCAAGTGAAGTGGCTACAGCTACAGTTACTGCAAAAGAT 1020
              ************************************************************

LP48_ffluc    GACGGCGTTAAACTAGAAATCGAATTAGCTCCAATGTATAGCTCTCGTCCACAATTCGTT 1080
LP125_ffluc   GACGGCGTTAAACTAGAAATCGAATTAGCTCCAATGTATAGCTCTCGTCCACAATTCGTT 1080
LP143_ffluc   GACGGCGTTAAACTAGAAATCGAATTAGCTCCAATGTATAGCTCTCGTCCACAATTCGTT 1077
A511_ffluc    GACGGCGTTAAACTAGAAATCGAATTAGCTCCAATGTATAGCTCTCGTCCACAATTCGTT 1077
LP124_ffluc   GACGGCGTTAAACTAGAAATCGAATTAGCTCCAATGTATAGCTCTCGTCCACAATTCGTT 1080
lp101_ffluc   GACGGCGTTAAACTAGAAATCGAATTAGCTCCAATGTATAGCTCTCGTCCACAATTCGTT 1080
LP99_ffluc    GACGGCGTTAAACTAGAAATCGAATTAGCTCCAATGTATAGCTCTCGTCCACAATTCGTT 1080
P100_ffluc    GACGGCGTTAAACTAGAAATCGAGTTAGCTCCAATGTACAGCTCCCGTCCACAATTCGTT 1080
              *********************** ************* ***** ****************
```

FIGURE 3 (Cont.)

```
L248_ffluc    TCAATCTATAGAAAAGGTGCAGAAACAGGTTTATTCTACCTAATCGCTCGTGTACCTGCT 1140
L2125_ffluc   TCAATCTATAGAAAAGGTGCAGAAACAGGTTTATTCTACCTAATCGCTCGTGTACCTGCT 1140
L2143_ffluc   TCAATCTATAGAAAAGGTGCAGAAACAGGTTTATTCTACCTAATCGCTCGTGTACCTGCT 1137
A511_ffluc    TCAATCTATAGAAAAGGTGCAGAAACAGGTTTATTCTACCTAATCGCTCGTGTACCTGCT 1137
L2124_ffluc   TCAATCTATAGAAAAGGTGCAGAAACAGGTTTATTCTACCTAATCGCTCGTGTACCTGCT 1140
lp101_ffluc   TCAATCTATAGAAAAGGTGCAGAAACAGGTTTATTCTACCTAATCGCTCGTGTACCTGCT 1140
L299_ffluc    TCAATCTATAGAAAAGGTGCAGAAACAGGTTTATTCTACCTAATCGCTCGTGTACCTGCT 1140
P100_ffluc    TCAATCTATAGAAAAGGTGCAGAAACAGGTTTATTCTACCTAATCGCTCGTGTACCTGCT 1140
              ************************************************************

L248_ffluc    AGCAAAGCAGAGAACAACGTAATCACTTTCTACGACTTAAACGACTCTATTCCTGAAACA 1200
L2125_ffluc   AGCAAAGCAGAGAACAACGTAATCACTTTCTACGACTTAAACGACTCTATTCCTGAAACA 1200
L2143_ffluc   AGCAAAGCAGAGAACAACGTAATCACTTTCTACGACTTAAACGACTCTATTCCTGAAACA 1197
A511_ffluc    AGCAAAGCAGAGAACAACGTAATCACTTTCTACGACTTAAACGACTCTATTCCTGAAACA 1197
L2124_ffluc   AGCAAAGCAGAGAACAACGTAATCACTTTCTACGACTTAAACGACTCTATTCCTGAAACA 1200
lp101_ffluc   AGCAAAGCAGAGAACAACGTAATCACTTTCTACGACTTAAACGACTCTATTCCTGAAACA 1200
L299_ffluc    AGCAAAGCAGAGAACAACGTAATCACTTTCTACGACTTAAACGACTCTATTCCTGAAACA 1200
P100_ffluc    AGCAAAGCAGAGAACAACGTAATCACTTTCTATGACTTAAACGACTCTATTCCTGAAACA 1200
              ******************************** ***************************

L248_ffluc    GTAGACGTATTCGTTGGTGAAATGTCGGCTAACGTAGTACACTTGTTTGAATTACTACCA 1260
L2125_ffluc   GTAGACGTATTCGTTGGTGAAATGTCGGCTAACGTAGTACACTTGTTTGAATTACTACCA 1260
L2143_ffluc   GTAGACGTATTCGTTGGTGAAATGTCGGCTAACGTAGTACACTTGTTTGAATTACTACCA 1257
A511_ffluc    GTAGACGTATTCGTTGGTGAAATGTCGGCTAACGTAGTACACTTGTTTGAATTACTACCA 1257
L2124_ffluc   GTAGACGTATTCGTTGGTGAAATGTCGGCTAACGTAGTACACTTGTTTGAATTACTACCA 1260
lp101_ffluc   GTAGACGTATTCGTTGGTGAAATGTCGGCTAACGTAGTACACTTGTTTGAATTACTACCA 1260
L299_ffluc    GTAGACGTATTCGTTGGTGAAATGTCGGCTAACGTAGTACACTTGTTTGAATTACTACCA 1260
P100_ffluc    GTAGACGTATTCGTTGGTGAAATGTCTGCTAACGTAGTACACTTGTTTGAATTACTACCA 1260
              ************************* **********************************

L248_ffluc    ATGATGAGATTACCTCTAGCTCAAATTAACGCATCTGTTACATTTGCAGTTTTATGGTAT 1320
L2125_ffluc   ATGATGAGATTACCTCTAGCTCAAATTAACGCATCTGTTACATTTGCAGTTTTATGGTAT 1320
L2143_ffluc   ATGATGAGATTACCTCTAGCTCAAATTAACGCATCTGTTACATTTGCAGTTTTATGGTAT 1317
A511_ffluc    ATGATGAGATTACCTCTAGCTCAAATTAACGCATCTGTTACATTTGCAGTTTTATGGTAT 1317
L2124_ffluc   ATGATGAGATTACCTCTAGCTCAAATTAACGCATCTGTTACATTTGCAGTTTTATGGTAT 1320
lp101_ffluc   ATGATGAGATTACCTCTAGCTCAAATTAACGCATCTGTTACATTTGCAGTTTTATGGTAT 1320
L299_ffluc    ATGATGAGATTACCTCTAGCTCAAATTAACGCATCTGTTACATTTGCAGTTTTATGGTAT 1320
P100_ffluc    ATGATGAGATTACCTCTAGCTCAAATTAACGCATCTGTTACATTTGCAGTTTTATGGTAT 1320
              ************************************************************

L248_ffluc    GGCGCATTAGCTCTAAGAGCACCTAAGAAATGGGTACGTATTAGAAACGTTAAATATATT 1380
L2125_ffluc   GGCGCATTAGCTCTAAGAGCACCTAAGAAATGGGTACGTATTAGAAACGTTAAATATATT 1380
L2143_ffluc   GGCGCATTAGCTCTAAGAGCACCTAAGAAATGGGTACGTATTAGAAACGTTAAATATATT 1377
A511_ffluc    GGCGCATTAGCTCTAAGAGCACCTAAGAAATGGGTACGTATTAGAAACGTTAAATATATT 1377
L2124_ffluc   GGCGCATTAGCTCTAAGAGCACCTAAGAAATGGGTACGTATTAGAAACGTTAAATATATT 1380
lp101_ffluc   GGCGCATTAGCTCTAAGAGCACCTAAGAAATGGGTACGTATTAGAAACGTTAAATATATT 1380
L299_ffluc    GGCGCATTAGCTCTAAGAGCACCTAAGAAATGGGTACGTATTAGAAACGTTAAATATATT 1380
P100_ffluc    GGAGCATTAGCTCTAAGAGCACCTAAGAAATGGGTACGTATTAGAAACGTTAAATATATT 1380
              ** *********************************************************

L248_ffluc    CCTGTAAAAAACGTTCATAGCAACTAAGAGGAGGTAAATATATATGGAAGACGCCAAAAA 1440
L2125_ffluc   CCTGTAAAAAACGTTCATAGCAACTAAGAGGAGGTAAATATATATGGAAGACGCCAAAAA 1440
L2143_ffluc   CCTGTAAAAAACGTTCATAGCAACTAAGAGGAGGTAAATATATATGGAAGACGCCAAAAA 1437
A511_ffluc    CCTGTAAAAAACGTTCATAGCAACTAAGAGGAGGTAAATATATATGGAAGACGCCAAAAA 1437
L2124_ffluc   CCTGTAAAAAACGTTCATAGCAACTAAGAGGAGGTAAATATATATGGAAGACGCCAAAAA 1440
lp101_ffluc   CCTGTAAAAAACGTTCATAGCAACTAAGAGGAGGTAAATATATATGGAAGACGCCAAAAA 1440
L299_ffluc    CCTGTAAAAAACGTTCATAGCAACTAAGAGGAGGTAAATATATATGGAAGACGCCAAAAA 1440
P100_ffluc    CCTGTAAAAAACGTTCATAGCAACTAAGAGGAGGTAAATATATATGGAAGACGCCAAAAA 1440
              ************************************************************
```

FIGURE 3 (Cont.)

```
LP48_ffluc    CATAAAGAAAGGCCCGGCGCCATTCTATCCTCTAGAGGATGGAACCGCTGGAGAGCAACT 1500
LP123_ffluc   CATAAAGAAAGGCCCGGCGCCATTCTATCCTCTAGAGGATGGAACCGCTGGAGAGCAACT 1500
LP143_ffluc   CATAAAGAAAGGCCCGGCGCCATTCTATCCTCTAGAGGATGGAACCGCTGGAGAGCAACT 1497
A511_ffluc    CATAAAGAAAGGCCCGGCGCCATTCTATCCTCTAGAGGATGGAACCGCTGGAGAGCAACT 1497
LP124_ffluc   CATAAAGAAAGGCCCGGCGCCATTCTATCCTCTAGAGGATGGAACCGCTGGAGAGCAACT 1500
lp101_ffluc   CATAAAGAAAGGCCCGGCGCCATTCTATCCTCTAGAGGATGGAACCGCTGGAGAGCAACT 1500
LP99_ffluc    CATAAAGAAAGGCCCGGCGCCATTCTATCCTCTAGAGGATGGAACCGCTGGAGAGCAACT 1500
P100_ffluc    CATAAAGAAAGGCCCGGCGCCATTCTATCCTCTAGAGGATGGAACCGCTGGAGAGCAACT 1500
              ************************************************************

LP48_ffluc    GCATAAGGCTATGAAGAGATACGCCCTGGTTCCTGGAACAATTGCTTTTACAGATGCACA 1560
LP123_ffluc   GCATAAGGCTATGAAGAGATACGCCCTGGTTCCTGGAACAATTGCTTTTACAGATGCACA 1560
LP143_ffluc   GCATAAGGCTATGAAGAGATACGCCCTGGTTCCTGGAACAATTGCTTTTACAGATGCACA 1557
A511_ffluc    GCATAAGGCTATGAAGAGATACGCCCTGGTTCCTGGAACAATTGCTTTTACAGATGCACA 1557
LP124_ffluc   GCATAAGGCTATGAAGAGATACGCCCTGGTTCCTGGAACAATTGCTTTTACAGATGCACA 1560
lp101_ffluc   GCATAAGGCTATGAAGAGATACGCCCTGGTTCCTGGAACAATTGCTTTTACAGATGCACA 1560
LP99_ffluc    GCATAAGGCTATGAAGAGATACGCCCTGGTTCCTGGAACAATTGCTTTTACAGATGCACA 1560
P100_ffluc    GCATAAGGCTATGAAGAGATACGCCCTGGTTCCTGGAACAATTGCTTTTACAGATGCACA 1560
              ************************************************************

LP48_ffluc    TATCGAGGTGAACATCACGTACGCGGAATACTTCGAAATGTCCGTTCGGTTGGCAGAAGC 1620
LP123_ffluc   TATCGAGGTGAACATCACGTACGCGGAATACTTCGAAATGTCCGTTCGGTTGGCAGAAGC 1620
LP143_ffluc   TATCGAGGTGAACATCACGTACGCGGAATACTTCGAAATGTCCGTTCGGTTGGCAGAAGC 1617
A511_ffluc    TATCGAGGTGAACATCACGTACGCGGAATACTTCGAAATGTCCGTTCGGTTGGCAGAAGC 1617
LP124_ffluc   TATCGAGGTGAACATCACGTACGCGGAATACTTCGAAATGTCCGTTCGGTTGGCAGAAGC 1620
lp101_ffluc   TATCGAGGTGAACATCACGTACGCGGAATACTTCGAAATGTCCGTTCGGTTGGCAGAAGC 1620
LP99_ffluc    TATCGAGGTGAACATCACGTACGCGGAATACTTCGAAATGTCCGTTCGGTTGGCAGAAGC 1620
P100_ffluc    TATCGAGGTGAACATCACGTACGCGGAATACTTCGAAATGTCCGTTCGGTTGGCAGAAGC 1620
              ************************************************************

LP48_ffluc    TATGAAACGATATGGGCTGAATACAAATCACAGAATCGTCGTATGCAGTGAAAACTCTCT 1680
LP123_ffluc   TATGAAACGATATGGGCTGAATACAAATCACAGAATCGTCGTATGCAGTGAAAACTCTCT 1680
LP143_ffluc   TATGAAACGATATGGGCTGAATACAAATCACAGAATCGTCGTATGCAGTGAAAACTCTCT 1677
A511_ffluc    TATGAAACGATATGGGCTGAATACAAATCACAGAATCGTCGTATGCAGTGAAAACTCTCT 1677
LP124_ffluc   TATGAAACGATATGGGCTGAATACAAATCACAGAATCGTCGTATGCAGTGAAAACTCTCT 1680
lp101_ffluc   TATGAAACGATATGGGCTGAATACAAATCACAGAATCGTCGTATGCAGTGAAAACTCTCT 1680
LP99_ffluc    TATGAAACGATATGGGCTGAATACAAATCACAGAATCGTCGTATGCAGTGAAAACTCTCT 1680
P100_ffluc    TATGAAACGATATGGGCTGAATACAAATCACAGAATCGTCGTATGCAGTGAAAACTCTCT 1680
              ************************************************************

LP48_ffluc    TCAATTCTTTATGCCGGTGTTGGGCGCGTTATTTATCGGAGTTGCAGTTGCGCCCGCGAA 1740
LP123_ffluc   TCAATTCTTTATGCCGGTGTTGGGCGCGTTATTTATCGGAGTTGCAGTTGCGCCCGCGAA 1740
LP143_ffluc   TCAATTCTTTATGCCGGTGTTGGGCGCGTTATTTATCGGAGTTGCAGTTGCGCCCGCGAA 1737
A511_ffluc    TCAATTCTTTATGCCGGTGTTGGGCGCGTTATTTATCGGAGTTGCAGTTGCGCCCGCGAA 1737
LP124_ffluc   TCAATTCTTTATGCCGGTGTTGGGCGCGTTATTTATCGGAGTTGCAGTTGCGCCCGCGAA 1740
lp101_ffluc   TCAATTCTTTATGCCGGTGTTGGGCGCGTTATTTATCGGAGTTGCAGTTGCGCCCGCGAA 1740
LP99_ffluc    TCAATTCTTTATGCCGGTGTTGGGCGCGTTATTTATCGGAGTTGCAGTTGCGCCCGCGAA 1740
P100_ffluc    TCAATTCTTTATGCCGGTGTTGGGCGCGTTATTTATCGGAGTTGCAGTTGCGCCCGCGAA 1740
              ************************************************************

LP48_ffluc    CGACATTTATAATGAACGTGAATTGCTCAACAGTATGAACATTTCGCAGCCTACCGTAGT 1800
LP123_ffluc   CGACATTTATAATGAACGTGAATTGCTCAACAGTATGAACATTTCGCAGCCTACCGTAGT 1800
LP143_ffluc   CGACATTTATAATGAACGTGAATTGCTCAACAGTATGAACATTTCGCAGCCTACCGTAGT 1797
A511_ffluc    CGACATTTATAATGAACGTGAATTGCTCAACAGTATGAACATTTCGCAGCCTACCGTAGT 1797
LP124_ffluc   CGACATTTATAATGAACGTGAATTGCTCAACAGTATGAACATTTCGCAGCCTACCGTAGT 1800
lp101_ffluc   CGACATTTATAATGAACGTGAATTGCTCAACAGTATGAACATTTCGCAGCCTACCGTAGT 1800
LP99_ffluc    CGACATTTATAATGAACGTGAATTGCTCAACAGTATGAACATTTCGCAGCCTACCGTAGT 1800
P100_ffluc    CGACATTTATAATGAACGTGAATTGCTCAACAGTATGAACATTTCGCAGCCTACCGTAGT 1800
              ************************************************************
```

FIGURE 3 (Cont.)

```
LP48_ffluc    GTTTGTTTCCAAAAAGGGGTTGCAAAAAATTTTGAACGTGCAAAAAAAATTACCAATAAT 1860
LP125_ffluc   GTTTGTTTCCAAAAAGGGGTTGCAAAAAATTTTGAACGTGCAAAAAAAATTACCAATAAT 1860
LP143_ffluc   GTTTGTTTCCAAAAAGGGGTTGCAAAAAATTTTGAACGTGCAAAAAAAATTACCAATAAT 1857
A511_ffluc    GTTTGTTTCCAAAAAGGGGTTGCAAAAAATTTTGAACGTGCAAAAAAAATTACCAATAAT 1857
LP124_ffluc   GTTTGTTTCCAAAAAGGGGTTGCAAAAAATTTTGAACGTGCAAAAAAAATTACCAATAAT 1860
Lp101_ffluc   GTTTGTTTCCAAAAAGGGGTTGCAAAAAATTTTGAACGTGCAAAAAAAATTACCAATAAT 1860
LP99_ffluc    GTTTGTTTCCAAAAAGGGGTTGCAAAAAATTTTGAACGTGCAAAAAAAATTACCAATAAT 1860
P100_ffluc    GTTTGTTTCCAAAAAGGGGTTGCAAAAAATTTTGAACGTGCAAAAAAAATTACCAATAAT 1860
              ************************************************************

LP48_ffluc    CCAGAAAATTATTATCATGGATTCTAAAACGGATTACCAGGGATTTCAGTCGATGTACAC 1920
LP125_ffluc   CCAGAAAATTATTATCATGGATTCTAAAACGGATTACCAGGGATTTCAGTCGATGTACAC 1920
LP143_ffluc   CCAGAAAATTATTATCATGGATTCTAAAACGGATTACCAGGGATTTCAGTCGATGTACAC 1917
A511_ffluc    CCAGAAAATTATTATCATGGATTCTAAAACGGATTACCAGGGATTTCAGTCGATGTACAC 1917
LP124_ffluc   CCAGAAAATTATTATCATGGATTCTAAAACGGATTACCAGGGATTTCAGTCGATGTACAC 1920
Lp101_ffluc   CCAGAAAATTATTATCATGGATTCTAAAACGGATTACCAGGGATTTCAGTCGATGTACAC 1920
LP99_ffluc    CCAGAAAATTATTATCATGGATTCTAAAACGGATTACCAGGGATTTCAGTCGATGTACAC 1920
P100_ffluc    CCAGAAAATTATTATCATGGATTCTAAAACGGATTACCAGGGATTTCAGTCGATGTACAC 1920
              ************************************************************

LP48_ffluc    GTTCGTCACATCTCATCTACCTCCCGGTTTTAATGAATACGATTTTGTACCAGAGTCCTT 1980
LP125_ffluc   GTTCGTCACATCTCATCTACCTCCCGGTTTTAATGAATACGATTTTGTACCAGAGTCCTT 1980
LP143_ffluc   GTTCGTCACATCTCATCTACCTCCCGGTTTTAATGAATACGATTTTGTACCAGAGTCCTT 1977
A511_ffluc    GTTCGTCACATCTCATCTACCTCCCGGTTTTAATGAATACGATTTTGTACCAGAGTCCTT 1977
LP124_ffluc   GTTCGTCACATCTCATCTACCTCCCGGTTTTAATGAATACGATTTTGTACCAGAGTCCTT 1980
Lp101_ffluc   GTTCGTCACATCTCATCTACCTCCCGGTTTTAATGAATACGATTTTGTACCAGAGTCCTT 1980
LP99_ffluc    GTTCGTCACATCTCATCTACCTCCCGGTTTTAATGAATACGATTTTGTACCAGAGTCCTT 1980
P100_ffluc    GTTCGTCACATCTCATCTACCTCCCGGTTTTAATGAATACGATTTTGTACCAGAGTCCTT 1980
              ************************************************************

LP48_ffluc    TGATCGTGACAAAACAATTGCACTGATAATGAATTCCTCTGGATCTACTGGGTTACCTAA 2040
LP125_ffluc   TGATCGTGACAAAACAATTGCACTGATAATGAATTCCTCTGGATCTACTGGGTTACCTAA 2040
LP143_ffluc   TGATCGTGACAAAACAATTGCACTGATAATGAATTCCTCTGGATCTACTGGGTTACCTAA 2037
A511_ffluc    TGATCGTGACAAAACAATTGCACTGATAATGAATTCCTCTGGATCTACTGGGTTACCTAA 2037
LP124_ffluc   TGATCGTGACAAAACAATTGCACTGATAATGAATTCCTCTGGATCTACTGGGTTACCTAA 2040
Lp101_ffluc   TGATCGTGACAAAACAATTGCACTGATAATGAATTCCTCTGGATCTACTGGGTTACCTAA 2040
LP99_ffluc    TGATCGTGACAAAACAATTGCACTGATAATGAATTCCTCTGGATCTACTGGGTTACCTAA 2040
P100_ffluc    TGATCGTGACAAAACAATTGCACTGATAATGAATTCCTCTGGATCTACTGGGTTACCTAA 2040
              ************************************************************

LP48_ffluc    GGGTGTGGCCCTTCCGCATAGAACTGCCTGCGTCAGATTCTCGCATGCCAGAGATCCTAT 2100
LP125_ffluc   GGGTGTGGCCCTTCCGCATAGAACTGCCTGCGTCAGATTCTCGCATGCCAGAGATCCTAT 2100
LP143_ffluc   GGGTGTGGCCCTTCCGCATAGAACTGCCTGCGTCAGATTCTCGCATGCCAGAGATCCTAT 2097
A511_ffluc    GGGTGTGGCCCTTCCGCATAGAACTGCCTGCGTCAGATTCTCGCATGCCAGAGATCCTAT 2097
LP124_ffluc   GGGTGTGGCCCTTCCGCATAGAACTGCCTGCGTCAGATTCTCGCATGCCAGAGATCCTAT 2100
Lp101_ffluc   GGGTGTGGCCCTTCCGCATAGAACTGCCTGCGTCAGATTCTCGCATGCCAGAGATCCTAT 2100
LP99_ffluc    GGGTGTGGCCCTTCCGCATAGAACTGCCTGCGTCAGATTCTCGCATGCCAGAGATCCTAT 2100
P100_ffluc    GGGTGTGGCCCTTCCGCATAGAACTGCCTGCGTCAGATTCTCGCATGCCAGAGATCCTAT 2100
              ************************************************************

LP48_ffluc    TTTTGGCAATCAAATCATTCCGGATACTGCGATTTTAAGTGTTGTTCCATTCCATCACGG 2160
LP125_ffluc   TTTTGGCAATCAAATCATTCCGGATACTGCGATTTTAAGTGTTGTTCCATTCCATCACGG 2160
LP143_ffluc   TTTTGGCAATCAAATCATTCCGGATACTGCGATTTTAAGTGTTGTTCCATTCCATCACGG 2157
A511_ffluc    TTTTGGCAATCAAATCATTCCGGATACTGCGATTTTAAGTGTTGTTCCATTCCATCACGG 2157
LP124_ffluc   TTTTGGCAATCAAATCATTCCGGATACTGCGATTTTAAGTGTTGTTCCATTCCATCACGG 2160
Lp101_ffluc   TTTTGGCAATCAAATCATTCCGGATACTGCGATTTTAAGTGTTGTTCCATTCCATCACGG 2160
LP99_ffluc    TTTTGGCAATCAAATCATTCCGGATACTGCGATTTTAAGTGTTGTTCCATTCCATCACGG 2160
P100_ffluc    TTTTGGCAATCAAATCATTCCGGATACTGCGATTTTAAGTGTTGTTCCATTCCATCACGG 2160
              ************************************************************
```

FIGURE 3 (Cont.)

```
LP48_ffluc      TTTTGGAATGTTACTACACTCGGATATTTGATATGTGGATTTCGAGTCGTCTTAATGTA 2220
LP125_ffluc     TTTTGGAATGTTACTACACTCGGATATTTGATATGTGGATTTCGAGTCGTCTTAATGTA 2220
LP143_ffluc     TTTTGGAATGTTACTACACTCGGATATTTGATATGTGGATTTCGAGTCGTCTTAATGTA 2217
A511_ffluc      TTTTGGAATGTTACTACACTCGGATATTTGATATGTGGATTTCGAGTCGTCTTAATGTA 2217
LP124_ffluc     TTTTGGAATGTTACTACACTCGGATATTTGATATGTGGATTTCGAGTCGTCTTAATGTA 2220
Lp101_ffluc     TTTTGGAATGTTACTACACTCGGATATTTGATATGTGGATTTCGAGTCGTCTTAATGTA 2220
LP99_ffluc      TTTTGGAATGTTACTACACTCGGATATTTGATATGTGGATTTCGAGTCGTCTTAATGTA 2220
P100_ffluc      TTTTGGAATGTTACTACACTCGGATATTTGATATGTGGATTTCGAGTCGTCTTAATGTA 2220
                ************************************************************

LP48_ffluc      TAGATTTGAAGAAGAGCTGTTTTTACGATCCCTTCAGGATTACAAAATTCAAAGTGCGTT 2280
LP125_ffluc     TAGATTTGAAGAAGAGCTGTTTTTACGATCCCTTCAGGATTACAAAATTCAAAGTGCGTT 2280
LP143_ffluc     TAGATTTGAAGAAGAGCTGTTTTTACGATCCCTTCAGGATTACAAAATTCAAAGTGCGTT 2277
A511_ffluc      TAGATTTGAAGAAGAGCTGTTTTTACGATCCCTTCAGGATTACAAAATTCAAAGTGCGTT 2277
LP124_ffluc     TAGATTTGAAGAAGAGCTGTTTTTACGATCCCTTCAGGATTACAAAATTCAAAGTGCGTT 2280
Lp101_ffluc     TAGATTTGAAGAAGAGCTGTTTTTACGATCCCTTCAGGATTACAAAATTCAAAGTGCGTT 2280
LP99_ffluc      TAGATTTGAAGAAGAGCTGTTTTTACGATCCCTTCAGGATTACAAAATTCAAAGTGCGTT 2280
P100_ffluc      TAGATTTGAAGAAGAGCTGTTTTTACGATCCCTTCAGGATTACAAAATTCAAAGTGCGTT 2280
                ************************************************************

LP48_ffluc      GCTAGTACCAACCCTATTTTCATTCTTCGCCAAAAGCACTCTGATTGACAAATACGATTT 2340
LP125_ffluc     GCTAGTACCAACCCTATTTTCATTCTTCGCCAAAAGCACTCTGATTGACAAATACGATTT 2340
LP143_ffluc     GCTAGTACCAACCCTATTTTCATTCTTCGCCAAAAGCACTCTGATTGACAAATACGATTT 2337
A511_ffluc      GCTAGTACCAACCCTATTTTCATTCTTCGCCAAAAGCACTCTGATTGACAAATACGATTT 2337
LP124_ffluc     GCTAGTACCAACCCTATTTTCATTCTTCGCCAAAAGCACTCTGATTGACAAATACGATTT 2340
Lp101_ffluc     GCTAGTACCAACCCTATTTTCATTCTTCGCCAAAAGCACTCTGATTGACAAATACGATTT 2340
LP99_ffluc      GCTAGTACCAACCCTATTTTCATTCTTCGCCAAAAGCACTCTGATTGACAAATACGATTT 2340
P100_ffluc      GCTAGTACCAACCCTATTTTCATTCTTCGCCAAAAGCACTCTGATTGACAAATACGATTT 2340
                ************************************************************

LP48_ffluc      ATCTAATTTACACGAAATTGCTTCTGGGGGCGCACCTCTTTCGAAAGAAGTCGGGGAAGC 2400
LP125_ffluc     ATCTAATTTACACGAAATTGCTTCTGGGGGCGCACCTCTTTCGAAAGAAGTCGGGGAAGC 2400
LP143_ffluc     ATCTAATTTACACGAAATTGCTTCTGGGGGCGCACCTCTTTCGAAAGAAGTCGGGGAAGC 2397
A511_ffluc      ATCTAATTTACACGAAATTGCTTCTGGGGGCGCACCTCTTTCGAAAGAAGTCGGGGAAGC 2397
LP124_ffluc     ATCTAATTTACACGAAATTGCTTCTGGGGGCGCACCTCTTTCGAAAGAAGTCGGGGAAGC 2400
Lp101_ffluc     ATCTAATTTACACGAAATTGCTTCTGGGGGCGCACCTCTTTCGAAAGAAGTCGGGGAAGC 2400
LP99_ffluc      ATCTAATTTACACGAAATTGCTTCTGGGGGCGCACCTCTTTCGAAAGAAGTCGGGGAAGC 2400
P100_ffluc      ATCTAATTTACACGAAATTGCTTCTGGGGGCGCACCTCTTTCGAAAGAAGTCGGGGAAGC 2400
                ************************************************************

LP48_ffluc      GGTTGCAAAACGCTTCCATCTTCCAGGGATACGACAAGGATATGGGCTCACTGAGACTAC 2460
LP125_ffluc     GGTTGCAAAACGCTTCCATCTTCCAGGGATACGACAAGGATATGGGCTCACTGAGACTAC 2460
LP143_ffluc     GGTTGCAAAACGCTTCCATCTTCCAGGGATACGACAAGGATATGGGCTCACTGAGACTAC 2457
A511_ffluc      GGTTGCAAAACGCTTCCATCTTCCAGGGATACGACAAGGATATGGGCTCACTGAGACTAC 2457
LP124_ffluc     GGTTGCAAAACGCTTCCATCTTCCAGGGATACGACAAGGATATGGGCTCACTGAGACTAC 2460
Lp101_ffluc     GGTTGCAAAACGCTTCCATCTTCCAGGGATACGACAAGGATATGGGCTCACTGAGACTAC 2460
LP99_ffluc      GGTTGCAAAACGCTTCCATCTTCCAGGGATACGACAAGGATATGGGCTCACTGAGACTAC 2460
P100_ffluc      GGTTGCAAAACGCTTCCATCTTCCAGGGATACGACAAGGATATGGGCTCACTGAGACTAC 2460
                ************************************************************

LP48_ffluc      ATCAGCTATTCTGATTACACCCGAGGGGGATGATAAACCGGGCGCGGTCGGTAAAGTTGT 2520
LP125_ffluc     ATCAGCTATTCTGATTACACCCGAGGGGGATGATAAACCGGGCGCGGTCGGTAAAGTTGT 2520
LP143_ffluc     ATCAGCTATTCTGATTACACCCGAGGGGGATGATAAACCGGGCGCGGTCGGTAAAGTTGT 2517
A511_ffluc      ATCAGCTATTCTGATTACACCCGAGGGGGATGATAAACCGGGCGCGGTCGGTAAAGTTGT 2517
LP124_ffluc     ATCAGCTATTCTGATTACACCCGAGGGGGATGATAAACCGGGCGCGGTCGGTAAAGTTGT 2520
Lp101_ffluc     ATCAGCTATTCTGATTACACCCGAGGGGGATGATAAACCGGGCGCGGTCGGTAAAGTTGT 2520
LP99_ffluc      ATCAGCTATTCTGATTACACCCGAGGGGGATGATAAACCGGGCGCGGTCGGTAAAGTTGT 2520
P100_ffluc      ATCAGCTATTCTGATTACACCCGAGGGGGATGATAAACCGGGCGCGGTCGGTAAAGTTGT 2520
                ************************************************************
```

FIGURE 3 (Cont.)

```
LP48_ffluc    TCCATTTTTTGAAGCGAAGGTTGTGGATCTGGATACCGGGAAAACGCTGGGCGTTAATCA 2580
LP125_ffluc   TCCATTTTTTGAAGCGAAGGTTGTGGATCTGGATACCGGGAAAACGCTGGGCGTTAATCA 2580
LP143_ffluc   TCCATTTTTTGAAGCGAAGGTTGTGGATCTGGATACCGGGAAAACGCTGGGCGTTAATCA 2577
A511_ffluc    TCCATTTTTTGAAGCGAAGGTTGTGGATCTGGATACCGGGAAAACGCTGGGCGTTAATCA 2577
LP124_ffluc   TCCATTTTTTGAAGCGAAGGTTGTGGATCTGGATACCGGGAAAACGCTGGGCGTTAATCA 2580
lp101_ffluc   TCCATTTTTTGAAGCGAAGGTTGTGGATCTGGATACCGGGAAAACGCTGGGCGTTAATCA 2580
LP99_ffluc    TCCATTTTTTGAAGCGAAGGTTGTGGATCTGGATACCGGGAAAACGCTGGGCGTTAATCA 2580
P100_ffluc    TCCATTTTTTGAAGCGAAGGTTGTGGATCTGGATACCGGGAAAACGCTGGGCGTTAATCA 2580
              ************************************************************

LP48_ffluc    GAGAGGCGAATTATGTGTCAGAGGACCTATGATTATGTCCGGTTATGTAAACAATCCGGA 2640
LP125_ffluc   GAGAGGCGAATTATGTGTCAGAGGACCTATGATTATGTCCGGTTATGTAAACAATCCGGA 2640
LP143_ffluc   GAGAGGCGAATTATGTGTCAGAGGACCTATGATTATGTCCGGTTATGTAAACAATCCGGA 2637
A511_ffluc    GAGAGGCGAATTATGTGTCAGAGGACCTATGATTATGTCCGGTTATGTAAACAATCCGGA 2637
LP124_ffluc   GAGAGGCGAATTATGTGTCAGAGGACCTATGATTATGTCCGGTTATGTAAACAATCCGGA 2640
lp101_ffluc   GAGAGGCGAATTATGTGTCAGAGGACCTATGATTATGTCCGGTTATGTAAACAATCCGGA 2640
LP99_ffluc    GAGAGGCGAATTATGTGTCAGAGGACCTATGATTATGTCCGGTTATGTAAACAATCCGGA 2640
P100_ffluc    GAGAGGCGAATTATGTGTCAGAGGACCTATGATTATGTCCGGTTATGTAAACAATCCGGA 2640
              ************************************************************

LP48_ffluc    AGCGACCAACGCCTTGATTGACAAGGATGGATGGCTACATTCTGGAGACATAGCTTACTG 2700
LP125_ffluc   AGCGACCAACGCCTTGATTGACAAGGATGGATGGCTACATTCTGGAGACATAGCTTACTG 2700
LP143_ffluc   AGCGACCAACGCCTTGATTGACAAGGATGGATGGCTACATTCTGGAGACATAGCTTACTG 2697
A511_ffluc    AGCGACCAACGCCTTGATTGACAAGGATGGATGGCTACATTCTGGAGACATAGCTTACTG 2697
LP124_ffluc   AGCGACCAACGCCTTGATTGACAAGGATGGATGGCTACATTCTGGAGACATAGCTTACTG 2700
lp101_ffluc   AGCGACCAACGCCTTGATTGACAAGGATGGATGGCTACATTCTGGAGACATAGCTTACTG 2700
LP99_ffluc    AGCGACCAACGCCTTGATTGACAAGGATGGATGGCTACATTCTGGAGACATAGCTTACTG 2700
P100_ffluc    AGCGACCAACGCCTTGATTGACAAGGATGGATGGCTACATTCTGGAGACATAGCTTACTG 2700
              ************************************************************

LP48_ffluc    GGACGAAGACGAACACTTCTTCATAGTTGACCGCTTGAAGTCTTTAATTAAATACAAAGG 2760
LP125_ffluc   GGACGAAGACGAACACTTCTTCATAGTTGACCGCTTGAAGTCTTTAATTAAATACAAAGG 2760
LP143_ffluc   GGACGAAGACGAACACTTCTTCATAGTTGACCGCTTGAAGTCTTTAATTAAATACAAAGG 2757
A511_ffluc    GGACGAAGACGAACACTTCTTCATAGTTGACCGCTTGAAGTCTTTAATTAAATACAAAGG 2757
LP124_ffluc   GGACGAAGACGAACACTTCTTCATAGTTGACCGCTTGAAGTCTTTAATTAAATACAAAGG 2760
lp101_ffluc   GGACGAAGACGAACACTTCTTCATAGTTGACCGCTTGAAGTCTTTAATTAAATACAAAGG 2760
LP99_ffluc    GGACGAAGACGAACACTTCTTCATAGTTGACCGCTTGAAGTCTTTAATTAAATACAAAGG 2760
P100_ffluc    GGACGAAGACGAACACTTCTTCATAGTTGACCGCTTGAAGTCTTTAATTAAATACAAAGG 2760
              ************************************************************

LP48_ffluc    ATATCAGGTGGCCCCCGCTGAATTGGAATCGATATTGTTACAACACCCCAACATCTTCGA 2820
LP125_ffluc   ATATCAGGTGGCCCCCGCTGAATTGGAATCGATATTGTTACAACACCCCAACATCTTCGA 2820
LP143_ffluc   ATATCAGGTGGCCCCCGCTGAATTGGAATCGATATTGTTACAACACCCCAACATCTTCGA 2817
A511_ffluc    ATATCAGGTGGCCCCCGCTGAATTGGAATCGATATTGTTACAACACCCCAACATCTTCGA 2817
LP124_ffluc   ATATCAGGTGGCCCCCGCTGAATTGGAATCGATATTGTTACAACACCCCAACATCTTCGA 2820
lp101_ffluc   ATATCAGGTGGCCCCCGCTGAATTGGAATCGATATTGTTACAACACCCCAACATCTTCGA 2820
LP99_ffluc    ATATCAGGTGGCCCCCGCTGAATTGGAATCGATATTGTTACAACACCCCAACATCTTCGA 2820
P100_ffluc    ATATCAGGTGGCCCCCGCTGAATTGGAATCGATATTGTTACAACACCCCAACATCTTCGA 2820
              ************************************************************

LP48_ffluc    CGCGGGCGTGGCAGGTCTTCCCGACGATGACGCCGGTGAACTTCCAGCCGCCGTTGTTGT 2880
LP125_ffluc   CGCGGGCGTGGCAGGTCTTCCCGACGATGACGCCGGTGAACTTCCAGCCGCCGTTGTTGT 2880
LP143_ffluc   CGCGGGCGTGGCAGGTCTTCCCGACGATGACGCCGGTGAACTTCCCGCCGCCGTTGTTGT 2877
A511_ffluc    CGCGGGCGTGGCAGGTCTTCCCGACGATGACGCCGGTGAACTTCCCGCCGCCGTTGTTGT 2877
LP124_ffluc   CGCGGGCGTGGCAGGTCTTCCCGACGATGACGCCGGTGAACTTCCCGCCGCCGTTGTTGT 2880
lp101_ffluc   CGCGGGCGTGGCAGGTCTTCCCGACGATGACGCCGGTGAACTTCCCGCCGCCGTTGTTGT 2880
LP99_ffluc    CGCGGGCGTGGCAGGTCTTCCCGACGATGACGCCGGTGAACTTCCCGCCGCCGTTGTTGT 2880
P100_ffluc    CGCGGGCGTGGCAGGTCTTCCCGACGATGACGCCGGTGAACTTCCCGCCGCCGTTGTTGT 2880
              *******************************************  **************
```

FIGURE 3 (Cont.)

```
LP48_ffluc    TTTGGAGCACGGAAAGACGATGACGGAAAAAGAGATCGTGGATTACGTCGCCAGTCAAGT  2940
LP125_ffluc   TTTGGAGCACGGAAAGACGATGACGGAAAAAGAGATCGTGGATTACGTCGCCAGTCAAGT  2940
LP143_ffluc   TTTGGAGCACGGAAAGACGATGACGGAAAAAGAGATCGTGGATTACGTCGCCAGTCAAGT  2937
A511_ffluc    TTTGGAGCACGGAAAGACGATGACGGAAAAAGAGATCGTGGATTACGTCGCCAGTCAAGT  2937
LP124_ffluc   TTTGGAGCACGGAAAGACGATGACGGAAAAAGAGATCGTGGATTACGTCGCCAGTCAAGT  2940
Lp101_ffluc   TTTGGAGCACGGAAAGACGATGACGGAAAAAGAGATCGTGGATTACGTCGCCAGTCAAGT  2940
LP99_ffluc    TTTGGAGCACGGAAAGACGATGACGGAAAAAGAGATCGTGGATTACGTCGCCAGTCAAGT  2940
P100_ffluc    TTTGGAGCACGGAAAGACGATGACGGAAAAAGAGATCGTGGATTACGTCGCCAGTCAAGT  2940
              ************************************************************

LP48_ffluc    AACAACCGCGAAAAAGTTGCGCGGAGGAGTTGTGTTTGTGGACGAAGTACCGAAAGGTCT  3000
LP125_ffluc   AACAACCGCGAAAAAGTTGCGCGGAGGAGTTGTGTTTGTGGACGAAGTACCGAAAGGTCT  3000
LP143_ffluc   AACAACCGCGAAAAAGTTGCGCGGAGGAGTTGTGTTTGTGGACGAAGTACCGAAAGGTCT  2997
A511_ffluc    AACAACCGCGAAAAAGTTGCGCGGAGGAGTTGTGTTTGTGGACGAAGTACCGAAAGGTCT  2997
LP124_ffluc   AACAACCGCGAAAAAGTTGCGCGGAGGAGTTGTGTTTGTGGACGAAGTACCGAAAGGTCT  3000
Lp101_ffluc   AACAACCGCGAAAAAGTTGCGCGGAGGAGTTGTGTTTGTGGACGAAGTACCGAAAGGTCT  3000
LP99_ffluc    AACAACCGCGAAAAAGTTGCGCGGAGGAGTTGTGTTTGTGGACGAAGTACCGAAAGGTCT  3000
P100_ffluc    AACAACCGCGAAAAAGTTGCGCGGAGGAGTTGTGTTTGTGGACGAAGTACCGAAAGGTCT  3000
              ************************************************************

LP48_ffluc    TACCGGAAAACTCGACGCAAGAAAAATCAGAGAGATCCTCATAAAGGCCAAGAAGGGCGG  3060
LP125_ffluc   TACCGGAAAACTCGACGCAAGAAAAATCAGAGAGATCCTCATAAAGGCCAAGAAGGGCGG  3060
LP143_ffluc   TACCGGAAAACTCGACGCAAGAAAAATCAGAGAGATCCTCATAAAGGCCAAGAAGGGCGG  3057
A511_ffluc    TACCGGAAAACTCGACGCAAGAAAAATCAGAGAGATCCTCATAAAGGCCAAGAAGGGCGG  3057
LP124_ffluc   TACCGGAAAACTCGACGCAAGAAAAATCAGAGAGATCCTCATAAAGGCCAAGAAGGGCGG  3060
Lp101_ffluc   TACCGGAAAACTCGACGCAAGAAAAATCAGAGAGATCCTCATAAAGGCCAAGAAGGGCGG  3060
LP99_ffluc    TACCGGAAAACTCGACGCAAGAAAAATCAGAGAGATCCTCATAAAGGCCAAGAAGGGCGG  3060
P100_ffluc    TACCGGAAAACTCGACGCAAGAAAAATCAGAGAGATCCTCATAAAGGCCAAGAAGGGCGG  3060
              ************************************************************

LP48_ffluc    AAAGTCCAAATTGTAATAATTATAGGATAATTGAATAAAAACAGTATAGAGAGCAGATAA  3120
LP125_ffluc   AAAGTCCAAATTGTAATAATTATAGGATAATTGAATAAAAACAGTATAGAGAGCAGATAA  3120
LP143_ffluc   AAAGTCCAAATTGTAATAATTATAGGATAATTGAATAAAAACAGTATAGAGAGCAGATAA  3117
A511_ffluc    AAAGTCCAAATTGTAATAATTATAGGATAATTGAATAAAAACAGTATAGAGAGCAGATAA  3117
LP124_ffluc   AAAGTCCAAATTGTAATAATTATAGGATAATTGAATAAAAACAGTATAGAGAGCAGATAA  3120
Lp101_ffluc   AAAGTCCAAATTGTAATAATTATAGGATAATTGAATAAAAACAGTATAGAGAGCAGATAA  3120
LP99_ffluc    AAAGTCCAAATTGTAATAATTATAGGATAATTGAATAAAAACAGTATAGAGAGCAGATAA  3120
P100_ffluc    AAAGTCCAAATTGTAATAATTATAGGATAATTGAATAAAAACAGTATAGAGAGCAGATAA  3120
              ************************************************************

LP48_ffluc    ATACTGCTCTCTATTTTACTAATAAGGAGGATTTAAATTGCTAAAAAATACAAACTTAGC  3180
LP125_ffluc   ATACTGCTCTCTATTTTACTAATAAGGAGGATTTAAATTGCTAAAAAATACAAACTTAGC  3180
LP143_ffluc   ATACTGCTCTCTATTTTACTAATAAGGAGGATTTAAATTGCTAAAAAATACAAACTTAGC  3177
A511_ffluc    ATACTGCTCTCTATTTTACTAATAAGGAGGATTTAAATTGCTAAAAAATACAAACTTAGC  3177
LP124_ffluc   ATACTGCTCTCTATTTTACTAATAAGGAGGATTTAAATTGCTAAAAAATACAAACTTAGC  3180
Lp101_ffluc   ATACTGCTCTCTATTTTACTAATAAGGAGGATTTAAATTGCTAAAAAATACAAACTTAGC  3180
LP99_ffluc    ATACTGCTCTCTATTTTACTAATAAGGAGGATTTAAATTGCTAAAAAATACAAACTTAGC  3180
P100_ffluc    ATACTGCTCTCTATTTTACTAATAAGGAGGATTTAAATTGCTAAAAAATACAAACTTAGC  3180
              ************************************************************

LP48_ffluc    TAATTATAAAAAAGTGAATACACGGTTTGGAAATCTTAGTTTTGACGACAAAGGTATTTC  3240
LP125_ffluc   TAATTATAAAAAAGTGAATACACGGTTTGGAAATCTTAGTTTTGACGACAAAGGTATTTC  3240
LP143_ffluc   TAATTATAAAAAAGTGAATACACGGTTTGGAAATCTTAGTTTTGACGACAAAGGTATTTC  3237
A511_ffluc    TAATTATAAAAAAGTGAATACACGGTTTGGAAATCTTAGTTTTGACGACAAAGGTATTTC  3237
LP124_ffluc   TAATTATAAAAAAGTGAATACACGGTTTGGAAATCTTAGTTTTGACGACAAAGGTATTTC  3240
Lp101_ffluc   TAATTATAAAAAAGTGAATACACGGTTTGGAAATCTTAGTTTTGACGACAAAGGTATTTC  3240
LP99_ffluc    TAATTATAAAAAAGTGAATACACGGTTTGGAAATCTTAGTTTTGACGACAAAGGTATTTC  3240
P100_ffluc    TAATTATAAAAAAGTGAATACACGATTTGGAAATCTTAGTTTTGATGATAAAGGTATTTC  3240
              ************************ *************** *** ** **********
```

FIGURE 3 (Cont.)

```
LP48___ffluc     TAATGACTTAACGGAAGAACAGCAAAAAGAATTAGGTAAGCTTCGAGGATTCGAATATAT  3300
LP125__ffluc     TAATGACTTAACGGAAGAACAGCAAAAAGAATTAGGTAAGCTTCGAGGATTCGAATATAT  3300
LP143__ffluc     TAATGACTTAACGGAAGAACAGCAAAAAGAATTAGGTAAGCTTCGAGGATTCGAATATAT  3297
A511___ffluc     TAATGACTTAACGGAAGAACAGCAAAAAGAATTAGGTAAGCTTCGAGGATTCGAATATAT  3297
LP124__ffluc     TAATGACTTAACGGAAGAACAGCAAAAAGAATTAGGTAAGCTTCGAGGATTCGAATATAT  3300
lp101__ffluc     TAATGACTTAACGGAAGAACAGCAAAAAGAATTAGGTAAGCTTCGAGGATTCGAATATAT  3300
LP99___ffluc     TAATGACTTAACGGAAGAACAGCAAAAAGAATTAGGTAAGCTTCGAGGATTCGAATATAT  3300
P100___ffluc     TAATGACCTAACGGAAGAGCAGCAAAAAGAATTAGGTAAGCTTAGAGGATTCGAATATAT  3300
                 ****** ********** ********************** ******************

LP48___ffluc     TAAGACAGAACAGAAAACAAAAGAAGAACCTAAGAAAGAAGAACCTAAGAAAGAA-----  3355
LP125__ffluc     TAAGACAGAACAGAAAACAAAAGAAGAACCTAAGAAAGAAGAACCTAAGAAAGAA-----  3355
LP143__ffluc     TAAGACAGAACAGAAAACAAAAGAAGAACCTAAGAAAGAAGAACCTAAGAAAGAAGAACC  3357
A511___ffluc     TAAGACAGAACAGAAAACAAAAGAAGAACCTAAGAAAGAAGAACCTAAGAAAGAAGAACC  3357
LP124__ffluc     TAAGACAGAACAGAAAACAAAAGAAGAACCTAAGAAAGAAGAACCTAAGAAAGAAGAACC  3360
lp101__ffluc     TAAGACAGAACAGAAAACAAAAGAAGAACCTAAGAAAGAAGAACCTAAGAAAGAAGAACC  3360
LP99___ffluc     TAAGACAGAACAGAAAACAAAAGAAGAACCTAAGAAAGAAGAACCTAAGAAAGAAGAACC  3360
P100___ffluc     TAAGACAGAACAGAAAACGAAAGAAGAACCTAAGAAAGAAGAACCTAAGAAAGAA-----  3355
                 ****************** *************************************

LP48___ffluc     ---------------------------------------------------AGTAC  3360
LP125__ffluc     ---------------------------------------------------AGTAC  3360
LP143__ffluc     TAAGAAAGAAGAACCTAAGAAAGAAGAACCTAAGAAAGAAGAACCTAAGAAAGAAGTAC  3417
A511___ffluc     TAAGAAAGAAGAACCTAAGAAAGAAGAACCTAAGAAAGAAGAACCTAAGAAAGAAGTAC  3417
LP124__ffluc     TAAGAAAGAAGAACCTAAGAAAGAAGAACCTAAGAAAGAAGAACCTAAGAAAGAAGTAC  3420
lp101__ffluc     TAAGAAAGAAGAACCTAAGAAAGAAGAACCTAAGAAAGAAGAACCTAAGAAAGAAGTAC  3420
LP99___ffluc     TAAGAAAGAAGAACCTAAGAAAGAAGAACCTAAGAAAGAAGAACCTAAGAAAGAAGTAC  3420
P100___ffluc     ---------------------------------------------------AGTAC  3360
                                                                      *****

LP48___ffluc     AGAAAATGAATTAGACAGCTTCTTAGCTAAAGAGCCTTCAATCAAAGAATTAAAAGAATT  3420
LP125__ffluc     AGAAAATGAATTAGACAGCTTCTTAGCTAAAGAGCCTTCAATCAAAGAATTAAAAGAATT  3420
LP143__ffluc     AGAAAATGAATTAGACAGCTTCTTAGCTAAAGAGCCTTCAATCAAAGAATTAAAAGAATT  3477
A511___ffluc     AGAAAATGAATTAGACAGCTTCTTAGCTAAAGAGCCTTCAATCAAAGAATTAAAAGAATT  3477
LP124__ffluc     AGAAAATGAATTAGACAGCTTCTTAGCTAAAGAGCCTTCAATCAAAGAATTAAAAGAATT  3480
lp101__ffluc     AGAAAATGAATTAGACAGCTTCTTAGCTAAAGAGCCTTCAATCAAAGAATTAAAAGAATT  3480
LP99___ffluc     AGAAAATGAATTAGACAGCTTCTTAGCTAAAGAGCCTTCAATCAAAGAATTAAAAGAATT  3480
P100___ffluc     AGAAAATGAATTAGACAGCTTCTTAGCTAAAGAACCTTCAATCAAAGAATTAAAAGAATT  3420
                 ********************************* **************************

LP48___ffluc     TGCGAGTAAAAAAGGCATTAAAATTGAAAAAACTAAGAAAAATGATATAATTGAAGAACT  3480
LP125__ffluc     TGCGAGTAAAAAAGGCATTAAAATTGAAAAAACTAAGAAAAATGATATAATTGAAGAACT  3480
LP143__ffluc     TGCGAGTAAAAAAGGCATTAAAATTGAAAAAACTAAGAAAAATGATATAATTGAAGAACT  3537
A511___ffluc     TGCGAGTAAAAAAGGCATTAAAATTGAAAAAACTAAGAAAAATGATATAATTGAAGAACT  3537
LP124__ffluc     TGCGAGTAAAAAAGGCATTAAAATTGAAAAAACTAAGAAAAATGATATAATTGAAGAACT  3540
lp101__ffluc     TGCGAGTAAAAAAGGCATTAAAATTGAAAAAACTAAGAAAAATGATATAATTGAAGAACT  3540
LP99___ffluc     TGCGAGTAAAAAAGGCATTAAAATTGAAAAAACTAAGAAAAATGATATAATTGAAGAACT  3540
P100___ffluc     TGCGAGTAAAAAAGGCATTAAAATTGAAAAAACTAAGAAAAATGATATAATTGAAGAACT  3480
                 ************************************************************

LP48___ffluc     AAAGAGAGGGTAATGTATAATGTATGGAGGTTATGAAGGACAAGATTCTTACGAATACCC  3540
LP125__ffluc     AAAGAGAGGGTAATGTATAATGTATGGAGGTTATGAAGGACAAGATTCTTACGAATACCC  3540
LP143__ffluc     AAAGAGAGGGTAATGTATAATGTATGGAGGTTATGAAGGACAAGATTCTTACGAATACCC  3597
A511___ffluc     AAAGAGAGGGTAATGTATAATGTATGGAGGTTATGAAGGACAAGATTCTTACGAATACCC  3597
LP124__ffluc     AAAGAGAGGGTAATGTATAATGTATGGAGGTTATGAAGGACAAGATTCTTACGAATACCC  3600
lp101__ffluc     AAAGAGAGGGTAATGTATAATGTATGGAGGTTATGAAGGACAAGATTCTTACGAATACCC  3600
LP99___ffluc     AAAGAGAGGGTAATGTATAATGTATGGAGGTTATGAAGGACAAGATTCTTACGAATACCC  3600
P100___ffluc     AAAGAGAGGGTAATGTATAATGTATGGAGGTTATGAAGGACAAGATTCTTACGAATACCC  3540
                 ************************************************************
```

FIGURE 3 (Cont.)

```
LP48_ffluc     TTACTCACATGGGAACCCTAAGCATGTAGAGCCAGAAAAAGTTGACGAATATGTTCTTTC 3600
LP125_ffluc    TTACTCACATGGGAACCCTAAGCATGTAGAGCCAGAAAAAGTTGACGAATATGTTCTTTC 3600
LP143_ffluc    TTACTCACATGGGAACCCTAAGCATGTAGAGCCAGAAAAAGTTGACGAATATGTTCTTTC 3657
A511_ffluc     TTACTCACATGGGAACCCTAAGCATGTAGAGCCAGAAAAAGTTGACGAATATGTTCTTTC 3657
LP124_ffluc    TTACTCACATGGGAACCCTAAGCATGTAGAGCCAGAAAAAGTTGACGAATATGTTCTTTC 3660
lp101_ffluc    TTACTCACATGGGAACCCTAAGCATGTAGAGCCAGAAAAAGTTGACGAATATGTTCTTTC 3660
LP99_ffluc     TTACTCACATGGGAACCCTAAGCATGTAGAGCCAGAAAAAGTTGACGAATATGTTCTTTC 3660
P100_ffluc     TTACTCACACGGGAACCCTAAGCATGTAGAGCCAGAAAAAGTTGACGAATATGTTCTTTC 3600
               ********* **************************************************

LP48_ffluc     TGATTATGGTTGGACTGCGGAAACAATTAAAGCATACATGTATGGTGTTCGTGTAGTAGA 3660
LP125_ffluc    TGATTATGGTTGGACTGCGGAAACAATTAAAGCATACATGTATGGTGTTCGTGTAGTAGA 3660
LP143_ffluc    TGATTATGGTTGGACTGCGGAAACAATTAAAGCATACATGTATGGTGTTCGTGTAGTAGA 3717
A511_ffluc     TGATTATGGTTGGACTGCGGAAACAATTAAAGCATACATGTATGGTGTTCGTGTAGTAGA 3717
LP124_ffluc    TGATTATGGTTGGACTGCGGAAACAATTAAAGCATACATGTATGGTGTTCGTGTAGTAGA 3720
lp101_ffluc    TGATTATGGTTGGACTGCGGAAACAATTAAAGCATACATGTATGGTGTTCGTGTAGTAGA 3720
LP99_ffluc     TGATTATGGTTGGACTGCGGAAACAATTAAAGCATACATGTATGTGTTCGTGTAGTAGA  3720
P100_ffluc     TGATTATGGCTGGACTGCGGAAACAATTAAAGCATACATGTATGGTGTTCGTGTAGTAGA 3660
               ********* **************************************************

LP48_ffluc     CCCTGAAACAGGAGAGGAAATGGGAGACACCTTCTACAATCATATTATAGAGGTTGCCGT 3720
LP125_ffluc    CCCTGAAACAGGAGAGGAAATGGGAGACACCTTCTACAATCATATTATAGAGGTTGCCGT 3720
LP143_ffluc    CCCTGAAACAGGAGAGGAAATGGGAGACACCTTCTACAATCATATTATAGAGGTTGCCGT 3777
A511_ffluc     CCCTGAAACAGGAGAGGAAATGGGAGACACCTTCTACAATCATATTATAGAGGTTGCCGT 3777
LP124_ffluc    CCCTGAAACAGGAGAGGAAATGGGAGACACCTTCTACAATCATATTATAGAGGTTGCCGT 3780
lp101_ffluc    CCCTGAAACAGGAGAGGAAATGGGAGACACCTTCTACAATCATATTATAGAGGTTGCCGT 3780
LP99_ffluc     CCCTGAAACAGGAGAGGAAATGGGAGACACCTTCTACAATCATATTATAGAGGTTGCCGT 3780
P100_ffluc     CCCTGAAACAGGAGAGGAAATGGGAGACACCTTCTACAATCATATTATAGAGGTTGCCGT 3720
               ************************************************************

LP48_ffluc     TGATAAGGC 3729
LP125_ffluc    TGATAAGGC 3729
LP143_ffluc    TGATAAGGC 3786
A511_ffluc     TGATAAGGC 3786
LP124_ffluc    TGATAAGGC 3789
lp101_ffluc    TGATAAGGC 3789
LP99_ffluc     TGATAAGGC 3789
P100_ffluc     TGATAAGGC 3729
               *********
```

FIGURE 4

LP124_nluc (SEQ ID NO: 31); A511_nluc (SEQ ID NO: 33); LP125_nluc (SEQ ID NO: 32); LP40_nluc (SEQ ID NO: 35); P100_nluc (SEQ ID NO: 34)

```
LP124_nluc    ATGCCAAAAAATAACAAAGAAGAAGAAGTTAAAGAAGTAAACCTTAATTCAGTACAAGAG 60
A511_nluc     ATGCCAAAAAATAACAAA---GAAGAAGTTAAAGAAGTAAACCTTAATTCAGTACAAGAG 57
LP125_nluc    ATGCCAAAAAATAACAAAGAAGAAGAAGTTAAAGAAGTAAACCTTAATTCAGTACAAGAG 60
LP40_nluc     ATGCCAAAAAATAACAAAGAAGAAGAAGTTAAAGAAGTAAACCTTAATTCAGTACAAGAG 60
P100_nluc     ATGCCAAAAAATAACAAAGAAGAAGAAGTTAAAGAAGTAAACCTTAATTCAGTACAAGAG 60
              ******************   ***************************************

LP124_nluc    GACGCGTTAAAGTCCTTTACAACTGGTTATGGTATCACACCTGATACACAAACAGATGCA 120
A511_nluc     GATGCGTTAAAGTCCTTTACGACTGGTTATGGTATCACACCTGATACACAAACAGATGCA 117
LP125_nluc    GACGCGTTAAAGTCCTTTACAACTGGTTATGGTATCACACCTGATACACAAACAGATGCA 120
LP40_nluc     GATGCGTTAAAGTCCTTTACAACTGGTTATGGTATCACACCTGATACACAAACAGATGCA 120
P100_nluc     GACGCGTTAAAGTCCTTTACAACTGGTTATGGTATCACACCTGATACACAAACAGATGCA 120
              ** ***************** ***************************************

LP124_nluc    GGAGCATTAAGACGTGAGTTCCTAGACGACCAAATCTCAATGCTTACTTGGACAGAGAAT 180
A511_nluc     GGAGCATTAAGACGTGAGTTCCTAGACGACCAAATCTCAATGCTTACTTGGACAGAGAAT 177
LP125_nluc    GGAGCATTAAGACGTGAGTTCCTAGACGACCAAATCTCAATGCTTACTTGGACAGAGAAT 180
LP40_nluc     GGGGCACTAAGACGTGAGTTCCTAGACGACCAAATCTCAATGCTTACTTGGACAGAGAAT 180
P100_nluc     GGAGCATTAAGACGTGAGTTCCTAGACGACCAAATCTCAATGCTTACTTGGACAGAGAAT 180
              ** *** *************************************************** ***

LP124_nluc    GATTTAACATTCTATAAAGACATCGCTAAAAAACCAGCTACATCTACAGTAGCAAAATAC 240
A511_nluc     GATTTAACATTCTATAAAGACATCGCTAAAAAACCAGCTACATCTACAGTAGCAAAATAC 237
LP125_nluc    GATTTAACATTCTATAAAGACATCGCTAAAAAACCAGCTACATCTACAGTAGCAAAATAC 240
LP40_nluc     GATTTAACATTCTACAAAGACATCGCTAAAAAACCAGCTACATCTACAGTAGCAAAATAC 240
P100_nluc     GATTTAACATTCTATAAAGACATCGCTAAAAAACCAGCTACATCTACAGTAGCAAAATAC 240
              ************** *********************************************

LP124_nluc    GATGTATACATGCAACATGGTAAGGTAGGTCATACTAGATTTACTCGTGAGATTGGGGTA 300
A511_nluc     GATGTATACATGCAACATGGTAAGGTAGGTCATACTAGATTTACTCGTGAGATTGGGGTA 297
LP125_nluc    GATGTATACATGCAACATGGTAAGGTAGGTCATACTAGATTTACTCGTGAGATTGGGGTA 300
LP40_nluc     GATGTGTACATGCAACACGGTAAAGTAGGTCATACTAGATTTACTCGTGAGATTGGGGTA 300
P100_nluc     GATGTATACATGCAACATGGTAAGGTAGGTCATACTAGATTTACTCGTGAGATTGGGGTA 300
              ***** *********** ***** ************************************

LP124_nluc    GCACCAGTAAGTGACCCTAACATCCGTCAAAAAACAGTAAACATGAAATTTGCTTCCGAT 360
A511_nluc     GCACCAGTAAGTGACCCTAACATCCGTCAAAAAACAGTAAATATGAAATTTGCTTCCGAT 357
LP125_nluc    GCACCAGTAAGTGACCCTAACATCCGTCAAAAAACAGTAAACATGAAATTTGCTTCCGAT 360
LP40_nluc     GCACCAGTAAGTGACCCTAACATCCGTCAAAAAACAGTAAACATGAAATTTGCTTCTGAT 360
P100_nluc     GCACCAGTAAGTGACCCTAACATCCGTCAAAAAACAGTAAATATGAAATTTGCTTCCGAT 360
              ***************************************** *************** ***

LP124_nluc    ACTAAAAACATCAGTATCGCAGCAGGTCTAGTAAACAACATTCAAGACCCAATGCAAATT 420
A511_nluc     ACTAAAAACATCAGTATCGCAGCAGGTCTAGTAAACAACATTCAAGACCCAATGCAAATT 417
LP125_nluc    ACTAAAAACATCAGTATCGCAGCAGGTCTAGTAAACAACATTCAAGACCCAATGCAAATT 420
LP40_nluc     ACTAAAAATATTAGTATCGCAGCAGGTCTAGTAAACAACATTCAAGACCCTATGCAAATT 420
P100_nluc     ACTAAAAACATCAGTATCGCAGCAGGTCTAGTAAACAACATTCAAGACCCAATGCAAATT 420
              ******** ** ************************************** *********

LP124_nluc    TTGACTGACGATGCTATCGTAAATATTGCTAAAACAATTGAGTGGGCTTCATTCTTTGGA 480
A511_nluc     TTGACTGACGATGCTATCGTAAATATTGCTAAAACAATTGAGTGGGCTTCATTCTTTGGA 477
LP125_nluc    TTGACTGACGATGCTATCGTAAATATTGCTAAAACAATTGAGTGGGCTTCATTCTTTGGA 480
LP40_nluc     TTGACTGATGATGCTATCGTAAATATTGCTAAAACAATTGAGTGGGCTTCATTCTTTGGA 480
P100_nluc     TTGACTGACGATGCTATCGTAAATATTGCTAAAACAATTGAGTGGGCTTCATTCTTTGGA 480
              ******** ****************************************************
```

FIGURE 4 (Cont.)

```
LP124_nluc    GATTCTGACTTATCAGATAGCCCAGAACCACAAGCAGGACTAGAATTTGACGGCTTGGCT 540
A511_nluc     GATTCTGACTTATCAGATAGCCCAGAACCACAAGCAGGACTAGAATTTGACGGCTTGGCT 537
LP125_nluc    GATTCTGACTTATCAGATAGCCCAGAACCACAAGCAGGACTAGAATTTGACGGCTTGGCT 540
LP40_nluc     GATTCTGACTTATCAGATAGCCCAGAACCACAAGCAGGATTAGAATTTGATGGCTTGGCT 540
P100_nluc     GATTCTGACTTATCAGATAGCCCAGAACCACAAGCAGGACTAGAATTTGACGGCTTGGCT 540
              **************************************  ********* ********

LP124_nluc    AAACTTATTAACCAAGATAACGTTCATGATGCTCGTGGAGCTAGCTTGACTGAAAGCTTG 600
A511_nluc     AAACTTATTAACCAAGATAACGTTCATGATGCTCGTGGAGCTAGCTTGACTGAAAGCTTG 597
LP125_nluc    AAACTTATTAACCAAGATAACGTTCATGATGCTCGTGGAGCTAGCTTGACTGAAAGCTTG 600
LP40_nluc     AAACTTATTAACCAAGATAACGTTCATGATGCTCGTGGAGCTAGCTTGACTGAAAGCTTG 600
P100_nluc     AAACTTATTAACCAAGATAACGTTCATGATGCTCGTGGAGCTAGCTTGACTGAAAGCTTG 600
              ************************************************************

LP124_nluc    TTAAACCAAGCAGCAGTAATGATTAGTAAAGGTTATGGTACACCTACAGATGCTTACATG 660
A511_nluc     TTAAACCAAGCAGCAGTAATGATTAGTAAAGGTTATGGTACACCTACAGATGCTTACATG 657
LP125_nluc    TTAAACCAAGCAGCAGTAATGATTAGTAAAGGTTATGGTACACCTACAGATGCTTACATG 660
LP40_nluc     TTAAACCAAGCAGCAGTAATGATTAGTAAAGGTTATGGTACACCTACAGATGCTTACATG 660
P100_nluc     TTAAACCAAGCAGCAGTAATGATTAGTAAAGGTTATGGTACACCTACAGATGCTTACATG 660
              ************************************************************

LP124_nluc    CCAGTAGGGGTTCAAGCAGACTTTGTTAACCAACAACTTTCTAAACAAACACAACTTGTT 720
A511_nluc     CCAGTAGGGGTTCAAGCAGACTTTGTTAACCAACAACTTTCTAAACAAACACAACTTGTT 717
LP125_nluc    CCAGTAGGGGTTCAAGCAGACTTTGTTAACCAACAACTTTCTAAACAAACACAACTTGTT 720
LP40_nluc     CCAGTAGGGGTTCAAGCAGACTTTGTTAACCAACAACTTTCTAAACAAACACAACTTGTT 720
P100_nluc     CCAGTAGGGGTTCAAGCAGACTTTGTTAACCAACAACTTTCTAAACAAACACAGCTTGTT 720
              ***************************************************** *****

LP124_nluc    CGCGATAACGGAAACAACGTAAGCGTTGGTTTCAACATCCAAGGTTTCCATTCAGCTCGT 780
A511_nluc     CGCGATAACGGAAACAACGTAAGCGTTGGTTTCAACATCCAAGGTTTCCATTCAGCTCGT 777
LP125_nluc    CGTGATAACGGAAACAACGTAAGCGTTGGTTTCAACATCCAAGGTTTCCATTCAGCTCGT 780
LP40_nluc     CGCGATAACGGAAACAACGTAAGCGTTGGTTTCAACATCCAAGGTTTCCATTCAGCTCGT 780
P100_nluc     CGTGATAACGGAAACAACGTAAGCGTTGGTTTCAACATCCAAGGTTTCCATTCAGCTCGT 780
              ** *********************************************************

LP124_nluc    GGATTTATCAAACTTCACGGTTCTACAGTAATGGAAAACGAACAAATCTTAGATGAACGT 840
A511_nluc     GGATTTATCAAACTTCACGGTTCTACAGTAATGGAAAACGAACAAATCTTAGATGAACGT 837
LP125_nluc    GGATTTATCAAACTTCACGGTTCTACAGTAATGGAAAACGAACAAATCTTAGATGAACGT 840
LP40_nluc     GGATTTATCAAACTTCACGGTTCTACAGTAATGGAAAACGAACAAATCTTAGATGAACGT 840
P100_nluc     GGATTTATCAAACTTCACGGTTCTACAGTAATGGAAAACGAACAAATCTTAGATGAACGT 840
              ************************************************************

LP124_nluc    ATTCTTGCTTTACCAACAGCTCCACAACCAGCTAAGGTAACTGCAACACAAGAAGCAGGT 900
A511_nluc     ATTCTTGCTTTACCAACAGCTCCACAACCAGCTAAGGTAACTGCAACACAAGAAGCAGGT 897
LP125_nluc    ATTCTTGCTTTACCAACAGCTCCACAACCAGCTAAGGTAACTGCAACACAAGAAGCAGGT 900
LP40_nluc     ATTCTTGCTTTACCAACAGCTCCACAACCAGCTAAGGTAACTGCAACACAAGAAGCAGGT 900
P100_nluc     ATTCTTGCTTTACCAACAGCTCCACAACCAGCTAAGGTAACTGCAACACAAGAAGCAGGT 900
              ************************************************************

LP124_nluc    AAAAAGGACAATTTAGAGCAGAAGATTTAGCAGCACATGAATATAAAGTTGTTGTAAGT 960
A511_nluc     AAAAAGGACAATTTAGAGCAGAAGATTTAGCAGCACATGAATATAAAGTTGTTGTAAGT 957
LP125_nluc    AAAAAGGACAATTTAGAGCAGAAGATTTAGCAGCACATGAATATAAAGTTGTTGTAAGT 960
LP40_nluc     AAAAAGGACAATTTAGAGCAGAAGATTTAGCAGCACATGAATATAAAGTTGTTGTAAGT 960
P100_nluc     AAAAAGGACAATTTAGAGCAGAAGACTTAGCAGCACACGAATACAAAGTTGTTGTAAGT 960
              ************************* ********** ***** ***************

LP124_nluc    TCTGACGATGCAGAGTCTATTGCAAGTGAAGTGGCTACAGCTACAGTTACTGCAAAAGAT 1020
A511_nluc     TCTGACGATGCAGAGTCTATTGCAAGTGAAGTGGCTACAGCTACAGTTACTGCAAAAGAT 1017
LP125_nluc    TCTGACGATGCAGAGTCTATTGCAAGTGAAGTGGCTACAGCTACAGTTACTGCAAAAGAT 1020
LP40_nluc     TCTGACGATGCAGAGTCTATTGCAAGTGAAGTGGCTACAGCTACAGTTACTGCAAAAGAT 1020
P100_nluc     TCTGACGATGCAGAGTCTATTGCAAGTGAAGTGGCTACAGCTACAGTTACTGCAAAAGAT 1020
              ************************************************************
```

FIGURE 4 (Cont.)

```
LP124_nluc   GACGGCGTTAAACTAGAAATCGAATTAGCTCCAATGTATAGCTCTCGTCCACAATTCGTT 1080
A511_nluc    GACGGCGTTAAACTAGAAATCGAATTAGCTCCAATGTATAGCTCTCGTCCACAATTCGTT 1077
LP125_nluc   GACGGCGTTAAACTAGAAATCGAATTAGCTCCAATGTATAGCTCTCGTCCACAATTCGTT 1080
LP40_nluc    GACGGCGTTAAACTAGAAATCGAATTAGCTCCAATGTATAGCTCTCGTCCACAATTCGTT 1080
P100_nluc    GACGGCGTTAAACTAGAAATCGAGTTAGCTCCAATGTACAGCTCCCGTCCACAATTCGTT 1080
             *********************** ************** *** ****************

LP124_nluc   TCAATCTATAGAAAGGTGCAGAAACAGGTTTATTCTACCTAATCGCTCGTGTACCTGCT 1140
A511_nluc    TCAATCTATAGAAAGGTGCAGAAACAGGTTTATTCTACCTAATCGCTCGTGTACCTGCT 1137
LP125_nluc   TCAATCTATAGAAAGGTGCAGAAACAGGTTTATTCTACCTAATCGCTCGTGTACCTGCT 1140
LP40_nluc    TCAATCTATAGAAAGGTGCAGAAACAGGTTTATTCTACCTAATCGCTCGTGTACCTGCT 1140
P100_nluc    TCAATCTATAGAAAGGTGCAGAAACAGGTTTATTCTACCTAATCGCTCGTGTACCTGCT 1140
             ************************************************************

LP124_nluc   AGCAAAGCAGAGAACAACGTAATCACTTTCTACGACTTAAACGACTCTATTCCTGAAACA 1200
A511_nluc    AGCAAAGCAGAGAACAACGTAATCACTTTCTACGACTTAAACGACTCTATTCCTGAAACA 1197
LP125_nluc   AGCAAAGCAGAGAACAACGTAATCACTTTCTACGACTTAAACGACTCTATTCCTGAAACA 1200
LP40_nluc    AGCAAAGCAGAGAACAACGTAATCACTTTCTACGACTTAAACGACTCTATTCCTGAAACA 1200
P100_nluc    AGCAAAGCAGAGAACAACGTAATCACTTTCTATGACTTAAACGACTCTATTCCTGAAACA 1200
             ******************************** ***************************

LP124_nluc   GTAGACGTATTCGTTGGTGAAATGTCGGCTAACGTAGTACACTTGTTTGAATTACTACCA 1260
A511_nluc    GTAGACGTATTCGTTGGTGAAATGTCGGCTAACGTAGTACACTTGTTTGAATTACTACCA 1257
LP125_nluc   GTAGACGTATTCGTTGGTGAAATGTCGGCTAACGTAGTACACTTGTTTGAATTACTACCA 1260
LP40_nluc    GTAGACGTATTCGTTGGTGAAATGTCGGCTAACGTAGTACACTTGTTTGAATTACTACCA 1260
P100_nluc    GTAGACGTATTCGTTGGTGAAATGTCTGCTAACGTAGTACACTTGTTTGAATTACTACCA 1260
             ************************** *********************************

LP124_nluc   ATGATGAGATTACCTCTAGCTCAAATTAACGCATCTGTTACATTTGCAGTTTTATGGTAT 1320
A511_nluc    ATGATGAGATTACCTCTAGCTCAAATTAACGCATCTGTTACATTTGCAGTTTTATGGTAT 1317
LP125_nluc   ATGATGAGATTACCTCTAGCTCAAATTAACGCATCTGTTACATTTGCAGTTTTATGGTAT 1320
LP40_nluc    ATGATGAGATTACCTCTAGCTCAAATTAACGCATCTGTTACATTTGCAGTTTTATGGTAT 1320
P100_nluc    ATGATGAGATTACCTCTAGCTCAAATTAACGCATCTGTTACATTTGCAGTTTTATGGTAT 1320
             ************************************************************

LP124_nluc   GGCGCATTAGCTCTAAGAGCACCTAAGAAATGGGTACGTATTAGAAACGTTAAATATATT 1380
A511_nluc    GGCGCATTAGCTCTAAGAGCACCTAAGAAATGGGTACGTATTAGAAACGTTAAATATATT 1377
LP125_nluc   GGCGCATTAGCTCTAAGAGCACCTAAGAAATGGGTACGTATTAGAAACGTTAAATATATT 1380
LP40_nluc    GGCGCATTAGCTCTAAGAGCACCTAAGAAATGGGTACGTATTAGAAACGTTAAATATATT 1380
P100_nluc    GGAGCATTAGCTCTAAGAGCACCTAAGAAATGGGTACGTATTAGAAACGTTAAATATATT 1380
             ** *********************************************************

LP124_nluc   CCTGTAAAAAACGTTCATAGCAACTAATAATAAGAGGAGGTAAATATATATGGTCTTCAC 1440
A511_nluc    CCTGTAAAAAACGTTCATAGCAACTAA------GAGGAGGTAAATATATATGGTCTTCAC 1431
LP125_nluc   CCTGTAAAAAACGTTCATAGCAACTAATAATAAGAGGAGGTAAATATATATGGTCTTCAC 1440
LP40_nluc    CCTGTAAAAAACGTTCATAGCAACTAATAATAAGAGGAGGTAAATATATATGGTCTTCAC 1440
P100_nluc    CCTGTAAAAAACGTTCATAGCAACTAA------GAGGAGGTAAATATATATGGTCTTCAC 1434
             ***************************      ***************************

LP124_nluc   ACTCGAAGATTTCGTTGGGGACTGGCGACAGACAGCCGGCTACAACCTGGACCAAGTCCT 1500
A511_nluc    ACTCGAAGATTTCGTTGGGGACTGGCGACAGACAGCCGGCTACAACCTGGACCAAGTCCT 1491
LP125_nluc   ACTCGAAGATTTCGTTGGGGACTGGCGACAGACAGCCGGCTACAACCTGGACCAAGTCCT 1500
LP40_nluc    ACTCGAAGATTTCGTTGGGGACTGGCGACAGACAGCCGGCTACAACCTGGACCAAGTCCT 1500
P100_nluc    ACTCGAAGATTTCGTTGGGGACTGGCGACAGACAGCCGGCTACAACCTGGACCAAGTCCT 1494
             ************************************************************

LP124_nluc   TGAACAGGGAGGTGTGTCCAGTTTGTTTCAGAATCTCGGGGTGTCCGTAACTCCGATCCA 1560
A511_nluc    TGAACAGGGAGGTGTGTCCAGTTTGTTTCAGAATCTCGGGGTGTCCGTAACTCCGATCCA 1551
LP125_nluc   TGAACAGGGAGGTGTGTCCAGTTTGTTTCAGAATCTCGGGGTGTCCGTAACTCCGATCCA 1560
LP40_nluc    TGAACAGGGAGGTGTGTCCAGTTTGTTTCAGAATCTCGGGGTGTCCGTAACTCCGATCCA 1560
P100_nluc    TGAACAGGGAGGTGTGTCCAGTTTGTTTCAGAATCTCGGGGTGTCCGTAACTCCGATCCA 1554
             ************************************************************
```

FIGURE 4 (Cont.)

```
LP124_nluc    AAGGATTGTCCTGAGCGGTGAAAATGGGCTGAAGATCGACATCCATGTCATCATCCCGTA 1620
A511_nluc     AAGGATTGTCCTGAGCGGTGAAAATGGGCTGAAGATCGACATCCATGTAATCATCCCGTA 1611
LP125_nluc    AAGGATTGTCCTGAGCGGTGAAAATGGGCTGAAGATCGACATCCATGTCATCATCCCGTA 1620
LP40_nluc     AAGGATTGTCCTGAGCGGTGAAAATGGGCTGAAGATCGACATCCATGTCATCATCCCGTA 1620
P100_nluc     AAGGATTGTCCTGAGCGGTGAAAATGGGCTGAAGATCGACATCCATGTCATCATCCCGTA 1614
              *********************************************** ***********

LP124_nluc    TGAAGGTCTGAGCGGCGACCAAATGGGCCAGATCGAAAAAATTTTTAAGGTGGTGTACCC 1680
A511_nluc     TGAAGGTCTGAGCGGCGACCAAATGGGCCAGATCGAAAAAATTTTTAAGGTGGTGTACCC 1671
LP125_nluc    TGAAGGTCTGAGCGGCGACCAAATGGGCCAGATCGAAAAAATTTTTAAGGTGGTGTACCC 1680
LP40_nluc     TGAAGGTCTGAGCGGCGACCAAATGGGCCAGATCGAAAAAATTTTTAAGGTGGTGTACCC 1680
P100_nluc     TGAAGGTCTGAGCGGCGACCAAATGGGCCAGATCGAAAAAATTTTTAAGGTGGTGTACCC 1674
              ************************************************************

LP124_nluc    TGTGGATGATCATCACTTTAAGGTGATCCTGCACTATGGCACACTGGTAATCGACGGGGT 1740
A511_nluc     TGTGGATGATCATCACTTTAAGGTGATCCTGCACTATGGCACACTGGTAATCGACGGGGT 1731
LP125_nluc    TGTGGATGATCATCACTTTAAGGTGATCCTGCACTATGGCACACTGGTAATCGACGGGGT 1740
LP40_nluc     TGTGGATGATCATCACTTTAAGGTGATCCTGCACTATGGCACACTGGTAATCGACGGGGT 1740
P100_nluc     TGTGGATGATCATCACTTTAAGGTGATCCTGCACTATGGCACACTGGTAATCGACGGGGT 1734
              ************************************************************

LP124_nluc    TACGCCGAACATGATCGACTATTTCGGACGGCCGTATGAAGGCATCGCCGTGTTCGACGG 1800
A511_nluc     TACGCCGAACATGATCGACTATTTCGGACGGCCGTATGAAGGCATCGCCGTGTTCGACGG 1791
LP125_nluc    TACGCCGAACATGATCGACTATTTCGGACGGCCGTATGAAGGCATCGCCGTGTTCGACGG 1800
LP40_nluc     TACGCCGAACATGATCGACTATTTCGGACGGCCGTATGAAGGCATCGCCGTGTTCGACGG 1800
P100_nluc     TACGCCGAACATGATCGACTATTTCGGACGGCCGTATGAAGGCATCGCCGTGTTCGACGG 1794
              ************************************************************

LP124_nluc    CAAAAAGATCACTGTAACAGGGACCCTGTGGAACGGCAACAAAATTATCGACGAGCGCCT 1860
A511_nluc     CAAAAAGATCACTGTAACAGGGACCCTGTGGAACGGCAACAAAATTATCGACGAGCGCCT 1851
LP125_nluc    CAAAAAGATCACTGTAACAGGGACCCTGTGGAACGGCAACAAAATTATCGACGAGCGCCT 1860
LP40_nluc     CAAAAAGATCACTGTAACAGGGACCCTGTGGAACGGCAACAAAATTATCGACGAGCGCCT 1860
P100_nluc     CAAAAAGATCACTGTAACAGGGACCCTGTGGAACGGCAACAAAATTATCGACGAGCGCCT 1854
              ************************************************************

LP124_nluc    GATCAACCCCGACGGCTCCCTGCTGTTCCGAGTAACCATCAACGGAGTGACCGGCTGGCG 1920
A511_nluc     GATCAACCCCGACGGCTCCCTGCTGTTCCGAGTAACCATCAACGGAGTGACCGGCTGGCG 1911
LP125_nluc    GATCAACCCCGACGGCTCCCTGCTGTTCCGAGTAACCATCAACGGAGTGACCGGCTGGCG 1920
LP40_nluc     GATCAACCCCGACGGCTCCCTGCTGTTCCGAGTAACCATCAACGGAGTGACCGGCTGGCG 1920
P100_nluc     GATCAACCCCGACGGCTCCCTGCTGTTCCGAGTAACCATCAACGGAGTGACCGGCTGGCG 1914
              ************************************************************

LP124_nluc    GCTGTGCGAACGCATTCTGGCGTAATAATTATAGGATAATTGAATAAAAACAGTATAGAG 1980
A511_nluc     GCTGTGCGAACGCATTCTGGCGTAATAATTATAGGATAATTGAATAAAAACAGTATAGAG 1971
LP125_nluc    GCTGTGCGAACGCATTCTGGCGTAATAATTATAGGATAATTGAATAAAAACAGTATAGAG 1980
LP40_nluc     GCTGTGCGAACGCATTCTGGCGTAATAATTATAGGATAATTGAATAAAAACAGTATAGAG 1980
P100_nluc     GCTGTGCGAACGCATTCTGGCGTAATAATTATAGGATAATTGAATAAAAACAGTATAGAG 1974
              ************************************************************

LP124_nluc    AGCAGATAAATACTGCTCTCTATTTTACTAATAAGGAGGATTTAAATTGCTAAAAAATAC 2040
A511_nluc     AGCAGATAAATACTGCTCTCTATTTTACTAATAAGGAGGATTTAAATTGCTAAAAAATAC 2031
LP125_nluc    AGCAGATAAATACTGCTCTCTATTTTACTAATAAGGAGGATTTAAATTGCTAAAAAATAC 2040
LP40_nluc     AGCAGATAAATACTGCTCTCTATTTTACTAATAAGGAGGATTTAAATTGCTAAAAAATAC 2040
P100_nluc     AGCAGATAAATACTGCTCTCTATTTTACTAATAAGGAGGATTTAAATTGCTAAAAAATAC 2034
              ************************************************************

LP124_nluc    AAACTTAGCTAATTATAAAAAAGTGAATACACGGTTTGGAAATCTTAGTTTTGACGACAA 2100
A511_nluc     AAACTTAGCTAATTATAAAAAAGTGAATACACGGTTTGGAAATCTTAGTTTTGACGACAA 2091
LP125_nluc    AAACTTAGCTAATTATAAAAAAGTGAATACACGGTTTGGAAATCTTAGTTTTGACGACAA 2100
LP40_nluc     AAACTTAGCTAATTATAAAAAAGTGAATACACGGTTTGGAAATCTTAGTTTTGACGACAA 2100
P100_nluc     AAACTTAGCTAATTATAAAAAAGTGAATACACGATTTGGAAATCTTAGTTTTGATGATAA 2094
              ********************************* ******************* ** **
```

FIGURE 4 (Cont.)

```
LP124_nluc   AGGTATTTCTAATGACTTAACGGAAGAACAGCAAAAAGAATTAGGTAAGCTTCGAGGATT 2160
A511_nluc    AGGTATTTCTAATGACTTAACGGAAGAACAGCAAAAAGAATTAGGTAAGCTTCGAGGATT 2151
LP125_nluc   AGGTATTTCTAATGACTTAACGGAAGAACAGCAAAAAGAATTAGGTAAGCTTCGAGGATT 2160
LP40_nluc    AGGTATTTCTAATGACTTAACGGAAGAACAGCAAAAAGAATTAGGTAAGCTTCGAGGATT 2160
P100_nluc    AGGTATTTCTAATGACCTAACGGAAGAGCAGCAAAAAGAATTAGGTAAGCTTAGAGGATT 2154
             **************** ********* ************************* ******

LP124_nluc   CGAATATATTAAGACAGAACAGAAAACAAAAGAAGAACCTAAGAAAGAAGAACCTAAGAA 2220
A511_nluc    CGAATATATTAAGACAGAACAGAAAACAAAAGAAGAACCTAAGAAAGAAGAACCTAAGAA 2211
LP125_nluc   CGAATATATTAAGACAGAACAGAAAACAAAAGAAGAACCTAAGAAAGAAGAACCTAAGAA 2220
LP40_nluc    CGAATATATTAAGACAGAACAGAAAACAAAAGAAGAACCTAAGAAAGAAGAACCTAAGAA 2220
P100_nluc    CGAATATATTAAGACAGAACAGAAAACGAAAGAAGAACCTAAGAAAGAAGAACCTAAGAA 2214
             *************************** ********************************

LP124_nluc   AGAAGAACCTAAGAAAGAAGAACCTAAGAAAGAAGAACCTAAGAAAGAAGAACCTAAGAA 2280
A511_nluc    AGAAGAACCTAAGAAAGAAGAACCTAAGAAAGAAGAACCTAAGAAAGAAGAACCTAAGAA 2271
LP125_nluc   AGAA-------------------------------------------------------- 2224
LP40_nluc    AGAA---------------------------------------------GAACCTAAGAA 2235
P100_nluc    AGAA-------------------------------------------------------- 2218
             ****

LP124_nluc   AGAAAGTACAGAAAATGAATTAGACAGCTTCTTAGCTAAAGAGCCTTCAATCAAAGAATT 2340
A511_nluc    AGAAAGTACAGAAAATGAATTAGACAGCTTCTTAGCTAAAGAGCCTTCAATCAAAGAATT 2331
LP125_nluc   ----AGTACAGAAAATGAATTAGACAGCTTCTTAGCTAAAGAGCCTTCAATCAAAGAATT 2280
LP40_nluc    AGAAAGTACAGAAAATGAATTAGACAGCTTCTTAGCTAAAGAGCCTTCAATCAAAGAATT 2295
P100_nluc    ----AGTACAGAAAATGAATTAGACAGCTTCTTAGCTAAAGAACCTTCAATCAAAGAATT 2274
                 ************************************** ****************

LP124_nluc   AAAAGAATTTGCGAGTAAAAAAGGCATTAAAATTGAAAAAACTAAGAAAAATGATATAAT 2400
A511_nluc    AAAAGAATTTGCGAGTAAAAAAGGCATTAAAATTGAAAAAACTAAGAAAAATGATATAAT 2391
LP125_nluc   AAAAGAATTTGCGAGTAAAAAAGGCATTAAAATTGAAAAAACTAAGAAAAATGATATAAT 2340
LP40_nluc    AAAAGAATTTGCGAGTAAAAAAGGCATTAAAATTGAAAAAACTAAGAAAAACGATATAAT 2335
P100_nluc    AAAAGAATTTGCGAGTAAAAAAGGCATTAAAATTGAAAAAACTAAGAAAAATGATATAAT 2334
             *************************************************** *******

LP124_nluc   TGAAGAACTAAAGAGAGGGTAATGTATAATGTATGGAGGTTATGAAGGACAAGATTCTTA 2460
A511_nluc    TGAAGAACTAAAGAGAGGGTAATGTATAATGTATGGAGGTTATGAAGGACAAGATTCTTA 2451
LP125_nluc   TGAAGAACTAAAGAGAGGGTAATGTATAATGTATGGAGGTTATGAAGGACAAGATTCTTA 2400
LP40_nluc    TGAAGAACTAAAGAGAGGGTAATGTATAATGTATGGAGGTTATGAAGGACAAGATTCTTA 2415
P100_nluc    TGAAGAACTAAAGAGAGGGTAATGTACAATGTATGGAGGTTATGAAGGACAAGATTCTTA 2394
             ************************** *********************************

LP124_nluc   CGAATACCCTTACTCACATGGGAACCCTAAGCATGTAGAGCCAGAAAAAGTTGACGAATA 2520
A511_nluc    CGAATACCCTTACTCACATGGGAACCCTAAGCATGTAGAGCCAGAAAAAGTTGACGAATA 2511
LP125_nluc   CGAATACCCTTACTCACATGGGAACCCTAAGCATGTAGAGCCAGAAAAAGTTGACGAATA 2460
LP40_nluc    CGAATACCCTTACTCACATGGGAACCCTAAGCATGTAGAGCCAGAAAAAGTTGACGAATA 2475
P100_nluc    CGAATACCCTTACTCACACGGGAACCCTAAGCATGTAGAGCCAGAAAAAGTTGACGAATA 2454
             ****************** *****************************************

LP124_nluc   TGTTCTTTCTGATTATGGTTGGACTGCGGAAACAATTAAAGCATACATGTATGGTGTTCG 2580
A511_nluc    TGTTCTTTCTGATTATGGTTGGACTGCGGAAACAATTAAAGCATACATGTATGGTGTTCG 2571
LP125_nluc   TGTTCTTTCTGATTATGGTTGGACTGCGGAAACAATTAAAGCATACATGTATGGTGTTCG 2520
LP40_nluc    TGTTCTTTCTGATTATGGTTGGACTGCGGAAACAATTAAAGCATACATGTATGGTGTTCG 2535
P100_nluc    TGTTCTTTCTGATTATGGCTGGACTGCGGAAACAATTAAAGCATACATGTATGGTGTTCG 2514
             ****************** *****************************************

LP124_nluc   TGTAGTAGACCCTGAAACAGGAGAGGAAATGGGAGACACCTTCTACAATCATATTATAGA 2640
A511_nluc    TGTAGTAGACCCTGAAACAGGAGAGGAAATGGGAGACACCTTCTACAATCATATTATAGA 2631
LP125_nluc   TGTAGTAGACCCTGAAACAGGAGAGGAAATGGGAGACACCTTCTACAATCATATTATAGA 2580
LP40_nluc    TGTAGTAGACCCTGAAACAGGAGAGGAAATGGGAGACACCTTCTACAATCATATTATAGA 2595
P100_nluc    TGTAGTAGACCCTGAAACAGGAGAGGAAATGGGAGACACCTTCTACAATCATATTATAGA 2574
             ************************************************************
```

FIGURE 4 (Cont.)

```
LP124_nluc      GGTTGCCGTTGATAAGGC 2658
A511_nluc       GGTTGCCGTTGATAAGGC 2649
LP125_nluc      GGTTGCCGTTGATAAGGC 2598
LP40_nluc       GGTTGCCGTTGATAAGGC 2613
P100_nluc       GGTTGCCGTTGATAAGGC 2592
                ******************
```

METHODS OF MAKING RECOMBINANT PHAGE, COMPOSITIONS AND ARTICLES OF MANUFACTURE OF SAME FOR BACTERIAL DETECTION

RELATED APPLICATIONS

This application claims priority to, and the benefit of, U.S. Provisional Application No. 61/805,917, filed Mar. 27, 2013, the entire contents of which are incorporated herein in their entireties.

INCORPORATION-BY-REFERENCE OF SEQUENCE LISTING

The contents of the text file named "108310071_1.txt", which was created on Jun. 20, 2014 and is 119 KB in size, are hereby incorporated by reference in their entireties.

INTRODUCTION

Bacterial contamination and infection is a significant problem to public health and in many other areas. Methods and reagents to detect bacteria in medical, veterinary, agricultural, food processing, industrial and other contexts are therefore beneficial. Indeed, the annual worldwide bacterial in vitro diagnosis market is over $10 billion.

Bacterial food borne diseases pose a significant threat to human health, estimated to cause as many as about 76 million illnesses, 325,000 hospitalizations, and 5,000 deaths in the US annually.

For example, in 1996, juice that was contaminated with *Escherichia coli* was released into the public by a juice maker and resulted in one death and 66 illnesses. The company paid a $1.5 million fine, and the recall alone cost the company $6.5 million. In 2006, an *E. coli* 0157:H7 outbreak from contaminated spinach originating from California resulted in 205 illnesses and 3 deaths. In 2011 a listeriosis outbreak from cantaloupes from Colorado in July, August and September resulted in 30 deaths. That is the second deadliest recorded U.S. outbreak in terms of the number of deaths since the Centers for Disease Control and Prevention began tracking outbreaks in the 1970s. Another recall of cantaloupes in 2012 suggests that the food supply is still not safe and highlights the general and pervasive need for additional methods and reagents for testing the food supply to identify contamination.

Another example is bovine mastitis, an infection caused by bacterial cells that results in the inflammation of the bovine breast, reduction in milk yield and a decrease in milk quality. This condition is caused by the bacteria *Staphylococcus aureus* and *Staphylococcus agalactiae*. This reduction in milk yields and quality in the western world alone have been suggested to cause annual financial losses of $3.7 billion.

Another example is bovine tuberculosis (*Mycobacterium bovis*), a bacteria that causes financial loses worldwide. In 2005, for example, 12 of a herd of 55 cattle in a small Michigan farm tested positive for bovine tuberculosis. The farm was forced to destroy the entire herd of cattle, along with an entire herd of hogs. Tuberculosis testing in cattle requires the animal to be held for 2 days, and tests are false positive 5 percent of the time. Often entire herds have to be quarantined or destroyed. The annual worldwide financial losses have been estimated at $3 billion.

Tuberculosis is a leading cause of death worldwide. One third of the world's population is infected with *Mycobacterium tuberculosis*, the bacterium that causes tuberculosis. Every day 25,000 people are infected and 5,000 people die from the disease. Furthermore, due primarily to poor diagnosis, multidrug resistant strains of *M. tuberculosis* are emerging and the reemergence of tuberculosis as a worldwide epidemic has become a real threat. The worldwide annual market for tuberculosis diagnostics has been estimated at $1.8 billion.

MRSA is a drug-resistant version of the common *Staphylococcus aureus* bacteria and is carried by 2.5 million people in the US. A carrier can be a healthy individual, and still be highly contagious, due to the nature of the MRSA bacterium. The bacteria are highly contagious and spread by touch. Approximately 86% of all infections occur within hospitals, and these infections carry a 20% mortality rate. This bacterium costs an average of $21,000 over the standard costs to treat, and kills approximately 19,000 people in the US annually.

*Listeria monocytogenes* is an intracellular pathogen that can cause invasive disease in humans and animals. Approximately 99% of human listeriosis infections appear to be food borne. While *L. monocytogenes* has been isolated from a variety of raw and ready-to-eat foods, most human listeriosis infections appear to be caused by consumption of RTE foods that permit postcontamination growth of this pathogen. Listeriosis is estimated to be responsible for about 500 deaths per year in the United States, accounting for 28% of annual deaths attributable to known food-borne patho-gens, second only to deaths due to *Salmonella* infections.

Methods and systems exist for detecting microbial contamination. Such methods and systems suffer from a number of drawbacks, including the need in most cases to remove a potentially contaminated sample from the environment where it is collected and transferring it to a laboratory environment, where the sample is placed in a culture environment for enrichment and growth over a long period of time, ranging from many hours to days. Additionally, because these labs are frequently offsite there is often a delay in the shipping of a sample to a laboratory. Once enriched, samples are typically analyzed using expensive equipment, traditional culturing methods, PCR and other methods. Thus, current processes often comprise a large time lag between sampling and a result, during which time the sampled conditions may have changed and the results of the assay cannot be utilized to diagnose an infection in a patient or to act on contamination in a lot of manufactured food, for example. Accordingly, new testing methods and reagents would be useful.

Phage are viruses that have evolved in nature to use bacteria and archaea as a means of replicating themselves. A phage does this by attaching itself to a host microbe and injecting its genetic material into that host, inducing it to replicate the phage from tens to thousands of times. Some phage, called lytic phage, rupture the host microbe thereby releasing the progeny phage into the environment to seek out other microbes. The total phage replication time for infection of a microbe by parent phage, phage multiplication (amplification) in the microbe to produce progeny phage, and release of the progeny phage after lysis can take as little as a few minutes depending on the phage, the microbe, and the environmental conditions.

Methods of using phage to indicate the presence of bacteria that the phage infects have been described. In these methods, samples containing a bacteria are incubated with phage specific for that bacteria. The phage infect and replicate in the bacteria, resulting in production of a measurable signal. Some methods utilize the detection of progeny phage released from infected bacteria as a means of detection and identification. In such methods, progeny phage are not produced if the parent phage do not successfully infect the bacteria. Still other methods rely on the detection of a phage gene product rather than whole progeny phage. For example, a luciferase reporter phage that produces luciferase when it successfully infects host bacteria has been described. The luciferase then produces light that, if detected, indicates the presence of host bacteria in the sample. Other methods rely on the detection of bacterial debris that is released following a successful lytic infection of host bacteria by a specific bacteriophage. Despite the suggestion that methods of detecting heterologous gene products encoded by engineered phage can be used in bacteria diagnostics, that technology has yet to be employed in a non-laboratory setting to detect bacterial contamination.

The ability to identify and track bacterial contamination at both the species and subspecies has become increasingly important as a means to track outbreak strains and gather epidemiological data about contamination within food processing plants and finished goods, among many other settings. Identification of bacterial strains at the species level is based mainly on biochemical evidence. Subspecies determination is more poorly defined and no consensus method for determination exists. While there are multiple methods for subspecies determination, four methods are commonly used: serotyping, phage-typing, pulse-field gel electrophoresis, and ribotyping. These four methods all suffer from limitations, and though each system can classify a specific strain within a subgroup this classification does not necessarily ensure that all members of the subgroup share characteristics among the constituent members.

The specificity and sensitivity of a phage-based method of bacterial detection is determined in part by the host range of the engineered bacteriophage. The usefulness of a phage-based bacterial detection system depends on several factors including the existence of a defined host range of the phage used in the method. This disclosure meets these and other needs by providing engineered phage with defined host ranges that define sets of target microbes. This disclosure also provides sets of engineered phage that together define a host range of target microbes. The engineered phage and sets of phage are useful, for example, in methods of detecting target microbes. These and other aspects of this disclosure are provided.

SUMMARY

In a first aspect, this disclosure provides methods of detecting target microbes. The microbe may be an archaea or a bacteria.

In certain embodiments the methods comprise providing a sample; exposing the sample to a first type of phage capable of infecting a first set of target bacteria and comprising a heterologous nucleic acid sequence encoding a first marker; exposing the sample to a second type of phage capable of infecting a second set of target bacteria and comprising a heterologous nucleic acid sequence encoding a second marker; and assaying for the presence of the first marker and the second marker in the exposed sample. In some embodiments, detection of the first marker in the sample indicates the presence of bacteria of the first set of target bacteria in the sample. In some embodiments, detection of the second marker in the sample indicates the presence of bacteria of the second set of target bacteria in the sample. In some embodiments the first marker and the second marker are the same, and detection of the marker in the sample indicates the presence of bacteria of at least one of the first set of target bacteria and the second set of target bacteria in the sample.

In some embodiments, the first set of target bacteria and the second set of target bacteria independently comprise at least two species of a single genus of bacteria. In some embodiments, the first set of target bacteria and the second set of target bacteria independently comprise at least three species of a single genus of bacteria. In some embodiments, the first set of target bacteria and the second set of target bacteria independently comprise at least four species of a single genus of bacteria. In some embodiments, the single genus of bacteria is *Listeria*. In some embodiments, the first set of target bacteria and the second set of target bacteria comprise at least one species of bacteria in common. In some embodiments, the first set of target bacteria and the second set of target bacteria comprise at least two species of bacteria in common. In some embodiments, the first set of target bacteria and the second set of target bacteria comprise at least three species of bacteria in common. In some embodiments, the first set of target bacteria and the second set of target bacteria comprise at least four species of bacteria in common. In some embodiments, the species of *Listeria* are selected from *Listeria innocua, Listeria monocytogenes, Listeria seeligeri, Listeria ivanovii, Listeria grayi, Listeria marthii, Listeria rocourti* and *Listeria welshimeri*. In some embodiments, the species of *Listeria* are selected from *Listeria innocua, Listeria monocytogenes, Listeria seeligeri*, and *Listeria welshimeri*.

In some embodiments, the target bacteria comprise at least one sig B allelotype of *Listeria innocua* selected from 11, 22, 37, and 56. In some embodiments, the target bacteria comprise at least four allelotypes of *Listeria innocua*. In some embodiments, the at least four allelotypes of *Listeria innocua* are 11, 22, 37, and 56.

In some embodiments, the target bacteria comprise at least one ribotype of *Listeria monocytogenes* selected from DUP-10142, DUP-1030A, DUP-1030B, DUP-1038B, DUP-1039A, DUP-1039B, DUP-1039C, DUP-1042A, DUP-1042B, DUP-1042C, DUP-1043A, DUP-1044A, DUP-1044B, DUP-1044E, DUP-1045B, DUP-1052A, DUP-1053A, DUP-1062A, and DUP-1062D. In some embodiments, the target bacteria comprise at least nineteen ribotypes of *Listeria monocytogenes*. In some embodiments, the at least nineteen ribotypes of *Listeria monocytogenes* are DUP-10142, DUP-1030A, DUP-1030B, DUP-1038B, DUP-1039A, DUP-1039B, DUP-1039C, DUP-1042A, DUP-1042B, DUP-1042C, DUP-1043A, DUP-1044A, DUP-1044B, DUP-1044E, DUP-1045B, DUP-1052A, DUP-1053A, DUP-1062A, and DUP-1062D.

In some embodiments, the target bacteria comprise at least one sig B allelotype of *Listeria seeligeri* selected from 3, 20, 24, and 35. In some embodiments, the target bacteria comprise at least four allelotypes of *Listeria seeligeri*. In some embodiments, the at least four allelotypes of *Listeria seeligeri* are 3, 20, 24, and 35.

In some embodiments, the target bacteria comprise at least one sig B allelotype of *Listeria welshimeri* selected from 15, 27, 32, and 89. In some embodiments, the target bacteria comprise at least four allelotypes of *Listeria welshimeri*. In some embodiments, the at least four allelotypes of *Listeria welshimeri* are 15, 27, 32, and 89.

In some embodiments, the first set of target bacteria are all members of the same genus. In some embodiments, the second set of target bacteria are all members of the same genus. In some embodiments the target bacteria comprise members of more than one genus. In some embodiments, all of the target bacteria are *Listeria*. In some embodiments, the target bacteria do not include at least one of *Bacillus cereus, Bacillus megaterium, Bacillus subtilis, Enterococcus durans, Enterococcus faceium, Enterococcus hirae, Kocuria varians, Kurthia gibsonii, Kurthia zopfii, Rhodococcus equi, Staphylococcus aureus, Staphylococcus epidermidis, Staphylococ-* cus saprophyticus, Streptococcus equi, Streptococcus galloyticus, Lactobacillus casei, Lactobacillus buchneri, Lactobacillus lactus, Lactobacillus fermentum, Micrococcus lutues, Pseudomonas protogens, Pseudomonas florescens, Aeromonas sp, Serratia liquefaciens, Serratia proteamaculans, Serratia liquefaciens, Bacillaceae bacterium, Serratia proteamaculans, Pseudomonas florescens, Pseudomonas poae, Pseudomonas sp, Pseudomonas fragi, Providencia alcalifaciens, Serratia sp, Serratia grimesii, Hafnia sp., Serratia proteamaculans, Pseudomonas florescens, Chryseobacterium sp., Pseudomonas fragi, and Enterobacteriaceae. In some embodiments, the target bacteria do not include Bacillus cereus, Bacillus megaterium, Bacillus subtilis, Enterococcus durans, Enterococcus faceium, Enterococcus hirae, Kocuria varians, Kurthia gibsonii, Kurthia zopfii, Rhodococcus equi, Staphylococcus aureus, Staphylococcus epidermidis, Staphylococcus saprophyticus, Streptococcus equi, Streptococcus galloyticus, Lactobacillus casei, Lactobacillus buchneri, Lactobacillus lactus, Lactobacillus fermentum, Micrococcus lutues, Pseudomonas protogens, Pseudomonas florescens, Aeromonas sp, Serratia liquefaciens, Serratia proteamaculans, Serratia liquefaciens, Bacillaceae bacterium, Serratia proteamaculans, Pseudomonas florescens, Pseudomonas poae, Pseudomonas sp, Pseudomonas fragi, Providencia alcalifaciens, Serratia sp, Serratia grimesii, Hafnia sp., Serratia proteamaculans, Pseudomonas florescens, Chryseobacterium sp., Pseudomonas fragi, and Enterobacteriaceae.

In some embodiments, the methods further comprise exposing the sample to a third type of phage capable of infecting a third set of target bacteria and comprising a heterologous nucleic acid sequence encoding a third marker. In some embodiments, the methods further comprise exposing the sample to a fourth type of phage capable of infecting a fourth set of target bacteria and comprising a heterologous nucleic acid sequence encoding a fourth marker. In some embodiments, the methods further comprise exposing the sample to a fifth type of phage capable of infecting a fifth set of target bacteria and comprising a heterologous nucleic acid sequence encoding a fifth marker. In some embodiments, the methods further comprise exposing the sample to a sixth type of phage capable of infecting a sixth set of target bacteria and comprising a heterologous nucleic acid sequence encoding a sixth marker. In some embodiments, the methods further comprise exposing the sample to a seventh type of phage capable of infecting a seventh set of target bacteria and comprising a heterologous nucleic acid sequence encoding a seventh marker. In some embodiments, the methods further comprise exposing the sample to a eighth type of phage capable of infecting a eighth set of target bacteria and comprising a heterologous nucleic acid sequence encoding a eighth marker. In some embodiments, the methods further comprise exposing the sample to a ninth type of phage capable of infecting a ninth set of target bacteria and comprising a heterologous nucleic acid sequence encoding a ninth marker. In some embodiments, the methods further comprise exposing the sample to ten or more types of phage capable of infecting ten or more sets of target bacteria and comprising a heterologous nucleic acid sequences encoding ten or more markers. In some embodiments that utilize three or more types of phage, all of the three or more markers are different. In some embodiments that utilize three or more types of phage, all of the three or more markers are the same. In some embodiments that utilize three or more types of phage, two, three, four, five, six, seven, eight, or nine of the markers are the same.

In some embodiments, at least one type of phage used in the method is selected from A511, P100, LP40, LP44, LP48, LP99, LP101, LP124, LP125, and LP143, and derivatives thereof. In some embodiments, every type of phage used in the method is selected from A511, P100, LP40, LP44, LP48, LP99, LP101, LP124, LP125, and LP143, and derivatives thereof.

In some embodiments, the first marker is a screenable marker. In some embodiments, the first marker is a luciferase. In some embodiments, the luciferase is at least 70% identical to SEQ ID NO: 2. In some embodiments, the luciferase is at least 70% identical to SEQ ID NO: 4.

In some embodiments, the first type of phage is selected from LP48::ffluc, LP99::ffluc, LP101::ffluc, LP124::ffluc, LP125::ffluc, LP143::ffluc, A511::ffluc, and P100::ffluc, and derivatives of those phage. In some embodiments, the first type of phage is selected from LP40:nluc, LP124::nluc, LP125::nluc, A511::nluc, and P100::nluc.

In some embodiments, the second marker is a screenable marker. In some embodiments, the second marker is a luciferase. In some embodiments, the luciferase is at least 70% identical to SEQ ID NO: 2. In some embodiments, the luciferase is at least 70% identical to SEQ ID NO: 4.

In some embodiments, the second type of phage is selected from LP48::ffluc, LP99::ffluc, LP101::ffluc, LP124::ffluc, LP125::ffluc, LP143::ffluc, A511::ffluc, and P100::ffluc. In some embodiments, the second type of phage is selected from LP40:nluc, LP124::nluc, LP125::nluc, A511::nluc, and P100::nluc.

In some embodiments the method comprises contacting the sample with A511::nluc, P100::nluc, and LP124::nluc. In some embodiments the method comprises contacting the sample with A511::nluc and LP124::nluc. In some embodiments the method comprises contacting the sample with A511::nluc, LP40::nluc, and LP124::nluc.

In some embodiments, the method comprises exposing the sample to the first type of phage and the second type of phage at the same time.

In some embodiments, the sample is an environmental sample.

In some embodiments, the first marker is detected in the sample, indicating the presence of bacteria of the first set of target bacteria in the sample. In some embodiments, the second marker is detected in the sample, indicating the presence of bacteria of the second set of target bacteria in the sample. In some embodiments, the first marker and the second marker are the same, and the marker is detected in the sample, indicating the presence of bacteria of at least one of the first set of target bacteria and the second set of target bacteria in the sample.

In some embodiments, the false positive rate of the assay against environmental samples is 5% or less, 4% or less, 3% or less, 2% or less, or 1% or less. In some embodiments, the false negative rate of the assay against environmental samples is 5% or less, 4% or less, 3% or less, 2% or less, or 1% or less.

In some embodiments, the sample is exposed to metabolic stimulation conditions before it is exposed to the phage.

In some embodiments, the methods further comprise incubating the sample under metabolic stimulation conditions for a period of time before exposing the sample to the phage capable of infecting target bacteria.

In certain embodiments the methods comprise providing a sample; exposing the sample to at least one recombinant Listeria phage comprising a heterologous nucleic acid sequence encoding a marker, the recombinant Listeria phage selected from recombinant LP40 and derivatives thereof, recombinant LP48 and derivatives thereof, recombinant LP99 and derivatives thereof, recombinant LP101 and derivatives thereof, recombinant LP124 and derivatives thereof, recombinant LP125 and derivatives thereof, and recombinant LP143 and derivatives thereof; and assaying for the presence of the marker in the exposed sample. In some embodiments, the methods further comprise exposing the sample to at least one recombinant *Listeria* phage comprising a heterologous nucleic acid sequence encoding a marker, the recombinant *Listeria* phage selected from recombinant A511 and recombinant P100. In some embodiments, detection of the marker in the sample indicates the presence of *Listeria* in the sample.

In some embodiments, target bacteria of the recombinant *Listeria* phage comprise at least one species of *Listeria* selected from *Listeria innocua*, *Listeria monocytogenes*, *Listeria seeligeri*, *Listeria ivanovii*, *Listeria grayi*, *Listeria marthii*, *Listeria rocourti*, and *Listeria welshimeri*. In some embodiments, detection of the marker in the sample indicates the presence of the at least one species of *Listeria* selected from *Listeria innocua*, *Listeria monocytogenes*, *Listeria seeligeri*, *Listeria ivanovii*, *Listeria grayi*, *Listeria marthii*, *Listeria rocourti*, and *Listeria welshimeri* in the sample.

In some embodiments, target bacteria of the *Listeria* phage comprise at least one species of *Listeria* selected from *Listeria innocua*, *Listeria monocytogenes*, *Listeria seeligeri*, and *Listeria welshimeri*. In some embodiments, detection of the marker in the sample indicates the presence of the at least one species of *Listeria* selected from *Listeria innocua*, *Listeria monocytogenes*, *Listeria seeligeri*, and *Listeria welshimeri* in the sample.

In some embodiments, target bacteria of the *Listeria* phage comprise at least one sig B allelotype of *Listeria innocua* selected from 11, 22, 37, and 56, and detection of the marker in the sample indicates the presence of at least one sig B allelotype of *Listeria innocua* selected from 11, 22, 37, and 56. In some embodiments, the at least one *Listeria* phage is capable of infecting *Listeria innocua* sig B allelotypes 11, 22, 37, and 56.

In some embodiments, target bacteria of the *Listeria* phage comprise at least one ribotype of *Listeria monocytogenes* selected from DUP-10142, DUP-1030A, DUP-1030B, DUP-1038B, DUP-1039A, DUP-1039B, DUP-1039C, DUP-1042A, DUP-1042B, DUP-1042C, DUP-1043A, DUP-1044A, DUP-1044B, DUP-1044E, DUP-1045B, DUP-1052A, DUP-1053A, DUP-1062A, and DUP-1062D; and detection of the marker in the sample indicates the presence of at least one ribotype of *Listeria monocytogenes* selected from DUP-10142, DUP-1030A, DUP-1030B, DUP-1038B, DUP-1039A, DUP-1039B, DUP-1039C, DUP-1042A, DUP-1042B, DUP-1042C, DUP-1043A, DUP-1044A, DUP-1044B, DUP-1044E, DUP-1045B, DUP-1052A, DUP-1053A, DUP-1062A, and DUP-1062D. In some embodiments, target bacteria of the *Listeria* phage comprise *Listeria monocytogenes* ribotypes DUP-10142, DUP-1030A, DUP-1030B, DUP-1038B, DUP-1039A, DUP-1039B, DUP-1039C, DUP-1042A, DUP-1042B, DUP-1042C, DUP-1043A, DUP-1044A, DUP-1044B, DUP-1044E, DUP-1045B, DUP-1052A, DUP-1053A, DUP-1062A, and DUP-1062D.

In some embodiments, target bacteria of the *Listeria* phage comprise at least one sig B allelotype of *Listeria seeligeri* selected from 3, 20, 24, and 35, and detection of the marker in the sample indicates the presence of at least one sig B allelotype of *Listeria seeligeri* selected from 3, 20, 24, and 35. In some embodiments, target bacteria of the *Listeria* phage comprise *Listeria seeligeri* sig B allelotypes 3, 20, 24, and 35.

In some embodiments, target bacteria of the *Listeria* phage comprise at least one sig B allelotype of *Listeria welshimeri* selected from 15, 27, 32, and 89, and detection of the marker in the sample indicates the presence of at least one sig B allelotype of *Listeria welshimeri* selected from 15, 27, 32, and 89. In some embodiments, target bacteria of the *Listeria* phage comprise *Listeria welshimeri* sig B allelotypes 15, 27, 32, and 89.

In some embodiments, the target bacteria comprise at least two species of *Listeria* selected from *Listeria innocua*, *Listeria monocytogenes*, *Listeria seeligeri*, and *Listeria* welshimeri. In some embodiments, the target bacteria comprise at least three species of *Listeria* selected from *Listeria innocua*, *Listeria monocytogenes*, *Listeria seeligeri*, and *Listeria* welshimeri. In some embodiments, the target bacteria comprise at least four species of *Listeria* selected from *Listeria innocua*, *Listeria monocytogenes*, *Listeria seeligeri*, *Listeria ivanovii*, *Listeria grayi*, *Listeria marthii*, *Listeria rocourti*, and *Listeria welshimeri*. In some embodiments, the target bacteria do not include at least one of *Bacillus cereus*, *Bacillus megaterium*, *Bacillus subtilis*, *Enterococcus durans*, *Enterococcus faceium*, *Enterococcus hirae*, *Kocuria varians*, *Kurthia gibsonii*, *Kurthia zopfii*, *Rhodococcus equi*, *Staphylococcus aureus*, *Staphylococcus epidermidis*, *Staphylococcus saprophyticus*, *Streptococcus equi*, *Streptococcus galloyticus*, *Lactobacillus casei*, *Lactobacillus buchneri*, *Lactobacillus lactus*, *Lactobacillus fermentum*, *Micrococcus lutues*, *Pseudomonas protogens*, *Pseudomonas florescens*, *Aeromonas* sp, *Serratia liquefaciens*, *Serratia proteamaculans*, *Serratia liquefaciens*, Bacillaceae bacterium, *Serratia proteamaculans*, *Pseudomonas florescens*, *Pseudomonas poae*, *Pseudomonas* sp, *Pseudomonas fragi*, *Providencia alcalifaciens*, *Serratia* sp, *Serratia grimesii*, *Hafnia* sp., *Serratia proteamaculans*, *Pseudomonas florescens*, *Chryseobacterium* sp., *Pseudomonas fragi*, and Enterobacteriaceae. In some embodiments, the target bacteria do not include *Bacillus cereus*, *Bacillus megaterium*, *Bacillus subtilis*, *Enterococcus durans*, *Enterococcus faceium*, *Enterococcus hirae*, *Kocuria varians*, *Kurthia gibsonii*, *Kurthia zopfii*, *Rhodococcus equi*, *Staphylococcus aureus*, *Staphylococcus epidermidis*, *Staphylococcus saprophyticus*, *Streptococcus equi*, *Streptococcus galloyticus*, *Lactobacillus casei*, *Lactobacillus buchneri*, *Lactobacillus lactus*, *Lactobacillus fermentum*, *Micrococcus lutues*, *Pseudomonas protogens*, *Pseudomonas florescens*, *Aeromonas* sp, *Serratia liquefaciens*, *Serratia proteamaculans*, *Serratia liquefaciens*, Bacillaceae bacterium, *Serratia proteamaculans*, *Pseudomonas florescens*, *Pseudomonas poae*, *Pseudomonas* sp, *Pseudomonas fragi*, *Providencia alcalifaciens*, *Serratia* sp, *Serratia grimesii*, *Hafnia* sp., *Serratia proteamaculans*, *Pseudomonas florescens*, *Chryseobacterium* sp., *Pseudomonas fragi*, and Enterobacteriaceae. In some embodiments, all of the target bacteria are *Listeria*.

In some embodiments, the marker is a screenable marker. In some embodiments, the marker is a luciferase. In some embodiments, the luciferase is at least 70% identical to SEQ ID NO: 2. In some embodiments, the luciferase is at least 70% identical to SEQ ID NO: 4. In some embodiments, the phage is selected from LP48::ffluc, LP99::ffluc, LP101::ffluc, LP124::ffluc, LP125::ffluc, LP143::ffluc, A511::ffluc, and P100::ffluc. In some embodiments, the phage is selected from LP40::nluc, LP124::nluc, LP125::nluc, A511::nluc, and P100::nluc.

In some embodiments, the sample is an environmental sample.

In some embodiments, the marker is detected in the sample, indicating the presence of bacteria of the first set of target bacteria in the sample.

In some embodiments, the false positive rate of the assay against environmental samples is 5% or less, 4% or less, 3% or less, 2% or less, or 1% or less. In some embodiments, the false negative rate of the assay against environmental samples is 5% or less, 4% or less, 3% or less, 2% or less, or 1% or less. In some embodiments, the sample is exposed to metabolic stimulation conditions before the sample is exposed to the phage.

In another aspect, this disclosure provides recombinant *Listeria* phage comprising a heterologous nucleic acid sequence encoding a marker. In some embodiments, the recombinant *Listeria* phage is selected from recombinant LP40 and derivatives thereof, recombinant LP48 and derivatives thereof, recombinant LP99 and derivatives thereof, recombinant LP101 and derivatives thereof, recombinant LP124 and derivatives thereof, recombinant LP125 and derivatives thereof, and recombinant LP143 and derivatives thereof. In some embodiments, target bacteria of the recombinant *Listeria* phage comprise at least one species of *Listeria* selected from *Listeria innocua, Listeria monocytogenes, Listeria seeligeri, Listeria ivanovii, Listeria grayi, Listeria marthii, Listeria rocourti*, and *Listeria welshimeri*. In some embodiments, target bacteria of the recombinant *Listeria* phage comprise at least one species of *Listeria* selected from *Listeria innocua, Listeria monocytogenes, Listeria seeligeri*, and *Listeria welshimeri*.

In some embodiments, target bacteria of the *Listeria* phage comprise at least one sig B allelotype of *Listeria innocua* selected from 11, 22, 37, and 56 and producing the marker. In some embodiments, target bacteria of the *Listeria* phage comprise *Listeria innocua* sig B allelotypes 11, 22, 37, and 56.

In some embodiments, target bacteria of the *Listeria* phage comprise at least one ribotype of *Listeria monocytogenes* selected from DUP-10142, DUP-1030A, DUP-1030B, DUP-1038B, DUP-1039A, DUP-1039B, DUP-1039C, DUP-1042A, DUP-1042B, DUP-1042C, DUP-1043A, DUP-1044A, DUP-1044B, DUP-1044E, DUP-1045B, DUP-1052A, DUP-1053A, DUP-1062A, and DUP-1062D. In some embodiments, target bacteria of the *Listeria* phage comprise *Listeria monocytogenes* ribotypes DUP-10142, DUP-1030A, DUP-1030B, DUP-1038B, DUP-1039A, DUP-1039B, DUP-1039C, DUP-1042A, DUP-1042B, DUP-1042C, DUP-1043A, DUP-1044A, DUP-1044B, DUP-1044E, DUP-1045B, DUP-1052A, DUP-1053A, DUP-1062A, and DUP-1062D.

In some embodiments, target bacteria of the *Listeria* phage comprise at least one sig B allelotype of *Listeria seeligeri* selected from 3, 20, 24, and 35. In some embodiments, target bacteria of the *Listeria* phage comprise *Listeria seeligeri* sig B allelotypes 3, 20, 24, and 35.

In some embodiments, target bacteria of the *Listeria* phage comprise at least one sig B allelotype of *Listeria welshimeri* selected from 15, 27, 32, and 89. In some embodiments, target bacteria of the *Listeria* phage comprise *Listeria welshimeri* sig B allelotypes 15, 27, 32, and 89.

In some embodiments, target bacteria of the *Listeria* phage comprise at least two species of *Listeria* selected from *Listeria innocua, Listeria monocytogenes, Listeria seeligeri, Listeria ivanovii, Listeria grayi, Listeria marthii, Listeria rocourti*, and *Listeria welshimeri*. In some embodiments, target bacteria of the *Listeria* phage comprise at least three species of *Listeria* selected from *Listeria innocua, Listeria monocytogenes, Listeria seeligeri, Listeria ivanovii, Listeria grayi, Listeria marthii, Listeria rocourti*, and *Listeria welshimeri*. In some embodiments, target bacteria of the *Listeria* phage comprise *Listeria innocua, Listeria monocytogenes, Listeria seeligeri, Listeria ivanovii, Listeria grayi, Listeria marthii, Listeria rocourti*, and *Listeria welshimeri*. In some embodiments, the target bacteria do not include at least one of *Bacillus cereus, Bacillus megaterium, Bacillus subtilis, Enterococcus durans, Enterococcus faceium, Enterococcus hirae, Kocuria varians, Kurthia gibsonii, Kurthia zopfii, Rhodococcus equi, Staphylococcus aureus, Staphylococcus epidermidis, Staphylococcus saprophyticus, Streptococcus equi, Streptococcus galloyticus, Lactobacillus casei, Lactobacillus buchneri, Lactobacillus lactus, Lactobacillus fermentum, Micrococcus lutues, Pseudomonas protogens, Pseudomonas florescens, Aeromonas* sp, *Serratia liquefaciens, Serratia proteamaculans, Serratia liquefaciens*, Bacillaceae bacterium, *Serratia proteamaculans, Pseudomonas florescens, Pseudomonas poae, Pseudomonas* sp, *Pseudomonas fragi, Providencia alcalifaciens, Serratia* sp, *Serratia grimesii, Hafnia* sp., *Serratia proteamaculans, Pseudomonas florescens, Chryseobacterium* sp., *Pseudomonas fragi*, and Enterobacteriaceae. In some embodiments, the target bacteria do not include *Bacillus cereus, Bacillus megaterium, Bacillus subtilis, Enterococcus durans, Enterococcus faceium, Enterococcus hirae, Kocuria varians, Kurthia gibsonii, Kurthia zopfii, Rhodococcus equi, Staphylococcus aureus, Staphylococcus epidermidis, Staphylococcus saprophyticus, Streptococcus equi, Streptococcus galloyticus, Lactobacillus casei, Lactobacillus buchneri, Lactobacillus lactus, Lactobacillus fermentum, Micrococcus lutues, Pseudomonas protogens, Pseudomonas florescens, Aeromonas* sp, *Serratia liquefaciens, Serratia proteamaculans, Serratia liquefaciens*, Bacillaceae bacterium, *Serratia proteamaculans, Pseudomonas florescens, Pseudomonas poae, Pseudomonas* sp, *Pseudomonas fragi, Providencia alcalifaciens, Serratia* sp, *Serratia grimesii, Hafnia* sp., *Serratia proteamaculans, Pseudomonas florescens, Chryseobacterium* sp., *Pseudomonas fragi*, and Enterobacteriaceae. In some embodiments, all of the target bacteria of the *Listeria* phage are *Listeria*.

In some embodiments, the marker is a screenable marker. In some embodiments, the marker is a luciferase. In some embodiments, the luciferase is at least 70% identical to SEQ ID NO: 2. In some embodiments, the luciferase is at least 70% identical to SEQ ID NO: 4.

In some embodiments, the phage is selected from LP48:: ffluc, LP99::ffluc, LP101::ffluc, LP124::ffluc, LP125::ffluc, and LP143::ffluc. In some embodiments, the phage is selected from LP124::nluc and LP125::nluc.

In some embodiments the recombinant *Listeria* phage comprises a heterologous nucleic acid sequence encoding a luciferase that is at least 70% identical to SEQ ID NO: 2; and the recombinant *Listeria* phage is selected from recombinant A511 and derivatives thereof, recombinant P100 and derivatives thereof, recombinant LP40 and derivatives thereof, recombinant LP48 and derivatives thereof, recombinant LP99 and derivatives thereof, recombinant LP101 and derivatives thereof, recombinant LP124 and derivatives thereof, recombinant LP125 and derivatives thereof, and recombinant LP143 and derivatives thereof. In some embodiments, the recombinant *Listeria* phage is selected from LP48::ffluc, LP99::ffluc, LP101::ffluc, LP124::ffluc, LP125::ffluc, LP143::ffluc, A511::ffluc, and P100::ffluc.

In some embodiments the recombinant *Listeria* phage comprises a heterologous nucleic acid sequence encoding a luciferase at least 70% identical to SEQ ID NO: 4; and the recombinant *Listeria* phage is selected from recombinant A511 and derivatives thereof, recombinant P100 and derivatives thereof, recombinant LP40 and derivatives thereof, recombinant LP48 and derivatives thereof, recombinant LP99 and derivatives thereof, recombinant LP101 and derivatives thereof, recombinant LP124 and derivatives thereof, recombinant LP125 and derivatives thereof, and recombinant LP143 and derivatives thereof. In some embodiments, the recombinant *Listeria* phage is selected from LP124::nluc, LP125::nluc, A511::nluc, and P100::nluc.

In some embodiments, the recombinant *Listeria* phage detects target bacteria in environmental samples with a false positive rate of 5% or less, 4% or less, 3% or less, 2% or less, or 1% or less. In some embodiments, the recombinant *Listeria* phage detects target bacteria in environmental samples with a false negative rate of 5% or less, 4% or less, 3% or less, 2% or less, or 1% or less.

In another aspect, this disclosure provides compositions comprising recombinant *Listeria* phage. In some embodiments the composition comprises: at least one recombinant *Listeria* phage comprising a heterologous nucleic acid sequence encoding a marker, the recombinant *Listeria* phage selected from recombinant LP40 and derivatives thereof, recombinant LP48 and derivatives thereof, recombinant LP99 and derivatives thereof, recombinant LP101 and derivatives thereof, recombinant LP124 and derivatives thereof, recombinant LP125 and derivatives thereof, and recombinant LP143 and derivatives thereof; and at least one non-phage component selected from at least one of a) at least one compound selected from carbohydrates and related compounds, b) at least compound selected from nitrogen containing compounds, c) at least compound selected from nucleic acids and related compounds, d) at least compound selected from lipid, e) at least one inorganic compound, and f) at least one organic compound. In some embodiments, the composition comprises at least one of 1,2-Propanediol, 2-Aminoethanol, Glucuronamide, Tyramine, b-Phenylethylamine, L-Aspartic Acid, L-Proline, D-Alanine, D-Serine, L-Glutamic Acid, L-Asparagine, D-Aspartic Acid, L-Glutamine, Gly-Asp, D-Threonine, Gly-Glu, L-Serine, L-Threonine, L-Alanine, Ala-Gly, Gly-Pro, L-Arabinose, N-Acetyl-D-Glucosamine, D-Galactose, D-Trehalose, D-Mannose, Dulcitol, D-Sorbitol, Glycerol, L-Fucose, D,L-a-Glycerol, Phosphate, D-Xylose, D-Mannitol, D-Glucose-6-Phosphate, D-Ribose, L-Rhamnose, D-Fructose, a-D-Glucose, Maltose, D-Melibiose, Thymidine, a-Methyl-D-Galactoside, a-D-Lactose, Lactulosem Sucrose, Uridine, D-Glucose-1-Phosphate, D-Fructose-6-Phosphate, b-Methyl-D-Glucoside, Adonitol, Maltotriose, 2'-Deoxyadenosine, Adenosine, m-Inositol, D-Cellobiose, Inosine, N-Acetyl-D-Mannosamine, D-Psicose, L-Lyxose, D-Saccharic Acid, Succinic Acid, D-Glucuronic Acid, D-Gluconic Acid, D,L-Lactic Acid, Formic Acid, D-Galactonic Acid-g-Lactone, D,L-Malic Acid, Acetic Acid, D-Glucosaminic Acid, a-Ketoglutaric Acid, a-Ketobutyric Acid, m-Tartaric Acid, a-Hydroxyglutaric Acid-g-Lactone, a-Hydroxybutyric Acid, Citric Acid, Fumaric Acid, Bromosuccinic Acid, Propionic Acid, Mucic Acid, Glycolic Acid, Glyoxylic Acid, Tricarballylic Acid, Acetoacetic Acid, Mono-Methylsuccinate, D-Malic Acid, L-Malic Acid, p-Hydroxyphenyl Acetic Acid, m-Hydroxyphenyl Acetic Acid, Pyruvic Acid, L-Galactonic Acid-g-Lactone, D-Galacturonic Acid, Methylpyruvate, Tween 20, Tween 40, Tween 80. In some embodiments the composition comprises A511::nluc, P100::nluc, and LP124::nluc. In some embodiments the composition comprises A511::nluc and LP124::nluc. In some embodiments the composition comprises A511::nluc, LP40::nluc, and LP124::nluc.

In some embodiments the composition comprises: at least two recombinant *Listeria* phage comprising a heterologous nucleic acid sequence encoding a marker, the recombinant *Listeria* phage selected from recombinant A511 and derivatives thereof, recombinant P100 and derivatives thereof, recombinant LP40 and derivatives thereof, recombinant LP48 and derivatives thereof, recombinant LP99 and derivatives thereof, recombinant LP101 and derivatives thereof, recombinant LP124 and derivatives thereof, recombinant LP125 and derivatives thereof, and recombinant LP143 and derivatives thereof. In some embodiments the composition further comprises at least one non-phage component selected from at least one of a) at least one compound selected from carbohydrates and related compounds, b) at least compound selected from nitrogen containing compounds, c) at least compound selected from nucleic acids and related compounds, d) at least compound selected from lipid, e) at least one inorganic compound, and f) at least one organic compound. In some embodiments the composition comprises at least one of 1,2-Propanediol, 2-Aminoethanol, Glucuronamide, Tyramine, b-Phenylethylamine, L-Aspartic Acid, L-Proline, D-Alanine, D-Serine, L-Glutamic Acid, L-Asparagine, D-Aspartic Acid, L-Glutamine, Gly-Asp, D-Threonine, Gly-Glu, L-Serine, L-Threonine, L-Alanine, Ala-Gly, Gly-Pro, L-Arabinose, N-Acetyl-D-Glucosamine, D-Galactose, D-Trehalose, D-Mannose, Dulcitol, D-Sorbitol, Glycerol, L-Fucose, D,L-a-Glycerol, Phosphate, D-Xylose, D-Mannitol, D-Glucose-6-Phosphate, D-Ribose, L-Rhamnose, D-Fructose, a-D-Glucose, Maltose, D-Melibiose, Thymidine, a-Methyl-D-Galactoside, a-D-Lactose, Lactulosem Sucrose, Uridine, D-Glucose-1-Phosphate, D-Fructose-6-Phosphate, b-Methyl-D-Glucoside, Adonitol, Maltotriose, 2'-Deoxyadenosine, Adenosine, m-Inositol, D-Cellobiose, Inosine, N-Acetyl-D-Mannosamine, D-Psicose, L-Lyxose, D-Saccharic Acid, Succinic Acid, D-Glucuronic Acid, D-Gluconic Acid, D,L-Lactic Acid, Formic Acid, D-Galactonic Acid-g-Lactone, D,L-Malic Acid, Acetic Acid, D-Glucosaminic Acid, a-Ketoglutaric Acid, a-Ketobutyric Acid, m-Tartaric Acid, a-Hydroxyglutaric Acid-g-Lactone, a-Hydroxybutyric Acid, Citric Acid, Fumaric Acid, Bromosuccinic Acid, Propionic Acid, Mucic Acid, Glycolic Acid, Glyoxylic Acid, Tricarballylic Acid, Acetoacetic Acid, Mono-Methylsuccinate, D-Malic Acid, L-Malic Acid, p-Hydroxyphenyl Acetic Acid, m-Hydroxyphenyl Acetic Acid, Pyruvic Acid, L-Galactonic Acid-g-Lactone, D-Galacturonic Acid, Methylpyruvate, Tween 20, Tween 40, Tween 80.

In another aspect, this disclosure provides articles of manufacture. In some embodiments the article of manufacture comprises at least one recombinant *Listeria* phage comprising a heterologous nucleic acid sequence encoding a marker, the recombinant *Listeria* phage selected from recombinant LP40 and derivatives thereof, recombinant LP48 and derivatives thereof, recombinant LP99 and derivatives thereof, recombinant LP101 and derivatives thereof, recombinant LP124 and derivatives thereof, recombinant LP125 and derivatives thereof, and recombinant LP143 and derivatives thereof; and a solution comprising at least one non-phage component selected from at least one of a) at least one compound selected from carbohydrates and related compounds, b) at least compound selected from nitrogen containing compounds, c) at least compound selected from nucleic acids and related compounds, d) at least compound selected from lipid, e) at least one inorganic compound, and f) at least one organic compound. In some embodiments, the article of manufacture comprises a container comprising a solution comprising at least one of 1,2-Propanediol, 2-Aminoethanol, Glucuronamide, Tyramine, b-Phenylethylamine, L-Aspartic Acid, L-Proline, D-Alanine, D-Serine, L-Glutamic Acid, L-Asparagine, D-Aspartic Acid, L-Glutamine, Gly-Asp, D-Threonine, Gly-Glu, L-Serine, L-Threonine, L-Alanine, Ala-Gly, Gly-Pro, L-Arabinose, N-Acetyl-D-Glucosamine, D-Galactose, D-Trehalose, D-Mannose, Dulcitol, D-Sorbitol, Glycerol, L-Fucose, D,L-a-Glycerol, Phosphate, D-Xylose, D-Mannitol, D-Glucose-6-Phosphate, D-Ribose, L-Rhamnose, D-Fructose, a-D-Glucose, Maltose, D-Melibiose, Thymidine, a-Methyl-D-Galactoside, a-D-Lactose, Lactulosem Sucrose, Uridine, D-Glucose-1-Phosphate, D-Fructose-6-Phosphate, b-Methyl-D-Glucoside, Adonitol, Maltotriose, 2'-Deoxyadenosine, Adenosine, m-Inositol, D-Cellobiose, Inosine, N-Acetyl-D-Mannosamine, D-Psicose, L-Lyxose, D-Saccharic Acid, Succinic Acid, D-Glucuronic Acid, D-Gluconic Acid, D,L-Lactic Acid, Formic Acid, D-Galactonic Acid-g-Lactone, D,L-Malic Acid, Acetic Acid, D-Glucosaminic Acid, a-Ketoglutaric Acid, a-Ketobutyric Acid, m-Tartaric Acid, a-Hydroxyglutaric Acid-g-Lactone, a-Hydroxybutyric Acid, Citric Acid, Fumaric Acid, Bromosuccinic Acid, Propionic Acid, Mucic Acid, Glycolic Acid, Glyoxylic Acid, Tricarballylic Acid, Acetoacetic Acid, Mono-Methylsuccinate, D-Malic Acid, L-Malic Acid, p-Hydroxyphenyl Acetic Acid, m-Hydroxyphenyl Acetic Acid, Pyruvic Acid, L-Galactonic Acid-g-Lactone, D-Galacturonic Acid, Methylpyruvate, Tween 20, Tween 40, Tween 80. In some embodiments the article of manufacture comprises A511::nluc, P100::nluc, and LP124::nluc. In some embodiments the article of manufacture comprises A511:: nluc and LP124::nluc. In some embodiments the article of manufacture comprises A511::nluc, LP40::nluc, and LP124:: nluc.

In some embodiments the article of manufacture comprises at least two recombinant *Listeria* phage comprising a heterologous nucleic acid sequence encoding a marker, the recombinant *Listeria* phage selected from recombinant A511 and derivatives thereof, recombinant P100 and derivatives thereof, recombinant LP40 and derivatives thereof, recombinant LP48 and derivatives thereof, recombinant LP99 and derivatives thereof, recombinant LP101 and derivatives thereof, recombinant LP124 and derivatives thereof, recombinant LP125 and derivatives thereof, and recombinant LP143 and derivatives thereof; and a solution comprising at least one non-phage component selected from at least one of a) at least one compound selected from carbohydrates and related compounds, b) at least compound selected from nitrogen containing compounds, c) at least compound selected from nucleic acids and related compounds, d) at least compound selected from lipid, e) at least one inorganic compound, and f) at least one organic compound. In some embodiments the article of manufacture comprises a container comprising a solution comprising at least one of 1,2-Propanediol, 2-Aminoethanol, Glucuronamide, Tyramine, b-Phenylethylamine, L-Aspartic Acid, L-Proline, D-Alanine, D-Serine, L-Glutamic Acid, L-Asparagine, D-Aspartic Acid, L-Glutamine, Gly-Asp, D-Threonine, Gly-Glu, L-Serine, L-Threonine, L-Alanine, Ala-Gly, Gly-Pro, L-Arabinose, N-Acetyl-D-Glucosamine, D-Galactose, D-Trehalose, D-Mannose, Dulcitol, D-Sorbitol, Glycerol, L-Fucose, D,L-a-Glycerol, Phosphate, D-Xylose, D-Mannitol, D-Glucose-6-Phosphate, D-Ribose, L-Rhamnose, D-Fructose, a-D-Glucose, Maltose, D-Melibiose, Thymidine, a-Methyl-D-Galactoside, a-D-Lactose, Lactulosem Sucrose, Uridine, D-Glucose-1-Phosphate, D-Fructose-6-Phosphate, b-Methyl-D-Glucoside, Adonitol, Maltotriose, 2'-Deoxyadenosine, Adenosine, m-Inositol, D-Cellobiose, Inosine, N-Acetyl-D-Mannosamine, D-Psicose, L-Lyxose, D-Saccharic Acid, Succinic Acid, D-Glucuronic Acid, D-Gluconic Acid, D,L-Lactic Acid, Formic Acid, D-Galactonic Acid-g-Lactone, D,L-Malic Acid, Acetic Acid, D-Glucosaminic Acid, a-Ketoglutaric Acid, a-Ketobutyric Acid, m-Tartaric Acid, a-Hydroxyglutaric Acid-g-Lactone, a-Hydroxybutyric Acid, Citric Acid, Fumaric Acid, Bromosuccinic Acid, Propionic Acid, Mucic Acid, Glycolic Acid, Glyoxylic Acid, Tricarballylic Acid, Acetoacetic Acid, Mono-Methylsuccinate, D-Malic Acid, L-Malic Acid, p-Hydroxyphenyl Acetic Acid, m-Hydroxyphenyl Acetic Acid, Pyruvic Acid, L-Galactonic Acid-g-Lactone, D-Galacturonic Acid, Methylpyruvate, Tween 20, Tween 40, Tween 80.

In another aspect, this disclosure provides methods of identifying target microbes of a phage. The target microbes may be bacteria or archaea. In some embodiments, the methods comprise exposing a plurality of liquid culture samples of different bacterial types to the phage; and determining whether the phage infects the plurality of different bacterial types. In some embodiments, determining whether the phage infects the plurality of different bacterial types comprises measuring cell clearing in the samples. In some embodiments, cell clearing in a sample indicates the bacterial type in the sample is a target bacteria of the phage.

In some embodiments, the phage comprises a heterologous nucleic acid sequence encoding a first marker. In some embodiments, determining whether the phage infects the plurality of different bacterial types is by assaying for the presence of the marker in the plurality of samples. In some embodiments, detection of the marker in a sample indicates the bacterial type in the sample is a target bacteria of the phage.

BRIEF DESCRIPTION OF THE DRAWINGS

FIG. 1 is an alignment of cps gene sequences.

FIG. 2 is an alignment of the protein sequences encoded by the cps gene sequences of FIG. 1.

FIG. 3 is an alignment of inserted firefly luciferase coding sequences.

FIG. 4 is an alignment of inserted nano luc luciferase coding sequences.

DETAILED DESCRIPTION

Unless otherwise defined herein, scientific and technical terms used in connection with the present disclosure shall have the meanings that are commonly understood by those of ordinary skill in the art. Further, unless otherwise required by context, singular terms shall include the plural and plural terms shall include the singular. Generally, nomenclatures used in connection with, and techniques of, biochemistry, enzymology, molecular and cellular biology, microbiology, genetics and protein and nucleic acid chemistry and hybridization described herein are those well-known and commonly used in the art. Certain references and other documents cited herein are expressly incorporated herein by reference. Additionally, all Genbank or other sequence database records cited herein are hereby incorporated herein by reference. In case of conflict, the present specification, including definitions, will control. The materials, methods, and examples are illustrative only and not intended to be limiting.

The methods and techniques of the present disclosure are generally performed according to conventional methods well known in the art and as described in various general and more specific references that are cited and discussed throughout the present specification unless otherwise indicated. See, e.g., Sambrook et al., *Molecular Cloning: A Laboratory Manual*, 3d ed., Cold Spring Harbor Laboratory Press, Cold Spring Harbor, N.Y. (2001); Ausubel et al., *Current Protocols in Molecular Biology*, Greene Publishing Associates (1992, and Supplements to 2002); Taylor and Drickamer, *Introduction to Glycobiology*, Oxford Univ. Press (2003); *Worthington Enzyme Manual*, Worthington Biochemical Corp., Freehold, N.J.; *Handbook of Biochemistry: Section A Proteins*, Vol I, CRC Press (1976); *Handbook of Biochemistry: Section A*

*Proteins*, Vol II, CRC Press (1976); *Essentials of Glycobiology*, Cold Spring Harbor Laboratory Press (1999). Many molecular biology and genetic techniques applicable to phage are described in Clokie et al., *Bacteriophages: Methods and Protocols*, Vols. 1 and 2 (*Methods in Molecular Biology*, Vols. 501 and 502), Humana Press, New York, N.Y. (2009), which is hereby incorporated herein by reference.

This disclosure refers to sequence database entries (e.g., UniProt/SwissProt or GENBANK records) for certain amino acid and nucleic acid sequences that are published on the internet, as well as other information on the internet. The skilled artisan understands that information on the internet, including sequence database entries, is updated from time to time and that, for example, the reference number used to refer to a particular sequence can change. Where reference is made to a public database of sequence information or other information on the internet, it is understood that such changes can occur and particular embodiments of information on the internet can come and go. Because the skilled artisan can find equivalent information by searching on the internet, a reference to an internet web page address or a sequence database entry evidences the availability and public dissemination of the information in question.

Before the present phage, compositions, methods, and other embodiments are disclosed and described, it is to be understood that the terminology used herein is for the purpose of describing particular embodiments only and is not intended to be limiting. It must be noted that, as used in the specification and the appended claims, the singular forms "a," "an" and "the" include plural referents unless the context clearly dictates otherwise.

The term "comprising" as used herein is synonymous with "including" or "containing", and is inclusive or open-ended and does not exclude additional, unrecited members, elements or method steps.

As used herein, the term "in vitro" refers to events that occur in an artificial environment, e.g., in a test tube or reaction vessel, in cell culture, in a Petri dish, etc., rather than within an organism (e.g., animal, plant, or microbe).

As used herein, the term "in vivo" refers to events that occur within an organism (e.g., animal, plant, or microbe). An assay that occurs at least in part in vivo within a microbe may nonetheless occur in vitro if parts of the assay occur outside of the microbe in culture, for example.

As used herein, the term "isolated" refers to a substance or entity that has been (1) separated from at least some of the components with which it was associated when initially produced (whether in nature or in an experimental setting), and/or (2) produced, prepared, and/or manufactured by the hand of man. Isolated substances and/or entities may be separated from at least about 10%, about 20%, about 30%, about 40%, about 50%, about 60%, about 70%, about 80%, about 90%, or more of the other components with which they were initially associated. In some embodiments, isolated agents are more than about 80%, about 85%, about 90%, about 91%, about 92%, about 93%, about 94%, about 95%, about 96%, about 97%, about 98%, about 99%, or more than about 99% pure. As used herein, a substance is "pure" if it is substantially free of other components.

The term "peptide" as used herein refers to a short polypeptide, e.g., one that typically contains less than about 50 amino acids and more typically less than about 30 amino acids. The term as used herein encompasses analogs and mimetics that mimic structural and thus biological function.

The term "polypeptide" encompasses both naturally-occurring and non-naturally occurring proteins, and fragments, mutants, derivatives and analogs thereof. A polypeptide may be monomeric or polymeric. Further, a polypeptide may comprise a number of different domains each of which has one or more distinct activities. For the avoidance of doubt, a "polypeptide" may be any length greater two amino acids.

The term "isolated protein" or "isolated polypeptide" is a protein or polypeptide that by virtue of its origin or source of derivation (1) is not associated with naturally associated components that accompany it in its native state, (2) exists in a purity not found in nature, where purity can be adjudged with respect to the presence of other cellular material (e.g., is free of other proteins from the same species) (3) is expressed by a cell from a different species, or (4) does not occur in nature (e.g., it is a fragment of a polypeptide found in nature or it includes amino acid analogs or derivatives not found in nature or linkages other than standard peptide bonds). Thus, a polypeptide that is chemically synthesized or synthesized in a cellular system different from the cell from which it naturally originates will be "isolated" from its naturally associated components. A polypeptide or protein may also be rendered substantially free of naturally associated components by isolation, using protein purification techniques well known in the art. As thus defined, "isolated" does not necessarily require that the protein, polypeptide, peptide or oligopeptide so described has been physically removed from a cell in which it was synthesized.

The term "polypeptide fragment" as used herein refers to a polypeptide that has a deletion, e.g., an amino-terminal and/or carboxy-terminal deletion compared to a full-length polypeptide, such as a naturally occurring protein. In an embodiment, the polypeptide fragment is a contiguous sequence in which the amino acid sequence of the fragment is identical to the corresponding positions in the naturally-occurring sequence. Fragments typically are at least 5, 6, 7, 8, 9 or 10 amino acids long, or at least 12, 14, 16 or 18 amino acids long, or at least 20 amino acids long, or at least 25, 30, 35, 40 or 45, amino acids, or at least 50 or 60 amino acids long, or at least 70 amino acids long.

The term "fusion protein" refers to a polypeptide comprising a polypeptide or fragment coupled to heterologous amino acid sequences. Fusion proteins are useful because they can be constructed to contain two or more desired functional elements that can be from two or more different proteins. A fusion protein comprises at least 10 contiguous amino acids from a polypeptide of interest, or at least 20 or 30 amino acids, or at least 40, 50 or 60 amino acids, or at least 75, 100 or 125 amino acids. The heterologous polypeptide included within the fusion protein is usually at least 6 amino acids in length, or at least 8 amino acids in length, or at least 15, 20, or 25 amino acids in length. Fusions that include larger polypeptides, such as an IgG Fc region, and even entire proteins, such as the green fluorescent protein ("GFP") chromophore-containing proteins, have particular utility. Fusion proteins can be produced recombinantly by constructing a nucleic acid sequence which encodes the polypeptide or a fragment thereof in frame with a nucleic acid sequence encoding a different protein or peptide and then expressing the fusion protein. Alternatively, a fusion protein can be produced chemically by crosslinking the polypeptide or a fragment thereof to another protein.

As used herein, a protein has "homology" or is "homologous" to a second protein if the nucleic acid sequence that encodes the protein has a similar sequence to the nucleic acid sequence that encodes the second protein. Alternatively, a protein has homology to a second protein if the two proteins have similar amino acid sequences. (Thus, the term "homologous proteins" is defined to mean that the two proteins have similar amino acid sequences.) As used herein, homology between two regions of amino acid sequence (especially with respect to predicted structural similarities) is interpreted as implying similarity in function.

When "homologous" is used in reference to proteins or peptides, it is recognized that residue positions that are not identical often differ by conservative amino acid substitutions. A "conservative amino acid substitution" is one in which an amino acid residue is substituted by another amino acid residue having a side chain (R group) with similar chemical properties (e.g., charge or hydrophobicity). In general, a conservative amino acid substitution will not substantially change the functional properties of a protein. In cases where two or more amino acid sequences differ from each other by conservative substitutions, the percent sequence identity or degree of homology may be adjusted upwards to correct for the conservative nature of the substitution. Means for making this adjustment are well known to those of skill in the art. See, e.g., Pearson, 1994, Methods Mol. Biol. 24:307-31 and 25:365-89.

The following six groups each contain amino acids that are conservative substitutions for one another: 1) Serine, Threonine; 2) Aspartic Acid, Glutamic Acid; 3) Asparagine, Glutamine; 4) Arginine, Lysine; 5) Isoleucine, Leucine, Methionine, Alanine, Valine, and 6) Phenylalanine, Tyrosine, Tryptophan.

Sequence homology for polypeptides, which is also referred to as percent sequence identity, is typically measured using sequence analysis software. See, e.g., the Sequence Analysis Software Package of the Genetics Computer Group (GCG), University of Wisconsin Biotechnology Center, 910 University Avenue, Madison, Wis. 53705. Protein analysis software matches similar sequences using a measure of homology assigned to various substitutions, deletions and other modifications, including conservative amino acid substitutions. For instance, GCG contains programs such as "Gap" and "Bestfit" which can be used with default parameters to determine sequence homology or sequence identity between closely related polypeptides, such as homologous polypeptides from different species of organisms or between a wild-type protein and a mutein thereof. See, e.g., GCG Version 6.1.

An exemplary algorithm when comparing a particular polypeptide sequence to a database containing a large number of sequences from different organisms is the computer program BLAST (Altschul et al., J. Mol. Biol. 215:403-410 (1990); Gish and States, Nature Genet. 3:266-272 (1993); Madden et al., Meth. Enzymol. 266:131-141 (1996); Altschul et al., Nucleic Acids Res. 25:3389-3402 (1997); Zhang and Madden, Genome Res. 7:649-656 (1997)), especially blastp or tblastn (Altschul et al., Nucleic Acids Res. 25:3389-3402 (1997)).

Exemplary parameters for BLASTp are: Expectation value: 10 (default); Filter: seg (default); Cost to open a gap: 11 (default); Cost to extend a gap: 1 (default); Max. alignments: 100 (default); Word size: 11 (default); No. of descriptions: 100 (default); Penalty Matrix: BLOWSUM62. The length of polypeptide sequences compared for homology will generally be at least about 16 amino acid residues, or at least about 20 residues, or at least about 24 residues, or at least about 28 residues, or more than about 35 residues. When searching a database containing sequences from a large number of different organisms, it may be useful to compare amino acid sequences. Database searching using amino acid sequences can be measured by algorithms other than blastp known in the art. For instance, polypeptide sequences can be compared using FASTA, a program in GCG Version 6.1. FASTA provides alignments and percent sequence identity of the regions of the best overlap between the query and search sequences. Pearson, Methods Enzymol. 183:63-98 (1990). For example, percent sequence identity between amino acid sequences can be determined using FASTA with its default parameters (a word size of 2 and the PAM250 scoring matrix), as provided in GCG Version 6.1, herein incorporated by reference.

In some embodiments, polymeric molecules (e.g., a polypeptide sequence or nucleic acid sequence) are considered to be "homologous" to one another if their sequences are at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 99% identical. In some embodiments, polymeric molecules are considered to be "homologous" to one another if their sequences are at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 99% similar. The term "homologous" necessarily refers to a comparison between at least two sequences (nucleotides sequences or amino acid sequences). In some embodiments, two nucleotide sequences are considered to be homologous if the polypeptides they encode are at least about 50% identical, at least about 60% identical, at least about 70% identical, at least about 80% identical, or at least about 90% identical for at least one stretch of at least about 20 amino acids. In some embodiments, homologous nucleotide sequences are characterized by the ability to encode a stretch of at least 4-5 uniquely specified amino acids. Both the identity and the approximate spacing of these amino acids relative to one another must be considered for nucleotide sequences to be considered homologous. In some embodiments of nucleotide sequences less than 60 nucleotides in length, homology is determined by the ability to encode a stretch of at least 4-5 uniquely specified amino acids. In some embodiments, two protein sequences are considered to be homologous if the proteins are at least about 50% identical, at least about 60% identical, at least about 70% identical, at least about 80% identical, or at least about 90% identical for at least one stretch of at least about 20 amino acids.

As used herein, a "modified derivative" refers to polypeptides or fragments thereof that are substantially homologous in primary structural sequence to a reference polypeptide sequence but which include, e.g., in vivo or in vitro chemical and biochemical modifications or which incorporate amino acids that are not found in the reference polypeptide. Such modifications include, for example, acetylation, carboxylation, phosphorylation, glycosylation, ubiquitination, labeling, e.g., with radionuclides, and various enzymatic modifications, as will be readily appreciated by those skilled in the art. A variety of methods for labeling polypeptides and of substituents or labels useful for such purposes are well known in the art, and include radioactive isotopes such as $^{125}$I, $^{32}$P, $^{35}$S, and $^{3}$H, ligands that bind to labeled antiligands (e.g., antibodies), fluorophores, chemiluminescent agents, enzymes, and antiligands that can serve as specific binding pair members for a labeled ligand. The choice of label depends on the sensitivity required, ease of conjugation with the primer, stability requirements, and available instrumentation. Methods for labeling polypeptides are well known in the art. See, e.g., Ausubel et al., Current Protocols in Molecular Biology, Greene Publishing Associates (1992, and Supplements to 2002).

As used herein, "polypeptide mutant" or "mutein" refers to a polypeptide whose sequence contains an insertion, duplication, deletion, rearrangement or substitution of one or more amino acids compared to the amino acid sequence of a reference protein or polypeptide, such as a native or wild-type protein. A mutein may have one or more amino acid point substitutions, in which a single amino acid at a position has been changed to another amino acid, one or more insertions and/or deletions, in which one or more amino acids are inserted or deleted, respectively, in the sequence of the reference protein, and/or truncations of the amino acid sequence at either or both the amino or carboxy termini. A mutein may have the same or a different biological activity compared to the reference protein.

In some embodiments, a mutein has, for example, at least 70% overall sequence homology to its counterpart reference polypeptide or protein. In some embodiments, a mutein has at least 75%, at least 80%, at least 85%, or at least 90% overall sequence homology to the wild-type protein or polypeptide. In other embodiments, a mutein exhibits at least 95% sequence identity, or 98%, or 99%, or 99.5% or 99.9% overall sequence identity.

As used herein, "recombinant" refers to a biomolecule, e.g., a gene or protein, that (1) has been removed from its naturally occurring environment, (2) is not associated with all or a portion of a polynucleotide in which the gene is found in nature, (3) is operatively linked to a polynucleotide which it is not linked to in nature, or (4) does not occur in nature. The term "recombinant" can be used in reference to cloned DNA isolates, chemically synthesized polynucleotide analogs, or polynucleotide analogs that are biologically synthesized by heterologous systems, as well as proteins and/or mRNAs encoded by such nucleic acids. Thus, for example, a protein synthesized by a microorganism is recombinant, for example, if it is synthesized from an mRNA synthesized from a recombinant gene present in the cell. A phage is "recombinant" if it comprises a recombinant biomolecule. Thus, for example and without limitation, a phage is recombinant if the genome of the phage comprises a recombinant nucleic acid sequence.

The term "polynucleotide", "nucleic acid molecule", "nucleic acid", or "nucleic acid sequence" refers to a polymeric form of nucleotides of at least 10 bases in length. The term includes DNA molecules (e.g., cDNA or genomic or synthetic DNA) and RNA molecules (e.g., mRNA or synthetic RNA), as well as analogs of DNA or RNA containing non-natural nucleotide analogs, non-native internucleoside bonds, or both. The nucleic acid can be in any topological conformation. For instance, the nucleic acid can be single-stranded, double-stranded, triple-stranded, quadruplexed, partially double-stranded, branched, hairpinned, circular, or in a padlocked conformation. The nucleic acid (also referred to as polynucleotides) may include both sense and antisense strands of RNA, cDNA, genomic DNA, and synthetic forms and mixed polymers of the above. They may be modified chemically or biochemically or may contain non-natural or derivatized nucleotide bases, as will be readily appreciated by those of skill in the art. Such modifications include, for example, labels, methylation, substitution of one or more of the naturally occurring nucleotides with an analog, internucleotide modifications such as uncharged linkages (e.g., methyl phosphonates, phosphotriesters, phosphoramidates, carbamates, etc.), charged linkages (e.g., phosphorothioates, phosphorodithioates, etc.), pendent moieties (e.g., polypeptides), intercalators (e.g., acridine, psoralen, etc.), chelators, alkylators, and modified linkages (e.g., alpha anomeric nucleic acids, etc.) Also included are synthetic molecules that mimic polynucleotides in their ability to bind to a designated sequence via hydrogen bonding and other chemical interactions. Such molecules are known in the art and include, for example, those in which peptide linkages substitute for phosphate linkages in the backbone of the molecule. Other modifications can include, for example, analogs in which the ribose ring contains a bridging moiety or other structure such as the modifications found in "locked" nucleic acids.

A "synthetic" RNA, DNA or a mixed polymer is one created outside of a cell, for example one synthesized chemically.

The term "nucleic acid fragment" as used herein refers to a nucleic acid sequence that has a deletion, e.g., a 5'-terminal or 3'-terminal deletion compared to a full-length reference nucleotide sequence. In an embodiment, the nucleic acid fragment is a contiguous sequence in which the nucleotide sequence of the fragment is identical to the corresponding positions in the naturally-occurring sequence. In some embodiments fragments are at least 10, 15, 20, or 25 nucleotides long, or at least 20, 30, 40, 50, 60, 70, 80, 90, 100, 110, 120, 130, 140, or 150 nucleotides long. In some embodiments a fragment of a nucleic acid sequence is a fragment of an open reading frame sequence. In some embodiments such a fragment encodes a polypeptide fragment (as defined herein) of the protein encoded by the open reading frame nucleotide sequence.

As used herein, an endogenous nucleic acid sequence in the genome of an organism (including a phage) (or the encoded protein product of that sequence) is deemed "recombinant" herein if a heterologous sequence is placed adjacent to the endogenous nucleic acid sequence, such that the expression of this endogenous nucleic acid sequence is altered. In this context, a heterologous sequence is a sequence that is not naturally adjacent to the endogenous nucleic acid sequence, whether or not the heterologous sequence is itself endogenous (originating from the same host cell or progeny thereof) or exogenous (originating from a different host cell or progeny thereof). By way of example, a promoter sequence can be substituted (e.g., by homologous recombination) for the native promoter of a gene in the genome of a host cell, such that this gene has an altered expression pattern. This gene would now become "recombinant" because it is separated from at least some of the sequences that naturally flank it.

A nucleic acid is also considered "recombinant" if it contains any modifications that do not naturally occur to the corresponding nucleic acid in a genome. For instance, an endogenous coding sequence is considered "recombinant" if it contains an insertion, deletion or a point mutation introduced artificially, e.g., by human intervention. A "recombinant nucleic acid" also includes a nucleic acid integrated into a host cell chromosome at a heterologous site and a nucleic acid construct present as an episome. With reference to a phage, a "recombinant phage genome" is a phage genome that contains an insertion, deletion or a point mutation introduced artificially, e.g., by human intervention.

As used herein, the phrase "degenerate variant" of a reference nucleic acid sequence encompasses nucleic acid sequences that can be translated, according to the standard genetic code, to provide an amino acid sequence identical to that translated from the reference nucleic acid sequence. The term "degenerate oligonucleotide" or "degenerate primer" is used to signify an oligonucleotide capable of hybridizing with target nucleic acid sequences that are not necessarily identical in sequence but that are homologous to one another within one or more particular segments.

The term "percent sequence identity" or "identical" in the context of nucleic acid sequences refers to the residues in the two sequences which are the same when aligned for maximum correspondence. The length of sequence identity comparison may be over a stretch of at least about nine nucleotides, usually at least about 20 nucleotides, more usually at least about 24 nucleotides, typically at least about 28 nucleotides, more typically at least about 32, and even more typically at least about 36 or more nucleotides. There are a number of different algorithms known in the art which can be used to measure nucleotide sequence identity. For instance, polynucleotide sequences can be compared using FASTA, Gap or Bestfit, which are programs in Wisconsin Package Version 10.0, Genetics Computer Group (GCG), Madison, Wis. FASTA provides alignments and percent sequence identity of the regions of the best overlap between the query and search sequences. Pearson, Methods Enzymol. 183:63-98 (1990). For instance, percent sequence identity between nucleic acid sequences can be determined using FASTA with its default parameters (a word size of 6 and the NOPAM factor for the scoring matrix) or using Gap with its default parameters as provided in GCG Version 6.1, herein incorporated by reference. Alternatively, sequences can be compared using the computer program, BLAST (Altschul et al., J. Mol. Biol. 215:403-410 (1990); Gish and States, Nature Genet. 3:266-272 (1993); Madden et al., Meth. Enzymol. 266:131-141 (1996); Altschul et al., Nucleic Acids Res. 25:3389-3402 (1997); Zhang and Madden, Genome Res. 7:649-656 (1997)), especially blastp or tblastn (Altschul et al., Nucleic Acids Res. 25:3389-3402 (1997)).

The term "substantial homology" or "substantial similarity," when referring to a nucleic acid or fragment thereof, indicates that, when optimally aligned with appropriate nucleotide insertions or deletions with another nucleic acid (or its complementary strand), there is nucleotide sequence identity in at least about 50%, 60%, 70%, 80%, 85%, 90%, 95%, 96%, 97%, 98% or 99% of the nucleotide bases, as measured by any well-known algorithm of sequence identity, such as FASTA, BLAST or Gap, as discussed above.

Alternatively, substantial homology or similarity exists when a nucleic acid or fragment thereof hybridizes to another nucleic acid, to a strand of another nucleic acid, or to the complementary strand thereof, under stringent hybridization conditions. "Stringent hybridization conditions" and "stringent wash conditions" in the context of nucleic acid hybridization experiments depend upon a number of different physical parameters. Nucleic acid hybridization will be affected by such conditions as salt concentration, temperature, solvents, the base composition of the hybridizing species, length of the complementary regions, and the number of nucleotide base mismatches between the hybridizing nucleic acids, as will be readily appreciated by those skilled in the art. One having ordinary skill in the art knows how to vary these parameters to achieve a particular stringency of hybridization.

In general, "stringent hybridization" is performed at about 25° C. below the thermal melting point (Tm) for the specific DNA hybrid under a particular set of conditions. "Stringent washing" is performed at temperatures about 5° C. lower than the Tm for the specific DNA hybrid under a particular set of conditions. The Tm is the temperature at which 50% of the target sequence hybridizes to a perfectly matched probe. See Sambrook et al., Molecular Cloning: A Laboratory Manual, 2d ed., Cold Spring Harbor Laboratory Press, Cold Spring Harbor, N.Y. (1989), page 9.51. For purposes herein, "stringent conditions" are defined for solution phase hybridization as aqueous hybridization (i.e., free of formamide) in 6×SSC (where 20×SSC contains 3.0 M NaCl and 0.3 M sodium citrate), 1% SDS at 65° C. for 8-12 hours, followed by two washes in 0.2×SSC, 0.1% SDS at 65° C. for 20 minutes. It will be appreciated by the skilled worker that hybridization at 65° C. will occur at different rates depending on a number of factors including the length and percent identity of the sequences which are hybridizing.

As used herein, an "expression control sequence" refers to polynucleotide sequences that affect the expression of coding sequences to which they are operatively linked. Expression control sequences are sequences that control the transcription, post-transcriptional events and translation of nucleic acid sequences. Expression control sequences include appropriate transcription initiation, termination, promoter and enhancer sequences; efficient RNA processing signals such as splicing and polyadenylation signals; sequences that stabilize cytoplasmic mRNA; sequences that enhance translation efficiency (e.g., ribosome binding sites); sequences that enhance protein stability; and when desired, sequences that enhance protein secretion. The nature of such control sequences differs depending upon the host organism; in prokaryotes, such control sequences generally include promoter, ribosomal binding site, and transcription termination sequence. The term "control sequences" is intended to encompass, at a minimum, any component whose presence is essential for expression, and can also encompass an additional component whose presence is advantageous, for example, leader sequences and fusion partner sequences.

As used herein, "operatively linked" or "operably linked" expression control sequences refers to a linkage in which the expression control sequence is contiguous with the gene of interest to control the gene of interest, as well as expression control sequences that act in trans or at a distance to control the gene of interest.

As used herein, a "vector" is intended to refer to a nucleic acid molecule capable of transporting another nucleic acid to which it has been linked. One type of vector is a "plasmid," which generally refers to a circular double stranded DNA loop into which additional DNA segments may be ligated, but also includes linear double-stranded molecules such as those resulting from amplification by the polymerase chain reaction (PCR) or from treatment of a circular plasmid with a restriction enzyme. Other vectors include cosmids, bacterial artificial chromosomes (BAC) and yeast artificial chromosomes (YAC). Another type of vector is a viral vector, wherein additional DNA segments may be ligated into the viral genome (discussed in more detail below). Certain vectors are capable of autonomous replication in a host cell into which they are introduced (e.g., vectors having an origin of replication which functions in the host cell). Other vectors can be integrated into the genome of a host cell upon introduction into the host cell, and are thereby replicated along with the host genome. Moreover, certain vectors are capable of directing the expression of genes to which they are operatively linked. Such vectors are referred to herein as "recombinant expression vectors" (or simply "expression vectors").

The term "recombinant host cell" (or simply "recombinant cell" or "host cell"), as used herein, is intended to refer to a cell into which a recombinant nucleic acid such as a recombinant vector has been introduced. In some instances the word "cell" is replaced by a name specifying a type of cell. For example, a "recombinant microorganism" is a recombinant host cell that is a microorganism host cell. It should be understood that such terms are intended to refer not only to the particular subject cell but to the progeny of such a cell. Because certain modifications may occur in succeeding generations due to either mutation or environmental influences, such progeny may not, in fact, be identical to the parent cell, but are still included within the scope of the term "recombinant host cell," "recombinant cell," and "host cell", as used herein. A recombinant host cell may be an isolated cell or cell line grown in culture or may be a cell which resides in a living tissue or organism.

As used herein, "bacteriophage" refers to a virus that infects bacteria. Similarly, "archaeophage" refers to a virus that infects archaea. The term "phage" is used to refer to both types of viruses but in certain instances as indicated by the context may also be used as shorthand to refer to a bacteriophage or archeophage specifically. Bacteriophage and archeophage are obligate intracellular parasites that multiply inside bacteria/archaea by making use of some or all of the host biosynthetic machinery (i.e., viruses that infect bacteria). Though different bacteriophages and archeophages may contain different materials, they all contain nucleic acid and protein, and can under certain circumstances be encapsulated in a lipid membrane. Depending upon the phage, the nucleic acid may be either DNA or RNA but not both and it can exist in various forms.

As used herein, "heterologous nucleic acid sequence" is any sequence placed at a location in the genome where it does not normally occur. A heterologous nucleic acid sequence may comprise a sequence that does not naturally occur in a particular bacteria/archaea and/or phage or it may comprise only sequences naturally found in the bacteria/archaea and/or phage, but placed at a non-normally occurring location in the genome. In some embodiments the heterologous nucleic acid sequence is not a natural phage sequence; in some embodiments it is a natural phage sequence, albeit from a different phage; while in still other embodiments it is a sequence that occurs naturally in the genome of the starting phage but is then moved to another site where it does not naturally occur, rendering it a heterologous sequence at that new site.

A "starting phage" or "starting phage genome" is a phage isolated from a natural or human made environment that has not been modified by genetic engineering, or the genome of such a phage.

A "recombinant phage" or "recombinant phage genome" is a phage that comprises a genome that has been genetically modified by insertion of a heterologous nucleic acid sequence into the phage, or the genome of the phage. In some embodiments the genome of a starting phage is modified by recombinant DNA technology to introduce a heterologous nucleic acid sequence into the genome at a defined site. In some embodiments the heterologous sequence is introduced with no corresponding loss of endogenous phage genomic nucleotides. In other words, if bases N1 and N2 are adjacent in the starting phage genome the heterologous sequence is inserted between N1 and N2. Thus, in the resulting recombinant genome the heterologous sequence is flanked by nucleotides N1 and N2. In some cases the heterologous sequence is inserted and endogenous nucleotides are removed or replaced with the exogenous sequence. For example, in some embodiments the exogenous sequence is inserted in place of some or all of the endogenous sequence which is removed. In some embodiments endogenous sequences are removed from a position in the phage genome distant from the site(s) of insertion of exogenous sequences.

A "phage host cell" is a cell that can be infected by a phage to yield progeny phage particles.

"Operatively linked" or "operably linked" expression control sequences refers to a linkage in which the expression control sequence is contiguous with coding sequences of interest to control expression of the coding sequences of interest, as well as expression control sequences that act in trans or at a distance to control expression of the coding sequence.

A "coding sequence" or "open reading frame" is a sequence of nucleotides that encodes a polypeptide or protein. The termini of the coding sequence are a start codon and a stop codon.

The term "expression control sequence" as used herein refers to polynucleotide sequences which affect the expression of coding sequences to which they are operatively linked.

Expression control sequences are sequences which control the transcription, post-transcriptional events and translation of nucleic acid sequences. Expression control sequences include appropriate transcription initiation, termination, promoter and enhancer sequences; efficient RNA processing signals such as splicing and polyadenylation signals; sequences that stabilize cytoplasmic mRNA; sequences that enhance translation efficiency (e.g., ribosome binding sites); sequences that enhance protein stability; and when desired, sequences that enhance protein secretion. The nature of such control sequences differs depending upon the host organism; in prokaryotes, such control sequences generally include promoter, ribosomal binding site, and transcription termination sequence. The term "control sequences" is intended to include, at a minimum, all components whose presence is essential for expression, and can also include additional components whose presence is advantageous, for example, leader sequences and fusion partner sequences.

As used herein, a "phage genome" includes naturally occurring phage genomes and derivatives thereof. Generally (though not necessarily), the derivatives possess the ability to propagate in the same hosts as the parent. In some embodiments the only difference between a naturally occurring phage genome and a derivative phage genome is at least one of a deletion and an addition of nucleotides from at least one end of the phage genome if the genome is linear or at least one point in the genome if the genome is circular.

As used herein, "target bacteria" are bacteria that can be infected by a phage to yield a detectable output. For example, a detectable output includes cell lysis. Thus, lysis of bacterial cells by a phage indicates that the bacterial cells are "target bacteria" of that phage. Another example of a detectable output is expression of a marker following infection of a bacterial cell by a phage. Suitable markers include RNAs and polypeptides.

As used herein, a "marker" includes selectable and/or screenable markers. As used herein, a "selectable marker" is a marker that confers upon cells that possess the marker the ability to grow in the presence or absence of an agent that inhibits or stimulates, respectively, growth of similar cells that do not express the marker. Such cells can also be said to have a "selectable phenotype" by virtue of their expression of the selectable marker. For example, the ampicillin resistance gene (AmpR) confers the ability to grow in the presence of ampicillin on cells which possess and express the gene. (See Sutcliffe, J. G., *Proc Natl Acad Sci USA*. 1978 August; 75(8): 3737-3741.) Other nonlimiting examples include genes that confer resistance to chloramphenicol, kanamycin, and tetracycline. Other markers include URA3, TRP and LEU, which allow growth in the absence of said uracil, tryptophan and leucine, respectively.

As used herein, a "screenable marker" is a detectable label that that can be used as a basis to identify cells that express the marker. Such cells can also be said to have a "screenable phenotype" by virtue of their expression of the screenable marker. (In general selectable markers may also function as screenable markers in so far as the gene product of the selectable marker may be used as a basis to identify cells that express the marker independently of the function of the gene product to confer selectability on cells that express it.) Any molecule that can be differentially detected and encoded by the recombinant phage can serve as a screenable marker. A screenable marker can be a nucleic acid molecule or a portion thereof, such as an RNA or a DNA molecule that is single or double stranded. Alternatively, a screenable marker can be a protein or a portion thereof. Suitable protein markers include enzymes that catalyzes formation of a detectable reaction product. An example is a chemiluminescent protein such as luciferase or variations, such as luxAB, and β-galactosidase. Another example is the horseradish peroxidase enzyme. Proteins used to generate a luminescent signal fall into two broad categories: those that generate light directly (luciferases and related proteins) and those that are used to generate light indirectly as part of a chemical cascade (horseradish peroxidase). The most common bioluminescent proteins used in biological research are aequorin and luciferase. The former protein is derived from the jellyfish *Aequorea victoria* and can be used to determine calcium concentrations in solution. The luciferase family of proteins has been adapted for a broad range of experimental purposes. Luciferases from firefly and Renilla are the most commonly used in biological research. These proteins have also been genetically separated into two distinct functional domains that will generate light only when the proteins are closely co-localized. A variety of emission spectrum-shifted mutant derivatives of both of these proteins have been generated over the past decade. These have been used for multi-color imaging and co-localization within a living cell. The other groups of proteins used to generate chemiluminescent signal are peroxidases and phosphatases. Peroxidases generate peroxide that oxidizes luminol in a reaction that generates light. The most widely used of these is horseradish peroxidase (HRP), which has been used extensively for detection in western blots and ELISAs. A second group of proteins that have been employed in a similar fashion are alkaline phosphatases, which remove a phosphate from a substrate molecule, destabilizing it and initiating a cascade that results in the emission of light.

Other suitable screenable markers include fluorescent proteins. Fluorescent proteins include but are not limited to blue/UV fluorescent proteins (for example, TagBFP, Azurite, EBFP2, mKalama1, Sirius, Sapphire, and T-Sapphire), cyan fluorescent proteins (for example, ECFP, Cerulean, SCFP3A, mTurquoise, monomeric Midoriishi-Cyan, TagCFP, and mTFP1), green fluorescent proteins (for example, EGFP, Emerald, Superfolder GFP, Monomeric Azami Green, TagGFP2, mUKG, and mWasabi), yellow fluorescent proteins (for example, EYFP, Citrine, Venus, SYFP2, and TagYFP), orange fluorescent proteins (for example, Monomeric Kusabira-Orange, mKOκ, mKO2, mOrange, and mOrange2), red fluorescent proteins (for example, mRaspberry, mCherry, mStrawberry, mTangerine, tdTomato, TagRFP, TagRFP-T, mApple, and mRuby), far-red fluorescent proteins (for example, mPlum, HcRed-Tandem, mKate2, mNeptune, and NirFP), near-IR fluorescent proteins (for example, TagRFP657, IFP1.4, and iRFP), long stokes-shift proteins (for example, mKeima Red, LSS-mKate1, and LSS-mKate2), photoactivatible fluorescent proteins (for example, PA-GFP, PAmCherry1, and PATagRFP), photoconvertible fluorescent proteins (for example, Kaede (green), Kaede (red), KikGR1 (green), KikGR1 (red), PS-CFP2, PS-CFP2, mEos2 (green), mEos2 (red), PSmOrange, and PSmOrange), and photoswitchable fluorescent proteins (for example, Dronpa). Several variants and alternatives to the listed examples are also well known to those of skill in the art and may be substituted in appropriate applications.

Other suitable markers include epitopes. For example, a protein comprising an epitope that can be detected with an antibody or other binding molecule is an example of a screenable marker. An antibody that recognizes the epitope can be directly linked to a signal generating moiety (such as by covalent attachment of a chemiluminescent or fluorescent protein) or it can be detected using at least one additional binding reagent such as a secondary antibody, directly linked to a signal generating moiety, for example. In some embodiments the epitope is not present in the proteins of the phage or the target microorganism so detection of the epitope in a sample indicates that the protein comprising the epitope was produced by the microorganism following infection by the recombinant phage comprising a gene encoding the protein comprising the epitope. In other embodiments the marker may be a purification tag in the context of a protein that is naturally present in the target microorganism or the phage. For example, the tag (e.g., a 6-His tag) can be used to purify the heterologous protein from other bacterial or phage proteins and the purified protein can then be detected, for example using an antibody.

As used herein, an "environmental sample" is a sample obtained from any setting other than a laboratory cell culture setting. Generally, though not necessarily, an environmental sample is obtained from a setting that comprises at least one of a) a temperature that does not support maximum growth and/or metabolism of bacterial cells, b) a nutrient profile that does not support maximum growth and/or metabolism of bacterial cells, and c) bacterial cells that are not target bacteria for a phage used in an assay. In some embodiments some or all of the bacteria present in an environmental sample are not in a metabolically active state. Without limitation, environmental samples may be obtained from industrial plants, food processing plants, veterinary sources, food, livestock, medical settings and surfaces, schools, assisted living centers, cruise ships, other confined quarters and homes.

A. Recombinant Phage

This disclosure provides novel methods of assessing phage host-range. The methods were used to define target bacteria for a set of phage as described in the examples As a result of that analysis, the phage LP40, LP48, LP99, LP101, LP124, LP125, LP143, A511, and P100 were selected for engineering. The examples describe making recombinant versions of the phage LP40, LP48, LP99, LP101, LP124, LP125, LP143, A511, and P100, comprising a heterologous nucleic acid sequence encoding a marker. As demonstrated in the examples, those phage are useful, for example, to detect target bacteria, as further disclosed throughout this application.

Accordingly, this disclosure provides recombinant *Listeria* phage comprising a heterologous nucleic acid sequence encoding a marker. In some embodiments the recombinant phage comprises a genome comprising a region of at least 1 kb that comprises substantial homology to a region of at least 1 kb of the genome of at least one phage selected from LP40, LP48, LP99, LP101, LP124, LP125, LP143, A511, and P100. In some embodiments the region of homology comprises at least 2 kb, at least 3 kb, at least 4 kb, at least 5 kb, at least 6 kb, at least 7 kb, at least 8 kb, at least 9 kb, at least 10 kb, or more. In some embodiments the region of homology is the entire genome of the recombinant *Listeria* phage. In some embodiments the substantial homology is nucleotide sequence identity of at least 50%, 60%, 70%, 80%, 85%, 90%, 95%, 96%, 97%, 98% or 99% across the region of homology.

This disclosure provides the amino acid sequences of the cps gene of the phage LP40 (SEQ ID NO: 6), LP48 (SEQ ID NO: 8), LP99 (SEQ ID NO: 10), LP101 (SEQ ID NO: 12), LP124 (SEQ ID NO: 14), LP125 (SEQ ID NO: 16), LP143 (SEQ ID NO: 18), A511 (SEQ ID NO: 20), and P100 (SEQ ID NO: 22). Accordingly, in some embodiments this disclosure provides recombinant *Listeria* phage comprising a heterologous nucleic acid sequence encoding a marker, wherein the recombinant *Listeria* phage comprises a nucleic acid sequence that encodes a protein selected from SEQ ID NOS: 6, 8, 10, 12, 14, 16, 18, 20, and 22, and muteins thereof.

This disclosure also provides the nucleotide sequences of the open reading frames of the cps gene of the phage LP40

(SEQ ID NO: 5), LP48 (SEQ ID NO: 7), LP99 (SEQ ID NO: 9), LP101 (SEQ ID NO: 11), LP124 (SEQ ID NO: 13), LP125 (SEQ ID NO: 15), LP143 (SEQ ID NO: 17), A511 (SEQ ID NO: 19), and P100 (SEQ ID NO: 21). Accordingly, in some embodiments this disclosure provides recombinant *Listeria* phage comprising a heterologous nucleic acid sequence encoding a marker, wherein the recombinant *Listeria* phage comprises a nucleic acid sequence selected from SEQ ID NOS: 5, 7, 9, 11, 13, 15, 17, 19, and 21, and nucleic acid sequences comprising substantial homology thereto.

In some embodiments the recombinant *Listeria* phage comprising a heterologous nucleic acid sequence encoding a marker comprises a screenable marker. In some embodiments the marker is a luciferase. In some embodiments the luciferase is at least 70% identical to SEQ ID NO: 2. In some embodiments the luciferase is encoded by a nucleic acid sequence comprising SEQ ID NO: 1 or a nucleic acid sequence comprising substantial homology to SEQ ID NO: 1. In some embodiments the recombinant *Listeria* phage is selected from LP48::ffluc, LP99::ffluc, LP101::ffluc, LP124::ffluc, LP125::ffluc, LP143::ffluc, A511::ffluc, and P100::ffluc. In some embodiments the recombinant *Listeria* phage is selected from phage comprising genomes comprising substantial homology to at least one phage selected from LP48::ffluc, LP99::ffluc, LP101::ffluc, LP124::ffluc, LP125::ffluc, LP143::ffluc, A511::ffluc, and P100::ffluc.

In some embodiments the luciferase is at least 70% identical to SEQ ID NO: 4. In some embodiments the luciferase is encoded by a nucleic acid sequence comprising SEQ ID NO: 3 or a nucleic acid sequence comprising substantial homology to SEQ ID NO: 3. In some embodiments the recombinant *Listeria* phage is selected from LP::040::nluc, LP124::nluc, LP125::nluc, A511::nluc, and P100::nluc. In some embodiments the recombinant *Listeria* phage is selected from phage comprising genomes comprising substantial homology to at least one phage selected from LP::040::nluc, LP124::nluc, LP125::nluc, A511::nluc, and P100::nluc.

In some embodiments the heterologous nucleic acid sequence encoding a marker is operatively linked in the recombinant phage genome to at least one regulatory element that is also heterologous to the phage genome. In some embodiments expression of the heterologous nucleic acid sequence encoding a marker in target bacteria is controlled exclusively by regulatory elements that are heterologous to the phage genome.

In some embodiments the heterologous nucleic acid sequence encoding a marker is operatively linked in the recombinant phage genome to at least one regulatory element that is endogenous to the phage genome. In other words, the heterologous nucleic acid sequence encoding a marker is operatively linked to the endogenous regulatory element by virtue of the location in the starting phage genome where the heterologous nucleic acid sequence encoding a marker is placed. In some embodiments expression of the heterologous nucleic acid sequence encoding a marker in target bacteria is controlled exclusively by regulatory elements that are endogenous to the phage genome. In some embodiments expression of the heterologous nucleic acid sequence encoding a marker in target bacteria is controlled in part by regulatory elements that are endogenous to the phage genome and in part by regulatory elements that are heterologous to the phage genome.

In some embodiments the recombinant *Listeria* phage comprising a heterologous nucleic acid sequence encoding a marker comprises more than one heterologous nucleic acid sequence encoding a marker. In some embodiments the recombinant phage comprises multiple copies of the same nucleic acid sequence encoding a marker (i.e., copy encodes the same marker). In some embodiments the recombinant phage comprises copies of more than one type of nucleic acid sequence encoding a marker (i.e., at least two copies encode different markers). In some embodiments the more than one copy are positioned at adjacent locations in the recombinant phage genome. In other embodiments at least one (up to all) of the more than one copy are located at non-adjacent locations in the recombinant phage genome.

In some embodiments the length of the heterologous nucleic acid sequence is at least 100 bases, at least 200 based, at least 300 bases, at least 400 bases, at least 500 bases, at least 600 bases, at least 700 bases, at least 800 bases, at least 900 bases, at least 1.0 kilobase (kb), at least 1.1 kb, at least 1.2 kb, at least 1.3 kb, at least 1.4 kb, at least 1.5 kb, at least 1.6 kb, at least 1.7 kb, at least 1.8 kb, at least 1.9 kb, at least 2.0 kb, at least 2.1 kb, at least 2.2 kb, at least 2.3 kb, at least 2.4 kb, at least 2.5 kb, at least 2.6 kb, at least 2.7 kb, at least 2.8 kb, at least 2.9 kb, at least 3.0 kb, at least 3.1 kb, at least 3.2 kb, at least 3.3 kb, at least 3.4 kb, at least 3.5 kb, at least 3.6 kb, at least 3.7 kb, at least 3.8 kb, at least 3.9 kb, at least 4.0 kb, at least 4.5 kb, at least 5.0 kb, at least 5.5 kb, at least 5.5 kb, at least 6.0 kb, at least 6.5 kb, at least 7.0 kb, at least 7.5 kb, at least 8.0 kb, at least 8.5 kb, at least 9.0 kb, at least 9.5 kb, at least 10 kb, or more. In some embodiments the length of the heterologous nucleic acid sequence is 500 bases or less, 1.0 kb or less, 1.5 kb or less, 2.0 kb or less, 2.5 kb or less, 3.0 kb or less, 3.5 kb or less, 4.0 kb or less, 4.5 kb or less, 5.0 kb or less, 5.5 kb or less, 6.0 kb or less, 6.5 kb or less, 7.0 kb or less, 7.5 kb or less, 8.0 kb or less, 8.5 kb or less, 9.0 kb or less, 9.5 kb or less, or 10.0 kb or less. In some such embodiments the heterologous nucleic acid sequence comprises a length that is less than the maximum length of heterologous nucleic acid sequence that can be packaged into a phage particle encoded by the phage genome and comprising the phage genome.

In some embodiments the length of the heterologous nucleic acid sequence is from 100 to 500 bases, from 200 to 1,000 bases, from 500 to 1,000 bases, from 500 to 1,500 bases, from 1 kb to 2 kb, from 1.5 kb to 2.5 kb, from 2.0 kb to 3.0 kb, from 2.5 kb to 3.5 kb, from 3.0 kb to 4.0 kb, from 3.5 kb to 4.5 kb, from 4.0 kb to 5.0 kb, from 4.5 kb to 5.5 kb, from 5.0 kb to 6.0 kb, from 5.5 kb to 6.5 kb, from 6.0 kb to 7.0 kb, from 6.5 kb to 7.5 kb, from 7.0 kb to 8.0 kb, from 7.5 kb to 8.5 kb, from 8.0 kb to 9.0 kb, from 8.5 kb to 9.5 kb, or from 9.0 kb to 10.0 kb.

In some embodiments the ratio of the length of the heterologous nucleic acid sequence to the total length of the genome of the recombinant phage is at least 0.05, at least 0.10, at least 0.15, at least 0.20, or at least 0.25. In some embodiments the ratio of the length of the genome of the recombinant phage to the length of the genome of the corresponding starting phage is at least 1.05, at least 1.10, at least 1.15, at least 1.20, or at least 1.25.

In some embodiments the heterologous nucleic acid sequence is inserted into the starting phage genome with no loss of endogenous starting phage genome sequence. In some embodiments the inserted heterologous nucleic acid sequence replaces endogenous starting phage genome sequence. In some such embodiments the heterologous nucleic acid sequence replaces an amount of endogenous genomic sequence that is less than the length of the heterologous nucleic acid sequence. Thus, in such embodiments the length of the recombinant phage genome is longer than the length of the starting phage genome. In some such embodiments the heterologous nucleic acid sequence replaces an amount of endogenous genomic sequence that is greater than the length of the heterologous nucleic acid sequence. Thus, in such embodiments the length of the recombinant phage genome is shorter than the length of the starting phage genome. In some such embodiments the heterologous nucleic acid sequence replaces an amount of endogenous genomic sequence that is equal to the length of the heterologous nucleic acid sequence.

In some embodiments the protein or polypeptide encoded by a heterologous open reading frame is modified to reduce cleavage by proteases present in phage host cells. For example, computational algorithms can be used to identify known protease cleavage sites and the sequence of the open reading frame may be modified using conservative substitutions to remove these sites. Alternatively, directed mutagenesis is used to evolve the open reading frame sequence to encode a product that has an increased resistance to at least one protease present in a phage host cell or in the culture of a phage host cell.

This disclosure also provides isolated nucleic acids obtainable from a recombinant phage of this disclosure. In some embodiments the isolated nucleic acid is an isolated genome of a recombinant phage of this disclosure. In some embodiments the isolated nucleic acid comprises a fragment of less than the total genome of recombinant phage of this disclosure, the fragment comprising at least 10%, at least 20%, at least 30%, at least 40%, at least 50%, at least 60%, at least 70%, at least 80%, at least 90%, at least 95%, or at least 99% of the genome of the recombinant phage. In some embodiments the isolated nucleic acid comprises a fragment of less than the total genome of recombinant phage of this disclosure, the fragment comprising at least 20 bp, at least 50 bp, at least 100 bp, at least 500 bp, at least 1 kb, at least 2 kb, at least 3 kb, at least 4 kb, or at least 5 kb of the phage genome. In some embodiments the isolated nucleic acid comprises a fragment that is homolous to a fragment disclosed in this paragraph.

B. Methods of Making Recombinant Phage

Any method known in the art can be used to make genetically modified phage from starting phage. For example, U.S. Pat. No. 5,824,468 discloses methods of making genetically modified phage. Alternative methods are disclosed in co-pending application Ser. No. 13/627,060, filed Sep. 26, 2012, which is hereby incorporated herein by reference.

Example 5 describes a new method of making recombinant phage. This method is sometimes referred to herein as phage infective engineering (PIE). This method allows insertion of a heterologous nucleic acid sequence into any desired location of a phage genome. The PIE method utilizes a phage targeting vector (PTV) that is transformed into a phage host cell. The PTV comprises a heterologous nucleic acid sequence (such as an open reading frame encoding a marker) for insertion into a phage genome. The heterologous nucleic acid sequence is flanked by upstream and downstream homology regions, which are located adjacent to the desired insertion site. In some embodiments the homology regions in the vector are directly adjacent in a starting phage genome. Such embodiments allow insertion of the heterologous nucleic acid sequence into the phage genome without a loss of endogenous phage sequence. In some embodiments the homology regions in the vector flank a region of the starting phage genome that is not included in the vector. Such embodiments allow insertion of the heterologous nucleic acid sequence into the phage genome while deleting a region of the starting phage genome at the site of insertion. Such embodiments allow, for example, the replacement of an endogenous phage sequence with a replacement sequence. In some embodiments the starting sequence that is deleted and the replacement sequence display sequence homology, such as homology of at least 50%, 60%, 70%, 80%, 90%, 95%, 96%, 97%, 98%, 99% or higher.

The upstream homology region, downstream homology region, and heterologous nucleic acid sequence are combined in a vector to make a PTV. One example of a suitable vector is pMK4; however, skilled artisans are aware of many suitable vectors that may be used for this purpose. The plasmid may be isolated in any suitable host, such as *E. coli*. Upon verification, the plasmid is then transformed into a phage host cell. One example of such a cell useful for many *Listeria* phage is the *L. monocytogenes* strain EGD-e.

Once the PTV is successfully transformed into the phage host, the initial recombination was performed by incubating the transformed phage host cell with starting phage.

To assess whether recombination has occurred, the infection is assayed using any suitable method to identify recombinant phage that comprise the heterologous nucleic acid sequence. PCR is one method that may be used. Alternatively, if the heterologous nucleic acid sequence comprises an open reading frame the presence of transcripts encoded by that open reading frame, the presence of the encoded gene product, or functional readouts of the encoded gene product may be screened for in cultures of cells infected with the resultant phage to identify recombinant phage.

C. Phage Target Bacteria

The recombinant phage of this disclosure may be used to detect the presence of bacteria. Detection of target bacteria is based on the ability of the recombinant phage to bind to a target bacteria, transfer of the phage genome into the target bacteria, and expression of the heterologous nucleic acid sequence encoding a marker by the bacteria. Accordingly, the specificity of a method of detecting target bacteria using recombinant phage comprising a heterologous nucleic acid sequence encoding a marker is based on the range of bacterial types that support expression of the marker following exposure to the phage. Sometimes the range of bacterial types that support expression of the marker following exposure to the phage is referred to herein as the "host range" of the phage. The set of bacterial types that make up the host range of the phage is sometimes referred to herein as "target bacteria" for the phage.

This disclosure provides novel methods of assessing phage host range and thus of defining target bacteria for a phage. In certain embodiments the methods comprise exposing a candidate type of bacteria to a phage in a liquid culture. The ability of the phage to cause clearing of the culture, which reflects infection and lysis of bacteria in the culture by the phage, is an indication that the bacteria in the culture are target bacteria of the phage. As demonstrated in the examples this method is surprisingly more accurate in assessing the true phage host range for a phage than prior art plate-based plaque assays. In some embodiments herein, the "host range" of a phage or the "target bacteria" of a phage are defined based on a set of bacteria that a phage can clear in a liquid culture-based assay.

While the liquid culture method is an improvement over prior art methods and is very useful for many purposes, it does embody all aspects of methods of using a recombinant phage to detect target bacteria. Such methods rely on the ability of the recombinant phage to bind to a target bacteria, transfer of the phage genome into the target bacteria, and expression of the heterologous nucleic acid sequence encoding a marker by the bacteria. Accordingly, even if a phage is unable to lyse a liquid culture of a particular bacterial cell type the phage may nonetheless be able to bind to the bacteria type, transfer the phage genome into the target bacteria, and thus cause expression of a heterologous nucleic acid sequence encoding a marker by the bacteria. Indeed, as demonstrated by the examples assays that detect the presence of the marker in a type of bacteria following exposure to a recombinant phage are in some embodiments more sensitive even than liquid based host range assays. Accordingly, in some embodiments herein, the "host range" of a phage or the "target bacteria" of a phage are defined by a process that comprises 1) providing a recombinant phage comprising a heterologous nucleic acid sequence encoding a marker; 2) exposing a sample to the phage; and 3) assaying for the presence of the marker in the exposed sample. This type of assay is sometimes referred to herein generally as a "marker host range assay." In some embodiments assaying for the presence of the marker in the exposed sample is by a method comprising detection of an mRNA. In some embodiments assaying for the presence of the marker in the exposed sample is by a method comprising direct detection of marker protein, such as using an antibody. In some embodiments assaying for the presence of the marker in the exposed sample is by a method comprising functional detection of marker protein. For example, if the marker protein is a luciferase the exposed sample may be exposed to luciferin and production of light may be assayed. This method may be adapted to any type of marker disclosed herein and skilled artisans are aware that many variations on the detection method of the marker may be used.

Certain variables may modify the host range of phage under certain conditions. Conditions that sustain constant bacterial growth and therefore maximal bacteriophage infectivity are seldom found in environments where methods of detecting bacteria are useful. Oligotrophic environments and competition among microorganisms force bacteria to be able to adapt quickly to rough and changing situations. A particular lifestyle composed of continuous cycles of growth and starvation is commonly referred to as feast and famine. Bacteria have developed many different mechanisms to survive in nutrient-depleted and harsh environments, varying from producing a more resistant vegetative cell to complex developmental programs. As a consequence of prolonged starvation, certain bacterial species enter a dynamic non-proliferative state in which continuous cycles of growth and death occur until 'better times' come, a.k.a. restoration of favorable growth conditions and with them the favorable infective condition.

The infectivity of bacteriophages is determined in part not only by the specificity of their encoded tail fiber recognition proteins, but also by the environmental conditions that are present. That includes but is not limited to the metabolic state of the bacterium the bacteriophage is capable of recognizing. Furthermore it includes the chemical and physical composition of the environment that the bacteriophage and the bacterium experience when the phage contacts a bacterium. Environmental factors of the solution such as but not limited to pH, osmolarity, temperature, rheological properties and others all may impact the ability of a bacteriophage to infect a bacterium.

To account for these variables, the step of exposing a sample of bacteria to a phage in the liquid clearing host-range assay and the marker host range assay may be conducted under defined conditions. The defined conditions may comprise at least one of: a defined time duration, a defined temperature, and the presence of at least one of a) at least one compound selected from carbohydrates and related compounds, b) at least compound selected from nitrogen containing compounds, c) at least compound selected from nucleic acids and related compounds, d) at least compound selected from lipid, e) at least one inorganic compound, and f) at least one organic compound.

In some embodiments the carbohydrates and related compounds are selected from sugars such as glucose, mannose, and maltose. In some embodiments the carbohydrates and related compounds are selected from carboxy sugars that are degraded by the pentose phosphate pathway, which may but need not generate more moles of NADPH per mole consumed as compared to glucose. In some embodiments the carbohydrates and related compounds are selected from compounds feeding into central metabolism, such as but not limited to ketoglutarate, D-malic acid, or pyruvic acid. In some embodiments the carbohydrates and related compounds are selected from glycerol and other carbohydrate (or other) osmoprotectants that may but need not provide osmotic support to cells that exist in a potentially weakened or damaged state in the environment. In some embodiments glycerol functions as a volume excluder that increases the efficiency of phage infection. In some embodiments the carbohydrates and related compounds are selected from sugar alcohols, such as aminoethanol.

In some embodiments the nitrogen containing compounds are selected from ammonium, other amino acid building blocks, and free amino acids. The free amino acid may be any genome encoded standard amino acid or any non-standard amino acid. In some embodiments the amino acid is selected from glutamic acid and glutamine. In some embodiments the amino acid is selected from branched chain amino acids. In some embodiments the nitrogen containing compounds are selected from degradation products of branched amino acids such as propionic acid.

In some embodiments the nucleic acids and related compounds are selected from nucleotides, nucleosides, deoxynucleotides, and deoxynucleosides. In some embodiments the nucleic acids and related compounds are selected from metabolites of the nucleotide generation pathways such as inosine.

In some embodiments the lipid compounds are selected from fatty acids and related compounds. Tween 20, 40, and 80 are converted to fatty acids upon ester hydrolysis and can also be used. In some embodiments the lipid compounds are selected from lecithin and related compounds.

In some embodiments the inorganic compounds are selected from salts, such as for example thiosulfate.

In some embodiments the organic compounds are selected from aliphatics, aromatics, heterocyclics, and non-biogenic polymers.

In some embodiments the at least one compound is selected from:

| Compound | CAS # |
| --- | --- |
| 1,2-Propanediol | 57-55-6 |
| 2-Aminoethanol | 141-43-5 |
| Glucuronamide | 3789-97-7 |
| Tyramine | 60-19-5 |
| b-Phenylethylamine | 156-28-5 |
| L-Aspartic Acid | 3792-50-5 |
| L-Proline | 147-85-3 |
| D-Alanine | 338-69-2 |
| D-Serine | 312-84-5 |
| L-Glutamic Acid | 6106-04-3 |
| L-Asparagine | 70-47-3 |
| D-Aspartic Acid | 1783-96-6 |
| L-Glutamine | 56-85-9 |
| Gly-Asp | |
| D-Threonine | 632-20-2 |

-continued

| Compound | CAS # |
| --- | --- |
| Gly-Glu | 7412-78-4 |
| L-Serine | 56-45-1 |
| L-Threonine | 72-19-5 |
| L-Alanine | 56-41-7 |
| Ala-Gly | 687-69-4 |
| Gly-Pro | 704-15-4 |
| L-Arabinose | 87-72-9 |
| N-Acetyl-D-Glucosamine | 7512-17-6 |
| D-Galactose | 59-23-4 |
| D-Trehalose | 99-20-7 |
| D-Mannose | 3458-28-4 |
| Dulcitol | 608-66-2 |
| D-Sorbitol | 50-70-4 |
| Glycerol | 56-81-5 |
| L-Fucose | 2438-80-4 |
| D,L-a-Glycerol Phosphate | 3325-00-6 |
| D-Xylose | 58-86-6 |
| D-Mannitol | 69-65-8 |
| D-Glucose-6-Phosphate | 3671-99-6 |
| D-Ribose | 50-69-1 |
| L-Rhamnose | 3615-41-6 |
| D-Fructose | 57-48-7 |
| a-D-Glucose | 50-99-7 |
| Maltose | 69-79-4 |
| D-Melibiose | 585-99-9 |
| Thymidine | 50-89-5 |
| a-Methyl-D-Galactoside | 3396-99-4 |
| a-D-Lactose | 63-42-3 |
| Lactulose | 4618-18-2 |
| Sucrose | 57-50-1 |
| Uridine | 58-96-8 |
| D-Glucose-1-Phosphate | 56401-20-8 |
| D-Fructose-6-Phosphate | 26177-86-637250-85-4 |
| b-Methyl-D-Glucoside | 709-50-2 |
| Adonitol | 488-81-3 |
| Maltotriose | 1109-28-0 |
| 2'-Deoxyadenosine | 16373-93-6 |
| Adenosine | 58-61-7 |
| m-Inositol | 87-89-8 |
| D-Cellobiose | 528-50-7 |
| Inosine | 58-63-9 |
| N-Acetyl-D-Mannosamine | 7772-94-3 |
| D-Psicose | 551-68-8 |
| L-Lyxose | 1949-78-6 |
| D-Saccharic Acid | 576-42-1 |
| Succinic Acid | 6106-21-4 |
| D-Glucuronic Acid | 14984-34-0 |
| D-Gluconic Acid | 527-07-1 |
| D,L-Lactic Acid | 312-85-6 |
| Formic Acid | 141-53-7 |
| D-Galactonic Acid-g-Lactone | 2782-07-2 |
| D,L-Malic Acid | 6915-15-7 |
| Acetic Acid | 127-09-3 |
| D-Glucosaminic Acid | 3646-68-2 |
| a-Ketoglutaric Acid | 22202-68-2 |
| a-Ketobutyric Acid | 2013-26-5 |
| m-Tartaric Acid | 147-73-9 |
| a-Hydroxyglutaric Acid-g-Lactone | 21461-84-7 |
| a-Hydroxybutyric Acid | 19054-57-0 |
| Citric Acid | 6132-04-3 |
| Fumaric Acid | 17013-01-3 |
| Bromosuccinic Acid | 923-06-8 |
| Propionic Acid | 137-40-6 |
| Mucic Acid | 526-99-8 |
| Glycolic Acid | 79-14-1 |
| Glyoxylic Acid | 563-96-2 |
| Tricarballylic Acid | 99-14-9 |
| Acetoacetic Acid | 3483-11-2 |
| Mono-Methylsuccinate | 3878-55-5 |
| D-Malic Acid | 636-61-3 |
| L-Malic Acid | 138-09-0 |
| p-Hydroxyphenyl Acetic Acid | 156-38-7 |
| m-Hydroxyphenyl Acetic Acid | 621-37-4 |
| Pyruvic Acid | 113-24-6 |
| L-Galactonic Acid-g-Lactone | 1668-08-2 |
| D-Galacturonic Acid | 91510-62-2 |
| Methylpyruvate | 600-22-6 |
| Tween 20 | 9005-64-5 |
| Tween 40 | 9005-66-7 |
| Tween 80 | 9005-65-6 |

Another approach to modify the host range detected in a host range assay is to pretreat bacteria before exposing the bacterial samples to the phage. This allows for a decoupling of steps designed to modify the state of a bacterial cell (and possibly its susceptibility to phage infection) from conditions used for the infection itself. For example the metabolic rate may be increased during a pre-incubation step which in turn may increase at least one of the replicative, transcriptive, and translative functions that influence clearing or production of a marker following infection of a bacterial cell by a phage. Furthermore, it is possible that such an incubation period also changes the surface receptor expression, or changes the composition of the cell wall of the bacterium, which may also modify whether a phage can productively infect the bacteria.

Accordingly, in some embodiments samples of bacteria are incubated in metabolic stimulation conditions before exposure to the phage for the phage host range assay. In some embodiments exposure of the cells to metabolic stimulation conditions stimulates cell division in the cells. In some embodiments exposure of the cells to metabolic stimulation conditions does not stimulate cell division in the cells. In some embodiments, exposure of the cells to metabolic stimulation conditions stimulates at least one of the replicative, transcriptive, and translative functions that influence clearing or production of a marker following infection of a bacterial cell by a phage.

As used herein, "metabolic stimulation conditions" are conditions that promote development of a microorganism metabolic state in which the microorganism is permissive to infection and maintenance of a phage life cycle and/or infection followed by expression of a marker gene produce encoded by a heterologous nucleic acid sequence in the genome of the phage. In some embodiments the microorganism prior to exposure to the metabolic stimulation conditions is not permissive to infection and maintenance of a phage life cycle. In other embodiments the microorganism prior to exposure to the metabolic stimulation conditions is in a metabolic state that reduces its susceptibility to infection and maintenance of a phage life cycle compared to a comparable microorganism grown under log phase conditions. In such embodiments exposure of the microorganism to the metabolic stimulation conditions increases the susceptibility of the microorganism to infection and maintenance of a phage life cycle. In some embodiments metabolic stimulation conditions comprise at least one of a permissive temperature, pH, Po$_2$, and nutrient combination. In some embodiments the target microbe undergoes at least one cell division under metabolic stimulation conditions. In some embodiments the target microbe does not undergo at least one cell division under metabolic stimulation conditions.

In some embodiments the sample is exposed to metabolic stimulation conditions before the sample is contacted with a phage. In some such embodiments the sample is then removed from metabolic stimulation conditions prior to contacting with a phage while in other embodiments the sample is maintained under metabolic stimulation conditions when contacted by a phage. In some embodiments the sample is exposed to a first set of metabolic stimulation conditions for a first period of time and then transferred to a second set of metabolic stimulation conditions. In some embodiments the recombinant phage is exposed to the sample while the sample is maintained under the second set of metabolic stimulation conditions. In some embodiments the sample is exposed to metabolic stimulation conditions for from 5 minutes to 24 hours before the sample is contacted by a phage. In some embodiments the sample is exposed to metabolic stimulation conditions for from 5 minutes to 6 hours before the sample is contacted by a phage. In some embodiments the sample is exposed to metabolic stimulation conditions for from 10 minutes to 6 hours before the sample is contacted by a phage. In some embodiments the sample is exposed to metabolic stimulation conditions for from 20 minutes to 6 hours before the sample is contacted by a phage. In some embodiments the sample is exposed to metabolic stimulation conditions for from 30 minutes to 6 hours before the sample is contacted by a phage. In some embodiments the sample is exposed to metabolic stimulation conditions for from 1 to 6 hours before the sample is contacted by a phage. In some embodiments the sample is exposed to metabolic stimulation conditions for from 2 to 6 hours before the sample is contacted by a phage. In some embodiments the sample is exposed to metabolic stimulation conditions for from 2 to 12 hours before the sample is contacted by a phage. In some embodiments the sample is exposed to metabolic stimulation conditions for from 3 to 12 hours before the sample is contacted by a phage. In some embodiments the sample is exposed to metabolic stimulation conditions for from 6 to 12 hours before the sample is contacted by a phage. In some embodiments the sample is exposed to metabolic stimulation conditions for from 12 to 24 hours before the sample is contacted by a phage. In some embodiments the sample is exposed to metabolic stimulation conditions for at least 10 minutes, at least 20 minutes, at least 30 minutes, at least 40 minutes, at least 50 minutes, at least 1 hour, at least 1.5 hours, or at least 2 hours.

By conducting a host range analysis under at least one embodiment of conditions described in this section it is possible to define conditions that provide a useful level of sensitivity and/or selectivity for a method of detecting target bacteria. In some embodiments the conditions used for the host range analysis are also used for methods of detecting target bacteria using the phage when those phage are used to detect target bacteria in other contexts (i.e., when testing environmental samples).

D. Methods of Detecting Target Bacteria

The recombinant phage of this disclosure are useful to detect target microbes. This disclosure provides exemplary recombinant phage and methods of making further recombinant phage. This disclosure also defines the target bacteria of certain disclosed recombinant phage and provides methods of identifying the target bacteria of any phage, including any recombinant phage. Accordingly, this disclosure enables methods of detecting target microbes using recombinant phage. By, among other things, enabling a detailed characterization of the target bacteria of the recombinant phage this disclosure in certain embodiments provides useful methods not available in the prior art.

The methods are broadly applicable and in view of the teachings of this disclosure skilled artisans will understand how to apply the methods to detect any type of archaea and/or bacteria. In some embodiments the archaea is a Euryarchaeota. In some embodiments the archaea is a Crenarcheota. In some embodiments the bacteria is a member of a phyla selected from Actinobacteria, Aquificae, Armatimonadetes, Bacteroidetes, Caldiserica, Chlamydiae, Chloroflexi, Chrysiogenetes, Cyanobacteria, Deferribacteres, Deinococcus-Thermus, Dictyoglomi, Elusimicrobia, Fibrobacteres, Firmicutes, Fusobacteria, Gemmatimonadetes, Nitrospirae, Planctomycetes, Proteobacteria, Spirochaetes, Synergistets, Tenericutes, Thermodesulfobacteria, Thermotogae. In some embodiments the bacteria is at least one Firmicutes selected from *Bacillus, Listeria, Staphylococcus*. In some embodiments the bacteria is at least one Proteobacteria selected from *Acidobacillus, Aeromonas, Burkholderia, Neisseria, Shewanella, Citrobacter, Enterobacter, Erwinia, Escherichia, Klebsiella, Kluyvera, Morganella, Salmonella, Shigella, Yersinia, Coxiella, Rickettsia, Legionella, Avibacterium, Haemophilus, Pasteurella, Acinetobacter, Moraxella, Pseudomonas, Vibrio, Xanthomonas*. In some embodiments the bacteria is at least one Tenericutes selected from *Mycoplasma, Spiroplasma*, and *Ureaplasma*.

Common bacterial contaminates of food that are detected using the phage and methods disclosed herein include, without limitation, *Salmonella, E. coli* (including without limitation pathogenic *E. coli, E. coli* O157:H7, Shiga-toxin producing *E. coli, E. coli* O26, O *E. coli* 111, *E. coli* O103, *E. coli* O121, *E. coli* O45 and *E. coli* O145), coliform bacteria (which include without limitation, *Citrobacter, Enterobacter*, Hathia, *Klebsiella, Serratia*), *Shigella, Listeria, Clostridium* (including *Clostridium botulinum* and *Clostridium perfringens*), *Vibrio* (including *Vibrio cholera* and *Vibrio vulnificus*), Enterobacteriacae, *Staphylococcus* (including *Staphylococcus aureus* and *Staphylococcus epidermis*), *Bacillus* (including *Bacillus cereus*), *Campylobacter* (including *Campylobacter jejuni*), *Pseudomonas, Streptococcus, Acinetobacter, Klebsiella, Campylobacter*, and *Yersinia*.

In certain embodiments the methods comprise providing a sample; exposing the sample to a first type of phage capable of infecting a first set of target bacteria and comprising a heterologous nucleic acid sequence encoding a first marker; exposing the sample to a second type of phage capable of infecting a second set of target bacteria and comprising a heterologous nucleic acid sequence encoding a second marker; and assaying for the presence of the first marker and the second marker in the exposed sample. In some embodiments, detection of the first marker in the sample indicates the presence of bacteria of the first set of target bacteria in the sample. In some embodiments, detection of the second marker in the sample indicates the presence of bacteria of the second set of target bacteria in the sample. In some embodiments the first marker and the second marker are the same, and detection of the marker in the sample indicates the presence of bacteria of at least one of the first set of target bacteria and the second set of target bacteria in the sample.

In some embodiments, the first set of target bacteria and the second set of target bacteria independently comprise at least two species of a single genus of bacteria. In some embodiments, the first set of target bacteria and the second set of target bacteria independently comprise at least three species of a single genus of bacteria. In some embodiments, the first set of target bacteria and the second set of target bacteria independently comprise at least four species of a single genus of bacteria. In some embodiments, the single genus of bacteria is *Listeria*. In some embodiments, the first set of target bacteria and the second set of target bacteria comprise at least one species of bacteria in common. In some embodiments, the first set of target bacteria and the second set of target bacteria comprise at least two species of bacteria in common. In some embodiments, the first set of target bacteria and the second set of target bacteria comprise at least three species of bacteria in common. In some embodiments, the first set of target bacteria and the second set of target bacteria comprise at least four species of bacteria in common. In some embodiments, the species of *Listeria* are selected from *Listeria*

*innocua, Listeria monocytogenes, Listeria seeligeri, Listeria ivanovii, Listeria grayi, Listeria marthii, Listeria rocourti* and *Listeria welshimeri*. In some embodiments, the species of *Listeria* are selected from *Listeria innocua, Listeria monocytogenes, Listeria seeligeri*, and *Listeria welshimeri*.

In some embodiments, the target bacteria comprise at least one sig B allelotype of *Listeria innocua* selected from 11, 22, 37, and 56. In some embodiments, the target bacteria comprise at least four allelotypes of *Listeria innocua*. In some embodiments, the at least four allelotypes of *Listeria innocua* are 11, 22, 37, and 56.

In some embodiments, the target bacteria comprise at least one ribotype of *Listeria monocytogenes* selected from DUP-10142, DUP-1030A, DUP-1030B, DUP-1038B, DUP-1039A, DUP-1039B, DUP-1039C, DUP-1042A, DUP-1042B, DUP-1042C, DUP-1043A, DUP-1044A, DUP-1044B, DUP-1044E, DUP-1045B, DUP-1052A, DUP-1053A, DUP-1062A, and DUP-1062D. In some embodiments, the target bacteria comprise at least nineteen ribotypes of *Listeria monocytogenes*. In some embodiments, the at least nineteen ribotypes of *Listeria monocytogenes* are DUP-10142, DUP-1030A, DUP-1030B, DUP-1038B, DUP-1039A, DUP-1039B, DUP-1039C, DUP-1042A, DUP-1042B, DUP-1042C, DUP-1043A, DUP-1044A, DUP-1044B, DUP-1044E, DUP-1045B, DUP-1052A, DUP-1053A, DUP-1062A, and DUP-1062D.

In some embodiments, the target bacteria comprise at least one sig B allelotype of *Listeria seeligeri* selected from 3, 20, 24, and 35. In some embodiments, the target bacteria comprise at least four allelotypes of *Listeria seeligeri*. In some embodiments, the at least four allelotypes of *Listeria seeligeri* are 3, 20, 24, and 35.

In some embodiments, the target bacteria comprise at least one sig B allelotype of *Listeria welshimeri* selected from 15, 27, 32, and 89. In some embodiments, the target bacteria comprise at least four allelotypes of *Listeria welshimeri*. In some embodiments, the at least four allelotypes of *Listeria welshimeri* are 15, 27, 32, and 89.

In some embodiments, the first set of target bacteria are all members of the same genus. In some embodiments, the second set of target bacteria are all members of the same genus. In some embodiments, all of the target bacteria are *Listeria*. In some embodiments, the target bacteria do not include at least one of *Bacillus cereus, Bacillus megaterium, Bacillus subtilis, Enterococcus durans, Enterococcus faceium, Enterococcus hirae, Kocuria varians, Kurthia gibsonii, Kurthia zopfii, Rhodococcus equi, Staphylococcus aureus, Staphylococcus epidermidis, Staphylococcus saprophyticus, Streptococcus equi, Streptococcus galloyticus, Lactobacillus casei, Lactobacillus buchneri, Lactobacillus lactus, Lactobacillus fermentum, Micrococcus lutues, Pseudomonas protogens, Pseudomonas florescens, Aeromonas* sp, *Serratia liquefaciens, Serratia proteamaculans, Serratia liquefaciens*, Bacillaceae bacterium, *Serratia proteamaculans, Pseudomonas florescens, Pseudomonas poae, Pseudomonas* sp, *Pseudomonas fragi, Providencia alcalifaciens, Serratia* sp, *Serratia grimesii, Hafnia* sp., *Serratia proteamaculans, Pseudomonas florescens, Chryseobacterium* sp., *Pseudomonas fragi*, and Enterobacteriaceae. In some embodiments, the target bacteria do not include *Bacillus cereus, Bacillus megaterium, Bacillus subtilis, Enterococcus durans, Enterococcus faceium, Enterococcus hirae, Kocuria varians, Kurthia gibsonii, Kurthia zopfii, Rhodococcus equi, Staphylococcus aureus, Staphylococcus epidermidis, Staphylococcus saprophyticus, Streptococcus equi, Streptococcus galloyticus, Lactobacillus casei, Lactobacillus buchneri, Lactobacillus lactus, Lactobacillus fermentum, Micrococcus lutues, Pseudomonas protogens, Pseudomonas florescens, Aeromonas* sp, *Serratia liquefaciens, Serratia proteamaculans, Serratia liquefaciens*, Bacillaceae bacterium, *Serratia proteamaculans, Pseudomonas florescens, Pseudomonas poae, Pseudomonas* sp, *Pseudomonas fragi, Providencia alcalifaciens, Serratia* sp, *Serratia grimesii, Hafnia* sp., *Serratia proteamaculans, Pseudomonas florescens, Chryseobacterium* sp., *Pseudomonas fragi*, and Enterobacteriaceae.

In some embodiments, the methods further comprise exposing the sample to a third type of phage capable of infecting a third set of target bacteria and comprising a heterologous nucleic acid sequence encoding a third marker. In some embodiments, the methods further comprise exposing the sample to a fourth type of phage capable of infecting a fourth set of target bacteria and comprising a heterologous nucleic acid sequence encoding a fourth marker. In some embodiments, the methods further comprise exposing the sample to a fifth type of phage capable of infecting a fifth set of target bacteria and comprising a heterologous nucleic acid sequence encoding a fifth marker. In some embodiments, the methods further comprise exposing the sample to a sixth type of phage capable of infecting a sixth set of target bacteria and comprising a heterologous nucleic acid sequence encoding a sixth marker. In some embodiments, the methods further comprise exposing the sample to a seventh type of phage capable of infecting a seventh set of target bacteria and comprising a heterologous nucleic acid sequence encoding a seventh marker. In some embodiments, the methods further comprise exposing the sample to a eighth type of phage capable of infecting a eighth set of target bacteria and comprising a heterologous nucleic acid sequence encoding a eighth marker. In some embodiments, the methods further comprise exposing the sample to a ninth type of phage capable of infecting a ninth set of target bacteria and comprising a heterologous nucleic acid sequence encoding a ninth marker. In some embodiments, the methods further comprise exposing the sample to ten or more types of phage capable of infecting ten or more sets of target bacteria and comprising a heterologous nucleic acid sequences encoding ten or more markers. In some embodiments that utilize three or more types of phage, all of the three or more markers are different. In some embodiments that utilize three or more types of phage, all of the three or more markers are the same. In some embodiments that utilize three or more types of phage, two, three, four, five, six, seven, eight, or nine of the markers are the same.

In some embodiments, at least one type of phage used in the method is selected from A511, P100, LP40, LP48, LP99, LP101, LP124, LP125, and LP143, and derivatives thereof. In some embodiments, every type of phage used in the method is selected from A511, P100, LP40, LP48, LP99, LP101, LP124, LP125, and LP143, and derivatives thereof.

In some embodiments, the first marker is a screenable marker. In some embodiments, the first marker is a luciferase. In some embodiments, the luciferase is at least 70% identical to SEQ ID NO: 2. In some embodiments, the luciferase is at least 70% identical to SEQ ID NO: 4.

In some embodiments, the first type of phage is selected from LP48::ffluc, LP99::ffluc, LP101::ffluc, LP124::ffluc, LP125::ffluc, LP143::ffluc, A511::ffluc, and P100::ffluc, and derivatives of those phage. In some embodiments, the first type of phage is selected from LP40::nluc, LP124::nluc, LP125::nluc, A511::nluc, and P100::nluc.

In some embodiments, the second marker is a screenable marker. In some embodiments, the second marker is a luciferase. In some embodiments, the luciferase is at least 70% identical to SEQ ID NO: 2. In some embodiments, the luciferase is at least 70% identical to SEQ ID NO: 4.

In some embodiments, the second type of phage is selected from LP48::ffluc, LP99::ffluc, LP101::ffluc, LP124::ffluc, LP125::ffluc, LP143::ffluc, A511::ffluc, and P100::ffluc. In some embodiments, the second type of phage is selected from LP40::nluc, LP124::nluc, LP125::nluc, A511::nluc, and P100::nluc.

In some embodiments, the method comprises exposing the sample to the first type of phage and the second type of phage at the same time.

In some embodiments, the sample is an environmental sample.

In some embodiments, the first marker is detected in the sample, indicating the presence of bacteria of the first set of target bacteria in the sample. In some embodiments, the second marker is detected in the sample, indicating the presence of bacteria of the second set of target bacteria in the sample. In some embodiments, the first marker and the second marker are the same, and the marker is detected in the sample, indicating the presence of bacteria of at least one of the first set of target bacteria and the second set of target bacteria in the sample.

In some embodiments, the false positive rate of the assay against environmental samples is 5% or less, 4% or less, 3% or less, 2% or less, or 1% or less. In some embodiments, the false negative rate of the assay against environmental samples is 5% or less, 4% or less, 3% or less, 2% or less, or 1% or less.

In some embodiments, the sample is exposed to metabolic stimulation conditions before it is exposed to the phage.

In some embodiments, the methods further comprise incubating the sample under metabolic stimulation conditions for a period of time before exposing the sample to the phage capable of infecting target bacteria.

In certain embodiments the methods comprise providing a sample; exposing the sample to at least one recombinant *Listeria* phage comprising a heterologous nucleic acid sequence encoding a marker, the recombinant *Listeria* phage selected from recombinant LP40 and derivatives thereof, recombinant LP48 and derivatives thereof, recombinant LP99 and derivatives thereof, recombinant LP101 and derivatives thereof, recombinant LP124 and derivatives thereof, recombinant LP125 and derivatives thereof, and recombinant LP143 and derivatives thereof; and assaying for the presence of the marker in the exposed sample. In some embodiments, the methods further comprise exposing the sample to at least one recombinant *Listeria* phage comprising a heterologous nucleic acid sequence encoding a marker, the recombinant *Listeria* phage selected from recombinant A511 and recombinant P100. In some embodiments, detection of the marker in the sample indicates the presence of *Listeria* in the sample.

In some embodiments, target bacteria of the recombinant *Listeria* phage comprise at least one species of *Listeria* selected from *Listeria innocua, Listeria monocytogenes, Listeria seeligeri, Listeria ivanovii, Listeria grayi, Listeria marthii, Listeria rocourti*, and *Listeria welshimeri*. In some embodiments, detection of the marker in the sample indicates the presence of the at least one species of *Listeria* selected from *Listeria innocua, Listeria monocytogenes, Listeria seeligeri, Listeria ivanovii, Listeria grayi, Listeria marthii, Listeria* rocourti, and *Listeria welshimeri* in the sample.

In some embodiments, target bacteria of the *Listeria* phage comprise at least one species of *Listeria* selected from *Listeria innocua, Listeria monocytogenes, Listeria* seeligeri, and *Listeria welshimeri*. In some embodiments, detection of the marker in the sample indicates the presence of the at least one species of *Listeria* selected from *Listeria innocua, Listeria monocytogenes, Listeria seeligeri*, and *Listeria welshimeri* in the sample.

In some embodiments, target bacteria of the *Listeria* phage comprise at least one sig B allelotype of *Listeria innocua* selected from 11, 22, 37, and 56, and detection of the marker in the sample indicates the presence of at least one sig B allelotype of *Listeria* innocua selected from 11, 22, 37, and 56. In some embodiments, the at least one *Listeria* phage is capable of infecting *Listeria innocua* sig B allelotypes 11, 22, 37, and 56.

In some embodiments, target bacteria of the *Listeria* phage comprise at least one ribotype of *Listeria monocytogenes* selected from DUP-10142, DUP-1030A, DUP-1030B, DUP-1038B, DUP-1039A, DUP-1039B, DUP-1039C, DUP-1042A, DUP-1042B, DUP-1042C, DUP-1043A, DUP-1044A, DUP-1044B, DUP-1044E, DUP-1045B, DUP-1052A, DUP-1053A, DUP-1062A, and DUP-1062D; and detection of the marker in the sample indicates the presence of at least one ribotype of *Listeria monocytogenes* selected from DUP-10142, DUP-1030A, DUP-1030B, DUP-1038B, DUP-1039A, DUP-1039B, DUP-1039C, DUP-1042A, DUP-1042B, DUP-1042C, DUP-1043A, DUP-1044A, DUP-1044B, DUP-1044E, DUP-1045B, DUP-1052A, DUP-1053A, DUP-1062A, and DUP-1062D. In some embodiments, target bacteria of the *Listeria* phage comprise *Listeria monocytogenes* ribotypes DUP-10142, DUP-1030A, DUP-1030B, DUP-1038B, DUP-1039A, DUP-1039B, DUP-1039C, DUP-1042A, DUP-1042B, DUP-1042C, DUP-1043A, DUP-1044A, DUP-1044B, DUP-1044E, DUP-1045B, DUP-1052A, DUP-1053A, DUP-1062A, and DUP-1062D.

In some embodiments, target bacteria of the *Listeria* phage comprise at least one sig B allelotype of *Listeria seeligeri* selected from 3, 20, 24, and 35, and detection of the marker in the sample indicates the presence of at least one sig B allelotype of *Listeria* seeligeri selected from 3, 20, 24, and 35. In some embodiments, target bacteria of the *Listeria* phage comprise *Listeria seeligeri* sig B allelotypes 3, 20, 24, and 35.

In some embodiments, target bacteria of the *Listeria* phage comprise at least one sig B allelotype of *Listeria welshimeri* selected from 15, 27, 32, and 89, and detection of the marker in the sample indicates the presence of at least one sig B allelotype of *Listeria* welshimeri selected from 15, 27, 32, and 89. In some embodiments, target bacteria of the *Listeria* phage comprise *Listeria welshimeri* sig B allelotypes 15, 27, 32, and 89.

In some embodiments, the target bacteria comprise at least two species of *Listeria* selected from *Listeria innocua, Listeria monocytogenes, Listeria seeligeri*, and *Listeria* welshimeri. In some embodiments, the target bacteria comprise at least three species of *Listeria* selected from *Listeria innocua, Listeria monocytogenes, Listeria seeligeri*, and *Listeria* welshimeri. In some embodiments, the target bacteria comprise at least four species of *Listeria* selected from *Listeria innocua, Listeria monocytogenes, Listeria seeligeri, Listeria ivanovii, Listeria grayi, Listeria marthii, Listeria rocourti*, and *Listeria welshimeri*. In some embodiments, the target bacteria do not include at least one of *Bacillus cereus, Bacillus megaterium, Bacillus subtilis, Enterococcus durans, Enterococcus faceium, Enterococcus hirae, Kocuria varians, Kurthia gibsonii, Kurthia zopfii, Rhodococcus equi, Staphylococcus aureus, Staphylococcus epidermidis, Staphylococcus saprophyticus, Streptococcus equi, Streptococcus galloyticus, Lactobacillus casei, Lactobacillus buchneri, Lactobacillus lactus, Lactobacillus fermentum, Micrococcus lutues, Pseudomonas protogens, Pseudomonas florescens, Aeromonas sp, Serratia liquefaciens, Serratia proteamaculans, Serratia liquefaciens*, Bacillaceae bacterium, *Serratia proteamaculans, Pseudomonas florescens, Pseudomonas* poae, *Pseudomonas* sp, *Pseudomonas fragi*, *Providencia alcalifaciens*, *Serratia* sp, *Serratia grimesii*, *Hafnia* sp., *Serratia proteamaculans*, *Pseudomonas florescens*, *Chryseobacterium* sp., *Pseudomonas fragi*, and Enterobacteriaceae. In some embodiments, the target bacteria do not include *Bacillus cereus*, *Bacillus megaterium*, *Bacillus subtilis*, *Enterococcus durans*, *Enterococcus faceium*, *Enterococcus hirae*, *Kocuria varians*, *Kurthia gibsonii*, *Kurthia zopfii*, *Rhodococcus equi*, *Staphylococcus aureus*, *Staphylococcus epidermidis*, *Staphylococcus saprophyticus*, *Streptococcus equi*, *Streptococcus galloyticus*, *Lactobacillus casei*, *Lactobacillus buchneri*, *Lactobacillus lactus*, *Lactobacillus fermentum*, *Micrococcus lutues*, *Pseudomonas protogens*, *Pseudomonas florescens*, *Aeromonas* sp, *Serratia liquefaciens*, *Serratia proteamaculans*, *Serratia liquefaciens*, Bacillaceae bacterium, *Serratia proteamaculans*, *Pseudomonas florescens*, *Pseudomonas poae*, *Pseudomonas* sp, *Pseudomonas fragi*, *Providencia alcalifaciens*, *Serratia* sp, *Serratia grimesii*, *Hafnia* sp., *Serratia proteamaculans*, *Pseudomonas florescens*, *Chryseobacterium* sp., *Pseudomonas fragi*, and Enterobacteriaceae.

In some embodiments, the marker is a screenable marker. In some embodiments, the marker is a luciferase. In some embodiments, the luciferase is at least 70% identical to SEQ ID NO: 2. In some embodiments, the luciferase is at least 70% identical to SEQ ID NO: 4. In some embodiments, the phage is selected from LP48::ffluc, LP99::ffluc, LP101::ffluc, LP124::ffluc, LP125::ffluc, LP143::ffluc, A511::ffluc, and P100::ffluc. In some embodiments, the phage is selected from LP::40::nluc, LP124::nluc, LP125::nluc, A511::nluc, and P100::nluc.

In some embodiments, the sample is an environmental sample.

In some embodiments, the marker is detected in the sample, indicating the presence of bacteria of the first set of target bacteria in the sample.

In some embodiments, the false positive rate of the assay against environmental samples is 5% or less, 4% or less, 3% or less, 2% or less, or 1% or less. In some embodiments, the false negative rate of the assay against environmental samples is 5% or less, 4% or less, 3% or less, 2% or less, or 1% or less. In some embodiments, the sample is exposed to metabolic stimulation conditions before the sample is exposed to the phage.

In some embodiments the sample is exposed to the phage for a period of time before assaying for the presence of a marker in the exposed sample is conducted. In some embodiments the period of time is from 1 minute to 24 hours, from 5 minutes to 12 hours, from 5 minutes to 6 hours, from 5 minutes to 3 hours, from 5 minutes to 2 hours, from 5 minutes to 1 hour, from 5 minutes to 50 minutes, from 5 minutes to 40 minutes, from 5 minutes to 30 minutes, from 5 minutes to 20 minutes, or from 5 minutes to 10 minutes. In some embodiments the period of time is from 1 to 2 hours, from 1 to 4 hours, or from 2 to 4 hours. In some embodiments the period of time is for at least 1 minute, at least 5 minutes, at least 10 minutes, at least 20 minutes, at least 30 minutes, at least 40 minutes, at least 50 minutes, or at least 1 hour.

In some embodiments any phage and/or parts of phage in the exposed sample are substantially removed before the assaying for the presence of a marker in the exposed sample is conducted.

In some embodiments of the methods of this disclosure, the methods further comprise comparing a detected level of marker in a test sample to at least one of a positive control and a negative control. The positive and/or negative control may be used to calibrate the assay including for the purpose of defining a positive result and/or a negative result.

E. Compositions

The methods of assaying phage host range provided herein allow, in certain embodiments, for the characterization of the host range of phage—and thus definition of target bacteria for phage—at a resolution not provided by the prior art. One use of the methods and of phage characterized by the methods is to identify useful combinations of phage that may be used together is a system to detect target bacteria. In some embodiments such systems provide phage separately and the phage are then mixed before or during an assay. Alternatively, such systems comprise useful mixtures of phage, such as phage provided in a buffer for use in an assay. Compositions comprising useful combinations of phage are also, necessarily, produced during the assay in several embodiments. Accordingly, this disclosure also provides compositions that comprise phage.

In some embodiments the composition comprises: at least one recombinant *Listeria* phage comprising a heterologous nucleic acid sequence encoding a marker, the recombinant *Listeria* phage selected from recombinant LP40 and derivatives thereof, recombinant LP48 and derivatives thereof, recombinant LP99 and derivatives thereof, recombinant LP101 and derivatives thereof, recombinant LP124 and derivatives thereof, recombinant LP125 and derivatives thereof, and recombinant LP143 and derivatives thereof; and at least one non-phage component selected from at least one of a) at least one compound selected from carbohydrates and related compounds, b) at least compound selected from nitrogen containing compounds, c) at least compound selected from nucleic acids and related compounds, d) at least compound selected from lipid, e) at least one inorganic compound, and f) at least one organic compound. In some embodiments, the composition comprises at least one of 1,2-Propanediol, 2-Aminoethanol, Glucuronamide, Tyramine, b-Phenylethylamine, L-Aspartic Acid, L-Proline, D-Alanine, D-Serine, L-Glutamic Acid, L-Asparagine, D-Aspartic Acid, L-Glutamine, Gly-Asp, D-Threonine, Gly-Glu, L-Serine, L-Threonine, L-Alanine, Ala-Gly, Gly-Pro, L-Arabinose, N-Acetyl-D-Glucosamine, D-Galactose, D-Trehalose, D-Mannose, Dulcitol, D-Sorbitol, Glycerol, L-Fucose, D,L-a-Glycerol, Phosphate, D-Xylose, D-Mannitol, D-Glucose-6-Phosphate, D-Ribose, L-Rhamnose, D-Fructose, a-D-Glucose, Maltose, D-Melibiose, Thymidine, a-Methyl-D-Galactoside, a-D-Lactose, Lactulosem Sucrose, Uridine, D-Glucose-1-Phosphate, D-Fructose-6-Phosphate, b-Methyl-D-Glucoside, Adonitol, Maltotriose, 2'-Deoxyadenosine, Adenosine, m-Inositol, D-Cellobiose, Inosine, N-Acetyl-D-Mannosamine, D-Psicose, L-Lyxose, D-Saccharic Acid, Succinic Acid, D-Glucuronic Acid, D-Gluconic Acid, D,L-Lactic Acid, Formic Acid, D-Galactonic Acid-g-Lactone, D,L-Malic Acid, Acetic Acid, D-Glucosaminic Acid, a-Ketoglutaric Acid, a-Ketobutyric Acid, m-Tartaric Acid, a-Hydroxyglutaric Acid-g-Lactone, a-Hydroxybutyric Acid, Citric Acid, Fumaric Acid, Bromosuccinic Acid, Propionic Acid, Mucic Acid, Glycolic Acid, Glyoxylic Acid, Tricarballylic Acid, Acetoacetic Acid, Mono-Methylsuccinate, D-Malic Acid, L-Malic Acid, p-Hydroxyphenyl Acetic Acid, m-Hydroxyphenyl Acetic Acid, Pyruvic Acid, L-Galactonic Acid-g-Lactone, D-Galacturonic Acid, Methylpyruvate, Tween 20, Tween 40, Tween 80.

In some embodiments the composition comprises: at least two recombinant *Listeria* phage comprising a heterologous nucleic acid sequence encoding a marker, the recombinant *Listeria* phage selected from recombinant A511 and derivatives thereof, recombinant P100 and derivatives thereof, recombinant LP40 and derivatives thereof, recombinant LP44 and derivatives thereof, recombinant LP48 and derivatives thereof, recombinant LP99 and derivatives thereof, recombinant LP101 and derivatives thereof, recombinant LP124 and derivatives thereof, recombinant LP125 and derivatives thereof, and recombinant LP143 and derivatives thereof. In some embodiments the composition further comprises at least one non-phage component selected from at least one of a) at least one compound selected from carbohydrates and related compounds, b) at least compound selected from nitrogen containing compounds, c) at least compound selected from nucleic acids and related compounds, d) at least compound selected from lipid, e) at least one inorganic compound, and f) at least one organic compound. In some embodiments the composition comprises at least one of 1,2-Propanediol, 2-Aminoethanol, Glucuronamide, Tyramine, b-Phenylethylamine, L-Aspartic Acid, L-Proline, D-Alanine, D-Serine, L-Glutamic Acid, L-Asparagine, D-Aspartic Acid, L-Glutamine, Gly-Asp, D-Threonine, Gly-Glu, L-Serine, L-Threonine, L-Alanine, Ala-Gly, Gly-Pro, L-Arabinose, N-Acetyl-D-Glucosamine, D-Galactose, D-Trehalose, D-Mannose, Dulcitol, D-Sorbitol, Glycerol, L-Fucose, D,L-a-Glycerol, Phosphate, D-Xylose, D-Mannitol, D-Glucose-6-Phosphate, D-Ribose, L-Rhamnose, D-Fructose, a-D-Glucose, Maltose, D-Melibiose, Thymidine, a-Methyl-D-Galactoside, a-D-Lactose, Lactulosem Sucrose, Uridine, D-Glucose-1-Phosphate, D-Fructose-6-Phosphate, b-Methyl-D-Glucoside, Adonitol, Maltotriose, 2'-Deoxyadenosine, Adenosine, m-Inositol, D-Cellobiose, Inosine, N-Acetyl-D-Mannosamine, D-Psicose, L-Lyxose, D-Saccharic Acid, Succinic Acid, D-Glucuronic Acid, D-Gluconic Acid, D,L-Lactic Acid, Formic Acid, D-Galactonic Acid-g-Lactone, D,L-Malic Acid, Acetic Acid, D-Glucosaminic Acid, a-Ketoglutaric Acid, a-Ketobutyric Acid, m-Tartaric Acid, a-Hydroxyglutaric Acid-g-Lactone, a-Hydroxybutyric Acid, Citric Acid, Fumaric Acid, Bromosuccinic Acid, Propionic Acid, Mucic Acid, Glycolic Acid, Glyoxylic Acid, Tricarballylic Acid, Acetoacetic Acid, Mono-Methylsuccinate, D-Malic Acid, L-Malic Acid, p-Hydroxyphenyl Acetic Acid, m-Hydroxyphenyl Acetic Acid, Pyruvic Acid, L-Galactonic Acid-g-Lactone, D-Galacturonic Acid, Methylpyruvate, Tween 20, Tween 40, Tween 80.

In some embodiments the systems or compositions comprise at least two recombinant *Listeria* phage selected from recombinant LP40 and derivatives thereof, recombinant LP48 and derivatives thereof, recombinant LP99 and derivatives thereof, recombinant LP101 and derivatives thereof, recombinant LP124 and derivatives thereof, recombinant LP125 and derivatives thereof, and recombinant LP143 and derivatives thereof. In some embodiments the systems or compositions comprise at least three, four, five, six, seven, eight, nine, or more recombinant *Listeria* phage, selected from recombinant LP040 and derivatives thereof, recombinant LP048 and derivatives thereof, recombinant LP99 and derivatives thereof, recombinant LP101 and derivatives thereof, recombinant LP124 and derivatives thereof, recombinant LP125 and derivatives thereof, and recombinant LP143 and derivatives thereof.

F. Articles of Manufacture

In some embodiments the system and or composition comprising at least one recombinant *Listeria* phage comprising a heterologous nucleic acid sequence encoding a marker is provided in the form of an article of manufacture. Such an article of manufacture is useful, for example, as a means to provide the at least one nant *Listeria* phage comprising a heterologous nucleic acid sequence encoding a marker in combination with other components that can be used together to perform an assay to detect a target bacteria. In some embodiments the article of manufacture comprises at least one container comprising the at least one recombinant *Listeria* phage comprising a heterologous nucleic acid sequence encoding a marker.

In some embodiments the article of manufacture comprises at least one container comprising at least two recombinant *Listeria* phage selected from recombinant LP40 and derivatives thereof, recombinant LP48 and derivatives thereof, recombinant LP99 and derivatives thereof, recombinant LP101 and derivatives thereof, recombinant LP124 and derivatives thereof, recombinant LP125 and derivatives thereof, and recombinant LP143 and derivatives thereof. In some embodiments the systems or compositions comprise at least three, four, five, six, seven, eight, nine, or more recombinant *Listeria* phage, selected from recombinant LP40 and derivatives thereof, recombinant LP48 and derivatives thereof, recombinant LP99 and derivatives thereof, recombinant LP101 and derivatives thereof, recombinant LP124 and derivatives thereof, recombinant LP125 and derivatives thereof, and recombinant LP143 and derivatives thereof. In some embodiments in which the article of manufacture comprises more than one phage all of the phage are provided in separate containers. In other embodiments two or more of the phage are provided in combination in a single container.

In some embodiments the article of manufacture further comprises a solution comprising at least one non-phage component selected from at least one of a) at least one compound selected from carbohydrates and related compounds, b) at least compound selected from nitrogen containing compounds, c) at least compound selected from nucleic acids and related compounds, d) at least compound selected from lipid, e) at least one inorganic compound, and f) at least one organic compound. In some embodiments, the article of manufacture comprises a container comprising a solution comprising at least one of 1,2-Propanediol, 2-Aminoethanol, Glucuronamide, Tyramine, b-Phenylethylamine, L-Aspartic Acid, L-Proline, D-Alanine, D-Serine, L-Glutamic Acid, L-Asparagine, D-Aspartic Acid, L-Glutamine, Gly-Asp, D-Threonine, Gly-Glu, L-Serine, L-Threonine, L-Alanine, Ala-Gly, Gly-Pro, L-Arabinose, N-Acetyl-D-Glucosamine, D-Galactose, D-Trehalose, D-Mannose, Dulcitol, D-Sorbitol, Glycerol, L-Fucose, D,L-a-Glycerol, Phosphate, D-Xylose, D-Mannitol, D-Glucose-6-Phosphate, D-Ribose, L-Rhamnose, D-Fructose, a-D-Glucose, Maltose, D-Melibiose, Thymidine, a-Methyl-D-Galactoside, a-D-Lactose, Lactulosem Sucrose, Uridine, D-Glucose-1-Phosphate, D-Fructose-6-Phosphate, b-Methyl-D-Glucoside, Adonitol, Maltotriose, 2'-Deoxyadenosine, Adenosine, m-Inositol, D-Cellobiose, Inosine, N-Acetyl-D-Mannosamine, D-Psicose, L-Lyxose, D-Saccharic Acid, Succinic Acid, D-Glucuronic Acid, D-Gluconic Acid, D,L-Lactic Acid, Formic Acid, D-Galactonic Acid-g-Lactone, D,L-Malic Acid, Acetic Acid, D-Glucosaminic Acid, a-Ketoglutaric Acid, a-Ketobutyric Acid, m-Tartaric Acid, a-Hydroxyglutaric Acid-g-Lactone, a-Hydroxybutyric Acid, Citric Acid, Fumaric Acid, Bromosuccinic Acid, Propionic Acid, Mucic Acid, Glycolic Acid, Glyoxylic Acid, Tricarballylic Acid, Acetoacetic Acid, Mono-Methylsuccinate, D-Malic Acid, L-Malic Acid, p-Hydroxyphenyl Acetic Acid, m-Hydroxyphenyl Acetic Acid, Pyruvic Acid, L-Galactonic Acid-g-Lactone, D-Galacturonic Acid, Methylpyruvate, Tween 20, Tween 40, Tween 80. In some embodiments at least one recombinant *Listeria* phage present in the article of manufacture is present in the solution comprising at least one non-phage component. In other embodiments the phage and solution are provided separately and may, for example, be combined by a user.

EXAMPLES

The following examples serve to more fully describe the manner of using certain embodiments of the invention disclosed herein. These examples are presented for illustrative purposes and should not serve to limit the true scope of the invention disclosed herein.

Example 1

*Listeria* Panel

A bacterial strain panel comprising a diverse combination of *Listeria* species and subspecies was selected for characterization of *Listeria* phages. The panel comprises strains that have been isolated from various geographic and environmental niches including food processing plants and food retail locations. Special consideration was given to obtain bacterial strains from food processing environments with sufficient geographic separation to maximize natural variation within the bacterial strain panel.

The panel as assembled initially contained 272 *Listeria* isolates and represents the four major species of *Listeria* (*L. monocytogenes*, *L. innocua*, *L. welshimeri* and *L. seeligeri*) (Table 1). Within each species the panel comprises representative isolates of various subspecies to ensure sufficient depth of coverage to allow for meaningful extrapolation of the data to the subspecies in general. The selection of strains for the bacterial panel were based on the prevalence of particular strains within the food environment and associated with human disease. Environmental screening of retail food stores used allelotyping to identify the most commonly identified *Listeria* subspecies and identified that certain allelotypes were often highly represented among the population of species identified. (Williams, S. K. et al., J Food Prot 74, 63-77 (2011); Sauders, B. D. et al., Appl Environ Microbiol 78, 4420-4433 (2012).) Ten (10) *L. monocytogenes* strains from each of the most common ribotypes represented from isolates from food and human disease were selected for the collection. These populations are largely overlapping and have a strong correlation in prevalence and, therefore, represent the strains most useful to identify in food processing plants. When looking at breadth of coverage of *L. monocytogenes* strains based on ribotypes isolated in human disease and food processing plants, the panel as constructed represents ~86% and 91% coverage, respectively. The purpose for selecting 10 strains of each *L. monocytogenes* ribotype was to allow for the identification of natural variation within a group to ensure a reasonably complete coverage of the *L. monocytogenes* species.

To expand beyond *L. monocytogenes* and cover other species within the genus additional species and subspecies variation was considered to select further strains for the panel. Again, focus was placed on the species and subspecies that are commonly identified in food processing plants. Ten (10) isolates representing each of the most common allelotypes of *L. welshimeri*, *L. innocua* and *L. seeligeri* were selected. The panel as constructed covers 96% of the *L. innocua*, 98% of the *L. selelingri*, and 100% of the *L. welshimeri* ribotypes identified by Saunders et al. and provides an accurate representation of the *Listeria* genus. The *Listeria* host panel as assembled thus serves as a tool for the analysis of the host range of any bacteriophage against the *Listeria* genus. Accordingly, this panel can be used to define target bacteria of any given phage.

The genus, species, and subspecies of the members of the panel is provided in Table 1.

TABLE 1

| Identifier | Strain Name | Genus/Species | Subspecies |
|---|---|---|---|
| NP1900 | FSL R8-5085 | *Listeria innocua* | sig B allelotype 11 |
| NP1901 | FSL R8-5091 | *Listeria innocua* | sig B allelotype 11 |
| NP1902 | FSL R8-5098 | *Listeria innocua* | sig B allelotype 11 |
| NP1903 | FSL R8-5255 | *Listeria innocua* | sig B allelotype 11 |
| NP1904 | FSL R8-5293 | *Listeria innocua* | sig B allelotype 11 |
| NP1905 | FSL R8-5295 | *Listeria innocua* | sig B allelotype 11 |
| NP1906 | FSL R8-5306 | *Listeria innocua* | sig B allelotype 11 |
| NP1907 | FSL R8-5440 | *Listeria innocua* | sig B allelotype 11 |
| NP1908 | FSL R8-5442 | *Listeria innocua* | sig B allelotype 11 |
| NP1909 | FSL R8-5448 | *Listeria innocua* | sig B allelotype 11 |
| NP1912 | FSL R8-7061 | *Listeria innocua* | sig B allelotype 22 |
| NP1959 | FSL S4-158 | *Listeria innocua* | sig B allelotype 22 |
| NP1960 | FSL S10-784 | *Listeria innocua* | sig B allelotype 22 |
| NP1961 | FSL F6-1168 | *Listeria innocua* | sig B allelotype 22 |
| NP1962 | FSL R8-5961 | *Listeria innocua* | sig B allelotype 22 |
| NP1963 | FSL R8-6922 | *Listeria innocua* | sig B allelotype 22 |
| NP1964 | FSL R8-7352 | *Listeria innocua* | sig B allelotype 22 |
| NP1965 | FSL R8-5598 | *Listeria innocua* | sig B allelotype 22 |
| NP1966 | FSL R8-6733 | *Listeria innocua* | sig B allelotype 22 |
| NP1967 | FSL R8-5942 | *Listeria innocua* | sig B allelotype 22 |
| NP1915 | FSL R8-7548 | *Listeria innocua* | sig B allelotype 37 |
| NP1997 | FSL R8-5764 | *Listeria innocua* | sig B allelotype 37 |
| NP1998 | FSL R8-5802 | *Listeria innocua* | sig B allelotype 37 |
| NP1999 | FSL R8-6012 | *Listeria innocua* | sig B allelotype 37 |
| NP2000 | FSL R8-6355 | *Listeria innocua* | sig B allelotype 37 |
| NP2001 | FSL R8-6369 | *Listeria innocua* | sig B allelotype 37 |
| NP2002 | FSL R8-6476 | *Listeria innocua* | sig B allelotype 37 |
| NP2003 | FSL R8-7175 | *Listeria innocua* | sig B allelotype 37 |
| NP2004 | FSL R8-6888 | *Listeria innocua* | sig B allelotype 37 |
| NP2005 | FSL R8-6672 | *Listeria innocua* | sig B allelotype 37 |
| NP1916 | FSL R8-6667 | *Listeria innocua* | sig B allelotype 56 |
| NP2006 | FSL S10-1311 | *Listeria innocua* | sig B allelotype 56 |
| NP2007 | FSL F6-1159 | *Listeria innocua* | sig B allelotype 56 |
| NP2008 | FSL F6-1126 | *Listeria innocua* | sig B allelotype 56 |
| NP2009 | FSL S6-120 | *Listeria innocua* | sig B allelotype 56 |
| NP2010 | FSL R8-5594 | *Listeria innocua* | sig B allelotype 56 |
| NP2011 | FSL R8-7181 | *Listeria innocua* | sig B allelotype 56 |
| NP2012 | FSL R2-632 | *Listeria innocua* | sig B allelotype 56 |
| NP2013 | FSL L3-851 | *Listeria innocua* | sig B allelotype 56 |
| NP2014 | FSL S10-1377 | *Listeria innocua* | sig B allelotype 56 |
| NP 1869 | WSLC 3009 | *Listeria ivanovii* | sig B allelotype 73 |
| NP 1840 | FSL J1-208 | *Listeria monocytogenes* | ribotype DUP-10142 |
| NP 1839 | FSL F6-367 | *Listeria monocytogenes* | ribotype DUP-1030A |
| NP2024 | FSL F6-267 | *Listeria monocytogenes* | ribotype DUP-1030A |
| NP2025 | FSL F6-406 | *Listeria monocytogenes* | ribotype DUP-1030A |
| NP2026 | FSL H5-592 | *Listeria monocytogenes* | ribotype DUP-1030A |
| NP2027 | FSL H1-219 | *Listeria monocytogenes* | ribotype DUP-1030A |
| NP2028 | FSL H1-121 | *Listeria monocytogenes* | ribotype DUP-1030A |
| NP2029 | FSL W3-072 | *Listeria monocytogenes* | ribotype DUP-1030A |
| NP2030 | FSL N4-239 | *Listeria monocytogenes* | ribotype DUP-1030A |
| NP2031 | FSL N3-293 | *Listeria monocytogenes* | ribotype DUP-1030A |
| NP2032 | FSL F3-319 | *Listeria monocytogenes* | ribotype DUP-1030A |
| NP1879 | FSL N4-221 | *Listeria monocytogenes* | ribotype DUP-1030B |
| NP2033 | FSL F2-738 | *Listeria monocytogenes* | ribotype DUP-1030B |
| NP2034 | FSL N3-881 | *Listeria monocytogenes* | ribotype DUP-1030B |
| NP2035 | FSL N4-048 | *Listeria monocytogenes* | ribotype DUP-1030B |
| NP2036 | FSL N4-696 | *Listeria monocytogenes* | ribotype DUP-1030B |
| NP2037 | FSL N4-242 | *Listeria monocytogenes* | ribotype DUP-1030B |
| NP2038 | FSL H4-364 | *Listeria monocytogenes* | ribotype DUP-1030B |

TABLE 1-continued

| Identifier | Strain Name | Genus/Species | Subspecies |
|---|---|---|---|
| NP2039 | FSL H4-147 | Listeria monocytogenes | ribotype DUP-1030B |
| NP2040 | FSL H4-946 | Listeria monocytogenes | ribotype DUP-1030B |
| NP2041 | FSL S4-461 | Listeria monocytogenes | ribotype DUP-1030B |
| NP2042 | FSL F6-206 | Listeria monocytogenes | ribotype DUP-1038B |
| NP2043 | FSL F6-224 | Listeria monocytogenes | ribotype DUP-1038B |
| NP2044 | FSL L3-739 | Listeria monocytogenes | ribotype DUP-1038B |
| NP2045 | FSL N3-008 | Listeria monocytogenes | ribotype DUP-1038B |
| NP2046 | FSL N3-022 | Listeria monocytogenes | ribotype DUP-1038B |
| NP2047 | FSL J1-108 | Listeria monocytogenes | ribotype DUP-1038B |
| NP2048 | FSL J1-119 | Listeria monocytogenes | ribotype DUP-1038B |
| NP2049 | FSL C1-122 | Listeria monocytogenes | ribotype DUP-1038B |
| NP2050 | FSL J1-126 | Listeria monocytogenes | ribotype DUP-1038B |
| NP1880 | FSL L3-159 | Listeria monocytogenes | ribotype DUP-1039A |
| NP2051 | FSL F3-285 | Listeria monocytogenes | ribotype DUP-1039A |
| NP2052 | FSL R6-288 | Listeria monocytogenes | ribotype DUP-1039A |
| NP2053 | FSL N1-021 | Listeria monocytogenes | ribotype DUP-1039A |
| NP2054 | FSL H1-208 | Listeria monocytogenes | ribotype DUP-1039A |
| NP2055 | FSL N3-034 | Listeria monocytogenes | ribotype DUP-1039A |
| NP2056 | FSL L5-072 | Listeria monocytogenes | ribotype DUP-1039A |
| NP2057 | FSL S6-131 | Listeria monocytogenes | ribotype DUP-1039A |
| NP2058 | FSL N3-278 | Listeria monocytogenes | ribotype DUP-1039A |
| NP2059 | FSL R2-282 | Listeria monocytogenes | ribotype DUP-1039A |
| NP1881 | FSL T1-323 | Listeria monocytogenes | ribotype DUP-1039B |
| NP2060 | FSL H5-770 | Listeria monocytogenes | ribotype DUP-1039B |
| NP2061 | FSL F6-207 | Listeria monocytogenes | ribotype DUP-1039B |
| NP2062 | FSL F6-236 | Listeria monocytogenes | ribotype DUP-1039B |
| NP2063 | FSL H5-795 | Listeria monocytogenes | ribotype DUP-1039B |
| NP2064 | FSL N3-246 | Listeria monocytogenes | ribotype DUP-1039B |
| NP2065 | FSL R2-062 | Listeria monocytogenes | ribotype DUP-1039B |
| NP2066 | FSL R2-437 | Listeria monocytogenes | ribotype DUP-1039B |
| NP2067 | FSL M1-004 | Listeria monocytogenes | ribotype DUP-1039B |
| NP2068 | FSL L4-352 | Listeria monocytogenes | ribotype DUP-1039B |
| NP2069 | FSL F6-605 | Listeria monocytogenes | ribotype DUP-1039C |
| NP2070 | FSL V1-001 | Listeria monocytogenes | ribotype DUP-1039C |
| NP2071 | FSL F6-464 | Listeria monocytogenes | ribotype DUP-1039C |
| NP2072 | FSL R8-2748 | Listeria monocytogenes | ribotype DUP-1039C |
| NP2073 | FSL R6-908 | Listeria monocytogenes | ribotype DUP-1039C |
| NP2074 | FSL L3-802 | Listeria monocytogenes | ribotype DUP-1039C |
| NP2075 | FSL F3-056 | Listeria monocytogenes | ribotype DUP-1039C |
| NP2076 | FSL J2-020 | Listeria monocytogenes | ribotype DUP-1039C |
| NP2077 | FSL S4-914 | Listeria monocytogenes | ribotype DUP-1039C |
| NP1882 | FSL H5-725 | Listeria monocytogenes | ribotype DUP-1042A |
| NP2078 | FSL F6-467 | Listeria monocytogenes | ribotype DUP-1042A |
| NP2079 | FSL F6-655 | Listeria monocytogenes | ribotype DUP-1042A |
| NP2080 | FSL F6-352 | Listeria monocytogenes | ribotype DUP-1042A |
| NP2081 | FSL H5-781 | Listeria monocytogenes | ribotype DUP-1042A |
| NP2082 | FSL K2-147 | Listeria monocytogenes | ribotype DUP-1042A |
| NP2083 | FSL V1-026 | Listeria monocytogenes | ribotype DUP-1042A |
| NP2084 | FSL H5-572 | Listeria monocytogenes | ribotype DUP-1042A |
| NP2085 | FSL K2-065 | Listeria monocytogenes | ribotype DUP-1042A |
| NP2086 | FSL H4-120 | Listeria monocytogenes | ribotype DUP-1042A |
| NP2087 | FSL F6-184 | Listeria monocytogenes | ribotype DUP-1042B |
| NP2088 | FSL F6-191 | Listeria monocytogenes | ribotype DUP-1042B |
| NP2089 | FSL H1-099 | Listeria monocytogenes | ribotype DUP-1042B |
| NP2090 | FSL J1-116 | Listeria monocytogenes | ribotype DUP-1042B |
| NP2091 | FSL R2-192 | Listeria monocytogenes | ribotype DUP-1042B |
| NP2092 | FSL J1-225 | Listeria monocytogenes | ribotype DUP-1042B |
| NP2093 | FSL R2-500 | Listeria monocytogenes | ribotype DUP-1042B |
| NP2094 | FSL R2-501 | Listeria monocytogenes | ribotype DUP-1042B |
| NP2095 | FSL E1-159 | Listeria monocytogenes | ribotype DUP-1042B |
| NP2096 | FSL F6-355 | Listeria monocytogenes | ribotype DUP-1042C |
| NP2097 | FSL F6-382 | Listeria monocytogenes | ribotype DUP-1042C |
| NP2098 | FSL F3-200 | Listeria monocytogenes | ribotype DUP-1042C |
| NP2099 | FSL K2-143 | Listeria monocytogenes | ribotype DUP-1042C |
| NP2100 | FSL N1-176 | Listeria monocytogenes | ribotype DUP-1042C |
| NP2101 | FSL N1-417 | Listeria monocytogenes | ribotype DUP-1042C |
| NP2102 | FSL L3-051 | Listeria monocytogenes | ribotype DUP-1042C |
| NP2103 | FSL T1-107 | Listeria monocytogenes | ribotype DUP-1042C |
| NP2104 | FSL T1-408 | Listeria monocytogenes | ribotype DUP-1042C |
| NP1883 | FSL T1-922 | Listeria monocytogenes | ribotype DUP-1043A |
| NP2105 | FSL F6-396 | Listeria monocytogenes | ribotype DUP-1043A |
| NP2106 | FSL H5-806 | Listeria monocytogenes | ribotype DUP-1043A |
| NP2107 | FSL F6-551 | Listeria monocytogenes | ribotype DUP-1043A |
| NP2108 | FSL F6-446 | Listeria monocytogenes | ribotype DUP-1043A |
| NP2109 | FSL F6-315 | Listeria monocytogenes | ribotype DUP-1043A |
| NP2110 | FSL V1-022 | Listeria monocytogenes | ribotype DUP-1043A |
| NP2111 | FSL R2-132 | Listeria monocytogenes | ribotype DUP-1043A |
| NP2112 | FSL R2-273 | Listeria monocytogenes | ribotype DUP-1043A |

TABLE 1-continued

| Identifier | Strain Name | Genus/Species | Subspecies |
| --- | --- | --- | --- |
| NP2113 | FSL N3-277 | Listeria monocytogenes | ribotype DUP-1043A |
| NP1884 | FSL H1-251 | Listeria monocytogenes | ribotype DUP-1044A |
| NP2114 | FSL F6-358 | Listeria monocytogenes | ribotype DUP-1044A |
| NP2115 | FSL F6-194 | Listeria monocytogenes | ribotype DUP-1044A |
| NP2116 | FSL R2-763 | Listeria monocytogenes | ribotype DUP-1044A |
| NP2117 | FSL R2-765 | Listeria monocytogenes | ribotype DUP-1044A |
| NP2118 | FSL R2-764 | Listeria monocytogenes | ribotype DUP-1044A |
| NP2119 | FSL N1-225 | Listeria monocytogenes | ribotype DUP-1044A |
| NP2120 | FSL N1-227 | Listeria monocytogenes | ribotype DUP-1044A |
| NP2121 | FSL N1-048 | Listeria monocytogenes | ribotype DUP-1044A |
| NP2122 | FSL K2-131 | Listeria monocytogenes | ribotype DUP-1044A |
| NP1885 | FSL L3-501 | Listeria monocytogenes | ribotype DUP-1044B |
| NP2123 | FSL F6-222 | Listeria monocytogenes | ribotype DUP-1044B |
| NP2124 | FSL F6-249 | Listeria monocytogenes | ribotype DUP-1044B |
| NP2125 | FSL N3-065 | Listeria monocytogenes | ribotype DUP-1044B |
| NP2126 | FSL H4-699 | Listeria monocytogenes | ribotype DUP-1044B |
| NP2127 | FSL L4-241 | Listeria monocytogenes | ribotype DUP-1044B |
| NP2128 | FSL S4-643 | Listeria monocytogenes | ribotype DUP-1044B |
| NP2129 | FSL R2-073 | Listeria monocytogenes | ribotype DUP-1044B |
| NP2130 | FSL F3-224 | Listeria monocytogenes | ribotype DUP-1044B |
| NP2131 | FSL N4-334 | Listeria monocytogenes | ribotype DUP-1044B |
| NP1886 | FSL R2-069 | Listeria monocytogenes | ribotype DUP-1044E |
| NP2132 | FSL R2-070 | Listeria monocytogenes | ribotype DUP-1044E |
| NP1887 | FSL H1-030 | Listeria monocytogenes | ribotype DUP-1045B |
| NP2133 | FSL F6-421 | Listeria monocytogenes | ribotype DUP-1045B |
| NP2134 | FSL F6-449 | Listeria monocytogenes | ribotype DUP-1045B |
| NP2135 | FSL J2-054 | Listeria monocytogenes | ribotype DUP-1045B |
| NP2136 | FSL S4-024 | Listeria monocytogenes | ribotype DUP-1045B |
| NP2137 | FSL H1-111 | Listeria monocytogenes | ribotype DUP-1045B |
| NP2138 | FSL K2-022 | Listeria monocytogenes | ribotype DUP-1045B |
| NP2139 | FSL S4-066 | Listeria monocytogenes | ribotype DUP-1045B |
| NP2140 | FSL R2-067 | Listeria monocytogenes | ribotype DUP-1045B |
| NP2141 | FSL R2-293 | Listeria monocytogenes | ribotype DUP-1045B |
| NP2142 | FSL F6-323 | Listeria monocytogenes | ribotype DUP-1052A |
| NP2143 | FSL F6-216 | Listeria monocytogenes | ribotype DUP-1052A |
| NP2144 | FSL F6-321 | Listeria monocytogenes | ribotype DUP-1052A |
| NP2145 | FSL V1-117 | Listeria monocytogenes | ribotype DUP-1052A |
| NP2146 | FSL H5-846 | Listeria monocytogenes | ribotype DUP-1052A |
| NP2147 | FSL L3-055 | Listeria monocytogenes | ribotype DUP-1052A |
| NP2148 | FSL T1-313 | Listeria monocytogenes | ribotype DUP-1052A |
| NP2149 | FSL R8-0875 | Listeria monocytogenes | ribotype DUP-1052A |
| NP2150 | FSL R2-317 | Listeria monocytogenes | ribotype DUP-1052A |
| NP1888 | FSL L4-019 | Listeria monocytogenes | ribotype DUP-1053A |
| NP2151 | FSL F6-335 | Listeria monocytogenes | ribotype DUP-1053A |
| NP2152 | FSL R6-653 | Listeria monocytogenes | ribotype DUP-1053A |
| NP2153 | FSL L3-135 | Listeria monocytogenes | ribotype DUP-1053A |
| NP2154 | FSL L3-143 | Listeria monocytogenes | ribotype DUP-1053A |
| NP2155 | FSL L3-167 | Listeria monocytogenes | ribotype DUP-1053A |
| NP2156 | FSL N3-031 | Listeria monocytogenes | ribotype DUP-1053A |
| NP2157 | FSL J1-101 | Listeria monocytogenes | ribotype DUP-1053A |
| NP2158 | FSL F6-154 | Listeria monocytogenes | ribotype DUP-1053A |
| NP2159 | FSL R2-499 | Listeria monocytogenes | ribotype DUP-1053A |
| NP1889 | FSL T1-027 | Listeria monocytogenes | ribotype DUP-1062A |
| NP2160 | FSL F6-325 | Listeria monocytogenes | ribotype DUP-1062A |
| NP2161 | FSL F6-220 | Listeria monocytogenes | ribotype DUP-1062A |
| NP2162 | FSL F6-319 | Listeria monocytogenes | ribotype DUP-1062A |
| NP2163 | FSL F6-365 | Listeria monocytogenes | ribotype DUP-1062A |
| NP2164 | FSL F6-360 | Listeria monocytogenes | ribotype DUP-1062A |
| NP2165 | FSL F6-313 | Listeria monocytogenes | ribotype DUP-1062A |
| NP2166 | FSL R2-031 | Listeria monocytogenes | ribotype DUP-1062A |
| NP2167 | FSL R2-050 | Listeria monocytogenes | ribotype DUP-1062A |
| NP2168 | FSL R2-078 | Listeria monocytogenes | ribotype DUP-1062A |
| NP1890 | FSL T1-041 | Listeria monocytogenes | ribotype DUP-1062D |
| NP2169 | FSL F6-264 | Listeria monocytogenes | ribotype DUP-1062D |
| NP2170 | FSL F3-146 | Listeria monocytogenes | ribotype DUP-1062D |
| NP2171 | FSL F3-194 | Listeria monocytogenes | ribotype DUP-1062D |
| NP2172 | FSL H4-122 | Listeria monocytogenes | ribotype DUP-1062D |
| NP2173 | FSL H4-286 | Listeria monocytogenes | ribotype DUP-1062D |
| NP2174 | FSL R6-646 | Listeria monocytogenes | ribotype DUP-1062D |
| NP2175 | FSL T1-041 | Listeria monocytogenes | ribotype DUP-1062D |
| NP2176 | FSL F7-002 | Listeria monocytogenes | ribotype DUP-1062D |
| NP2177 | FSL X1-005 | Listeria monocytogenes | ribotype DUP-1062D |
| NP 1878 | EGD-e | Listeria monocytogenes | |
| NP1911 | FSL R8-7641 | Listeria seeligeri | sig B allelotype 20 |
| NP1950 | FSL S10-030 | Listeria seeligeri | sig B allelotype 20 |
| NP1951 | FSL S10-320 | Listeria seeligeri | sig B allelotype 20 |
| NP1952 | FSL S10-1602 | Listeria seeligeri | sig B allelotype 20 |
| NP1953 | FSL L5-075 | Listeria seeligeri | sig B allelotype 20 |
| NP1954 | FSL L5-046 | Listeria seeligeri | sig B allelotype 20 |
| NP1955 | FSL L5-104 | Listeria seeligeri | sig B allelotype 20 |
| NP1956 | FSL R8-7575 | Listeria seeligeri | sig B allelotype 20 |
| NP1957 | FSL S4-178 | Listeria seeligeri | sig B allelotype 20 |
| NP1958 | FSL S4-135 | Listeria seeligeri | sig B allelotype 20 |

TABLE 1-continued

| Identifier | Strain Name | Genus/Species | Subspecies |
|---|---|---|---|
| NP1913 | FSL R8-6826 | *Listeria seeligeri* | sig B allelotype 24 |
| NP1968 | FSL S10-034 | *Listeria seeligeri* | sig B allelotype 24 |
| NP1969 | FSL S10-1611 | *Listeria seeligeri* | sig B allelotype 24 |
| NP1970 | FSL L5-054 | *Listeria seeligeri* | sig B allelotype 24 |
| NP1971 | FSL L5-085 | *Listeria seeligeri* | sig B allelotype 24 |
| NP1972 | FSL R8-6868 | *Listeria seeligeri* | sig B allelotype 24 |
| NP1973 | FSL R8-6545 | *Listeria seeligeri* | sig B allelotype 24 |
| NP1974 | FSL R8-6949 | *Listeria seeligeri* | sig B allelotype 24 |
| NP1975 | FSL S4-167 | *Listeria seeligeri* | sig B allelotype 24 |
| NP1976 | FSL S4-180 | *Listeria seeligeri* | sig B allelotype 24 |
| NP1891 | FSL R8-5241 | *Listeria seeligeri* | sig B allelotype 3 |
| NP1892 | FSL R8-5247 | *Listeria seeligeri* | sig B allelotype 3 |
| NP1893 | FSL R8-5253 | *Listeria seeligeri* | sig B allelotype 3 |
| NP1894 | FSL R8-5513 | *Listeria seeligeri* | sig B allelotype 3 |
| NP1895 | FSL R8-6629 | *Listeria seeligeri* | sig B allelotype 3 |
| NP1896 | FSL R8-6635 | *Listeria seeligeri* | sig B allelotype 3 |
| NP1897 | FSL R8-6659 | *Listeria seeligeri* | sig B allelotype 3 |
| NP1898 | FSL R8-6665 | *Listeria seeligeri* | sig B allelotype 3 |
| NP1899 | FSL R8-6852 | *Listeria seeligeri* | sig B allelotype 3 |
| NP1990 | FSL H6-027 | *Listeria seeligeri* | sig B allelotype 35 |
| NP1991 | FSL H6-079 | *Listeria seeligeri* | sig B allelotype 35 |
| NP1992 | FSL H6-185 | *Listeria seeligeri* | sig B allelotype 35 |
| NP1993 | FSL R8-6874 | *Listeria seeligeri* | sig B allelotype 35 |
| NP1994 | FSLR8-6880 | *Listeria seeligeri* | sig B allelotype 35 |
| NP1995 | FSL R8-7629 | *Listeria seeligeri* | sig B allelotype 35 |
| NP1996 | FSL S4-544 | *Listeria seeligeri* | sig B allelotype 35 |
| NP1910 | FSL R8-7026 | *Listeria welshimeri* | sig B allelotype 15 |
| NP1945 | FSL L5-079 | *Listeria welshimeri* | sig B allelotype 15 |
| NP1946 | FSL S10-1450 | *Listeria welshimeri* | sig B allelotype 15 |
| NP1947 | FSL S10-1451 | *Listeria welshimeri* | sig B allelotype 15 |
| NP1948 | FSL S4-081 | *Listeria welshimeri* | sig B allelotype 15 |
| NP1949 | FSL S4-101 | *Listeria welshimeri* | sig B allelotype 15 |
| NP1977 | FSL N1-064 | *Listeria welshimeri* | sig B allelotype 27 |
| NP1978 | FSL R8-8163 | *Listeria welshimeri* | sig B allelotype 27 |
| NP1979 | FSL R8-7524 | *Listeria welshimeri* | sig B allelotype 27 |
| NP1980 | FSL R8-7486 | *Listeria welshimeri* | sig B allelotype 27 |
| NP1981 | FSL R8-6035 | *Listeria welshimeri* | sig B allelotype 27 |
| NP1982 | FSL R8-5807 | *Listeria welshimeri* | sig B allelotype 27 |
| NP1983 | FSL S4-182 | *Listeria welshimeri* | sig B allelotype 27 |
| NP1984 | FSL R2-630 | *Listeria welshimeri* | sig B allelotype 27 |
| NP1985 | FSL F6-1131 | *Listeria welshimeri* | sig B allelotype 27 |
| NP1914 | FSL R8-7454 | *Listeria welshimeri* | sig B allelotype 32 |
| NP1986 | FSL R8-7041 | *Listeria welshimeri* | sig B allelotype 32 |
| NP1987 | FSL R8-5837 | *Listeria welshimeri* | sig B allelotype 32 |
| NP1988 | FSL R8-6136 | *Listeria welshimeri* | sig B allelotype 32 |
| NP1989 | FSL S4-289 | *Listeria welshimeri* | sig B allelotype 32 |
| NP1917 | FSL R8-1903 | *Listeria welshimeri* | sig B allelotype 89 |
| NP2015 | FSL S10-114 | *Listeria welshimeri* | sig B allelotype 89 |
| NP2016 | FSL S10-115 | *Listeria welshimeri* | sig B allelotype 89 |
| NP2017 | FSL S10-117 | *Listeria welshimeri* | sig B allelotype 89 |
| NP2018 | FSL S10-119 | *Listeria welshimeri* | sig B allelotype 89 |
| NP2019 | FSL S10-121 | *Listeria welshimeri* | sig B allelotype 89 |
| NP2020 | FSL R8-0056 | *Listeria welshimeri* | sig B allelotype 89 |
| NP2021 | FSL R8-1198 | *Listeria welshimeri* | sig B allelotype 89 |
| NP2022 | FSL R8-7403 | *Listeria welshimeri* | sig B allelotype 89 |
| NP2023 | FSL R2-631 | *Listeria welshimeri* | sig B allelotype 89 |

Example 2

Plate-Based Phage Host Range Assay

In order to quantify the host range a given bacteriophage the plaque forming efficiency of the bacteriophage on a given isolate was standardized to a reference strain for the bacteriophage, normally the strain used for bacteriophage production. To determine the plaque forming efficiency a dilution series for the phage is generated and titered on each host. Before the work reported herein, this was the standard method of phage host range analysis. See, e.g., Sambrook et al., *Molecular Cloning: A Laboratory Manual,* 3d ed., Cold Spring Harbor Laboratory Press, Cold Spring Harbor, N.Y. (2001).

The *Listeria* bacterial strain panel was used to determine the host range for a particular bacteriophage. To do this a culture of each *Listeria* strain to be tested was started in 5 ml of LBL1 and grown overnight at 30 C in an orbital shaker and allowed to grow for 16 hours. For each bacterial host strain 30 µl of the 16-hour culture was mixed with 270 µl of fresh LBL1 medium. To each cell dilution, 4 ml of LBL1 soft agar was added and overlayed onto LBL1 agar in 100 mm petri dish. The soft agar overlay was allowed to cool and solidify at room temperature. Additionally, a reference strain (FSL F6-367 for A511 and P100) was treated in a similar manner to the host range isolates. A 10-fold dilution series of the bacteriophage in LBL1 medium was prepared from $10^{-1}$ to $10^{-8}$. 5 µl of each dilution of the bacteriophage was spotted onto the soft agar overlay and the liquid was allowed to adsorb and then the plate was incubated at 30 C for 16 hours. After incubation the plaques present at each dilution series were counted and compared to the reference strain to provide an efficiency of plaquing for each host range isolate. The host range was represented as a percentage of the titer observed on the experimental host compared to the reference strain. Bacterial strains that showed a plaquing efficiency greater than 10% (Table 2, dark gray shading) of the reference strain were considered to be within the host range. Bacterial strains that showed a plaquing efficiency less than 10% but greater than 0.01% (Table 2, light gray shade) of the reference strain were considered to be weakly susceptible to the phage. Bacterial strains that showed a plaquing efficiency less than 0.01% (Table 2, unshaded) of the reference strain were considered to be outside of the host range for a phage. A phenomenon that was seen for many of the bacterial strains tested was what has been described in the literature and art as "extra cellular killing" (ECK) (Table 2, black), see e.g. Shaw et al. (J Immunol Methods. 1983; 56(1):75-83). A strain was defined as demonstrating ECK for a particular phage when at high phage concentration completely cleared the lawn, however, subsequent dilutions did not produce clearing.

The plate-based host range determination allowed for a rough approximation of the host range of A511 and P100 against the *Listeria* isolate library. Of the 272 strains tested in the bacterial strain library 67 and 120 strains supported plaque formation by A511 and P100, respectively (Table 2). The greatest limitations of this method were the length of time needed to process the entire library for a give bacteriophage and the inability to determine the entire host range due to the ECK phenomenon. For the bacteriophage A511 and P100, of the 272 bacterial strains in the host range panel tested, 117 and 42, respectively, showed ECK and hence provided no information about the host range for these strains. Additionally, in view of the ECK phenomenon and because of the general differences between bacteria growing on a plate and bacteria growing in a liquid culture, it was hypothesized that the plate-based method for determining host range may not represent the host range for a liquid-based application.

Example 3

A Liquid Culture Phage Host Range Assay

The prevalence of the extra-cellular killing (ECK) phenomenon demonstrated by both A511 and P100 in the plate-based host range method demonstrates that the plate based is not as useful as it could be for determining the host range for either phage. To overcome those deficiencies a novel liquid-based host range assay was developed. The liquid-based host range assay is an end point assay where the ability of a phage to infect a particular bacterial isolate is determined by comparing the optical density of a culture with or without bacteriophage.

The *Listeria* host panel strain collection (Table 1) was struck out on Brain Heart Infusion (BHI) agar plates and single colonies were inoculated in 1 ml BHI liquid in a 2-ml 96-deep well dish, covered with a sterile breathable sterile membrane and grown at 30 C for 16 hours. Each of the 16-hour cultures from the 96-well plates were diluted 1:10,000 in 198 µl of LBL1 in a 300 µl flat-bottom optical 96-well plate and then either $1 \times 10^5$ pfu of the bacteriophage or an equivalent volume of LBL1 was added to each well of the 96-well plate. This concentration of bacteriophage and bacterial cell dilutions was to approximate a multiplicity of infection (MOI) of 1 in each well. After addition of the phage or control, the plates were incubated at 26 C with shaking at 50 rpm for 16-hours. Plates were placed in a 96-well plate reader (Biotek Eon Microplate Reader) and agitated for 3 seconds with orbital shaking to resuspend cells that had settled out of culture. After the agitation, the optical density of each well was measure at 600 nm (OD600) wavelength light. The ratio of OD600 of the bacterial isolate in the presence of bacteriophage to the uninfected bacterial isolate culture was used as a metric to determine the efficiency of infection for a bacterial strain. A bacterial strain with a ratio of less than or equal to 0.4 (Table 2, dark gray shade) was considered to be sensitive to infection by the bacteriophage.

The liquid-based host range assay identified 192 and 153 bacterial strains sensitive to A511 and P100, respectively, of the 272 strains in the bacterial strain panel (Table 2). This data shows that A511 is capable of infecting approximately 70% and P100 is capable of infecting approximately 58% of the host range panel. In comparison to the liquid-based host range, the plate-based host range method identified 62 and 120 bacterial strains that demonstrated a plaquing-efficiency for A511 and P100, respectively. Of the strains identified in the plate-based host range methods, only 8 A511-sensitive bacterial strains and 3 P100-sensitive bacterial strains did not show clearance in the liquid-based clearance assay. Because the liquid-based assay is an endpoint assay and represents a kinetic interaction between bacteriophage infection and bacterial cell growth certain bacterial strains with increased cell growth rates may be able to saturate a culture even though the strain is susceptible to infection and this may explain the reason why a small number of strains identified in the plaque-based assay were not identified in the liquid assay.

The additional strains identified by the liquid-based host range assay were due to the ability to collect data on strains that demonstrated an ECK phenotype in the plate-based host range assay. The large number of strains that demonstrated this phenotype created a large amount of unknown information regarding the host range for A511 and P100. The liquid-based assay eliminated the ECK phenomenon, one of the large drawbacks of the plate-based host range method. Two factors contributed to the lack of ECK. First the concentration of phages used in the liquid-based assay is a set concentration that is lower than the concentrations of phage that demonstrated ECK in the plate-based host range assay. Second, the delocalized concentration of bacteriophage within the liquid infection and the low MOI decreases the number of interactions between the bacterial cells and bacteriophage. The limited interaction decreases the possibility of non-productive encounters and lowers super-infection, or infection by multiple bacteriophages of a cell. By eliminating ECK, the sensitivity for measuring susceptibility of a particular bacterial cell to a bacteriophage was increased substantially and provided a more accurate representation of the host range of a bacteriophage across the *Listeria* species.

The liquid-based host range assay showed substantial advances over the prior method of using a plate-based system for determining host range of a bacteriophage. Previous literature did not report the ability of growing these bacteriophages in a format other than a plate-based method. The liquid format is also useful because the speed with which the liquid-based host range assay can be performed increases the speed of determining the host range of a bacteriophage from 7-10 days for the panel as it was assembled to several hours of hands on labor. Additionally, the high-throughput nature of the scoring of host susceptibility allowed for multiple bacteriophage host ranges to be determined concurrently, a possibility that did not exist previously. The ability to process multiple bacteriophages concurrently allowed for a more direct comparison of bacteriophages by minimizing variation between bacterial culture physiology and media lots. Together, the increased speed and direct bacteriophage characterizations allowed for rapid processing of multiple phages and prioritization for bacteriophage engineering described herein. Moreover, the liquid-based host range assay allowed for a more accurate representation of the functional determination of a potential bacteriophage in a predicted product compared to a plate-based host range assay. The combination of the increased speed, ability for more direct comparison and ability to assess functionality of a bacteriophage in a more direct method to the final product makes the liquid-based host range assay significantly more useful than the plate-based host range method in most contexts.

The efficacy of a cocktail of a P100 and A511 bacteriophage can be determined by the ability of each of the bacteriophages to infect a particular strain. Infections of the host panel with a cocktail of P100 and A511 show the additive host range expected from the extrapolation of the individual host ranges. Based on observations regarding the bacteriophage concentration required for optimum luciferase production during the course of infection, the concentration of bacteriophage added was maintained at a constant total phage concentration of $1 \times 10^7$ whether a single bacteriophage or multiple phage cocktail was used for infections. The cocktail of A511 and P100 shows coverage of 74% of the panel constructed, while the individual bacteriophages show 70% and 55% coverage, respectively. (Table 2.) This increased coverage of the panel arises from the face that while the phages have largely overlapping coverage the subset of strains susceptible to P100 infection is not full encompassed within the A511 strains. The ability to extrapolate function of a bacteriophage cocktail from the individual liquid-based host range provides as a powerful tool to identify and prioritize new bacteriophages for engineering to build a more complete cocktail.

The function of a bacteriophage cocktail of P100 and A511 on samples collected from environmental samples cannot be strictly inferred from the host panel assembled. The sites sampled in environmental testing represent diverse populations of bacteria and often have more than one species or subspecies of *Listeria* present at an individual location. Environmental sampling at food processing plants with geographic and source diversity identified 31 samples that have been confirmed positive for *Listeria* using a culture based method of detection at a third-party laboratory. Of these 31 positive samples, 10 samples contained multiple *Listeria* species or subspecies. The A511 and P100 cocktail was capable of detecting 24 of the 31 (77%) of the positive samples. The correlation between the liquid-based host range results and the environmental samples collected allows for further iterations on the bacteriophage cocktail to be made in order to gain more complete coverage of the *Listeria* genus and validated the usefulness of the liquid-based host range method.

Example 4

Host Range Characterization of Additional *Listeria* Phages

Construction of a *Listeria* host strain panel and development of a rapid liquid-based host range assay allowed for the rapid screening of additional bacteriophages to identify those bacteriophages that would increase the breadth of coverage of the *Listeria* genus. Twenty five additional bacteriophages were screened against the host panel in the liquid-based host range assay and analyzed for host susceptibility based on clearance versus an uninfected control. The data are presented in Table 3. Strains were considered within host range if they demonstrated a ratio of 0.4 or less (shaded dark gray). During the determination of the OD600 of the cultures there was no correction for the absorbance of the growth medium or culture plate, therefore, a ratio of 0.09 constituted a completely cleared culture by infection. Because of variations in the maximum OD600 obtained by different *Listeria* strains a conservative ratio of 0.4 was chosen to denote *Listeria* strains that were sensitive to a given bacteriophage. Strains that had a OD600 ratio of greater than 0.4 were considered to be outside of host range (Table 3, unshaded). From these twenty five bacteriophages assayed, seven (7) bacteriophages were selected to proceed into engineering based on the criteria that they provided useful host panel coverage, had genome sequence availability for development of phage targeting vectors and were capable of infecting *L. monocytogenes* strain EGD-e, the strain of *Listeria* most amenable to transformation.

The seven bacteriophages selected in addition to A511 and P100 were LP44, LP40, LP48, LP99, LP101, LP124, LP125, and LP143. No individual phage assayed covers more than 78% of the *Listeria* host strain panel. In combination, the bacteriophages cover approximately 92% of the host strain panel as assayed by liquid-based host range assay (Table 3). This combinatorial approach allows for the construction of a bacteriophage cocktail that provides the necessary coverage of the *Listeria* species to provide a reliable determination of the presence of *Listeria* in environmental sample collection.

After engineering the genome of the phages with two different genetic payloads, Firefly Luciferase and Nanoluciferase, the host range of these phages was retested to ensure that the genome modifications did not affect the fitness of the phages or compromise their ability to infect the target bacteria. To examine the result of combining bacteriophages in an infection the liquid-based host range assay was used to test the combinatorial effects of phage infection. For these infections the final concentration of phage was maintained at a constant $1\times10^5$ pfu consisting of equal amounts of each of the phage within the cocktail (i.e.—a two phage cocktail would consist of $5\times10^4$ pfu of each of the two component phages.

Example 5

Engineering *Listeria* Phage

A novel phage engineering method was developed to create recombinant phage. This method is sometimes refereed to herein as Phage Infective Engineering (PIE). This method allows insertion of a heterologous nucleic acid sequence into any desired location of a phage genome. The initial site chosen for insertion was that used in Loessner, et al. (Appl. Environ Microbiol., 62:1133-1140), downstream of the major capsid protein gene cps. The coding sequence for the firefly luciferase (SEQ ID NO: 1) or the nano luc luciferase (SEQ ID NO: 3) was inserted at this location.

The PIE method uses Phage Targeting Vectors PTVs which include the luciferase gene sequence flanked by ~1 KB of phage sequence directly upstream and downstream of the desired insertion site (referred to as an upstream homology region (UHR) and downstream homology region (DHR)). Each of these inserts was created using PCR primers that would amplify the desired amplicon, while adding 20 bp of homology to facilitate assembly. Plasmids were assembled using the GeneArt Seamless Assembly Kit (Life Technologies). The 3 inserts (UHR, luc, DHR) were assembled into the gram positive/gram negative shuttle vector pMK4, which was restriction-digested with SmaI and PstI (NEB).

The A511 phage genome sequence is available in Genbank (NC_009811). A511 phage may be obtained from ATCC (PTA-4608™).

The PIE method was used to insert the firefly luciferase gene (SEQ ID NO: 1) directly after the stop codon of the cps gene of A511, between bases 46,695 and 46,696 of the genomic sequence. No sequence was deleted from the phage genome. A 16 bp sequence containing a ribosome-binding site (<u>GAGGAGG</u>TAAATATAT) was placed before the start (ATG) of the firefly luciferase gene.

To engineer phage A511, 1276 bases of the cps gene were amplified using oligos "pMAK upf" and "pMAK upr", forming the fragment "A511 UHR". The luciferase gene was amplified using primers "pMAK lucf" and "pMAK lucr", creating the fragment "A511 luc". The primer "pMAK lucf" also added a ribosome binding site (Shine-Dalgarno) upstream of the luciferase gene. The 1140 bp immediately after the cps stop codon was amplified using "pMAK dnf" and "pMAK dnr", named "A511 DHR".

These 3 amplicons were recombineered into pMK4 which had been restriction digested with SmaI/PstI using the GeneArt Seamless Assembly Kit, according to the manufacturer's instructions. Once isolated in *e. coli*, the plasmid was sequenced to verify correct amplification and assembly. Upon verification, the plasmid was transformed into the *L. monocytogenes* strain EGD-e and selected on BHI-chloramphenicol (10 µg/ml) agar plates.

Once the PTV was successfully transformed into EGD-e, the initial recombination was performed: An overnight culture of the A511::FF PTV-containing EGD-e was diluted 1:100 and allowed to grow to an OD600 of 0.1. This culture was then diluted back to an OD600 of 0.02 and mixed with 1e5 pfu/ml of wild-type A511 phage in a 2 ml volume. This infection was cultured at 30° C., shaken at 50 rpm overnight.

To assess whether recombination had occurred, the infection was assayed on the following day. First, the lysate was mixed with chloroform to kill any remaining cells, and to destroy the background luciferase made by the PTV. The phage is chloroform-resistant, which is a common trait in bacteriophages. 4% v/v CHCl3 was added to the lysate, vortexed, spun down, and the supernatant was recovered. A test infection was done, adding a 1:10 dilution of an overnight culture of EGD-e was mixed with the recombinant lysate (90 µl cell dilution, 10 µl phage lysate). A control infection was set up without cells. The infections were incubated statically at 30° C. for 3 hr, then assayed for luminescence on the Glomax 20/20. 20 µl of the infection was mixed with 100 µl of Promega Lucifase Assay Reagent (20 µl of lysate and 20 µl of NanoGlo for the NanoLuc phages), then read using a 10 second integration (1 s for NanoGlo). The recombinant lysate produced light, indicating that there were recombinant phage in the lysate.

In order to enrich and isolate the recombinant phage, it needed to be separated away from the wild-type phages present in the recombinant lysate. Successive rounds of dilution and division were employed. Lysates were made with 10-fold dilutions of input phages, and screened for the presence of recombinant phage by assaying the lysates for luciferase activity.

The recombination efficiency was estimated to be 1:1e5 to 1:1e6. In order to isolate a pure recombinant lysate, the methods described in (Appl. Environ Microbiol. 62:1133-1140) were modified as follows. The initial recombinant lysate was titered. 20 1-ml lysates were set up each with 1e6, 1e5, and 1e4 pfu/ml of the recombinant lysate: 1 ml EGD-e @OD 0.02, 1eX phages; O/N, 30 C, 50 rpm. On the following day, the CHCl3 treatment was done, as described above, for each lysate. The lysates were used to set up infections as above. Each lysate was assayed on the Glomax 20/20 (20 µl infection, 100 µl Reagent for FF, 20 µl infection, 20 µl NanoGlo for nluc). The goal was to locate the lysate that was made with the fewest number of phages that exhibits luminescence upon infection. Once this lysate was identified, it was titered and used to set up lysates with 1e3, 1e2 and 1e1 pfu/ml. Once a luminescent lysate was isolated that had been made with 1e2 phages, this lysate was plated for single plaques. Plaques were picked into SM buffer. These "soakates" were diluted 1:10 in dH2O and assayed by PCR using "DBONO360" and "DBONO361" to look for the presence of recombinant junctions between the luciferase gene and phage sequence.

The P100 phage genomic sequence is available in Genbank (DQ004855). P100 may be obtained from ATCC (PTA-4383™).

The luciferase insertion site for P100 was also downstream of the same cps gene. The location of the firefly luciferase insertion in P100 is between base 13,196 and 13,197 of the P100 genomic sequence.

P100 was engineered in the same manner as A511 with the following exceptions: the "P100 DHR" fragment was amplified using the primers "pMAK dnf" and "pMAK dnr P100". The single recombinant plaque was identified by picking the plaque into 100 µl SM buffer. 10 µl of this soakate was mixed with 50 µl of luciferin and luminescence was seen on the luminometer. This method of identifying positives was utilized in subsequent recombinant phage isolation.

The following phages were engineered using the firefly luciferase gene and the methods described for A511::ffluc: LP48, LP124, LP125, LP99, LP101, LP143.

The following phages were engineered using the NanoLuc gene: A511, P100, LP40, LP124 and LP125.

The PTV for A511::nluc was constructed by amplifying the following PCR fragments: Using an A511 lysate as the template, the UHR fragment was generated using oligos pMAK upf and DBONO356; the DHR fragment was amplified using oligos DBONO359 and pMAK dnr. Using the Promega plasmid pNL1.1 as a template, the NanoLuc fragment was amplified using oligos DBONO357 and DBONO358. The assembly and subsequent PIE methods were similar to those described.

The PTV and engineering for P100::nluc was performed in the same way as for A511::nluc, with the exception that the DHR fragment was amplified using the oligo pMAK dnr P100 rather than pMAK dnr.

The PTVs for LP124, LP125, and LP40 were constructed in the same way as A511::nluc, with the following changes. The DHR fragment amplified was shorter to allow for more efficient assembly of the plasmid, using oligos DBONO359 and DBONO382. Also, the insertion site was modified by adding two additional stop codons (TAATAA) directly downstream of the cps gene of these phages. These 6 bases were added by creating additional primers DBONO379 and DBONO380. The UHR fragments for these phages were amplified using oligos pMAK upf and DBONO380. The NanoLuc fragments were amplified using oligos DBONO379 and DBONO358.

The following oligonucleotides were used in the PIE methods:

pMAK upf:
(SEQ ID NO: 36)
TTACGCCAAGCTTGGCTGCAACGTGAGTTCCTAGACGACC pMAK upr:
(SEQ ID NO: 37)
ATGTTTTTGGCGTCTTCCATATATATTTACCTCCTCTTAGTTGCTA
TGAACGTTTT pMAK lucf:
(SEQ ID NO: 38)
AAAACGTTCATAGCAACTAAGAGGAGGTAAATATATATGGAAGACG
CCAAAAACAT pMAK lucr:
(SEQ ID NO: 39)
ATTCAATTATCCTATAATTATTACAATTTGGACTTTCCGC pMAK dnf:
(SEQ ID NO: 40)
GCGGAAAGTCCAAATTGTAATAATTATAGGATAATTGAAT pMAK dnr:
(SEQ ID NO: 41)
ACGACGGCCAGTGAATTCCCAGTTACTAACTGCTCTAATG pMAK dnr P100:
(SEQ ID NO: 42)
ACGACGGCCAGTGAATTCCCAGTTACTAACTGTTCTAATG

DBONO360:
(SEQ ID NO: 43)
CCTCTAGCTCAAATTAACGCATCTGT

DBONO361:
(SEQ ID NO: 44)
TGGCTCTACATGCTTAGGGTTCC

DBONO356:
(SEQ ID NO: 45)
TCTTCGAGTGTGAAGACCATATATATTTACCTCCTCTTAGTTGC

DBONO357:
(SEQ ID NO: 46)
CTAAGAGGAGGTAAATATATATGGTCTTCACACTCGAAGATTT

DBONO358:
(SEQ ID NO: 47)
ATTCAATTATCCTATAATTATTACGCCAGAATGCGTTCGC

DBONO359:
(SEQ ID NO: 48)
GCGAACGCATTCTGGCGTAATAATTATAGGATAATTGAATAAA

DBONO379:
(SEQ ID NO: 49)
AAAACGTTCATAGCAACTAATAATAAGAGGAGGTAAATATATGG
TCTTCACACTCGAAGATTT

DBONO380:
(SEQ ID NO: 49)
ATATTTACCTCCTCTTATTATTAGTTGCTATGAACGTTTTTACAGG

DBONO382:
(SEQ ID NO: 50)
ACGACGGCCAGTGAATTCCCTCGTGGTGTTCTGACTCCCG

In subsequent experiments some modifications were made to the method. During PTV construction it was discovered that the DHR fragment was often missing from the assembled plasmid. This was overcome by shortening the length of the fragment used, utilizing oligo DBONO382.

In a modified approach, following determining the titer of the recombinant lysate, the enrichment process was sometimes conducted as follows and was used to make the nano luc phages.

96-well microtiter plates were used to grow the PIE lysates at a 200 µl volume. For the FF lysates, the initial step was making 96 lysates at 1e6 pfu/lysate (5e6 pfu/ml), 96 at 1e5, and 95 at 1e4. For the NanoLuc phages, it was found that the recombination efficiency of the recombinant lysate was significantly higher, and that dilutions down to 1e0 pfu/lysate could be used. These lysates were made by incubating at 30° C., shaking at 50 rpm overnight. The lysates were assayed using the appropriate luciferase assay system (ff or nanoglo). Instead of using the lysates to infect fresh cells, it was found that the background signal of the lysate itself was an indication of the presence of recombinant phage.

Upon identification of a lysate made from the fewest number of phages, that lysate was used to set up new 96-well lysates using fewer phages. Once an approximate recombinant frequency of 1:10-1:100 was reached, the phages were plated on agar plates to isolate single plaques as described above.

These methods were used to create recombinant phage comprising either a heterologous open reading frame encoding the ff luciferase or an open reading frame encoding the nano luc luciferase. In order to confirm the integrity of the inserted payload and the surrounding sequence in the engineered phages, a fragment was amplified by PCR and sequenced. This fragment spanned the inserted sequence, beginning in the cps gene, crossing through the firefly or nanoluc gene, and crossing into the downstream sequence. The full cps gene was also PCR amplified using oligos DBONO398 and pMAK upr

DBONO398:
(SEQ ID NO: 57)
TGCTATATTATAGGAACATGGGAA.

The gene was sequenced using oligos DBONO273, DBONO398, and pMAK upr.

The PCR fragment was amplified using primers:

DBONO273:
(SEQ ID NO: 51)
TGCTTACATGCCAGTAGGGGT;
and

DBONO382:
(SEQ ID NO: 50)
ACGACGGCCAGTGAATTCCCTCGTGGTGTTCTGACTCCCG

The nanoluc phages were sequenced using oligos:

DBONO273;

DBONO382;

DBONO361:
(SEQ ID NO: 44)
TGGCTCTACATGCTTAGGGTTCC;

DBONO360:
(SEQ ID NO: 43)
CCTCTAGCTCAAATTAACGCATCTGT;

DBONO362:
(SEQ ID NO: 52)
GTATGAAGGTCTGAGCGGCG
and

DBONO363:
(SEQ ID NO: 53)
GATCTGGCCCATTTGGTCGC.

The firefly phages were sequenced using oligos:

DBONO273;

DBONO382;

DBONO360;

DBONO361;

DBONO274:
(SEQ ID NO: 54)
CGCATAGAACTGCCTGCGTC;

DBONO151:
(SEQ ID NO: 55)
CACCCCAACATCTTCGACGC;
and

DBONO152:
(SEQ ID NO: 56)
GCGCAACTGCAACTCCGATA

Sequencing was performed by Genewiz, Inc. Using the Geneious software package, alignments were made and a consensus sequence was generated for each phage.

The following engineered phages have been created and the insertion site regions sequenced as described above:
Phages Containing an Inserted Firefly Luciferase:
LP48::ffluc (SEQ ID NO: 23);
LP99::ffluc (SEQ ID NO: 24);
LP101::ffluc (SEQ ID NO: 25);
LP124::ffluc (SEQ ID NO: 26);
LP125::ffluc (SEQ ID NO: 27);
LP143::ffluc (SEQ ID NO: 28);
A511::ffluc (SEQ ID NO: 29); and
P100::ffluc (SEQ ID NO: 30).
Phages Containing an Inserted Nano Luc Luciferase:
LP124::nluc (SEQ ID NO: 31);
LP125::nluc (SEQ ID NO: 32);
A511::nluc (SEQ ID NO: 33);
P100::nluc (SEQ ID NO: 34).

The insertion site regions of the phages comprising an inserted firefly luciferase coding sequence are aligned in FIG. 3. Each sequence includes the following parts.

|  | LP48 | LP99 | LP101 | LP124 | LP125 | LP143 | A511 | P100 |
| --- | --- | --- | --- | --- | --- | --- | --- | --- |
| cps gene | 1-1407 | 1-1407 | 1-1407 | 1-1407 | 1-1407 | 1-1404 | 1-1404 | 1-1407 |
| RBS (inserted) | 1408-1423 | 1408-1423 | 1408-1423 | 1408-1423 | 1408-1423 | 1405-1420 | 1405-1420 | 1408-1423 |

-continued

|  | LP48 | LP99 | LP101 | LP124 | LP125 | LP143 | A511 | P100 |
|---|---|---|---|---|---|---|---|---|
| Firefly Luciferase | 1424-3076 | 1424-3076 | 1424-3076 | 1424-3076 | 1424-3076 | 1421-3073 | 1421-3073 | 1424-3076 |
| Downstream genes | 3077-3729 | 3077-3789 | 3077-3789 | 3077-3789 | 3077-3729 | 3074-3786 | 3074-3786 | 3077-3729 |

The insertion site regions of the phages comprising an inserted nano luc luciferase coding sequence are aligned in FIG. 4. Each sequence includes the following parts.

|  | LP124::nluc | LP125::nluc | A511::nluc | P100::nluc | LP40::nluc |
|---|---|---|---|---|---|
| cps gene | 1-1407 | 1-1407 | 1-1404 | 1-1407 | 1-1407 |
| additional stop codons (inserted) | 1408-1413 | 1408-1413 | n/a | n/a | 1408-1413 |
| RBS (inserted) | 1414-1429 | 1414-1429 | 1405-1420 | 1408-1423 | 1414-1429 |
| NanoLuc | 1430-1945 | 1430-1945 | 1421-1936 | 1424-1939 | 1430-1945 |
| Downstream genes | 1946-2658 | 1946-2598 | 1937-2649 | 1940-2592 | 1946-2613 |

The cps open reading frames and encoded proteins for each phage are:

| Phage | Cps Gene Sequence | Cps Protein Sequence |
|---|---|---|
| LP40 | 5 | 6 |
| LP48 | 7 | 8 |
| LP99 | 9 | 10 |
| LP101 | 11 | 12 |
| LP124 | 13 | 14 |
| LP125 | 15 | 16 |
| LP143 | 17 | 18 |
| A511 | 19 | 20 |
| P100 | 21 | 22 |

The cps gene sequences are aligned in FIG. 1 and the protein sequences in FIG. 2. The cps genes of the engineered phage display a relatively high degree of homology.

All of the above phages were engineered using the methods described above. Partial genome sequences showed that the primers used for A511 could be used to create PTVs for LP48, LP124, and LP125. No genome sequence was available at the time for LP99, LP101 or LP143. Using the A511 PTV primers, it was possible to amplify the appropriate fragments for PTV construction in the same manner as A511. This reflects homology between the cps gene regions across those phages. The luciferase gene insertion site was at the same location (after the cps gene stop codon TAA) as in A511::ffluc.

Example 6

Host Range Characterization of Combinations of *Listeria* Phages

After engineering the genome of the phages with two different genetic payloads, Firefly Luciferase and Nanoluciferase, the host range of these phages was retested to ensure that the genome modifications did not affect the fitness of the phages or compromise their ability to provide coverage across the *Listeria* strain host panel. Engineered phages were tested in the liquid-based host range assay and compared to non-modified bacteriophages. The engineered bacteriophages did not show a change in their host range compared to the non-modified wild-type versions (Table 4).

The identification of bacteriophages that, when their individual host range profiles were combined, provided the necessary coverage of the *Listeria* genus raised the question of whether the phages when used in a combinatorial infection would provide the additive coverage expected or whether the presence of additional bacteriophages in an infection would diminish the ability of a single bacteriophage to infect a susceptible strain. To test this, combinations of bacteriophages (cocktails) were tested for the ability of a bacteriophage cocktail to provide clearance in the liquid-based host range assay. For these infections the final concentration of phage was maintained at a constant $1 \times 10^5$ pfu consisting of equal amounts of each of the phage within the cocktail (i.e.—a two phage cocktail would consist of $5 \times 10^4$ pfu of each of the two component phages). The combination of bacteriophages in a cocktail (either a two, three or four bacteriophage cocktail) did not cause a loss of host range and provided the expected additive effects of the host range of the individual bacteriophages (Table 4). The additive effect of the bacteriophages was independent of the genomic modifications as neither the engineered Firefly luciferase and Nanoluc luciferase expressing bacteriophages had an altered liquid-based host range compared to the unengineered bacteriophages.

Example 7

Comparison of Liquid-Based Host Range Versus Marker-Based Host Range

The ability of a bacteriophage to clear an actively growing culture is determined by a number of factors including the rate of growth of a particular strain and the rate of bacteriophage replication, in addition to the ability of the bacteriophage to infect a specific strain. Therefore, the output of culture clearance measure used in the liquid culture method disclosed herein is potentially more restrictive than the host range that could be determined by exposing bacterial strains to an recombinant phage comprising a heterologous nucleic acid sequence encoding a marker and assaying for marker production. One example of such a marker is luciferase. Therefore, the host range was determined for phage LP124:nluc by both the liquid-based host range assay and by an infection based luciferase detection assay. To carry out the infection based assay, the *Listeria* host panel strain collection was struck out on Brain Heart Infusion (BHI) agar plates and single colonies were inoculated in 1 ml BHI liquid in a 2-ml 96-deep well dish, covered with a sterile breathable sterile membrane and grown at 30 C for 16 hours. Each of the 16-hour cultures from the 96-well plates were diluted 1:10,000 in 198 µl of BHI. For the infection, 12.5 µl of the culture dilution were mixed added to 12.5 µl of LP124:nluc at a concentration of $1 \times 10^7$ pfu/ml in a opaque luminescence reader plate and incubated at 30 C for 3 hours. After three hours the level of luminescence was detected using a Promega Glomax 96-well plate reader using Promega NanoGlo reaction following manufacturer's recommendations.

Table 5 shows the host range determined by the two methods. A strain was considered to be within host range for the clearance assay if the ratio of infected culture OD600 to the uninfected culture OD600 was less than 0.4. For the luciferase detection-based host range assay strains were stratified in three categories, high RLU strains (Table 5, dark gray shading), medium RLU strains (Table 5, light gray shading), and low RLU strains (Table 5, unshaded). Based on the performance of the assay a strain was considered to be within the host range of the bacteriophage if the RLU measurement was greater than 10,000 Random Light Units (RLU) (Table 5, light gray shading). This luciferase activity cut-off was used because it characterizes a useful level of sensitivity in bacterial assays. Based on these criteria the liquid-based host range clearance, LP124 shows a broad host range by clearing 50.5% (140 of 276) of the Listeria strains tested. By the luciferase detection assay, 78.2% (216 of 276) of the Listeria strains tested showed high RLU levels.

The comparison between the ability of LP124::nluc to clear cultures of the Listeria host-panel to the RLU output shows that the host range measured using marker expression is greater than that defined using the liquid-based host range. This could be for several reasons. First, a bacterial strain that is not cleared by the infection but that produces light may have a growth rate that outpaces the ability of the bacteriophage to infect and replicate. In this case, the strain would never succumb completely to bacteriophage because the number of uninfected cells would outpace the bacteriophage in the culture. Second, the bacteriophage may be able to carry out the initial steps of infection (i.e. attachment, injection of DNA and translation of viral proteins) but be unable to complete the infection process (i.e. virion assembly, release from the cell). Because the bacteriophage life-cycle can be separated into discrete steps, a bacteriophage is capable to produce phage encoded proteins, in this case luciferase, without clearance of the culture or producing additional bacteriophage. While additional strains that produce luciferase without producing bacteriophage would not fall within the classical definition of host range for a bacteriophage, the strains do meet inclusion in the host range definition for the purpose of this disclosure because the host range that matters in methods of detecting target bacteria using a phage comprising a heterologous nucleic acid sequence encoding a marker is the types of bacteria that support marker production. This increased host-range observed when using the engineered bacteriophage is an advantageous byproduct of the engineering process and could not be determined a priori for the Listeria host panel.

One possible concern raised by the ability of a bacteriophage to produce light in a bacterial strain that it could not clear from a liquid-based culture is that other off-target bacterial genera may also produce luciferase in the presence of engineered phages. These bacterial species would not have been considered to be in host range of these phages because of an inability to produce bacteriophage in response to bacteriophage infections. However, the increased sensitivity for detecting early stages of infection with the engineered phages could, at least theoretically, result in production of marker (in this case luciferase—assayed by light production) in strains of bacteria not identified as hosts using the liquid culture method, for example. To address this issue, a panel of bacterial species closely related to Listeria was assembled (Table 6). This panel consisted of other Gram-positive organisms phylogenetically similar to Listeria. To determine if these strains were able to produce light in the presence of the engineered bacteriophage each of the species were grown for 16 hours under appropriate growth conditions (Table 6). The strains were diluted to a concentration of $10^5$ cfu/ml and then 90 µl of cells were mixed with 10 µl of a bacteriophage cocktail at $1 \times 10^7$ pfu/ml and incubated for 3 hours at 30 C. The reactions were then measured for the presence of luciferase using the standard protocol. None of the bacterial species tested had detectable levels of RLU (Table 6) demonstrating that the ability of the bacteriophages to show RLUs in strains that they do not clear is not a strictly off-target effect that will decrease the accuracy of a bacteriophage reporter based assay.

A second question was whether these bacteria species that were phylogenetically similar to Listeria would decrease the sensitivity of the engineered bacteriophages to detect Listeria when the Listeria and non-Listeria bacteria species were present together in an assay. To examine this possibility the related bacterial species were grown as above and diluted to a concentration of $10^5$ cfu/ml. A Listeria strain was struck out on Brain Heart Infusion (BHI) agar plates and single colonies were inoculated in 5 ml BHI liquid and grown at 30 C for 16 hours. The overnight culture was diluter 1:5 in fresh 0.5×BHI medium and grown for 2 hours at 30 C shaking at 200 rpm in an orbital shaker. After two hours a 10-fold serial dilution of the culture was made. To perform the test 10 µl of the Listeria serial dilution that should represent ~10 cfu total was mixed with 20 µl of the potentially inhibitory bacterial species and 10 µl of the bacteriophage cocktail (A511::nluc/LP124::nluc/P100::nluc) and the mixture was incubated for 3 hours at 30 C. After the incubation the reaction was assayed for the presence of luciferase using the Promega Glomax 20/20 luminometer and Promega NanoGlo reaction as suggested. These assays showed that there was no decrease in the ability to detect Listeria in the presence of $10^4$ greater numbers of competing bacteria (Table 6) demonstrating the sensitivity of the assay is not affected by the presence of non-target bacteria in samples.

This selection of bacteria was a limited set and did not represent all of the bacteria that could be present during environmental sampling. To generate a more exhaustive sample of bacterial species that may decrease the sensitivity and accuracy of the bacteriophage cocktail, environmental samples were collected from food processing plants and bacterial species were isolated from environmental swabs to determine the effect of these species on performance of the assay. To isolate bacterial species that were present, environmental samples were plated onto both Brain Heart Infusion Agar or R2A agar and grown overnight at 30 C. Bacteria that were present on the plates were identified based on colony morphology and struck to purity on BHI agar plates. Pure cultures of the bacterial species were grown in BHI medium at 30 C for 16 hours. The cultures were diluted to a concentration of $10^5$ cfu/ml and tested for both the production of luciferase in the presence of the bacteriophage cocktail and inhibition of Listeria infection by the bacteriophage cocktail as above. None of the bacterial species, consisting of both Gram-positive and Gram-negative bacteria, showed any luciferase production in the presence of the bacteriophage (Table 7). Additionally, incubation of Listeria in the presence of the collected samples failed to show any decrease in the production of luciferase, demonstrating that the environmentally collected bacteria do not decrease the sensitivity or accuracy of the assay.

Example 8

Design of Phage Compositions

The increased host range observed by the RLU-based luciferase detection assay compared to the liquid-based host range assay identified a novel method for distinguishing differences between the host range of bacteriophages. Additionally, the RLU-based luciferase detection assay as a means to assess phage host range allows for a highly accurate assessment of the target bacteria identified by an engineered bacteriophage under conditions similar to those of methods of detecting target bacteria. One way this information may be used is to identify useful combinations of phage that can be combined to make a combination of phage having a useful cumulative host range.

To determine the additive effect of including LP124::nluc in a bacteriophage cocktail a RLU-based luciferase detection assay was compared between A511::nluc and LP124::nluc for a portion of the *Listeria* host range panel. LP124::nluc had a larger RLU-based host range (detects 77 of 96 strains, 80.2%) compared to A511:nluc (detects 37 of 96 strains, 38.5%) (Table 8). Moreover, LP124:nluc produces greater than 100-times higher RLU values compared to A511:nluc in 73 of 96 strains (76%). This increased RLU output from LP124:nluc infections predicts that a bacteriophage cocktail that contains both A511 and LP124:nluc would have greater sensitivity and accuracy over a A511:nluc alone.

To test whether LP124::nluc would increase the levels of RLU produced in the presence of A511 and P100 the RLU values were compared between samples infected with both a two-phage cocktail (A511::nluc/P100::nluc) and a three-phage cocktail (A511::nluc/P100::nluc/LP124::nluc). To test this, 1 ml of complex environmental samples grown in UVM medium were pelleted by centrifugation. The supernatant was removed and the cells were resuspended in 100 μl of either the two-phage or three-phage cocktail at a total bacteriophage concentration of 1×10$^7$ and incubated at 30 C. RLU levels were measured by using Promega NanoGlo reagent and the Promega 20/20 luminometer. As for the *Listeria* host panel, the environmental samples showed higher levels of RLU in the presence of the three-phage cocktail than the two-phage cocktail (Table 9). This increase in the RLU output of the infection demonstrates a clear advantage from having LP124::nluc present over P100::nluc and A511::nluc alone.

The increased host range and RLU output of the three-phage compared to the two-phage cocktail suggested that a cocktail of A511::nluc and LP124::nluc would provide useful coverage against environmental samples. To determine the ability of the cocktail to identify *Listeria* relevant to food processing plants environmental sampling was conducted in various food processing plants in the United States. These food processing plants represented seafood, dairy, meat and produce processing plants and were geographically diverse in their location. After environmental collection was performed, *Listeria* that were present in the environmental samples were isolated using a modified USDA isolation method. The *Listeria* were struck out on BHI agar plates and a single colony was used to inoculate 1 ml of 0.5×BHI medium in a 2 ml deep well dish and covered with a sterile breathable membrane and incubated for 16 hours at 30 C. Each of the 16-hour cultures from the 96-well plated were diluted 1:10,000 in 198 μl of BHI. For the infection, 12.5 μl of the culture dilution were mixed added to 12.5 μl of a bacteriophage cocktail containing A511::nluc and LP124::nluc at a total bacteriophage concentration of 1×10$^7$ pfu/ml in a opaque luminescence reader plate and incubated at 30 C for 3 hours. After three hours the level of luminescence was detected using a Promega Glomax 96-well plate reader using Promega NanoGlo reaction following manufacturer's recommendations. Concurrently, a liquid-based host range assay was performed to compare the RLU output to culture clearance.

Based on the liquid-based host range assay the bacteriophage cocktail was able to clear the bacterial culture in 25 of 100 strains (25%). This decreased level of clearance is due to a greater growth rate for the environmentally isolated strains compared to commone lab isolates tested in the *Listeria* host range panel. The RLU based host range assay identified 75 of 100 strains (75%) (Table 10). These environmental samples represented complex microbiological communities and had multiple *Listeria* isolates per environmental sample. The presence of multiple strains of *Listeria* within these microbiological communities improves the sensitivity of the assay. In this example the environmental samples were collected using sponges and the sponges were incubated for up to 24 h with media, after which an aliquot was removed and assayed for the presence or absence of the bacterial population to be detected. Based on the ability of the bacteriophage cocktail to identify individual *Listeria* strains identified from the same environmental samples it would have been predicted that the bacteriophage cocktail of A511 and LP124:nluc would be able to detect 48 of 57 (84.2%) *Listeria* positive sponges. When the environmental sponge was incubated in a growth medium and a sample of the enriched sample is tested using the assay the bacteriophage cocktail containing A511 and LP124:nluc was able to detect 49 of 57 (85.9%) *Listeria*-positive sponges. This increased sensitivity demonstrates that the presence of multiple *Listeria* strains, including those out of host range for the bacteriophage cocktail, does not diminish the sensitivity of the assay to detect *Listeria* strains that are sensitive to the bacteriophage cocktail.

TABLE 2

| NP # | A511 Plate | P100 Plate | Avg A511 | Avg P100 | A511/P100 Cocktail |
|---|---|---|---|---|---|
| NP1900 | ▮ | 0.00 | 0.09 | 1.03 | 0.29 |
| NP1901 | 0.75 | 0.17 | 0.15 | 0.10 | 0.10 |
| NP1902 | ▮ | ▮ | 0.10 | 1.04 | 0.30 |
| NP1903 | 0.75 | 0.03 | 0.09 | 0.11 | 0.10 |
| NP1904 | ▮ | ▮ | 0.09 | 0.11 | 0.11 |
| NP1905 | ▮ | ▮ | 0.16 | 0.12 | 0.12 |
| NP1906 | ▮ | ▮ | 0.10 | 1.08 | 0.79 |
| NP1907 | ▮ | 0.00 | 0.09 | 1.05 | 0.30 |
| NP1908 | 0.45 | 0.17 | 0.19 | 0.10 | 0.11 |
| NP1909 | ▮ | 0.00 | 0.09 | 1.00 | 0.10 |
| NP1912 | ▮ | 0.00 | 0.10 | 0.93 | 0.28 |
| NP1959 | 0.28 | 0.20 | 0.09 | 0.09 | 0.10 |
| NP1960 | 0.00 | 0.00 | 0.09 | 0.91 | 0.15 |
| NP1961 | ▮ | 0.20 | 0.11 | 0.10 | 0.12 |
| NP1962 | ▮ | 0.00 | 0.09 | 0.91 | 0.34 |
| NP1963 | 0.12 | 0.90 | 0.09 | 0.09 | 0.12 |
| NP1964 | 0.80 | 1.40 | 0.09 | 0.09 | 0.10 |
| NP1965 | 0.20 | 0.30 | 0.09 | 0.09 | 0.10 |
| NP1966 | ▮ | 0.20 | 0.09 | 0.10 | 0.11 |
| NP1967 | 1.40 | 0.50 | 0.10 | 0.09 | 0.10 |
| NP1915 | 0.10 | ▮ | 0.77 | 0.10 | 0.11 |
| NP1997 | 0.05 | 0.00 | 0.09 | 0.11 | 0.11 |

TABLE 2-continued

| | | | | | |
|---|---|---|---|---|---|
| NP1998 | 0.10 | | 0.09 | 0.10 | 0.11 |
| NP1999 | 0.10 | 0.70 | 0.09 | 0.14 | 0.11 |
| NP2000 | 0.10 | 0.00 | 0.09 | 0.10 | 0.11 |
| NP2001 | 0.05 | 1.00 | 0.10 | 0.11 | 0.11 |
| NP2002 | | | 0.10 | 0.98 | 0.28 |
| NP2003 | | 0.00 | 0.16 | 1.03 | 0.09 |
| NP2004 | | 0.00 | 0.13 | 1.00 | 0.10 |
| NP2005 | | 0.00 | 0.31 | 0.89 | 0.13 |
| NP1916 | | 0.00 | 0.41 | 0.90 | 1.01 |
| NP2006 | | 0.00 | 0.12 | 0.77 | 0.09 |
| NP2007 | 0.06 | 10.00 | 0.09 | 0.09 | 0.11 |
| NP2008 | 0.10 | 1.00 | 0.09 | 0.09 | 0.11 |
| NP2009 | 0.25 | 0.90 | 0.09 | 0.11 | 0.11 |
| NP2010 | | 0.00 | 0.29 | 0.76 | 0.09 |
| NP2011 | | 0.00 | 0.45 | 0.78 | 1.00 |
| NP2012 | 0.00 | 0.00 | 0.57 | 1.04 | 1.04 |
| NP2013 | 0.00 | 0.00 | 0.49 | 1.00 | 1.04 |
| NP2014 | | 0.00 | 0.39 | 0.84 | 0.10 |
| NP1869 | 0.10 | 1.71 | 0.13 | 0.21 | 0.13 |
| NP1840 | | | 1.02 | 1.17 | 1.05 |
| NP1839 | 1.00 | 1.00 | 0.24 | 0.35 | 0.14 |
| NP2024 | 4.00 | 0.50 | 0.10 | 0.10 | 0.11 |
| NP2025 | 1.20 | 0.33 | 0.09 | 0.09 | 0.11 |
| NP2026 | 1.10 | 0.33 | 0.56 | 0.57 | 0.26 |
| NP2027 | 0.00 | 0.27 | 0.10 | 0.12 | 0.12 |
| NP2028 | 1.00 | 0.33 | 0.09 | 0.09 | 0.12 |
| NP2029 | | | 0.21 | 0.98 | 0.12 |
| NP2030 | 0.00 | 1.33 | 0.10 | 0.09 | 0.12 |
| NP2031 | 0.10 | 0.27 | 0.09 | 0.09 | 0.11 |
| NP2032 | 1.00 | 0.33 | 0.08 | 0.09 | 0.12 |
| NP1879 | 0.20 | 0.50 | 1.05 | 0.13 | 0.20 |
| NP2033 | 1.00 | 0.67 | 0.10 | 0.11 | 0.10 |
| NP2034 | 0.90 | 3.33 | 0.10 | 0.11 | 0.11 |
| NP2035 | 2.00 | 0.30 | 0.10 | 0.11 | 0.11 |
| NP2036 | 1.00 | 0.33 | 0.09 | 0.09 | 0.12 |
| NP2037 | 1.00 | 0.33 | 0.10 | 0.11 | 0.11 |
| NP2038 | | 1.00 | 1.04 | 0.11 | 0.23 |
| NP2039 | | 0.33 | 0.99 | 0.10 | 0.24 |
| NP2040 | | 0.33 | 0.89 | 0.10 | 0.23 |
| NP2041 | 1.50 | 0.33 | 0.10 | 0.12 | 0.12 |
| NP2042 | | 0.17 | 0.15 | 0.09 | 0.13 |
| NP2043 | | 1.33 | 0.09 | 0.09 | 0.10 |
| NP2044 | | 0.00 | 0.09 | 0.09 | 0.26 |
| NP2045 | | 3.33 | 0.20 | 0.20 | 0.11 |
| NP2046 | 0.00 | 0.07 | 0.09 | 0.09 | 0.11 |
| NP2047 | | 0.17 | 0.10 | 0.10 | 0.13 |
| NP2048 | | 0.33 | 0.13 | 0.10 | 0.17 |
| NP2049 | | 0.33 | 0.10 | 0.09 | 0.21 |
| NP2050 | | 0.27 | 0.10 | 0.09 | 0.12 |
| NP1880 | 0.00 | 0.00 | 1.01 | 1.07 | 1.07 |
| NP2051 | | 0.33 | 0.90 | 0.09 | 0.19 |
| NP2052 | 1.00 | 0.07 | 0.09 | 0.09 | 0.10 |
| NP2053 | 0.30 | 0.33 | 0.09 | 0.09 | 0.12 |
| NP2054 | 0.30 | 0.07 | 0.09 | 0.09 | 0.16 |
| NP2055 | 2.00 | 0.43 | 0.09 | 0.09 | 0.10 |
| NP2056 | 1.20 | 0.10 | 0.09 | 0.09 | 0.12 |
| NP2057 | | 0.33 | 0.97 | 0.09 | 0.28 |
| NP2058 | | 0.10 | 0.97 | 0.10 | 0.25 |
| NP2059 | 0.09 | 0.17 | 0.12 | 0.13 | 0.14 |
| NP1881 | 0.00 | 0.00 | 0.17 | 1.05 | 0.14 |
| NP2060 | 0.00 | | 0.44 | 0.95 | 0.98 |
| NP2061 | | | 0.12 | 0.89 | 0.12 |
| NP2062 | | | 0.12 | 0.90 | 0.13 |
| NP2063 | | | 0.96 | 1.03 | 1.25 |
| NP2064 | | 0.01 | 0.09 | 0.09 | 0.25 |
| NP2065 | | | 0.11 | 0.97 | 0.09 |
| NP2066 | | | 0.49 | 1.02 | 0.96 |
| NP2067 | 0.00 | 0.00 | 1.06 | 1.08 | 0.93 |
| NP1868 | | | 1.12 | 1.11 | 1.05 |
| NP2069 | | | 0.19 | 1.04 | 0.17 |
| NP2070 | | 0.27 | 0.45 | 0.10 | 0.11 |
| NP2071 | 0.00 | 0.00 | 1.14 | 1.14 | 1.21 |
| NP2072 | 0.60 | 0.33 | 0.10 | 0.11 | 0.12 |
| NP2073 | | | 0.63 | 1.12 | 1.07 |
| NP2074 | 0.10 | 0.33 | 0.18 | 0.11 | 0.16 |
| NP2075 | | 0.03 | 0.12 | 0.91 | 0.79 |
| NP2076 | 1.20 | 0.27 | 0.09 | 0.10 | 0.11 |
| NP2077 | 0.00 | 0.17 | 0.14 | 0.10 | 0.11 |
| NP1882 | 0.95 | 0.58 | 0.93 | 0.11 | 0.12 |
| NP2078 | | | 0.11 | 0.77 | 0.17 |
| NP2079 | | | 1.04 | 1.07 | 1.04 |
| NP2080 | 0.00 | 0.00 | 1.04 | 1.05 | 1.02 |
| NP2081 | 0.00 | 0.00 | 1.00 | 0.98 | 1.01 |
| NP2082 | 0.00 | 0.00 | 1.07 | 1.06 | 1.02 |
| NP2083 | | | 0.13 | 0.36 | 0.89 |
| NP2084 | | | 0.14 | 1.00 | 0.17 |
| NP2085 | 0.00 | 0.00 | 1.01 | 1.00 | 0.95 |
| NP2086 | | | 0.19 | 1.06 | 0.17 |
| NP2087 | 0.00 | 0.00 | 0.96 | 0.96 | 1.16 |
| NP2088 | 0.20 | 0.60 | 0.11 | 0.11 | 0.15 |
| NP2089 | 0.00 | 0.00 | 0.90 | 1.00 | 1.06 |
| NP2090 | 0.50 | 0.40 | 0.12 | 0.12 | 0.17 |
| NP2091 | 0.01 | 0.01 | 0.10 | 0.16 | 0.49 |
| NP2092 | 0.50 | 1.00 | 0.09 | 0.09 | 0.10 |
| NP2093 | | 1.00 | 0.25 | 0.09 | 0.10 |
| NP2094 | | 1.00 | 0.09 | 0.09 | 0.10 |
| NP2095 | 1.00 | 0.20 | 0.14 | 0.18 | 0.22 |
| NP2096 | | 0.30 | 0.13 | 0.09 | 0.10 |
| NP2097 | 0.00 | 0.70 | 0.12 | 0.10 | 0.11 |
| NP2098 | | 0.00 | 0.12 | 0.09 | 0.13 |
| NP2099 | 0.00 | 0.20 | 0.12 | 0.09 | 0.11 |
| NP2100 | 0.00 | 0.00 | 0.97 | 1.00 | 0.99 |
| NP2101 | | 0.00 | 0.91 | 1.02 | 1.04 |
| NP2102 | | 0.00 | 0.98 | 1.02 | 1.01 |
| NP2103 | 0.00 | 0.00 | 1.02 | 1.01 | 0.98 |
| NP2104 | | 0.00 | 0.98 | 1.02 | 1.03 |
| NP1883 | 0.00 | 0.00 | 0.40 | 0.94 | 1.00 |
| NP2105 | 0.00 | 0.00 | 1.05 | 1.03 | 1.02 |
| NP2106 | | | 0.79 | 1.04 | 1.01 |
| NP2107 | 0.00 | 0.00 | 1.07 | 1.12 | 1.03 |
| NP2108 | 0.00 | 0.00 | 1.05 | 1.11 | 1.01 |
| NP2109 | | | 0.10 | 1.09 | 0.10 |
| NP2110 | 0.00 | 0.00 | 0.92 | 0.84 | 1.06 |
| NP2111 | | | 0.71 | 0.92 | 1.12 |
| NP2112 | 0.00 | 0.00 | 1.00 | 0.92 | 1.05 |
| NP2113 | 2.00 | 0.30 | 0.09 | 0.09 | 0.10 |
| NP1884 | 0.00 | | 0.10 | 1.09 | 0.20 |
| NP2114 | | | 0.09 | 0.48 | 0.09 |
| NP2115 | | | 0.09 | 0.97 | 0.09 |
| NP2116 | | | 0.09 | 1.03 | 0.09 |
| NP2117 | | | 0.10 | 0.88 | 0.10 |
| NP2118 | | | 0.10 | 1.01 | 0.10 |
| NP2119 | | | 0.09 | 0.86 | 0.09 |
| NP2120 | | | 0.11 | 1.06 | 0.11 |
| NP2121 | | 0.00 | 0.09 | 0.98 | 0.09 |
| NP2122 | | | 0.09 | 0.88 | 0.09 |

TABLE 2-continued

| | | | | | |
|---|---|---|---|---|---|
| NP1885 | | | 0.94 | | |
| NP2123 | | | | | |
| NP2124 | | | | | |
| NP2125 | | | | | |
| NP2126 | | | 0.52 | | |
| NP2127 | | | 0.93 | 1.06 | 1.08 |
| NP2128 | | | | | |
| NP2129 | | | | | |
| NP2130 | | | | | |
| NP2131 | 0.00 | | | | |
| NP1886 | 0.00 | 0.00 | 0.47 | 0.96 | 1.04 |
| NP2132 | 0.00 | 0.00 | 1.03 | 1.02 | 1.03 |
| NP1887 | | 0.00 | 1.02 | 0.99 | 1.00 |
| NP2133 | | | 1.07 | | |
| NP2134 | | 0.00 | 1.06 | 1.12 | 1.16 |
| NP2135 | 0.00 | | | | |
| NP2136 | | | 0.86 | | |
| NP2137 | | | 0.85 | | |
| NP2138 | | 0.00 | 0.98 | 1.01 | 1.00 |
| NP2139 | | | | | |
| NP2140 | | | 0.96 | 0.97 | 1.08 |
| NP2141 | | | | | |
| NP2142 | | | 0.71 | 1.06 | 1.02 |
| NP2143 | | | 0.90 | 1.05 | 1.03 |
| NP2144 | 0.00 | 0.00 | | | |
| NP2145 | 0.00 | 0.00 | | | |
| NP2146 | | | 0.94 | 0.94 | 1.12 |
| NP2147 | | 0.00 | | | |
| NP2148 | 0.00 | | | | |
| NP2149 | 0.00 | 0.00 | 1.12 | 1.18 | 1.01 |
| NP2150 | 0.00 | 0.00 | 0.73 | 1.12 | 1.11 |
| NP1888 | | | | 0.97 | |
| NP2151 | 0.00 | 0.00 | 1.13 | 1.07 | 1.04 |
| NP2152 | | | | | |
| NP2153 | | 0.00 | 0.81 | 1.01 | 1.05 |
| NP2154 | | 0.00 | 1.06 | 1.00 | 1.09 |
| NP2155 | 0.00 | 0.00 | 0.74 | 1.00 | 1.10 |
| NP2156 | | | | | |
| NP2157 | | | | | |
| NP2158 | 0.00 | | | | |
| NP2159 | 0.00 | 0.00 | 1.11 | 1.10 | 1.23 |
| NP1889 | | | 1.02 | | |
| NP2160 | | 0.00 | | | |
| NP2161 | | | | | |
| NP2162 | | | | | |
| NP2163 | | | | | |
| NP2164 | | | 1.05 | 1.11 | 0.96 |
| NP2165 | | | 0.44 | 0.95 | 1.16 |
| NP2166 | 0.00 | 0.00 | | | |
| NP2167 | | | | | |
| NP2168 | | | | | |
| NP1890 | 0.00 | 0.00 | 0.89 | 1.02 | 1.04 |
| NP2169 | | | | | |
| NP2170 | | | | | |
| NP2171 | | | | | |
| NP2172 | | | | | |
| NP2173 | | | | | |
| NP2174 | | | | | |
| NP2175 | 0.00 | 0.00 | 1.08 | 1.05 | 1.05 |
| NP2176 | 0.00 | 0.00 | 1.07 | 1.06 | 1.08 |
| NP2177 | | | 1.08 | 1.06 | 0.91 |
| NP1878 | | | | | |
| NP1911 | 0.00 | | | 0.54 | |
| NP1950 | | | | | |
| NP1951 | | | | | |
| NP1952 | 0.05 | | | | |
| NP1953 | | | | | |
| NP1954 | | | | | |
| NP1955 | | 0.00 | | | |
| NP1956 | | 0.00 | | 1.03 | |
| NP1957 | 0.00 | | | | |
| NP1958 | | | | | |
| NP1913 | | 0.00 | | 0.78 | |
| NP1968 | | | | | |
| NP1969 | | | | | |
| NP1970 | 0.08 | | | | |
| NP1971 | | | | | |
| NP1972 | 0.00 | 0.00 | 1.11 | 1.22 | 0.92 |
| NP1973 | | 0.00 | 0.22 | 0.73 | |
| NP1974 | | 0.00 | 0.23 | 0.70 | |
| NP1975 | | | 0.95 | 1.03 | 1.12 |
| NP1976 | | | | | |
| NP1891 | 0.00 | 0.00 | 0.99 | 1.03 | 0.95 |
| NP1892 | 0.00 | 0.00 | 1.01 | 1.04 | 0.96 |
| NP1893 | 0.00 | 0.00 | 1.00 | 1.04 | 0.97 |
| NP1894 | 0.00 | | | 0.99 | |
| NP1895 | | | | | |
| NP1896 | | | | | |
| NP1897 | | | | | |
| NP1898 | | | 0.99 | | |
| NP1899 | 0.00 | 0.00 | | 1.04 | |
| NP1990 | | 0.00 | | 1.07 | 0.59 |
| NP1991 | | 0.00 | | 1.03 | |
| NP1992 | | 0.00 | | 1.07 | |
| NP1993 | | 0.00 | | 1.04 | |
| NP1994 | | 0.00 | | 0.99 | |
| NP1995 | | 0.00 | | 0.93 | |
| NP1996 | 0.05 | | | | |
| NP1910 | | | | | |
| NP1945 | | | | | |
| NP1946 | 0.00 | | | | |
| NP1947 | 0.00 | | | | |
| NP1948 | 0.00 | | | | 0.47 |
| NP1949 | | | | | |
| NP1977 | 0.06 | | | | |
| NP1978 | | 0.00 | 0.44 | 1.04 | 1.10 |
| NP1979 | 0.00 | 0.00 | 0.52 | 1.01 | 1.04 |
| NP1980 | | | 0.27 | 1.04 | |
| NP1981 | | 0.00 | 0.39 | 0.84 | |
| NP1982 | | 0.00 | 0.35 | 0.87 | |
| NP1983 | | | | | |
| NP1984 | 0.00 | 0.00 | 0.27 | 0.95 | |
| NP1985 | | 0.00 | 0.63 | 1.05 | 1.01 |
| NP1914 | | | | | |
| NP1986 | | | | | |
| NP1987 | | | | | |
| NP1988 | 0.00 | | | | |
| NP1989 | 0.00 | | 0.83 | | |
| NP1917 | | 0.00 | | 1.00 | |
| NP2015 | 0.00 | 0.00 | | | |
| NP2016 | 0.00 | 0.00 | | | |
| NP2017 | | | | | |
| NP2018 | | 0.00 | | | |
| NP2019 | | | | | |
| NP2020 | 0.00 | | | | 0.83 |
| NP2021 | 0.00 | 0.00 | 0.26 | 1.06 | |
| NP2022 | | 0.00 | | 1.07 | |
| NP2023 | | 0.00 | 0.44 | 0.98 | 1.03 |

TABLE 3A

| NP # | LP14 | LP20 | LP30 | LP34 | LP39 | LP40 | LP44 |
|---|---|---|---|---|---|---|---|
| 1900 | 1.18 | 0.09 | 1.01 | 1.14 | 1.14 | 0.52 | 0.24 |
| 1901 | 1.11 | 0.18 | 1.00 | 0.12 | 1.14 | 0.98 | 0.09 |
| 1902 | 1.10 | 0.13 | 0.99 | 0.22 | 1.15 | 0.95 | 0.09 |
| 1903 | 1.10 | 0.11 | 1.01 | 0.13 | 1.13 | 0.95 | 0.09 |
| 1904 | 1.11 | 0.10 | 1.02 | 0.11 | 1.13 | 0.85 | 0.14 |
| 1905 | 1.12 | 0.10 | 1.01 | 0.19 | 1.12 | 0.87 | 0.13 |
| 1906 | 1.08 | 0.16 | 0.99 | 0.10 | 1.08 | 0.91 | 0.09 |
| 1907 | 1.14 | 0.10 | 1.02 | 1.11 | 1.12 | 0.22 | 0.25 |
| 1908 | 1.03 | 0.12 | 1.05 | 0.11 | 1.03 | 0.89 | 0.09 |
| 1909 | 1.08 | 0.09 | 0.95 | 1.05 | 1.07 | 0.21 | 0.16 |
| 1912 | 1.23 | 0.10 | 0.98 | 1.31 | 1.21 | 0.24 | 0.17 |
| 1959 | 1.02 | 0.22 | 1.04 | 0.10 | 0.99 | 0.97 | 0.22 |
| 1960 | 0.11 | 0.18 | 0.76 | 0.11 | 1.04 | 0.93 | 0.09 |
| 1961 | 0.94 | 0.09 | 0.88 | 0.12 | 1.25 | 0.87 | 0.10 |
| 1962 | 1.08 | 0.09 | 1.09 | 1.30 | 1.30 | 0.19 | 0.25 |
| 1963 | 0.97 | 0.09 | 1.02 | 0.13 | 1.22 | 0.78 | 0.23 |
| 1964 | 1.04 | 0.10 | 1.11 | 0.10 | 1.11 | 0.93 | 0.30 |
| 1965 | 1.04 | 0.11 | 0.97 | 0.10 | 1.13 | 0.87 | 0.23 |
| 1966 | 1.09 | 0.22 | 0.98 | 0.11 | 1.19 | 1.02 | 0.28 |
| 1967 | 1.00 | 0.42 | 1.16 | 0.11 | 1.16 | 0.95 | 0.18 |
| 1915 | 1.15 | 0.09 | 0.70 | 0.22 | 1.12 | 0.89 | 0.16 |
| 1997 | 1.08 | 0.09 | 0.11 | 0.10 | 1.06 | 0.93 | 0.18 |
| 1998 | 1.07 | 0.09 | 0.11 | 0.10 | 1.07 | 0.88 | 0.18 |
| 1999 | 1.06 | 0.09 | 0.16 | 0.10 | 1.05 | 0.91 | 0.25 |
| 2000 | 1.07 | 0.09 | 0.11 | 0.10 | 1.05 | 0.94 | 0.33 |
| 2001 | 1.08 | 0.10 | 0.14 | 0.11 | 1.06 | 0.89 | 0.19 |
| 2002 | 1.04 | 1.10 | 1.03 | 0.14 | 1.06 | 0.72 | 0.13 |
| 2003 | 1.05 | 0.09 | 0.73 | 0.10 | 1.05 | 0.80 | 0.22 |
| 2004 | 1.03 | 0.09 | 0.20 | 0.12 | 1.00 | 1.10 | 0.16 |
| 2005 | 1.05 | 0.10 | 0.16 | 0.11 | 1.04 | 0.98 | 0.21 |
| 1916 | 1.17 | 0.47 | 1.02 | 0.14 | 1.04 | 0.44 | 0.18 |
| 2006 | 1.08 | 0.25 | 1.04 | 0.11 | 0.90 | 0.31 | 0.23 |
| 2007 | 0.10 | 0.27 | 0.11 | 0.13 | 1.00 | 0.47 | 0.09 |
| 2008 | 0.10 | 0.16 | 0.11 | 0.09 | 1.01 | 0.45 | 0.10 |
| 2009 | 1.08 | 0.40 | 0.10 | 0.10 | 1.07 | 0.86 | 0.09 |
| 2010 | 1.01 | 0.18 | 1.16 | 0.10 | 0.91 | 0.26 | 0.20 |
| 2011 | 1.04 | 0.31 | 0.97 | 0.11 | 0.92 | 0.40 | 0.22 |
| 2012 | 1.06 | 0.34 | 0.99 | 1.02 | 1.07 | 0.61 | 0.32 |
| 2013 | 1.06 | 0.36 | 0.98 | 1.05 | 1.07 | 0.67 | 0.30 |
| 2014 | 1.04 | 0.33 | 0.98 | 0.11 | 0.96 | 0.42 | 0.27 |
| 1869 | 0.83 | 0.22 | 1.01 | 0.21 | 0.15 | 0.13 | 0.13 |
| 1840 | 1.04 | 0.38 | 0.14 | 0.24 | 1.09 | 0.41 | 0.32 |
| 1839 | 1.16 | 1.56 | 1.02 | 1.12 | 0.16 | 0.21 | 0.95 |
| 2024 | 1.00 | 1.16 | 0.20 | 0.95 | 0.10 | 0.08 | 1.02 |
| 2025 | 1.04 | 1.13 | 0.20 | 1.02 | 0.33 | 0.08 | 1.05 |
| 2026 | 1.05 | 1.35 | 0.52 | 0.17 | 0.21 | 0.44 | 1.05 |
| 2027 | 1.04 | 1.06 | 0.63 | 1.01 | 0.27 | 0.08 | 1.01 |
| 2028 | 0.98 | 1.12 | 0.16 | 0.99 | 0.19 | 0.10 | 0.99 |
| 2029 | 1.10 | 1.17 | 0.97 | 1.09 | 0.16 | 0.10 | 0.94 |
| 2030 | 1.03 | 1.22 | 0.25 | 0.90 | 0.12 | 0.09 | 0.84 |
| 2031 | 1.00 | 1.06 | 0.94 | 1.03 | 0.11 | 0.08 | 0.89 |
| 2032 | 0.26 | 1.12 | 0.15 | 1.04 | 0.10 | 0.08 | 0.96 |
| 1878 | 1.15 | 1.18 | 1.08 | 1.15 | 0.15 | 0.08 | 1.03 |
| 2033 | 1.01 | 1.21 | 0.18 | 0.98 | 0.20 | 0.09 | 1.01 |
| 2034 | 1.04 | 1.10 | 0.16 | 1.06 | 0.15 | 0.09 | 0.96 |
| 2035 | 1.02 | 1.19 | 0.14 | 1.02 | 0.16 | 0.09 | 0.97 |
| 2036 | 1.01 | 1.11 | 0.23 | 1.02 | 0.12 | 0.09 | 0.98 |
| 2037 | 0.99 | 1.09 | 0.17 | 1.05 | 0.13 | 0.09 | 0.92 |
| 2038 | 1.02 | 1.07 | 1.08 | 1.05 | 0.19 | 0.11 | 0.94 |
| 2039 | 1.06 | 1.02 | 1.03 | 1.03 | 0.22 | 0.10 | 0.93 |
| 2040 | 0.99 | 1.09 | 1.02 | 1.25 | 0.23 | 0.11 | 0.91 |
| 2041 | 1.13 | 1.10 | 0.20 | 1.15 | 0.12 | 0.11 | 1.01 |
| 2042 | 1.08 | 0.94 | 0.10 | 1.03 | 1.04 | 0.81 | 0.12 |
| 2043 | 1.05 | 1.09 | 0.83 | 1.08 | 1.05 | 0.65 | 0.11 |
| 2044 | 1.08 | 1.00 | 0.28 | 1.10 | 1.08 | 0.48 | 0.10 |
| 2045 | 1.03 | 0.45 | 0.10 | 0.19 | 1.04 | 0.26 | 0.09 |
| 2046 | 1.03 | 0.75 | 0.10 | 0.27 | 1.03 | 0.35 | 0.09 |
| 2047 | 1.00 | 1.12 | 0.10 | 1.07 | 1.00 | 0.44 | 0.09 |
| 2048 | 1.01 | 0.32 | 0.23 | 0.12 | 1.01 | 0.23 | 0.23 |
| 2049 | 1.07 | 0.97 | 1.06 | 1.14 | 1.12 | 0.58 | 0.12 |
| 2050 | 1.04 | 0.86 | 0.99 | 1.13 | 1.08 | 0.43 | 0.09 |
| 1880 | 1.15 | 1.05 | 1.08 | 1.15 | 1.15 | 0.09 | 1.03 |
| 2051 | 1.05 | 1.10 | 1.00 | 1.13 | 0.16 | 0.09 | 0.93 |
| 2052 | 1.06 | 1.15 | 0.18 | 1.08 | 0.15 | 0.10 | 0.94 |
| 2053 | 1.00 | 1.15 | 0.23 | 1.04 | 0.45 | 0.11 | 1.04 |
| 2054 | 1.11 | 1.14 | 0.77 | 1.17 | 0.18 | 0.11 | 0.96 |
| 2055 | 0.98 | 1.09 | 0.18 | 1.06 | 0.19 | 0.09 | 0.97 |
| 2056 | 1.21 | 1.07 | 0.25 | 1.21 | 0.12 | 0.10 | 0.99 |
| 2057 | 1.17 | 1.04 | 1.03 | 1.06 | 0.13 | 0.10 | 1.02 |
| 2058 | 1.16 | 1.14 | 1.01 | 1.12 | 0.16 | 0.10 | 0.95 |
| 2059 | 0.92 | 1.08 | 0.17 | 1.00 | 0.11 | 0.10 | 1.11 |
| 1881 | 1.15 | 1.24 | 1.13 | 1.09 | 1.13 | 0.08 | 1.01 |
| 2060 | 1.13 | 1.14 | 1.06 | 1.08 | 0.16 | 0.11 | 1.06 |
| 2061 | 1.15 | 1.32 | 1.08 | 1.09 | 0.20 | 0.10 | 1.04 |
| 2062 | 1.14 | 1.10 | 0.98 | 1.06 | 0.11 | 0.10 | 1.06 |
| 2063 | 1.06 | 1.06 | 1.02 | 1.11 | 0.21 | 0.10 | 1.08 |
| 2064 | 0.95 | 1.09 | 1.03 | 1.21 | 0.17 | 0.09 | 1.00 |
| 2065 | 0.98 | 1.12 | 1.04 | 1.01 | 0.13 | 0.11 | 1.04 |
| 2066 | 0.88 | 1.19 | 1.07 | 0.95 | 0.12 | 0.10 | 0.96 |
| 2067 | 0.89 | 1.09 | 0.99 | 0.94 | 0.91 | 0.90 | 1.00 |
| 2068 | 0.88 | 1.06 | 1.08 | 0.97 | 0.93 | 0.10 | 1.03 |
| 2069 | 0.90 | 1.07 | 1.13 | 1.07 | 0.96 | 0.12 | 1.05 |
| 2070 | 0.93 | 1.19 | 1.20 | 1.08 | 0.12 | 0.10 | 1.06 |
| 2071 | 0.92 | 1.18 | 1.09 | 1.03 | 1.09 | 0.95 | 1.01 |
| 2072 | 0.96 | 1.18 | 0.32 | 1.09 | 0.14 | 0.11 | 1.08 |
| 2073 | 1.04 | 1.21 | 1.04 | 1.09 | 0.29 | 0.11 | 1.06 |
| 2074 | 1.11 | 1.10 | 1.00 | 1.01 | 0.16 | 0.11 | 0.49 |
| 2075 | 1.01 | 1.30 | 1.03 | 1.20 | 0.17 | 0.11 | 1.04 |
| 2076 | 1.07 | 1.05 | 0.24 | 0.77 | 0.12 | 0.10 | 1.01 |
| 2077 | 1.13 | 1.11 | 1.08 | 1.17 | 0.13 | 0.09 | 1.02 |
| 1882 | 1.06 | 1.04 | 1.03 | 1.02 | 0.12 | 0.09 | 1.00 |
| 2078 | 1.08 | 1.05 | 1.06 | 1.11 | 0.14 | 0.09 | 1.03 |
| 2079 | 1.04 | 1.10 | 1.09 | 1.07 | 1.00 | 0.09 | 1.03 |
| 2080 | 1.05 | 1.05 | 1.08 | 1.09 | 0.16 | 0.10 | 1.06 |
| 2081 | 1.05 | 1.06 | 1.08 | 1.11 | 1.02 | 1.10 | 1.08 |
| 2082 | 1.02 | 1.08 | 1.06 | 1.07 | 0.98 | 1.17 | 1.06 |
| 2083 | 1.02 | 1.08 | 1.04 | 1.07 | 0.25 | 0.10 | 1.04 |
| 2084 | 0.97 | 1.09 | 1.06 | 1.01 | 0.14 | 0.09 | 1.05 |
| 2085 | 1.04 | 1.07 | 1.08 | 1.06 | 0.12 | 0.10 | 1.10 |
| 2086 | 1.06 | 0.97 | 1.07 | 0.96 | 0.12 | 0.11 | 1.08 |
| 2087 | 1.03 | 1.21 | 1.22 | 1.05 | 1.12 | 1.12 | 1.03 |
| 2088 | 1.02 | 1.00 | 0.22 | 0.72 | 0.81 | 0.35 | 0.10 |
| 2089 | 1.05 | 1.03 | 1.22 | 1.02 | 0.91 | 0.98 | 1.04 |
| 2090 | 1.13 | 1.04 | 0.72 | 0.99 | 1.07 | 0.37 | 0.11 |
| 2091 | 1.07 | 1.09 | 1.10 | 1.04 | 0.16 | 0.11 | 1.05 |
| 2092 | 0.89 | 1.01 | 0.18 | 0.11 | 0.99 | 0.58 | 0.10 |
| 2093 | 1.05 | 0.98 | 1.05 | 1.08 | 1.01 | 0.82 | 0.09 |
| 2094 | 1.08 | 1.00 | 0.87 | 1.03 | 0.95 | 0.78 | 0.09 |
| 2095 | 1.09 | 1.08 | 0.24 | 1.08 | 1.02 | 0.11 | 1.07 |
| 2096 | 1.09 | 1.10 | 1.11 | 1.05 | 0.24 | 0.09 | 1.06 |
| 2097 | 0.93 | 1.04 | 1.11 | 1.05 | 0.12 | 0.10 | 1.04 |
| 2098 | 1.13 | 1.05 | 1.07 | 0.94 | 0.18 | 0.10 | 1.06 |

TABLE 3A-continued

| | | | | | | | |
|---|---|---|---|---|---|---|---|
| 2099 | 0.98 | 1.15 | 0.97 | 1.16 | 0.15 | 0.10 | 0.99 |
| 2100 | 1.06 | 1.06 | 1.13 | 1.05 | 0.12 | 0.10 | 1.04 |
| 2101 | 1.07 | 1.09 | 1.09 | 1.07 | 1.15 | 0.71 | 1.09 |
| 2102 | 1.06 | 1.08 | 1.10 | 1.04 | 1.09 | 0.70 | 1.06 |
| 2103 | 1.10 | 1.07 | 1.08 | 1.07 | 0.20 | 0.09 | 1.06 |
| 2104 | 1.06 | 1.09 | 1.10 | 1.05 | 1.16 | 0.75 | 1.07 |
| 1883 | 1.13 | 1.08 | 1.04 | 1.06 | 1.11 | 0.90 | 1.07 |
| 2105 | 1.08 | 1.12 | 1.07 | 1.06 | 1.07 | 0.10 | 1.04 |
| 2106 | 1.13 | 1.11 | 1.07 | 1.11 | 0.13 | 0.09 | 1.05 |
| 2107 | 1.06 | 1.09 | 1.07 | 1.00 | 1.00 | 0.10 | 1.05 |
| 2108 | 1.09 | 1.13 | 1.03 | 1.04 | 1.11 | 1.09 | 1.05 |
| 2109 | 1.22 | 1.23 | 1.06 | 1.04 | 1.10 | 0.13 | 0.09 |
| 2110 | 1.00 | 1.17 | 1.12 | 0.94 | 1.02 | 1.04 | 1.04 |
| 2111 | 1.00 | 1.25 | 0.98 | 1.11 | 0.24 | 0.10 | 1.00 |
| 2112 | 1.00 | 1.14 | 1.07 | 1.01 | 0.99 | 0.92 | 1.01 |
| 2113 | 0.63 | 1.16 | 0.18 | 1.03 | 0.14 | 0.09 | 1.03 |
| 1884 | 1.00 | 1.02 | 1.01 | 0.94 | 1.04 | 0.50 | 0.19 |
| 2114 | 1.03 | 1.13 | 1.07 | 0.48 | 1.02 | 0.54 | 0.09 |
| 2115 | 1.03 | 1.15 | 0.91 | 0.95 | 0.96 | 0.53 | 0.09 |
| 2116 | 1.02 | 1.11 | 1.03 | 0.92 | 1.03 | 0.70 | 0.10 |
| 2117 | 1.06 | 1.10 | 1.02 | 0.98 | 1.07 | 0.60 | 0.13 |
| 2118 | 1.03 | 1.11 | 0.96 | 0.96 | 1.05 | 0.69 | 0.11 |
| 2119 | 1.05 | 1.19 | 0.89 | 0.51 | 1.02 | 0.31 | 0.09 |
| 2120 | 1.07 | 1.12 | 1.01 | 1.08 | 1.05 | 0.12 | 0.10 |
| 2121 | 1.00 | 1.16 | 1.05 | 0.99 | 1.02 | 0.51 | 0.10 |
| 2122 | 1.11 | 1.12 | 0.97 | 0.99 | 1.00 | 0.55 | 0.09 |
| 1885 | 1.13 | 0.96 | 1.05 | 1.12 | 0.11 | 0.10 | 1.04 |
| 2123 | 1.05 | 1.13 | 0.18 | 1.04 | 1.17 | 0.44 | 0.09 |
| 2124 | 1.08 | 1.03 | 0.15 | 0.10 | 1.05 | 0.28 | 0.09 |
| 2125 | 1.04 | 1.02 | 0.09 | 0.95 | 1.06 | 0.74 | 0.10 |
| 2126 | 1.04 | 1.12 | 1.07 | 1.08 | 0.13 | 0.10 | 1.03 |
| 2127 | 1.02 | 1.14 | 1.09 | 1.10 | 0.98 | 0.10 | 1.04 |
| 2128 | 1.07 | 1.01 | 0.10 | 1.05 | 1.08 | 0.74 | 0.09 |
| 2129 | 1.06 | 1.04 | 1.02 | 1.08 | 1.07 | 0.32 | 0.09 |
| 2130 | 1.10 | 1.03 | 0.13 | 1.12 | 1.10 | 0.26 | 0.09 |
| 2131 | 1.07 | 1.08 | 0.09 | 1.07 | 1.03 | 0.79 | 0.10 |
| 1886 | 1.02 | 1.06 | 0.95 | 1.13 | 0.17 | 0.09 | 0.92 |
| 2132 | 1.05 | 1.07 | 1.10 | 1.04 | 0.14 | 0.09 | 1.06 |
| 1887 | 0.99 | 1.20 | 1.01 | 1.05 | 0.22 | 0.09 | 0.94 |
| 2133 | 1.09 | 1.12 | 1.13 | 1.20 | 0.12 | 0.11 | 1.11 |
| 2134 | 1.11 | 1.12 | 1.18 | 0.83 | 0.84 | 0.45 | 1.15 |
| 2135 | 1.01 | 1.15 | 1.02 | 1.02 | 0.24 | 0.09 | 1.00 |
| 2136 | 0.93 | 1.02 | 1.07 | 0.95 | 0.09 | 0.10 | 1.01 |
| 2137 | 1.04 | 1.06 | 1.08 | 1.03 | 0.13 | 0.09 | 1.04 |
| 2138 | 1.15 | 1.12 | 0.98 | 1.15 | 1.07 | 1.07 | 0.96 |
| 2139 | 1.06 | 1.09 | 1.14 | 1.09 | 0.12 | 0.09 | 1.11 |
| 2140 | 1.00 | 1.06 | 1.27 | 1.00 | 1.00 | 0.10 | 1.05 |
| 2141 | 0.99 | 1.21 | 1.25 | 1.11 | 0.13 | 0.10 | 1.17 |
| 2142 | 1.08 | 1.14 | 1.19 | 1.12 | 0.14 | 0.10 | 1.11 |
| 2143 | 1.09 | 1.13 | 1.21 | 1.12 | 0.13 | 0.10 | 1.14 |
| 2148 | 1.13 | 1.10 | 0.20 | 1.09 | 0.24 | 0.10 | 1.00 |
| 2149 | 1.07 | 1.12 | 0.95 | 1.08 | 1.05 | 0.97 | 0.95 |
| 2150 | 1.13 | 1.16 | 1.11 | 1.09 | 0.17 | 0.11 | 1.11 |
| 2164 | 1.05 | 1.13 | 0.27 | 1.05 | 0.21 | 0.11 | 1.08 |
| 2165 | 1.04 | 1.12 | 0.16 | 1.11 | 0.20 | 0.10 | 1.14 |
| 2166 | 0.98 | 1.14 | 1.17 | 0.92 | 0.16 | 0.11 | 1.16 |
| 2167 | 1.12 | 1.15 | 0.31 | 1.25 | 0.17 | 0.09 | 1.03 |
| 1888 | 1.18 | 1.17 | 1.07 | 1.16 | 0.11 | 0.09 | 0.98 |
| 2151 | 1.12 | 1.24 | 1.09 | 1.06 | 0.18 | 0.11 | 1.07 |
| 2152 | 1.13 | 1.09 | 0.22 | 1.08 | 0.12 | 0.11 | 1.21 |
| 2153 | 1.12 | 1.06 | 1.03 | 1.06 | 0.17 | 0.11 | 1.01 |
| 2154 | 1.07 | 1.21 | 1.08 | 1.09 | 0.13 | 0.11 | 1.03 |
| 2155 | 1.09 | 1.11 | 0.96 | 1.05 | 0.18 | 0.11 | 1.03 |
| 2156 | 1.11 | 1.12 | 1.11 | 0.98 | 0.21 | 0.09 | 1.34 |
| 2157 | 1.16 | 1.24 | 0.14 | 1.15 | 0.12 | 0.09 | 0.94 |
| 2158 | 0.94 | 1.05 | 0.29 | 0.90 | 0.12 | 0.10 | 1.07 |
| 2159 | 0.90 | 1.11 | 1.10 | 0.99 | 0.11 | 0.12 | 1.09 |
| 1889 | 1.18 | 1.19 | 1.03 | 1.15 | 0.19 | 0.09 | 0.99 |
| 2144 | 1.09 | 1.11 | 1.11 | 1.10 | 0.19 | 0.10 | 1.09 |
| 2145 | 1.10 | 1.10 | 1.17 | 1.13 | 0.12 | 0.10 | 1.12 |
| 2146 | 1.07 | 1.13 | 0.23 | 1.10 | 0.17 | 0.09 | 1.10 |
| 2147 | 0.97 | 1.10 | 1.13 | 0.98 | 0.18 | 0.12 | 1.05 |
| 2160 | 0.99 | 1.11 | 0.18 | 1.10 | 0.21 | 0.12 | 1.11 |
| 2161 | 1.05 | 1.13 | 0.18 | 1.16 | 0.25 | 0.11 | 1.14 |
| 2162 | 1.10 | 1.10 | 0.28 | 1.15 | 0.22 | 0.11 | 1.12 |
| 2163 | 1.04 | 1.16 | 0.27 | 1.08 | 0.30 | 0.11 | 1.19 |
| 2168 | 0.96 | 1.17 | 0.24 | 0.97 | 0.31 | 0.10 | 0.99 |
| 1890 | 1.15 | 1.14 | 1.06 | 1.13 | 0.19 | 0.09 | 1.00 |
| 2169 | 1.13 | 1.16 | 0.46 | 1.11 | 0.18 | 0.12 | 1.09 |
| 2170 | 1.08 | 1.07 | 0.16 | 1.10 | 0.19 | 0.10 | 1.07 |
| 2171 | 1.04 | 1.10 | 0.23 | 1.14 | 0.26 | 0.11 | 1.07 |
| 2172 | 1.06 | 1.10 | 0.20 | 1.19 | 1.04 | 0.11 | 1.10 |
| 2173 | 1.11 | 1.16 | 0.13 | 1.16 | 0.68 | 0.10 | 1.05 |
| 2174 | 1.09 | 1.07 | 0.23 | 1.12 | 0.10 | 0.11 | 1.05 |
| 2175 | 1.05 | 1.08 | 1.06 | 1.12 | 0.19 | 0.10 | 1.10 |
| 2176 | 1.17 | 1.10 | 1.08 | 1.11 | 1.09 | 0.10 | 1.08 |
| 2177 | 1.13 | 1.12 | 1.03 | 1.14 | 1.12 | 1.07 | 1.04 |
| 1879 | 1.28 | 1.07 | 1.04 | 0.68 | 0.13 | 0.08 | 1.14 |
| 1911 | 1.10 | 0.11 | 1.02 | 1.06 | 1.10 | 0.21 | 0.11 |
| 1950 | 1.08 | 1.06 | 1.12 | 1.09 | 0.10 | 0.09 | 1.09 |
| 1951 | 1.33 | 1.00 | 1.02 | 0.80 | 0.78 | 1.05 | 1.00 |
| 1952 | 0.95 | 1.02 | 1.02 | 0.10 | 0.12 | 0.10 | 0.11 |
| 1953 | 0.16 | 0.10 | 1.01 | 0.09 | 0.94 | 0.73 | 0.10 |
| 1954 | 1.03 | 0.10 | 1.00 | 1.08 | 0.11 | 0.09 | 1.02 |
| 1955 | 0.79 | 0.10 | 1.02 | 0.10 | 0.94 | 0.74 | 0.11 |
| 1956 | 1.09 | 0.10 | 1.02 | 1.17 | 1.14 | 0.14 | 0.10 |
| 1957 | 0.99 | 0.99 | 1.14 | 1.06 | 0.15 | 0.10 | 1.12 |
| 1958 | 1.00 | 1.05 | 1.08 | 1.03 | 0.10 | 0.09 | 1.04 |
| 1913 | 1.05 | 0.09 | 1.15 | 1.09 | 1.03 | 0.16 | 0.11 |
| 1968 | 1.09 | 1.14 | 1.07 | 0.11 | 0.14 | 0.10 | 0.11 |
| 1969 | 1.17 | 1.05 | 1.02 | 1.19 | 1.30 | 0.11 | 1.02 |
| 1970 | 1.14 | 1.17 | 1.08 | 0.11 | 0.10 | 0.09 | 0.14 |
| 1971 | 1.07 | 1.10 | 1.00 | 1.08 | 0.13 | 0.09 | 1.06 |
| 1972 | 1.26 | 0.09 | 0.96 | 1.07 | 1.11 | 0.15 | 0.10 |
| 1973 | 1.25 | 0.10 | 1.15 | 0.81 | 1.24 | 0.21 | 0.11 |
| 1974 | 1.16 | 0.10 | 1.05 | 0.94 | 1.10 | 0.14 | 0.10 |
| 1975 | 0.88 | 1.01 | 1.00 | 0.87 | 0.92 | 0.09 | 0.92 |
| 1976 | 0.92 | 1.02 | 0.97 | 0.97 | 0.82 | 0.09 | 1.00 |
| 1891 | 1.16 | 1.12 | 1.03 | 1.16 | 1.13 | 1.02 | 1.12 |
| 1892 | 1.12 | 1.14 | 1.06 | 1.12 | 1.12 | 1.00 | 0.99 |
| 1893 | 1.12 | 1.09 | 1.04 | 1.14 | 0.23 | 0.09 | 1.00 |
| 1894 | 1.16 | 1.02 | 1.05 | 1.15 | 1.16 | 1.04 | 1.12 |
| 1895 | 1.08 | 1.13 | 1.04 | 1.00 | 0.19 | 0.09 | 1.09 |
| 1896 | 1.09 | 1.05 | 1.02 | 1.02 | 0.18 | 0.10 | 1.03 |
| 1897 | 1.11 | 1.03 | 1.05 | 0.37 | 0.17 | 0.10 | 0.99 |
| 1898 | 0.91 | 0.94 | 1.10 | 1.04 | 0.23 | 0.09 | 0.96 |
| 1899 | 1.09 | 1.00 | 1.04 | 0.99 | 1.00 | 0.97 | 1.05 |
| 1990 | 1.00 | 0.09 | 1.05 | 0.30 | 1.00 | 0.09 | 0.09 |
| 1991 | 1.03 | 0.09 | 1.02 | 0.26 | 1.01 | 0.09 | 0.09 |
| 1992 | 1.02 | 0.09 | 1.03 | 0.38 | 1.10 | 0.09 | 0.09 |
| 1993 | 1.13 | 0.10 | 0.92 | 0.11 | 0.10 | 0.10 | 0.08 |
| 1994 | 1.06 | 0.10 | 1.08 | 0.09 | 0.12 | 0.09 | 0.09 |
| 1995 | 1.04 | 0.10 | 1.14 | 0.10 | 0.10 | 0.09 | 0.09 |
| 1996 | 1.04 | 0.09 | 0.09 | 0.09 | 1.01 | 0.09 | 0.09 |

TABLE 3A-continued

| | | | | | | | |
|---|---|---|---|---|---|---|---|
| 1910 | 0.11 | 0.09 | 0.23 | 0.11 | 1.13 | 0.62 | 0.09 |
| 1945 | 1.14 | 1.10 | 1.05 | 0.15 | 0.20 | 0.08 | 0.90 |
| 1946 | 0.10 | 0.23 | 1.04 | 0.10 | 1.10 | 0.89 | 0.09 |
| 1947 | 0.10 | 0.29 | 0.95 | 0.15 | 1.04 | 0.72 | 0.10 |
| 1948 | 0.16 | 0.18 | 0.72 | 0.11 | 1.13 | 0.89 | 0.11 |
| 1949 | 0.17 | 0.09 | 0.22 | 0.11 | 1.09 | 0.53 | 0.09 |
| 1977 | 0.13 | 0.79 | 1.05 | 0.10 | 0.96 | 1.00 | 0.09 |
| 1978 | 0.95 | 0.75 | 1.03 | 0.96 | 1.00 | 0.80 | 0.37 |
| 1979 | 0.95 | 0.70 | 1.06 | 0.85 | 0.98 | 0.78 | 0.32 |
| 1980 | 1.01 | 0.92 | 1.09 | 1.01 | 1.04 | 0.78 | 0.82 |
| 1981 | 0.98 | 0.70 | 1.14 | 0.93 | 0.94 | 0.78 | 0.37 |
| 1982 | 1.05 | 0.90 | 1.09 | 1.03 | 1.11 | 0.94 | 0.34 |
| 1983 | 0.95 | 1.14 | 0.96 | 0.94 | 0.12 | 0.10 | 0.10 |
| 1984 | 1.05 | 0.79 | 1.03 | 1.05 | 1.04 | 0.88 | 0.27 |
| 1985 | 0.11 | 1.00 | 0.98 | 0.09 | 1.02 | 0.85 | 0.09 |
| 1914 | 1.19 | 1.05 | 1.03 | 0.11 | 1.12 | 0.86 | 0.11 |
| 1986 | 1.04 | 0.85 | 1.04 | 0.10 | 1.02 | 0.81 | 0.13 |
| 1987 | 1.04 | 0.83 | 1.03 | 0.09 | 1.02 | 0.85 | 0.12 |
| 1988 | 1.03 | 0.58 | 1.07 | 0.09 | 1.01 | 0.88 | 0.13 |
| 1989 | 1.01 | 1.07 | 1.01 | 0.11 | 0.22 | 0.08 | 0.15 |
| 1917 | 1.14 | 0.78 | 1.05 | 1.16 | 1.16 | 0.89 | 0.68 |
| 2015 | 0.99 | 0.46 | 1.08 | 0.10 | 1.04 | 0.89 | 0.10 |
| 2016 | 0.72 | 0.46 | 1.00 | 0.10 | 0.99 | 0.77 | 0.10 |
| 2017 | 1.12 | 0.43 | 0.93 | 0.12 | 1.24 | 0.80 | 0.10 |
| 2018 | 1.10 | 0.40 | 1.07 | 0.12 | 1.19 | 0.77 | 0.11 |
| 2019 | 1.09 | 0.53 | 1.11 | 0.11 | 1.10 | 0.74 | 0.11 |
| 2020 | 1.10 | 0.65 | 1.12 | 0.11 | 1.09 | 0.87 | 0.43 |
| 2021 | 1.08 | 0.50 | 1.10 | 1.09 | 1.08 | 0.79 | 0.36 |
| 2022 | 1.05 | 0.55 | 1.08 | 1.06 | 1.06 | 0.84 | 0.36 |
| 2023 | 1.03 | 1.07 | 1.05 | 1.09 | 1.04 | 0.98 | 0.51 |

TABLE 3B

| NP # | LP48 | LP49 | LP54 | LP56 | LP95 | LP99 | LP101 |
|---|---|---|---|---|---|---|---|
| 1900 | 0.91 | 0.93 | 0.09 | 0.71 | 0.89 | 0.37 | 0.20 |
| 1901 | 0.13 | 0.95 | 0.13 | 1.01 | 0.09 | 0.09 | 0.10 |
| 1902 | 1.00 | 0.88 | 0.12 | 1.04 | 0.70 | 0.09 | 0.13 |
| 1903 | 0.13 | 0.88 | 0.10 | 1.02 | 0.10 | 0.10 | 0.10 |
| 1904 | 0.19 | 0.87 | 0.10 | 0.95 | 0.10 | 0.09 | 0.84 |
| 1905 | 0.18 | 0.94 | 0.10 | 1.01 | 0.11 | 0.09 | 0.90 |
| 1906 | 0.99 | 0.86 | 0.11 | 1.03 | 0.70 | 0.09 | 0.12 |
| 1907 | 0.94 | 0.79 | 0.10 | 0.77 | 0.98 | 0.39 | 0.15 |
| 1908 | 0.13 | 0.97 | 0.11 | 0.95 | 0.09 | 0.09 | 0.16 |
| 1909 | 0.91 | 0.82 | 0.09 | 0.72 | 0.97 | 0.40 | 0.17 |
| 1912 | 1.03 | 0.55 | 0.17 | 0.61 | 0.74 | 0.29 | 0.17 |
| 1959 | 0.14 | 1.01 | 0.22 | 0.93 | 0.09 | 0.08 | 0.10 |
| 1960 | 0.75 | 0.96 | 0.11 | 1.00 | 0.10 | 0.10 | 0.10 |
| 1961 | 0.18 | 0.97 | 0.09 | 0.89 | 0.09 | 0.09 | 0.10 |
| 1962 | 1.22 | 0.58 | 0.09 | 0.48 | 0.63 | 0.17 | 0.27 |
| 1963 | 0.12 | 0.89 | 0.09 | 0.93 | 0.08 | 0.08 | 0.09 |
| 1964 | 0.12 | 1.04 | 0.09 | 0.94 | 0.08 | 0.08 | 0.09 |
| 1965 | 0.12 | 0.92 | 0.09 | 1.02 | 0.09 | 0.08 | 0.09 |
| 1966 | 0.19 | 1.05 | 0.13 | 0.96 | 0.08 | 0.08 | 0.91 |
| 1967 | 0.17 | 1.08 | 0.18 | 1.00 | 0.09 | 0.08 | 0.49 |
| 1915 | 0.09 | 0.92 | 0.09 | 1.26 | 0.12 | 0.09 | 0.09 |
| 1997 | 0.10 | 0.95 | 0.09 | 0.99 | 0.10 | 0.09 | 0.09 |
| 1998 | 0.10 | 0.94 | 0.09 | 1.10 | 0.11 | 0.09 | 0.09 |

TABLE 3B-continued

| | | | | | | | |
|---|---|---|---|---|---|---|---|
| 1999 | 0.11 | 0.94 | 0.09 | 1.11 | 0.10 | 0.09 | 0.10 |
| 2000 | 0.10 | 0.96 | 0.09 | 1.07 | 0.10 | 0.09 | 0.09 |
| 2001 | 0.10 | 0.97 | 0.10 | 1.04 | 0.10 | 0.09 | 0.09 |
| 2002 | 0.21 | 0.95 | 1.08 | 0.89 | 0.12 | 0.09 | 0.17 |
| 2003 | 0.83 | 0.94 | 0.09 | 1.04 | 0.22 | 0.09 | 0.09 |
| 2004 | 0.88 | 1.12 | 0.10 | 1.00 | 1.05 | 0.10 | 0.11 |
| 2005 | 0.92 | 0.90 | 0.10 | 1.07 | 1.08 | 0.12 | 0.11 |
| 1916 | 1.04 | 0.63 | 0.48 | 0.59 | 0.88 | 0.53 | 0.45 |
| 2006 | 0.94 | 0.72 | 0.13 | 0.86 | 0.95 | 0.46 | 0.22 |
| 2007 | 0.23 | 0.96 | 0.11 | 0.51 | 0.12 | 0.09 | 0.11 |
| 2008 | 0.25 | 0.89 | 0.11 | 0.65 | 0.12 | 0.10 | 0.11 |
| 2009 | 0.37 | 0.96 | 0.13 | 0.88 | 0.14 | 0.10 | 0.10 |
| 2010 | 0.82 | 0.72 | 0.12 | 0.86 | 1.24 | 0.59 | 0.20 |
| 2011 | 0.89 | 0.99 | 0.14 | 0.56 | 0.82 | 0.57 | 0.35 |
| 2012 | 0.85 | 0.96 | 0.20 | 0.87 | 0.96 | 0.41 | 0.41 |
| 2013 | 0.99 | 0.93 | 0.16 | 0.89 | 1.03 | 0.88 | 0.40 |
| 2014 | 0.95 | 0.83 | 0.14 | 0.59 | 0.70 | 0.63 | 0.44 |
| 1869 | 0.17 | 0.28 | 0.22 | 0.57 | 0.15 | 0.12 | 0.13 |
| 1840 | 1.00 | 0.99 | 0.85 | 0.85 | 1.05 | 0.48 | 0.26 |
| 1839 | 0.29 | 0.29 | 1.21 | 0.48 | 0.46 | 0.16 | 0.21 |
| 2024 | 0.09 | 0.54 | 1.10 | 0.10 | 0.10 | 0.11 | 0.08 |
| 2025 | 0.10 | 0.79 | 1.14 | 0.11 | 0.11 | 0.10 | 0.08 |
| 2026 | 0.46 | 0.50 | 1.32 | 0.60 | 0.60 | 0.32 | 0.45 |
| 2027 | 0.12 | 0.09 | 1.13 | 0.15 | 0.11 | 0.10 | 0.10 |
| 2028 | 0.10 | 0.10 | 1.07 | 0.10 | 0.09 | 0.09 | 0.11 |
| 2029 | 1.04 | 1.00 | 1.08 | 0.10 | 0.10 | 0.12 | 0.11 |
| 2030 | 0.09 | 0.49 | 1.21 | 0.10 | 0.09 | 0.10 | 0.09 |
| 2031 | 0.09 | 0.62 | 1.04 | 0.09 | 0.09 | 0.09 | 0.09 |
| 2032 | 0.10 | 0.69 | 1.11 | 0.10 | 0.09 | 0.09 | 0.08 |
| 1878 | 0.12 | 0.87 | 1.14 | 0.52 | 0.11 | 0.10 | 0.14 |
| 2033 | 0.10 | 0.72 | 1.10 | 0.10 | 0.10 | 0.11 | 0.09 |
| 2034 | 0.11 | 0.72 | 1.21 | 0.11 | 0.10 | 0.10 | 0.09 |
| 2035 | 0.10 | 0.73 | 1.09 | 0.11 | 0.10 | 0.09 | 0.09 |
| 2036 | 0.09 | 0.50 | 1.10 | 0.10 | 0.10 | 0.09 | 0.08 |
| 2037 | 0.10 | 0.77 | 1.10 | 0.11 | 0.10 | 0.10 | 0.09 |
| 2038 | 0.12 | 1.03 | 1.12 | 0.88 | 0.10 | 0.10 | 0.21 |
| 2039 | 0.11 | 0.88 | 1.03 | 0.15 | 0.10 | 0.10 | 0.12 |
| 2040 | 0.11 | 1.11 | 1.18 | 1.11 | 0.11 | 0.10 | 0.31 |
| 2041 | 0.10 | 0.52 | 1.21 | 0.11 | 0.10 | 0.10 | 0.12 |
| 2042 | 0.09 | 0.96 | 1.08 | 0.91 | 0.09 | 0.10 | 0.46 |
| 2043 | 0.09 | 0.98 | 1.01 | 0.94 | 0.10 | 0.09 | 0.33 |
| 2044 | 0.09 | 0.81 | 1.00 | 0.85 | 0.10 | 0.10 | 0.31 |
| 2045 | 0.10 | 0.86 | 0.35 | 0.57 | 0.10 | 0.10 | 0.21 |
| 2046 | 0.09 | 0.90 | 0.72 | 0.90 | 0.11 | 0.10 | 0.26 |
| 2047 | 0.11 | 1.02 | 1.11 | 0.95 | 0.11 | 0.11 | 0.26 |
| 2048 | 0.20 | 0.60 | 0.33 | 0.57 | 0.19 | 0.11 | 0.19 |
| 2049 | 0.09 | 1.07 | 1.01 | 0.97 | 0.10 | 0.10 | 0.39 |
| 2050 | 0.09 | 1.05 | 0.75 | 0.90 | 0.10 | 0.10 | 0.34 |
| 1880 | 1.13 | 0.87 | 1.16 | 1.01 | 0.73 | 0.10 | 0.94 |
| 2051 | 0.11 | 0.83 | 1.11 | 0.27 | 0.10 | 0.10 | 0.17 |

TABLE 3B-continued

| | | | | | | | |
|---|---|---|---|---|---|---|---|
| 2052 | 0.09 | 0.41 | 1.08 | 0.10 | 0.10 | 0.11 | 0.11 |
| 2053 | 0.10 | 0.78 | 1.17 | 1.08 | 0.10 | 0.11 | 0.31 |
| 2054 | 0.11 | 0.12 | 0.99 | 0.13 | 0.10 | 0.10 | 0.15 |
| 2055 | 0.09 | 0.60 | 1.04 | 0.10 | 0.09 | 0.09 | 0.09 |
| 2056 | 0.09 | 0.09 | 1.10 | 0.10 | 0.09 | 0.11 | 0.10 |
| 2057 | 0.10 | 0.94 | 1.09 | 0.56 | 0.10 | 0.10 | 0.21 |
| 2058 | 0.11 | 1.02 | 1.16 | 1.02 | 0.10 | 0.11 | 0.53 |
| 2059 | 0.10 | 0.51 | 1.08 | 0.11 | 0.10 | 0.10 | 0.10 |
| 1881 | 0.91 | 0.78 | 1.11 | 1.11 | 0.96 | 0.10 | 0.85 |
| 2060 | 1.05 | 1.16 | 1.12 | 0.12 | 0.13 | 0.10 | 0.13 |
| 2061 | 0.96 | 1.09 | 1.21 | 0.12 | 0.13 | 0.10 | 0.13 |
| 2062 | 1.05 | 1.03 | 1.14 | 0.12 | 0.13 | 0.11 | 0.13 |
| 2063 | 0.94 | 1.05 | 1.14 | 0.14 | 1.05 | 0.41 | 0.12 |
| 2064 | 0.22 | 0.43 | 1.13 | 0.10 | 0.09 | 0.09 | 0.09 |
| 2065 | 0.98 | 1.10 | 1.13 | 0.12 | 0.13 | 0.12 | 0.13 |
| 2066 | 1.04 | 1.03 | 1.19 | 0.13 | 0.15 | 0.13 | 0.12 |
| 2067 | 1.01 | 1.03 | 1.08 | 1.15 | 1.13 | 0.99 | 1.02 |
| 2068 | 0.90 | 1.06 | 1.16 | 1.18 | 1.17 | 0.11 | 0.96 |
| 2069 | 0.93 | 1.01 | 1.10 | 1.13 | 0.30 | 0.11 | 1.02 |
| 2070 | 0.09 | 0.93 | 1.26 | 0.12 | 0.11 | 0.10 | 0.18 |
| 2071 | 0.85 | 1.01 | 1.19 | 1.21 | 1.12 | 1.09 | 1.03 |
| 2072 | 0.10 | 0.57 | 1.14 | 0.13 | 0.11 | 0.11 | 0.11 |
| 2073 | 0.95 | 0.46 | 1.15 | 1.06 | 1.06 | 0.09 | 0.99 |
| 2074 | 0.08 | 0.69 | 0.99 | 0.11 | 0.10 | 0.12 | 0.11 |
| 2075 | 1.05 | 1.12 | 1.29 | 0.13 | 0.13 | 0.10 | 0.13 |
| 2076 | 0.10 | 0.87 | 1.11 | 1.11 | 0.11 | 0.09 | 0.99 |
| 2077 | 0.09 | 0.75 | 1.14 | 0.12 | 0.11 | 0.09 | 0.09 |
| 1882 | 0.10 | 0.48 | 1.07 | 0.11 | 0.10 | 0.09 | 0.09 |
| 2078 | 1.04 | 1.09 | 1.08 | 0.13 | 0.16 | 0.09 | 0.11 |
| 2079 | 1.07 | 0.89 | 1.14 | 1.17 | 1.16 | 0.14 | 0.89 |
| 2080 | 1.04 | 1.01 | 1.14 | 0.12 | 1.05 | 0.94 | 0.11 |
| 2081 | 1.04 | 0.96 | 1.15 | 1.13 | 1.12 | 0.99 | 0.91 |
| 2082 | 1.09 | 0.98 | 1.13 | 1.11 | 1.10 | 1.08 | 0.98 |
| 2083 | 1.07 | 0.94 | 1.05 | 0.11 | 0.12 | 0.10 | 0.10 |
| 2084 | 1.10 | 0.95 | 1.10 | 0.11 | 0.12 | 0.09 | 0.11 |
| 2085 | 1.07 | 1.03 | 1.14 | 0.12 | 1.07 | 0.98 | 0.11 |
| 2086 | 1.04 | 0.99 | 1.10 | 0.11 | 0.12 | 0.10 | 0.12 |
| 2087 | 1.01 | 0.95 | 1.20 | 0.98 | 1.00 | 1.08 | 1.17 |
| 2088 | 0.20 | 0.97 | 0.92 | 0.76 | 0.12 | 0.11 | 0.28 |
| 2089 | 1.10 | 0.92 | 1.08 | 1.16 | 1.11 | 0.95 | 0.98 |
| 2090 | 0.19 | 0.84 | 1.01 | 0.58 | 0.12 | 0.12 | 0.31 |
| 2091 | 1.05 | 0.90 | 1.15 | 0.12 | 0.13 | 0.10 | 0.10 |
| 2092 | 0.10 | 0.92 | 1.08 | 0.92 | 0.10 | 0.09 | 0.35 |
| 2093 | 0.09 | 0.96 | 1.07 | 1.03 | 0.11 | 0.09 | 0.49 |
| 2094 | 0.10 | 0.91 | 1.13 | 0.06 | 0.11 | 0.09 | 0.42 |
| 2095 | 0.13 | 1.02 | 1.09 | 0.14 | 0.12 | 0.13 | 0.11 |
| 2096 | 0.10 | 0.94 | 1.15 | 0.12 | 0.11 | 0.09 | 0.09 |
| 2097 | 0.10 | 0.38 | 1.19 | 0.11 | 0.10 | 0.09 | 0.10 |
| 2098 | 0.09 | 0.82 | 1.14 | 0.10 | 0.10 | 0.09 | 0.11 |
| 2099 | 0.10 | 0.76 | 1.17 | 0.11 | 0.11 | 0.09 | 0.11 |
| 2100 | 1.04 | 0.99 | 1.10 | 0.13 | 1.15 | 0.96 | 0.11 |
| 2101 | 1.05 | 0.96 | 1.18 | 1.22 | 1.22 | 0.93 | 0.85 |
| 2102 | 1.07 | 1.05 | 1.08 | 1.27 | 1.16 | 0.92 | 1.10 |
| 2103 | 1.05 | 1.01 | 1.16 | 0.15 | 1.11 | 0.96 | 0.10 |
| 2104 | 1.10 | 0.83 | 1.09 | 1.25 | 1.22 | 0.96 | 0.92 |
| 1883 | 0.96 | 0.91 | 1.08 | 1.04 | 1.06 | 1.10 | 0.88 |
| 2105 | 1.04 | 1.08 | 1.19 | 1.16 | 1.11 | 0.96 | 1.00 |
| 2106 | 1.12 | 1.10 | 1.08 | 0.14 | 1.06 | 0.10 | 0.10 |
| 2107 | 1.07 | 1.01 | 1.11 | 1.05 | 1.01 | 0.97 | 0.93 |
| 2108 | 1.07 | 1.00 | 1.10 | 1.05 | 1.10 | 0.97 | 1.00 |
| 2109 | 1.05 | 0.94 | 1.23 | 0.65 | 1.09 | 0.10 | 0.11 |
| 2110 | 1.05 | 1.03 | 1.11 | 1.00 | 1.01 | 0.91 | 1.10 |
| 2111 | 0.94 | 0.95 | 1.28 | 0.11 | 0.35 | 0.09 | 0.10 |
| 2112 | 1.01 | 1.00 | 1.19 | 1.15 | 1.09 | 0.93 | 0.97 |
| 2113 | 0.09 | 0.96 | 1.17 | 0.10 | 0.10 | 0.09 | 0.09 |
| 1884 | 0.98 | 0.88 | 0.99 | 0.90 | 1.02 | 0.09 | 0.34 |
| 2114 | 1.02 | 0.97 | 1.14 | 1.01 | 1.05 | 0.09 | 0.36 |
| 2115 | 1.04 | 1.07 | 1.17 | 1.09 | 1.04 | 0.09 | 0.36 |
| 2116 | 1.02 | 1.00 | 1.19 | 1.06 | 1.04 | 0.09 | 0.50 |
| 2117 | 1.08 | 1.08 | 1.16 | 1.00 | 0.87 | 0.09 | 0.32 |
| 2118 | 1.02 | 0.99 | 1.22 | 1.00 | 1.03 | 0.09 | 0.38 |
| 2119 | 1.03 | 1.01 | 1.24 | 0.58 | 0.55 | 0.10 | 0.20 |
| 2120 | 0.97 | 1.01 | 1.16 | 0.66 | 0.99 | 0.10 | 0.11 |
| 2121 | 0.95 | 1.01 | 1.17 | 1.07 | 1.09 | 0.09 | 0.32 |
| 2122 | 0.99 | 1.00 | 1.14 | 0.95 | 1.01 | 0.09 | 0.34 |
| 1885 | 0.09 | 0.72 | 0.94 | 0.10 | 0.10 | 0.09 | 0.09 |
| 2123 | 0.09 | 1.03 | 1.08 | 0.95 | 0.09 | 0.09 | 0.31 |
| 2124 | 0.10 | 1.02 | 1.05 | 0.84 | 0.10 | 0.09 | 0.22 |
| 2125 | 0.10 | 0.97 | 0.99 | 0.86 | 0.09 | 0.09 | 0.32 |
| 2126 | 0.11 | 0.95 | 1.14 | 0.26 | 0.10 | 0.10 | 0.16 |
| 2127 | 1.08 | 0.94 | 1.17 | 1.02 | 0.96 | 0.10 | 1.16 |
| 2128 | 0.10 | 0.96 | 0.97 | 1.04 | 0.11 | 0.09 | 0.29 |
| 2129 | 0.10 | 0.95 | 0.98 | 0.95 | 0.10 | 0.09 | 0.30 |
| 2130 | 0.10 | 1.01 | 1.12 | 0.91 | 0.11 | 0.09 | 0.25 |
| 2131 | 0.10 | 1.10 | 1.05 | 1.03 | 0.11 | 0.09 | 0.37 |
| 1886 | 1.06 | 0.97 | 1.00 | 0.11 | 0.97 | 1.06 | 0.10 |
| 2132 | 1.20 | 0.94 | 1.09 | 0.13 | 1.18 | 0.98 | 0.10 |
| 1887 | 1.12 | 0.91 | 1.08 | 0.11 | 0.31 | 0.11 | 0.09 |
| 2133 | 0.11 | 0.65 | 1.15 | 0.12 | 0.10 | 0.11 | 0.11 |
| 2134 | 1.10 | 0.91 | 1.18 | 1.00 | 1.08 | 0.85 | 1.13 |
| 2135 | 0.09 | 0.75 | 1.11 | 0.11 | 0.10 | 0.09 | 0.10 |
| 2136 | 0.09 | 0.91 | 1.15 | 0.11 | 0.10 | 0.09 | 0.10 |
| 2137 | 0.10 | 0.79 | 1.13 | 0.11 | 0.10 | 0.10 | 0.10 |

TABLE 3B-continued

| | | | | | | | |
|---|---|---|---|---|---|---|---|
| 2138 | 0.99 | 0.92 | 1.12 | 1.11 | 1.10 | 0.97 | 1.05 |
| 2139 | 0.10 | 0.56 | 1.09 | 0.14 | 0.11 | 0.10 | 0.10 |
| 2140 | 0.94 | 0.84 | 1.04 | 1.09 | 1.07 | 0.10 | 0.97 |
| 2141 | 0.09 | 0.47 | 1.13 | 0.11 | 0.10 | 0.10 | 0.11 |
| 2142 | 0.98 | 1.00 | 1.19 | 0.12 | 0.85 | 0.10 | 0.11 |
| 2143 | 0.99 | 1.05 | 1.17 | 0.15 | 0.99 | 0.11 | 0.11 |
| 2148 | 0.10 | 0.82 | 1.06 | 0.11 | 0.09 | 0.09 | 0.10 |
| 2149 | 1.06 | 0.99 | 1.04 | 1.01 | 1.02 | 0.95 | 1.00 |
| 2150 | 1.09 | 1.01 | 1.11 | 0.12 | 0.25 | 0.09 | 0.12 |
| 2164 | 0.10 | 0.51 | 1.17 | 0.11 | 0.09 | 0.11 | 0.11 |
| 2165 | 0.10 | 0.77 | 1.21 | 0.10 | 0.09 | 0.10 | 0.11 |
| 2166 | 0.95 | 1.02 | 1.06 | 0.11 | 1.01 | 1.10 | 0.12 |
| 2167 | 0.09 | 0.87 | 1.02 | 0.11 | 0.10 | 0.08 | 0.10 |
| 1888 | 0.98 | 0.95 | 1.12 | 0.11 | 0.18 | 0.12 | 0.09 |
| 2151 | 1.08 | 1.12 | 1.22 | 0.12 | 0.20 | 0.11 | 0.12 |
| 2152 | 0.10 | 1.03 | 1.14 | 0.11 | 0.10 | 0.09 | 0.11 |
| 2153 | 1.06 | 0.90 | 1.02 | 0.11 | 0.15 | 0.12 | 0.11 |
| 2154 | 1.07 | 1.16 | 1.17 | 0.13 | 0.20 | 0.09 | 0.12 |
| 2155 | 1.14 | 1.09 | 1.21 | 0.11 | 0.15 | 0.12 | 0.11 |
| 2156 | 0.10 | 0.87 | 0.98 | 0.11 | 0.10 | 0.10 | 0.10 |
| 2157 | 0.10 | 0.96 | 1.10 | 0.10 | 0.09 | 0.09 | 0.10 |
| 2158 | 0.09 | 0.98 | 1.06 | 0.11 | 0.10 | 0.09 | 0.11 |
| 2159 | 1.16 | 1.20 | 1.13 | 0.13 | 0.25 | 0.11 | 0.13 |
| 1889 | 0.10 | 0.63 | 1.08 | 0.10 | 0.09 | 0.11 | 0.10 |
| 2144 | 1.06 | 0.84 | 1.13 | 0.11 | 1.07 | 1.21 | 0.10 |
| 2145 | 0.77 | 0.90 | 1.14 | 1.04 | 0.94 | 0.10 | 0.94 |
| 2146 | 0.10 | 0.88 | 1.13 | 0.12 | 0.10 | 0.09 | 0.11 |
| 2147 | 0.12 | 1.03 | 1.11 | 0.14 | 0.10 | 0.10 | 0.13 |
| 2160 | 0.11 | 1.14 | 0.55 | 0.12 | 0.10 | 0.10 | 0.13 |
| 2161 | 0.10 | 1.06 | 1.17 | 0.11 | 0.10 | 0.10 | 0.11 |
| 2162 | 0.11 | 1.05 | 1.07 | 1.11 | 0.10 | 0.10 | 0.11 |
| 2163 | 0.11 | 1.00 | 1.17 | 0.11 | 0.10 | 0.10 | 0.12 |
| 2168 | 0.10 | 1.03 | 1.10 | 0.11 | 0.10 | 0.08 | 0.11 |
| 1890 | 0.90 | 0.87 | 1.10 | 0.81 | 1.00 | 1.06 | 0.19 |
| 2169 | 0.11 | 1.15 | 1.12 | 0.11 | 0.11 | 0.51 | 0.13 |
| 2170 | 0.10 | 1.01 | 1.16 | 0.38 | 0.11 | 0.09 | 0.18 |
| 2171 | 0.10 | 0.98 | 1.12 | 0.57 | 0.10 | 0.10 | 0.15 |
| 2172 | 0.11 | 0.95 | 1.16 | 1.20 | 0.11 | 0.09 | 1.07 |
| 2173 | 0.11 | 1.11 | 1.26 | 1.11 | 0.10 | 0.09 | 0.98 |
| 2174 | 0.07 | 0.88 | 1.15 | 0.11 | 0.10 | 0.30 | 0.10 |
| 2175 | 1.13 | 1.02 | 1.14 | 0.25 | 1.13 | 0.97 | 0.21 |
| 2176 | 1.09 | 1.05 | 1.15 | 1.09 | 0.75 | 0.09 | 1.05 |
| 2177 | 1.00 | 1.09 | 1.14 | 1.11 | 1.04 | 0.98 | 0.97 |
| 1879 | 0.11 | 0.66 | 1.03 | 0.10 | 0.10 | 0.10 | 0.09 |
| 1911 | 0.99 | 0.68 | 0.11 | 0.37 | 0.50 | 0.13 | 0.14 |
| 1950 | 0.10 | 1.00 | 0.98 | 0.09 | 0.09 | 0.08 | 0.09 |
| 1951 | 1.24 | 1.02 | 0.98 | 0.98 | 0.98 | 0.91 | 1.07 |
| 1952 | 0.10 | 0.97 | 1.00 | 0.09 | 0.09 | 0.09 | 0.10 |
| 1953 | 1.01 | 1.12 | 0.09 | 0.92 | 0.88 | 0.91 | 0.12 |
| 1954 | 0.09 | 0.92 | 1.05 | 0.10 | 0.10 | 0.09 | 0.09 |
| 1955 | 1.07 | 1.08 | 0.10 | 0.78 | 0.83 | 0.77 | 0.12 |
| 1956 | 1.09 | 0.62 | 0.10 | 0.38 | 0.56 | 0.11 | 0.12 |
| 1957 | 0.09 | 1.02 | 1.00 | 0.10 | 0.10 | 0.09 | 0.09 |
| 1958 | 0.09 | 0.98 | 1.07 | 0.09 | 0.09 | 0.09 | 0.09 |
| 1913 | 1.04 | 0.72 | 0.11 | 0.23 | 0.39 | 0.12 | 0.11 |
| 1968 | 0.09 | 0.96 | 1.02 | 0.09 | 0.08 | 0.09 | 0.10 |
| 1969 | 0.10 | 1.03 | 1.04 | 0.96 | 0.08 | 0.09 | 1.05 |
| 1970 | 0.09 | 0.88 | 1.05 | 0.09 | 0.09 | 0.08 | 0.09 |
| 1971 | 0.09 | 0.92 | 1.10 | 0.09 | 0.09 | 0.08 | 0.09 |
| 1972 | 1.01 | 0.39 | 0.09 | 0.23 | 0.36 | 0.09 | 0.12 |
| 1973 | 1.20 | 0.70 | 0.09 | 0.45 | 0.40 | 0.310 | 0.19 |
| 1974 | 1.08 | 0.76 | 0.10 | 0.24 | 0.35 | 0.11 | 0.11 |
| 1975 | 0.09 | 0.87 | 1.00 | 1.14 | 0.10 | 0.12 | 0.65 |
| 1976 | 0.09 | 0.87 | 0.97 | 1.03 | 0.09 | 0.08 | 0.92 |
| 1891 | 1.03 | 0.99 | 1.07 | 1.14 | 0.95 | 1.02 | 0.88 |
| 1892 | 0.95 | 0.96 | 1.07 | 1.08 | 0.99 | 1.04 | 0.88 |
| 1893 | 0.90 | 0.90 | 1.06 | 0.11 | 1.00 | 1.04 | 0.09 |
| 1894 | 0.97 | 0.99 | 1.02 | 1.09 | 1.09 | 1.03 | 0.89 |
| 1895 | 0.11 | 0.28 | 1.02 | 0.13 | 0.14 | 0.10 | 0.10 |
| 1896 | 0.10 | 0.25 | 1.00 | 0.11 | 0.10 | 0.11 | 0.10 |
| 1897 | 0.09 | 0.32 | 0.98 | 0.09 | 0.09 | 0.09 | 0.10 |
| 1898 | 0.09 | 0.38 | 0.90 | 0.11 | 0.09 | 0.08 | 0.09 |
| 1899 | 1.00 | 0.96 | 0.98 | 1.04 | 0.94 | 1.05 | 0.96 |
| 1990 | 0.74 | 0.63 | 0.09 | 0.15 | 0.90 | 0.10 | 0.09 |
| 1991 | 0.80 | 0.32 | 0.10 | 0.15 | 0.88 | 0.10 | 0.09 |
| 1992 | 0.80 | 0.37 | 0.10 | 0.17 | 1.05 | 0.10 | 0.09 |
| 1993 | 0.94 | 0.22 | 0.09 | 0.12 | 1.14 | 0.10 | 0.10 |
| 1994 | 0.93 | 0.19 | 0.10 | 0.16 | 1.08 | 0.10 | 0.09 |
| 1995 | 0.94 | 0.27 | 0.10 | 0.14 | 1.18 | 0.10 | 0.09 |
| 1996 | 0.88 | 0.82 | 0.09 | 0.48 | 0.30 | 0.09 | 0.09 |
| 1910 | 0.24 | 0.92 | 0.10 | 1.08 | 0.12 | 0.09 | 0.09 |
| 1945 | 0.09 | 0.15 | 0.73 | 0.14 | 0.12 | 0.09 | 0.09 |
| 1946 | 0.11 | 0.98 | 0.13 | 1.24 | 0.11 | 0.09 | 0.08 |
| 1947 | 0.10 | 0.83 | 0.12 | 1.16 | 0.11 | 0.09 | 0.08 |
| 1948 | 0.92 | 0.94 | 0.30 | 1.21 | 1.28 | 0.97 | 0.09 |
| 1949 | 0.33 | 0.89 | 0.09 | 0.88 | 0.10 | 0.09 | 0.09 |
| 1977 | 0.87 | 0.91 | 0.66 | 1.05 | 0.27 | 0.19 | 0.09 |
| 1978 | 0.90 | 0.88 | 0.43 | 1.10 | 1.15 | 1.10 | 0.79 |
| 1979 | 0.95 | 0.83 | 0.49 | 0.95 | 1.00 | 0.96 | 0.80 |
| 1980 | 1.02 | 0.77 | 0.80 | 1.09 | 1.05 | 1.00 | 0.80 |
| 1981 | 1.03 | 0.85 | 0.49 | 1.03 | 1.06 | 0.92 | 0.78 |
| 1982 | 0.98 | 0.96 | 0.64 | 1.19 | 1.11 | 0.97 | 0.90 |
| 1983 | 0.10 | 0.16 | 1.09 | 0.13 | 0.11 | 0.09 | 0.11 |
| 1984 | 0.97 | 0.94 | 0.48 | 1.08 | 1.10 | 0.83 | 0.81 |

TABLE 3B-continued

| | | | | | | | |
|---|---|---|---|---|---|---|---|
| 1985 | 0.88 | 0.88 | 0.83 | 1.15 | 1.11 | 0.93 | 0.08 |
| 1914 | 0.25 | 0.93 | 1.05 | 1.18 | 0.14 | 0.10 | 0.23 |
| 1986 | 0.27 | 0.94 | 0.53 | 1.18 | 0.15 | 0.10 | 0.28 |
| 1987 | 0.26 | 0.94 | 0.59 | 1.13 | 0.14 | 0.10 | 0.31 |
| 1988 | 0.28 | 0.87 | 0.42 | 0.95 | 0.12 | 0.10 | 0.31 |
| 1989 | 0.10 | 0.28 | 1.05 | 0.14 | 0.11 | 0.09 | 0.09 |
| 1917 | 0.95 | 0.92 | 0.50 | 0.86 | 1.01 | 0.70 | 0.80 |
| 2015 | 0.86 | 0.95 | 0.39 | 0.88 | 0.80 | 0.21 | 0.16 |
| 2016 | 0.89 | 0.97 | 0.32 | 1.00 | 0.83 | 0.22 | 0.24 |
| 2017 | 0.97 | 0.77 | 0.29 | 0.97 | 0.85 | 0.23 | 0.19 |
| 2018 | 0.88 | 0.87 | 0.36 | 1.14 | 0.73 | 0.21 | 0.13 |
| 2019 | 1.09 | 0.79 | 0.44 | 1.10 | 0.72 | 0.19 | 0.12 |
| 2020 | 0.84 | 0.88 | 0.59 | 0.95 | 0.22 | 0.15 | 0.78 |
| 2021 | 0.94 | 0.95 | 0.34 | 1.06 | 0.93 | 0.45 | 0.69 |
| 2022 | 0.92 | 0.93 | 0.37 | 1.08 | 1.03 | 0.57 | 0.72 |
| 2023 | 1.04 | 1.05 | 0.99 | 1.15 | 1.10 | 0.18 | 0.97 |

TABLE 3C

| NP # | LP103 | LP106 | LP109 | LP114 | LP124 | LP125 |
|---|---|---|---|---|---|---|
| 1900 | 1.25 | 1.16 | 1.06 | 0.97 | 0.66 | 1.18 |
| 1901 | 1.10 | 0.16 | 0.12 | 0.09 | 0.10 | 1.14 |
| 1902 | 1.14 | 1.20 | 0.13 | 0.10 | 0.36 | 1.17 |
| 1903 | 1.10 | 0.28 | 0.12 | 0.10 | 0.11 | 1.12 |
| 1904 | 1.12 | 0.22 | 0.77 | 0.11 | 0.11 | 1.09 |
| 1905 | 1.11 | 0.23 | 0.95 | 0.11 | 0.11 | 1.14 |
| 1906 | 1.17 | 0.98 | 0.12 | 0.10 | 0.76 | 1.08 |
| 1907 | 1.22 | 1.16 | 1.02 | 0.96 | 0.76 | 1.07 |
| 1908 | 1.10 | 0.11 | 0.12 | 0.09 | 0.10 | 0.73 |
| 1909 | 1.26 | 1.05 | 0.95 | 0.88 | 0.73 | 1.00 |
| 1912 | 1.08 | 1.27 | 1.15 | 1.08 | 0.71 | 1.13 |
| 1959 | 0.09 | 0.10 | 0.09 | 1.00 | 0.09 | 1.06 |
| 1960 | 0.20 | 0.38 | 0.09 | 0.08 | 0.13 | 0.94 |
| 1961 | 0.16 | 0.16 | 0.08 | 0.95 | 0.12 | 1.00 |
| 1962 | 0.91 | 1.21 | 1.01 | 1.15 | 0.25 | 1.06 |
| 1963 | 0.08 | 0.10 | 0.09 | 1.00 | 0.09 | 1.00 |
| 1964 | 0.08 | 0.11 | 0.09 | 1.08 | 0.09 | 1.06 |
| 1965 | 0.08 | 0.10 | 0.08 | 1.03 | 0.09 | 1.01 |
| 1966 | 0.10 | 0.12 | 0.08 | 0.97 | 0.10 | 1.06 |
| 1967 | 0.09 | 0.13 | 0.10 | 1.14 | 0.10 | 1.03 |
| 1915 | 0.09 | 0.23 | 0.09 | 0.12 | 0.10 | 0.10 |
| 1997 | 0.09 | 0.10 | 0.09 | 1.03 | 0.09 | 0.10 |
| 1998 | 0.09 | 0.11 | 0.09 | 1.03 | 0.10 | 0.10 |
| 1999 | 0.09 | 0.10 | 0.09 | 1.00 | 0.09 | 0.11 |
| 2000 | 0.09 | 0.10 | 0.09 | 1.02 | 0.09 | 0.09 |
| 2001 | 0.09 | 0.23 | 0.09 | 1.02 | 0.10 | 0.10 |
| 2002 | 0.10 | 0.12 | 0.09 | 0.97 | 0.10 | 0.77 |
| 2003 | 0.97 | 1.04 | 0.09 | 1.10 | 0.09 | 1.10 |

TABLE 3C-continued

| | | | | | | |
|---|---|---|---|---|---|---|
| 2004 | 1.06 | 1.06 | 0.09 | 0.96 | 0.09 | 1.06 |
| 2005 | 1.12 | 1.17 | 0.09 | 1.10 | 0.10 | 1.02 |
| 1916 | 1.08 | 1.04 | 1.14 | 1.11 | 0.73 | 1.07 |
| 2006 | 0.97 | 0.99 | 0.77 | 1.00 | 0.59 | 1.18 |
| 2007 | 0.14 | 0.23 | 0.10 | 0.10 | 0.11 | 1.11 |
| 2008 | 0.18 | 0.20 | 0.10 | 0.10 | 0.11 | 1.08 |
| 2009 | 0.28 | 0.45 | 0.09 | 0.09 | 0.14 | 1.05 |
| 2010 | 1.24 | 0.84 | 0.74 | 0.98 | 0.57 | 1.13 |
| 2011 | 0.94 | 0.86 | 0.88 | 1.02 | 0.59 | 1.14 |
| 2012 | 1.06 | 1.04 | 0.94 | 1.01 | 0.91 | 1.03 |
| 2013 | 1.06 | 1.04 | 0.92 | 0.98 | 0.89 | 1.03 |
| 2014 | 1.01 | 0.89 | 0.78 | 1.01 | 0.63 | 1.08 |
| 1869 | 0.13 | 0.14 | 0.13 | 0.13 | 0.22 | 0.62 |
| 1840 | 1.19 | 1.08 | 0.16 | 0.13 | 1.02 | 1.10 |
| 1839 | 0.17 | 0.15 | 1.07 | 1.23 | 0.21 | 0.17 |
| 2024 | 0.09 | 0.10 | 1.00 | 1.09 | 0.10 | 0.09 |
| 2025 | 0.09 | 0.18 | 1.04 | 1.14 | 0.09 | 0.09 |
| 2026 | 0.30 | 0.16 | 0.97 | 1.05 | 0.26 | 0.32 |
| 2027 | 0.10 | 0.20 | 1.09 | 1.11 | 0.09 | 0.09 |
| 2028 | 0.09 | 0.15 | 0.97 | 0.95 | 0.09 | 0.09 |
| 2029 | 0.47 | 0.29 | 1.11 | 0.99 | 0.15 | 0.11 |
| 2030 | 0.09 | 0.24 | 0.90 | 0.96 | 0.10 | 0.10 |
| 2031 | 0.08 | 0.11 | 0.92 | 0.91 | 0.10 | 0.10 |
| 2032 | 0.09 | 0.19 | 1.05 | 0.93 | 0.09 | 0.10 |
| 1878 | 0.10 | 0.11 | 0.95 | 0.98 | 0.11 | 0.11 |
| 2033 | 0.10 | 0.10 | 1.15 | 0.97 | 0.10 | 0.10 |
| 2034 | 0.09 | 0.15 | 0.95 | 0.99 | 0.10 | 0.12 |
| 2035 | 0.09 | 0.12 | 1.08 | 0.93 | 0.10 | 0.11 |
| 2036 | 0.09 | 0.15 | 1.14 | 0.95 | 0.09 | 0.11 |
| 2037 | 0.09 | 0.10 | 1.09 | 0.94 | 0.10 | 0.10 |
| 2038 | 0.09 | 0.28 | 0.96 | 0.91 | 0.09 | 0.10 |
| 2039 | 0.09 | 0.23 | 1.07 | 0.94 | 0.09 | 0.10 |
| 2040 | 0.09 | 0.12 | 0.90 | 1.07 | 0.10 | 0.11 |
| 2041 | 0.10 | 0.16 | 1.14 | 0.99 | 0.10 | 0.10 |
| 2042 | 0.09 | 0.16 | 0.91 | 0.98 | 0.10 | 0.10 |
| 2043 | 0.09 | 0.10 | 0.89 | 0.99 | 0.09 | 0.09 |
| 2044 | 0.09 | 0.14 | 1.01 | 1.03 | 0.09 | 0.10 |
| 2045 | 0.10 | 0.11 | 0.75 | 0.93 | 0.13 | 0.10 |
| 2046 | 0.09 | 0.10 | 0.94 | 1.08 | 0.10 | 0.09 |
| 2047 | 0.11 | 0.11 | 0.96 | 0.91 | 0.11 | 0.12 |
| 2048 | 0.10 | 0.10 | 0.30 | 0.95 | 0.13 | 0.12 |
| 2049 | 0.09 | 0.15 | 1.03 | 0.93 | 0.09 | 0.09 |
| 2050 | 0.10 | 0.13 | 0.98 | 0.90 | 0.10 | 0.10 |
| 1880 | 1.26 | 1.16 | 0.98 | 1.03 | 1.07 | 1.12 |

TABLE 3C-continued

| | | | | | | |
|---|---|---|---|---|---|---|
| 2051 | 0.10 | 0.11 | 0.98 | 0.91 | 0.10 | 0.10 |
| 2052 | 0.10 | 0.24 | 0.98 | 0.86 | 0.10 | 0.10 |
| 2053 | 0.11 | 0.34 | 1.12 | 1.07 | 0.10 | 0.10 |
| 2054 | 0.10 | 0.13 | 1.07 | 1.10 | 0.11 | 0.11 |
| 2055 | 0.09 | 0.23 | 1.02 | 1.15 | 0.09 | 0.09 |
| 2056 | 0.10 | 0.17 | 1.03 | 0.99 | 0.09 | 0.10 |
| 2057 | 0.10 | 0.11 | 1.03 | 0.98 | 0.09 | 0.10 |
| 2058 | 0.11 | 0.11 | 1.00 | 0.96 | 0.10 | 0.10 |
| 2059 | 0.10 | 0.16 | 1.10 | 1.09 | 0.10 | 0.22 |
| 1881 | 1.23 | 1.16 | 0.93 | 0.97 | 1.06 | 1.20 |
| 2060 | 0.51 | 0.19 | 1.07 | 1.04 | 0.14 | 0.11 |
| 2061 | 0.25 | 0.23 | 1.08 | 1.03 | 0.14 | 0.26 |
| 2062 | 0.28 | 0.18 | 1.06 | 1.25 | 0.13 | 0.12 |
| 2063 | 0.99 | 0.87 | 1.05 | 1.16 | 1.06 | 0.96 |
| 2064 | 0.14 | 0.30 | 1.05 | 1.24 | 0.09 | 0.09 |
| 2065 | 0.42 | 0.15 | 1.07 | 1.02 | 0.14 | 0.11 |
| 2066 | 0.38 | 0.11 | 1.00 | 1.11 | 0.17 | 0.10 |
| 2067 | 1.14 | 1.08 | 0.96 | 1.10 | 1.10 | 0.94 |
| 2068 | 0.98 | 1.17 | 1.03 | 1.12 | 1.17 | 0.97 |
| 2069 | 0.70 | 0.25 | 1.08 | 1.33 | 0.36 | 0.11 |
| 2070 | 0.09 | 0.20 | 1.12 | 1.21 | 0.11 | 0.11 |
| 2071 | 0.93 | 0.92 | 1.06 | 0.94 | 1.05 | 0.97 |
| 2072 | 0.11 | 0.16 | 1.07 | 0.96 | 0.11 | 0.10 |
| 2073 | 0.90 | 0.20 | 1.14 | 0.89 | 1.09 | 0.31 |
| 2074 | 0.11 | 0.12 | 1.13 | 0.57 | 0.09 | 0.11 |
| 2075 | 0.23 | 0.24 | 1.13 | 1.14 | 0.15 | 0.13 |
| 2076 | 0.08 | 0.21 | 0.96 | 1.04 | 0.09 | 0.10 |
| 2077 | 0.09 | 0.11 | 0.97 | 1.01 | 0.10 | 0.10 |
| 1882 | 0.09 | 0.10 | 0.99 | 0.97 | 0.10 | 0.10 |
| 2078 | 0.19 | 0.16 | 1.10 | 1.02 | 0.15 | 0.13 |
| 2079 | 0.94 | 1.03 | 1.02 | 1.08 | 1.11 | 1.07 |
| 2080 | 0.93 | 1.03 | 1.04 | 1.06 | 1.03 | 1.07 |
| 2081 | 0.96 | 1.02 | 0.94 | 0.99 | 1.02 | 1.02 |
| 2082 | 1.03 | 0.99 | 1.01 | 1.07 | 1.09 | 0.98 |
| 2083 | 0.15 | 0.12 | 1.05 | 1.09 | 0.13 | 0.09 |
| 2084 | 0.16 | 0.10 | 1.05 | 1.04 | 0.13 | 0.14 |
| 2085 | 1.00 | 1.09 | 1.09 | 1.20 | 1.10 | 0.97 |
| 2086 | 0.17 | 0.14 | 1.12 | 1.19 | 0.11 | 0.21 |
| 2087 | 1.16 | 1.011 | 1.13 | 1.18 | 1.08 | 0.11 |
| 2088 | 0.12 | 0.16 | 0.96 | 1.07 | 0.13 | 0.17 |
| 2089 | 1.03 | 0.95 | 0.97 | 1.09 | 1.12 | 1.01 |
| 2090 | 0.12 | 0.14 | 1.10 | 1.04 | 0.12 | 0.12 |
| 2091 | 0.13 | 0.23 | 1.02 | 1.06 | 0.15 | 0.10 |
| 2092 | 0.08 | 0.10 | 1.04 | 1.07 | 0.09 | 0.10 |
| 2093 | 0.08 | 0.09 | 0.94 | 1.05 | 0.09 | 0.10 |
| 2094 | 0.08 | 0.09 | 1.01 | 1.05 | 0.09 | 0.09 |
| 2095 | 0.11 | 0.86 | 1.05 | 1.05 | 0.11 | 0.10 |
| 2096 | 0.09 | 0.19 | 1.05 | 1.19 | 0.09 | 0.09 |
| 2097 | 0.09 | 0.13 | 1.09 | 1.07 | 0.09 | 0.09 |
| 2098 | 0.09 | 0.12 | 1.12 | 1.13 | 0.09 | 0.10 |
| 2099 | 0.09 | 0.28 | 1.12 | 1.07 | 0.10 | 0.09 |
| 2100 | 1.07 | 1.07 | 1.08 | 1.08 | 1.10 | 1.09 |
| 2101 | 0.97 | 1.07 | 1.02 | 1.14 | 1.06 | 1.10 |
| 2102 | 0.97 | 0.97 | 0.96 | 1.07 | 1.11 | 1.02 |
| 2103 | 1.00 | 1.04 | 1.11 | 1.07 | 1.12 | 0.99 |
| 2104 | 0.99 | 1.03 | 0.95 | 1.15 | 1.14 | 1.08 |
| 1883 | 1.22 | 1.13 | 1.00 | 0.96 | 1.02 | 1.06 |
| 2105 | 1.02 | 1.06 | 0.99 | 1.15 | 1.18 | 0.94 |
| 2106 | 1.00 | 0.67 | 1.14 | 1.15 | 1.00 | 0.12 |
| 2107 | 0.98 | 1.02 | 1.02 | 1.25 | 1.11 | 0.92 |
| 2108 | 1.12 | 1.03 | 0.96 | 1.15 | 1.05 | 1.10 |
| 2109 | 0.92 | 1.04 | 1.06 | 1.16 | 1.10 | 0.93 |
| 2110 | 0.97 | 1.14 | 1.17 | 1.15 | 1.11 | 0.94 |
| 2111 | 1.05 | 0.37 | 1.05 | 1.12 | 0.34 | 0.12 |
| 2112 | 1.02 | 0.99 | 1.13 | 1.14 | 1.12 | 1.15 |
| 2113 | 0.08 | 0.09 | 1.07 | 1.10 | 0.10 | 0.10 |
| 1884 | 1.12 | 1.01 | 1.12 | 0.93 | 0.98 | 1.05 |
| 2114 | 0.97 | 0.92 | 1.01 | 1.20 | 1.06 | 1.09 |
| 2115 | 0.98 | 0.99 | 1.12 | 1.18 | 1.08 | 1.09 |
| 2116 | 1.13 | 0.87 | 1.00 | 1.15 | 1.10 | 1.14 |
| 2117 | 1.03 | 1.01 | 0.96 | 1.12 | 1.03 | 1.04 |
| 2118 | 1.06 | 1.05 | 1.03 | 1.11 | 1.13 | 1.01 |
| 2119 | 1.11 | 1.00 | 1.07 | 1.10 | 1.15 | 0.97 |
| 2120 | 0.99 | 1.05 | 1.02 | 1.18 | 1.04 | 0.95 |
| 2121 | 0.97 | 0.96 | 1.02 | 1.09 | 1.11 | 1.03 |
| 2122 | 0.86 | 1.09 | 1.21 | 1.13 | 1.12 | 0.92 |
| 1885 | 0.10 | 0.16 | 1.06 | 0.96 | 0.09 | 0.09 |
| 2123 | 0.09 | 0.12 | 1.01 | 0.98 | 0.09 | 0.09 |
| 2124 | 0.09 | 0.10 | 1.03 | 1.17 | 0.09 | 0.10 |
| 2125 | 0.09 | 0.09 | 1.03 | 0.15 | 0.09 | 0.10 |
| 2126 | 0.09 | 0.15 | 1.04 | 1.13 | 0.10 | 0.09 |
| 2127 | 1.03 | 1.03 | 1.03 | 1.14 | 1.01 | 0.97 |
| 2128 | 0.09 | 0.09 | 1.00 | 0.14 | 0.09 | 0.09 |
| 2129 | 0.09 | 0.14 | 1.01 | 0.17 | 0.09 | 0.11 |
| 2130 | 0.09 | 0.19 | 1.00 | 1.16 | 0.10 | 0.11 |
| 2131 | 0.09 | 0.13 | 1.02 | 0.14 | 0.09 | 0.10 |
| 1886 | 0.98 | 1.14 | 0.94 | 1.13 | 1.00 | 1.05 |
| 2132 | 0.92 | 1.05 | 1.04 | 1.10 | 1.01 | 1.04 |
| 1887 | 1.14 | 0.12 | 0.93 | 0.92 | 0.36 | 0.10 |
| 2133 | 0.10 | 0.18 | 1.02 | 1.03 | 0.10 | 0.09 |
| 2134 | 0.88 | 0.85 | 1.01 | 1.26 | 1.11 | 0.89 |
| 2135 | 0.09 | 0.16 | 1.05 | 1.15 | 0.09 | 0.09 |
| 2136 | 0.09 | 0.13 | 0.11 | 1.02 | 0.09 | 0.08 |
| 2137 | 0.09 | 0.16 | 1.21 | 1.20 | 0.10 | 0.09 |

TABLE 3C-continued

| | | | | | | |
|---|---|---|---|---|---|---|
| 2138 | 0.97 | 1.14 | 1.04 | 1.20 | 1.03 | 0.97 |
| 2139 | 0.10 | 0.27 | 1.03 | 1.17 | 0.10 | 0.09 |
| 2140 | 0.86 | 0.18 | 1.08 | 1.09 | 0.54 | 0.17 |
| 2141 | 0.09 | 0.16 | 1.18 | 1.25 | 0.10 | 0.09 |
| 2142 | 1.00 | 0.13 | 1.05 | 1.19 | 1.03 | 0.10 |
| 2143 | 1.06 | 0.50 | 1.03 | 1.32 | 0.98 | 0.15 |
| 2148 | 0.09 | 0.23 | 1.13 | 1.09 | 0.10 | 0.10 |
| 2149 | 0.92 | 1.07 | 1.08 | 1.00 | 0.96 | 1.06 |
| 2150 | 0.78 | 0.32 | 0.99 | 1.11 | 0.60 | 0.19 |
| 2164 | 0.10 | 0.20 | 1.07 | 1.20 | 0.10 | 0.09 |
| 2165 | 0.10 | 0.15 | 0.97 | 1.27 | 0.10 | 0.08 |
| 2166 | 1.12 | 0.93 | 1.03 | 1.37 | 1.06 | 1.03 |
| 2167 | 0.08 | 0.11 | 1.04 | 1.09 | 0.10 | 0.10 |
| 1888 | 1.13 | 0.12 | 1.02 | 0.97 | 0.19 | 0.11 |
| 2151 | 0.92 | 0.15 | 1.15 | 1.09 | 0.54 | 0.11 |
| 2152 | 0.09 | 0.11 | 1.11 | 1.18 | 0.10 | 0.11 |
| 2153 | 0.44 | 0.23 | 1.22 | 1.07 | 0.14 | 0.10 |
| 2154 | 0.90 | 0.25 | 1.39 | 1.12 | 0.22 | 0.11 |
| 2155 | 0.44 | 0.13 | 1.20 | 1.05 | 0.15 | 0.12 |
| 2156 | 0.10 | 0.12 | 1.16 | 1.06 | 0.09 | 0.09 |
| 2157 | 0.09 | 0.11 | 1.17 | 1.20 | 0.09 | 0.09 |
| 2158 | 0.09 | 0.14 | 1.22 | 1.17 | 0.09 | 0.09 |
| 2159 | 1.05 | 0.20 | 1.00 | 1.09 | 0.21 | 0.13 |
| 1889 | 0.10 | 0.18 | 0.99 | 0.97 | 0.10 | 0.11 |
| 2144 | 1.18 | 1.14 | 1.22 | 1.21 | 1.11 | 0.99 |
| 2145 | 0.11 | 0.85 | 1.02 | 1.26 | 0.71 | 0.10 |
| 2146 | 0.09 | 0.14 | 1.15 | 1.16 | 0.10 | 0.09 |
| 2147 | 0.11 | 0.23 | 1.10 | 1.15 | 0.10 | 0.11 |
| 2160 | 0.11 | 0.18 | 1.05 | 1.08 | 0.10 | 0.09 |
| 2161 | 0.10 | 0.28 | 1.05 | 1.15 | 0.10 | 0.10 |
| 2162 | 0.10 | 0.23 | 1.03 | 1.20 | 0.10 | 0.09 |
| 2163 | 0.10 | 0.19 | 1.07 | 1.22 | 0.10 | 0.10 |
| 2168 | 0.08 | 0.41 | 1.05 | 1.06 | 0.10 | 0.09 |
| 1890 | 1.20 | 1.10 | 1.00 | 0.97 | 1.04 | 1.13 |
| 2169 | 0.50 | 0.11 | 1.64 | 1.19 | 0.10 | 0.10 |
| 2170 | 0.08 | 0.16 | 1.09 | 1.08 | 0.10 | 0.09 |
| 2171 | 0.10 | 0.30 | 1.13 | 0.12 | 0.10 | 0.09 |
| 2172 | 0.10 | 0.13 | 1.12 | 1.06 | 0.10 | 0.09 |
| 2173 | 0.09 | 0.11 | 1.06 | 1.04 | 0.11 | 0.09 |
| 2174 | 0.31 | 0.13 | 1.04 | 1.02 | 0.09 | 0.09 |
| 2175 | 0.09 | 1.21 | 1.04 | 1.15 | 1.14 | 0.89 |
| 2176 | 0.84 | 0.43 | 1.15 | 1.13 | 0.65 | 0.14 |
| 2177 | 1.00 | 1.14 | 1.02 | 1.03 | 1.12 | 0.95 |
| 1879 | 0.10 | 0.43 | 0.99 | 1.01 | 0.10 | 0.12 |
| 1911 | 1.18 | 1.03 | 1.06 | 1.09 | 0.27 | 1.13 |
| 1950 | 0.08 | 0.15 | 1.01 | 1.18 | 0.09 | 0.08 |
| 1951 | 0.89 | 0.91 | 1.00 | 1.02 | 1.07 | 0.09 |
| 1952 | 0.09 | 0.12 | 0.38 | 0.17 | 0.09 | 0.09 |
| 1953 | 1.11 | 1.00 | 0.14 | 0.09 | 0.76 | 0.97 |
| 1954 | 0.09 | 0.14 | 0.92 | 0.98 | 0.09 | 0.09 |
| 1955 | 1.09 | 0.10 | 0.14 | 0.09 | 0.74 | 1.01 |
| 1956 | 1.10 | 0.95 | 0.90 | 1.02 | 0.16 | 0.98 |
| 1957 | 0.09 | 0.23 | 1.18 | 1.04 | 0.09 | 0.09 |
| 1958 | 0.09 | 0.14 | 1.03 | 1.07 | 0.09 | 0.09 |
| 1913 | 1.23 | 0.98 | 0.91 | 1.07 | 0.45 | 1.00 |
| 1968 | 0.09 | 0.14 | 0.26 | 0.15 | 0.09 | 0.10 |
| 1969 | 0.09 | 0.14 | 1.16 | 1.02 | 0.10 | 0.10 |
| 1970 | 0.08 | 0.15 | 0.12 | 0.17 | 0.09 | 0.10 |
| 1971 | 0.07 | 0.13 | 1.16 | 0.98 | 0.09 | 0.09 |
| 1972 | 0.89 | 0.34 | 0.93 | 0.94 | 0.13 | 1.00 |
| 1973 | 1.14 | 0.30 | 0.65 | 1.02 | 0.17 | 1.01 |
| 1974 | 0.98 | 0.96 | 0.76 | 0.82 | 0.15 | 1.05 |
| 1975 | 0.11 | 0.13 | 0.95 | 0.85 | 0.09 | 0.10 |
| 1976 | 0.08 | 0.27 | 0.83 | 0.85 | 0.09 | 0.10 |
| 1891 | 1.07 | 1.13 | 1.02 | 1.06 | 1.04 | 1.12 |
| 1892 | 1.12 | 1.13 | 1.17 | 1.02 | 1.03 | 1.06 |
| 1893 | 1.11 | 1.11 | 1.19 | 0.96 | 1.02 | 1.12 |
| 1894 | 1.13 | 1.14 | 1.04 | 1.01 | 1.05 | 1.03 |
| 1895 | 0.10 | 0.15 | 1.09 | 1.00 | 0.11 | 0.11 |
| 1896 | 0.11 | 0.14 | 1.13 | 1.03 | 0.11 | 0.10 |
| 1897 | 0.08 | 0.12 | 1.01 | 1.04 | 0.09 | 0.09 |
| 1898 | 0.08 | 0.23 | 0.97 | 1.00 | 0.08 | 0.10 |
| 1899 | 1.14 | 1.03 | 1.00 | 0.99 | 0.97 | 1.20 |
| 1990 | 0.94 | 1.01 | 0.95 | 0.90 | 0.46 | 1.00 |
| 1991 | 0.96 | 0.97 | 0.99 | 0.91 | 0.40 | 1.03 |
| 1992 | 0.92 | 1.08 | 0.82 | 0.94 | 0.36 | 1.03 |
| 1993 | 1.02 | 1.11 | 0.86 | 1.01 | 0.11 | 0.95 |
| 1994 | 1.13 | 0.98 | 1.05 | 0.98 | 0.10 | 1.08 |
| 1995 | 1.10 | 1.03 | 0.84 | 0.97 | 0.10 | 1.09 |
| 1996 | 0.76 | 0.14 | 0.09 | 0.09 | 0.20 | 1.07 |
| 1910 | 0.14 | 0.36 | 0.09 | 0.09 | 0.09 | 1.14 |
| 1945 | 0.09 | 0.19 | 0.97 | 1.04 | 0.09 | 0.10 |
| 1946 | 0.10 | 0.13 | 0.09 | 0.09 | 0.09 | 1.14 |
| 1947 | 0.09 | 0.10 | 0.10 | 0.10 | 0.10 | 1.14 |
| 1948 | 1.09 | 1.19 | 0.09 | 0.09 | 0.59 | 1.07 |
| 1949 | 0.15 | 0.70 | 0.09 | 0.09 | 0.11 | 1.07 |
| 1977 | 0.89 | 0.56 | 0.69 | 0.09 | 0.34 | 1.04 |
| 1978 | 1.12 | 1.15 | 0.99 | 0.90 | 1.03 | 1.06 |
| 1979 | 1.11 | 1.09 | 1.01 | 0.85 | 0.99 | 1.05 |
| 1980 | 1.00 | 1.18 | 0.94 | 1.01 | 1.01 | 1.08 |
| 1981 | 0.95 | 1.09 | 1.08 | 1.12 | 0.96 | 0.98 |
| 1982 | 1.07 | 1.19 | 1.08 | 1.10 | 1.08 | 1.02 |
| 1983 | 0.09 | 0.14 | 0.88 | 0.11 | 0.09 | 0.10 |
| 1984 | 1.05 | 1.07 | 0.83 | 1.02 | 0.98 | 1.03 |
| 1985 | 1.04 | 1.04 | 0.34 | 0.09 | 1.02 | 1.03 |

TABLE 3C-continued

| | | | | | |
|---|---|---|---|---|---|
| 1914 | 0.17 | 0.16 | 0.09 | 0.12 | 0.16 | 1.16 |
| 1986 | 0.16 | 0.11 | 0.09 | 0.12 | 0.14 | 1.03 |
| 1987 | 0.15 | 0.12 | 0.09 | 0.11 | 0.12 | 1.06 |
| 1988 | 0.16 | 0.11 | 0.09 | 0.12 | 0.12 | 1.01 |
| 1989 | 0.09 | 0.15 | 0.12 | 0.31 | 0.10 | 0.09 |
| 1917 | 1.17 | 1.15 | 1.02 | 1.03 | 1.03 | 1.04 |
| 2015 | 0.98 | 0.98 | 0.12 | 0.10 | 0.83 | 1.02 |
| 2016 | 1.00 | 0.96 | 0.13 | 0.10 | 0.83 | 1.05 |
| 2017 | 0.97 | 1.11 | 0.14 | 0.10 | 0.81 | 0.98 |
| 2018 | 1.01 | 1.25 | 0.15 | 0.11 | 0.85 | 0.98 |
| 2019 | 1.05 | 1.05 | 0.13 | 0.11 | 0.94 | 0.98 |
| 2020 | 0.69 | 0.78 | 1.09 | 1.21 | 0.30 | 0.99 |
| 2021 | 1.05 | 1.10 | 1.05 | 1.19 | 0.96 | 1.06 |
| 2022 | 1.10 | 1.06 | 1.06 | 1.14 | 0.96 | 0.98 |
| 2023 | 1.10 | 1.03 | 1.01 | 0.99 | 1.11 | 0.95 |

TABLE 3D

| NP # | LP128 | LP129 | LP141 | LP143 | LP177 |
|---|---|---|---|---|---|
| 1900 | 0.54 | 1.01 | 1.10 | 0.30 | 0.79 |
| 1901 | 0.10 | 0.09 | 0.10 | 0.10 | 0.09 |
| 1902 | 0.10 | 0.09 | 0.10 | 0.36 | 0.55 |
| 1903 | 0.10 | 0.09 | 0.11 | 0.10 | 0.10 |
| 1904 | 0.10 | 0.10 | 0.10 | 0.11 | 0.10 |
| 1905 | 0.10 | 0.10 | 0.11 | 0.10 | 0.10 |
| 1906 | 0.09 | 0.10 | 0.10 | 0.20 | 0.48 |
| 1907 | 0.55 | 1.11 | 1.02 | 0.28 | 0.64 |
| 1908 | 0.09 | 0.09 | 0.11 | 0.11 | 0.09 |
| 1909 | 0.53 | 1.26 | 1.11 | 0.17 | 0.76 |
| 1912 | 0.56 | 0.75 | 1.10 | 0.62 | 0.61 |
| 1959 | 0.60 | 0.96 | 0.84 | 0.09 | 0.09 |
| 1960 | 0.09 | 0.09 | 0.10 | 0.11 | 0.10 |
| 1961 | 0.48 | 0.96 | 0.95 | 0.12 | 0.09 |
| 1962 | 0.44 | 0.62 | 0.85 | 0.12 | 0.52 |
| 1963 | 0.61 | 0.91 | 0.86 | 0.09 | 0.08 |
| 1964 | 0.72 | 0.97 | 0.95 | 0.09 | 0.08 |
| 1965 | 0.47 | 0.92 | 0.93 | 0.09 | 0.08 |
| 1966 | 0.63 | 0.79 | 0.98 | 0.09 | 0.08 |
| 1967 | 0.45 | 0.95 | 0.89 | 0.09 | 0.09 |
| 1915 | 0.67 | 0.75 | 1.04 | 0.09 | 0.12 |
| 1997 | 0.64 | 0.84 | 1.07 | 0.09 | 0.10 |
| 1998 | 0.76 | 0.95 | 0.74 | 0.09 | 0.11 |
| 1999 | 0.98 | 0.90 | 0.95 | 0.09 | 0.10 |
| 2000 | 0.77 | 1.02 | 0.94 | 0.09 | 0.10 |
| 2001 | 0.59 | 0.85 | 0.97 | 0.10 | 0.11 |
| 2002 | 0.59 | 1.07 | 1.14 | 0.11 | 0.11 |
| 2003 | 0.57 | 1.00 | 1.04 | 0.10 | 1.01 |

TABLE 3D-continued

| 2004 | 0.54 | 0.36 | 1.16 | 0.10 | 0.23 |
|---|---|---|---|---|---|
| 2005 | 0.45 | 0.99 | 1.18 | 0.11 | 1.08 |
| 1916 | 0.16 | 0.65 | 0.16 | 0.68 | 0.72 |
| 2006 | 0.20 | 0.53 | 0.29 | 0.39 | 0.78 |
| 2007 | 0.11 | 0.09 | 0.10 | 0.11 | 0.13 |
| 2008 | 0.11 | 0.09 | 0.10 | 0.11 | 0.13 |
| 2009 | 0.10 | 0.09 | 0.28 | 0.12 | 0.13 |
| 2010 | 0.20 | 0.79 | 0.66 | 0.30 | 0.90 |
| 2011 | 0.14 | 0.65 | 0.46 | 0.44 | 0.56 |
| 2012 | 0.79 | 1.11 | 1.14 | 0.43 | 0.81 |
| 2013 | 0.86 | 1.02 | 1.10 | 0.44 | 0.89 |
| 2014 | 0.13 | 0.84 | 0.25 | 0.43 | 0.51 |
| 1869 | 0.15 | 0.12 | 0.13 | 0.22 | 0.14 |
| 1840 | 0.10 | 0.10 | 0.11 | 1.06 | 1.10 |
| 1839 | 1.21 | 0.98 | 1.28 | 0.18 | 0.47 |
| 2024 | 1.06 | 1.09 | 1.07 | 0.10 | 0.10 |
| 2025 | 1.13 | 1.18 | 1.07 | 0.09 | 0.11 |
| 2026 | 1.10 | 0.72 | 1.02 | 0.28 | 0.61 |
| 2027 | 1.09 | 1.09 | 1.06 | 0.10 | 0.11 |
| 2028 | 1.02 | 1.01 | 1.02 | 0.10 | 0.09 |
| 2029 | 1.04 | 1.11 | 1.12 | 0.20 | 0.14 |
| 2030 | 1.01 | 1.01 | 1.06 | 0.10 | 0.09 |
| 2031 | 1.00 | 1.02 | 1.01 | 0.10 | 0.09 |
| 2032 | 1.01 | 0.99 | 1.13 | 0.10 | 0.09 |
| 1878 | 1.14 | 1.22 | 1.20 | 0.11 | 0.11 |
| 2033 | 1.10 | 1.02 | 1.03 | 0.10 | 0.10 |
| 2034 | 1.09 | 0.98 | 1.01 | 0.10 | 0.10 |
| 2035 | 1.10 | 0.96 | 1.00 | 0.10 | 0.10 |
| 2036 | 1.07 | 0.95 | 1.09 | 0.09 | 0.10 |
| 2037 | 1.10 | 1.04 | 1.16 | 0.10 | 0.10 |
| 2038 | 1.09 | 0.98 | 1.00 | 0.09 | 0.10 |
| 2039 | 1.13 | 0.93 | 1.10 | 0.09 | 0.10 |
| 2040 | 1.27 | 0.96 | 1.02 | 0.10 | 0.11 |
| 2041 | 1.09 | 1.03 | 1.09 | 0.10 | 0.10 |
| 2042 | 0.24 | 1.07 | 1.09 | 0.10 | 0.09 |
| 2043 | 0.23 | 1.12 | 1.10 | 0.09 | 0.10 |
| 2044 | 0.29 | 1.24 | 1.17 | 0.09 | 0.11 |
| 2045 | 0.19 | 0.85 | 1.18 | 0.14 | 0.10 |
| 2046 | 0.18 | 1.09 | 1.20 | 0.10 | 0.10 |
| 2047 | 0.25 | 1.01 | 1.24 | 0.11 | 0.11 |
| 2048 | 0.23 | 0.44 | 0.95 | 0.14 | 0.19 |
| 2049 | 0.28 | 1.04 | 1.05 | 0.09 | 0.10 |
| 2050 | 0.20 | 1.07 | 1.05 | 0.10 | 0.10 |
| 1880 | 1.02 | 1.10 | 1.17 | 1.06 | 0.84 |
| 2051 | 1.11 | 1.03 | 0.98 | 0.10 | 0.10 |
| 2052 | 1.12 | 1.05 | 1.24 | 0.10 | 0.10 |

TABLE 3D-continued

| | | | | | |
|---|---|---|---|---|---|
| 2053 | 1.07 | 1.11 | 1.21 | 0.10 | 0.10 |
| 2054 | 1.03 | 0.98 | 1.11 | 0.12 | 0.09 |
| 2055 | 1.02 | 1.02 | 1.17 | 0.09 | 0.09 |
| 2056 | 1.03 | 1.08 | 1.34 | 0.10 | 0.09 |
| 2057 | 1.00 | 1.05 | 1.13 | 0.10 | 0.10 |
| 2058 | 1.02 | 1.18 | 1.07 | 0.10 | 0.10 |
| 2059 | 1.09 | 1.00 | 1.05 | 0.10 | 0.10 |
| 1881 | 1.13 | 1.20 | 1.00 | 1.07 | 1.02 |
| | | | | | |
| 2060 | 1.07 | 0.97 | 1.10 | 0.30 | 0.11 |
| 2061 | 1.07 | 1.02 | 0.97 | 0.18 | 0.11 |
| 2062 | 1.09 | 0.99 | 0.93 | 0.18 | 0.12 |
| 2063 | 0.95 | 0.93 | 0.92 | 1.17 | 1.06 |
| 2064 | 0.99 | 0.82 | 1.00 | 0.09 | 0.09 |
| 2065 | 1.03 | 1.06 | 1.07 | 0.16 | 0.11 |
| 2066 | 1.00 | 0.99 | 1.04 | 0.18 | 0.13 |
| 2067 | 1.15 | 1.01 | 1.08 | 1.05 | 1.21 |
| | | | | | |
| 2068 | 1.14 | 1.07 | 1.02 | 1.27 | 1.21 |
| 2069 | 1.13 | 0.92 | 1.04 | 0.52 | 0.25 |
| 2070 | 1.13 | 1.02 | 0.93 | 0.11 | 0.11 |
| 2071 | 1.17 | 1.22 | 1.03 | 1.18 | 1.17 |
| 2072 | 1.11 | 1.32 | 1.03 | 0.10 | 0.12 |
| 2073 | 1.06 | 0.98 | 0.92 | 1.26 | 1.04 |
| 2074 | 1.08 | 1.03 | 1.48 | 0.09 | 0.10 |
| 2075 | 0.99 | 1.07 | 1.05 | 0.18 | 0.12 |
| | | | | | |
| 2076 | 1.06 | 0.97 | 1.02 | 0.10 | 0.10 |
| 2077 | 1.16 | 1.06 | 1.04 | 0.09 | 0.11 |
| 1882 | 1.07 | 1.22 | 0.99 | 0.10 | 0.10 |
| 2078 | 1.07 | 0.94 | 0.97 | 0.14 | 0.14 |
| 2079 | 1.21 | 0.84 | 0.98 | 1.09 | 1.14 |
| 2080 | 1.08 | 0.84 | 0.96 | 1.13 | 1.09 |
| 2081 | 1.26 | 0.99 | 1.03 | 1.06 | 1.23 |
| 2082 | 1.11 | 1.05 | 1.04 | 1.07 | 1.14 |
| | | | | | |
| 2083 | 1.05 | 1.18 | 1.02 | 0.13 | 0.12 |
| 2084 | 1.07 | 1.03 | 0.99 | 0.13 | 0.12 |
| 2085 | 1.09 | 1.02 | 0.99 | 1.17 | 1.12 |
| 2086 | 1.09 | 1.14 | 1.06 | 0.11 | 0.12 |
| 2087 | 0.92 | 1.02 | 0.95 | 1.22 | 1.00 |
| 2088 | 0.32 | 0.89 | 0.99 | 0.14 | 0.12 |
| 2089 | 1.09 | 1.01 | 0.97 | 1.09 | 1.14 |
| 2090 | 0.36 | 0.81 | 1.00 | 0.12 | 0.11 |
| | | | | | |
| 2091 | 1.11 | 1.00 | 1.02 | 0.11 | 0.12 |
| 2092 | 0.33 | 1.00 | 1.05 | 0.09 | 0.11 |
| 2093 | 0.37 | 1.08 | 1.03 | 0.09 | 0.11 |
| 2094 | 0.41 | 1.03 | 1.00 | 0.09 | 0.11 |
| 2095 | 1.17 | 1.01 | 1.08 | 0.11 | 0.12 |
| 2096 | 1.18 | 1.01 | 1.11 | 0.09 | 0.11 |
| 2097 | 1.12 | 0.98 | 0.98 | 0.10 | 0.10 |

TABLE 3D-continued

| | | | | | |
|---|---|---|---|---|---|
| 2098 | 1.03 | 0.95 | 0.92 | 0.09 | 0.09 |
| 2099 | 1.16 | 0.91 | 0.99 | 0.10 | 0.11 |
| 2100 | 1.29 | 1.03 | 1.03 | 1.04 | 1.12 |
| 2101 | 1.29 | 1.04 | 1.00 | 1.07 | 1.18 |
| 2102 | 1.31 | 0.99 | 0.98 | 1.05 | 1.19 |
| 2103 | 1.18 | 0.99 | 0.99 | 1.05 | 1.12 |
| 2104 | 1.25 | 1.00 | 1.01 | 1.03 | 1.22 |
| | | | | | |
| 1883 | 1.04 | 1.11 | 0.90 | 1.16 | 1.06 |
| 2105 | 1.15 | 1.10 | 1.03 | 1.17 | 1.11 |
| 2106 | 1.25 | 1.09 | 1.16 | 0.92 | 1.01 |
| 2107 | 1.16 | 0.97 | 1.01 | 1.16 | 1.13 |
| 2108 | 1.12 | 1.00 | 1.03 | 1.10 | 1.09 |
| 2109 | 0.21 | 0.99 | 1.05 | 1.25 | 1.07 |
| 2110 | 1.03 | 1.05 | 0.96 | 1.17 | 1.00 |
| 2111 | 1.02 | 0.95 | 0.83 | 0.77 | 0.35 |
| | | | | | |
| 2112 | 1.12 | 1.00 | 0.99 | 1.19 | 1.10 |
| 2113 | 1.08 | 0.99 | 1.00 | 0.10 | 0.10 |
| 1884 | 0.19 | 1.05 | 0.84 | 0.98 | 0.97 |
| 2114 | 0.27 | 0.92 | 0.98 | 1.10 | 1.07 |
| 2115 | 0.26 | 0.95 | 0.97 | 1.10 | 1.02 |
| 2116 | 0.26 | 0.98 | 0.99 | 1.11 | 1.12 |
| 2117 | 0.40 | 1.03 | 1.00 | 1.11 | 0.84 |
| 2118 | 0.21 | 1.01 | 1.00 | 1.16 | 0.99 |
| | | | | | |
| 2119 | 0.15 | 1.04 | 1.11 | 1.10 | 0.47 |
| 2120 | 0.22 | 0.95 | 1.02 | 1.13 | 1.08 |
| 2121 | 0.21 | 0.97 | 1.17 | 1.17 | 1.04 |
| 2122 | 0.15 | 1.07 | 0.98 | 1.19 | 0.88 |
| 1885 | 1.01 | 1.09 | 1.02 | 0.09 | 0.09 |
| 2123 | 0.10 | 0.14 | 1.04 | 0.09 | 0.09 |
| 2124 | 0.16 | 0.86 | 1.09 | 0.09 | 0.10 |
| 2125 | 0.10 | 0.13 | 0.32 | 0.09 | 0.09 |
| | | | | | |
| 2126 | 1.14 | 1.10 | 1.20 | 0.10 | 0.11 |
| 2127 | 1.08 | 0.97 | 1.06 | 1.09 | 1.03 |
| 2128 | 0.11 | 0.12 | 0.31 | 0.09 | 0.11 |
| 2129 | 0.11 | 0.13 | 0.49 | 0.09 | 0.10 |
| 2130 | 0.25 | 0.85 | 1.15 | 0.10 | 0.11 |
| 2131 | 0.12 | 0.12 | 0.32 | 0.09 | 0.11 |
| 1886 | 1.01 | 0.98 | 0.95 | 1.01 | 0.99 |
| | | | | | |
| 2132 | 1.25 | 0.96 | 1.11 | 1.03 | 1.17 |
| 1887 | 1.08 | 1.04 | 0.99 | 1.17 | 0.12 |
| 2133 | 1.10 | 1.00 | 1.10 | 0.10 | 0.10 |
| 2134 | 1.00 | 0.94 | 1.03 | 1.24 | 1.07 |
| 2135 | 1.02 | 1.14 | 1.00 | 0.09 | 0.09 |
| 2136 | 1.05 | 1.10 | 0.97 | 0.09 | 0.10 |
| 2137 | 1.07 | 1.13 | 0.97 | 0.09 | 0.10 |

TABLE 3D-continued

| | | | | | |
|---|---|---|---|---|---|
| 2138 | 1.09 | 1.03 | 0.84 | 1.08 | 1.09 |
| 2139 | 1.10 | 1.03 | 1.11 | 0.09 | 0.10 |
| 2140 | 1.08 | 1.00 | 0.93 | 0.88 | 1.08 |
| 2141 | 1.03 | 0.96 | 0.96 | 0.11 | 0.10 |
| 2142 | 1.08 | 1.05 | 1.18 | 0.83 | 0.96 |
| 2143 | 1.11 | 1.07 | 1.00 | 1.03 | 1.07 |
| 2148 | 1.08 | 1.08 | 1.00 | 0.09 | 0.10 |
| 2149 | 1.02 | 1.18 | 0.96 | 1.06 | 1.17 |
| 2150 | 1.10 | 1.00 | 0.86 | 0.71 | 0.31 |
| 2164 | 1.06 | 1.06 | 0.98 | 0.10 | 0.09 |
| 2165 | 1.04 | 1.03 | 0.97 | 0.10 | 0.09 |
| 2166 | 1.02 | 1.15 | 1.24 | 1.09 | 0.97 |
| 2167 | 1.07 | 0.80 | 0.92 | 0.10 | 0.10 |
| 1888 | 1.08 | 1.14 | 1.09 | 0.22 | 0.19 |
| 2151 | 1.15 | 0.94 | 0.90 | 0.36 | 0.28 |
| 2152 | 1.10 | 0.97 | 1.05 | 0.10 | 0.10 |
| 2153 | 1.09 | 1.03 | 0.95 | 0.16 | 0.15 |
| 2154 | 1.11 | 0.95 | 0.85 | 0.29 | 0.30 |
| 2155 | 1.06 | 1.07 | 1.18 | 0.19 | 0.17 |
| 2156 | 0.99 | 0.95 | 1.02 | 0.09 | 0.10 |
| 2157 | 1.01 | 1.07 | 0.99 | 0.09 | 0.09 |
| 2158 | 0.97 | 0.81 | 0.91 | 0.09 | 0.10 |
| 2159 | 1.06 | 0.93 | 1.09 | 0.40 | 0.35 |
| 1889 | 1.03 | 1.09 | 1.09 | 0.10 | 0.09 |
| 2144 | 1.10 | 1.11 | 1.04 | 1.07 | 1.08 |
| 2145 | 1.03 | 1.07 | 1.06 | 0.64 | 0.94 |
| 2146 | 1.05 | 1.04 | 1.05 | 0.10 | 0.10 |
| 2147 | 1.06 | 0.98 | 0.99 | 0.10 | 0.10 |
| 2160 | 1.01 | 0.89 | 1.05 | 0.10 | 0.10 |
| 2161 | 1.06 | 0.95 | 1.08 | 0.10 | 0.10 |
| 2162 | 1.02 | 0.96 | 1.05 | 0.10 | 0.09 |
| 2163 | 0.98 | 0.92 | 0.97 | 0.10 | 0.10 |
| 2168 | 1.13 | 0.93 | 0.93 | 0.10 | 0.10 |
| 1890 | 1.06 | 1.12 | 1.07 | 1.03 | 1.01 |
| 2169 | 1.12 | 0.90 | 1.11 | 0.10 | 0.10 |
| 2170 | 1.12 | 0.82 | 0.94 | 0.10 | 0.11 |
| 2171 | 1.10 | 0.86 | 0.91 | 0.11 | 0.11 |
| 2172 | 1.15 | 0.83 | 1.07 | 0.10 | 0.12 |
| 2173 | 1.03 | 0.84 | 0.95 | 0.11 | 0.10 |
| 2174 | 1.09 | 3.35 | 3.43 | 0.10 | 0.10 |
| 2175 | 1.14 | 0.91 | 0.97 | 1.11 | 1.11 |
| 2176 | 0.98 | 0.95 | 0.97 | 0.58 | 0.89 |
| 2177 | 1.02 | 1.01 | 1.08 | 1.18 | 1.05 |
| 1879 | 0.99 | 1.30 | 1.20 | 0.10 | 0.09 |
| 1911 | 0.18 | 0.94 | 1.23 | 0.14 | 0.30 |
| 1950 | 0.91 | 1.08 | 1.07 | 0.09 | 0.09 |
| 1951 | 0.98 | 0.89 | 0.98 | 1.00 | 0.98 |
| 1952 | 0.10 | 0.11 | 0.98 | 0.09 | 0.09 |
| 1953 | 0.10 | 0.09 | 0.11 | 0.27 | 0.79 |
| 1954 | 1.02 | 1.06 | 1.05 | 0.09 | 0.10 |
| 1955 | 0.09 | 0.09 | 0.11 | 0.27 | 0.81 |
| 1956 | 0.19 | 0.96 | 1.00 | 0.10 | 0.28 |
| 1957 | 1.09 | 0.92 | 0.96 | 0.09 | 0.09 |
| 1958 | 1.02 | 0.99 | 0.92 | 0.09 | 0.09 |
| 1913 | 0.17 | 0.97 | 1.18 | 0.35 | 0.20 |
| 1968 | 0.09 | 0.11 | 0.99 | 0.09 | 0.08 |
| 1969 | 0.92 | 0.99 | 0.86 | 0.10 | 0.08 |
| 1970 | 0.11 | 0.20 | 0.97 | 0.09 | 0.08 |
| 1971 | 0.98 | 0.84 | 0.87 | 0.08 | 0.09 |
| 1972 | 0.17 | 0.21 | 0.95 | 0.11 | 0.20 |
| 1973 | 0.24 | 0.79 | 0.95 | 0.11 | 0.27 |
| 1974 | 0.18 | 0.81 | 0.95 | 0.11 | 0.20 |
| 1975 | 1.14 | 1.26 | 1.27 | 0.09 | 0.19 |
| 1976 | 1.03 | 1.00 | 0.89 | 0.09 | 0.09 |
| 1891 | 1.07 | 1.06 | 1.02 | 1.06 | 1.14 |
| 1892 | 1.15 | 1.13 | 1.00 | 1.04 | 1.11 |
| 1893 | 1.09 | 1.11 | 0.95 | 1.13 | 1.09 |
| 1894 | 1.15 | 1.05 | 0.92 | 1.02 | 1.14 |
| 1895 | 1.11 | 1.08 | 0.95 | 0.11 | 0.11 |
| 1896 | 0.99 | 0.95 | 0.91 | 0.09 | 0.10 |
| 1897 | 0.98 | 1.01 | 0.97 | 0.09 | 0.09 |
| 1898 | 1.07 | 0.96 | 0.85 | 0.08 | 0.09 |
| 1899 | 0.99 | 0.99 | 1.07 | 1.00 | 1.03 |
| 1990 | 0.12 | 0.27 | 1.11 | 0.09 | 0.20 |
| 1991 | 0.12 | 0.31 | 1.12 | 0.10 | 0.19 |
| 1992 | 0.13 | 0.28 | 1.07 | 0.09 | 0.22 |
| 1993 | 0.11 | 0.21 | 1.16 | 0.10 | 0.58 |
| 1994 | 0.11 | 0.28 | 1.08 | 0.09 | 1.16 |
| 1995 | 0.13 | 0.22 | 1.05 | 0.10 | 0.71 |
| 1996 | 0.11 | 0.09 | 0.10 | 0.09 | 0.33 |
| 1910 | 0.11 | 0.09 | 0.10 | 0.09 | 0.12 |
| 1945 | 0.35 | 0.81 | 0.99 | 0.09 | 0.12 |
| 1946 | 0.11 | 0.09 | 0.09 | 0.09 | 0.11 |
| 1947 | 0.11 | 0.09 | 0.09 | 0.09 | 0.11 |
| 1948 | 0.11 | 0.09 | 0.09 | 0.31 | 1.04 |
| 1949 | 0.09 | 0.09 | 0.09 | 0.10 | 0.10 |
| 1977 | 0.09 | 0.10 | 0.10 | 0.31 | 0.26 |
| 1978 | 1.10 | 1.10 | 1.17 | 1.00 | 1.06 |
| 1979 | 0.95 | 1.10 | 0.97 | 0.87 | 0.85 |
| 1980 | 1.08 | 1.06 | 0.98 | 0.99 | 0.98 |
| 1981 | 1.01 | 0.97 | 0.93 | 0.87 | 0.93 |
| 1982 | 0.97 | 1.06 | 0.93 | 1.10 | 1.13 |
| 1983 | 0.11 | 1.02 | 0.91 | 0.10 | 0.11 |
| 1984 | 0.95 | 1.05 | 1.04 | 0.94 | 1.00 |
| 1985 | 0.10 | 0.08 | 0.09 | 1.00 | 1.01 |
| 1914 | 0.11 | 0.10 | 0.11 | 0.15 | 0.14 |
| 1986 | 0.11 | 0.09 | 0.13 | 0.14 | 0.15 |

TABLE 3D-continued

| | | | | | |
|---|---|---|---|---|---|
| 1987 | 0.11 | 0.09 | 0.12 | 0.14 | 0.14 |
| 1988 | 0.10 | 0.09 | 0.11 | 0.13 | 0.12 |
| 1989 | 0.13 | 0.98 | 1.04 | 0.10 | 0.11 |
| 1917 | 0.81 | 1.20 | 0.90 | 1.05 | 0.71 |
| 2015 | 0.10 | 0.11 | 0.22 | 0.67 | 0.55 |
| 2016 | 0.11 | 0.11 | 0.21 | 0.61 | 0.58 |
| 2017 | 0.10 | 0.11 | 0.22 | 0.58 | 0.56 |
| 2018 | 0.11 | 0.10 | 0.27 | 0.66 | 0.77 |
| 2019 | 0.11 | 0.10 | 0.24 | 0.74 | 0.59 |
| 2020 | 0.30 | 1.11 | 0.13 | 0.25 | 0.22 |
| 2021 | 0.78 | 1.09 | 1.18 | 0.82 | 0.88 |
| 2022 | 0.82 | 1.16 | 1.11 | 0.79 | 0.96 |
| 2023 | 1.04 | 1.04 | 1.09 | 1.03 | 1.08 |

TABLE 4

A

| NP # | A511:ff | P100:ff | LP48:ff | LP125:ff | A511:ff, P100:ff, LP48:ff | A511:ff, P100:ff, LP48:ff, LP125:ff |
|---|---|---|---|---|---|---|
| 1839 | 0.15 | 0.14 | 0.19 | 0.14 | 0.14 | 0.18 |
| 1840 | 1.01 | 1.03 | 1.01 | 1.06 | 1.02 | 1.04 |
| 1869 | 0.14 | 0.13 | 0.15 | 0.90 | 0.16 | 0.14 |
| 1878 | 1.02 | 0.19 | 1.01 | 1.14 | 0.26 | 0.22 |
| 1879 | 0.12 | 0.11 | 0.12 | 0.13 | 0.12 | 0.12 |
| 1880 | 1.00 | 1.05 | 0.96 | 1.06 | 1.06 | 1.02 |
| 1881 | 1.07 | 1.09 | 1.04 | 1.16 | 1.08 | 1.04 |
| 1882 | 0.76 | 0.11 | 0.22 | 0.42 | 0.14 | 0.15 |
| 1883 | 1.08 | 1.09 | 1.08 | 1.08 | 1.02 | 1.04 |
| 1884 | 1.05 | 1.03 | 1.06 | 1.07 | 1.03 | 1.01 |
| 1885 | 0.12 | 0.10 | 0.11 | 0.11 | 0.11 | 0.10 |
| 1886 | 0.99 | 1.09 | 1.00 | 1.06 | 1.09 | 1.04 |
| 1887 | 1.02 | 1.07 | 1.17 | 0.98 | 1.11 | 1.05 |
| 1888 | 0.98 | 1.05 | 1.04 | 1.02 | 1.11 | 1.01 |
| 1889 | 0.13 | 0.11 | 0.12 | 0.13 | 0.12 | 0.13 |
| 1890 | 1.04 | 1.05 | 1.07 | 1.06 | 1.13 | 1.06 |
| 1891 | 1.01 | 1.02 | 1.00 | 1.06 | 1.08 | 1.03 |
| 1892 | 0.98 | 0.97 | 0.98 | 1.06 | 1.05 | 1.01 |
| 1893 | 1.01 | 1.00 | 1.02 | 1.07 | 1.06 | 1.01 |
| 1894 | 1.03 | 1.05 | 1.02 | 1.08 | 1.06 | 1.04 |
| 1895 | 0.13 | 0.11 | 0.13 | 0.13 | 0.12 | 0.12 |
| 1896 | 0.12 | 0.11 | 0.12 | 0.17 | 0.11 | 0.12 |
| 1897 | 0.18 | 0.16 | 0.16 | 0.19 | 0.16 | 0.16 |
| 1898 | 0.10 | 0.10 | 0.10 | 0.10 | 0.10 | 0.10 |
| 1899 | 1.07 | 1.07 | 1.05 | 1.04 | 1.08 | 0.98 |
| 1900 | 1.06 | 1.07 | 1.05 | 1.03 | 1.14 | 1.00 |
| 1901 | 0.11 | 0.10 | 0.12 | 1.01 | 0.11 | 0.11 |
| 1902 | 1.02 | 1.05 | 1.03 | 1.03 | 1.05 | 0.98 |
| 1903 | 0.11 | 0.11 | 0.11 | 1.03 | 0.14 | 0.11 |
| 1904 | 0.11 | 0.12 | 0.16 | 1.04 | 0.12 | 0.12 |
| 1905 | 0.11 | 0.12 | 0.16 | 1.05 | 0.12 | 0.12 |
| 1906 | 1.04 | 1.07 | 1.04 | 1.04 | 1.04 | 0.66 |
| 1907 | 1.04 | 1.09 | 1.03 | 1.05 | 1.05 | 0.98 |
| 1908 | 0.11 | 0.10 | 0.12 | 1.04 | 0.11 | 0.11 |
| 1909 | 0.99 | 1.01 | 1.00 | 1.01 | 1.00 | 0.94 |
| 1910 | 0.17 | 0.14 | 0.25 | 0.96 | 0.19 | 0.18 |
| 1911 | 1.06 | 1.02 | 1.06 | 1.07 | 1.20 | 1.01 |

TABLE 4-continued

| 1912 | 1.04 | 0.97 | 1.02 | 1.02 | 1.13 | 1.05 |
|---|---|---|---|---|---|---|
| 1913 | 0.99 | 0.98 | 0.96 | 0.95 | 1.13 | 0.96 |
| 1914 | 0.92 | 0.13 | 0.56 | 1.14 | 0.27 | 0.20 |
| 1915 | 0.14 | 0.11 | 0.11 | 0.13 | 0.12 | 0.12 |
| 1916 | 1.07 | 1.06 | 1.05 | 1.12 | 1.23 | 1.02 |
| 1917 | 1.02 | 0.99 | 1.06 | 1.09 | 1.09 | 1.02 |
| 1945 | 0.12 | 0.10 | 0.11 | 0.16 | 0.10 | 0.10 |
| 1946 | 0.75 | 0.14 | 0.85 | 1.09 | 0.20 | 0.24 |
| 1947 | 0.85 | 0.15 | 0.87 | 1.15 | 0.21 | 0.20 |
| 1948 | 0.43 | 0.99 | 1.05 | 1.04 | 0.43 | 0.85 |
| 1949 | 0.13 | 0.13 | 0.17 | 1.07 | 0.14 | 0.12 |
| 1950 | 0.09 | 0.09 | 0.09 | 0.09 | 0.10 | 0.09 |
| 1951 | 1.02 | 1.00 | 1.00 | 1.00 | 1.00 | 1.00 |
| 1952 | 0.11 | 0.09 | 0.09 | 0.09 | 0.10 | 0.09 |
| 1953 | 0.11 | 0.10 | 0.98 | 1.08 | 0.13 | 0.12 |
| 1954 | 0.09 | 0.09 | 0.09 | 0.09 | 0.09 | 0.09 |
| 1955 | 0.11 | 0.10 | 0.97 | 1.10 | 0.12 | 0.12 |
| 1956 | 0.97 | 0.87 | 0.97 | 1.02 | 0.98 | 0.94 |
| 1957 | 0.13 | 0.10 | 0.66 | 0.17 | 0.10 | 0.10 |
| 1958 | 0.09 | 0.09 | 0.09 | 0.10 | 0.09 | 0.09 |
| 1959 | 0.10 | 0.10 | 0.12 | 1.03 | 0.10 | 0.10 |
| 1960 | 0.14 | 0.93 | 0.19 | 1.00 | 0.19 | 0.18 |
| 1961 | 0.12 | 0.16 | 1.01 | 1.25 | 0.12 | 0.12 |
| 1962 | 1.10 | 1.17 | 1.13 | 1.21 | 1.17 | 1.10 |
| 1963 | 0.13 | 0.10 | 0.13 | 1.09 | 0.12 | 0.12 |
| 1964 | 0.11 | 0.10 | 0.13 | 1.09 | 0.12 | 0.12 |
| 1965 | 0.12 | 0.10 | 0.13 | 1.13 | 0.12 | 0.12 |
| 1966 | 0.11 | 0.10 | 0.16 | 1.00 | 0.11 | 0.11 |
| 1967 | 0.12 | 0.10 | 0.23 | 1.05 | 0.12 | 0.12 |
| 1968 | 0.11 | 0.10 | 0.10 | 0.10 | 0.10 | 0.10 |
| 1969 | 0.12 | 0.10 | 0.10 | 0.10 | 0.10 | 0.10 |
| 1970 | 0.09 | 0.08 | 0.08 | 0.09 | 0.09 | 0.08 |
| 1971 | 0.09 | 0.08 | 0.09 | 0.09 | 0.08 | 0.08 |
| 1972 | 1.08 | 1.02 | 1.10 | 1.46 | 1.10 | 1.14 |
| 1973 | 1.10 | 1.08 | 1.08 | 1.11 | 1.11 | 1.11 |
| 1974 | 1.14 | 1.15 | 1.15 | 1.14 | 1.27 | 1.14 |
| 1975 | 0.97 | 0.96 | 0.97 | 0.98 | 0.58 | 0.99 |
| 1976 | 0.12 | 0.10 | 0.10 | 0.10 | 0.10 | 0.10 |
| 1977 | 0.13 | 0.11 | 0.90 | 1.03 | 0.15 | 0.15 |
| 1978 | 1.10 | 1.04 | 1.08 | 1.08 | 1.17 | 1.15 |
| 1979 | 1.14 | 1.12 | 1.11 | 1.16 | 1.26 | 1.21 |
| 1980 | 1.01 | 1.09 | 1.04 | 1.12 | 1.11 | 1.08 |
| 1981 | 1.16 | 1.21 | 1.09 | 1.14 | 1.18 | 1.15 |
| 1982 | 1.01 | 1.08 | 0.94 | 1.03 | 1.04 | 1.00 |
| 1983 | 0.43 | 0.14 | 0.39 | 0.34 | 0.18 | 0.16 |
| 1984 | 1.06 | 1.03 | 1.05 | 1.05 | 1.06 | 1.06 |
| 1985 | 1.00 | 1.03 | 1.02 | 1.01 | 1.04 | 1.02 |
| 1986 | 0.86 | 0.12 | 0.60 | 1.06 | 0.14 | 0.14 |
| 1987 | 0.81 | 0.12 | 0.61 | 1.02 | 0.13 | 0.15 |
| 1988 | 0.81 | 0.12 | 0.42 | 1.06 | 0.14 | 0.15 |
| 1989 | 0.96 | 0.17 | 0.76 | 0.71 | 0.22 | 0.26 |
| 1990 | 1.07 | 1.04 | 1.04 | 1.10 | 1.06 | 1.03 |
| 1991 | 1.03 | 1.03 | 1.00 | 1.06 | 1.01 | 0.98 |
| 1992 | 0.98 | 1.02 | 0.99 | 1.04 | 1.04 | 0.96 |
| 1993 | 1.00 | 1.02 | 1.12 | 1.20 | 1.36 | 1.04 |
| 1994 | 1.02 | 1.06 | 0.96 | 0.98 | 1.14 | 0.98 |
| 1995 | 1.03 | 1.00 | 1.02 | 1.02 | 1.07 | 1.01 |
| 1996 | 0.10 | 0.09 | 0.87 | 1.05 | 0.09 | 0.09 |
| 1997 | 0.12 | 0.10 | 0.10 | 0.12 | 0.10 | 0.11 |

TABLE 4-continued

| | | | | | | |
|---|---|---|---|---|---|---|
| 1998 | 0.12 | 0.10 | 0.10 | 0.11 | 0.10 | 0.10 |
| 1999 | 0.13 | 0.13 | 0.10 | 0.51 | 0.11 | 0.12 |
| 2000 | 0.13 | 0.10 | 0.10 | 0.12 | 0.11 | 0.11 |
| 2001 | 0.12 | 0.10 | 0.10 | 0.12 | 0.11 | 0.11 |
| 2002 | 0.30 | 1.03 | 1.03 | 1.04 | 0.80 | 0.72 |
| 2003 | 1.00 | 1.01 | 1.01 | 1.03 | 1.01 | 0.95 |
| 2004 | 1.02 | 1.04 | 1.03 | 1.03 | 1.01 | 0.98 |
| 2005 | 0.98 | 1.00 | 1.02 | 1.00 | 1.12 | 1.00 |
| 2006 | 1.07 | 1.11 | 0.94 | 1.03 | 1.12 | 0.94 |
| 2007 | 0.12 | 0.13 | 0.18 | 1.01 | 0.13 | 0.12 |
| 2008 | 0.12 | 0.13 | 0.19 | 1.03 | 0.13 | 0.12 |
| 2009 | 0.11 | 0.13 | 0.21 | 0.98 | 0.12 | 0.11 |
| 2010 | 0.96 | 1.07 | 0.98 | 1.12 | 1.20 | 0.92 |
| 2011 | 0.97 | 1.01 | 0.95 | 0.98 | 1.09 | 0.90 |
| 2012 | 1.02 | 1.02 | 1.05 | 1.01 | 1.05 | 0.99 |
| 2013 | 0.96 | 1.01 | 1.01 | 0.97 | 1.02 | 0.95 |
| 2014 | 0.94 | 1.07 | 1.00 | 1.05 | 1.15 | 0.90 |
| 2015 | 0.98 | 1.03 | 1.03 | 1.01 | 0.99 | 0.96 |
| 2016 | 1.00 | 1.02 | 1.03 | 1.06 | 1.02 | 0.99 |
| 2017 | 0.95 | 0.93 | 0.98 | 0.99 | 1.04 | 0.96 |
| 2018 | 0.89 | 0.93 | 0.87 | 0.93 | 0.91 | 0.86 |
| 2019 | 1.00 | 0.99 | 0.97 | 1.03 | 1.06 | 0.98 |
| 2020 | 1.03 | 0.89 | 0.97 | 1.07 | 0.96 | 0.89 |
| 2021 | 0.98 | 1.01 | 0.98 | 1.01 | 1.04 | 0.98 |
| 2022 | 1.02 | 1.04 | 1.00 | 1.05 | 1.06 | 1.01 |
| 2023 | 1.12 | 1.05 | 1.03 | 1.06 | 1.10 | 1.11 |
| 2024 | 0.11 | 0.10 | 0.10 | 0.11 | 0.10 | 0.10 |
| 2025 | 0.12 | 0.11 | 0.11 | 0.11 | 0.11 | 0.11 |
| 2026 | 0.55 | 0.55 | 0.55 | 0.56 | 0.55 | 0.55 |
| 2027 | 0.13 | 0.11 | 0.13 | 0.15 | 0.13 | 0.13 |
| 2028 | 0.11 | 0.10 | 0.10 | 0.10 | 0.10 | 0.10 |
| 2029 | 0.98 | 0.91 | 1.06 | 1.02 | 1.07 | 1.04 |
| 2030 | 0.12 | 0.09 | 0.10 | 0.10 | 0.10 | 0.10 |
| 2031 | 0.21 | 0.10 | 0.16 | 0.23 | 0.11 | 0.12 |
| 2032 | 0.11 | 0.10 | 0.11 | 0.10 | 0.10 | 0.10 |
| 2033 | 0.11 | 0.10 | 0.10 | 0.10 | 0.11 | 0.10 |
| 2034 | 0.11 | 0.10 | 0.11 | 0.10 | 0.10 | 0.10 |
| 2035 | 0.10 | 0.09 | 0.10 | 0.10 | 0.10 | 0.10 |
| 2036 | 0.11 | 0.10 | 0.10 | 0.10 | 0.10 | 0.10 |
| 2037 | 0.10 | 0.10 | 0.10 | 0.10 | 0.10 | 0.10 |
| 2038 | 0.99 | 0.18 | 1.04 | 0.86 | 0.22 | 0.19 |
| 2039 | 1.04 | 0.18 | 0.96 | 0.75 | 0.23 | 0.23 |
| 2040 | 1.01 | 0.15 | 1.07 | 1.09 | 0.25 | 0.24 |
| 2041 | 0.11 | 0.10 | 0.11 | 0.11 | 0.11 | 0.10 |
| 2042 | 0.60 | 0.10 | 0.78 | 0.96 | 0.25 | 0.20 |
| 2043 | 1.02 | 0.10 | 0.65 | 0.95 | 0.11 | 0.10 |
| 2044 | 1.03 | 0.11 | 0.82 | 1.04 | 0.19 | 0.13 |
| 2045 | 1.00 | 0.10 | 0.16 | 1.01 | 0.11 | 0.11 |
| 2046 | 1.12 | 0.11 | 0.66 | 1.07 | 0.12 | 0.12 |
| 2047 | 0.99 | 0.12 | 0.84 | 0.99 | 0.14 | 0.13 |
| 2048 | 1.21 | 0.22 | 1.08 | 1.36 | 0.25 | 0.27 |
| 2049 | 0.97 | 0.10 | 0.79 | 1.00 | 0.12 | 0.12 |
| 2050 | 1.14 | 0.11 | 0.99 | 1.16 | 0.12 | 0.13 |
| 2051 | 0.99 | 0.19 | 1.02 | 0.90 | 0.23 | 0.23 |
| 2052 | 0.12 | 0.10 | 0.11 | 0.10 | 0.10 | 0.10 |
| 2053 | 0.10 | 0.10 | 0.10 | 0.11 | 0.11 | 0.10 |
| 2054 | 0.14 | 0.13 | 0.14 | 0.16 | 0.14 | 0.14 |
| 2055 | 0.11 | 0.09 | 0.11 | 0.10 | 0.10 | 0.10 |
| 2056 | 0.13 | 0.11 | 0.12 | 0.12 | 0.12 | 0.12 |
| 2057 | 1.06 | 0.20 | 1.07 | 1.07 | 0.32 | 0.29 |
| 2058 | 1.00 | 0.24 | 1.12 | 1.04 | 0.28 | 0.29 |
| 2059 | 0.11 | 0.10 | 0.11 | 0.12 | 0.10 | 0.10 |
| 2060 | 1.19 | 1.18 | 1.26 | 1.19 | 1.28 | 1.28 |
| 2061 | 1.03 | 0.91 | 1.07 | 0.98 | 1.01 | 0.95 |
| 2062 | 1.13 | 1.08 | 1.15 | 1.07 | 1.12 | 1.08 |
| 2063 | 1.00 | 1.00 | 1.06 | 1.04 | 1.17 | 1.04 |
| 2064 | 1.09 | 0.87 | 1.15 | 1.24 | 1.13 | 1.24 |
| 2065 | 0.96 | 0.97 | 0.94 | 0.86 | 0.93 | 0.96 |
| 2066 | 1.00 | 1.08 | 1.09 | 1.18 | 1.16 | 1.13 |
| 2067 | 1.14 | 1.09 | 1.18 | 1.18 | 1.13 | 1.15 |
| 2068 | 1.10 | 1.02 | 1.05 | 1.11 | 1.08 | 1.09 |
| 2069 | 1.11 | 1.13 | 1.08 | 1.26 | 1.09 | 1.16 |
| 2070 | 0.99 | 0.10 | 0.20 | 0.21 | 0.11 | 0.11 |
| 2071 | 1.13 | 1.12 | 1.03 | 1.20 | 1.21 | 1.15 |
| 2072 | 0.14 | 0.12 | 0.13 | 0.12 | 0.12 | 0.12 |
| 2073 | 1.01 | 0.99 | 0.98 | 1.11 | 1.08 | 1.05 |
| 2074 | 1.04 | 0.12 | 0.80 | 0.87 | 0.14 | 0.15 |
| 2075 | 1.00 | 1.00 | 1.04 | 1.17 | 1.04 | 1.07 |
| 2076 | 0.11 | 0.10 | 0.11 | 0.10 | 0.10 | 0.10 |
| 2077 | 0.34 | 0.11 | 0.27 | 0.22 | 0.12 | 0.12 |
| 2078 | 0.97 | 0.97 | 0.97 | 0.98 | 0.99 | 1.01 |
| 2079 | 1.06 | 1.06 | 1.07 | 1.07 | 1.04 | 1.06 |
| 2080 | 1.01 | 1.02 | 1.02 | 1.03 | 1.02 | 1.05 |
| 2081 | 1.03 | 1.03 | 1.07 | 1.05 | 1.02 | 1.04 |
| 2082 | 1.05 | 1.06 | 1.07 | 1.03 | 1.02 | 1.06 |
| 2083 | 1.08 | 1.07 | 1.05 | 1.04 | 1.03 | 1.09 |
| 2084 | 1.00 | 1.03 | 1.02 | 1.03 | 1.05 | 1.05 |
| 2085 | 1.09 | 1.06 | 1.02 | 1.09 | 0.97 | 1.11 |
| 2086 | 1.06 | 1.07 | 1.10 | 1.13 | 1.18 | 1.11 |
| 2087 | 1.01 | 1.30 | 0.94 | 0.97 | 1.08 | 1.01 |
| 2088 | 0.18 | 0.13 | 0.53 | 0.87 | 0.16 | 0.16 |
| 2089 | 1.09 | 1.19 | 1.12 | 1.08 | 1.11 | 1.07 |
| 2090 | 0.15 | 0.11 | 0.34 | 0.74 | 0.13 | 0.14 |
| 2091 | 1.04 | 1.06 | 1.06 | 1.04 | 1.06 | 1.03 |
| 2092 | 0.11 | 0.09 | 0.11 | 0.16 | 0.10 | 0.10 |
| 2093 | 0.80 | 0.09 | 0.82 | 0.88 | 0.09 | 0.09 |
| 2095 | 0.15 | 0.12 | 0.14 | 0.14 | 0.14 | 0.14 |
| 2096 | 0.67 | 0.09 | 0.38 | 0.67 | 0.09 | 0.09 |
| 2097 | 0.39 | 0.10 | 0.28 | 0.47 | 0.10 | 0.10 |
| 2098 | 0.57 | 0.09 | 0.43 | 0.61 | 0.09 | 0.10 |
| 2099 | 0.47 | 0.10 | 0.23 | 0.26 | 0.10 | 0.10 |
| 2100 | 1.02 | 1.03 | 1.00 | 1.03 | 1.02 | 1.01 |
| 2101 | 1.05 | 1.04 | 1.05 | 1.05 | 1.03 | 1.01 |
| 2102 | 1.00 | 0.98 | 1.00 | 0.99 | 0.99 | 0.98 |
| 2103 | 1.02 | 1.03 | 1.07 | 1.04 | 1.05 | 1.07 |
| 2104 | 0.98 | 0.99 | 0.99 | 0.98 | 0.98 | 0.99 |
| 2105 | 1.03 | 1.06 | 1.02 | 1.07 | 1.01 | 0.99 |
| 2106 | 1.00 | 0.98 | 1.01 | 1.00 | 1.00 | 1.02 |
| 2107 | 1.01 | 1.00 | 0.99 | 1.00 | 0.98 | 0.98 |
| 2108 | 1.00 | 0.98 | 1.01 | 0.96 | 1.01 | 1.01 |
| 2109 | 1.00 | 1.00 | 1.02 | 0.99 | 0.99 | 1.02 |
| 2110 | 1.01 | 0.96 | 1.02 | 0.98 | 1.04 | 1.00 |
| 2111 | 1.02 | 1.07 | 0.98 | 1.05 | 1.05 | 1.04 |
| 2112 | 1.00 | 1.03 | 1.06 | 1.03 | 1.01 | 1.04 |
| 2113 | 0.12 | 0.10 | 0.10 | 0.10 | 0.10 | 0.10 |
| 2114 | 0.98 | 0.99 | 1.00 | 1.01 | 0.98 | 1.02 |
| 2115 | 1.00 | 1.06 | 1.03 | 1.06 | 1.01 | 1.03 |
| 2116 | 0.98 | 0.97 | 0.98 | 0.98 | 0.95 | 1.01 |
| 2117 | 0.99 | 1.04 | 1.05 | 1.02 | 1.01 | 0.92 |
| 2118 | 0.93 | 0.97 | 1.00 | 0.96 | 0.95 | 1.02 |
| 2119 | 1.08 | 1.05 | 1.07 | 1.06 | 1.03 | 0.95 |
| 2120 | 0.92 | 0.95 | 0.98 | 0.98 | 0.95 | 1.01 |
| 2121 | 1.13 | 1.16 | 1.18 | 1.22 | 1.12 | 1.20 |
| 2122 | 1.03 | 0.97 | 1.02 | 1.03 | 1.08 | 1.01 |
| 2123 | 0.10 | 0.10 | 0.10 | 0.10 | 0.10 | 0.10 |

TABLE 4-continued

| | | | | | | |
|---|---|---|---|---|---|---|
| 2124 | 0.11 | 0.09 | 0.10 | 0.10 | 0.10 | 0.10 |
| 2125 | 0.10 | 0.10 | 0.10 | 0.10 | 0.10 | 0.10 |
| 2126 | 1.00 | 0.17 | 1.06 | 0.86 | 0.22 | 0.21 |
| 2127 | 1.07 | 1.13 | 1.10 | 1.06 | 1.08 | 1.05 |
| 2128 | 0.09 | 0.09 | 0.09 | 0.09 | 0.09 | 0.09 |
| 2129 | 0.10 | 0.10 | 0.10 | 0.10 | 0.09 | 0.10 |
| 2130 | 0.09 | 0.09 | 0.10 | 0.10 | 0.09 | 0.09 |
| 2131 | 0.10 | 0.10 | 0.09 | 0.24 | 0.09 | 0.10 |
| 2132 | 0.93 | 1.00 | 1.00 | 0.95 | 1.00 | 0.98 |
| 2133 | 1.07 | 0.12 | 0.14 | 0.14 | 0.13 | 0.14 |
| 2134 | 1.09 | 0.96 | 0.97 | 0.99 | 1.06 | 0.98 |
| 2135 | 0.57 | 0.15 | 0.96 | 1.09 | 0.16 | 0.23 |
| 2136 | 1.07 | 0.10 | 0.11 | 0.12 | 0.10 | 0.11 |
| 2137 | 1.14 | 0.11 | 0.12 | 0.13 | 0.11 | 0.11 |
| 2138 | 1.11 | 1.06 | 1.02 | 1.04 | 1.05 | 1.04 |
| 2139 | 0.75 | 0.11 | 0.24 | 0.14 | 0.13 | 0.13 |
| 2140 | 1.02 | 1.05 | 1.05 | 1.05 | 0.98 | 1.05 |
| 2141 | 0.84 | 0.14 | 1.04 | 0.99 | 0.16 | 0.16 |
| 2142 | 0.99 | 1.02 | 1.06 | 1.03 | 0.94 | 0.95 |
| 2143 | 1.16 | 1.14 | 1.21 | 1.15 | 1.11 | 1.10 |
| 2164 | 0.10 | 0.10 | 0.11 | 0.11 | 0.10 | 0.10 |
| 2165 | 0.13 | 0.12 | 0.14 | 0.14 | 0.13 | 0.13 |
| 2166 | 1.04 | 1.00 | 1.09 | 1.09 | 1.10 | 1.08 |
| 2167 | 0.15 | 0.11 | 0.11 | 0.11 | 0.11 | 0.13 |
| 2148 | 0.11 | 0.10 | 0.11 | 0.12 | 0.10 | 0.10 |
| 2149 | 0.96 | 1.13 | 0.97 | 1.07 | 1.06 | 1.00 |
| 2150 | 0.93 | 1.05 | 0.95 | 1.03 | 1.02 | 1.04 |
| 2151 | 0.93 | 0.94 | 0.97 | 1.02 | 1.01 | 1.01 |
| 2152 | 0.10 | 0.09 | 0.09 | 0.10 | 0.10 | 0.09 |
| 2153 | 1.03 | 1.10 | 1.12 | 1.11 | 1.09 | 1.10 |
| 2154 | 0.93 | 1.03 | 1.12 | 1.02 | 1.01 | 1.10 |
| 2155 | 0.98 | 1.11 | 1.07 | 1.13 | 1.11 | 1.10 |
| 2156 | 0.12 | 0.09 | 0.09 | 0.10 | 0.09 | 0.09 |
| 2157 | 0.45 | 0.44 | 0.45 | 0.46 | 0.44 | 0.45 |
| 2158 | 0.12 | 0.10 | 0.11 | 0.11 | 0.10 | 0.11 |
| 2159 | 1.02 | 1.10 | 1.09 | 1.13 | 1.21 | 1.16 |
| 2160 | 0.17 | 0.12 | 0.13 | 0.14 | 0.13 | 0.13 |
| 2161 | 0.14 | 0.10 | 0.11 | 0.11 | 0.11 | 0.11 |
| 2162 | 0.14 | 0.10 | 0.11 | 0.11 | 0.12 | 0.11 |
| 2163 | 0.13 | 0.11 | 0.10 | 0.11 | 0.11 | 0.11 |
| 2144 | 1.03 | 1.00 | 1.03 | 1.07 | 1.13 | 1.14 |
| 2145 | 1.05 | 1.09 | 1.05 | 1.12 | 1.17 | 1.18 |
| 2146 | 0.12 | 0.10 | 0.11 | 0.11 | 0.10 | 0.10 |
| 2147 | 1.09 | 0.13 | 0.18 | 1.04 | 0.17 | 0.17 |
| 2168 | 0.13 | 0.12 | 0.13 | 0.13 | 0.12 | 0.11 |
| 2169 | 0.13 | 0.13 | 0.13 | 0.12 | 0.13 | 0.12 |
| 2170 | 0.11 | 0.09 | 0.11 | 0.10 | 0.10 | 0.11 |
| 2171 | 0.12 | 0.12 | 0.13 | 0.12 | 0.12 | 0.11 |
| 2172 | 0.11 | 0.13 | 0.21 | 0.20 | 0.12 | 0.12 |
| 2173 | 0.12 | 0.12 | 0.17 | 0.26 | 0.11 | 0.11 |
| 2174 | 0.11 | 0.10 | 0.11 | 0.11 | 0.11 | 0.10 |
| 2175 | 0.97 | 0.97 | 1.01 | 1.01 | 0.97 | 0.94 |
| 2176 | 1.03 | 1.01 | 1.00 | 1.02 | 1.00 | 1.00 |
| 2177 | 0.98 | 0.90 | 0.95 | 0.99 | 0.95 | 0.89 |

B

| NP # | P100 and A511:nluc | LP124:nluc | A511, P100, 124:nluc | LP124:nluc RLU |
|---|---|---|---|---|
| 1839 | 0.14 | 0.27 | 0.31 | 4.14E+08 |
| 1840 | 1.05 | 1.11 | 1.04 | 5.68E+02 |
| 1869 | 0.13 | 0.20 | 0.17 | 4.63E+08 |
| 1878 | 0.20 | 0.55 | 0.65 | 2.43E+08 |
| 1879 | 0.12 | 0.10 | 0.10 | |
| 1880 | 1.07 | 1.01 | 1.09 | 1.16E+06 |
| 1881 | 1.00 | 0.96 | 1.08 | 2.41E+06 |
| 1882 | 0.12 | 0.20 | 0.23 | 8.90E+05 |
| 1883 | 1.00 | 1.12 | 1.03 | 8.22E+02 |
| 1884 | 1.05 | 1.04 | 1.01 | 1.14E+04 |
| 1885 | 0.12 | 0.09 | 0.09 | 9.07E+08 |
| 1886 | 1.04 | 1.02 | 0.96 | 4.83E+02 |
| 1887 | 1.00 | 0.94 | 1.08 | 5.87E+05 |
| 1888 | 0.94 | 0.88 | 1.00 | 3.72E+06 |
| 1889 | 0.10 | 0.10 | 0.10 | 7.50E+08 |
| 1890 | 1.04 | 0.96 | 1.01 | 1.32E+03 |
| 1891 | 0.95 | 0.90 | 1.13 | 4.48E+02 |
| 1892 | 0.96 | 1.00 | 1.04 | 5.21E+02 |
| 1893 | 0.97 | 1.03 | 1.07 | 5.34E+02 |
| 1894 | 0.96 | 0.90 | 1.05 | 4.04E+02 |
| 1895 | 0.12 | 0.11 | 0.15 | 1.18E+09 |
| 1896 | 0.12 | 0.10 | 0.15 | 1.18E+09 |
| 1897 | 0.10 | 0.11 | 0.10 | 1.20E+09 |
| 1898 | 0.10 | 0.13 | 0.10 | 1.18E+09 |
| 1899 | 0.98 | 1.16 | 1.09 | 7.88E+02 |
| 1900 | 0.94 | 0.88 | 1.06 | 6.40E+02 |
| 1901 | 0.10 | 0.09 | 0.10 | 5.17E+08 |
| 1902 | 1.02 | 1.00 | 0.57 | 2.88E+06 |
| 1903 | 0.10 | 0.11 | 0.10 | 4.89E+08 |
| 1904 | 0.11 | 0.13 | 0.10 | 1.03E+08 |
| 1905 | 0.12 | 0.16 | 0.11 | 1.12E+08 |
| 1906 | 0.79 | 0.91 | 1.06 | 3.11E+06 |
| 1907 | 0.98 | 0.98 | 1.07 | 6.91E+02 |
| 1908 | 0.11 | 0.11 | 0.12 | 4.99E+08 |
| 1909 | 1.10 | 0.98 | 1.02 | 6.89E+02 |
| 1910 | 0.11 | 0.11 | 0.13 | 1.36E+09 |
| 1911 | 1.05 | 0.92 | 1.10 | 4.16E+05 |
| 1912 | 1.08 | 1.07 | 1.11 | 4.00E+02 |
| 1913 | 1.15 | 1.59 | 0.97 | 6.22E+02 |
| 1914 | 0.11 | 0.17 | 0.11 | 3.71E+08 |
| 1915 | 0.11 | 0.10 | 0.11 | 2.25E+08 |
| 1916 | 1.01 | 0.89 | 0.99 | 1.88E+04 |
| 1917 | 1.10 | 0.89 | 1.05 | 1.18E+06 |
| 1945 | 0.10 | 0.12 | 0.09 | 1.07E+09 |
| 1946 | 0.17 | 0.30 | 0.79 | 8.28E+04 |
| 1947 | 0.12 | 0.31 | 0.54 | 1.08E+05 |
| 1948 | 0.47 | 0.79 | 0.56 | 1.68E+04 |
| 1949 | 0.11 | 0.14 | 0.13 | 9.51E+08 |
| 1950 | 0.09 | 0.11 | 0.12 | 1.14E09 |
| 1951 | 1.02 | 1.00 | 1.02 | 8.32E+02 |
| 1952 | 0.10 | 0.14 | 0.10 | 1.26E+09 |
| 1953 | 0.10 | 1.22 | 0.10 | 1.31E+08 |
| 1954 | 0.10 | 0.13 | 0.11 | 7.70E+08 |
| 1955 | 0.10 | 1.04 | 0.10 | 1.15E+06 |
| 1956 | 1.07 | 1.08 | 1.01 | 1.50E06 |
| 1957 | 0.10 | 0.14 | 0.10 | 3.15E+07 |
| 1958 | 0.10 | 0.13 | 0.11 | 8.58E+08 |
| 1959 | 0.10 | 0.12 | 0.11 | 4.59E+08 |
| 1960 | 0.15 | 0.14 | 0.14 | 6.09E+08 |
| 1961 | 0.12 | 0.12 | 0.13 | 1.49E+08 |
| 1962 | 1.04 | 0.97 | 1.41 | 9.90E+02 |
| 1963 | 0.12 | 0.10 | 0.11 | 1.13E+09 |
| 1964 | 0.10 | 0.10 | 0.11 | 1.24E+09 |
| 1965 | 0.10 | 0.10 | 0.09 | 1.31E+09 |
| 1966 | 0.11 | 0.09 | 0.10 | 8.83E+08 |
| 1967 | 0.10 | 0.10 | 0.10 | 5.14E+08 |
| 1968 | 0.09 | 0.12 | 0.12 | 1.08E+09 |

TABLE 4-continued

| | | | |
|---|---|---|---|
| 1969 | 0.09 | 0.12 | 0.12 | 1.19E+09 |
| 1970 | 0.08 | 0.09 | 0.10 | 9.52E+08 |
| 1971 | 0.09 | 0.10 | 0.10 | 1.71E+09 |
| 1972 | 0.92 | 0.75 | 1.68 | 2.46E+06 |
| 1973 | 1.10 | 1.02 | 1.80 | 1.27E+03 |
| 1974 | 1.11 | 0.96 | 1.08 | 5.58E+02 |
| 1975 | 1.12 | 0.10 | 0.12 | 2.05E+09 |
| 1976 | 0.11 | 0.11 | 0.12 | 1.01E+09 |
| 1977 | 0.11 | 0.78 | 0.13 | 9.36E+08 |
| 1978 | 1.10 | 1.04 | 1.17 | 4.25E+03 |
| 1979 | 1.04 | 0.90 | 1.08 | 8.68E+02 |
| 1980 | 0.99 | 0.93 | 1.14 | 1.01E+06 |
| 1981 | 1.59 | 0.78 | 1.18 | 8.87E+02 |
| 1982 | 1.03 | 1.02 | 0.98 | 2.26E+04 |
| 1983 | 0.16 | 0.26 | 0.25 | 1.10E+05 |
| 1984 | 1.01 | 1.14 | 0.99 | 5.70E+05 |
| 1985 | 1.01 | 1.07 | 1.00 | 3.71E+05 |
| 1986 | 0.11 | 0.17 | 0.11 | 4.42E+08 |
| 1987 | 0.11 | 0.16 | 0.11 | 4.19E+08 |
| 1988 | 0.11 | 0.16 | 0.12 | 5.10E+08 |
| 1989 | 0.21 | 0.35 | 0.70 | 7.94E+03 |
| 1990 | 0.59 | 1.05 | 1.03 | 5.21E+02 |
| 1991 | 0.97 | 1.08 | 0.97 | 7.81E+02 |
| 1992 | 0.98 | 1.06 | 0.98 | 5.54E+02 |
| 1993 | 1.10 | 1.05 | 1.08 | 5.49E+02 |
| 1994 | 0.99 | 1.12 | 1.05 | 6.11E+02 |
| 1995 | 1.05 | 1.07 | 1.07 | 6.58E+02 |
| 1996 | 0.10 | 0.40 | 0.09 | 9.57E+08 |
| 1997 | 0.11 | 0.10 | 0.11 | 1.03E+09 |
| 1998 | 0.11 | 0.10 | 0.11 | 7.04E+08 |
| 1999 | 0.11 | 0.10 | 0.13 | 7.03E+08 |
| 2000 | 0.11 | 0.12 | 0.12 | 7.44E+08 |
| 2001 | 0.11 | 0.85 | 0.20 | 7.40E+08 |
| 2002 | 0.28 | 0.14 | 0.55 | 2.40E+08 |
| 2003 | 1.06 | 1.08 | 1.07 | 2.97E+06 |
| 2004 | 1.06 | 1.00 | 1.12 | 2.48E+06 |
| 2005 | 1.09 | 1.02 | 1.07 | 1.91E+06 |
| 2006 | 1.01 | 1.39 | 1.08 | 2.27E+03 |
| 2007 | 0.11 | 0.15 | 0.11 | 1.03E+09 |
| 2008 | 0.11 | 0.15 | 0.12 | 1.49E+09 |
| 2009 | 0.11 | 0.14 | 0.10 | 7.14E+08 |
| 2010 | 1.00 | 1.16 | 1.15 | 1.41E+05 |
| 2011 | 1.00 | 1.18 | 1.18 | 9.53E+04 |
| 2012 | 1.04 | 1.06 | 1.04 | 1.96E+03 |
| 2013 | 1.04 | 1.05 | 1.05 | 4.57E+03 |
| 2014 | 0.95 | 1.18 | 1.18 | 6.58E+04 |
| 2015 | 0.95 | 1.04 | 1.00 | 9.04E+04 |
| 2016 | 1.01 | 1.17 | 0.93 | 1.18E+05 |
| 2017 | 1.05 | 0.91 | 1.32 | 1.27E+05 |
| 2018 | 1.12 | 1.15 | 0.99 | 1.63E+05 |
| 2019 | 1.00 | 1.15 | 1.02 | 5.09E+04 |
| 2020 | 0.83 | 0.67 | 0.74 | 1.33E+08 |
| 2021 | 1.05 | 1.05 | 1.04 | 8.08E+03 |
| 2022 | 1.04 | 1.12 | 1.05 | 1.60E+04 |
| 2023 | 1.03 | 1.06 | 0.96 | 2.05E+05 |
| 2024 | 0.11 | 0.10 | 0.09 | 2.00E+09 |
| 2025 | 0.11 | 0.10 | 0.10 | 9.29E+08 |
| 2026 | 0.26 | 0.42 | 0.41 | 8.12E+07 |
| 2027 | 0.12 | 0.13 | 0.10 | 2.18E+09 |
| 2028 | 0.12 | 0.10 | 0.09 | 5.25E+08 |
| 2029 | 1.12 | 1.06 | 0.98 | 8.97E+05 |
| 2030 | 0.12 | 0.11 | 0.10 | 4.29E+06 |
| 2031 | 0.11 | 0.15 | 0.20 | 3.22E+05 |
| 2032 | 0.12 | 0.11 | 0.09 | 8.40E+08 |
| 2033 | 0.10 | 0.10 | 0.09 | 8.34E+08 |
| 2034 | 0.11 | 0.10 | 0.09 | 9.17E+08 |
| 2035 | 0.11 | 0.09 | 0.09 | 1.02E+09 |
| 2036 | 0.12 | 0.10 | 0.09 | 1.25E+09 |
| 2037 | 0.11 | 0.10 | 0.09 | 8.85E+08 |
| 2038 | 0.23 | 0.57 | 0.26 | 8.38E+03 |
| 2039 | 0.24 | 0.57 | 0.37 | 1.71E+04 |
| 2040 | 0.23 | 0.38 | 0.56 | 2.20E+04 |
| 2041 | 0.12 | 0.10 | 0.10 | 7.90E+08 |
| 2042 | 0.13 | 0.29 | 0.56 | 2.60E+06 |
| 2043 | 0.10 | 0.15 | 0.25 | 1.51E+06 |
| 2044 | 0.26 | 0.15 | 0.31 | 1.54E+06 |
| 2045 | 0.11 | 0.71 | 0.38 | 1.85E+06 |
| 2046 | 0.11 | 0.19 | 0.34 | 3.69E+05 |
| 2047 | 0.13 | 0.16 | 0.29 | 5.60E+05 |
| 2048 | 0.17 | 0.91 | 0.73 | 5.59E+03 |
| 2049 | 0.21 | 0.13 | 0.33 | 5.39E+05 |
| 2050 | 0.12 | 0.16 | 0.28 | 6.97E+05 |
| 2051 | 0.19 | 0.52 | 0.48 | 2.43E+04 |
| 2052 | 0.10 | 0.10 | 0.10 | 5.51E+08 |
| 2053 | 0.12 | 0.12 | 0.11 | 2.63E+08 |
| 2054 | 0.16 | 0.13 | 0.11 | 2.25E+09 |
| 2055 | 0.10 | 0.10 | 0.10 | 1.79E+09 |
| 2056 | 0.12 | 0.09 | 0.10 | 1.24E+09 |
| 2057 | 0.28 | 0.53 | 0.54 | 1.38E+04 |
| 2058 | 0.25 | 0.69 | 0.65 | 2.17E+04 |
| 2059 | 0.14 | 0.10 | 0.10 | 1.94E+09 |
| 2060 | 0.98 | 0.88 | 0.97 | 1.62E+06 |
| 2061 | 1.00 | 0.69 | 0.93 | 2.51E+06 |
| 2062 | 1.03 | 0.39 | 1.01 | 3.04E+06 |
| 2063 | 1.25 | 0.96 | 0.99 | 8.85E+05 |
| 2064 | 0.25 | 0.12 | 0.13 | 1.21E+09 |
| 2065 | 0.90 | 0.35 | 0.95 | 2.52E+06 |
| 2066 | 0.96 | 0.19 | 1.12 | 1.77E+06 |
| 2067 | 0.93 | 1.48 | 1.42 | 5.81E+02 |
| 2068 | 1.05 | 1.02 | 1.07 | 1.34E+06 |
| 2069 | 0.92 | 0.95 | 1.15 | 1.63E+06 |
| 2070 | 0.11 | 0.13 | 0.16 | 6.71E+08 |
| 2071 | 1.21 | 1.40 | 1.07 | 2.29E+03 |
| 2072 | 0.12 | 0.12 | 0.11 | 8.04E+08 |
| 2073 | 1.07 | 0.94 | 1.13 | 1.32E+09 |
| 2074 | 0.16 | 0.22 | 0.51 | 7.06E+06 |
| 2075 | 0.79 | 0.40 | 0.51 | 3.07E+06 |
| 2076 | 0.11 | 0.09 | 0.10 | 2.65E+09 |
| 2077 | 0.11 | 0.19 | 0.41 | 7.24E+05 |
| 2078 | 1.01 | 0.39 | 1.05 | 4.00E+08 |
| 2079 | 1.04 | 1.06 | 1.09 | 2.89E+04 |
| 2080 | 1.02 | 1.02 | 1.11 | 6.69E+02 |
| 2081 | 1.01 | 1.15 | 1.58 | 5.28E+02 |

TABLE 4-continued

| | | | | |
|---|---|---|---|---|
| 2082 | 1.02 | 1.05 | 1.11 | 5.89E+02 |
| 2083 | 0.89 | 0.18 | 0.99 | 1.30E+09 |
| 2084 | 1.02 | 0.49 | 1.04 | 8.76E+08 |
| 2085 | 0.95 | 1.11 | 0.98 | 4.66E+03 |
| 2086 | 1.17 | 0.25 | 0.99 | 1.15E+09 |
| 2087 | 1.16 | 1.13 | 1.09 | 9.13E+02 |
| 2088 | 0.15 | 0.19 | 0.15 | 1.93E+09 |
| 2089 | 1.06 | 1.15 | 1.08 | 1.55E+04 |
| 2090 | 0.17 | 0.24 | 0.14 | 2.09E+09 |
| 2091 | 0.49 | 0.19 | 0.68 | 7.86E+08 |
| 2092 | 0.10 | 0.10 | 0.10 | 1.93E+09 |
| 2093 | 0.10 | 0.42 | 0.54 | 5.39E+05 |
| 2094 | 0.10 | 0.43 | 0.64 | 6.93E+04 |
| 2095 | 0.22 | 0.13 | 0.10 | 7.54E+08 |
| 2096 | 0.10 | 0.21 | 0.30 | 2.01E+05 |
| 2097 | 0.11 | 0.23 | 0.20 | 5.42E+06 |
| 2098 | 0.13 | 0.30 | 0.24 | 1.89E+05 |
| 2099 | 0.11 | 0.24 | 0.41 | 1.80E+04 |
| 2100 | 0.99 | 1.13 | 1.06 | 9.19E+02 |
| 2101 | 1.04 | 1.05 | 1.06 | 2.03E+03 |
| 2102 | 1.01 | 1.09 | 1.03 | 7.52E+03 |
| 2103 | 0.98 | 1.26 | 1.07 | 1.80E+03 |
| 2104 | 1.03 | 1.02 | 1.06 | 2.07E+03 |
| 2105 | 1.02 | 1.09 | 1.02 | 8.50E+02 |
| 2106 | 1.01 | 1.19 | 1.03 | 7.00E+06 |
| 2107 | 1.03 | 1.34 | 1.02 | 1.20E+03 |
| 2108 | 1.01 | 1.09 | 0.98 | 7.31E+02 |
| 2109 | 1.04 | 1.15 | 1.06 | 1.35E+03 |
| 2110 | 1.06 | 0.99 | 1.05 | 1.23E+03 |
| 2111 | 1.12 | 0.99 | 1.05 | 4.33E+05 |
| 2112 | 1.05 | 1.09 | 1.01 | 9.46E+02 |
| 2113 | 0.10 | 0.09 | 0.09 | 8.06E+08 |
| 2114 | 1.06 | 0.94 | 1.02 | 3.13E+04 |
| 2115 | 1.08 | 0.99 | 0.94 | 9.25E+03 |
| 2116 | 1.04 | 1.01 | 1.05 | 1.23E+04 |
| 2117 | 1.04 | 0.78 | 1.03 | 3.64E+04 |
| 2118 | 1.05 | 1.00 | 1.02 | 1.31E+04 |
| 2119 | 1.08 | 0.48 | 0.72 | 2.41E+05 |
| 2120 | 1.05 | 0.48 | 0.78 | 1.13E+04 |
| 2121 | 1.03 | 0.62 | 1.04 | 6.97E+03 |
| 2122 | 1.10 | 0.39 | 1.05 | 7.79E+03 |
| 2123 | 0.11 | 0.09 | 0.10 | 1.19E+09 |
| 2124 | 0.11 | 0.09 | 0.10 | 1.84E+09 |
| 2125 | 0.10 | 0.10 | 0.09 | 1.04E+09 |
| 2126 | 0.22 | 0.50 | 0.66 | 1.52E+05 |
| 2127 | 1.08 | 1.05 | 1.08 | 1.40E+06 |
| 2128 | 0.10 | 0.10 | 0.09 | 9.27E+08 |
| 2129 | 0.10 | 0.10 | 0.09 | 9.59E+08 |
| 2130 | 0.10 | 0.10 | 0.09 | 1.10E+09 |
| 2131 | 0.10 | 0.10 | 0.09 | 8.76E+08 |
| 2132 | 1.03 | 1.21 | 1.01 | 8.98E+03 |
| 2133 | 0.12 | 0.12 | 0.10 | 7.24E+08 |
| 2134 | 1.16 | 1.07 | 1.10 | 4.11E+03 |
| 2135 | 0.18 | 0.33 | 0.32 | 6.59E+05 |
| 2136 | 0.10 | 0.09 | 0.09 | 1.73E+09 |
| 2137 | 0.10 | 0.09 | 0.09 | 1.13E+09 |
| 2138 | 1.00 | 1.16 | 0.99 | 2.04E+04 |
| 2139 | 0.12 | 0.09 | 0.10 | 7.09E+08 |
| 2140 | 1.08 | 0.85 | 1.02 | 8.84E+04 |
| 2141 | 0.18 | 0.19 | 0.72 | 2.03E+04 |
| 2142 | 1.02 | 0.88 | 1.01 | 1.19E+06 |
| 2143 | 1.03 | 0.54 | 1.02 | 2.61E+06 |
| 2164 | 0.11 | 0.11 | 0.09 | 3.17E+08 |
| 2165 | 0.11 | 0.11 | 0.09 | 3.67E+08 |
| 2166 | 1.12 | 0.56 | 1.04 | 2.34E+04 |
| 2167 | 0.15 | 0.13 | 0.10 | 9.74E+08 |
| 2148 | 0.10 | 0.12 | 0.10 | 2.01E+09 |
| 2149 | 1.01 | 1.06 | 1.12 | 9.57E+03 |
| 2150 | 1.11 | 1.09 | 1.06 | 8.18E+05 |
| 2151 | 1.04 | 1.07 | 1.05 | 8.33E+05 |
| 2152 | 0.14 | 0.09 | 0.10 | 6.38E+08 |
| 2153 | 1.05 | 0.85 | 1.06 | 1.12E+06 |
| 2154 | 1.09 | 0.98 | 1.09 | 1.31E+06 |
| 2155 | 1.10 | 0.50 | 1.12 | 9.99E+05 |
| 2156 | 0.13 | 0.11 | 0.09 | 9.04E+08 |
| 2157 | 0.10 | 0.37 | 0.17 | 7.10E+07 |
| 2158 | 0.12 | 0.10 | 0.10 | 6.65E+08 |
| 2159 | 1.23 | 0.87 | 1.10 | 1.01E+06 |
| 2160 | 0.14 | 0.12 | 0.13 | 6.33E+08 |
| 2161 | 0.17 | 0.15 | 0.11 | 3.43E+08 |
| 2162 | 0.12 | 0.12 | 0.11 | 6.64E+08 |
| 2163 | 0.16 | 0.10 | 0.12 | 1.23E+09 |
| 2144 | 0.96 | 1.09 | 1.13 | 8.40E+03 |
| 2145 | 1.16 | 0.55 | 1.17 | 1.41E+07 |
| 2146 | 0.13 | 0.11 | 0.11 | 1.48E+09 |
| 2147 | 0.16 | 0.15 | 0.17 | 1.08E+09 |
| 2168 | 0.14 | 0.09 | 0.11 | 7.92E+08 |
| 2169 | 0.14 | 0.11 | 0.12 | 1.49E+09 |
| 2170 | 0.13 | 0.10 | 0.11 | 2.46E+09 |
| 2171 | 0.11 | 0.09 | 0.11 | 1.83E+09 |
| 2172 | 0.11 | 0.10 | 0.24 | 1.23E+09 |
| 2173 | 0.11 | 0.10 | 0.11 | 1.68E+09 |
| 2174 | 0.11 | 0.09 | 0.10 | 1.48E+09 |
| 2175 | 1.05 | 1.04 | 1.08 | 1.44E+04 |
| 2176 | 1.08 | 0.97 | 1.03 | 1.51E+06 |
| 2177 | 0.91 | 1.30 | 1.02 | 1.31E+03 |

TABLE 5

| NP # | LP124:nluc clearance | LP124:nluc RLU |
|---|---|---|
| 1839 | 0.27 | 4.14E+08 |
| 1840 | 1.11 | 5.68E+02 |
| 1869 | 0.20 | 4.63E+08 |
| 1878 | 0.10 | 2.43E+08 |
| 1879 | 0.55 | |
| 1880 | 1.01 | 1.16E+06 |
| 1881 | 0.96 | 2.41E+06 |
| 1882 | 0.20 | 8.90E+05 |
| 1883 | 1.12 | 8.22E+02 |
| 1884 | 1.04 | 1.14E+04 |
| 1885 | 0.09 | 9.07E+08 |
| 1886 | 1.02 | 4.83E+02 |
| 1887 | 0.94 | 5.87E+05 |
| 1888 | 0.88 | 3.72E+06 |
| 1889 | 0.10 | 7.50E+08 |
| 1890 | 0.96 | 1.32E+03 |
| 1891 | 0.90 | 4.48E+02 |
| 1892 | 1.00 | 5.21E+02 |
| 1893 | 1.03 | 5.34E+02 |
| 1894 | 0.90 | 4.04E+02 |
| 1895 | 0.11 | 1.18E+09 |

TABLE 5-continued

| | | |
|---|---|---|
| 1896 | 0.10 | 1.18E+09 |
| 1897 | 0.11 | 1.20E+09 |
| 1898 | 0.13 | 1.18E+09 |
| 1899 | 1.16 | 7.88E+02 |
| 1900 | 0.88 | 6.40E+02 |
| 1901 | 0.09 | 5.17E+08 |
| 1902 | 1.00 | 2.88E+06 |
| 1903 | 0.11 | 4.89E+08 |
| 1904 | 0.13 | 1.03E+08 |
| 1905 | 0.16 | 1.12E+08 |
| 1906 | 0.91 | 3.11E+06 |
| 1907 | 0.98 | 6.91E+02 |
| 1908 | 0.11 | 4.99E+08 |
| 1909 | 0.98 | 6.89E+02 |
| 1910 | 0.11 | 1.36E+09 |
| 1911 | 0.92 | 4.16E+05 |
| 1912 | 1.07 | 4.00E+02 |
| 1913 | 1.59 | 6.22E+02 |
| 1914 | 0.17 | 3.71E+08 |
| 1915 | 0.10 | 2.25E+08 |
| 1916 | 0.89 | 1.88E+04 |
| 1917 | 0.89 | 1.18E+06 |
| 1945 | 0.12 | 1.07E+09 |
| 1946 | 0.30 | 8.28E+04 |
| 1947 | 0.31 | 1.08E+05 |
| 1948 | 0.79 | 1.68E+04 |
| 1949 | 0.14 | 9.51E+08 |
| 1950 | 0.11 | 1.14E+09 |
| 1951 | 1.00 | 8.32E+02 |
| 1952 | 0.14 | 1.26E+09 |
| 1953 | 1.22 | 1.31E+08 |
| 1954 | 0.13 | 7.70E+08 |
| 1955 | 1.04 | 1.15E+08 |
| 1956 | 1.08 | 1.50E+06 |
| 1957 | 0.14 | 3.15E+07 |
| 1958 | 0.13 | 8.58E+08 |
| 1959 | 0.12 | 4.59E+08 |
| 1960 | 0.14 | 6.09E+08 |
| 1961 | 0.12 | 1.49E+08 |
| 1962 | 0.97 | 9.90E+08 |
| 1963 | 0.10 | 1.13E+09 |
| 1964 | 0.10 | 1.24E+09 |
| 1965 | 0.10 | 1.31E+09 |
| 1966 | 0.09 | 8.83E+08 |
| 1967 | 0.10 | 5.14E+08 |
| 1968 | 0.12 | 1.08E+09 |
| 1969 | 0.12 | 1.19E+09 |
| 1970 | 0.09 | 9.52E+08 |
| 1971 | 0.10 | 1.17E+09 |
| 1972 | 0.75 | 2.46E+06 |
| 1973 | 1.02 | 1.27E+03 |
| 1974 | 0.96 | 5.58E+02 |
| 1975 | 0.10 | 2.05E+09 |
| 1976 | 0.11 | 1.01E+09 |
| 1977 | 0.78 | 9.36E+08 |
| 1978 | 1.04 | 4.25E+03 |
| 1979 | 0.90 | 8.68E+02 |
| 1980 | 0.93 | 1.01E+06 |
| 1981 | 0.78 | 8.87E+02 |
| 1982 | 1.02 | 2.26E+04 |
| 1983 | 0.26 | 1.10E+05 |
| 1984 | 0.14 | 5.70E+05 |
| 1985 | 1.07 | 3.71E+05 |
| 1986 | 0.17 | 4.42E+08 |
| 1987 | 0.16 | 4.19E+08 |
| 1988 | 0.16 | 5.10E+08 |
| 1989 | 0.35 | 7.94E+03 |
| 1990 | 1.05 | 5.21E+02 |
| 1991 | 1.08 | 7.81E+02 |
| 1992 | 1.06 | 5.54E+02 |
| 1993 | 1.05 | 5.49E+02 |
| 1994 | 1.12 | 6.11E+02 |
| 1995 | 1.07 | 6.58E+02 |
| 1996 | 0.40 | 9.57E+08 |
| 1997 | 0.10 | 1.03E+09 |
| 1998 | 0.10 | 7.04E+08 |
| 1999 | 0.10 | 7.03E+08 |
| 2000 | 0.12 | 7.44E+08 |
| 2001 | 0.85 | 7.40E+08 |
| 2002 | 0.14 | 2.40E+08 |
| 2003 | 1.08 | 2.97E+06 |
| 2004 | 1.00 | 2.48E+06 |
| 2005 | 1.02 | 1.91E+06 |
| 2006 | 1.39 | 2.27E+03 |
| 2007 | 0.15 | 1.03E+09 |
| 2008 | 0.15 | 1.49E+09 |
| 2009 | 0.14 | 7.14E+08 |
| 2010 | 1.16 | 1.41E+05 |
| 2011 | 1.18 | 9.53E+04 |
| 2012 | 1.06 | 1.96E+03 |
| 2013 | 1.05 | 4.57E+03 |
| 2014 | 1.18 | 6.58E+04 |
| 2015 | 1.04 | 9.04E+04 |
| 2016 | 1.17 | 1.18E+05 |
| 2017 | 0.91 | 1.27E+05 |
| 2018 | 1.15 | 1.63E+05 |
| 2019 | 1.15 | 5.09E+04 |
| 2020 | 0.67 | 1.33E+08 |
| 2021 | 1.05 | 8.08E+03 |
| 2022 | 1.12 | 1.60E+04 |
| 2023 | 1.06 | 2.05E+05 |
| 2024 | 0.10 | 2.00E+09 |
| 2025 | 0.10 | 9.29E+08 |
| 2026 | 0.42 | 8.12E+07 |
| 2027 | 0.13 | 2.18E+09 |
| 2028 | 0.10 | 5.25E+08 |
| 2029 | 1.06 | 8.97E+05 |
| 2030 | 0.11 | 4.29E+06 |
| 2031 | 0.15 | 3.22E+05 |
| 2032 | 0.11 | 8.40E+08 |
| 2033 | 0.10 | 8.34E+08 |
| 2034 | 0.10 | 9.17E+08 |
| 2035 | 0.09 | 1.02E+09 |
| 2036 | 0.10 | 1.25E+09 |
| 2037 | 0.10 | 8.85E+08 |
| 2038 | 0.57 | 8.38E+03 |
| 2039 | 0.57 | 1.71E+04 |
| 2040 | 0.38 | 2.20E+04 |
| 2041 | 0.10 | 7.90E+08 |
| 2042 | 0.29 | 2.60E+06 |
| 2043 | 0.15 | 1.51E+06 |
| 2044 | 0.15 | 1.54E+06 |
| 2045 | 0.71 | 1.85E+06 |
| 2046 | 0.19 | 3.69E+05 |
| 2047 | 0.16 | 5.60E+05 |
| 2048 | 0.91 | 5.59E+03 |
| 2049 | 0.13 | 5.39E+05 |
| 2050 | 0.16 | 6.97E+05 |
| 2051 | 0.52 | 2.43E+04 |
| 2052 | 0.10 | 5.51E+08 |
| 2053 | 0.12 | 2.63E+08 |
| 2054 | 0.13 | 2.25E+09 |
| 2055 | 0.10 | 1.79E+09 |
| 2056 | 0.09 | 1.24E+09 |
| 2057 | 0.53 | 1.38E+04 |
| 2058 | 0.69 | 2.17E+04 |
| 2059 | 0.10 | 1.94E+09 |
| 2060 | 0.88 | 1.62E+06 |
| 2061 | 0.69 | 2.51E+06 |
| 2062 | 0.39 | 3.04E+06 |
| 2063 | 0.96 | 8.85E+05 |

TABLE 5-continued

| | | |
|---|---|---|
| 2064 | 0.12 | 1.21E+09 |
| 2065 | 0.35 | 2.52E+06 |
| 2066 | 0.19 | 1.77E+06 |
| 2067 | 1.48 | 5.81E+02 |
| 2068 | 1.02 | 1.34E+06 |
| 2069 | 0.95 | 1.63E+06 |
| 2070 | 0.13 | 6.71E+08 |
| 2071 | 1.40 | 2.29E+03 |
| 2072 | 0.12 | 8.04E+08 |
| 2073 | 0.94 | 1.32E+09 |
| 2074 | 0.22 | 7.06E+06 |
| 2075 | 0.40 | 3.07E+06 |
| 2076 | 0.09 | 2.65E+09 |
| 2077 | 0.19 | 7.24E+05 |
| 2078 | 0.39 | 4.00E+08 |
| 2079 | 1.06 | 2.89E+04 |
| 2080 | 1.02 | 6.69E+02 |
| 2081 | 1.15 | 5.28E+02 |
| 2082 | 1.05 | 5.89E+02 |
| 2083 | 0.18 | 1.30E+09 |
| 2084 | 0.49 | 8.76E+08 |
| 2085 | 1.11 | 4.66E+03 |
| 2086 | 0.25 | 1.15E+09 |
| 2087 | 1.13 | 9.13E+02 |
| 2088 | 0.19 | 1.93E+09 |
| 2089 | 1.15 | 1.55E+04 |
| 2090 | 0.24 | 2.09E+09 |
| 2091 | 0.19 | 7.86E+08 |
| 2092 | 0.10 | 1.93E+09 |
| 2093 | 0.42 | 5.39E+05 |
| 2094 | 0.43 | 6.93E+04 |
| 2095 | 0.13 | 7.54E+08 |
| 2096 | 0.21 | 2.01E+05 |
| 2097 | 0.23 | 5.42E+06 |
| 2098 | 0.30 | 1.89E+05 |
| 2099 | 0.24 | 1.80E+04 |
| 2100 | 1.13 | 9.19E+02 |
| 2101 | 1.05 | 2.03E+03 |
| 2102 | 1.09 | 7.52E+03 |
| 2103 | 1.26 | 1.80E+03 |
| 2104 | 1.02 | 2.07E+03 |
| 2105 | 1.09 | 8.50E+02 |
| 2106 | 1.19 | 7.00E+06 |
| 2107 | 1.34 | 1.20E+03 |
| 2108 | 1.09 | 7.31E+02 |
| 2109 | 1.15 | 1.35E+03 |
| 2110 | 0.99 | 1.23E+03 |
| 2111 | 0.99 | 4.33E+05 |
| 2112 | 1.09 | 9.46E+02 |
| 2113 | 0.09 | 8.06E+08 |
| 2114 | 0.94 | 3.13E+04 |
| 2115 | 0.99 | 9.25E+03 |
| 2116 | 1.01 | 1.23E+04 |
| 2117 | 0.78 | 3.64E+04 |
| 2118 | 1.00 | 1.31E+04 |
| 2119 | 0.48 | 2.41E+05 |
| 2120 | 0.48 | 1.13E+04 |
| 2121 | 0.62 | 6.97E+03 |
| 2122 | 0.39 | 7.79E+03 |
| 2123 | 0.09 | 1.19E+09 |
| 2124 | 0.09 | 1.84E+09 |
| 2125 | 0.10 | 1.04E+09 |
| 2126 | 0.50 | 1.52E+05 |
| 2127 | 1.05 | 1.40E+06 |
| 2128 | 0.10 | 9.27E+08 |
| 2129 | 0.10 | 9.59E+08 |
| 2130 | 0.10 | 1.10E+09 |
| 2131 | 0.10 | 8.76E+08 |
| 2132 | 1.21 | 8.98E+03 |
| 2133 | 0.12 | 7.24E+08 |
| 2134 | 1.07 | 4.11E+03 |
| 2135 | 0.33 | 6.59E+05 |
| 2136 | 0.09 | 1.73E+09 |
| 2137 | 0.09 | 1.13E+09 |
| 2138 | 1.16 | 2.04E+04 |
| 2139 | 0.09 | 7.09E+08 |
| 2140 | 0.85 | 8.74E+04 |
| 2141 | 0.19 | 2.03E+04 |
| 2142 | 0.88 | 1.19E+06 |
| 2143 | 0.54 | 2.61E+06 |
| 2164 | 0.11 | 3.17E+08 |
| 2165 | 0.11 | 3.67E+08 |
| 2166 | 0.56 | 2.34E+04 |
| 2167 | 0.13 | 9.74E+08 |
| 2148 | 0.12 | 2.01E+09 |
| 2149 | 1.06 | 9.57E+03 |
| 2150 | 1.09 | 8.18E+05 |
| 2151 | 1.07 | 8.33E+05 |
| 2152 | 0.09 | 6.38E+08 |
| 2153 | 0.85 | 1.12E+06 |
| 2154 | 0.98 | 1.31E+06 |
| 2155 | 0.50 | 9.99E+05 |
| 2156 | 0.11 | 9.04E+08 |
| 2157 | 0.37 | 7.10E+07 |
| 2158 | 0.10 | 6.65E+08 |
| 2159 | 0.87 | 1.01E+06 |
| 2160 | 0.12 | 6.33E+08 |
| 2161 | 0.15 | 3.43E+08 |
| 2162 | 0.12 | 6.64E+08 |
| 2163 | 0.10 | 1.23E+09 |
| 2144 | 1.09 | 8.40E+03 |
| 2145 | 0.55 | 1.41E+07 |
| 2146 | 0.11 | 1.48E+09 |
| 2147 | 0.15 | 1.08E+09 |
| 2168 | 0.09 | 7.92E+08 |
| 2169 | 0.11 | 1.49E+09 |
| 2170 | 0.10 | 2.46E+09 |
| 2171 | 0.09 | 1.83E+09 |
| 2172 | 0.10 | 1.23E+09 |
| 2173 | 0.10 | 1.68E+09 |
| 2174 | 0.09 | 1.48E+09 |
| 2175 | 1.04 | 1.44E+04 |
| 2176 | 0.97 | 1.51E+06 |
| 2177 | 1.30 | 1.31E+03 |
| 2178 | 0.85 | 3.67E+04 |

TABLE 6

| Species | Growth Medium | Growth Temperature | $10^5$ negative cfu | $10^1$ Listeria/$10^5$ negative cfu |
|---|---|---|---|---|
| Bacillus cereus | Nutrient Broth | 30 C. | 53 | 3756 |
| Bacillus megaterium | Nutrient Broth | 30 C. | 74 | 4814 |
| Bacillus subtilis | Nutrient Broth | 30 C. | 56 | 1982 |
| Enterococcus durans | Brain Heart Infusion | 37 C. | 57 | 3507 |
| Enterococcus faceium | Brain Heart Infusion | 37 C. | 55 | 8735 |
| Enterococcus hirae | Brain Heart Infusion | 37 C. | 57 | 6145 |
| Kocuria varians | Nutrient Broth | 30 C. | 52 | 6283 |

TABLE 6-continued

| Species | Growth Medium | Growth Temperature | $10^5$ negative cfu | $10^1$ Listeria/$10^5$ negative cfu |
|---|---|---|---|---|
| Kurthia gibsonii | Brain Heart Infusion | 30 C. | 44 | 4420 |
| Kurthia zopfii | Nutrient Broth | 26 C. | 54 | 7226 |
| Rhodococcus equi | Brain Heart Infusion | 37 C. | 61 | 4367 |
| Staphylococcus aureus | Tryptic Soy Broth | 37 C. | 55 | 3575 |
| Staphylococcus epidermidis | Tryptic Soy Broth | 37 C. | 51 | 4544 |
| Staphylococcus saprophyticus | Nutrient Broth | 37 C. | 59 | 4434 |
| Streptococcus equi | Brain Heart Infusion | 37 C. | 63 | 3368 |
| Streptococcus galloyticus | Brain Heart Infusion | 37 C. | 64 | 5287 |
| Lactobacillus casei | MRS | 37 C., 5% $CO_2$ | 59 | 5320 |
| Lactobacillus buchneri | MRS | 37 C., 5% $CO_3$ | 53 | 6331 |
| Lactobacillus lactus | MRS | 37 C., 5% $CO_4$ | 67 | 5065 |
| Lactobacillus fermentum | MRS | 37 C., 5% $CO_5$ | 67 | 4318 |
| Micrococcus lutues | Tryptic Soy Broth | 30 C. | 79 | 3322 |

TABLE 7

| Sample # | Species | $10^5$ negative cfu | $10^1$ Listeria/$10^5$ negative cfu |
|---|---|---|---|
| 2501-1 | Pseudomonas protogens | 253 | 3513 |
| 250-2 | Pseudomonas florescens | 285 | 1737 |
| 251(2)-1 | Pseudomonas florescens | 236 | 2903 |
| 251(2)-2 | Aeromonas sp | 240 | 1790 |
| 261(1)-1 | Serratia liquefaciens | 318 | 6165 |
| 261(1)-2 | Serratia proteamaculans | 260 | 4614 |
| 261(2)-1 | Serratia liquefaciens | 296 | 2421 |
| 261(2)-2 | Bacillaceae bacterium | 320 | 5289 |
| 289-1 | Serratia proteamaculans | 273 | 3487 |
| 289-2 | Pseudomonas florescens | 279 | 5161 |
| 289-3 | Pseudomonas poae | 241 | 1922 |
| 290(1)-1 | Pseudomonas sp | 241 | 1965 |
| 290(1)-2 | Pseudomonas sp | 271 | 2178 |
| 290(2)-1 | Pseudomonas fragi | 223 | 3052 |
| 290(3)-1 | Pseudomonas sp | 272 | 2560 |
| 291(1)-1 | Providencia alcalifaciens | 262 | 4963 |
| 291(1)-2 | Serratia sp | 272 | 3827 |
| 291(2)-1 | Serratia grimesii | 240 | 3302 |
| 291(2)-2 | Serratia sp | 213 | 3086 |
| 291-1 | Serratia sp | 270 | 2430 |
| 293-1 | Serratia sp, Hafnia sp. | 243 | 2989 |
| 293-2 | Serratia proteamaculans | 259 | 3254 |
| 296-4 | Serratia proteamaculans | 304 | 2314 |
| 304-1 | Pseudomonas florescens | 272 | 2639 |
| 304-2 | Chryseobacterium sp. | 269 | 2911 |
| 306-1 | Pseudomonas fragi | 266 | 3212 |
| 306-2 | Enterobacteriaceae | 273 | 4358 |

TABLE 8

| NP # | A511:nluc | LP124:nluc | LP124/A511 RLU output |
|---|---|---|---|
| 1997 | 5.13E+05 | 1.03E+09 | 2.01E+03 |
| 1998 | 4.47E+05 | 7.04E+08 | 1.58E+03 |
| 1999 | 4.15E+05 | 7.03E+08 | 1.69E+03 |
| 2000 | 4.60E+05 | 7.44E+08 | 1.62E+03 |
| 2001 | 3.76E+05 | 7.40E+08 | 1.97E+03 |
| 2002 | 4.39E+05 | 2.40E+08 | 5.47E+02 |
| 2003 | 1.25E+02 | 2.97E+06 | 2.38E+04 |
| 2004 | 1.69E+02 | 2.48E+06 | 1.47E+04 |
| 2005 | 8.90E+01 | 1.91E+06 | 2.15E+04 |
| 2006 | 1.90E+01 | 2.27E+03 | 1.20E+02 |
| 2007 | 4.55E+06 | 1.03E+09 | 2.27E+02 |
| 2008 | 4.69E+06 | 1.49E+09 | 3.18E+02 |
| 2009 | 8.22E+06 | 7.14E+08 | 8.68E+01 |
| 2010 | 5.70E+01 | 1.41E+05 | 2.48E+03 |
| 2011 | 1.20E+01 | 9.53E+04 | 7.94E+03 |
| 2012 | 1.50E+01 | 1.96E+03 | 1.31E+02 |
| 2013 | 1.20E+01 | 4.57E+03 | 3.81E+02 |
| 2014 | 9.00E+00 | 6.58E+04 | 7.31E+03 |
| 1869 | 6.15E+06 | 4.63E+08 | 7.52E+01 |
| 1840 | 4.20E+01 | 5.68E+02 | 1.35E+01 |
| 1839 | 4.84E+06 | 4.14E+08 | 8.54E+01 |
| 2024 | 7.74E+06 | 2.00E+09 | 2.58E+02 |
| 2025 | 2.50E+06 | 9.29E+08 | 3.71E+02 |
| 2026 | 9.99E+05 | 8.12E+07 | 8.13E+01 |
| 2027 | 1.74E+06 | 2.18E+09 | 1.25E+03 |
| 2028 | 5.89E+06 | 5.25E+08 | 8.91E+01 |
| 2029 | 3.46E+02 | 8.97E+05 | 2.59E+03 |
| 2030 | 9.18E+06 | 4.29E+06 | 4.68E-01 |
| 2031 | 3.36E+03 | 3.22E+05 | 9.57E+01 |
| 2032 | 5.53E+06 | 8.40E+08 | 1.52E+02 |
| 2033 | 5.22E+06 | 8.34E+08 | 1.60E+02 |
| 2034 | 4.50E+06 | 9.17E+08 | 2.04E+02 |
| 2035 | 3.66E+06 | 1.02E+09 | 2.78E+02 |
| 2036 | 6.27E+06 | 1.25E+09 | 2.00E+02 |
| 2037 | 3.65E+06 | 8.85E+08 | 2.42E+02 |
| 2038 | 4.60E+01 | 8.38E+03 | 1.82E+02 |
| 2039 | 3.10E+01 | 1.71E+04 | 5.50E+02 |
| 2040 | 4.40E+01 | 2.20E+04 | 4.99E+02 |
| 2041 | 6.25E+06 | 7.90E+08 | 1.26E+02 |
| 2042 | 1.38E+03 | 2.60E+06 | 1.89E+03 |
| 2043 | 3.65E+02 | 1.51E+06 | 4.13E+03 |
| 2044 | 7.03E+02 | 1.54E+06 | 2.19E+03 |
| 2045 | 4.52E+02 | 1.85E+06 | 4.10E+03 |
| 2046 | 7.35E+02 | 3.69E+05 | 5.02E+02 |
| 2047 | 2.18E+02 | 5.60E+05 | 2.57E+03 |
| 2048 | 2.01E+02 | 5.59E+03 | 2.78E+01 |
| 2049 | 3.10E+02 | 5.39E+05 | 1.74E+03 |
| 2050 | 5.27E+02 | 6.97E+05 | 1.32E+03 |
| 2051 | 7.00E+00 | 2.43E+04 | 3.47E+03 |
| 2052 | 8.15E+06 | 5.51E+08 | 6.76E+01 |
| 2053 | 6.19E+06 | 2.63E+08 | 4.25E+01 |

TABLE 8-continued

| | | | |
|---|---|---|---|
| 2054 | 2.47E+06 | 2.25E+09 | 9.13E+02 |
| 2055 | 1.06E+07 | 1.79E+09 | 1.69E+02 |
| 2056 | 3.54E+06 | 1.24E+09 | 3.52E+02 |
| 2057 | 4.40E+01 | 1.38E+04 | 3.14E+02 |
| 2058 | 8.00E+00 | 2.17E+04 | 2.72E+03 |
| 2059 | 8.19E+06 | 1.94E+09 | 2.37E+02 |
| 2060 | 1.13E+03 | 1.62E+06 | 1.43E+03 |
| 2061 | 1.20E+03 | 2.51E+06 | 2.08E+03 |
| 2062 | 8.02E+02 | 3.04E+06 | 3.79E+03 |
| 2063 | 1.49E+03 | 8.85E+05 | 5.96E+02 |
| 2064 | 1.02E+04 | 1.21E+09 | 1.19E+05 |
| 2065 | 1.01E+03 | 2.52E+06 | 2.50E+03 |
| 1973 | 4.40E+01 | 1.27E+03 | 2.88E+01 |
| 1974 | 9.00E+00 | 5.58E+02 | 6.20E+01 |
| 1975 | 1.40E+01 | 2.05E+09 | 1.47E+08 |
| 1976 | 1.16E+07 | 1.01E+09 | 8.72E+01 |
| 1990 | 1.40E+01 | 5.21E+02 | 3.72E+01 |
| 1991 | 6.00E+00 | 7.81E+02 | 1.30E+02 |
| 1992 | 1.00E+01 | 5.54E+02 | 5.54E+01 |
| 1993 | 8.00E+00 | 5.49E+02 | 6.86E+01 |
| 1994 | 9.00E+00 | 6.11E+02 | 6.79E+01 |
| 1995 | 8.00E+00 | 6.58E+02 | 8.23E+01 |
| 1996 | 5.07E+06 | 9.57E+08 | 1.89E+02 |
| 1977 | 6.55E+06 | 9.36E+08 | 1.43E+02 |
| 1978 | 2.00E+01 | 4.25E+03 | 2.12E+02 |
| 1979 | 8.00E+00 | 8.68E+02 | 1.09E+02 |
| 1980 | 1.45E+03 | 1.01E+06 | 7.00E+02 |
| 1981 | 1.00E+01 | 8.87E+02 | 8.87E+01 |
| 1982 | 3.30E+01 | 2.26E+04 | 6.85E+02 |
| 1983 | 1.47E+03 | 1.10E+05 | 7.52E+01 |
| 1984 | 2.07E+02 | 5.70E+05 | 2.75E+03 |
| 1985 | 5.78E+02 | 3.71E+05 | 6.42E+02 |
| 1986 | 1.27E+06 | 4.42E+08 | 3.49E+02 |
| 1987 | 1.13E+06 | 4.19E+08 | 3.72E+02 |
| 1988 | 1.32E+06 | 5.10E+08 | 3.87E+02 |
| 1989 | 5.02E+02 | 7.94E+03 | 1.58E+01 |
| 2015 | 1.00E+02 | 9.04E+04 | 9.04E+02 |
| 2016 | 1.49E+02 | 1.18E+05 | 7.90E+02 |
| 2017 | 1.18E+02 | 1.27E+05 | 1.08E+03 |
| 2018 | 1.34E+02 | 1.63E+05 | 1.22E+03 |
| 2019 | 1.46E+02 | 5.09E+04 | 3.48E+02 |
| 2020 | 1.40E+02 | 1.33E+08 | 9.48E+05 |
| 2021 | 8.20E+01 | 8.08E+03 | 9.86E+01 |
| 2022 | 3.60E+01 | 1.60E+04 | 4.45E+02 |
| 2023 | 4.40E+01 | 2.05E+05 | 4.67E+03 |

TABLE 9

| Sample # | A511/P100 cocktail RLU | A511/P100/LP124 cocktail RLU | Signal Ratio of 3-phage/2-phage |
|---|---|---|---|
| 398 | 1164 | 2212 | 1.9 |
| 399 | 11459 | 27183 | 2.4 |
| 401 | 2100 | 3058 | 1.5 |
| 402 | 113103 | 217389 | 1.9 |
| 403 | 46219 | 58768 | 1.3 |
| 405 | 9988 | 24151 | 2.4 |
| 407 | 2732 | 5329 | 2.0 |
| 426 | 64717 | 444121 | 6.9 |
| 427 | 75896 | 613358 | 8.1 |

TABLE 10

| NP # | A511/LP124 Clearance | A511/LP124 RLU |
|---|---|---|
| 2180 | 0.51 | 9425355 |
| 2181 | 0.91 | 4829460 |
| 2182 | 0.97 | 22478532 |
| 2183 | 0.21 | 1178748672 |
| 2184 | 0.95 | 8949 |
| 2185 | 1.08 | 3540 |
| 2186 | 0.93 | 13285696 |
| 2187 | 0.87 | 1446053376 |
| 2188 | 0.11 | 1317144704 |
| 2189 | 0.15 | 1227835136 |
| 2190 | 0.60 | 11299 |
| 2191 | 0.09 | 1444555254 |
| 2192 | 0.69 | 5535 |
| 2193 | 0.75 | 1314372736 |
| 2194 | 0.95 | 33425 |
| 2195 | 0.63 | 483384224 |
| 2196 | 0.11 | 1402767616 |
| 2197 | 0.97 | 12005105 |
| 2198 | 1.00 | 4624066 |
| 2199 | 1.05 | 13923259 |
| 2201 | 1.04 | 17701700 |
| 2200 | 1.09 | 13959437 |
| 2202 | 1.01 | 18058374 |
| 2203 | 1.19 | 15579639 |
| 2204 | 0.93 | 1058 |
| 2217 | 1.08 | 738479 |
| 2218 | 0.60 | 3828983 |
| 2222 | 0.89 | 3141 |
| 2234 | 1.47 | 111 |
| 2235 | 1.00 | 553 |
| 2236 | 1.18 | 1656 |
| 2237 | 0.12 | 624961 |
| 2238 | 0.56 | 25193 |
| 2239 | 0.97 | 39008 |
| 2242 | 0.96 | 152481 |
| 2243 | 0.97 | 1249 |
| 2244 | 0.10 | 1478536320 |
| 2246 | 0.93 | 12594 |
| 2248 | 0.43 | 36580156 |
| 2249 | 0.17 | 43955716 |
| 2250 | 0.60 | 236283 |
| 2251 | 1.02 | 1681 |
| 2253 | 1.05 | 31609824 |
| 2254 | 0.98 | 1130 |
| 2256 | 0.98 | 30291 |
| 2257 | 1.06 | 134811 |
| 2258 | 1.00 | 1072 |
| 2260 | 0.17 | 38230508 |
| 2262 | 1.03 | 6718 |
| 2263 | 0.67 | 152658896 |
| 2265 | 0.89 | 1923 |
| 2267 | 0.92 | 86490696 |
| 2269 | 0.15 | 239873472 |
| 2270 | 0.13 | 1182304128 |
| 2271 | 0.98 | 9737881 |
| 2272 | 0.34 | 28609152 |
| 2275 | 0.91 | 22955124 |
| 2278 | 0.16 | 36394420 |
| 2281 | 1.17 | 8376739 |
| 2282 | 0.13 | 1877224464 |

TABLE 10-continued

| | | |
|---|---|---|
| 2283 | 0.79 | 4552574 |
| 2284 | 0.33 | 400019616 |
| 2287 | 0.12 | 334971200 |
| 2290 | 0.14 | 83818688 |
| 2291 | 0.45 | 11715284 |
| 2293 | 1.05 | 457 |
| 2295 | 0.97 | 45340 |
| 2296 | 0.91 | 13112 |
| 2298 | 0.66 | 153830 |
| 2299 | 1.01 | 586 |
| 2301 | 1.13 | 567 |
| 2302 | 0.56 | 3343962 |
| 2303 | 0.37 | 3420569 |
| 2305 | 0.15 | 331570720 |
| 2306 | 1.12 | 1588 |
| 2307 | 1.10 | 12765 |
| 2308 | 1.10 | 4390 |
| 2309 | 1.17 | 6388 |
| 2310 | 1.20 | 3387 |
| 2311 | 1.06 | 33898140 |
| 2312 | 0.19 | 19504462 |
| 2313 | 1.12 | 1712 |
| 2314 | 1.04 | 6168 |
| 2316 | 0.11 | 71091864 |
| 2318 | 0.11 | 337684704 |
| 2319 | 0.11 | 476671232 |
| 2320 | 0.99 | 5048 |
| 2321 | 1.02 | 4614 |
| 2323 | 0.60 | 10705072 |
| 2325 | 0.79 | 10092227 |
| 2327 | 0.90 | 175424880 |
| 2330 | 1.07 | 236237904 |
| 2331 | 0.92 | 3027250 |
| 2333 | 1.06 | 19965 |
| 2334 | 1.03 | 11160 |
| 2335 | 0.13 | 8174093 |
| 2336 | 0.61 | 38853036 |
| 2337 | 0.75 | 17568558 |
| 2340 | 0.16 | 92967936 |
| 2341 | 0.69 | 11054598 |

DEPOSIT OF BIOLOGICAL MATERIALS

The recombinant phages described herein were deposited on May 16, 2013 with the American Type Culture Collection (ATCC®). The address of ATCC® is: American Type Culture Collection (ATCC®), Patent Depository, 10801 University Boulevard, Manassas, Va. 20110-2209 USA. The deposits were made under the terms of the Budapest Treaty on the International Recognition of the Deposit of Microorganisms for the Purposes of Patent Procedure. The ATCC Patent Deposit Designations for the deposits are provided in Table 11.

TABLE 11

| PHAGE | ATCC ® Patent Deposit Designation |
|---|---|
| LP48::ffluc | PTA-120333 |
| LP125::ffluc | PTA-120334 |
| LP40::nluc | PTA-120335 |
| A511::nluc | PTA-120336 |
| P100::ffluc | PTA-120337 |
| LP124::nluc | PTA-120338 |
| LP101::ffluc | PTA-120339 |
| LP99::ffluc | PTA-120340 |
| LP143::ffluc | PTA-120341 |
| A511::ffluc | PTA-120342 |
| P100::nluc | PTA-120343 |
| LP124:ffluc | PTA-120344 |
| LP125::nluc | PTA-120345 |

INFORMAL SEQUENCE LISTING

```
SEQ ID NO: 1-FF luc open reading frame
ATGGAAGACGCCAAAAACATAAAGAAAGGCCCGGCGCCATTCTATCCTCTAGAGGATGGAACCGCTG
GAGAGCAACTGCATAAGGCTATGAAGAGATACGCCCTGGTTCCTGGAACAATTGCTTTTACAGATGCA
CATATCGAGGTGAACATCACGTACGCGGAATACTTCGAAATGTCCGTTCGGTTGGCAGAAGCTATGAA
ACGATATGGGCTGAATACAAATCACAGAATCGTCGTATGCAGTGAAAACTCTCTTCAATTCTTTATGCC
GGTGTTGGGCGCGTTATTTATCGGAGTTGCAGTTGCGCCCGCGAACGACATTTATAATGAACGTGAAT
TGCTCAACAGTATGAACATTTCGCAGCCTACCGTAGTGTTTGTTTCCAAAAAGGGGTTGCAAAAAATTT
TGAACGTGCAAAAAAAATTACCAATAATCCAGAAATTATTATCATGGATTCTAAAACGGATTACCAG
GGATTTCAGTCGATGTACACGTTCGTCACATCTCATCTACCTCCCGGTTTTAATGAATACGATTTTGTA
CCAGAGTCCTTTGATCGTGACAAAACAATTGCACTGATAATGAATTCCTCTGGATCTACTGGGTTACCT
AAGGGTGTGGCCCTTCCGCATAGAACTGCCTGCGTCAGATTCTCGCATGCCAGAGATCCTATTTTTGGC
AATCAAATCATTCCGGATACTGCGATTTTAAGTGTTGTTCCATTCCATCACGGTTTTGGAATGTTTACT
ACACTCGGATATTTGATATGTGGATTTCGAGTCGTCTTAATGTATAGATTTGAAGAAGAGCTGTTTTTA
CGATCCCTTCAGGATTACAAAATTCAAAGTGCGTTGCTAGTACCAACCCTATTTTCATTCTTCGCCAAA
AGCACTCTGATTGACAAATACGATTTATCTAATTTACACGAAATTGCTTCTGGGGGCGCACCTCTTTCG
AAAGAAGTCGGGGAAGCGGTTGCAAAACGCTTCCATCTTCCAGGGATACGACAAGGATATGGGCTCA
CTGAGACTACATCAGCTATTCTGATTACACCCGAGGGGGATGATAAACCGGGCGCGGTCGGTAAAGTT
GTTCCATTTTTTGAAGCGAAGGTTGTGGATCTGGATACCGGGAAAACGCTGGGCGTTAATCAGAGAGG
CGAATTATGTGTCAGAGGACCTATGATTATGTCCGGTTATGTAAACAATCCGGAAGCGACCAACGCCT
TGATTGACAAGGATGGATGGCTACATTCTGGAGACATAGCTTACTGGGACGAAGACGAACACTTCTTC
ATAGTTGACCGCTTGAAGTCTTTAATTAAATACAAAGGATATCAGGTGGCCCCCGCTGAATTGGAATC
GATATTGTTACAACACCCCAACATCTTCGACGCGGGCGTGGCAGGTCTTCCCGACGATGACGCCGGTG
AACTTCCCGCCGCCGTTGTTGTTTTGGAGCACGGAAAGACGATGACGGAAAAAGAGATCGTGGATTAC
GTCGCCAGTCAAGTAACAACCGCGAAAAAGTTGCGCGGAGGAGTTGTGTTTGTGGACGAAGTACCGA
```

```
AAGGTCTTACCGGAAAACTCGACGCAAGAAAAATCAGAGAGATCCTCATAAAGGCCAAGAAGGGCGG
AAAGTCCAAATTGTAA

SEQ ID NO: 2-FF luc amino acid sequence
MEDAKNIKKGPAPFYPLEDGTAGEQLHKAMKRYALVPGTIAFTDAHIEVNITYAEYFEMSVRLAEAMKRY
GLNTNHRIVVCSENSLQFFMPVLGALFIGVAVAPANDIYNERELLNSMNISQPTVVFVSKKGLQKILNVQKK
LPIIQKIIIMDSKTDYQGFQSMYTFVTSHLPPGFNEYDFVPESFDRDKTIALIMNSSGSTGLPKGVALPHRTAC
VRFSHARDPIFGNQIIPDTAILSVVPFHHGFGMFTTLGYLICGFRVVLMYRFEEELFLRSLQDYKIQSALLVPT
LFSFFAKSTLIDKYDLSNLHEIASGGAPLSKEVGEAVAKRFHLPGIRQGYGLTETTSAILITPEGDDKPGAVG
KVVPFFEAKVVDLDTGKTLGVNQRGELCVRGPMIMSGYVNNPEATNALIDKDGWLHSGDIAYWDEDEHF
FIVDRLKSLIKYKGYQVAPAELESILLQHPNIFDAGVAGLPDDDAGELPAAVVVLEHGKTMTEKEIVDYVA
SQVTTAKKLRGGVVFVDEVPKGLTGKLDARKIREILIKAKKGGKSKL SEQ ID NO: 3-Nano luc open reading frame
ATGGTCTTCACACTCGAAGATTTCGTTGGGGACTGGCGACAGACAGCCGGCTACAACCTGGACCAAGT
CCTTGAACAGGGAGGTGTGTCCAGTTTGTTTCAGAATCTCGGGGTGTCCGTAACTCCGATCCAAAGGA
TTGTCCTGAGCGGTGAAAATGGGCTGAAGATCGACATCCATGTCATCATCCCGTATGAAGGTCTGAGC
GGCGACCAAATGGGCCAGATCGAAAAAATTTTTAAGGTGGTGTACCCTGTGGATGATCATCACTTTAA
GGTGATCCTGCACTATGGCACACTGGTAATCGACGGGGTTACGCCGAACATGATCGACTATTTCGGAC
GGCCGTATGAAGGCATCGCCGTGTTCGACGGCAAAAAGATCACTGTAACAGGGACCCTGTGGAACGG
CAACAAAATTATCGACGAGCGCCTGATCAACCCCGACGGCTCCCTGCTGTTCCGAGTAACCATCAACG
GAGTGACCGGCTGGCGGCTGTGCGAACGCATTCTGGCGTAA SEQ ID NO: 4-Nano luc amino acid sequence
MVFTLEDFVGDWRQTAGYNLDQVLEQGGVSSLFQNLGVSVTPIQRIVLSGENGLKIDIHVIIPYEGLSGDQM
GQIEKIFKVVYPVDDHHFKVILHYGTLVIDGVTPNMIDYFGRPYEGIAVFDGKKITVTGTLWNGNKIIDERLI
NPDGSLLFRVTINGVTGWRLCERILA SEQ ID NO: 5-LP040 Cps open reading frame
ATGCCAAAAAATAACAAAGAAGAAGAAGTTAAAGAAGTAAACCTTAATTCAGTACAAGAGGATGCGT
TAAAGTCCTTTACAACTGGTTATGGTATCACACCTGATACACAAACAGATGCAGGGGCACTAAGACGT
GAGTTCCTAGACGACCAAATCTCAATGCTTACTTGGACAAAGAATGATTTAACATTCTACAAAGACAT
CGCTAAAAAACCAGCTACATCTACAGTAGCAAAATACGATGTGTACATGCAACACGGTAAAGTAGGT
CATACTAGATTTACTCGTGAGATTGGGGTAGCACCAGTAAGTGACCCTAACATCCGTCAAAAAACAGT
AAACATGAAATTTGCTTCTGATACTAAAAATATTAGTATCGCAGCAGGTCTAGTAAACAACATTCAAG
ACCCTATGCAAATTTTGACTGATGATGCTATCGTAAATATCGCTAAAACAATTGAGTGGGCTTCATTCT
TTGGAGATTCTGACTTATCAGATAGCCCAGAACCACAAGCAGGATTAGAATTTGATGGCTTGGCTAAA
CTTATTAACCAAGATAACGTTCATGATGCTCGTGGAGCTAGCTTGACTGAAAGCTTGTTAAACCAAGC
AGCAGTAATGATTAGTAAAGGTTATGGTACACCTACAGATGCTTACATGCCAGTAGGGGTTCAAGCAG
ACTTTGTTAACCAACAACTTTCTAAACAAACACAACTTGTTCGCGATAACGGAAACAACGTAAGCGTT
GGTTTCAACATCCAAGGTTTCCATTCAGCTCGTGGATTTATCAAACTTCACGGTTCTACAGTAATGGAA
AACGAACAAATCTTAGATGAACGTATTCTTGCTTTACCAACAGCTCCACAACCAGCTAAGGTAACTGC
AACACAAGAAGCAGGTAAAAAGGACAATTTAGAGCAGAAGATTTAGCAGCACATGAATATAAAGTT
GTTGTAAGTTCTGACGATGCAGAGTCTATTGCAAGTGAAGTGGCTACAGCTACAGTTACTGCAAAAGA
TGACGGCGTTAAACTAGAAATCGAATTAGCTCCAATGTATAGCTCTCGTCCACAATTCGTTTCAATCTA
TAGAAAAGGTGCAGAAACAGGGTTTATTCTACCTAATCGCTCGTGTACCTGCTAGCAAAGCAGAGAACA
ACGTAATCACTTTCTACGACTTAAACGACTCTATTCCTGAAACAGTAGACGTATTCGTTGGTGAAATGT
CGGCTAACGTAGTACACTTGTTTGAATTACTACCAATGATGAGATTACCTCTAGCTCAAATTAACGCAT
CTGTTACATTTGCAGTTTTATGGTATGGCGCATTAGCTCTAAGAGCACCTAAGAAATGGGTACGTATTA
GAAACGTTAAATATATTCCTGTAAAAAACGTTCATAGCAACTAA SEQ ID NO: 6-LP40 Cps protein
MPKNNKEEEVKEVNLNSVQEDALKSFTTGYGITPDTQTDAGALRREFLDDQISMLTWTENDLTFYKDIAK
KPATSTVAKYDVYMQHGKVGHTRFTREIGVAPVSDPNIRQKTVNMKFASDTKNISIAAGLVNNIQDPMQIL
TDDAIVNIAKTIEWASFFGDSDLSDSPEPQAGLEFDGLAKLINQDNVHDARGASLTESLLNQAAVMISKGY
GTPTDAYMPVGVQADFVNQQLSKQTQLVRDNGNNVSVGFNIQGFHSARGFIKLHGSTVMENEQILDERIL
ALPTAPQPAKVTATQEAGKKGQFRAEDLAAHEYKVVVSSDDAESIASEVATATVTAKDDGVKLEIELAPM
YSSRPQFVSIYRKGAETGLFYLIARVPASKAENNVITFYDLNDSIPETVDVFVGEMSANVVHLFELLPMMRL
PLAQINASVTFAVLWYGALALRAPKKWVRIRNVKYIPVKNVHSN SEQ ID NO: 7-LP48 Cps open reading frame
ATGCCAAAAAATAACAAAGAAGAAGAAGTTAAAGAAGTAAACCTTAATTCAGTACAAGAGGACGCGT
TAAAGTCCTTTACAACTGGTTATGGTATCACACCTGATACACAAACAGATGCAGGAGCATTAAGACGT
GAGTTCCTAGACGACCAAATCTCAATGCTTACTTGGACAGAGAATGATTTAACATTCTATAAAGACAT
CGCTAAAAAACCAGCTACATCTACAGTAGCAAAATACGATGTATACATGCAACATGGTAAGGTAGGTC
ATACTAGATTTACTCGTGAGATTGGGGTAGCACCAGTAAGTGACCCTAACATCCGTCAAAAAACAGTA
AACATGAAATTTGCTTCCGATACTAAAAACATCAGTATCGCAGCAGGTCTAGTAAACAACATTCAAGA
CCCAATGCAAATTTTGACTGACGATGCTATCGTAAATATTGCTAAAACAATTGAGTGGCTTCATTCTT
TGGAGATTCTGACTTATCAGATAGCCCAGAACCACAAGCAGGACTAGAATTTGACGGCTTGGCTAAAC
TTATTAACCAAGATAACGTTCATGATGCTCGTGGAGCTAGCTTGACTGAAAGCTTGTTAAACCAAGCA
GCAGTAATGATTAGTAAAGGTTATGGTACACCTACAGATGCTTACATGCCAGTAGGGGTTCAAGCAGA
CTTTGTTAACCAACAACTTTCTAAACAAACACAACTTGTTCGCGATAACGGAAACAACGTAAGCGTTG
GTTTCAACATCCAAGGTTTCCATTCAGCTCGTGGATTTATCAAACTTCACGGTTCTACAGTAATGGAAA
CGAACAAATCTTAGATGAACGTATTCTTGCTTTACCAACAGCTCCACAACCAGCTAAGGTAACTGCA
ACACAAGAAGCAGGTAAAAAGGACAATTTAGAGCAGAAGATTTAGCAGCACATGAATATAAAGTTG
TTGTAAGTTCTGACGATGCAGAGTCTATTGCAAGTGAAGTGGCTACAGCTACAGTTACTGCAAAAGAT
GACGGCGTTAAACTAGAAATCGAATTAGCTCCAATGTATAGCTCTCGTCCACAATTCGTTTCAATCTAT
```

| INFORMAL SEQUENCE LISTING |
| --- |

AGAAAAGGTGCAGAAACAGGTTTATTCTACCTAATCGCTCGTGTACCTGCTAGCAAAGCAGAGAACAA
CGTAATCACTTTCTACGACTTAAACGACTCTATTCCTGAAACAGTAGACGTATTCGTTGGTGAAATGTC
GGCTAACGTAGTACACTTGTTTGAATTACTACCAATGATGAGATTACCTCTAGCTCAAATTAACGCATC
TGTTACATTTGCAGTTTTATGGTATGGCGCATTAGCTCTAAGAGCACCTAAGAAATGGGTACGTATTAG
AAACGTTAAATATATTCCTGTAAAAAACGTTCATAGCAACTAA

SEQ ID NO: 8-LP48 protein
MPKNNKEEEVKEVNLNSVQEDALKSFTTGYGITPDTQTDAGALRREFLDDQISMLTWTENDLTFYKDIAK
KPATSTVAKYDVYMQHGKVGHTRFTREIGVAPVSDPNIRQKTVNMKFASDTKNISIAAGLVNNIQDPMQIL
TDDAIVNIAKTIEWASFFGDSDLSDSPEPQAGLEFDGLAKLINQDNVHDARGASLTESLLNQAAVMISKGY
GTPTDAYMPVGVQADFVNQQLSKQTQLVRDNGNNVSVGFNIQGFHSARGFIKLHGSTVMENEQILDERIL
ALPTAPQPAKVTATQEAGKKGQFRAEDLAAHEYKVVVSSDDAESIASEVATATVTAKDDGVKLEIELAPM
YSSRPQFVSIYRKGAETGLFYLIARVPASKAENNVITFYDLNDSIPETVDVFVGEMSANVVHLFELLPMMRL
PLAQINASVTFAVLWYGALALRAPKKWVRIRNVKYIPVKNVHSN SEQ ID NO: 9-LP099 Cps open reading frame
ATGCCAAAAAATAACAAAGAAGAAGAAGTTAAAGAAGTAAACCTTAATTCAGTACAAGAGGACGCGT
TAAAGTCCTTTACAACTGGTTATGGTATCACACCTGATACACAAACAGATGCAGGAGCATTAAGACGT
GAGTTCCTAGACGACCAAATCTCAATGCTTACTTGGACAGAGAATGATTTAACATTCTATAAAGACAT
CGCTAAAAAACCAGCTACATCTACAGTAGCAAAATACGATGTATACATGCAACATGGTAAGGTAGGTC
ATACTAGATTTACTCGTGAGATTGGGGTAGCACCAGTAAGTGACCCTAACATCCGTCAAAAAACAGTA
AACATGAAATTTGCTTCCGATACTAAAAACATCAGTATCGCAGCAGGTCTAGTAAACAACATTCAAGA
CCCAATGCAAATTTTGACTGACGATGCTATCGTAAATATTGCTAAAACAATTGAGTGGGCTTCATTCTT
TGGAGATTCTGACTTATCAGATAGCCCAGAACCACAAGCAGGACTAGAATTTGACGGCTTGGCTAAAC
TTATTAACCAAGATAACGTTCATGATGCTCGTGGAGCTAGCTTGACTGAAAGCTTGTTAAACCAAGCA
GCAGTAATGATTAGTAAAGGTTATGGTACACCTACAGATGCTTACATGCCAGTAGGGGTTCAAGCAGA
CTTTGTTAACCAACAACTTTCTAAACAAACACAACTTGTTCGCGATAACGGAAACAACGTAAGCGTTG
GTTTCAACATCCAAGGTTTCCATTCAGCTCGTGGATTTATCAAACTTCACGGTTCTACAGTAATGGAAA
ACGAACAAATCTTAGATGAACGTATTCTTGCTTTACCAACAGCTCCACAACCAGCTAAGGTAACTGCA
ACACAAGAAGCAGGTAAAAAAGGACAATTTAGAGCAGAAGATTTAGCAGCACATGAATATAAAGTTG
TTGTAAGTTCTGACGATGCAGAGTCTATTGCAAGTGAAGTGGCTACAGCTACAGTTACTGCAAAAGAT
GACGGCGTTAAACTAGAAATCGAATTAGCTCCAATGTATAGCTCTCGTCCACAATTCGTTTCAATCTAT
AGAAAAGGTGCAGAAACAGGTTTATTCTACCTAATCGCTCGTGTACCTGCTAGCAAAGCAGAGAACAA
CGTAATCACTTTCTACGACTTAAACGACTCTATTCCTGAAACAGTAGACGTATTCGTTGGTGAAATGTC
GGCTAACGTAGTACACTTGTTTGAATTACTACCAATGATGAGATTACCTCTAGCTCAAATTAACGCATC
TGTTACATTTGCAGTTTTATGGTATGGCGCATTAGCTCTAAGAGCACCTAAGAAATGGGTACGTATTAG
AAACGTTAAATATATTCCTGTAAAAAACGTTCATAGCAACTAA SEQ ID NO: 10-LP099 Cps protein
MPKNNKEEEVKEVNLNSVQEDALKSFTTGYGITPDTQTDAGALRREFLDDQISMLTWTENDLTFYKDIAK
KPATSTVAKYDVYMQHGKVGHTRFTREIGVAPVSDPNIRQKTVNMKFASDTKNISIAAGLVNNIQDPMQIL
TDDAIVNIAKTIEWASFFGDSDLSDSPEPQAGLEFDGLAKLINQDNVHDARGASLTESLLNQAAVMISKGY
GTPTDAYMPVGVQADFVNQQLSKQTQLVRDNGNNVSVGFNIQGFHSARGFIKLHGSTVMENEQILDERIL
ALPTAPQPAKVTATQEAGKKGQFRAEDLAAHEYKVVVSSDDAESIASEVATATVTAKDDGVKLEIELAPM
YSSRPQFVSIYRKGAETGLFYLIARVPASKAENNVITFYDLNDSIPETVDVFVGEMSANVVHLFELLPMMRL
PLAQINASVTFAVLWYGALALRAPKKWVRIRNVKYIPVKNVHSN SEQ ID NO: 11-LP101 Cps open reading frame
ATGCCAAAAAATAACAAAGAAGAAGAAGTTAAAGAAGTAAACCTTAATTCAGTACAAGAGGACGCGT
TAAAGTCCTTTACAACTGGTTATGGTATCACACCTGATACACAAACAGATGCAGGAGCATTAAGACGT
GAGTTCCTAGACGACCAAATCTCAATGCTTACTTGGACAGAGAATGATTTAACATTCTATAAAGACAT
CGCTAAAAAACCAGCTACATCTACAGTAGCAAAATACGATGTATACATGCAACATGGTAAGGTAGGTC
ATACTAGATTTACTCGTGAGATTGGGGTAGCACCAGTAAGTGACCCTAACATCCGTCAAAAAACAGTA
AACATGAAATTTGCTTCCGATACTAAAAACATCAGTATCGCAGCAGGTCTAGTAAACAACATTCAAGA
CCCAATGCAAATTTTGACTGACGATGCTATCGTAAATATTGCTAAAACAATTGAGTGGGCTTCATTCTT
TGGAGATTCTGACTTATCAGATAGCCCAGAACCACAAGCAGGACTAGAATTTGACGGCTTGGCTAAAC
TTATTAACCAAGATAACGTTCATGATGCTCGTGGAGCTAGCTTGACTGAAAGCTTGTTAAACCAAGCA
GCAGTAATGATTAGTAAAGGTTATGGTACACCTACAGATGCTTACATGCCAGTAGGGGTTCAAGCAGA
CTTTGTTAACCAACAACTTTCTAAACAAACACAACTTGTTCGCGATAACGGAAACAACGTAAGCGTTG
GTTTCAACATCCAAGGTTTCCATTCAGCTCGTGGATTTATCAAACTTCACGGTTCTACAGTAATGGAAA
ACGAACAAATCTTAGATGAACGTATTCTTGCTTTACCAACAGCTCCACAACCAGCTAAGGTAACTGCA
ACACAAGAAGCAGGTAAAAAAGGACAATTTAGAGCAGAAGATTTAGCAGCACATGAATATAAAGTTG
TTGTAAGTTCTGACGATGCAGAGTCTATTGCAAGTGAAGTGGCTACAGCTACAGTTACTGCAAAAGAT
GACGGCGTTAAACTAGAAATCGAATTAGCTCCAATGTATAGCTCTCGTCCACAATTCGTTTCAATCTAT
AGAAAAGGTGCAGAAACAGGTTTATTCTACCTAATCGCTCGTGTACCTGCTAGCAAAGCAGAGAACAA
CGTAATCACTTTCTACGACTTAAACGACTCTATTCCTGAAACAGTAGACGTATTCGTTGGTGAAATGTC
GGCTAACGTAGTACACTTGTTTGAATTACTACCAATGATGAGATTACCTCTAGCTCAAATTAACGCATC
TGTTACATTTGCAGTTTTATGGTATGGCGCATTAGCTCTAAGAGCACCTAAGAAATGGGTACGTATTAG
AAACGTTAAATATATTCCTGTAAAAAACGTTCATAGCAACTAA SEQ ID NO: 12-LP101 Cps protein
MPKNNKEEEVKEVNLNSVQEDALKSFTTGYGITPDTQTDAGALRREFLDDQISMLTWTENDLTFYKDIAK
KPATSTVAKYDVYMQHGKVGHTRFTREIGVAPVSDPNIRQKTVNMKFASDTKNISIAAGLVNNIQDPMQIL
TDDAIVNIAKTIEWASFFGDSDLSDSPEPQAGLEFDGLAKLINQDNVHDARGASLTESLLNQAAVMISKGY
GTPTDAYMPVGVQADFVNQQLSKQTQLVRDNGNNVSVGFNIQGFHSARGFIKLHGSTVMENEQILDERIL
ALPTAPQPAKVTATQEAGKKGQFRAEDLAAHEYKVVVSSDDAESIASEVATATVTAKDDGVKLEIELAPM

INFORMAL SEQUENCE LISTING

YSSRPQFVSIYRKGAETGLFYLIARVPASKAENNVITFYDLNDSIPETVDVFVGEMSANVVHLFELLPMMRL
PLAQINASVTFAVLWYGALALRAPKKWVRIRNVKYIPVKNVHSN

SEQ ID NO: 13-LP124 Cps open reading frame
ATGCCAAAAAATAACAAAGAAGAAGAAGTTAAAGAAGTAAACCTTAATTCAGTACAAGAGGACGCGT
TAAAGTCCTTTACAACTGGTTATGGTATCACACCTGATACACAAACAGATGCAGGAGCATTAAGACGT
GAGTTCCTAGACGACCAAATCTCAATGCTTACTTGGACAGAGAATGATTTAACATTCTATAAAGACAT
CGCTAAAAAACCAGCTACATCTACAGTAGCAAAATACGATGTATACATGCAACATGGTAAGGTAGGTC
ATACTAGATTTACTCGTGAGATTGGGGTAGCACCAGTAAGTGACCCTAACATCCGTCAAAAAACAGTA
AACATGAAATTTGCTTCCGATACTAAAAACATCAGTATCGCAGCAGGTCTAGTAAACAACATTCAAGA
CCCAATGCAAATTTTGACTGACGATGCTATCGTAAATATTGCTAAAACAATTGAGTGGGCTTCATTCTT
TGGAGATTCTGACTTATCAGATAGCCCAGAACCACAAGCAGGACTAGAATTTGACGGCTTGGCTAAAC
TTATTAACCAAGATAACGTTCATGATGCTCGTGGAGCTAGCTTGACTGAAAGCTTGTTAAACCAAGCA
GCAGTAATGATTAGTAAAGGTTATGGTACACCTACAGATGCTTACATGCCAGTAGGGGTTCAAGCAGA
CTTTGTTAACCAACAACTTTCTAAACAAACACAACTTGTTCGCGATAACGGAAACAACGTAAGCGTTG
GTTTCAACATCCAAGGTTTCCATTCAGCTCGTGGATTTATCAAACTTCACGGTTCTACAGTAATGGAAA
ACGAACAAATCTTAGATGAACGTATTCTTGCTTTACCAACAGCTCCACAACCAGCTAAGGTAACTGCA
ACACAAGAAGCAGGTAAAAAAGGACAATTTAGAGCAGAAGATTTAGCAGCACATGAATATAAAGTTG
TTGTAAGTTCTGACGATGCAGAGTCTATTGCAAGTGAAGTGGCTACAGCTACAGTTACTGCAAAAGAT
GACGGCGTTAAACTAGAAATCGAATTAGCTCCAATGTATAGCTCTCGTCCACAATTCGTTTCAATCTAT
AGAAAAGGTGCAGAAACAGGTTTATTCTACCTAATCGCTCGTGTACCTGCTAGCAAAGCAGAGAACAA
CGTAATCACTTTCTACGACTTAAACGACTCTATTCCTGAAACAGTAGACGTATTCGTTGGTGAAATGTC
GGCTAACGTAGTACACTTGTTTGAATTACTACCAATGATGAGATTACCTCTAGCTCAAATTAACGCATC
TGTTACATTTGCAGTTTTATGGTATGGCGCATTAGCTCTAAGAGCACCTAAGAAATGGGTACGTATTAG
AAACGTTAAATATATTCCTGTAAAAAACGTTCATAGCAACTAA SEQ ID NO: 14-LP124 Cps protein
MPKNNKEEEVKEVNLNSVQEDALKSFTTGYGITPDTQTDAGALRREFLDDQISMLTWTENDLTFYKDIAK
KPATSTVAKYDVYMQHGKVGHTRFTREIGVAPVSDPNIRQKTVNMKFASDTKNISIAAGLVNNIQDPMQIL
TDDAIVNIAKTIEWASFFGDSDLSDSPEPQAGLEFDGLAKLINQDNVHDARGASLTESLLNQAAVMISKGY
GTPTDAYMPVGVQADFVNQQLSKQTQLVRDNGNNVSVGFNIQGFHSARGFIKLHGSTVMENEQILDERIL
ALPTAPQPAKVTATQEAGKKGQFRAEDLAAHEYKVVVSSDDAESIASEVATATVTAKDDGVKLEIELAPM
YSSRPQFVSIYRKGAETGLFYLIARVPASKAENNVITFYDLNDSIPETVDVFVGEMSANVVHLFELLPMMRL
PLAQINASVTFAVLWYGALALRAPKKWVRIRNVKYIPVKNVHSN SEQ ID NO: 15-LP125 Cps open reading frame
ATGCCAAAAAATAACAAAGAAGAAGAAGTTAAAGAAGTAAACCTTAATTCAGTACAAGAGGACGCGT
TAAAGTCCTTTACAACTGGTTATGGTATCACACCTGATACACAAACAGATGCAGGAGCATTAAGACGT
GAGTTCCTAGACGACCAAATCTCAATGCTTACTTGGACAGAGAATGATTTAACATTCTATAAAGACAT
CGCTAAAAAACCAGCTACATCTACAGTAGCAAAATACGATGTATACATGCAACATGGTAAGGTAGGTC
ATACTAGATTTACTCGTGAGATTGGGGTAGCACCAGTAAGTGACCCTAACATCCGTCAAAAAACAGTA
AACATGAAATTTGCTTCCGATACTAAAAACATCAGTATCGCAGCAGGTCTAGTAAACAACATTCAAGA
CCCAATGCAAATTTTGACTGACGATGCTATCGTAAATATTGCTAAAACAATTGAGTGGGCTTCATTCTT
TGGAGATTCTGACTTATCAGATAGCCCAGAACCACAAGCAGGACTAGAATTTGACGGCTTGGCTAAAC
TTATTAACCAAGATAACGTTCATGATGCTCGTGGAGCTAGCTTGACTGAAAGCTTGTTAAACCAAGCA
GCAGTAATGATTAGTAAAGGTTATGGTACACCTACAGATGCTTACATGCCAGTAGGGGTTCAAGCAGA
CTTTGTTAACCAACAACTTTCTAAACAAACACAACTTGTTCGTGATAACGGAAACAACGTAAGCGTTG
GTTTCAACATCCAAGGTTTCCATTCAGCTCGTGGATTTATCAAACTTCACGGTTCTACAGTAATGGAAA
ACGAACAAATCTTAGATGAACGTATTCTTGCTTTACCAACAGCTCCACAACCAGCTAAGGTAACTGCA
ACACAAGAAGCAGGTAAAAAAGGACAATTTAGAGCAGAAGATTTAGCAGCACATGAATATAAAGTTG
TTGTAAGTTCTGACGATGCAGAGTCTATTGCAAGTGAAGTGGCTACAGCTACAGTTACTGCAAAAGAT
GACGGCGTTAAACTAGAAATCGAATTAGCTCCAATGTATAGCTCTCGTCCACAATTCGTTTCAATCTAT
AGAAAAGGTGCAGAAACAGGTTTATTCTACCTAATCGCTCGTGTACCTGCTAGCAAAGCAGAGAACAA
CGTAATCACTTTCTACGACTTAAACGACTCTATTCCTGAAACAGTAGACGTATTCGTTGGTGAAATGTC
GGCTAACGTAGTACACTTGTTTGAATTACTACCAATGATGAGATTACCTCTAGCTCAAATTAACGCATC
TGTTACATTTGCAGTTTTATGGTATGGCGCATTAGCTCTAAGAGCACCTAAGAAATGGGTACGTATTAG
AAACGTTAAATATATTCCTGTAAAAAACGTTCATAGCAACTAA SEQ ID NO: 16-LP125 Cps protein
MPKNNKEEEVKEVNLNSVQEDALKSFTTGYGITPDTQTDAGALRREFLDDQISMLTWTENDLTFYKDIAK
KPATSTVAKYDVYMQHGKVGHTRFTREIGVAPVSDPNIRQKTVNMKFASDTKNISIAAGLVNNIQDPMQIL
TDDAIVNIAKTIEWASFFGDSDLSDSPEPQAGLEFDGLAKLINQDNVHDARGASLTESLLNQAAVMISKGY
GTPTDAYMPVGVQADFVNQQLSKQTQLVRDNGNNVSVGFNIQGFHSARGFIKLHGSTVMENEQILDERIL
ALPTAPQPAKVTATQEAGKKGQFRAEDLAAHEYKVVVSSDDAESIASEVATATVTAKDDGVKLEIELAPM
YSSRPQFVSIYRKGAETGLFYLIARVPASKAENNVITFYDLNDSIPETVDVFVGEMSANVVHLFELLPMMRL
PLAQINASVTFAVLWYGALALRAPKKWVRIRNVKYIPVKNVHSN SEQ ID NO: 17-LP143 Cps open reading frame
ATGCCAAAAAATAACAAAGAAGAAGTTAAAGAAGTAAACCTTAATTCAGTACAAGAGGATGCGTTAA
AGTCCTTTACGACTGGTTATGGTATCACACCTGATACACAAACAGATGCAGGAGCATTAAGACGTGAG
TTCCTAGACGACCAAATCTCAATGCTTACTTGGACAGAGAATGATTTAACATTCTATAAAGACATCGCT
AAAAAACCAGCTACATCTACAGTAGCAAAATACGATGTATACATGCAACATGGTAAGGTAGGTCATA
CTAGATTTACTCGTGAGATTGGGGTAGCACCAGTAAGTGACCCTAACATCCGTCAAAAAACAGTAAAT
ATGAAATTTGCTTCCGATACTAAAAACATCAGTATCGCAGCAGGTCTAGTAAACAACATTCAAGACCC
AATGCAAATTTTGACTGACGATGCTATCGTAAATATTGCTAAAACAATTGAGTGGGCTTCATTCTTTGG
AGATTCTGACTTATCAGATAGCCCAGAACCACAAGCAGGACTAGAATTTGACGGCTTGGCTAAACTTA
TTAACCAAGATAACGTTCATGATGCTCGTGGAGCTAGCTTGACTGAAAGCTTGTTAAACCAAGCAGCA GTAATGATTAGTAAAGGTTATGGTACACCTACAGATGCTTACATGCCAGTAGGGGTTCAAGCAGACTT
TGTTAACCAACAACTTTCTAAACAAACACAACTTGTTCGCGATAACGGAAACAACGTAAGCGTTGGTT
TCAACATCCAAGGTTTCCATTCAGCTCGTGGATTTATCAAACTTCACGGTTCTACAGTAATGGAAAACG
AACAAATCTTAGATGAACGTATTCTTGCTTTACCAACAGCTCCACAACCAGCTAAGGTAACTGCAACA
CAAGAAGCAGGTAAAAAGGACAATTTAGAGCAGAAGATTTAGCAGCACATGAATATAAAGTTGTTG
TAAGTTCTGACGATGCAGAGTCTATTGCAAGTGAAGTGGCTACAGCTACAGTTACTGCAAAAGATGAC
GGCGTTAAACTAGAAATCGAATTAGCTCCAATGTATAGCTCTCGTCCACAATTCGTTTCAATCTATAGA
AAAGGTGCAGAAACAGGTTTATTCTACCTAATCGCTCGTGTACCTGCTAGCAAAGCAGAGAACAACGT
AATCACTTTCTACGACTTAAACGACTCTATTCCTGAAACAGTAGACGTATTCGTTGGTGAAATGTCGGC
TAACGTAGTACACTTGTTTGAATTACTACCAATGATGAGATTACCTCTAGCTCAAATTAACGCATCTGT
TACATTTGCAGTTTATGGTATGGCGCATTAGCTCTAAGAGCACCTAAGAAATGGGTACGTATTAGAA
ACGTTAAATATATTCCTGTAAAAAACGTTCATAGCAACTAA SEQ ID NO: 18-LP143 Cps protein
MPKNNKEEVKEVNLNSVQEDALKSFTTGYGITPDTQTDAGALRREFLDDQISMLTWTENDLTFYKDIAKK
PATSTVAKYDVYMQHGKVGHTRFTREIGVAPVSDPNIRQKTVNMKFASDTKNISIAAGLVNNIQDPMQILT
DDAIVNIAKTIEWASFFGDSDLSDSPEPQAGLEFDGLAKLINQDNVHDARGASLTESLLNQAAVMISKGYG
TPTDAYMPVGVQADFVNQQLSKQTQLVRDNGNNVSVGFNIQGFHSARGFIKLHGSTVMENEQILDERILAL
PTAPQPAKVTATQEAGKKGQFRAEDLAAHEYKVVVSSDDAESIASEVATATVTAKDDGVKLEIELAPMYS
SRPQFVSIYRKGAETGLFYLIARVPASKAENNVITFYDLNDSIPETVDVFVGEMSANVVHLFELLPMMRLPL
AQINASVTFAVLWYGALALRAPKKWVRIRNVKYIPVKNVHSN SEQ ID NO: 19-A511 Cps open reading frame
ATGCCAAAAAATAACAAAGAAGAAGTTAAAGAAGTAAACCTTAATTCAGTACAAGAGGATGCGTTAA
AGTCCTTTACGACTGGTTATGGTATCACACCTGATACACAAACAGATGCAGGAGCATTAAGACGTGAG
TTCCTAGACGACCAAATCTCAATGCTTACTTGGACAGAGAATGATTTAACATTCTATAAAGACATCGCT
AAAAAACCAGCTACATCTACAGTAGCAAAATACGATGTATACATGCAACATGGTAAGGTAGGTCATA
CTAGATTTACTCGTGAGATTGGGGTAGCACCAGTAAGTGACCCTAACATCCGTCAAAAAACAGTAAAT
ATGAAATTTGCTTCCGATACTAAAAACATCAGTATCGCAGCAGGTCTAGTAAACAACATTCAAGACCC
AATGCAAATTTTGACTGACGATGCTATCGTAAATATTGCTAAAACAATTGAGTGGGCTTCATTCTTTGG
AGATTCTGACTTATCAGATAGCCCAGAACCACAAGCAGGACTAGAATTTGACGGCTTGGCTAAACTTA
TTAACCAAGATAACGTTCATGATGCTCGTGGAGCTAGCTTGACTGAAAGCTTGTTAAACCAAGCAGA
GTAATGATTAGTAAAGGTTATGGTACACCTACAGATGCTTACATGCCAGTAGGGGTTCAAGCAGACTT
TGTTAACCAACAACTTTCTAAACAAACACAACTTGTTCGCGATAACGGAAACAACGTAAGCGTTGGTT
TCAACATCCAAGGTTTCCATTCAGCTCGTGGATTTATCAAACTTCACGGTTCTACAGTAATGGAAAACG
AACAAATCTTAGATGAACGTATTCTTGCTTTACCAACAGCTCCACAACCAGCTAAGGTAACTGCAACA
CAAGAAGCAGGTAAAAAGGACAATTTAGAGCAGAAGATTTAGCAGCACATGAATATAAAGTTGTTG
TAAGTTCTGACGATGCAGAGTCTATTGCAAGTGAAGTGGCTACAGCTACAGTTACTGCAAAAGATGAC
GGCGTTAAACTAGAAATCGAATTAGCTCCAATGTATAGCTCTCGTCCACAATTCGTTTCAATCTATAGA
AAAGGTGCAGAAACAGGTTTATTCTACCTAATCGCTCGTGTACCTGCTAGCAAAGCAGAGAACAACGT
AATCACTTTCTACGACTTAAACGACTCTATTCCTGAAACAGTAGACGTATTCGTTGGTGAAATGTCGGC
TAACGTAGTACACTTGTTTGAATTACTACCAATGATGAGATTACCTCTAGCTCAAATTAACGCATCTGT
TACATTTGCAGTTTATGGTATGGCGCATTAGCTCTAAGAGCACCTAAGAAATGGGTACGTATTAGAA
ACGTTAAATATATTCCTGTAAAAAACGTTCATAGCAACTAA SEQ ID NO: 20-A511 Cps protein
MPKNNKEEVKEVNLNSVQEDALKSFTTGYGITPDTQTDAGALRREFLDDQISMLTWTENDLTFYKDIAKK
PATSTVAKYDVYMQHGKVGHTRFTREIGVAPVSDPNIRQKTVNMKFASDTKNISIAAGLVNNIQDPMQILT
DDAIVNIAKTIEWASFFGDSDLSDSPEPQAGLEFDGLAKLINQDNVHDARGASLTESLLNQAAVMISKGYG
TPTDAYMPVGVQADFVNQQLSKQTQLVRDNGNNVSVGFNIQGFHSARGFIKLHGSTVMENEQILDERILAL
PTAPQPAKVTATQEAGKKGQFRAEDLAAHEYKVVVSSDDAESIASEVATATVTAKDDGVKLEIELAPMYS
SRPQFVSIYRKGAETGLFYLIARVPASKAENNVITFYDLNDSIPETVDVFVGEMSANVVHLFELLPMMRLPL
AQINASVTFAVLWYGALALRAPKKWVRIRNVKYIPVKNVHSN SEQ ID NO: 21-P100 Cps open reading frame
ATGCCAAAAAATAACAAAGAAGAAGAAGTTAAAGAAGTAAACCTTAATTCAGTACAAGAGGACGCGT
TAAAGTCCTTTACAACTGGTTATGGTATCACACCTGATACACAAACAGATGCAGGAGCATTAAGACGT
GAGTTCCTAGACGACCAAATCTCAATGCTTACTTGGACAGAGAATGATTTAACATTCTATAAAGACAT
CGCTAAAAAACCAGCTACATCTACAGTAGCAAAATACGATGTATACATGCAACATGGTAAGGTAGGTC
ATACTAGATTTACTCGTGAGATTGGGGTAGCACCAGTAAGTGACCCTAACATCCGTCAAAAAACAGTA
AATATGAAATTTGCTTCCGATACTAAAAACATCAGTATCGCAGCAGGTCTAGTAAACAACATTCAAGA
CCCAATGCAAATTTTGACTGACGATGCTATCGTAAATATTGCTAAAACAATTGAGTGGGCTTCATTCTT
TGGAGATTCTGACTTATCAGATAGCCCAGAACCACAAGCAGGACTAGAATTTGACGGCTTGGCTAAAC
TTATTAACCAAGATAACGTTCATGATGCTCGTGGAGCTAGCTTGACTGAAAGCTTGTTAAACCAAGCA
GCAGTAATGATTAGTAAAGGTTATGGTACACCTACAGATGCTTACATGCCAGTAGGGGTTCAAGCAGA
CTTTGTTAACCAACAACTTTCTAAACAAACACAGCTTGTTCGTGATAACGGAAACAACGTAAGCGTTG
GTTTCAACATCCAAGGTTTCCATTCAGCTCGTGGATTTATCAAACTTCACGGTTCTACAGTAATGGAAA
ACGAACAAATCTTAGATGAACGTATTCTTGCTTTACCAACAGCTCCACAACCAGCTAAGGTAACTGCA
ACACAAGAAGCAGGTAAAAAGGACAATTTAGAGCAGAAGACTTAGCAGCACACGAATACAAAGTTG
TTGTAAGTTCTGACGATGCAGAGTCTATTGCAAGTGAAGTGGCTACAGCTACAGTTACTGCAAAAGAT
GACGGCGTTAAACTAGAAATCGAGTTAGCTCCAATGTACAGCTCCCGTCCACAATTCGTTTCAATCTAT
AGAAAAGGTGCAGAAACAGGTTTATTCTACCTAATCGCTCGTGTACCTGCTAGCAAAGCAGAGAACAA
CGTAATCACTTTCTATGACTTAAACGACTCTATTCCTGAAACAGTAGACGTATTCGTTGGTGAAATGTC
TGCTAACGTAGTACACTTGTTTGAATTACTACCAATGATGAGATTACCTCTAGCTCAAATTAACGCATC
TGTTACATTTGCAGTTTATGGTATGGAGCATTAGCTCTAAGAGCACCTAAGAAATGGGTACGTATTAG
AAACGTTAAATATATTCCTGTAAAAAACGTTCATAGCAACTAA

INFORMAL SEQUENCE LISTING

SEQ ID NO: 22-P100 Cps protein
MPKNNKEEEVKEVNLNSVQEDALKSFTTGYGITPDTQTDAGALRREFLDDQISMLTWTENDLTFYKDIAK
KPATSTVAKYDVYMQHGKVGHTRFTREIGVAPVSDPNIRQKTVNMKFASDTKNISIAAGLVNNIQDPMQIL
TDDAIVNIAKTIEWASFFGDSDLSDSPEPQAGLEFDGLAKLINQDNVHDARGASLTESLLNQAAVMISKGY
GTPTDAYMPVGVQADFVNQQLSKQTQLVRDNGNNVSVGFNIQGFHSARGFIKLHGSTVMENEQILDERIL
ALPTAPQPAKVTATQEAGKKGQFRAEDLAAHEYKVVVSSDDAESIASEVATATVTAKDDGVKLEIELAPM
YSSRPQFVSIYRKGAETGLFYLIARVPASKAENNVITFYDLNDSIPETVDVFVGEMSANVVHLFELLPMMRL
PLAQINASVTFAVLWYGALALRAPKKWVRIRNVKYIPVKNVHSN SEQ ID NO: 23-LP48::ffluc
ATGCCAAAAAATAACAAAGAAGAAGAAGTTAAAGAAGTAAACCTTAATTCAGTACAAGAGGACGCGT
TAAAGTCCTTTACAACTGGTTATGGTATCACACCTGATACACAAACAGATGCAGGAGCATTAAGACGT
GAGTTCCTAGACGACCAAATCTCAATGCTTACTTGGACAGAGAATGATTTAACATTCTATAAAGACAT
CGCTAAAAAACCAGCTACATCTACAGTAGCAAAATACGATGTATACATGCAACATGGTAAGGTAGGTC
ATACTAGATTTACTCGTGAGATTGGGGTAGCACCAGTAAGTGACCCTAACATCCGTCAAAAAACAGTA
AACATGAAATTTGCTTCCGATACTAAAAACATCAGTATCGCAGCAGGTCTAGTAAACAACATTCAAGA
CCCAATGCAAATTTGACTGACGATGCTATCGTAAATATTGCTAAAACAATTGAGTGGGCTTCATTCTT
TGGAGATTCTGACTTATCAGATAGCCCAGAACCACAAGCAGGACTAGAATTTGACGGCTTGGCTAAAC
TTATTAACCAAGATAACGTTCATGATGCTCGTGGAGCTAGCTTGACTGAAAGCTTGTTAAACCAAGCA
GCAGTAATGATTAGTAAAGGTTATGGTACACCTACAGATGCTTACATGCCAGTAGGGGTTCAAGCAGA
CTTTGTTAACCAACAACTTTCTAAACAAACACAACTTGTTCGCGATAACGGAAACAACGTAAGCGTTG
GTTTCAACATCCAAGGTTTCCATTCAGCTCGTGGATTTATCAAACTTCACGGTTCTACAGTAATGGAAA
ACGAACAAATCTTAGATGAACGTATTCTTGCTTTACCAACAGCTCCACAACCAGCTAAGGTAACTGCA
ACACAAGAAGCAGGTAAAAAAGGACAATTTAGAGCAGAAGATTTAGCAGCACATGAATATAAAGTTG
TTGTAAGTTCTGACGATGCAGAGTCTATTGCAAGTGAAGTGGCTACAGCTACAGTTACTGCAAAAGAT
GACGGCGTTAAACTAGAAATCGAATTAGCTCCAATGTATAGCTCTCGTCCACAATTCGTTTCAATCTAT
AGAAAAGGTGCAGAAACAGGTTTATTCTACCTAATCGCTCGTGTACCTGCTAGCAAAGCAGAGAACAA
CGTAATCACTTTCTACGACTTAAACGACTCTATTCCTGAAACAGTAGACGTATTCGTTGGTGAAATGTC
GGCTAACGTAGTACACTTGTTTGAATTACTACCAATGATGAGATTACCTCTAGCTCAAATTAACGCATC
TGTTACATTTGCAGTTTTATGGTATGGCGCATTAGCTCTAAGAGCACCTAAGAAATGGGTACGTATTAG
AAACGTTAAATATATTCCTGTAAAAAACGTTCATAGCAACTAAGAGGAGGTAAATATATATGGAAGAC
GCCAAAAACATAAAGAAAGGCCCGGCGCCATTCTATCCTCTAGAGGATGAACCGCTGGAGAGCAAC
TGCATAAGGCTATGAAGAGATACGCCCTGGTTCCTGGAACAATTGCTTTTACAGATGCACATATCGAG
GTGAACATCACGTACGCGGAATACTTCGAAATGTCCGTTCGGTTGGCAGAAGCTATGAAACGATATGG
GCTGAATACAAATCACAGAATCGTCGTATGCAGTGAAAACTCTCTTCAATTCTTTATGCCGGTGTTGGG
CGCGTTATTTATCGGAGTTGCAGTTGCGCCCGCGAACGACATTTATAATGAACGTGAATTGCTCAACA
GTATGAACATTTCGCAGCCTACCGTAGTGTTTGTTTCCAAAAAGGGGTTGCAAAAAATTTTGAACGTG
CAAAAAAAATTACCAATAATCCAGAAAATTATTATCATGGATTCTAAAACGGATTACCAGGGATTTCA
GTCGATGTACACGTTCGTCACATCTCATCTACCTCCCGGTTTTAATGAATACGATTTTGTACCAGAGTC
CTTTGATCGTGACAAAACAATTGCACTGATAATGAATTCCTCTGGATCTACTGGGTTACCTAAGGGTGT
GGCCCTTCCGCATAGAACTGCCTGCGTCAGATTCTCGCATGCCAGAGATCCTATTTTTGGCAATCAAAT
CATTCCGGATACTGCGATTTTAAGTGTTGTTCCATTCCATCACGGTTTTGGAATGTTTACTACACTCGG
ATATTTGATATGTGGATTTCGAGTCGTCTTAATGTATAGATTTGAAGAAGAGCTGTTTTTACGATCCCT
TCAGGATTACAAAATTCAAAGTGCGTTGCTAGTACCAACCCTATTTTCATTCTTCGCCAAAAGCACTCT
GATTGACAAATACGATTTATCTAATTTACACGAAATTGCTTCTGGGGGCGCACCTCTTTCGAAAGAAGT
CGGGGAAGCGGTTGCAAAACGCTTCCATCTTCCAGGGGATACGACAAGCGATATGGGCTCACTGAGACTA
CATCAGCTATTCTGATTACACCCGAGGGGGATGATAAACCGGGCGCGGTCGGTAAAGTTGTTCCATTT
TTTGAAGCGAAGGTTGTGGATCTGGATACCGGGAAAACGCTGGGCGTTAATCAGAGAGGCGAATTAT
GTGTCAGAGGACCTATGATTATGTCCGGTTATGTAAACAATCCGGAAGCGACCAACGCCTTGATTGAC
AAGGATGGATGGCTACATTCTGGAGACATAGCTTACTGGGACGAAGACGAACACTTCTTCATAGTTGA
CCGCTTGAAGTCTTTAATTAAATACAAAGGATATCAGGTGGCCCCCGCTGAATTGGAATCGATATTGTT
ACAACACCCCAACATCTTCGACGCGGGCGTGGCAGGTCTTCCCGACGATGACGCCGGTGAACTTCCAG
CCGCCGTTGTTGTTTTGGAGCACGGAAAGACGATGACGGAAAAAGAGATCGTGGATTACGTCGCCAGT
CAAGTAACAACCGCGAAAAAGTTGCGCGGAGGAGTTGTGTTTGTGGACGAAGTACCGAAAGGTCTTA
CCGGAAAACTCGACGCAAGAAAATCAGAGAGATCCTCATAAAGGCCAAGAAGGGCGGAAAGTCCA
AATTGTAATAATTATAGGATAATTGAATAAAAACAGTATAGAGAGCAGATAAATACTGCTCTCTATTT
TACTAATAAGGAGGATTTAAATTGCTAAAAAATACAAACTTAGCTAATTATAAAAAAGTGAATACACG
GTTTGGAAATCTTAGTTTTGACGACAAAGGTATTTCTAATGACTTAACGGAAGAACAGCAAAAAGAAT
TAGGTAAGCTTCGAGGATTCGAATATATTAAGACAGAACAGAAAACAAAAGAAGAACCTAAGAAAGA
AGAACCTAAGAAAGAAGTACAGAAAATGAATTAGACAGCTTCTTAGCTAAAGAGCCTTCAATCAAA
GAATTAAAAGAATTTGCGAGTAAAAAAGGCATTAAAATTGAAAAAACTAAGAAAAATGATATAATTG
AAGAACTAAAGAGAGGGTAATGTATAATGTATGGAGGTTATGAAGGACAAGATTCTTACGAATACCC
TTACTCACATGGGAACCCTAAGCATGTAGAGCCAGAAAAAGTTGACGAATATGTTCTTTCTGATTATG
GTTGGACTGCGGAAACAATTAAAGCATACATGTATGGTGTTCGTGTAGTAGACCCTGAAACAGGAGAG
GAAATGGGAGACACCTTCTACAATCATATTATAGAGGTTGCCGTTGATAAGGC SEQ ID NO: 24-LP99::ffluc
ATGCCAAAAAATAACAAAGAAGAAGAAGTTAAAGAAGTAAACCTTAATTCAGTACAAGAGGACGCGT
TAAAGTCCTTTACAACTGGTTATGGTATCACACCTGATACACAAACAGATGCAGGAGCATTAAGACGT
GAGTTCCTAGACGACCAAATCTCAATGCTTACTTGGACAGAGAATGATTTAACATTCTATAAAGACAT
CGCTAAAAAACCAGCTACATCTACAGTAGCAAAATACGATGTATACATGCAACATGGTAAGGTAGGTC
ATACTAGATTTACTCGTGAGATTGGGGTAGCACCAGTAAGTGACCCTAACATCCGTCAAAAAACAGTA
AACATGAAATTTGCTTCCGATACTAAAAACATCAGTATCGCAGCAGGTCTAGTAAACAACATTCAAGA
CCCAATGCAAATTTGACTGACGATGCTATCGTAAATATTGCTAAAACAATTGAGTGGGCTTCATTCTT
TGGAGATTCTGACTTATCAGATAGCCCAGAACCACAAGCAGGACTAGAATTTGACGGCTTGGCTAAAC
TTATTAACCAAGATAACGTTCATGATGCTCGTGGAGCTAGCTTGACTGAAAGCTTGTTAAACCAAGCA
GCAGTAATGATTAGTAAAGGTTATGGTACACCTACAGATGCTTACATGCCAGTAGGGGTTCAAGCAGA

| INFORMAL SEQUENCE LISTING |
|---|
| CTTTGTTAACCAACAACTTTCTAAACAAACACAACTTGTTCGCGATAACGGAAACAACGTAAGCGTTG |
| GTTTCAACATCCAAGGTTTCCATTCAGCTCGTGGATTTATCAAACTTCACGGTTCTACAGTAATGGAAA |
| ACGAACAAATCTTAGATGAACGTATTCTTGCTTTACCAACAGCTCCACAACCAGCTAAGGTAACTGCA |
| ACACAAGAAGCAGGTAAAAAAGGACAATTTAGAGCAGAAGATTTAGCAGCACATGAATATAAAGTTG |
| TTGTAAGTTCTGACGATGCAGAGTCTATTGCAAGTGAAGTGGCTACAGCTACAGTTACTGCAAAAGAT |
| GACGGCGTTAAACTAGAAATCGAATTAGCTCCAATGTATAGCTCTCGTCCACAATTCGTTTCAATCTAT |
| AGAAAAGGTGCAGAAACAGGTTTATTCTACCTAATCGCTCGTGTACCTGCTAGCAAAGCAGAGAACAA |
| CGTAATCACTTTCTACGACTTAAACGACTCTATTCCTGAAACAGTAGACGTATTCGTTGGTGAAATGTC |
| GGCTAACGTAGTACACTTGTTTGAATTACTACCAATGATGAGATTACCTCTAGCTCAAATTAACGCATC |
| TGTTACATTTGCAGTTTATGGTATGGCGCATTAGCTCTAAGAGCACCTAAGAAATGGGTACGTATTAG |
| AAACGTTAAATATATTCCTGTAAAAAACGTTCATAGCAACTAAGAGGAGGTAAATATATATGGAAGAC |
| GCCAAAAACATAAAGAAAGGCCCGGCGCCATTCTATCCTCTAGAGGATGGAACCGCTGGAGAGCAAC |
| TGCATAAGGCTATGAAGAGATACGCCCTGGTTCCTGGAACAATTGCTTTTACAGATGCACATATCGAG |
| GTGAACATCACGTACGCGGAATACTTCGAAATGTCCGTTCGGTTGGCAGAAGCTATGAAACGATATGG |
| GCTGAATACAAATCACAGAATCGTCGTATGCAGTGAAAACTCTCTTCAATTCTTTATGCCGGTGTTGGG |
| CGCGTTATTTATCGGAGTTGCAGTTGCGCCCGCGAACGACATTTATAATGAACGTGAATTGCTCAACA |
| GTATGAACATTTCGCAGCCTACCGTAGTGTTTGTTTCCAAAAAGGGGTTGCAAAAAATTTTGAACGTG |
| CAAAAAAAATTACCAATAATCCAGAAAATTATTATCATGGATTCTAAAACGGATTACCAGGGATTTCA |
| GTCGATGTACACGTTCGTCACATCTCATCTACCTCCCGGTTTTAATGAATACGATTTTGTACCAGAGTC |
| CTTTGATCGTGACAAAACAATTGCACTGATAATGAATTCCTCTGGATCTACTGGGTTACCTAAGGGTGT |
| GGCCCTTCCGCATAGAACTGCCTGCGTCAGATTCTCGCATGCCAGAGATCCTATTTTTGGCAATCAAAT |
| CATTCCGGATACTGCGATTTTAAGTGTTGTTCCATTCCATCACGGTTTTGGAATGTTTACTACACTCGG |
| ATATTTGATATGTGGATTTCGAGTCGTCTTAATGTATAGATTTGAAGAAGAGCTGTTTTTACGATCCCT |
| TCAGGATTACAAAATTCAAAGTGCGTTGCTAGTACCAACCCTATTTTCATTCTTCGCCAAAAGCACTCT |
| GATTGACAAATACGATTTATCTAATTTACACGAAATTGCTTCTGGGGGCGCACCTCTTTCGAAAGAAGT |
| CGGGGAAGCGGTTGCAAAACGCTTCCATCTTCCAGGGATACGACAAGGATATGGGCTCACTGAGACTA |
| CATCAGCTATTCTGATTACACCCGAGGGGGATGATAAACCGGGCGCGGTCGGTAAAGTTGTTCCATTT |
| TTTGAAGCGAAGGTTGTGGATCTGGATACCGGGAAAACGCTGGGCGTTAATCAGAGAGGCGAATTAT |
| GTGTCAGAGGACCTATGATTATGTCCGGTTATGTAAACAATCCGGAAGCGACCAACGCCTTGATTGAC |
| AAGGATGGATGGCTACATTCTGGAGACATAGCTTACTGGGACGAAGACGAACACTTCTTCATAGTTGA |
| CCGCTTGAAGTCTTTAATTAAATACAAAGGATATCAGGTGGCCCCCGCTGAATTGGAATCGATATTGTT |
| ACAACACCCCAACATCTTCGACGCGGGCGTGGCAGGTCTTCCCGACGATGACGCCGGTGAACTTCCCG |
| CCGCCGTTGTTGTTTTGGAGCACGGAAAGACGATGACGGAAAAAGAGATCGTGGATTACGTCGCCAGT |
| CAAGTAACAACCGCGAAAAAGTTGCGCGGAGGAGTTGTGTTTGTGGACGAAGTACCGAAAGGTCTTA |
| CCGGAAAACTCGACGCAAGAAAATCAGAGAGATCCTCATAAAGGCCAAGAAGGGCGGAAAGTCCA |
| AATTGTAATAATTATAGGATAATTGAATAAAAACAGTATAGAGCAGATAATACTGCTCTCTATTT |
| TACTAATAAGGAGGATTTAAATTGCTAAAAAATACAAACTTAGCTAATTATAAAAAAGTGAATACACG |
| GTTTGGAAATCTTAGTTTTGACGACAAAGGTATTTCTAATGACTTAACGGAAGAACAGCAAAAAGAAT |
| TAGGTAAGCTTCGAGGATTCGAATATATTAAGACAGAACAGAAAACAAAAGAAGAACCTAAGAAAGA |
| AGAACCTAAGAAAGAAGAACCTAAGAAAGAAGAACCTAAGAAAGAAGAACCTAAGAAAGAAGAACC |
| TAAGAAAGAAAGTACAGAAAATGAATTAGACAGCTTCTTAGCTAAAGAAGCCTTCAATCAAAGAATTA |
| AAAGAATTTGCGAGTAAAAAAGGCATTAAAATTGAAAAAACTAAGAAAAATGATATAATTGAAGAAC |
| TAAAGAGAGGGTAATGTATAATGTATGGAGGTTATGAAGGACAAGATTCTTACGAATACCCTTACTCA |
| CATGGGAACCCTAAGCATGTAGAGCCAGAAAAAGTTGACGAATATGTTCTTTCTGATTATGGTTGGAC |
| TGCGGAAACAATTAAAGCATACATGTATGGTGTTCGTGTAGTAGACCCTGAAACAGGAGAGGAAATG |
| GGAGACACCTTCTACAATCATATTATAGAGGTTGCCGTTGATAAGGC |

SEQ ID NO: 25-LP101::ffluc
ATGCCAAAAAATAACAAGAAGAAGAAGTTAAAGAAGTAAACCTTAATTCAGTACAAGAGGACGCGT
TAAAGTCCTTTACAACTGGTTATGGTATCACACCTGATACACAAACAGATGCAGGAGCATTAAGACGT
GAGTTCCTAGACGACCAAATCTCAATGCTTACTTGGACAGAGAATGATTTAACATTCTATAAAGACAT
CGCTAAAAAACCAGCTACATCTACAGTAGCAAAATACGATGTATACATGCAACATGGTAAGGTAGGTC
ATACTAGATTTACTCGTGAGATTGGGGTAGCACCAGTAAGTGACCCTAACATCCGTCAAAAAACAGTA
AACATGAAATTTGCTTCCGATACTAAAAACATCAGTATCGCAGCAGGTCTAGTAAACAACATTCAAGA
CCCAATGCAAATTTTGACTGACGATGCTATCGTAAATATTGCTAAACAATTGAGTGGGCTTCATTCTT
TGGAGATTCTGACTTATCAGATAGCCCAGAACCACAAGCAGGACTAGAATTTGACGGCTTGGCTAAAC
TTATTAACCAAGATAACGTTCATGATGCTCGTGGAGCTAGCTTGACTGAAAAGCTTGTTAAACAAGCA
GCAGTAATGATTAGTAAAGGTTATGGTACACCTACAGATGCTTACATGCCAGTAGGGGTTCAAGCAGA
CTTTGTTAACCAACAACTTTCTAAACAAACACAACTTGTTCGCGATAACGGAAACAACGTAAGCGTTG
GTTTCAACATCCAAGGTTTCCATTCAGCTCGTGGATTTATCAAACTTCACGGTTCTACAGTAATGGAAA
ACGAACAAATCTTAGATGAACGTATTCTTGCTTTACCAACAGCTCCACAACCAGCTAAGGTAACTGCA
ACACAAGAAGCAGGTAAAAAAGGACAATTTAGAGCAGAAGATTTAGCAGCACATGAATATAAAGTTG
TTGTAAGTTCTGACGATGCAGAGTCTATTGCAAGTGAAGTGGCTACAGCTACAGTTACTGCAAAAGAT
GACGGCGTTAAACTAGAAATCGAATTAGCTCCAATGTATAGCTCTCGTCCACAATTCGTTTCAATCTAT
AGAAAAGGTGCAGAAACAGGTTTATTCTACCTAATCGCTCGTGTACCTGCTAGCAAAGCAGAGAACAA
CGTAATCACTTTCTACGACTTAAACGACTCTATTCCTGAAACAGTAGACGTATTCGTTGGTGAAATGTC
GGCTAACGTAGTACACTTGTTTGAATTACTACCAATGATGAGATTACCTCTAGCTCAAATTAACGCATC
TGTTACATTTGCAGTTTATGGTATGGCGCATTAGCTCTAAGAGCACCTAAGAAATGGGTACGTATTAG
AAACGTTAAATATATTCCTGTAAAAAACGTTCATAGCAACTAAGAGGAGGTAAATATATATGGAAGAC
GCCAAAAACATAAAGAAAGGCCCGGCGCCATTCTATCCTCTAGAGGATGGAACCGCTGGAGAGCAAC
TGCATAAGGCTATGAAGAGATACGCCCTGGTTCCTGGAACAATTGCTTTTACAGATGCACATATCGAG
GTGAACATCACGTACGCGGAATACTTCGAAATGTCCGTTCGGTTGGCAGAAGCTATGAAACGATATGG
GCTGAATACAAATCACAGAATCGTCGTATGCAGTGAAAACTCTCTTCAATTCTTTATGCCGGTGTTGGG
CGCGTTATTTATCGGAGTTGCAGTTGCGCCCGCGAACGACATTTATAATGAACGTGAATTGCTCAACA
GTATGAACATTTCGCAGCCTACCGTAGTGTTTGTTTCCAAAAAGGGGTTGCAAAAAATTTTGAACGTG
CAAAAAAAATTACCAATAATCCAGAAAATTATTATCATGGATTCTAAAACGGATTACCAGGGATTTCA
GTCGATGTACACGTTCGTCACATCTCATCTACCTCCCGGTTTTAATGAATACGATTTTGTACCAGAGTC

| INFORMAL SEQUENCE LISTING |
|---|
| CTTTGATCGTGACAAAACAATTGCACTGATAATGAATTCCTCTGGATCTACTGGGTTACCTAAGGGTGT |
| GGCCCTTCCGCATAGAACTGCCTGCGTCAGATTCTCGCATGCCAGAGATCCTATTTTTGGCAATCAAAT |
| CATTCCGGATACTGCGATTTTAAGTGTTGTTCCATTCCATCACGGTTTTGGAATGTTTACTACACTCGG |
| ATATTTGATATGTGGATTTCGAGTCGTCTTAATGTATAGATTTGAAGAAGAGCTGTTTTTACGATCCCT |
| TCAGGATTACAAAATTCAAAGTGCGTTGCTAGTACCAACCCTATTTTCATTCTTCGCCAAAAGCACTCT |
| GATTGACAAATACGATTTATCTAATTTACACGAAATTGCTTCTGGGGGCGCACCTCTTTCGAAAGAAGT |
| CGGGGAAGCGGTTGCAAAACGCTTCCATCTTCCAGGGATACGACAAGGATATGGGCTCACTGAGACTA |
| CATCAGCTATTCTGATTACACCCGAGGGGGATGATAAACCGGGCGCGGTCGGTAAAGTTGTTCCATTT |
| TTTGAAGCGAAGGTTGTGGATCTGGATACCGGGAAAACGCTGGGCGTTAATCAGAGAGGCGAATTAT |
| GTGTCAGAGGACCTATGATTATGTCCGGTTATGTAAACAATCCGGAAGCGACCAACGCCTTGATTGAC |
| AAGGATGGATGGCTACATTCTGGAGACATAGCTTACTGGGACGAAGACGAACACTTCTTCATAGTTGA |
| CCGCTTGAAGTCTTTAATTAAATACAAAGGATATCAGGTGGCCCCCGCTGAATTGGAATCGATATTGTT |
| ACAACACCCCAACATCTTCGACGCGGGCGTGGCAGGTCTTCCCGACGATGACGCCGGTGAACTTCCCG |
| CCGCCGTTGTTGTTTGGAGCACGGAAAGACGATGACGGAAAAAGAGATCGTGGATTACGTCGCCAGT |
| CAAGTAACAACCGCGAAAAAGTTGCGCGGAGGAGTTGTGTTTGTGGACGAAGTACCGAAAGGTCTTA |
| CCGGAAAACTCGACGCAAGAAAAATCAGAGAGATCCTCATAAAGGCCAAGAAGGGCGGAAAGTCCA |
| AATTGTAATAATTATAGGATAATTGAATAAAAACAGTATAGAGAGCAGATAAATACTGCTCTCTATTT |
| TACTAATAAGGAGGATTTAAATTGCTAAAAAATACAAACTTAGCTAATTATAAAAAAGTGAATACACG |
| GTTTGGAAATCTTAGTTTTGACGACAAAGGTATTTCTAATGACTTAACGGAAGAACAGCAAAAAGAAT |
| TAGGTAAGCTTCGAGGATTCGAATATATTAAGACAGAACAGAAACAAAAGAAGAACCTAAGAAAGA |
| AGAACCTAAGAAAGAAGAACCTAAGAAAGAAGAACCTAAGAAAGAAGAACCTAAGAAAGAAGAACC |
| TAAGAAAGAAAGTACAGAAAATGAATTAGACAGCTTCTTAGCTAAAGAGCCTTCAATCAAAGAATTA |
| AAAGAATTTGCGAGTAAAAAAGGCATTAAAATTGAAAAAACTAAGAAAAATGATATAATTGAAGAAC |
| TAAAGAGAGGGTAATGTATAATGTATGGAGGTTATGAAGGACAAGATTCTTACGAATACCCTTACTCA |
| CATGGGAACCCTAAGCATGTAGAGCCAGAAAAAGTTGACGAATATGTTCTTTCTGATTATGGTTGGAC |
| TGCGGAAACAATTAAAGCATACATGTATGGTGTTCGTGTAGTAGACCCTGAAACAGGAGAGGAAATG |
| GGAGACACCTTCTACAATCATATTATAGAGGTTGCCGTTGATAAGGC |

SEQ ID NO: 26-LP124::ffluc
| ATGCCAAAAAATAACAAAGAAGAAGAAGTTAAAGAAGTAAAACCTTAATTCAGTACAAGAGGACGCGT |
|---|
| TAAAGTCCTTTACAACTGGTTATGGTATCACACCTGATACACAAACAGATGCAGGAGCATTAAGACGT |
| GAGTTCCTAGACGACCAAATCTCAATGCTTACTTGGACAGAGAATGATTTAACATTCTATAAAGACAT |
| CGCTAAAAAACCAGCTACATCTACAGTAGCAAAATACGATGTATACATGCAACATGGTAAGGTAGGTC |
| ATACTAGATTACTCGTGAGATTGGGGTAGCACCAGTAAGTGACCCTAACATCCGTCAAAAAACAGTA |
| AACATGAAATTTGCTTCCGATACTAAAAACATCAGTATCGCAGCAGGTCTAGTAAACAACATTCAAGA |
| CCCAATGCAAATTTTGACTGACGATGCTATCGTAAATATTGCTAAAACAATTGAGTGGGCTTCATTCTT |
| TGGAGATTCTGACTTATCAGATAGCCCAGAACCACAAGCAGGACTAGAATTTGACGGCTTGGCTAAAC |
| TTATTAACCAAGATAACGTTCATGATGCTCGTGGAGCTAGCTTGACTGAAAGCTTGTTAAACCAAGCA |
| GCAGTAATGATTAGTAAAGGTTATGGTACACCTACAGATGCTTACATGCCAGTAGGGGTTCAAGCAGA |
| CTTTGTTAACCAACAACTTTCTAAACAAACAACAACTTGTTCGCGATAACGGAACAACGTAAGCGTTG |
| GTTTCAACATCCAAGGTTTCCATTCAGCTCGTGGATTTATCAAACTTCACGGTTCTACAGTAATGAAA |
| ACGAACAAATCTTAGATGAACGTATTCTTGCTTTACCAACAGCTCCACAACCAGCTAAGGTAACTGCA |
| ACACAAGAAGCAGGTAAAAAAGGACAATTTAGAGCAGAAGATTTAGCAGCACATGAATATAAAGTTG |
| TTGTAAGTTCTGACGATGCAGAGTCTATTGCAAGTGAAGTGGCTACAGCTACAGTTACTGCAAAAGAT |
| GACGGCGTTAAACTAGAAATCGAATTAGCTCCAATGTATAGCTCTCGTCCACAATTCGTTTCAATCTAT |
| AGAAAAGGTGCAGAAACAGGTTTATTCTACCTAATCGCTCGTGTACCTGCTAGCAAAGCAGAGAACAA |
| CGTAATCACTTTCTACGACTTAAACGACTCTATTCCTGAAACAGTAGACGTATTCGTTGGTGAAATGTC |
| GGCTAACGTAGTACACTTGTTTGAATTACTACCAATGATGAGATTACCTCTAGCTCAAATTAACGCATC |
| TGTTACATTTGCAGTTTTATGGTATGGCCATTAGCTCTAAGAGCACCTAAGAAATGGGTACGTATTAG |
| AAACGTTAAATATATTCCTGTAAAAAACGTTCATAGCAACTAAGAGGAGGTAAATATATATGGAAGAC |
| GCCAAAAACATAAAGAAAGGCCCGGCGCCATTCTATCCTCTAGAGGATGGAACCGCTGGAGAGCAAC |
| TGCATAAGGCTATGAAGAGATACGCCCTGGTTCCTGGAACAATTGCTTTTACAGATGCACATATCGAG |
| GTGAACATCACGTACGCGGAATACTTCGAAATGTCCGTTCGGTTGGCAGAAGCTATGAAACGATATGG |
| GCTGAATACAAATCACAGAATCGTCGTATGCAGTGAAAACTCTCTTCAATTCTTTATGCCGGTGTTGGG |
| CGCGTTATTTATCGGAGTTGCAGTTGCGCCCGCGAACGACATTTATAATGAACGTGAATTGCTCAACA |
| GTATGAACATTTCGCAGCCTACCGTAGTGTTTGTTTCCAAAAAGGGGTTGCAAAAAATTTTGAACGTG |
| CAAAAAAAATTACCAATAATCCAGAAAATTATTATCATGGATTCTAAAACGGATTACCAGGGATTTCA |
| GTCGATGTACACGTTCGTCACATCTCATCTACCTCCCGGTTTTAATGAATACGATTTTGTACCAGAGTC |
| CTTTGATCGTGACAAAACAATTGCACTGATAATGAATTCCTCTGGATCTACTGGGTTACCTAAGGGTGT |
| GGCCCTTCCGCATAGAACTGCCTGCGTCAGATTCTCGCATGCCAGAGATCCTATTTTTGGCAATCAAAT |
| CATTCCGGATACTGCGATTTTAAGTGTTGTTCCATTCCATCACGGTTTTGGAATGTTTACTACACTCGG |
| ATATTTGATATGTGGATTTCGAGTCGTCTTAATGTATAGATTTGAAGAAGAGCTGTTTTTACGATCCCT |
| TCAGGATTACAAAATTCAAAGTGCGTTGCTAGTACCAACCCTATTTTCATTCTTCGCCAAAAGCACTCT |
| GATTGACAAATACGATTTATCTAATTTACACGAAATTGCTTCTGGGGGCGCACCTCTTTCGAAAGAAGT |
| CGGGGAAGCGGTTGCAAAACGCTTCCATCTTCCAGGGATACGACAAGGATATGGGCTCACTGAGACTA |
| CATCAGCTATTCTGATTACACCCGAGGGGGATGATAAACCGGGCGCGGTCGGTAAAGTTGTTCCATTT |
| TTTGAAGCGAAGGTTGTGGATCTGGATACCGGGAAAACGCTGGGCGTTAATCAGAGAGGCGAATTAT |
| GTGTCAGAGGACCTATGATTATGTCCGGTTATGTAAACAATCCGGAAGCGACCAACGCCTTGATTGAC |
| AAGGATGGATGGCTACATTCTGGAGACATAGCTTACTGGGACGAAGACGAACACTTCTTCATAGTTGA |
| CCGCTTGAAGTCTTTAATTAAATACAAAGGATATCAGGTGGCCCCCGCTGAATTGGAATCGATATTGTT |
| ACAACACCCCAACATCTTCGACGCGGGCGTGGCAGGTCTTCCCGACGATGACGCCGGTGAACTTCCCG |
| CCGCCGTTGTTGTTTGGAGCACGGAAAGACGATGACGGAAAAAGAGATCGTGGATTACGTCGCCAGT |
| CAAGTAACAACCGCGAAAAAGTTGCGCGGAGGAGTTGTGTTTGTGGACGAAGTACCGAAAGGTCTTA |
| CCGGAAAACTCGACGCAAGAAAAATCAGAGAGATCCTCATAAAGGCCAAGAAGGGCGGAAAGTCCA |
| AATTGTAATAATTATAGGATAATTGAATAAAAACAGTATAGAGAGCAGATAAATACTGCTCTCTATTT |
| TACTAATAAGGAGGATTTAAATTGCTAAAAAATACAAACTTAGCTAATTATAAAAAAGTGAATACACG |
| GTTTGGAAATCTTAGTTTTGACGACAAAGGTATTTCTAATGACTTAACGGAAGAACAGCAAAAAGAAT |

| INFORMAL SEQUENCE LISTING |
| --- |
| TAGGTAAGCTTCGAGGATTCGAATATATTAAGACAGAACAGAAAACAAAAGAAGAACCTAAGAAAGA
AGAACCTAAGAAAGAAGAACCTAAGAAAGAAGAACCTAAGAAAGAAGAACCTAAGAAAGAAGAACC
TAAGAAAGAAAGTACAGAAAATGAATTAGACAGCTTCTTAGCTAAAGAGCCTTCAATCAAAGAATTA
AAAGAATTTGCGAGTAAAAAAGGCATTAAAATTGAAAAAACTAAGAAAAATGATATAATTGAAGAAC
TAAAGAGAGGGTAATGTATAATGTATGGAGGTTATGAAGGACAAGATTCTTACGAATACCCTTACTCA
CATGGGAACCCTAAGCATGTAGAGCCAGAAAAAGTTGACGAATATGTTCTTTCTGATTATGGTTGGAC
TGCGGAAACAATTAAAGCATACATGTATGGTGTTCGTGTAGTAGACCCTGAAACAGGAGAGGAAATG
GGAGACACCTTCTACAATCATATTATAGAGGTTGCCGTTGATAAGGC

SEQ ID NO: 27-LP125::ffluc
ATGCCAAAAAATAACAAAGAAGAAGTTAAAGAAGTAAACCTTAATTCAGTACAAGAGGACGCGT
TAAAGTCCTTTACAACTGGTTATGGTATCACACCTGATACACAAACAGATGCAGGAGCATTAAGACGT
GAGTTCCTAGACGACCAAATCTCAATGCTTACTTGGACAGAGAATGATTTAACATTCTATAAAGACAT
CGCTAAAAAACCAGCTACATCTACAGTAGCAAAATACGATGTATACATGCAACATGGTAAGGTAGGTC
ATACTAGATTTACTCGTGAGATTGGGGTAGCACCAGTAAGTGACCCTAACATCCGTCAAAAAACAGTA
AACATGAAATTTGCTTCCGATACTAAAAACATCAGTATCGCAGCAGGTCTAGTAAACAACATTCAAGA
CCCAATGCAAATTTGACTGACGATGCTATCGTAAATATTGCTAAAACAATTGAGTGGGCTTCATTCTT
TGGAGATTCTGACTTATCAGATAGCCCAGAACCACAAGCAGGACTAGAATTTGACGGCTTGGCTAAAC
TTATTAACCAAGATAACGTTCATGATGCTCGTGGAGCTAGCTTGACTGAAAGCTTGTTAAACCAAGCA
GCAGTAATGATTAGTAAAGGTTATGGTACACCTACAGATGCTTACATGCCAGTAGGGGTTCAAGCAGA
CTTTGTTAACCAACAACTTTCTAAACAAACACAACTTGTTCGTGATAACGGAAACAACGTAAGCGTTG
GTTTCAACATCCAAGGTTTCCATTCAGCTCGTGGATTATCAAACTTCACGGTTCTACAGTAATGGAAA
ACGAACAAATCTTAGATGAACGTATTCTTGCTTTACCAACAGCTCCACAACCAGCTAAGGTAACTGCA
ACACAAGAAGCAGGTAAAAAAGGCACAATTTAGAGCAGAAGATTTAGCAGCACATGAATATAAAGTTG
TTGTAAGTTCTGACGATGCAGAGTCTATTGCAAGTGAAGTGGCTACAGCTACAGTTACTGCAAAAGAT
GACGGCGTTAAACTAGAAATCGAATTAGCTCCAATGTATAGCTCTCGTCCACAATTCGTTTCAATCTAT
AGAAAAGGTGCAGAAACAGGTTTATTCTACCTAATCGCTCGTGTACCTGCTAGCAAAGCAGAGAACAA
CGTAATCACTTTCTACGACTTAAACGACTCTATTCCTGAAACAGTAGACGTATTCGTTGGTGAAATGTC
GGCTAACGTAGTACACTTGTTTGAATTACTACCAATGATGAGATTACCTCTAGCTCAAATTAACGCATC
TGTTACATTTGCAGTTTTATGGTATGGCGCATTAGCTCTAAGAGCACCTAAGAAATGGGTACGTATTAG
AAACGTTAAATATATTCCTGTAAAAAACGTTCATAGCAACTAAGAGGAGGTAAATATATATGGAAGAC
GCCAAAAACATAAAGAAAGGCCCGGCGCCATTCTATCCTCTAGAGGATGAACCGCTGGAGAGCAAC
TGCATAAGGCTATGAAGAGATACGCCCTGGTTCCTGGAACAATTGCTTTTACAGATGCACATATCGAG
GTGAACATCACGTACGCGGAATACTTCGAAATGTCCGTTCGGTTGGCAGAAGCTATGAAACGATATGG
GCTGAATACAAATCACAGAATCGTCGTATGCAGTGAAAACTCTCTTCAATTCTTTATGCCGGTGTTGGG
CGCGTTATTTATCGGAGTTGCAGTTGCGCCCGCGAACGACATTTATAATGAACGTGAATTGCTCAACA
GTATGAACATTTCGCAGCCTACCGTAGTGTTTGTTTCCAAAAAGGGGTTGCAAAAAATTTTGAACGTG
CAAAAAAAATTACCAATAATCCAGAAAATTATTATCATGGATTCTAAAACGGATTACCAGGGATTTCA
GTCGATGTACACGTTCGTCACATCTCATCTACCTCCCGGTTTTAATGAATACGATTTTGTACCAGAGTC
CTTTGATCGTGACAAAACAATTGCACTGATAATGAATTCCTCTGGATCTACTGGGTTACCTAAGGGTGT
GGCCCTTCCGCATAGAACTGCCTGCGTCAGATTCTCGCATGCCAGAGATCCTATTTTTGGCAATCAAAT
CATTCCGGATACTGCGATTTTAAGTGTTGTTCCATTCCATCACGGTTTTGGAATGTTTACTACACTCGG
ATATTTGATATGTGGATTTCGAGTCGTCTTAATGTATAGATTTGAAGAAGAGCTGTTTTTACGATCCCT
TCAGGATTACAAAATTCAAAGTGCGTTGCTAGTACCAACCCTATTTTCATTCTTCGCCAAAAGCACTCT
GATTGACAAATACGATTTATCTAATTTACACGAAATTGCTTCTGGGGGCGCACCTCTTTCGAAAGAAGT
CGGGGAAGCGGTTGCAAAACGCTTCCATCTTCCAGGGATACGACAAGGATATGGGCTCACTGAGACTA
CATCAGCTATTCTGATTACACCCGAGGGGGATGATAAACCGGGCGCGGTCGGTAAAGTTGTTCCATTT
TTTGAAGCGAAGGTTGTGGATCTGGATACCGGGAAAACGCTGGGCGTTAATCAGAGAGGCGAATTAT
GTGTCAGAGGACCTATGATTATGTCCGGTTATGTAAACAATCCGGAAGCGACCAACGCCTTGATTGAC
AAGGATGGATGGCTACATTCTGGAGACATAGCTTACTGGGACGAAGACGAACACTTCTTCATAGTTGA
CCGCTTGAAGTCTTTAATTAAATACAAAGGATATCAGGTGGCCCCCGCTGAATTGGAATCGATATTGTT
ACAACACCCCAACATCTTCGACGCGGGCGTGGCAGGTCTTCCCGACGATGACGCCGGTGAACTTCCAG
CCGCCGTTGTTGTTTTGGAGCACGGAAAGACGATGACGGAAAAAGAGATCGTGGATTACGTCGCCAGT
CAAGTAACAACCGCGAAAAAGTTGCGCGGAGGAGTTGTGTTTGTGGACGAAGTACCGAAAGGTCTTA
CCGGAAAACTCGACGCAAGAAAATCAGAGAGATCCTCATAAAGGCCAAGAAGGGCGGAAAGTCCA
AATTGTAATAATTATAGGATAATTGAATAAAAACAGTATAGAGAGCAGATAAATACTGCTCTCTATTT
TACTAATAAGGAGGATTTAAATTGCTAAAAAATACAAACTTAACTAATTATAAAAAGTGAATACACG
GTTTGGAAATCTTAGTTTTGACGACAAAGGTATTTCTAATGACTTAACGGAAGAACAGCAAAAAGAAT
TAGGTAAGCTTCGAGGATTCGAATATATTAAGACAGAACAGAAAACAAAAGAAGAACCTAAGAAAGA
AGAACCTAAGAAAGAAGTACAGAAAATGAATTAGACAGCTTCTTAGCTAAAGAGCCTTCAATCAAA
GAATTAAAAGAATTTGCGAGTAAAAAAGGCATTAAAATTGAAAAAACTAAGAAAAATGATATAATTG
AAGAACTAAAGAGAGGGTAATGTATAATGTATGGAGGTTATGAAGGACAAGATTCTTACGAATACCC
TTACTCACATGGGAACCCTAAGCATGTAGAGCCAGAAAAAGTTGACGAATATGTTCTTTCTGATTATG
GTTGGACTGCGGAAACAATTAAAGCATACATGTATGGTGTTCGTGTAGTAGACCCTGAAACAGGAGAG
GAAATGGGAGACACCTTCTACAATCATATTATAGAGGTTGCCGTTGATAAGGC SEQ ID NO: 28-LP143::ffluc
ATGCCAAAAAATAACAAAGAAGAAGTTAAAGAAGTAAACCTTAATTCAGTACAAGAGGATGCGTTAA
AGTCCTTTACGACTGGTTATGGTATCACACCTGATACACAAACAGATGCAGGAGCATTAAGACGTGAG
TTCCTAGACGACCAAATCTCAATGCTTACTTGGACAGAGAATGATTTAACATTCTATAAAGACATCGCT
AAAAAACCAGCTACATCTACAGTAGCAAAATACGATGTATACATGCAACATGGTAAGGTAGGTCATA
CTAGATTTACTCGTGAGATTGGGGTAGCACCAGTAAGTGACCCTAACATCCGTCAAAAAACAGTAAAT
ATGAAATTTGCTTCCGATACTAAAAACATCAGTATCGCAGCAGGTCTAGTAAACAACATTCAAGACCC
AATGCAAATTTGACTGACGATGCTATCGTAAATATTGCTAAAACAATTGAGTGGGCTTCATTCTTTGG
AGATTCTGACTTATCAGATAGCCCAGAACCACAAGCAGGACTAGAATTTGACGGCTTGGCTAAACTTA
TTAACCAAGATAACGTTCATGATGCTCGTGGAGCTAGCTTGACTGAAAGCTTGTTAAACCAAGCAGCA
GTAATGATTAGTAAAGGTTATGGTACACCTACAGATGCTTACATGCCAGTAGGGGTTCAAGCAGACTT |

| INFORMAL SEQUENCE LISTING |
|---|
| TGTTAACCAACAACTTTCTAAACAAACACAACTTGTTCGCGATAACGGAAACAACGTAAGCGTTGGTT |
| TCAACATCCAAGGTTTCCATTCAGCTCGTGGATTTATCAAACTTCACGGTTCTACAGTAATGGAAAACG |
| AACAAATCTTAGATGAACGTATTCTTGCTTTACCAACAGCTCCACAACCAGCTAAGGTAACTGCAACA |
| CAAGAAGCAGGTAAAAAAGGACAATTTAGAGCAGAAGATTTAGCAGCACATGAATATAAAGTTGTTG |
| TAAGTTCTGACGATGCAGAGTCTATTGCAAGTGAAGTGGCTACAGCTACAGTTACTGCAAAAGATGAC |
| GGCGTTAAACTAGAAATCGAATTAGCTCCAATGTATAGCTCTCGTCCACAATTCGTTTCAATCTATAGA |
| AAAGGTGCAGAAACAGGTTTATTCTACCTAATCGCTCGTGTACCTGCTAGCAAAGCAGAGAACAACGT |
| AATCACTTTCTACGACTTAAACGACTCTATTCCTGAAACAGTAGACGTATTCGTTGGTGAAATGTCGGC |
| TAACGTAGTACACTTGTTTGAATTACTACCAATGATGAGATTACCTCTAGCTCAAATTAACGCATCTGT |
| TACATTTGCAGTTTTATGGTATGGCGCATTAGCTCTAAGAGCACCTAAGAAATGGGTACGTATTAGAA |
| ACGTTAAATATATTCCTGTAAAAAACGTTCATAGCAACTAAGAGGAGGTAAATATATATGGAAGACGC |
| CAAAAACATAAAGAAAGGCCCGGCGCCATTCTATCCTCTAGAGGATGGAACCGCTGGAGAGCAACTG |
| CATAAGGCTATGAAGAGATACGCCCTGGTTCCTGGAACAATTGCTTTTACAGATGCACATATCGAGGT |
| GAACATCACGTACGCGGAATACTTCGAAATGTCCGTTCGGTTGGCAGAAGCTATGAAACGATATGGGC |
| TGAATACAAATCACAGAATCGTCGTATGCAGTGAAAACTCTCTTCAATTCTTTATGCCGGTGTTGGGCG |
| CGTTATTTATCGGAGTTGCAGTTGCGCCCGCGAACGACATTTATAATGAACGTGAATTGCTCAACAGT |
| ATGAACATTTCGCAGCCTACCGTAGTGTTTGTTTCCAAAAAGGGGTTGCAAAAAATTTTGAACGTGCA |
| AAAAAAATTACCAATAATCCAGAAAATTATTATCATGGATTCTAAAACGGATTACCAGGGATTTCAGT |
| CGATGTACACGTTCGTCACATCTCATCTACCTCCCGGTTTTAATGAATACGATTTTGTACCAGAGTCCT |
| TTGATCTGACAAAACAATTGCACTGATAATGAATTCCTCTGACGTACTGGGTTACCTAAGGGTGTG |
| GCCCTTCCGCATAGAACTGCCTGCGTCAGATTCTCGCATGCCAGAGATCCTATTTTTGGCAATCAAATC |
| ATTCCGGATACTGCGATTTTAAGTGTTGTTCCATTCCATCACGGTTTTGGAATGTTTACTACACTCGGAT |
| ATTTGATATGTGGATTTCGAGTCGTCTTAATGTATAGATTTGAAGAAGAGCTGTTTTTACGATCCCTTC |
| AGGATTACAAAATTCAAAGTGCGTTGCTAGTACCAACCCTATTTTCATTCTTCGCCAAAAGCACTCTGA |
| TTGACAAATACGATTTATCTAATTTACACGAAATTGCTTCTGGGGGCGCACCTCTTTCGAAAGAAGTCG |
| GGGAAGCGGTTGCAAAACGCTTCCATCTTCCAGGGATACGACAAGGATATGGGCTCACTGAGACTACA |
| TCAGCTATTCTGATTACACCCGAGGGGGATGATAAACCGGGCGCGGTCGGTAAAGTTGTTCCATTTTTT |
| GAAGCGAAGGTTGTGGATCTGGATACCGGGAAAACGCTGGGCGTTAATCAGAGAGGCGAATTATGTG |
| TCAGAGGACCTATGATTATGTCCGGTTATGTAAACAATCCGGAAGCGACCAACGCCTTGATTGACAAG |
| GATGGATGGCTACATTCTGGAGACATAGCTTACTGGGACGAAGACGAACACTTCTTCATAGTTGACCG |
| CTTGAAGTCTTTAATTAAATACAAAGGATATCAGGTGGCCCCCGCTGAATTGGAATCGATATTGTTAC |
| AACACCCCAACATCTTCGACGCGGGCGTGGCAGGTCTTCCCGACGATGACGCCGGTGAACTTCCCGCC |
| GCCGTTGTTGTTTTGGAGCACGGAAAGACGATGACGGAAAAAGAGATCGTGGATTACGTCGCCAGTCA |
| AGTAACAACCGCGAAAAAGTTGCGCGGAGGAGTTGTGTTTGTGGACGAAGTACCGAAAGGTCTTACC |
| GGAAAACTCGACGCAAGAAAATCAGAGAGATCCTCATAAAGGCCAAGAAGGGCGGAAAGTCCAAA |
| TTGTAATAATTATAGGATAATTGAATAAAAACAGTATAGAGCAGATAAATACTGCTCTCTATTTTA |
| CTAATAAGGAGGATTTAAATTGCTAAAAAATACAAACTTAGCTAATTATAAAAAAGTGAATACACGGT |
| TTGGAAATCTTAGTTTTGACGACAAAGGTATTTCTAATGACTTAACGGAAGAACAGCAAAAAGAATTA |
| GGTAAGCTTCGAGGATTCGAATATATTAAGACAGAACAGAAAACAAAAGAAGAACCTAAGAAAGAA |
| GAACCTAAGAAAGAAGAACCTAAGAAAGAAGAACCTAAGAAAGAAGAACCTAAGAAAGAAGAACCT |
| AAGAAAGAAAGTACAGAAAATGAATTAGACAGCTTCTTAGCTAAAGAGCCTTCAATCAAAGAATTAA |
| AAGAATTTGCGAGTAAAAAAGGCATTAAAATTGAAAAAACTAAGAAAAATGATATAATTGAAGAACT |
| AAAGAGAGGGTAATGTATAATGTATGGAGGTTATGAAGGACAAGATTCTTACGAATACCCTTACTCAC |
| ATGGGAACCCTAAGCATGTAGAGCCAGAAAAAGTTGACGAATATGTTCTTTCTGATTATGGTTGGACT |
| GCGGAAACAATTAAAGCATACATGTATGGTGTTCGTGTAGTAGACCCTGAAACAGGAGAGGAAATGG |
| GAGACACCTTCTACAATCATATTATAGAGGTTGCCGTTGATAAGGC |

SEQ ID NO: 29-A511::ffluc
ATGCCAAAAAATAACAAAGAAGAAGTTAAAGAAGTAAACCTTAATTCAGTACAAGAGGATGCGTTAA
AGTCCTTTACGACTGGTTATGGTATCACACCTGATACACAAACAGATGCAGGAGCATTAAGACGTGAG
TTCCTAGACGACCAAATCTCAATGCTTACTTGGACAGAGAATGATTTAACATTCTATAAAGACATCGCT
AAAAAACCAGCTACATCTACAGTAGCAAAATACGATGTATACATGCAACATGGTAAGGTAGGTCATA
CTAGATTTACTCGTGAGATTGGGGTAGCACCAGTAAGTGACCCTAACATCCGTCAAAAAACAGTAAAT
ATGAAATTTGCTTCCGATACTAAAAACATCAGTATCGCAGCAGGTCTAGTAAACAACATTCAAGACCC
AATGCAAATTTTGACTGACGATGCTATCGTAAATATTGCTAAAACAATTGAGTGGGCTTCATTCTTTGG
AGATTCTGACTTATCAGATAGCCCAGAACCACAAGCAGGACTAGAATTTGACGGCTTGGCTAAACTTA
TTAACCAAGATAACGTTCATGATGCTCGTGGAGCTAGCTTACATGCCAGTAGGGGTTCAAGCAGACTT
TGTTAACCAACAACTTTCTAAACAAACACAACTTGTTCGCGATAACGGAAACAACGTAAGCGTTGGTT
TCAACATCCAAGGTTTCCATTCAGCTCGTGGATTTATCAAACTTCACGGTTCTACAGTAATGGAAAACG
AACAAATCTTAGATGAACGTATTCTTGCTTTACCAACAGCTCCAGCTAAGGTAACTGCAACA
CAAGAAGCAGGTAAAAAAGGACAATTTAGAGCAGAAGATTTAGCAGCACATGAATATAAAGTTGTTG
TAAGTTCTGACGATGCAGAGTCTATTGCAAGTGAAGTGGCTACAGCTACAGTTACTGCAAAAGATGAC
GGCGTTAAACTAGAAATCGAATTAGCTCCAATGTATAGCTCTCGTCCACAATTCGTTTCAATCTATAGA
AAAGGTGCAGAAACAGGTTTATTCTACCTAATCGCTCGTGTACCTGCTAGCAAAGCAGAGAACAACGT
AATCACTTTCTACGACTTAAACGACTCTATTCCTGAAACAGTAGACGTATTCGTTGGTGAAATGTCGGC
TAACGTAGTACACTTGTTTGAATTACTACCAATGATGAGATTACCTCTAGCTCAAATTAACGCATCTGT
TACATTTGCAGTTTTATGGTATGGCGCATTAGCTCTAAGAGCACCTAAGAAATGGGTACGTATTAGAA
ACGTTAAATATATTCCTGTAAAAAACGTTCATAGCAACTAAGAGGAGGTAAATATATATGGAAGACGC
CAAAAACATAAAGAAAGGCCCGGCGCCATTCTATCCTCTAGAGGATGGAACCGCTGGAGAGCAACTG
CATAAGGCTATGAAGAGATACGCCCTGGTTCCTGGAACAATTGCTTTTACAGATGCACATATCGAGGT
GAACATCACGTACGCGGAATACTTCGAAATGTCCGTTCGGTTGGCAGAAGCTATGAAACGATATGGGC
TGAATACAAATCACAGAATCGTCGTATGCAGTGAAAACTCTCTTCAATTCTTTATGCCGGTGTTGGGCG
CGTTATTTATCGGAGTTGCAGTTGCGCCCGCGAACGACATTTATAATGAACGTGAATTGCTCAACAGT
ATGAACATTTCGCAGCCTACCGTAGTGTTTGTTTCCAAAAAGGGGTTGCAAAAAATTTTGAACGTGCA
AAAAAAATTACCAATAATCCAGAAAATTATTATCATGGATTCTAAAACGGATTACCAGGGATTTCAGT
CGATGTACACGTTCGTCACATCTCATCTACCTCCCGGTTTTAATGAATACGATTTTGTACCAGAGTCCT -continued

INFORMAL SEQUENCE LISTING

TTGATCGTGACAAAACAATTGCACTGATAATGAATTCCTCTGGATCTACTGGGTTACCTAAGGGTGTG
GCCCTTCCGCATAGAACTGCCTGCGTCAGATTCTCGCATGCCAGAGATCCTATTTTTGGCAATCAAATC
ATTCCGGATACTGCGATTTTAAGTGTTGTTCCATTCCATCACGGTTTTGGAATGTTTACTACACTCGGAT
ATTTGATATGTGGATTTCGAGTCGTCTTAATGTATAGATTTGAAGAAGAGCTGTTTTTACGATCCCTTC
AGGATTACAAAATTCAAAGTGCGTTGCTAGTACCAACCCTATTTTCATTCTTCGCCAAAAGCACTCTGA
TTGACAAATACGATTTATCTAATTTACACGAAATTGCTTCTGGGGGCGCACCTCTTTCGAAAGAAGTCG
GGGGAAGCGGTTGCAAAACGCTTCCATCTTCCAGGGATACGACAAGGATATGGGCTCACTGAGACTACA
TCAGCTATTCTGATTACACCCGAGGGGGATGATAAACCGGGCGCGGTCGGTAAAGTTGTTCCATTTTTT
GAAGCGAAGGTTGTGGATCTGGATACCGGGAAAACGCTGGGCGTTAATCAGAGAGGCGAATTATGTG
TCAGAGGACCTATGATTATGTCCGGTTATGTAAACAATCCGGAAGCGACCAACGCCTTGATTGACAAG
GATGGATGGCTACATTCTGGAGACATAGCTTACTGGGACGAAGACGAACACTTCTTCATAGTTGACCG
CTTGAAGTCTTTAATTAAATACAAAGGATATCAGGTGGCCCCCGCTGAATTGGAATCGATATTGTTAC
AACACCCCAACATCTTCGACGCGGGCGTGGCAGGTCTTCCCGACGATGACGCCGGTGAACTTCCCGCC
GCCGTTGTTGTTTTGGAGCACGGAAAGACGATGACGGAAAAAGAGATCGTGGATTACGTCGCCAGTCA
AGTAACAACCGCGAAAAAGTTGCGCGGAGGAGTTGTGTTTGTGGACGAAGTACCGAAAGGTCTTACC
GGAAAACTCGACGCAAGAAAAATCAGAGAGATCCTCATAAAGGCCAAGAAGGGCGGAAAGTCCAAA
TTGTAATAATTATAGGATAATTGAATAAAAACAGTATAGAGAGCAGATAAATACTGCTCTCTATTTTA
CTAATAAGGAGGATTTAAATTGCTAAAAAATACAAACTTAGCTAATTATAAAAAAGTGAATACACGGT
TTGGAAATCTTAGTTTTGACGACAAAGGTATTTCTAATGACTTAACGGAAGAACAGCAAAAAGAATTA
GGTAAGCTTCGAGGATTCGAATATATTAAGACAGAACAGAAAACAAAAGAAGAACCTAAGAAAGAA
GAACCTAAGAAAGAAGAACCTAAGAAAGAAGAACCTAAGAAAGAAGAACCTAAGAAAGAAGAACCT
AAGAAAGAAAGTACAGAAAATGAATTAGACAGCTTCTTAGCTAAAGAAGCCTTCAATCAAAGAATTAA
AAGAATTTGCGAGTAAAAAAGGCATTAAAATTGAAAAAACTAAGAAAAATGATATAATTGAAGAACT
AAAGAGAGGGTAATGTATAATGTATGGAGGTTATGAAGGACAAGATTCTTACGAATACCCTTACTCAC
ATGGGAACCCTAAGCATGTAGAGCCAGAAAAAGTTGACGAATATGTTCTTTCTGATTATGGTTGGACT
GCGGAAACAATTAAAGCATACATGTATGGTGTTCGTGTAGTAGACCCTGAAACAGGAGAGGAAATGG
GAGACACCTTCTACAATCATATTATAGAGGTTGCCGTTGATAAGGC

SEQ ID NO: 30-P100::ffluc
ATGCCAAAAAATAACAAAGAAGAAGAAGTTAAAGAAGTAAACCTTAATTCAGTACAAGAGGACGCGT
TAAAGTCCTTTACAACTGGTTATGGTATCACACCTGATACACAAACAGATGCAGGAGCATTAAGACGT
GAGTTCCTAGACGACCAAATCTCAATGCTTACTTGGACAGAGAATGATTTAACATTCTATAAAGACAT
CGCTAAAAAACCAGCTACATCTACAGTAGCAAAATACGATGTATACATGCAACATGGTAAGGTAGGTC
ATACTAGATTACTCGTGAGATTGGGGTAGCACCAGTAAGTGACCCTAACATCCGTCAAAAAACAGTA
AATATGAAATTTGCTTCCGATACTAAAAACATCAGTATCGCAGCAGGTCTAGTAAACAACATTCAAGA
CCCAATGCAAATTTTGACTGACGATGCTATCGTAAATATTGCTAAAACAATTGAGTGGGCTTCATTCTT
TGGAGATTCTGACTTATCAGATAGCCCAGAACCACAAGCAGGACTAGAATTTGACGGCTTGGCTAAAC
TTATTAACCAAGATAACGTTCATGATGCTCGTGGAGCTAGCTTGACTGAAAGCTTGTTAAACCAAGCA
GCAGTAATGATTAGTAAAGGTTATGGTACACCTACAGATGCTTACATGCCAGTAGGGGTTCAAGCAGA
CTTTGTTAACCAACAACTTTCTAAACAAACACAGCTTGTTCGTGATAACGGAAACAACGTAAGCGTTG
GTTTCAACATCCAAGGTTTCCATTCAGCTCGTGGATTTATCAAACTTCACGGTTCTACAGTAATGGAAA
ACGAACAAATCTTAGATGAACGTATTCTTGCTTTACCAACAGCTCCACAACCAGCTAAGGTAACTGCA
ACACAAGAAGCAGGTAAAAAAGGACAATTTAGAGCAGAAGACTTAGCAGCACACGAATACAAAGTTG
TTGTAAGTTCTGACGATGCAGAGTCTATTGCAAGTGAAGTGGCTACAGCTACAGTTACTGCAAAAGAT
GACGGCGTTAAACTAGAAATCGAGTTAGCTCCAATGTACAGCTCCCGTCCACAATTCGTTTCAATCTAT
AGAAAAGGTGCAGAAACAGGTTTATTCTACCTAATCGCTCGTGTACCTGCTAGCAAAGCAGAGAACAA
CGTAATCACTTTCTATGACTTAAACGACTCTATTCCTGAAACAGTAGACGTATTCGTTGGTGAAATGTC
TGCTAACGTAGTACACTTGTTTGAATTACTACCAATGATGAGATTACCTCTAGCTCAAATTAACGCATC
TGTTACATTTGCAGTTTTATGGTATGGAGCATTAGCTCTAAGAGCACCTAAGAAATGGGTACGTATTAG
AAACGTTAAATATATTCCTGTAAAAAACGTTCATAGCAACTAAGAGGAGGTAAATATATATGGAAGAC
GCCAAAAACATAAAGAAAGGCCCGGCGCCATTCTATCCTCTAGAGGATGGAACCGCTGGAGAGCAAC
TGCATAAGGCTATGAAGAGATACGCCCTGGTTCCTGGAACAATTGCTTTTACAGATGCACATATCGAG
GTGAACATCACGTACGCGGAATACTTCGAAATGTCCGTTCGGTTGGCAGAAGCTATGAAACGATATGG
GCTGAATACAAATCACAGAATCGTCGTATGCAGTGAAAACTCTCTTCAATTCTTTATGCCGGTGTTGGG
CGCGTTATTTATCGGAGTTGCAGTTGCGCCCGCGAACGACATTTATAATGAACGTGAATTGCTCAACA
GTATGAACATTTCGCAGCCTACCGTAGTGTTTGTTTCCAAAAAGGGGTTGCAAAAAATTTTGAACGTG
CAAAAAAAATTACCAATAATCCAGAAAATTATTATCATGGATTCTAAAACGGATTACCAGGGATTTCA
GTCGATGTACACGTTCGTCACATCTCATCTACCTCCCGGTTTTAATGAATACGATTTTGTACCAGAGTC
CTTTGATCGTGACAAAACAATTGCACTGATAATGAATTCCTCTGGATCTACTGGGTTACCTAAGGGTGT
GGCCCTTCCGCATAGAACTGCCTGCGTCAGATTCTCGCATGCCAGAGATCCTATTTTTGGCAATCAAAT
CATTCCGGATACTGCGATTTTAAGTGTTGTTCCATTCCATCACGGTTTTGGAATGTTTACTACACTCGG
ATATTTGATATGTGGATTTCGAGTCGTCTTAATGTATAGATTTGAAGAAGAGCTGTTTTTACGATCCCT
TCAGGATTACAAAATTCAAAGTGCGTTGCTAGTACCAACCCTATTTTCATTCTTCGCCAAAAGCACTCT
GATTGACAAATACGATTTATCTAATTTACACGAAATTGCTTCTGGGGGCGCACCTCTTTCGAAAGAAGT
CGGGGAAGCGGTTGCAAAACGCTTCCATCTTCCAGGGATACGACAAGGATATGGGCTCACTGAGACTA
CATCAGCTATTCTGATTACACCCGAGGGGGATGATAAACCGGGCGCGGTCGGTAAAGTTGTTCCATTT
TTTGAAGCGAAGGTTGTGGATCTGGATACCGGGAAAACGCTGGGCGTTAATCAGAGAGGCGAATTAT
GTGTCAGAGGACCTATGATTATGTCCGGTTATGTAAACAATCCGGAAGCGACCAACGCCTTGATTGAC
AAGGATGGATGGCTACATTCTGGAGACATAGCTTACTGGGACGAAGACGAACACTTCTTCATAGTTGA
CCGCTTGAAGTCTTTAATTAAATACAAAGGATATCAGGTGGCCCCCGCTGAATTGGAATCGATATTGTT
ACAACACCCCAACATCTTCGACGCGGGCGTGGCAGGTCTTCCCGACGATGACGCCGGTGAACTTCCCG
CCGCCGTTGTTGTTTTGGAGCACGGAAAGACGATGACGGAAAAAGAGATCGTGGATTACGTCGCCAGT
CAAGTAACAACCGCGAAAAAGTTGCGCGGAGGAGTTGTGTTTGTGGACGAAGTACCGAAAGGTCTTA
CCGGAAAACTCGACGCAAGAAAAATCAGAGAGATCCTCATAAAGGCCAAGAAGGGCGGAAAGTCCA AATTGTAATAATTATAGGATAATTGAATAAAAACAGTATAGAGAGCAGATAAATACTGCTCTCTATTT
TACTAATAAGGAGGATTTAAATTGCTAAAAAATACAAACTTAGCTAATTATAAAAAAGTGAATACACG
ATTTGGAAATCTTAGTTTTGATGATAAAGGTATTTCTAATGACCTAACGGAAGAGCAGCAAAAAGAAT
TAGGTAAGCTTAGAGGATTCGAATATATTAAGACAGAACAGAAAACGAAAGAAGAACCTAAGAAAGA
AGAACCTAAGAAAGAAAGTACAGAAAATGAATTAGACAGCTTCTTAGCTAAAGAACCTTCAATCAAA
GAATTAAAAGAATTTGCGAGTAAAAAAGGCATTAAAATTGAAAAAACTAAGAAAAATGATATAATTG
AAGAACTAAAGAGAGGGTAATGTACAATGTATGGAGGTTATGAAGGACAAGATTCTTACGAATACCC
TTACTCACACGGGAACCCTAAGCATGTAGAGCCAGAAAAAGTTGACGAATATGTTCTTTCTGATTATG
GCTGGACTGCGGAAACAATTAAAGCATACATGTATGGTGTTCGTGTAGTAGACCCTGAAACAGGAGA
GGAAATGGGAGACACCTTCTACAATCATATTATAGAGGTTGCCGTTGATAAGGC SEQ ID NO: 31-LP124::nluc
ATGCCAAAAAATAACAAAGAAGAAGAAGTTAAAGAAGTAAACCTTAATTCAGTACAAGAGGACGCGT
TAAAGTCCTTTACAACTGGTTATGGTATCACACCTGATACACAAACAGATGCAGGAGCATTAAGACGT
GAGTTCCTAGACGACCAAATCTCAATGCTTACTTGGACAGAGAATGATTTAACATTCTATAAAGACAT
CGCTAAAAAACCAGCTACATCTACAGTAGCAAAATACGATGTATACATGCAACATGGTAAGGTAGGTC
ATACTAGATTTACTCGTGAGATTGGGGTAGCACCAGTAAGTGACCCTAACATCCGTCAAAAAACAGTA
AACATGAAATTTGCTTCCGATACTAAAAACATCAGTATCGCAGCAGGTCTAGTAAACAACATTCAAGA
CCCAATGCAAATTTTGACTGACGATGCTATCGTAAATATTGCTAAACAATTGAGTGGGCTTCATTCTT
TGGAGATTCTGACTTATCAGATAGCCCAGAACCACAAGCAGGACTAGAATTTGACGGCTTGGCTAAAC
TTATTAACCAAGATAACGTTCATGATGCTCGTGGAGCTAGCTTGACTGAAAGCTTGTTAAACCAAGCA
GCAGTAATGATTAGTAAAGGTTATGGTACACCTACAGATGCTTACATGCCAGTAGGGGTTCAAGCAGA
CTTTGTTAACCAACAACTTTCTAAACAAACACAACTTGTTCGCGATAACGGAAACAACGTAAGCGTTG
GTTTCAACATCCAAGGTTTCCATTCAGCTCGTGGATTTATCAAACTTCACGGTTCTACAGTAATGGAAA
ACGAACAAATCTTAGATGAACGTATTCTTGCTTTACCAACAGCTCCACAACCAGCTAAGGTAACTGCA
ACACAAGAAGCAGGTAAAAAAGGACAATTTAGAGCAGAAGATTTAGCAGCACATGAATATAAAGTTG
TTGTAAGTTCTGACGATGCAGAGTCTATTGCAAGTGAAGTGGCTACAGCTACAGTTACTGCAAAAGAT
GACGGCGTTAAACTAGAAATCGAATTAGCTCCAATGTATAGCTCTCGTCCACAATTCGTTTCAATCTAT
AGAAAAGGTGCAGAAACAGGTTTATTCTACCTAATCGCTCGTGTACCTGCTAGCAAAGCAGAGAACAA
CGTAATCACTTTCTACGACTTAAACGACTCTATTCCTGAAACAGTAGACGTATTCGTTGGTGAAATGTC
GGCTAACGTAGTACACTTGTTTGAATTACTACCAATGATGAGATTACCTCTAGCTCAAATTAACGCATC
TGTTACATTTGCAGTTTTATGGTATGGCGCATTAGCTCTCAAGAGCACCTAAGAAATGGGTACGTATTAG
AAACGTTAAATATATTCCTGTAAAAAACGTTCATAGCAACTAATAATAAGAGGAGGTAAATATATATG
GTCTTCACACTCGAAGATTTCGTTGGGGACTGCCGACAGACAGCCGGCTACAACCTGGACCAAGTCCT
TGAACAGGGAGGTGTGTCCAGTTTGTTTCAGAATCTCGGGGTGTCCGTAACTCCGATCCAAAGGATTG
TCCTGAGCGGTGAAAATGGGCTGAAGATCGACATCCATGTCATCATCCCGTATGAAGGTCTGAGCGGC
GACCAAATGGGCCAGATCGAAAAAATTTTTAAGGTGGTGTACCCATGGATGATCATCACTTTAAGGT
GATCCTGCACTATGGCACACTGGTAATCGACGGGGTTACGCCGAACATGATCGACTATTTCGGACGGC
CGTATGAAGGCATCGCCGTGTTCGACGGCAAAAAGATCACTGTAACAGGGACCCTGTGGAACGGCAA
CAAAATTATCGACGAGCGCCTGATCAACCCCGACGGCTCCCTGCTGTTCCGAGTAACCATCAACGGAG
TGACCGGCTGGCGGCTGTGCGAACGCATTCTGGCGTAATAATTATAGGATAATTGAATAAAAACAGTA
TAGAGAGCAGATAAATACTGCTCTCTATTTTACTAATAAGGAGGATTTAAATTGCTAAAAAATACAAA
CTTAGCTAATTATAAAAAAGTGAATACACGGTTTGGAAATCTTAGTTTTGACGACAAAGGTATTTCTA
ATGACTTAACGGAAGAACAGCAAAAAGAATTAGGTAAGCTTCGAGGATTCGAATATATTAAGACAGA
ACAGAAAACAAAGAAGAACCTAAGAAAGAAGAACCTAAGAAAGAAGAACCTAAGAAAGAAGAACC
TAAGAAAGAAGAACCTAAGAAAGAAGAACCTAAGAAAGAAAGTACAGAAAATGAATTAGACAGCTT
CTTAGCTAAAGAGCCTTCAATCAAAGAATTAAAAGAATTTGCGAGTAAAAAAGGCATTAAAATTGAA
AAAACTAAGAAAAATGATATAATTGAAGAACTAAAGAGAGGGTAATGTATAATGTATGGAGGTTATG
AAGGACAAGATTCTTACGAATACCCTTACTCACATGGGAACCCTAAGCATGTAGAGCCAGAAAAAGTT
GACGAATATGTTCTTTCTGATTATGGTTGGACTGCGGAAACAATTAAAGCATACATGTATGGTGTTCGT
GTAGTAGACCCTGAAACAGGAGAGGAAATGGGAGACACCTTCTACAATCATATTATAGAGGTTGCCGT
TGATAAGGC SEQ ID NO: 32-LP125::nluc
ATGCCAAAAAATAACAAAGAAGAAGAAGTTAAAGAAGTAAACCTTAATTCAGTACAAGAGGACGCGT
TAAAGTCCTTTACAACTGGTTATGGTATCACACCTGATACACAAACAGATGCAGGAGCATTAAGACGT
GAGTTCCTAGACGACCAAATCTCAATGCTTACTTGGACAGAGAATGATTTAACATTCTATAAAGACAT
CGCTAAAAAACCAGCTACATCTACAGTAGCAAAATACGATGTATACATGCAACATGGTAAGGTAGGTC
ATACTAGATTTACTCGTGAGATTGGGGTAGCACCAGTAAGTGACCCTAACATCCGTCAAAAAACAGTA
AACATGAAATTTGCTTCCGATACTAAAAACATCAGTATCGCAGCAGGTCTAGTAAACAACATTCAAGA
CCCAATGCAAATTTTGACTGACGATGCTATCGTAAATATTGCTAAACAATTGAGTGGGCTTCATTCTT
TGGAGATTCTGACTTATCAGATAGCCCAGAACCACAAGCAGGACTAGAATTTGACGGCTTGGCTAAAC
TTATTAACCAAGATAACGTTCATGATGCTCGTGGAGCTAGCTTGACTGAAAGCTTGTTAAACCAAGCA
GCAGTAATGATTAGTAAAGGTTATGGTACACCTACAGATGCTTACATGCCAGTAGGGGTTCAAGCAGA
CTTTGTTAACCAACAACTTTCTAAACAAACACAACTTGTTCGTGATAACGGAAACAACGTAAGCGTTG
GTTTCAACATCCAAGGTTTCCATTCAGCTCGTGGATTTATCAAACTTCACGGTTCTACAGTAATGGAAA
ACGAACAAATCTTAGATGAACGTATTCTTGCTTTACCAACAGCTCCACAACCAGCTAAGGTAACTGCA
ACACAAGAAGCAGGTAAAAAAGGACAATTTAGAGCAGAAGATTTAGCAGCACATGAATATAAAGTTG
TTGTAAGTTCTGACGATGCAGAGTCTATTGCAAGTGAAGTGGCTACAGCTACAGTTACTGCAAAAGAT
GACGGCGTTAAACTAGAAATCGAATTAGCTCCAATGTATAGCTCTCGTCCACAATTCGTTTCAATCTAT
AGAAAAGGTGCAGAAACAGGTTTATTCTACCTAATCGCTCGTGTACCTGCTAGCAAAGCAGAGAACAA
CGTAATCACTTTCTACGACTTAAACGACTCTATTCCTGAAACAGTAGACGTATTCGTTGGTGAAATGTC
GGCTAACGTAGTACACTTGTTTGAATTACTACCAATGATGAGATTACCTCTAGCTCAAATTAACGCATC
TGTTACATTTGCAGTTTTATGGTATGGCGCATTAGCTCTAAGAGCACCTAAGAAATGGGTACGTATTAG -continued

INFORMAL SEQUENCE LISTING

AAACGTTAAATATATTCCTGTAAAAAACGTTCATAGCAACTAATAATAAGAGGAGGTAAATATATATG
GTCTTCACACTCGAAGATTTCGTTGGGGACTGGCGACAGACAGCCGGCTACAACCTGGACCAAGTCCT
TGAACAGGGAGGTGTGTCCAGTTTGTTTCAGAATCTCGGGGTGTCCGTAACTCCGATCCAAAGGATTG
TCCTGAGCGGTGAAAATGGGCTGAAGATCGACATCCATGTCATCATCCCGTATGAAGGTCTGAGCGGC
GACCAAATGGGCCAGATCGAAAAAATTTTTAAGGTGGTGTACCCTGTGGATGATCATCACTTTAAGGT
GATCCTGCACTATGGCACACTGGTAATCGACGGGGTTACGCCGAACATGATCGACTATTTCGGACGGC
CGTATGAAGGCATCGCCGTGTTCGACGGCAAAAAGATCACTGTAACAGGGACCCTGTGGAACGGCAA
CAAAATTATCGACGAGCGCCTGATCAACCCCGACGGCTCCCTGCTGTTCCGAGTAACCATCAACGGAG
TGACCGGCTGGCGGCTGTGCGAACGCATTCTGGCGTAATAATTATAGGATAATTGAATAAAAACAGTA
TAGAGAGCAGATAAATACTGCTCTCTATTTTACTAATAAGGAGGATTTAAATTGCTAAAAAATACAAA
CTTAGCTAATTATAAAAAAGTGAATACACGGTTTGGAAATCTTAGTTTTGACGACAAAGGTATTTCTA
ATGACTTAACGGAAGAACAGCAAAAAGAATTAGGTAAGCTTCGAGGATTCGAATATATTAAGACAGA
ACAGAAAACAAAAGAAGAACCTAAGAAAGAAGAACCTAAGAAAGAAAGTACAGAAATGAATTAGA
CAGCTTCTTAGCTAAAGAGCCTTCAATCAAAGAATTAAAAGAATTTGCGAGTAAAAAAGGCATTAAAA
TTGAAAAAACTAAGAAAAATGATATAATTGAAGAACTAAAGAGAGGGTAATGTATAATGTATGGAGG
TTATGAAGGACAAGATTCTTACGAATACCCTTACTCACATGGGAACCCTAAGCATGTAGAGCCAGAAA
AAGTTGACGAATATGTTCTTTCTGATTATGGTTGGACTGCGGAAACAATTAAAGCATACATGTATGGT
GTTCGTGTAGTAGACCCTGAAACAGGAGAGGAAATGGGAGACACCTTCTACAATCATATTATAGAGGT
TGCCGTTGATAAGGC

SEQ ID NO: 33-A511::nluc
ATGCCAAAAAATAACAAAGAAGAAGTTAAAGAAGTAAACCTTAATTCAGTACAAGAGGATGCGTTAA
AGTCCTTTACGACTGGTTATGGTATCACACCTGATACACAAACAGATGCAGGAGCATTAAGACGTGAG
TTCCTAGACGACCAAATCTCAATGCTTACTTGGACAGAGAATGATTTAACATTCTATAAAGACATCGCT
AAAAAACCAGCTACATCTACAGTAGCAAAATACGATGTATACATGCAACATGGTAAGGTAGGTCATA
CTAGATTTACTCGTGAGATTGGGGTAGCACCAGTAAGTGACCCTAACATCCGTCAAAAAACAGTAAAT
ATGAAATTTGCTTCCGATACTAAAAACATCAGTATCGCAGCAGGTCTAGTAAACAACATTCAAGACCC
AATGCAAATTTTGACTGACGATGCTATCGTAAATATTGCTAAAACAATTGAGTGGGCTTCATTCTTTGG
AGATTCTGACTTATCAGATAGCCCAGAACCACAAGCAGGACTAGAATTTGACGGCTTGGCTAAACTTA
TTAACCAAGATAACGTTCATGATGCTCGTGGAGCTAGCTTGACTGAAAGCTTGTTAAACCAAGCAGCA
GTAATGATTAGTAAAGGTTATGGTACACCTACAGATGCTTACATGCCAGTAGGGGTTCAAGCAGACTT
TGTTAACCAACAACTTTCTAAACAAACACAACTTGTTCGCGATAACGGAAACAACGTAAGCGTTGGTT
TCAACATCCAAGGTTTCCATTCAGCTCGTGGATTTATCAAACTTCACGGTTCTACAGTAATGGAAAACG
AACAAATCTTAGATGAACGTATTCTTGCTTTACCAACAGCTCCACAACCAGCTAAGGTAACTGCAACA
CAAGAAGCAGGTAAAAAAGGACAATTTAGAGCAGAAGATTTAGCAGCACATGAATATAAAGTTGTTG
TAAGTTCTGACGATGCAGAGTCTATTGCAAGTGAAGTGGCTACAGCTACAGTTACTGCAAAAGATGAC
GGCGTTAAACTAGAAATCGAATTAGCTCCAATGTATAGCTCTCGTCCACAATTCGTTTCAATCTATAGA
AAAGGTGCAGAAACAGGTTTATTCTACCTAATCGCTCGTGTACCTGCTAGCAAAGCAGAGAACAACGT
AATCACTTTCTACGACTTAAACGACTCTATTCCTGAAACAGTAGACGTATTCGTTGGTGAAATGTCGGC
TAACGTAGTACACTTGTTTGAATTACTACCAATGATGAGATTACCTCTAGCTCAAATTAACGCATCTGT
TACATTTGCAGTTTTATGGTATGGCGCATTAGCTCTAAGAGCACCTAAGAAATGGGTACGTATTAGAA
ACGTTAAATATATTCCTGTAAAAAACGTTCATAGCAACTAAGAGGAGGTAAATATATATGGTCTTCAC
ACTCGAAGATTTCGTTGGGGACTGGCGACAGACAGCCGGCTACAACCTGGACCAAGTCCTTGAACAGG
GAGGTGTGTCCAGTTTGTTTCAGAATCTCGGGGTGTCCGTAACTCCGATCCAAAGGATTGTCCTGAGCG
GTGAAAATGGGCTGAAGATCGACATCCATGTAATCATCCCGTATGAAGGTCTGAGCGGCGACCAAATG
GGCCAGATCGAAAAAATTTTTAAGGTGGTGTACCCTGTGGATGATCATCACTTTAAGGTGATCCTGCA
CTATGGCACACTGGTAATCGACGGGGTTACGCCGAACATGATCGACTATTTCGGACGGCCGTATGAAG
GCATCGCCGTGTTCGACGGCAAAAAGATCACTGTAACAGGGACCCTGTGGAACGGCAACAAAATTAT
CGACGAGCGCCTGATCAACCCCGACGGCTCCCTGCTGTTCCGAGTAACCATCAACGGAGTGACCGGCT
GGCGGCTGTGCGAACGCATTCTGGCGTAATAATTATAGGATAATTGAATAAAAACAGTATAGAGAGC
AGATAAATACTGCTCTCTATTTTACTAATAAGGAGGATTTAAATTGCTAAAAAATACAAACTTAGCTA
ATTATAAAAAAGTGAATACACGGTTTGGAAATCTTAGTTTTGACGACAAAGGTATTTCTAATGACTTA
ACGGAAGAACAGCAAAAAGAATTAGGTAAGCTTCGAGGATTCGAATATATTAAGACAGAACAGAAAA
CAAAAGAAGAACCTAAGAAAGAAGAACCTAAGAAAGAAGAACCTAAGAAAGAAGAACCTAAGAAAG
AAGAACCTAAGAAAGAAGAACCTAAGAAAGAAAGTACAGAAATGAATTAGACAGCTTCTTAGCTAA
AGAGCCTTCAATCAAAGAATTAAAAGAATTTGCGAGTAAAAAAGGCATTAAAATTGAAAAACTAAG
AAAAATGATATAATTGAAGAACTAAAGAGAGGGTAATGTATAATGTATGGAGGTTATGAAGGACAAG
ATTCTTACGAATACCCTTACTCACATGGGAACCCTAAGCATGTAGAGCCAGAAAAGTTGACGAATAT
GTTCTTTCTGATTATGGTTGGACTGCGGAAACAATTAAAGCATACATGTATGGTGTTCGTGTAGTAGAC
CCTGAAACAGGAGAGGAAATGGGAGACACCTTCTACAATCATATTATAGAGGTTGCCGTTGATAAGGC SEQ ID NO: 34-P100::nluc
ATGCCAAAAAATAACAAAGAAGAAGTTAAAGAAGTAAACCTTAATTCAGTACAAGAGGACGCGT
TAAAGTCCTTTACAACTGGTTATGGTATCACACCTGATACACAAACAGATGCAGGAGCATTAAGACGT
GAGTTCCTAGACGACCAAATCTCAATGCTTACTTGGACAGAGAATGATTTAACATTCTATAAAGACAT
CGCTAAAAAACCAGCTACATCTACAGTAGCAAAATACGATGTATACATGCAACATGGTAAGGTAGGTC
ATACTAGATTTACTCGTGAGATTGGGGTAGCACCAGTAAGTGACCCTAACATCCGTCAAAAAACAGTA
AATATGAAATTTGCTTCCGATACTAAAAACATCAGTATCGCAGCAGGTCTAGTAAACAACATTCAAGA
CCCAATGCAAATTTTGACTGACGATGCTATCGTAAATATTGCTAAAACAATTGAGTGGGCTTCATTCTT
TGGAGATTCTGACTTATCAGATAGCCCAGAACCACAAGCAGGACTAGAATTTGACGGCTTGGCTAAAC
TTATTAACCAAGATAACGTTCATGATGCTCGTGGAGCTAGCTTGACTGAAAGCTTGTTAAACCAAGCA
GCAGTAATGATTAGTAAAGGTTATGGTACACCTACAGATGCTTACATGCCAGTAGGGGTTCAAGCAGA
CTTTGTTAACCAACAACTTTCTAAACAAACACAGCTTGTTCGTGATAACGGAAACAACGTAAGCGTTG

INFORMAL SEQUENCE LISTING

```
GTTTCAACATCCAAGGTTTCCATTCAGCTCGTGGATTTATCAAACTTCACGGTTCTACAGTAATGGAAA
ACGAACAAATCTTAGATGAACGTATTCTTGCTTTACCAACAGCTCCACAACCAGCTAAGGTAACTGCA
ACACAAGAAGCAGGTAAAAAAGGACAATTTAGAGCAGAAGACTTAGCAGCACACGAATACAAAGTTG
TTGTAAGTTCTGACGATGCAGAGTCTATTGCAAGTGAAGTGGCTACAGCTACAGTTACTGCAAAAGAT
GACGGCGTTAAACTAGAAATCGAGTTAGCTCCAATGTACAGCTCCCGTCCACAATTCGTTTCAATCTAT
AGAAAAGGTGCAGAAACAGGTTTATTCTACCTAATCGCTCGTGTACCTGCTAGCAAAGCAGAGAACAA
CGTAATCACTTTCTATGACTTAAACGACTCTATTCCTGAAACAGTAGACGTATTCGTTGGTGAAATGTC
TGCTAACGTAGTACACTTGTTTGAATTACTACCAATGATGAGATTACCTCTAGCTCAAATTAACGCATC
TGTTACATTTGCAGTTTTATGGTATGGAGCATTAGCTCTAAGAGCACCTAAGAAATGGGTACGTATTAG
AAACGTTAAATATATTCCTGTAAAAAACGTTCATAGCAACTAAGAGGAGGTAAATATATATGGTCTTC
ACACTCGAAGATTTCGTTGGGGACTGGCGACAGACAGCCGGCTACAACCTGGACCAAGTCCTTGAACA
GGGAGGTGTGTCCAGTTTGTTTCAGAATCTCGGGGTGTCCGTAACTCCGATCCAAAGGATTGTCCTGA
GCGGTGAAATGGGCTGAAGATCGACATCCATGTCATCATCCCGTATGAAGGTCTGAGCGGCGACCAA
ATGGGCCAGATCGAAAAATTTTTAAGGTGGTGTACCCTGTGGATGATCATCACTTTAAGGTGATCCT
GCACTATGGCACACTGGTAATCGACGGGGTTACGCCGAACATGATCGACTATTTCGGACGGCCGTATG
AAGGCATCGCCGTGTTCGACGGCAAAAAGATCACTGTAACAGGGACCCTGTGGAACGGCAACAAAT
TATCGACGAGCGCCTGATCAACCCCGACGGCTCCCTGCTGTTCCGAGTAACCATCAACGGAGTGACCG
GCTGGCGGCTGTGCGAACGCATTCTGGCGTAATAATTATAGGATAATTGAATAAAAACAGTATAGAGA
GCAGATAAATACTGCTCTCTATTTTACTAATAAGGAGGATTTAAATTGCTAAAAAATACAAACTTAGC
TAATTATAAAAAAGTGAATACACGATTTGGAAATCTTAGTTTTGATGATAAAGGTATTTCTAATGACCT
AACGGAAGAGCAGCAAAAAGAATTAGGTAAGCTTAGAGGATTCGAATATATTAAGACAGAACAGAAA
ACGAAAGAAGAACCTAAGAAAGAAGAACCTAAGAAAGAAGTACAGAAAATGAATTAGACAGCTTC
TTAGCTAAAGAACCTTCAATCAAAGAATTAAAAGAATTTGCGAGTAAAAAAGGCATTAAAATTGAAA
AAACTAAGAAAAATGATATAATTGAAGAACTAAAGAGGGGTAATGTACAATGTATGGAGGTTATGA
AGGACAAGATTCTTACGAATACCCTTACTCACACGGGAACCCTAAGCATGTAGAGCCAGAAAAAGTTG
ACGAATATGTTCTTTCTGATTATGGCTGGACTGCGGAAACAATTAAAGCATACATGTATGGTGTTCGTG
TAGTAGACCCTGAAACAGGAGAGGAAATGGGAGACACCTTCTACAATCATATTATAGAGGTTGCCGTT
GATAAGGC

SEQ ID NO: 35-LP40::nluc
ATGCCAAAAAATAACAAAGAAGAAGAAGTTAAAGAAGTAAACCTTAATTCAGTACAAGAGGATGCGT
TAAAGTCCTTTACAACTGGTTATGGTATCACACCTGATACACAAACAGATGCAGGGGCACTAAGACGT
GAGTTCCTAGACGACCAAATCTCAATGCTTACTTGGACAGAAAATGATTTAACATTCTACAAAGACAT
CGCTAAAAAACCAGCTACATCTACAGTAGCAAATACGATGTGTACATGCAACACGGTAAAGTAGGT
CATACTAGATTTACTCGTGAGATTGGGGTAGCACCAGTAAGTGACCCTAACATCCGTCAAAAAACAGT
AAACATGAAATTTGCTTCTGATACTAAAAATATTAGTATCGCAGCAGGTCTAGTAAACAACATTCAAG
ACCCTATGCAAATTTTGACTGATGATGCTATCGTAAATATCGCTAAAACAATTGAGTGGGCTTCATTCT
TTGGAGATTCTGACTTATCAGATAGCCCAGAACCACAAGCAGGATTAGAATTTGATGGCTTGGCTAAA
CTTATTAACCAAGATAACGTTCATGATGCTCGTGGAGCTAGCTTGACTGAAAGCTTGTTAAACCAAGC
AGCAGTAATGATTAGTAAAGGTTATGGTACACCTACAGATGCTTACATGCCAGTAGGGGTTCAAGCAG
ACTTTGTTAACCAACAACTTTCTAAACAAACACAACTTGTTCGCGATAACGGAAACAACGTAAGCGTT
GGTTTCAACATCCAAGGTTTCCATTCAGCTCGTGGATTTATCAAACTTCACGGTTCTACAGTAATGGAA
AACGAACAAATCTTAGATGAACGTATTCTTGCTTTACCAACAGCTCCACAACCAGCTAAGGTAACTGC
AACACAAGAAGCAGGTAAAAAAGGACAATTTAGAGCAGAAGATTTAGCAGCACATGAATATAAAGTT
GTTGTAAGTTCTGACGATGCAGAGTCTATTGCAAGTGAAGTGGCTACAGCTACAGTTACTGCAAAAGA
TGACGGCGTTAAACTAGAAATCGAATTAGCTCCAATGTATAGCTCTCGTCCACAATTCGTTTCAATCTA
TAGAAAAGGTGCAGAAACAGGTTTATTCTACCTAATCGCTCGTGTACCTGCTAGCAAAGCAGAGAACA
ACGTAATCACTTTCTACGACTTAAACGACTCTATTCCTGAAACAGTAGACGTATTCGTTGGTGAAATGT
CGGCTAACGTAGTACACTTGTTTGAATTACTACCAATGATGAGATTACCTCTAGCTCAAATTAACGCAT
CTGTTACATTTGCAGTTTTATGGTATGGCGCATTAGCTCTAAGAGCACCTAAGAAATGGGTACGTATTA
GAAACGTTAAATATATTCCTGTAAAAAACGTTCATAGCAACTAATAATAAGAGGAGGTAAATATATAT
GGTCTTCACACTCGAAGATTTCGTTGGGGACTGGCGACAGACAGCCGGCTACAACCTGGACCAAGTCC
TTGAACAGGGAGGTGTGTCCAGTTTGTTTCAGAATCTCGGGGTGTCCGTAACTCCGATCCAAAGGATT
GTCCTGAGCGGTGAAATGGGCTGAAGATCGACATCCATGTCATCATCCCGTATGAAGGTCTGAGCGG
CGACCAAATGGGCCAGATCGAAAAATTTTTAAGGTGGTGTACCCTGTGGATGATCATCACTTTAAGG
TGATCCTGCACTATGGCACACTGGTAATCGACGGGGTTACGCCGAACATGATCGACTATTTCGGACGG
CCGTATGAAGGCATCGCCGTGTTCGACGGCAAAAAGATCACTGTAACAGGGACCCTGTGGAACGGCA
ACAAAATTATCGACGAGCGCCTGATCAACCCCGACGGCTCCCTGCTGTTCCGAGTAACCATCAACGGA
GTGACCGGCTGGCGGCTGTGCGAACGCATTCTGGCGTAATAATTATAGGATAATTGAATAAAAACAGT
ATAGAGAGCAGATAAATACTGCTCTCTATTTTACTAATAAGGAGGATTTAAATTGCTAAAAAATACAA
ACTTAGCTAATTATAAAAAAGTGAATACACGGTTTGGAAATCTTAGTTTTGACGACAAAGGTATTTCT
AATGACTTAACGGAAGAACAGCAAAAAGAATTAGGTAAGCTTCGAGGATTCGAATATATTAAGACAG
AACAGAAACAAAAGAAGAACCTAAGAAAGAAGAACCTAAGAAAGAAGAACCTAAGAAAGAAGTA
CAGAAAATGAATTAGACAGCTTCTTAGCTAAAGAGCCTTCAATCAAAGAATTAAAAGAATTTGCGAGT
AAAAAAGGCATTAAAATTGAAAAAACTAAGAAAAACGATATAATTGAAGAACTAAAGAGAGGGTAA
TGTATAATGTATGGAGGTTATGAAGGACAAGATTCTTACGAATACCCTTACTCACATGGGAACCCTAA
GCATGTAGAGCCAGAAAAAGTTGACGAATATGTTCTTTCTGATTATGGTTGGACTGCGGAAACAATTA
AAGCATACATGTATGGTGTTCGTGTAGTAGACCCTGAAACAGGAGAGGAAATGGGAGACACCTTCTAC
AATCATATTATAGAGGTTGCCGTTGATAAGGC
```

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A composition comprising A511, LP40, and LP124 recombinant *Listeria* phage, each recombinant phage comprising a heterologous nucleic acid sequence encoding a luciferase that is at least 70% identical to SEQ ID NO: 4, a β-galactosidase, or a horseradish peroxidase.

2. An article of manufacture comprising A511, LP40, and LP124 recombinant *Listeria* phage, each recombinant phage comprising a heterologous nucleic acid sequence encoding a luciferase that is at least 70% identical to SEQ ID NOs 4, a β-galactosidase, or a horseradish peroxidase; and a solution comprising at least one non-phage component selected from at least one of a) at least one compound selected from carbohydrates and related compounds, b) at least one compound selected from nitrogen containing compounds, c) at least one compound selected from nucleic acids and related compounds, d) at least one compound selected from lipid, e) at least one inorganic compound, and f) at least one organic compound.

3. The composition of claim 1, wherein said composition provides increased *Listeria* species host range detection in comparison to the host range of a single recombinant *Listeria* phage.

4. The composition of claim 1, wherein said composition provides increased sensitivity for the detection of *Listeria* species in comparison to the sensitivity of a single recombinant *Listeria* phage.

5. The article of manufacture of claim 2, wherein said article of manufacture provides increased *Listeria* species host range detection in comparison to the host range of a single recombinant *Listeria* phage.

6. The article of manufacture of claim 2, wherein said article of manufacture provides increased sensitivity for the detection of *Listeria* species in comparison to the sensitivity of a single recombinant *Listeria* phage.

7. A method of detecting target bacteria, comprising:
exposing a sample to the composition of claim 1; and
assaying for the presence of the luciferase, β-galactosidase or horseradish peroxidase in the exposed sample.

8. A method of detecting target bacteria, comprising:
exposing a sample to the article of manufacture of claim 2; and
assaying for the presence of the luciferase, β-galactosidase or horseradish peroxidase in the exposed sample.

* * * * *

SEQUENCE LISTING

<160> NUMBER OF SEQ ID NOS: 35

<210> SEQ ID NO 1
<211> LENGTH: 1653
<212> TYPE: DNA
<213> ORGANISM: Xenorhabdus luminescens

<400> SEQUENCE: 1

```
atggaagacg ccaaaaacat aaagaaaggc ccggcgccat tctatcctct agaggatgga        60
accgctggag agcaactgca taaggctatg aagagatacg ccctggttcc tggaacaatt       120
gcttttacag atgcacatat cgaggtgaac atcacgtacg cggaatactt cgaaatgtcc       180
gttcggttgg cagaagctat gaaacgatat gggctgaata caaatcacag aatcgtcgta       240
tgcagtgaaa actctcttca attctttatg ccggtgttgg gcgcgttatt tatcggagtt       300
gcagttgcgc ccgcgaacga catttataat gaacgtgaat tgctcaacag tatgaacatt       360
tcgcagccta ccgtagtgtt tgtttccaaa aagggggttgc aaaaaatttt gaacgtgcaa       420
aaaaaattac caataatcca gaaaattatt atcatggatt ctaaaacgga ttaccaggga       480
tttcagtcga tgtacacgtt cgtcacatct catctacctc ccgttttaa tgaatacgat       540
tttgtaccag agtcctttga tcgtgacaaa acaattgcac tgataatgaa ttcctctgga       600
tctactgggt tacctaaggg tgtggccctt ccgcatagaa ctgcctgcgt cagattctcg       660
catgccagag atcctatttt tggcaatcaa atcattccgg atactgcgat tttaagtgtt       720
gttccattcc atcacggttt tggaatgttt actacactcg atatttgat atgtggattt       780
cgagtcgtct taatgtatag atttgaagaa gagctgtttt tacgatccct tcaggattac       840
aaaattcaaa gtgcgttgct agtaccaacc ctatttcat tcttcgccaa agcactctg        900
attgacaaat acgatttatc taatttacac gaaattgctt ctgggggcgc acctctttcg       960
aaagaagtcg gggaagcggt tgcaaaacgc ttccatcttc cagggatacg acaaggatat      1020
gggctcactg agactacatc agctattctg attacacccg aggggatgat aaaccgggc       1080
gcggtcggta agttgttcc attttttgaa gcgaaggttg tggatctgga taccgggaaa      1140
acgctgggcg ttaatcagag aggcgaatta tgtgtcagag acctatgat tatgtccggt      1200
tatgtaaaca atccggaagc gaccaacgcc ttgattgaca aggatggatg gctacattct      1260
ggagacatag cttactggga cgaagacgaa cacttcttca tagttgaccg cttgaagtct      1320
ttaattaaat acaaaggata tcaggtggcc cccgctgaat ggaatcgat attgttacaa       1380
caccccaaca tcttcgacgc gggcgtggca ggtcttcccg acgatgacgc cggtgaactt      1440
cccgccgccg ttgttgtttt ggagcacgga aagacgatga cggaaaaaga gatcgtggat      1500
tacgtcgcca gtcaagtaac aaccgcgaaa aagttgcgcg gagagttgt gtttgtggac      1560
gaagtaccga aggtcttac cggaaaactc gacgcaagaa aaatcagaga gatcctcata      1620
aaggccaaga agggcggaaa gtccaaattg taa                                   1653
```

<210> SEQ ID NO 2
<211> LENGTH: 550
<212> TYPE: PRT
<213> ORGANISM: Xenorhabdus luminescens

<400> SEQUENCE: 2

```
Met Glu Asp Ala Lys Asn Ile Lys Lys Gly Pro Ala Pro Phe Tyr Pro
1               5                   10                  15

Leu Glu Asp Gly Thr Ala Gly Glu Gln Leu His Lys Ala Met Lys Arg
            20                  25                  30
```

-continued

```
Tyr Ala Leu Val Pro Gly Thr Ile Ala Phe Thr Asp Ala His Ile Glu
         35                  40                  45
Val Asn Ile Thr Tyr Ala Glu Tyr Phe Glu Met Ser Val Arg Leu Ala
 50                  55                  60
Glu Ala Met Lys Arg Tyr Gly Leu Asn Thr Asn His Arg Ile Val Val
 65                  70                  75                  80
Cys Ser Glu Asn Ser Leu Gln Phe Phe Met Pro Val Leu Gly Ala Leu
                 85                  90                  95
Phe Ile Gly Val Ala Val Ala Pro Ala Asn Asp Ile Tyr Asn Glu Arg
                100                 105                 110
Glu Leu Leu Asn Ser Met Asn Ile Ser Gln Pro Thr Val Val Phe Val
             115                 120                 125
Ser Lys Lys Gly Leu Gln Lys Ile Leu Asn Val Gln Lys Lys Leu Pro
130                 135                 140
Ile Ile Gln Lys Ile Ile Ile Met Asp Ser Lys Thr Asp Tyr Gln Gly
145                 150                 155                 160
Phe Gln Ser Met Tyr Thr Phe Val Thr Ser His Leu Pro Pro Gly Phe
                165                 170                 175
Asn Glu Tyr Asp Phe Val Pro Glu Ser Phe Asp Arg Asp Lys Thr Ile
                180                 185                 190
Ala Leu Ile Met Asn Ser Ser Gly Ser Thr Gly Leu Pro Lys Gly Val
             195                 200                 205
Ala Leu Pro His Arg Thr Ala Cys Val Arg Phe Ser His Ala Arg Asp
210                 215                 220
Pro Ile Phe Gly Asn Gln Ile Ile Pro Asp Thr Ala Ile Leu Ser Val
225                 230                 235                 240
Val Pro Phe His His Gly Phe Gly Met Phe Thr Thr Leu Gly Tyr Leu
                245                 250                 255
Ile Cys Gly Phe Arg Val Val Leu Met Tyr Arg Phe Glu Glu Glu Leu
                260                 265                 270
Phe Leu Arg Ser Leu Gln Asp Tyr Lys Ile Gln Ser Ala Leu Leu Val
             275                 280                 285
Pro Thr Leu Phe Ser Phe Phe Ala Lys Ser Thr Leu Ile Asp Lys Tyr
290                 295                 300
Asp Leu Ser Asn Leu His Glu Ile Ala Ser Gly Gly Ala Pro Leu Ser
305                 310                 315                 320
Lys Glu Val Gly Glu Ala Val Ala Lys Arg Phe His Leu Pro Gly Ile
                325                 330                 335
Arg Gln Gly Tyr Gly Leu Thr Glu Thr Thr Ser Ala Ile Leu Ile Thr
                340                 345                 350
Pro Glu Gly Asp Asp Lys Pro Gly Ala Val Gly Lys Val Val Pro Phe
             355                 360                 365
Phe Glu Ala Lys Val Val Asp Leu Asp Thr Gly Lys Thr Leu Gly Val
370                 375                 380
Asn Gln Arg Gly Glu Leu Cys Val Arg Gly Pro Met Ile Met Ser Gly
385                 390                 395                 400
Tyr Val Asn Asn Pro Glu Ala Thr Asn Ala Leu Ile Asp Lys Asp Gly
                405                 410                 415
Trp Leu His Ser Gly Asp Ile Ala Tyr Trp Asp Glu Asp Glu His Phe
                420                 425                 430
Phe Ile Val Asp Arg Leu Lys Ser Leu Ile Lys Tyr Lys Gly Tyr Gln
             435                 440                 445
```

Val Ala Pro Ala Glu Leu Glu Ser Ile Leu Leu Gln His Pro Asn Ile
    450                 455                 460

Phe Asp Ala Gly Val Ala Gly Leu Pro Asp Asp Ala Gly Glu Leu
465                 470                 475                 480

Pro Ala Ala Val Val Leu Glu His Gly Lys Thr Met Thr Glu Lys
                485                 490                 495

Glu Ile Val Asp Tyr Val Ala Ser Gln Val Thr Thr Ala Lys Lys Leu
            500                 505                 510

Arg Gly Gly Val Val Phe Val Asp Glu Val Pro Lys Gly Leu Thr Gly
                515                 520                 525

Lys Leu Asp Ala Arg Lys Ile Arg Glu Ile Leu Ile Lys Ala Lys Lys
    530                 535                 540

Gly Gly Lys Ser Lys Leu
545                 550

<210> SEQ ID NO 3
<211> LENGTH: 516
<212> TYPE: DNA
<213> ORGANISM: Artificial
<220> FEATURE:
<223> OTHER INFORMATION: Recombinant luciferase

<400> SEQUENCE: 3
atggtcttca cactcgaaga tttcgttggg gactggcgac agacagccgg ctacaacctg      60
gaccaagtcc ttgaacaggg aggtgtgtcc agtttgtttc agaatctcgg ggtgtccgta     120
actccgatcc aaaggattgt cctgagcggt gaaaatgggc tgaagatcga catccatgtc     180
atcatcccgt atgaaggtct gagcggcgac caaatgggcc agatcgaaaa aatttttaag     240
gtggtgtacc ctgtggatga tcatcacttt aaggtgatcc tgcactatgg cacactggta     300
atcgacgggg ttacgccgaa catgatcgac tatttcggac ggccgtatga aggcatcgcc     360
gtgttcgacg gcaaaaagat cactgtaaca gggaccctgt ggaacggcaa caaaattatc     420
gacgagcgcc tgatcaaccc cgacggctcc ctgctgttcc gagtaaccat caacggagtg     480
accggctggc ggctgtgcga acgcattctg gcgtaa                              516

<210> SEQ ID NO 4
<211> LENGTH: 171
<212> TYPE: PRT
<213> ORGANISM: Artificial
<220> FEATURE:
<223> OTHER INFORMATION: recombinant luciferase

<400> SEQUENCE: 4

Met Val Phe Thr Leu Glu Asp Phe Val Gly Asp Trp Arg Gln Thr Ala
1               5                   10                  15

Gly Tyr Asn Leu Asp Gln Val Leu Glu Gln Gly Gly Val Ser Ser Leu
            20                  25                  30

Phe Gln Asn Leu Gly Val Ser Val Thr Pro Ile Gln Arg Ile Val Leu
        35                  40                  45

Ser Gly Glu Asn Gly Leu Lys Ile Asp Ile His Val Ile Ile Pro Tyr
    50                  55                  60

Glu Gly Leu Ser Gly Asp Gln Met Gly Gln Ile Glu Lys Ile Phe Lys
65                  70                  75                  80

Val Val Tyr Pro Val Asp Asp His His Phe Lys Val Ile Leu His Tyr
                85                  90                  95

Gly Thr Leu Val Ile Asp Gly Val Thr Pro Asn Met Ile Asp Tyr Phe
            100                 105                 110

```
Gly Arg Pro Tyr Glu Gly Ile Ala Val Phe Asp Gly Lys Lys Ile Thr
            115                 120                 125

Val Thr Gly Thr Leu Trp Asn Gly Asn Lys Ile Ile Asp Glu Arg Leu
    130                 135                 140

Ile Asn Pro Asp Gly Ser Leu Leu Phe Arg Val Thr Ile Asn Gly Val
145                 150                 155                 160

Thr Gly Trp Arg Leu Cys Glu Arg Ile Leu Ala
                165                 170
```

<210> SEQ ID NO 5
<211> LENGTH: 1407
<212> TYPE: DNA
<213> ORGANISM: LP40 Phage

<400> SEQUENCE: 5

```
atgccaaaaa ataacaaaga agaagaagtt aaagaagtaa accttaattc agtacaagag      60
gatgcgttaa gtcctttac aactggttat ggtatcacac ctgatacaca aacagatgca     120
ggggcactaa gacgtgagtt cctagacgac caaatctcaa tgcttacttg gacagaaaat     180
gatttaacat tctacaaaga catcgctaaa aaaccagcta catctacagt agcaaaatac     240
gatgtgtaca tgcaacacgg taaagtaggt catactagat ttactcgtga gattggggta     300
gcaccagtaa gtgaccctaa catccgtcaa aaaacagtaa acatgaaatt tgcttctgat     360
actaaaaata ttagtatcgc agcaggtcta gtaaacaaca ttcaagaccc tatgcaaatt     420
ttgactgatg atgctatcgt aaatatcgct aaaacaattg agtgggcttc attctttgga     480
gattctgact tatcagatag cccagaacca caagcaggat tagaatttga tggcttggct     540
aaacttatta accaagataa cgttcatgat gctcgtggag ctagcttgac tgaaagcttg     600
ttaaaccaag cagcagtaat gattagtaaa ggttatggta cacctacaga tgcttacatg     660
ccagtagggg ttcaagcaga ctttgttaac caacaacttt ctaaacaaac acaacttgtt     720
cgcgataacg gaaacaacgt aagcgttggt ttcaacatcc aaggtttcca ttcagctcgt     780
ggatttatca aacttcacgg ttctacagta atggaaaacg aacaaatctt agatgaacgt     840
attcttgctt taccaacagc tccacaacca gctaaggtaa ctgcaacaca agaagcaggt     900
aaaaaaggac aatttagagc agaagattta gcagcacatg aatataaagt tgttgtaagt     960
tctgacgatg cagagtctat tgcaagtgaa gtggctacag ctacagttac tgcaaaagat    1020
gacggcgtta aactagaaat cgaattagct ccaatgtata gctctcgtcc acaattcgtt    1080
tcaatctata gaaaaggtgc agaaacaggt ttattctacc taatcgctcg tgtacctgct    1140
agcaaagcag agaacaacgt aatcactttc tacgacttaa cgactctat tcctgaaaca    1200
gtagacgtat tcgttggtga atgtcggct aacgtagtac acttgtttga attactacca    1260
atgatgagat tacctctagc tcaaattaac gcatctgtta catttgcagt tttatggtat    1320
ggcgcattag ctctaagagc acctaagaaa tgggtacgta ttagaaacgt taaatatatt    1380
cctgtaaaaa acgttcatag caactaa                                        1407
```

<210> SEQ ID NO 6
<211> LENGTH: 468
<212> TYPE: PRT
<213> ORGANISM: LP40 Phage

<400> SEQUENCE: 6

```
Met Pro Lys Asn Asn Lys Glu Glu Glu Val Lys Glu Val Asn Leu Asn
1               5                   10                  15
```

-continued

```
Ser Val Gln Glu Asp Ala Leu Lys Ser Phe Thr Thr Gly Tyr Gly Ile
            20                  25                  30

Thr Pro Asp Thr Gln Thr Asp Ala Gly Ala Leu Arg Arg Glu Phe Leu
        35                  40                  45

Asp Asp Gln Ile Ser Met Leu Thr Trp Thr Glu Asn Asp Leu Thr Phe
50                  55                  60

Tyr Lys Asp Ile Ala Lys Lys Pro Ala Thr Ser Thr Val Ala Lys Tyr
65                  70                  75                  80

Asp Val Tyr Met Gln His Gly Lys Val Gly His Thr Arg Phe Thr Arg
                85                  90                  95

Glu Ile Gly Val Ala Pro Val Ser Asp Pro Asn Ile Arg Gln Lys Thr
            100                 105                 110

Val Asn Met Lys Phe Ala Ser Asp Thr Lys Asn Ile Ser Ile Ala Ala
        115                 120                 125

Gly Leu Val Asn Ile Gln Asp Pro Met Gln Ile Leu Thr Asp Asp
130                 135                 140

Ala Ile Val Asn Ile Ala Lys Thr Ile Glu Trp Ala Ser Phe Phe Gly
145                 150                 155                 160

Asp Ser Asp Leu Ser Asp Ser Pro Glu Pro Gln Ala Gly Leu Glu Phe
                165                 170                 175

Asp Gly Leu Ala Lys Leu Ile Asn Gln Asp Asn Val His Asp Ala Arg
            180                 185                 190

Gly Ala Ser Leu Thr Glu Ser Leu Leu Asn Gln Ala Ala Val Met Ile
        195                 200                 205

Ser Lys Gly Tyr Gly Thr Pro Thr Asp Ala Tyr Met Pro Val Gly Val
210                 215                 220

Gln Ala Asp Phe Val Asn Gln Gln Leu Ser Lys Gln Thr Gln Leu Val
225                 230                 235                 240

Arg Asp Asn Gly Asn Asn Val Ser Val Gly Phe Asn Ile Gln Gly Phe
                245                 250                 255

His Ser Ala Arg Gly Phe Ile Lys Leu His Gly Ser Thr Val Met Glu
            260                 265                 270

Asn Glu Gln Ile Leu Asp Glu Arg Ile Leu Ala Leu Pro Thr Ala Pro
        275                 280                 285

Gln Pro Ala Lys Val Thr Ala Thr Gln Glu Ala Gly Lys Lys Gly Gln
290                 295                 300

Phe Arg Ala Glu Asp Leu Ala Ala His Glu Tyr Lys Val Val Val Ser
305                 310                 315                 320

Ser Asp Asp Ala Glu Ser Ile Ala Ser Glu Val Ala Thr Ala Thr Val
                325                 330                 335

Thr Ala Lys Asp Asp Gly Val Lys Leu Glu Ile Glu Leu Ala Pro Met
            340                 345                 350

Tyr Ser Ser Arg Pro Gln Phe Val Ser Ile Tyr Arg Lys Gly Ala Glu
        355                 360                 365

Thr Gly Leu Phe Tyr Leu Ile Ala Arg Val Pro Ala Ser Lys Ala Glu
370                 375                 380

Asn Asn Val Ile Thr Phe Tyr Asp Leu Asn Asp Ser Ile Pro Glu Thr
385                 390                 395                 400

Val Asp Val Phe Val Gly Glu Met Ser Ala Asn Val Val His Leu Phe
                405                 410                 415

Glu Leu Leu Pro Met Met Arg Leu Pro Leu Ala Gln Ile Asn Ala Ser
            420                 425                 430
```

```
Val Thr Phe Ala Val Leu Trp Tyr Gly Ala Leu Ala Leu Arg Ala Pro
            435                 440                 445

Lys Lys Trp Val Arg Ile Arg Asn Val Lys Tyr Ile Pro Val Lys Asn
        450                 455                 460

Val His Ser Asn
465
```

<210> SEQ ID NO 7
<211> LENGTH: 1407
<212> TYPE: DNA
<213> ORGANISM: LP48 Phage

<400> SEQUENCE: 7

```
atgccaaaaa ataacaaaga agaagaagtt aaagaagtaa accttaattc agtacaagag      60
gacgcgttaa agtcctttac aactggttat ggtatcacac ctgatacaca aacagatgca     120
ggagcattaa gacgtgagtt cctagacgac caaatctcaa tgcttacttg gacagagaat     180
gatttaacat tctataaaga catcgctaaa aaaccagcta catctacagt agcaaaatac     240
gatgtataca tgcaacatgg taaggtaggt catactagat ttactcgtga gattggggta     300
gcaccagtaa gtgaccctaa catccgtcaa aaaacagtaa acatgaaatt tgcttccgat     360
actaaaaaca tcagtatcgc agcaggtcta gtaaacaaca ttcaagaccc aatgcaaatt     420
ttgactgacg atgctatcgt aaatattgct aaaacaattg agtgggcttc attctttgga     480
gattctgact tatcagatag cccagaacca caagcaggac tagaatttga cggcttggct     540
aaacttatta accaagataa cgttcatgat gctcgtggag ctagcttgac tgaaagcttg     600
ttaaaccaag cagcagtaat gattagtaaa ggttatggta cacctacaga tgcttacatg     660
ccagtagggg ttcaagcaga ctttgttaac caacaacttt ctaaacaaac acaacttgtt     720
cgcgataacg gaaacaacgt aagcgttggt ttcaacatcc aaggtttcca ttcagctcgt     780
ggatttatca aacttcacgg ttctacagta atggaaaacg aacaaatctt agatgaacgt     840
attcttgctt taccaacagc tccacaacca gctaaggtaa ctgcaacaca agaagcaggt     900
aaaaaaggac aatttagagc agaagattta gcagcacatg aatataaagt tgttgtaagt     960
tctgacgatg cagagtctat tgcaagtgaa gtggctacag ctacagttac tgcaaaagat    1020
gacggcgtta aactagaaat cgaattagct ccaatgtata gctctcgtcc acaattcgtt    1080
tcaatctata gaaaggtgc agaaacaggt ttattctacc taatcgctcg tgtacctgct    1140
agcaaagcag agaacaacgt aatcactttc tacgacttaa cgactctat tcctgaaaca    1200
gtagacgtat tcgttggtga aatgtcggct aactagtac acttgtttga attactacca    1260
atgatgagat tacctctagc tcaaattaac gcatctgtta catttgcagt tttatggtat    1320
ggcgcattag ctctaagagc acctaagaaa tgggtacgta ttagaaacgt taaatatatt    1380
cctgtaaaaa acgttcatag caactaa                                         1407
```

<210> SEQ ID NO 8
<211> LENGTH: 468
<212> TYPE: PRT
<213> ORGANISM: LP48 Phage

<400> SEQUENCE: 8

```
Met Pro Lys Asn Asn Lys Glu Glu Val Lys Glu Val Asn Leu Asn
1               5                  10                  15

Ser Val Gln Glu Asp Ala Leu Lys Ser Phe Thr Thr Gly Tyr Gly Ile
            20                  25                  30
```

```
Thr Pro Asp Thr Gln Thr Asp Ala Gly Ala Leu Arg Arg Glu Phe Leu
         35                  40                  45

Asp Asp Gln Ile Ser Met Leu Thr Trp Thr Glu Asn Asp Leu Thr Phe
 50                  55                  60

Tyr Lys Asp Ile Ala Lys Lys Pro Ala Thr Ser Thr Val Ala Lys Tyr
 65                  70                  75                  80

Asp Val Tyr Met Gln His Gly Lys Val Gly His Thr Arg Phe Thr Arg
                 85                  90                  95

Glu Ile Gly Val Ala Pro Val Ser Asp Pro Asn Ile Arg Gln Lys Thr
                100                 105                 110

Val Asn Met Lys Phe Ala Ser Asp Thr Lys Asn Ile Ser Ile Ala Ala
             115                 120                 125

Gly Leu Val Asn Asn Ile Gln Asp Pro Met Gln Ile Leu Thr Asp Asp
130                 135                 140

Ala Ile Val Asn Ile Ala Lys Thr Ile Glu Trp Ala Ser Phe Phe Gly
145                 150                 155                 160

Asp Ser Asp Leu Ser Asp Ser Pro Glu Pro Gln Ala Gly Leu Glu Phe
                165                 170                 175

Asp Gly Leu Ala Lys Leu Ile Asn Gln Asp Asn Val His Asp Ala Arg
            180                 185                 190

Gly Ala Ser Leu Thr Glu Ser Leu Leu Asn Gln Ala Ala Val Met Ile
        195                 200                 205

Ser Lys Gly Tyr Gly Thr Pro Thr Asp Ala Tyr Met Pro Val Gly Val
    210                 215                 220

Gln Ala Asp Phe Val Asn Gln Gln Leu Ser Lys Gln Thr Gln Leu Val
225                 230                 235                 240

Arg Asp Asn Gly Asn Asn Val Ser Val Gly Phe Asn Ile Gln Gly Phe
                245                 250                 255

His Ser Ala Arg Gly Phe Ile Lys Leu His Gly Ser Thr Val Met Glu
            260                 265                 270

Asn Glu Gln Ile Leu Asp Glu Arg Ile Leu Ala Leu Pro Thr Ala Pro
        275                 280                 285

Gln Pro Ala Lys Val Thr Ala Thr Gln Glu Ala Gly Lys Lys Gly Gln
    290                 295                 300

Phe Arg Ala Glu Asp Leu Ala Ala His Glu Tyr Lys Val Val Ser
305                 310                 315                 320

Ser Asp Asp Ala Glu Ser Ile Ala Ser Glu Val Ala Thr Ala Thr Val
                325                 330                 335

Thr Ala Lys Asp Asp Gly Val Lys Leu Glu Ile Glu Leu Ala Pro Met
            340                 345                 350

Tyr Ser Ser Arg Pro Gln Phe Val Ser Ile Tyr Arg Lys Gly Ala Glu
        355                 360                 365

Thr Gly Leu Phe Tyr Leu Ile Ala Arg Val Pro Ala Ser Lys Ala Glu
370                 375                 380

Asn Asn Val Ile Thr Phe Tyr Asp Leu Asn Asp Ser Ile Pro Glu Thr
385                 390                 395                 400

Val Asp Val Phe Val Gly Glu Met Ser Ala Asn Val His Leu Phe
                405                 410                 415

Glu Leu Leu Pro Met Met Arg Leu Pro Leu Ala Gln Ile Asn Ala Ser
            420                 425                 430

Val Thr Phe Ala Val Leu Trp Tyr Gly Ala Leu Ala Leu Arg Ala Pro
        435                 440                 445

Lys Lys Trp Val Arg Ile Arg Asn Val Lys Tyr Ile Pro Val Lys Asn
```

Val His Ser Asn
465

<210> SEQ ID NO 9
<211> LENGTH: 1407
<212> TYPE: DNA
<213> ORGANISM: LP099 Phage

<400> SEQUENCE: 9

```
atgccaaaaa ataacaaaga agaagaagtt aaagaagtaa accttaattc agtacaagag      60
gacgcgttaa agtcctttac aactggttat ggtatcacac ctgatacaca aacagatgca     120
ggagcattaa gacgtgagtt cctagacgac caaatctcaa tgcttacttg gacagagaat     180
gatttaacat tctataaaga catcgctaaa aaaccagcta catctacagt agcaaaatac     240
gatgtataca tgcaacatgg taaggtaggt catactagat ttactcgtga gattggggta     300
gcaccagtaa gtgaccctaa catccgtcaa aaaacagtaa acatgaaatt tgcttccgat     360
actaaaaaca tcagtatcgc agcaggtcta gtaaacaaca ttcaagaccc aatgcaaatt     420
ttgactgacg atgctatcgt aaatattgct aaaacaattg agtgggcttc attctttgga     480
gattctgact tatcagatag cccagaacca caagcaggac tagaatttga cggcttggct     540
aaacttatta accaagataa cgttcatgat gctcgtggag ctagcttgac tgaaagcttg     600
ttaaaccaag cagcagtaat gattagtaaa ggttatggta cacctacaga tgcttacatg     660
ccagtagggg ttcaagcaga ctttgttaac caacaacttt ctaaacaaac acaacttgtt     720
cgcgataacg gaaacaacgt aagcgttggt ttcaacatcc aaggtttcca ttcagctcgt     780
ggatttatca aacttcacgg ttctacagta atggaaaacg aacaaatctt agatgaacgt     840
attcttgctt taccaacagc tccacaacca gctaaggtaa ctgcaacaca agaagcaggt     900
aaaaaaggac aatttagagc agaagattta gcagcacatg aatataaagt tgttgtaagt     960
tctgacgatg cagagtctat tgcaagtgaa gtggctacag ctacagttac tgcaaaagat    1020
gacggcgtta actagaaat cgaattagct ccaatgtata gctctcgtcc acaattcgtt    1080
tcaatctata gaaaaggtgc agaaacaggt ttattctacc taatcgctcg tgtacctgct    1140
agcaaagcag agaacaacgt aatcactttc tacgacttaa cgactctctat tcctgaaaca    1200
gtagacgtat tcgttggtga atgtcggct aacgtagtac acttgtttga attactacca    1260
atgatgagat acctctagc tcaaattaac gcatctgtta catttgcagt tttatggtat    1320
ggcgcattag ctctaagagc acctaagaaa tgggtacgta ttagaaacgt taaatatatt    1380
cctgtaaaaa acgttcatag caactaa                                         1407
```

<210> SEQ ID NO 10
<211> LENGTH: 468
<212> TYPE: PRT
<213> ORGANISM: LP099 Phage

<400> SEQUENCE: 10

Met Pro Lys Asn Asn Lys Glu Glu Val Lys Glu Val Asn Leu Asn
1               5                   10                  15

Ser Val Gln Glu Asp Ala Leu Lys Ser Phe Thr Thr Gly Tyr Gly Ile
            20                  25                  30

Thr Pro Asp Thr Gln Thr Asp Ala Gly Ala Leu Arg Arg Glu Phe Leu
        35                  40                  45

Asp Asp Gln Ile Ser Met Leu Thr Trp Thr Glu Asn Asp Leu Thr Phe

```
                 50                  55                  60
Tyr Lys Asp Ile Ala Lys Pro Ala Thr Ser Thr Val Ala Lys Tyr
 65                  70                  75                  80

Asp Val Tyr Met Gln His Gly Lys Val Gly His Thr Arg Phe Thr Arg
                 85                  90                  95

Glu Ile Gly Val Ala Pro Val Ser Asp Pro Asn Ile Arg Gln Lys Thr
                100                 105                 110

Val Asn Met Lys Phe Ala Ser Asp Thr Lys Asn Ile Ser Ile Ala Ala
                115                 120                 125

Gly Leu Val Asn Asn Ile Gln Asp Pro Met Gln Ile Leu Thr Asp Asp
130                 135                 140

Ala Ile Val Asn Ile Ala Lys Thr Ile Glu Trp Ala Ser Phe Phe Gly
145                 150                 155                 160

Asp Ser Asp Leu Ser Asp Ser Pro Glu Pro Gln Ala Gly Leu Glu Phe
                165                 170                 175

Asp Gly Leu Ala Lys Leu Ile Asn Gln Asp Asn Val His Asp Ala Arg
                180                 185                 190

Gly Ala Ser Leu Thr Glu Ser Leu Leu Asn Gln Ala Ala Val Met Ile
                195                 200                 205

Ser Lys Gly Tyr Gly Thr Pro Thr Asp Ala Tyr Met Pro Val Gly Val
210                 215                 220

Gln Ala Asp Phe Val Asn Gln Gln Leu Ser Lys Gln Thr Gln Leu Val
225                 230                 235                 240

Arg Asp Asn Gly Asn Asn Val Ser Val Gly Phe Asn Ile Gln Gly Phe
                245                 250                 255

His Ser Ala Arg Gly Phe Ile Lys Leu His Gly Ser Thr Val Met Glu
                260                 265                 270

Asn Glu Gln Ile Leu Asp Glu Arg Ile Leu Ala Leu Pro Thr Ala Pro
                275                 280                 285

Gln Pro Ala Lys Val Thr Ala Thr Gln Glu Ala Gly Lys Lys Gly Gln
                290                 295                 300

Phe Arg Ala Glu Asp Leu Ala Ala His Glu Tyr Lys Val Val Ser
305                 310                 315                 320

Ser Asp Asp Ala Glu Ser Ile Ala Ser Glu Val Ala Thr Ala Thr Val
                325                 330                 335

Thr Ala Lys Asp Asp Gly Val Lys Leu Glu Ile Glu Leu Ala Pro Met
                340                 345                 350

Tyr Ser Ser Arg Pro Gln Phe Val Ser Ile Tyr Arg Lys Gly Ala Glu
                355                 360                 365

Thr Gly Leu Phe Tyr Leu Ile Ala Arg Val Pro Ala Ser Lys Ala Glu
                370                 375                 380

Asn Asn Val Ile Thr Phe Tyr Asp Leu Asn Asp Ser Ile Pro Glu Thr
385                 390                 395                 400

Val Asp Val Phe Val Gly Glu Met Ser Ala Asn Val Val His Leu Phe
                405                 410                 415

Glu Leu Leu Pro Met Met Arg Leu Pro Leu Ala Gln Ile Asn Ala Ser
                420                 425                 430

Val Thr Phe Ala Val Leu Trp Tyr Gly Ala Leu Ala Leu Arg Ala Pro
                435                 440                 445

Lys Lys Trp Val Arg Ile Arg Asn Val Lys Tyr Ile Pro Val Lys Asn
450                 455                 460

Val His Ser Asn
465
```

<210> SEQ ID NO 11
<211> LENGTH: 1407
<212> TYPE: DNA
<213> ORGANISM: LP101 Phage

<400> SEQUENCE: 11

```
atgccaaaaa ataacaaaga agaagaagtt aaagaagtaa accttaattc agtacaagag      60
gacgcgttaa agtcctttac aactggttat ggtatcacac ctgatacaca aacagatgca     120
ggagcattaa gacgtgagtt cctagacgac caaatctcaa tgcttacttg gacagagaat     180
gatttaacat tctataaaga catcgctaaa aaaccagcta catctacagt agcaaaatac     240
gatgtataca tgcaacatgg taaggtaggt catactagat ttactcgtga gattggggta     300
gcaccagtaa gtgaccctaa catccgtcaa aaaacagtaa acatgaaatt tgcttccgat     360
actaaaaaca tcagtatcgc agcaggtcta gtaaacaaca ttcaagaccc aatgcaaatt     420
ttgactgacg atgctatcgt aaatattgct aaaacaattg agtgggcttc attctttgga     480
gattctgact tatcagatag cccagaacca caagcaggac tagaatttga cggcttggct     540
aaacttatta accaagataa cgttcatgat gctcgtggag ctagcttgac tgaaagcttg     600
ttaaaccaag cagcagtaat gattagtaaa ggttatggta cacctacaga tgcttacatg     660
ccagtagggg ttcaagcaga ctttgttaac caacaacttt ctaaacaaac acaacttgtt     720
cgcgataacg gaaacaacgt aagcgttggt ttcaacatcc aaggtttcca ttcagctcgt     780
ggatttatca aacttcacgg ttctacagta atggaaaacg aacaaatctt agatgaacgt     840
attcttgctt taccaacagc tccacaacca gctaaggtaa ctgcaacaca agaagcaggt     900
aaaaaaggac aatttagagc agaagattta gcagcacatg aatataaagt tgttgtaagt     960
tctgacgatg cagagtctat tgcaagtgaa gtggctacag ctacagttac tgcaaaagat    1020
gacggcgtta aactagaaat cgaattagct ccaatgtata gctctcgtcc acaattcgtt    1080
tcaatctata gaaaaggtgc agaaacaggt ttattctacc taatcgctcg tgtacctgct    1140
agcaaagcag agaacaacgt aatcacttc tacgacttaa acgactctat tcctgaaaca    1200
gtagacgtat tcgttggtga atgtcggct aacgtagtac acttgtttga attactacca    1260
atgatgagat tacctctagc tcaaattaac gcatctgtta catttgcagt tttatggtat    1320
ggcgcattag ctctaagagc acctaagaaa tgggtacgta ttagaaacgt taaatatatt    1380
cctgtaaaaa acgttcatag caactaa                                        1407
```

<210> SEQ ID NO 12
<211> LENGTH: 468
<212> TYPE: PRT
<213> ORGANISM: LP101 Phage

<400> SEQUENCE: 12

```
Met Pro Lys Asn Asn Lys Glu Glu Val Lys Glu Val Asn Leu Asn
1               5                   10                  15

Ser Val Gln Glu Asp Ala Leu Lys Ser Phe Thr Thr Gly Tyr Gly Ile
            20                  25                  30

Thr Pro Asp Thr Gln Thr Asp Ala Gly Ala Leu Arg Arg Glu Phe Leu
        35                  40                  45

Asp Asp Gln Ile Ser Met Leu Thr Trp Thr Glu Asn Asp Leu Thr Phe
    50                  55                  60

Tyr Lys Asp Ile Ala Lys Lys Pro Ala Thr Ser Thr Val Ala Lys Tyr
65                  70                  75                  80
```

```
Asp Val Tyr Met Gln His Gly Lys Val Gly His Thr Arg Phe Thr Arg
                85                  90                  95

Glu Ile Gly Val Ala Pro Val Ser Asp Pro Asn Ile Arg Gln Lys Thr
            100                 105                 110

Val Asn Met Lys Phe Ala Ser Asp Thr Lys Asn Ile Ser Ile Ala Ala
        115                 120                 125

Gly Leu Val Asn Asn Ile Gln Asp Pro Met Gln Ile Leu Thr Asp Asp
    130                 135                 140

Ala Ile Val Asn Ile Ala Lys Thr Ile Glu Trp Ala Ser Phe Phe Gly
145                 150                 155                 160

Asp Ser Asp Leu Ser Asp Ser Pro Glu Pro Gln Ala Gly Leu Glu Phe
                165                 170                 175

Asp Gly Leu Ala Lys Leu Ile Asn Gln Asp Asn Val His Asp Ala Arg
            180                 185                 190

Gly Ala Ser Leu Thr Glu Ser Leu Leu Asn Gln Ala Ala Val Met Ile
        195                 200                 205

Ser Lys Gly Tyr Gly Thr Pro Thr Asp Ala Tyr Met Pro Val Gly Val
    210                 215                 220

Gln Ala Asp Phe Val Asn Gln Gln Leu Ser Lys Gln Thr Gln Leu Val
225                 230                 235                 240

Arg Asp Asn Gly Asn Asn Val Ser Val Gly Phe Asn Ile Gln Gly Phe
                245                 250                 255

His Ser Ala Arg Gly Phe Ile Lys Leu His Gly Ser Thr Val Met Glu
            260                 265                 270

Asn Glu Gln Ile Leu Asp Glu Arg Ile Leu Ala Leu Pro Thr Ala Pro
        275                 280                 285

Gln Pro Ala Lys Val Thr Ala Thr Gln Glu Ala Gly Lys Lys Gly Gln
    290                 295                 300

Phe Arg Ala Glu Asp Leu Ala Ala His Glu Tyr Lys Val Val Ser
305                 310                 315                 320

Ser Asp Asp Ala Glu Ser Ile Ala Ser Glu Val Ala Thr Ala Thr Val
                325                 330                 335

Thr Ala Lys Asp Asp Gly Val Lys Leu Glu Ile Glu Leu Ala Pro Met
            340                 345                 350

Tyr Ser Ser Arg Pro Gln Phe Val Ser Ile Tyr Arg Lys Gly Ala Glu
        355                 360                 365

Thr Gly Leu Phe Tyr Leu Ile Ala Arg Val Pro Ala Ser Lys Ala Glu
    370                 375                 380

Asn Asn Val Ile Thr Phe Tyr Asp Leu Asn Asp Ser Ile Pro Glu Thr
385                 390                 395                 400

Val Asp Val Phe Val Gly Glu Met Ser Ala Asn Val Val His Leu Phe
                405                 410                 415

Glu Leu Leu Pro Met Met Arg Leu Pro Leu Ala Gln Ile Asn Ala Ser
            420                 425                 430

Val Thr Phe Ala Val Leu Trp Tyr Gly Ala Leu Ala Leu Arg Ala Pro
        435                 440                 445

Lys Lys Trp Val Arg Ile Arg Asn Val Lys Tyr Ile Pro Val Lys Asn
    450                 455                 460

Val His Ser Asn
465

<210> SEQ ID NO 13
<211> LENGTH: 1407
```

-continued

```
<212> TYPE: DNA
<213> ORGANISM: LP124 Phage

<400> SEQUENCE: 13
atgccaaaaa ataacaaaga agaagaagtt aaagaagtaa accttaattc agtacaagag      60
gacgcgttaa agtcctttac aactggttat ggtatcacac ctgatacaca aacagatgca     120
ggagcattaa gacgtgagtt cctagacgac caaatctcaa tgcttacttg gacagagaat     180
gatttaacat tctataaaga catcgctaaa aaaccagcta catctacagt agcaaaatac     240
gatgtataca tgcaacatgg taaggtaggt catactagat ttactcgtga gattggggta     300
gcaccagtaa gtgaccctaa catccgtcaa aaaacagtaa acatgaaatt tgcttccgat     360
actaaaaaca tcagtatcgc agcaggtcta gtaaacaaca ttcaagaccc aatgcaaatt     420
ttgactgacg atgctatcgt aaatattgct aaaacaattg agtgggcttc attctttgga     480
gattctgact tatcagatag cccagaacca caagcaggac tagaatttga cggcttggct     540
aaacttatta accaagataa cgttcatgat gctcgtggag ctagcttgac tgaaagcttg     600
ttaaaccaag cagcagtaat gattagtaaa ggttatggta cacctacaga tgcttacatg     660
ccagtagggg ttcaagcaga ctttgttaac caacaacttt ctaaacaaac acaacttgtt     720
cgcgataacg gaaacaacgt aagcgttggt ttcaacatcc aaggtttcca ttcagctcgt     780
ggatttatca aacttcacgg ttctacagta atggaaaacg aacaaatctt agatgaacgt     840
attcttgctt taccaacagc tccacaacca gctaaggtaa ctgcaacaca agaagcaggt     900
aaaaaaggac aatttagagc agaagattta gcagcacatg aatataaagt tgttgtaagt     960
tctgacgatg cagagtctat tgcaagtgaa gtggctacag ctacagttac tgcaaaagat    1020
gacggcgtta aactagaaat cgaattagct ccaatgtata gctctcgtcc acaattcgtt    1080
tcaatctata gaaaaggtgc agaaacaggt ttattctacc taatcgctcg tgtacctgct    1140
agcaaagcag agaacaacgt aatcactttc tacgacttaa acgactctat tcctgaaaca    1200
gtagacgtat tcgttggtga atgtcggct aacgtagtac acttgtttga attactacca    1260
atgatgagat tacctctagc tcaaattaac gcatctgtta catttgcagt tttatggtat    1320
ggcgcattag ctctaagagc acctaagaaa tgggtacgta ttagaaacgt taaatatatt    1380
cctgtaaaaa acgttcatag caactaa                                        1407

<210> SEQ ID NO 14
<211> LENGTH: 468
<212> TYPE: PRT
<213> ORGANISM: LP124 Phage

<400> SEQUENCE: 14

Met Pro Lys Asn Asn Lys Glu Glu Val Lys Glu Val Asn Leu Asn
1               5                   10                  15

Ser Val Gln Glu Asp Ala Leu Lys Ser Phe Thr Thr Gly Tyr Gly Ile
                20                  25                  30

Thr Pro Asp Thr Gln Thr Asp Ala Gly Ala Leu Arg Arg Glu Phe Leu
            35                  40                  45

Asp Asp Gln Ile Ser Met Leu Thr Trp Thr Glu Asn Asp Leu Thr Phe
        50                  55                  60

Tyr Lys Asp Ile Ala Lys Lys Pro Ala Thr Ser Thr Val Ala Lys Tyr
65                  70                  75                  80

Asp Val Tyr Met Gln His Gly Lys Val Gly His Thr Arg Phe Thr Arg
                85                  90                  95
```

Glu Ile Gly Val Ala Pro Val Ser Asp Pro Asn Ile Arg Gln Lys Thr
100                 105                 110

Val Asn Met Lys Phe Ala Ser Asp Thr Lys Asn Ile Ser Ile Ala Ala
        115                 120                 125

Gly Leu Val Asn Ile Gln Asp Pro Met Gln Ile Leu Thr Asp Asp
130                 135                 140

Ala Ile Val Asn Ile Ala Lys Thr Ile Glu Trp Ala Ser Phe Phe Gly
145                 150                 155                 160

Asp Ser Asp Leu Ser Asp Ser Pro Glu Pro Gln Ala Gly Leu Glu Phe
                165                 170                 175

Asp Gly Leu Ala Lys Leu Ile Asn Gln Asp Asn Val His Asp Ala Arg
            180                 185                 190

Gly Ala Ser Leu Thr Glu Ser Leu Leu Asn Gln Ala Ala Val Met Ile
        195                 200                 205

Ser Lys Gly Tyr Gly Thr Pro Thr Asp Ala Tyr Met Pro Val Gly Val
210                 215                 220

Gln Ala Asp Phe Val Asn Gln Gln Leu Ser Lys Gln Thr Gln Leu Val
225                 230                 235                 240

Arg Asp Asn Gly Asn Asn Val Ser Val Gly Phe Asn Ile Gln Gly Phe
                245                 250                 255

His Ser Ala Arg Gly Phe Ile Lys Leu His Gly Ser Thr Val Met Glu
            260                 265                 270

Asn Glu Gln Ile Leu Asp Glu Arg Ile Leu Ala Leu Pro Thr Ala Pro
        275                 280                 285

Gln Pro Ala Lys Val Thr Ala Thr Gln Glu Ala Gly Lys Lys Gly Gln
290                 295                 300

Phe Arg Ala Glu Asp Leu Ala Ala His Glu Tyr Lys Val Val Ser
305                 310                 315                 320

Ser Asp Asp Ala Glu Ser Ile Ala Ser Glu Val Ala Thr Ala Thr Val
                325                 330                 335

Thr Ala Lys Asp Asp Gly Val Lys Leu Glu Ile Glu Leu Ala Pro Met
            340                 345                 350

Tyr Ser Ser Arg Pro Gln Phe Val Ser Ile Tyr Arg Lys Gly Ala Glu
        355                 360                 365

Thr Gly Leu Phe Tyr Leu Ile Ala Arg Val Pro Ala Ser Lys Ala Glu
370                 375                 380

Asn Asn Val Ile Thr Phe Tyr Asp Leu Asn Asp Ser Ile Pro Glu Thr
385                 390                 395                 400

Val Asp Val Phe Val Gly Glu Met Ser Ala Asn Val Val His Leu Phe
                405                 410                 415

Glu Leu Leu Pro Met Met Arg Leu Pro Leu Ala Gln Ile Asn Ala Ser
            420                 425                 430

Val Thr Phe Ala Val Leu Trp Tyr Gly Ala Leu Ala Leu Arg Ala Pro
        435                 440                 445

Lys Lys Trp Val Arg Ile Arg Asn Val Lys Tyr Ile Pro Val Lys Asn
450                 455                 460

Val His Ser Asn
465

<210> SEQ ID NO 15
<211> LENGTH: 1407
<212> TYPE: DNA
<213> ORGANISM: LP125 Phage

<400> SEQUENCE: 15

-continued

```
atgccaaaaa ataacaaaga agaagaagtt aaagaagtaa accttaattc agtacaagag      60
gacgcgttaa agtcctttac aactggttat ggtatcacac ctgatacaca aacagatgca     120
ggagcattaa gacgtgagtt cctagacgac caaatctcaa tgcttacttg gacagagaat     180
gatttaacat tctataaaga catcgctaaa aaaccagcta catctacagt agcaaaatac     240
gatgtataca tgcaacatgg taaggtaggt catactagat ttactcgtga gattggggta     300
gcaccagtaa gtgaccctaa catccgtcaa aaaacagtaa acatgaaatt tgcttccgat     360
actaaaaaca tcagtatcgc agcaggtcta gtaaacaaca ttcaagaccc aatgcaaatt     420
ttgactgacg atgctatcgt aaatattgct aaaacaattg agtgggcttc attctttgga     480
gattctgact tatcagatag cccagaacca caagcaggac tagaatttga cggcttggct     540
aaacttatta accaagataa cgttcatgat gctcgtggag ctagcttgac tgaaagcttg     600
ttaaaccaag cagcagtaat gattagtaaa ggttatggta cacctacaga tgcttacatg     660
ccagtagggg ttcaagcaga ctttgttaac caacaacttt ctaaacaaac acaacttgtt     720
cgtgataacg gaaacaacgt aagcgttggt ttcaacatcc aaggtttcca ttcagctcgt     780
ggatttatca aacttcacgg ttctacagta atggaaaacg aacaaatctt agatgaacgt     840
attcttgctt taccaacagc tccacaacca gctaaggtaa ctgcaacaca agaagcaggt     900
aaaaaaggac aatttagagc agaagattta gcagcacatg aatataaagt tgttgtaagt     960
tctgacgatg cagagtctat tgcaagtgaa gtggctacag ctacagttac tgcaaaagat    1020
gacggcgtta aactagaaat cgaattagct ccaatgtata gctctcgtcc acaattcgtt    1080
tcaatctata gaaaaggtgc agaaacaggt ttattctacc taatcgctcg tgtacctgct    1140
agcaaagcag agaacaacgt aatcactttc tacgacttaa acgactctat tcctgaaaca    1200
gtagacgtat tcgttggtga atgtcggct aacgtagtac acttgtttga attactacca    1260
atgatgagat tacctctagc tcaaattaac gcatctgtta catttgcagt tttatggtat    1320
ggcgcattag ctctaagagc acctaagaaa tgggtacgta ttagaaacgt taaatatatt    1380
cctgtaaaaa acgttcatag caactaa                                        1407
```

<210> SEQ ID NO 16
<211> LENGTH: 468
<212> TYPE: PRT
<213> ORGANISM: LP125 Phage

<400> SEQUENCE: 16

Met Pro Lys Asn Asn Lys Glu Glu Val Lys Glu Val Asn Leu Asn
1               5                   10                  15

Ser Val Gln Glu Asp Ala Leu Lys Ser Phe Thr Thr Gly Tyr Gly Ile
            20                  25                  30

Thr Pro Asp Thr Gln Thr Asp Ala Gly Ala Leu Arg Arg Glu Phe Leu
        35                  40                  45

Asp Asp Gln Ile Ser Met Leu Thr Trp Thr Glu Asn Asp Leu Thr Phe
    50                  55                  60

Tyr Lys Asp Ile Ala Lys Lys Pro Ala Thr Ser Thr Val Ala Lys Tyr
65                  70                  75                  80

Asp Val Tyr Met Gln His Gly Lys Val Gly His Thr Arg Phe Thr Arg
                85                  90                  95

Glu Ile Gly Val Ala Pro Val Ser Asp Pro Asn Ile Arg Gln Lys Thr
            100                 105                 110

Val Asn Met Lys Phe Ala Ser Asp Thr Lys Asn Ile Ser Ile Ala Ala

```
                    115                 120                 125
Gly Leu Val Asn Asn Ile Gln Asp Pro Met Gln Ile Leu Thr Asp Asp
            130                 135                 140

Ala Ile Val Asn Ile Ala Lys Thr Ile Glu Trp Ala Ser Phe Phe Gly
145                 150                 155                 160

Asp Ser Asp Leu Ser Asp Ser Pro Glu Pro Gln Ala Gly Leu Glu Phe
                165                 170                 175

Asp Gly Leu Ala Lys Leu Ile Asn Gln Asp Asn Val His Asp Ala Arg
            180                 185                 190

Gly Ala Ser Leu Thr Glu Ser Leu Leu Asn Gln Ala Ala Val Met Ile
        195                 200                 205

Ser Lys Gly Tyr Gly Thr Pro Thr Asp Ala Tyr Met Pro Val Gly Val
    210                 215                 220

Gln Ala Asp Phe Val Asn Gln Gln Leu Ser Lys Gln Thr Gln Leu Val
225                 230                 235                 240

Arg Asp Asn Gly Asn Asn Val Ser Val Gly Phe Asn Ile Gln Gly Phe
                245                 250                 255

His Ser Ala Arg Gly Phe Ile Lys Leu His Gly Ser Thr Val Met Glu
            260                 265                 270

Asn Glu Gln Ile Leu Asp Glu Arg Ile Leu Ala Leu Pro Thr Ala Pro
        275                 280                 285

Gln Pro Ala Lys Val Thr Ala Thr Gln Glu Ala Gly Lys Lys Gly Gln
    290                 295                 300

Phe Arg Ala Glu Asp Leu Ala Ala His Glu Tyr Lys Val Val Val Ser
305                 310                 315                 320

Ser Asp Asp Ala Glu Ser Ile Ala Ser Glu Val Ala Thr Ala Thr Val
                325                 330                 335

Thr Ala Lys Asp Asp Gly Val Lys Leu Glu Ile Glu Leu Ala Pro Met
            340                 345                 350

Tyr Ser Ser Arg Pro Gln Phe Val Ser Ile Tyr Arg Lys Gly Ala Glu
        355                 360                 365

Thr Gly Leu Phe Tyr Leu Ile Ala Arg Val Pro Ala Ser Lys Ala Glu
    370                 375                 380

Asn Asn Val Ile Thr Phe Tyr Asp Leu Asn Asp Ser Ile Pro Glu Thr
385                 390                 395                 400

Val Asp Val Phe Val Gly Glu Met Ser Ala Asn Val His Leu Phe
                405                 410                 415

Glu Leu Leu Pro Met Met Arg Leu Pro Leu Ala Gln Ile Asn Ala Ser
            420                 425                 430

Val Thr Phe Ala Val Leu Trp Tyr Gly Ala Leu Ala Leu Arg Ala Pro
        435                 440                 445

Lys Lys Trp Val Arg Ile Arg Asn Val Lys Tyr Ile Pro Val Lys Asn
    450                 455                 460

Val His Ser Asn
465

<210> SEQ ID NO 17
<211> LENGTH: 1404
<212> TYPE: DNA
<213> ORGANISM: LP143 Phage

<400> SEQUENCE: 17
atgccaaaaa ataacaaaga agaagttaaa gaagtaaacc ttaattcagt acaagaggat      60
gcgttaaagt cctttacgac tggttatggt atcacacctg atacacaaac agatgcagga     120
```

-continued

```
gcattaagac gtgagttcct agacgaccaa atctcaatgc ttacttggac agagaatgat    180
ttaacattct ataaagacat cgctaaaaaa ccagctacat ctacagtagc aaaatacgat    240
gtatacatgc aacatggtaa ggtaggtcat actagattta ctcgtgagat tggggtagca    300
ccagtaagtg accctaacat ccgtcaaaaa acagtaaata tgaaatttgc ttccgatact    360
aaaaacatca gtatcgcagc aggtctagta acaacattc aagacccaat gcaaattttg     420
actgacgatg ctatcgtaaa tattgctaaa acaattgagt gggcttcatt ctttggagat    480
tctgacttat cagatagccc agaaccacaa gcaggactag aatttgacgg cttggctaaa    540
cttattaacc aagataacgt tcatgatgct cgtggagcta gcttgactga aagcttgtta    600
aaccaagcag cagtaatgat tagtaaaggt tatggtacac ctacagatgc ttacatgcca    660
gtaggggttc aagcagactt tgttaaccaa caactttcta aacaaacaca acttgttcgc    720
gataacggaa acaacgtaag cgttggtttc aacatccaag gtttccattc agctcgtgga    780
tttatcaaac ttcacggttc tacagtaatg gaaaacgaac aaatcttaga tgaacgtatt    840
cttgctttac caacagctcc acaaccagct aaggtaactg caacacaaga agcaggtaaa    900
aaaggacaat ttagagcaga agatttagca gcacatgaat ataaagttgt tgtaagttct    960
gacgatgcag agtctattgc aagtgaagtg gctacagcta cagttactgc aaaagatgac   1020
ggcgttaaac tagaaatcga attagctcca atgtatagct ctcgtccaca attcgtttca   1080
atctatagaa aaggtgcaga aacaggttta ttctacctaa tcgctcgtgt acctgctagc   1140
aaagcagaga acaacgtaat cactttctac gacttaaacg actctattcc tgaaacagta   1200
gacgtattcg ttggtgaaat gtcggctaac gtagtacact tgtttgaatt actaccaatg   1260
atgagattac ctctagctca aattaacgca tctgttacat ttgcagtttt atggtatggc   1320
gcattagctc taagagcacc taagaaatgg gtacgtatta gaaacgttaa atatattcct   1380
gtaaaaaacg ttcatagcaa ctaa                                           1404
```

<210> SEQ ID NO 18
<211> LENGTH: 467
<212> TYPE: PRT
<213> ORGANISM: LP143 Phage

<400> SEQUENCE: 18

```
Met Pro Lys Asn Asn Lys Glu Glu Val Lys Glu Val Asn Leu Asn Ser
1               5                   10                  15

Val Gln Glu Asp Ala Leu Lys Ser Phe Thr Thr Gly Tyr Gly Ile Thr
            20                  25                  30

Pro Asp Thr Gln Thr Asp Ala Gly Ala Leu Arg Arg Glu Phe Leu Asp
        35                  40                  45

Asp Gln Ile Ser Met Leu Thr Trp Thr Glu Asn Asp Leu Thr Phe Tyr
    50                  55                  60

Lys Asp Ile Ala Lys Lys Pro Ala Thr Ser Thr Val Ala Lys Tyr Asp
65                  70                  75                  80

Val Tyr Met Gln His Gly Lys Val Gly His Thr Arg Phe Thr Arg Glu
                85                  90                  95

Ile Gly Val Ala Pro Val Ser Asp Pro Asn Ile Arg Gln Lys Thr Val
            100                 105                 110

Asn Met Lys Phe Ala Ser Asp Thr Lys Asn Ile Ser Ile Ala Ala Gly
        115                 120                 125

Leu Val Asn Asn Ile Gln Asp Pro Met Gln Ile Leu Thr Asp Asp Ala
    130                 135                 140
```

Ile Val Asn Ile Ala Lys Thr Ile Glu Trp Ala Ser Phe Phe Gly Asp
145                 150                 155                 160

Ser Asp Leu Ser Asp Ser Pro Glu Pro Gln Ala Gly Leu Glu Phe Asp
            165                 170                 175

Gly Leu Ala Lys Leu Ile Asn Gln Asp Asn Val His Asp Ala Arg Gly
        180                 185                 190

Ala Ser Leu Thr Glu Ser Leu Leu Asn Gln Ala Ala Val Met Ile Ser
    195                 200                 205

Lys Gly Tyr Gly Thr Pro Thr Asp Ala Tyr Met Pro Val Gly Val Gln
210                 215                 220

Ala Asp Phe Val Asn Gln Leu Ser Lys Gln Thr Gln Leu Val Arg
225                 230                 235                 240

Asp Asn Gly Asn Asn Val Ser Val Gly Phe Asn Ile Gln Gly Phe His
                245                 250                 255

Ser Ala Arg Gly Phe Ile Lys Leu His Gly Ser Thr Val Met Glu Asn
            260                 265                 270

Glu Gln Ile Leu Asp Glu Arg Ile Leu Ala Leu Pro Thr Ala Pro Gln
        275                 280                 285

Pro Ala Lys Val Thr Ala Thr Gln Glu Ala Gly Lys Lys Gly Gln Phe
    290                 295                 300

Arg Ala Glu Asp Leu Ala Ala His Glu Tyr Lys Val Val Ser Ser
305                 310                 315                 320

Asp Asp Ala Glu Ser Ile Ala Ser Glu Val Ala Thr Ala Thr Val Thr
                325                 330                 335

Ala Lys Asp Asp Gly Val Lys Leu Glu Ile Glu Leu Ala Pro Met Tyr
            340                 345                 350

Ser Ser Arg Pro Gln Phe Val Ser Ile Tyr Arg Lys Gly Ala Glu Thr
        355                 360                 365

Gly Leu Phe Tyr Leu Ile Ala Arg Val Pro Ala Ser Lys Ala Glu Asn
    370                 375                 380

Asn Val Ile Thr Phe Tyr Asp Leu Asn Asp Ser Ile Pro Glu Thr Val
385                 390                 395                 400

Asp Val Phe Val Gly Glu Met Ser Ala Asn Val His Leu Phe Glu
                405                 410                 415

Leu Leu Pro Met Met Arg Leu Pro Leu Ala Gln Ile Asn Ala Ser Val
            420                 425                 430

Thr Phe Ala Val Leu Trp Tyr Gly Ala Leu Leu Arg Ala Pro Lys
        435                 440                 445

Lys Trp Val Arg Ile Arg Asn Val Lys Tyr Ile Pro Val Lys Asn Val
450                 455                 460

His Ser Asn
465

<210> SEQ ID NO 19
<211> LENGTH: 1404
<212> TYPE: DNA
<213> ORGANISM: A511 Phage

<400> SEQUENCE: 19
atgccaaaaa ataacaaaga agaagttaaa gaagtaaacc ttaattcagt acaagaggat       60
gcgttaaagt cctttacgac tggttatggt atcacacctg atacacaaac agatgcagga      120
gcattaagac gtgagttcct agacgaccaa atctcaatgc ttacttggac agagaatgat      180
ttaacattct ataagacat cgctaaaaaa ccagctacat ctacagtagc aaaatacgat      240

-continued

```
gtatacatgc aacatggtaa ggtaggtcat actagattta ctcgtgagat tggggtagca    300
ccagtaagtg accctaacat ccgtcaaaaa acagtaaata tgaaatttgc ttccgatact    360
aaaaacatca gtatcgcagc aggtctagta acaacattc aagacccaat gcaaattttg     420
actgacgatg ctatcgtaaa tattgctaaa acaattgagt gggcttcatt ctttggagat    480
tctgacttat cagatagccc agaaccacaa gcaggactag aatttgacgg cttggctaaa    540
cttattaacc aagataacgt tcatgatgct cgtggagcta gcttgactga agcttgtta     600 aaccaagcag cagtaatgat tagtaaaggt tatggtacac ctacagatgc ttacatgcca    660
gtaggggttc aagcagactt tgttaaccaa caactttcta aacaaacaca acttgttcgc    720
gataacggaa acaacgtaag cgttggtttc aacatccaag gtttccattc agctcgtgga    780
tttatcaaac ttcacggttc tacagtaatg gaaaacgaac aaatcttaga tgaacgtatt    840
cttgctttac caacagctcc acaaccagct aaggtaactg caacacaaga agcaggtaaa    900
aaaggacaat ttagagcaga agatttagca gcacatgaat ataaagttgt tgtaagttct    960
gacgatgcag agtctattgc aagtgaagtg gctacagcta cagttactgc aaaagatgac   1020
ggcgttaaac tagaaatcga attagctcca atgtatagct ctcgtccaca attcgtttca   1080
atctatagaa aaggtgcaga acaggtttta ttctacctaa tcgctcgtgt acctgctagc   1140
aaagcagaga acaacgtaat cactttctac gacttaaacg actctattcc tgaaacagta   1200
gacgtattcg ttggtgaaat gtcggctaac gtagtacact tgtttgaatt actaccaatg   1260
atgagattac ctctagctca aattaacgca tctgttacat ttgcagtttt atggtatggc   1320
gcattagctc taagagcacc taagaaatgg gtacgtatta gaaacgttaa atatattcct   1380
gtaaaaaacg ttcatagcaa ctaa                                          1404
```

<210> SEQ ID NO 20
<211> LENGTH: 467
<212> TYPE: PRT
<213> ORGANISM: A511 Phage

<400> SEQUENCE: 20

```
Met Pro Lys Asn Asn Lys Glu Glu Val Lys Glu Val Asn Leu Asn Ser
1               5                   10                  15

Val Gln Glu Asp Ala Leu Lys Ser Phe Thr Thr Gly Tyr Gly Ile Thr
            20                  25                  30

Pro Asp Thr Gln Thr Asp Ala Gly Ala Leu Arg Arg Glu Phe Leu Asp
        35                  40                  45

Asp Gln Ile Ser Met Leu Thr Trp Thr Glu Asn Asp Leu Thr Phe Tyr
    50                  55                  60

Lys Asp Ile Ala Lys Lys Pro Ala Thr Ser Thr Val Ala Lys Tyr Asp
65                  70                  75                  80

Val Tyr Met Gln His Gly Lys Val Gly His Thr Arg Phe Thr Arg Glu
                85                  90                  95

Ile Gly Val Ala Pro Val Ser Asp Pro Asn Ile Arg Gln Lys Thr Val
            100                 105                 110

Asn Met Lys Phe Ala Ser Asp Thr Lys Asn Ile Ser Ile Ala Ala Gly
        115                 120                 125

Leu Val Asn Asn Ile Gln Asp Pro Met Gln Ile Leu Thr Asp Asp Ala
    130                 135                 140

Ile Val Asn Ile Ala Lys Thr Ile Glu Trp Ala Ser Phe Phe Gly Asp
145                 150                 155                 160
```

```
Ser Asp Leu Ser Asp Ser Pro Glu Pro Gln Ala Gly Leu Glu Phe Asp
            165                 170                 175
Gly Leu Ala Lys Leu Ile Asn Gln Asp Asn Val His Asp Ala Arg Gly
        180                 185                 190
Ala Ser Leu Thr Glu Ser Leu Leu Asn Gln Ala Ala Val Met Ile Ser
    195                 200                 205
Lys Gly Tyr Gly Thr Pro Thr Asp Ala Tyr Met Pro Val Gly Val Gln
210                 215                 220
Ala Asp Phe Val Asn Gln Leu Ser Lys Gln Thr Gln Leu Val Arg
225                 230                 235                 240
Asp Asn Gly Asn Asn Val Ser Val Gly Phe Asn Ile Gln Gly Phe His
                245                 250                 255
Ser Ala Arg Gly Phe Ile Lys Leu His Gly Ser Thr Val Met Glu Asn
            260                 265                 270
Glu Gln Ile Leu Asp Glu Arg Ile Leu Ala Leu Pro Thr Ala Pro Gln
        275                 280                 285
Pro Ala Lys Val Thr Ala Thr Gln Glu Ala Gly Lys Lys Gly Gln Phe
    290                 295                 300
Arg Ala Glu Asp Leu Ala Ala His Glu Tyr Lys Val Val Ser Ser
305                 310                 315                 320
Asp Asp Ala Glu Ser Ile Ala Ser Glu Val Ala Thr Ala Thr Val Thr
                325                 330                 335
Ala Lys Asp Asp Gly Val Lys Leu Glu Ile Glu Leu Ala Pro Met Tyr
            340                 345                 350
Ser Ser Arg Pro Gln Phe Val Ser Ile Tyr Arg Lys Gly Ala Glu Thr
        355                 360                 365
Gly Leu Phe Tyr Leu Ile Ala Arg Val Pro Ala Ser Lys Ala Glu Asn
    370                 375                 380
Asn Val Ile Thr Phe Tyr Asp Leu Asn Asp Ser Ile Pro Glu Thr Val
385                 390                 395                 400
Asp Val Phe Val Gly Glu Met Ser Ala Asn Val His Leu Phe Glu
                405                 410                 415
Leu Leu Pro Met Met Arg Leu Pro Leu Ala Gln Ile Asn Ala Ser Val
            420                 425                 430
Thr Phe Ala Val Leu Trp Tyr Gly Ala Leu Ala Leu Arg Ala Pro Lys
        435                 440                 445
Lys Trp Val Arg Ile Arg Asn Val Lys Tyr Ile Pro Val Lys Asn Val
    450                 455                 460
His Ser Asn
465

<210> SEQ ID NO 21
<211> LENGTH: 1407
<212> TYPE: DNA
<213> ORGANISM: P100 Phage

<400> SEQUENCE: 21
atgccaaaaa ataacaaaga agaagaagtt aaagaagtaa accttaattc agtacaagag     60
gacgcgttaa agtcctttac aactggttat ggtatcacac ctgatacaca aacagatgca    120
ggagcattaa gacgtgagtt cctagacgac caaatctcaa tgcttacttg gacagagaat    180
gatttaacat tctataaaga catcgctaaa aaaccagcta catctacagt agcaaaatac    240
gatgtataca tgcaacatgg taaggtaggt catactagat ttactcgtga gattggggta    300
gcaccagtaa gtgaccctaa catccgtcaa aaaacagtaa atatgaaatt tgcttccgat    360
```

```
actaaaaaca tcagtatcgc agcaggtcta gtaaacaaca ttcaagaccc aatgcaaatt      420
ttgactgacg atgctatcgt aaatattgct aaaacaattg agtgggcttc attctttgga      480
gattctgact tatcagatag cccagaacca caagcaggac tagaatttga cggcttggct      540
aaacttatta accaagataa cgttcatgat gctcgtggag ctagcttgac tgaaagcttg      600
ttaaaccaag cagcagtaat gattagtaaa ggttatggta cacctacaga tgcttacatg      660
ccagtagggg ttcaagcaga ctttgttaac caacaacttt ctaaacaaac acagcttgtt      720
cgtgataacg gaaacaacgt aagcgttggt ttcaacatcc aaggtttcca ttcagctcgt      780
ggatttatca aacttcacgg ttctacagta atggaaaacg aacaaatctt agatgaacgt      840
attcttgctt taccaacagc tccacaacca gctaaggtaa ctgcaacaca agaagcaggt      900
aaaaaaggac aatttagagc agaagactta gcagcacacg aatacaaagt tgttgtaagt      960
tctgacgatg cagagtctat tgcaagtgaa gtggctacag ctacagttac tgcaaaagat     1020
gacggcgtta aactagaaat cgagttagct ccaatgtaca gctcccgtcc acaattcgtt     1080
tcaatctata gaaaaggtgc agaaacaggt ttattctacc taatcgctcg tgtacctgct     1140
agcaaagcag agaacaacgt aatcactttc tatgacttaa cgactctat tcctgaaaca     1200
gtagacgtat tcgttggtga aatgtctgct aacgtagtac acttgtttga attactacca     1260
atgatgagat tacctctagc tcaaattaac gcatctgtta catttgcagt tttatggtat     1320
ggagcattag ctctaagagc acctaagaaa tgggtacgta ttagaaacgt taaatatatt     1380
cctgtaaaaa acgttcatag caactaa                                         1407
```

<210> SEQ ID NO 22
<211> LENGTH: 468
<212> TYPE: PRT
<213> ORGANISM: P100 Phage

<400> SEQUENCE: 22

```
Met Pro Lys Asn Asn Lys Glu Glu Val Lys Glu Val Asn Leu Asn
1               5                   10                  15

Ser Val Gln Glu Asp Ala Leu Lys Ser Phe Thr Thr Gly Tyr Gly Ile
            20                  25                  30

Thr Pro Asp Thr Gln Thr Asp Ala Gly Ala Leu Arg Arg Glu Phe Leu
        35                  40                  45

Asp Asp Gln Ile Ser Met Leu Thr Trp Thr Glu Asn Asp Leu Thr Phe
    50                  55                  60

Tyr Lys Asp Ile Ala Lys Lys Pro Ala Thr Ser Thr Val Ala Lys Tyr
65                  70                  75                  80

Asp Val Tyr Met Gln His Gly Lys Val Gly His Thr Arg Phe Thr Arg
                85                  90                  95

Glu Ile Gly Val Ala Pro Val Ser Asp Pro Asn Ile Arg Gln Lys Thr
            100                 105                 110

Val Asn Met Lys Phe Ala Ser Asp Thr Lys Asn Ile Ser Ile Ala Ala
        115                 120                 125

Gly Leu Val Asn Asn Ile Gln Asp Pro Met Gln Ile Leu Thr Asp Asp
    130                 135                 140

Ala Ile Val Asn Ile Ala Lys Thr Ile Glu Trp Ala Ser Phe Phe Gly
145                 150                 155                 160

Asp Ser Asp Leu Ser Asp Ser Pro Glu Pro Gln Ala Gly Leu Glu Phe
                165                 170                 175

Asp Gly Leu Ala Lys Leu Ile Asn Gln Asp Asn Val His Asp Ala Arg
```

```
            180                 185                 190
Gly Ala Ser Leu Thr Glu Ser Leu Leu Asn Gln Ala Ala Val Met Ile
            195                 200                 205

Ser Lys Gly Tyr Gly Thr Pro Thr Asp Ala Tyr Met Pro Val Gly Val
210                 215                 220

Gln Ala Asp Phe Val Asn Gln Gln Leu Ser Lys Gln Thr Gln Leu Val
225                 230                 235                 240

Arg Asp Asn Gly Asn Asn Val Ser Val Gly Phe Asn Ile Gln Gly Phe
                245                 250                 255

His Ser Ala Arg Gly Phe Ile Lys Leu His Gly Ser Thr Val Met Glu
            260                 265                 270

Asn Glu Gln Ile Leu Asp Glu Arg Ile Leu Ala Leu Pro Thr Ala Pro
        275                 280                 285

Gln Pro Ala Lys Val Thr Ala Thr Gln Glu Ala Gly Lys Lys Gly Gln
    290                 295                 300

Phe Arg Ala Glu Asp Leu Ala Ala His Glu Tyr Lys Val Val Val Ser
305                 310                 315                 320

Ser Asp Asp Ala Glu Ser Ile Ala Ser Glu Val Ala Thr Ala Thr Val
                325                 330                 335

Thr Ala Lys Asp Asp Gly Val Lys Leu Glu Ile Glu Leu Ala Pro Met
            340                 345                 350

Tyr Ser Arg Pro Gln Phe Val Ser Ile Tyr Arg Lys Gly Ala Glu
        355                 360                 365

Thr Gly Leu Phe Tyr Leu Ile Ala Arg Val Pro Ala Ser Lys Ala Glu
    370                 375                 380

Asn Asn Val Ile Thr Phe Tyr Asp Leu Asn Asp Ser Ile Pro Glu Thr
385                 390                 395                 400

Val Asp Val Phe Val Gly Glu Met Ser Ala Asn Val His Leu Phe
                405                 410                 415

Glu Leu Leu Pro Met Met Arg Leu Pro Leu Ala Gln Ile Asn Ala Ser
            420                 425                 430

Val Thr Phe Ala Val Leu Trp Tyr Gly Ala Leu Ala Leu Arg Ala Pro
        435                 440                 445

Lys Lys Trp Val Arg Ile Arg Asn Val Lys Tyr Ile Pro Val Lys Asn
    450                 455                 460

Val His Ser Asn
465

<210> SEQ ID NO 23
<211> LENGTH: 3729
<212> TYPE: DNA
<213> ORGANISM: Artificial
<220> FEATURE:
<223> OTHER INFORMATION: Recombinant Phage

<400> SEQUENCE: 23
atgccaaaaa ataacaaaga agaagaagtt aaagaagtaa accttaattc agtacaagag      60
gacgcgttaa agtcctttac aactggttat ggtatcacac ctgatacaca aacagatgca     120
ggagcattaa gacgtgagtt cctagacgac caaatctcaa tgcttacttg gacagagaat     180
gatttaacat tctataagga catcgctaaa aaaccagcta catctacagt agcaaaatac     240 gatgtatacca tgcaacatgg taaggtaggt catactagat ttactcgtga gattggggta     300
gcaccagtaa gtgaccctaa catccgtcaa aaaacagtaa acatgaaatt tgcttccgat     360
actaaaaaca tcagtatcgc agcaggtcta gtaaacaaca ttcaagaccc aatgcaaatt     420
```

```
ttgactgacg atgctatcgt aaatattgct aaaacaattg agtgggcttc attctttgga     480
gattctgact tatcagatag cccagaacca caagcaggac tagaatttga cggcttggct     540
aaacttatta accaagataa cgttcatgat gctcgtggag ctagcttgac tgaaagcttg     600
ttaaaccaag cagcagtaat gattagtaaa ggttatggta cacctacaga tgcttacatg     660
ccagtagggg ttcaagcaga ctttgttaac caacaacttt ctaaacaaac acaacttgtt     720
cgcgataacg gaaacaacgt aagcgttggt ttcaacatcc aaggtttcca ttcagctcgt     780
ggatttatca aacttcacgg ttctacagta atggaaaacg aacaaatctt agatgaacgt     840
attcttgctt taccaacagc tccacaacca gctaaggtaa ctgcaacaca agaagcaggt     900
aaaaaaggac aatttagagc agaagattta gcagcacatg aatataaagt tgttgtaagt     960
tctgacgatg cagagtctat tgcaagtgaa gtggctacag ctacagttac tgcaaaagat    1020
gacggcgtta aactagaaat cgaattagct ccaatgtata gctctcgtcc acaattcgtt    1080
tcaatctata gaaaggtgc agaaacaggt ttattctacc taatcgctcg tgtacctgct     1140
agcaaagcag agaacaacgt aatcactttc tacgacttaa cgactctat tcctgaaaca      1200 gtagacgtat tcgttggtga aatgtcggct aacgtagtac acttgtttga attactacca    1260
atgatgagat tacctctagc tcaaattaac gcatctgtta catttgcagt tttatggtat    1320
ggcgcattag ctctaagagc acctaagaaa tgggtacgta ttagaaacgt taaatatatt    1380
cctgtaaaaa acgttcatag caactaagag gaggtaaata tatatggaag acgccaaaaa    1440
cataaagaaa ggcccggcgc cattctatcc tctagaggat ggaaccgctg gagagcaact    1500
gcataaggct atgaagagat acgcctggt tcctggaaca attgctttta cagatgcaca     1560
tatcgaggtg aacatcacgt acgcggaata cttcgaaatg tccgttcggt tggcagaagc    1620
tatgaaacga tatgggctga atacaaatca cagaatcgtc gtatgcagtg aaaactctct    1680
tcaattcttt atgccggtgt tgggcgcgtt atttatcgga gttgcagttg cgcccgcgaa    1740
cgacatttat aatgaacgtg aattgctcaa cagtatgaac atttcgcagc ctaccgtagt    1800
gtttgtttcc aaaaaggggt tgcaaaaaat tttgaacgtg caaaaaaaat taccaataat    1860
ccagaaaatt attatcatgg attctaaaac ggattaccag ggatttcagt cgatgtacac    1920
gttcgtcaca tctcatctac ctcccggttt taatgaatac gattttgtac cagagtcctt    1980
tgatcgtgac aaaacaattg cactgataat gaattcctct ggatctactg ggttacctaa    2040
gggtgtggcc cttccgcata gaactgcctg cgtcagattc tcgcatgcca gagatcctat    2100
ttttggcaat caaatcattc cggatactgc gattttaagt gttgttccat tccatcacgg    2160
ttttggaatg tttactacac tcggatattt gatatgtgga tttcgagtcg tcttaatgta    2220
tagatttgaa gaagagctgt ttttacgatc ccttcaggat tacaaaattc aaagtgcgtt    2280
gctagtacca acccctatttt cattcttcgc caaaagcact ctgattgaca aatacgattt    2340
atctaattta cacgaaattg cttctggggg cgcacctctt tcgaaagaag tcggggaagc    2400
ggttgcaaaa cgcttccatc ttccagggat acgacaagga tatgggctca ctgagactac    2460
atcagctatt ctgattacac ccgaggggga tgataaaccg ggcgcggtcg gtaaagttgt    2520 tccattttt gaagcgaagg ttgtggatct ggataccggg aaaacgctgg gcgttaatca    2580
gagaggcgaa ttatgtgtca gaggacctat gattatgtcc ggttatgtaa acaatccgga    2640
agcgaccaac gccttgattg acaaggatgg atggctacat tctggagaca tagcttactg    2700
ggacgaagac gaacacttct tcatagttga ccgcttgaag tctttaatta aatacaaagg    2760
```

-continued

| | |
|---|---|
| atatcaggtg gcccccgctg aattggaatc gatattgtta caacacccca acatcttcga | 2820 |
| cgcgggcgtg gcaggtcttc ccgacgatga cgccggtgaa cttccagccg ccgttgttgt | 2880 |
| tttggagcac ggaaagacga tgacggaaaa agagatcgtg gattacgtcg ccagtcaagt | 2940 |
| aacaaccgcg aaaagttgc gcggaggagt tgtgtttgtg gacgaagtac cgaaaggtct | 3000 |
| taccggaaaa ctcgacgcaa gaaaaatcag agagatcctc ataaaggcca agaagggcgg | 3060 |
| aaagtccaaa ttgtaataat tataggataa ttgaataaaa acagtataga gagcagataa | 3120 |
| atactgctct ctatttact aataaggagg atttaaattg ctaaaaata caaacttagc | 3180 |
| taattataaa aaagtgaata cacggtttgg aaatcttagt tttgacgaca aaggtatttc | 3240 |
| taatgactta acggaagaac agcaaaaaga attaggtaag cttcgaggat tcgaatatat | 3300 |
| taagacagaa cagaaaacaa aagaagaacc taagaaagaa gaacctaaga aagaaagtac | 3360 |
| agaaaatgaa ttagacagct tcttagctaa agagccttca atcaaagaat taaaagaatt | 3420 |
| tgcgagtaaa aaaggcatta aaattgaaaa aactaagaaa aatgatataa ttgaagaact | 3480 |
| aaagagaggg taatgtataa tgtatggagg ttatgaagga caagattctt acgaatacc | 3540 |
| ttactcacat gggaacccta agcatgtaga gccagaaaaa gttgacgaat atgttctttc | 3600 |
| tgattatggt tggactgcgg aaacaattaa agcatacatg tatggtgttc gtgtagtaga | 3660 |
| ccctgaaaca ggagaggaaa tgggagacac cttctacaat catattatag aggttgccgt | 3720 |
| tgataaggc | 3729 |

<210> SEQ ID NO 24
<211> LENGTH: 3789
<212> TYPE: DNA
<213> ORGANISM: Artificial
<220> FEATURE:
<223> OTHER INFORMATION: Recombinant Phage

<400> SEQUENCE: 24

| | |
|---|---|
| atgccaaaaa ataacaaaga agaagaagtt aaagaagtaa accttaattc agtacaagag | 60 |
| gacgcgttaa agtcctttac aactggttat ggtatcacac ctgatacaca aacagatgca | 120 |
| ggagcattaa gacgtgagtt cctagacgac caaatctcaa tgcttacttg gacagagaat | 180 |
| gatttaacat tctataaaga catcgctaaa aaaccagcta catctacagt agcaaaatac | 240 |
| gatgtataca tgcaacatgg taaggtaggt catactagat ttactcgtga gattggggta | 300 |
| gcaccagtaa gtgaccctaa catccgtcaa aaaacagtaa acatgaaatt tgcttccgat | 360 |
| actaaaaaca tcagtatcgc agcaggtcta gtaaacaaca ttcaagaccc aatgcaaatt | 420 |
| ttgactgacg atgctatcgt aaatattgct aaaacaattg agtgggcttc attctttgga | 480 |
| gattctgact tatcagatag cccagaacca caagcaggac tagaatttga cggcttggct | 540 |
| aaacttatta ccaagataa cgttcatgat gctcgtggag ctagcttgac tgaaagcttg | 600 |
| ttaaaccaag cagcagtaat gattagtaaa ggttatggta cacctacaga tgcttacatg | 660 |
| ccagtagggg ttcaagcaga ctttgttaac caacaacttt ctaaacaaac acaacttgtt | 720 |
| cgcgataacg gaaacaacgt aagcgttggt ttcaacatcc aaggtttcca ttcagctcgt | 780 |
| ggatttatca aacttcacgg ttctacagta atggaaaacg aacaaatctt agatgaacgt | 840 |
| attcttgctt taccaacagc tccacaacca gctaaggtaa ctgcaacaca agaagcaggt | 900 |
| aaaaaaggac aatttagagc agaagattta gcagcacatg aatataaagt tgttgtaagt | 960 |
| tctgacgatg cagagtctat tgcaagtgaa gtggctacag ctacagttac tgcaaaagat | 1020 |
| gacggcgtta aactagaaat cgaattagct ccaatgtata gctctcgtcc acaattcgtt | 1080 |

```
tcaatctata gaaaaggtgc agaaacaggt ttattctacc taatcgctcg tgtacctgct   1140
agcaaagcag agaacaacgt aatcactttc tacgacttaa acgactctat tcctgaaaca   1200
gtagacgtat tcgttggtga aatgtcggct aacgtagtac acttgtttga attactacca   1260
atgatgagat tacctctagc tcaaattaac gcatctgtta catttgcagt tttatggtat   1320
ggcgcattag ctctaagagc acctaagaaa tgggtacgta ttagaaacgt taaatatatt   1380
cctgtaaaaa acgttcatag caactaagag gaggtaaata tatatggaag acgccaaaaa   1440
cataaagaaa ggcccggcgc cattctatcc tctagaggat ggaaccgctg gagagcaact   1500
gcataaggct atgaagagat acgccctggt tcctggaaca attgctttta cagatgcaca   1560
tatcgaggtg aacatcacgt acgcggaata cttcgaaatg tccgttcggt tggcagaagc   1620
tatgaaacga tatgggctga atacaaatca cagaatcgtc gtatgcagtg aaaactctct   1680
tcaattcttt atgccggtgt tgggcgcgtt atttatcgga gttgcagttg cgcccgcgaa   1740
cgacatttat aatgaacgtg aattgctcaa cagtatgaac atttcgcagc ctaccgtagt   1800
gtttgtttcc aaaaagggt tgcaaaaaat tttgaacgtg caaaaaaaat taccaataat   1860
ccagaaaatt attatcatgg attctaaaac ggattaccag ggatttcagt cgatgtacac   1920
gttcgtcaca tctcatctac ctcccggttt taatgaatac gattttgtac cagagtcctt   1980
tgatcgtgac aaaacaattg cactgataat gaattcctct ggatctactg ggttacctaa   2040
gggtgtggcc cttccgcata gaactgcctg cgtcagattc tcgcatgcca gagatcctat   2100
ttttggcaat caaatcattc cggatactgc gattttaagt gttgttccat tccatcacgg   2160
ttttggaatg tttactacac tcggatattt gatatgtgga tttcgagtcg tcttaatgta   2220
tagatttgaa gaagagctgt ttttacgatc ccttcaggat tacaaaattc aaagtgcgtt   2280
gctagtacca accctatttt cattcttcgc caaaagcact ctgattgaca aatacgattt   2340
atctaattta cacgaaattg cttctggggg cgcacctctt tcgaaagaag tcggggaagc   2400
ggttgcaaaa cgcttccatc ttccagggat acgacaagga tatgggctca ctgagactac   2460
atcagctatt ctgattacac ccgagggga tgataaaccg ggcgcggtcg gtaaagttgt   2520 tccattttt gaagcgaagg ttgtggatct ggataccggg aaaacgctgg gcgttaatca   2580
gagaggcgaa ttatgtgtca gaggacctat gattatgtcc ggttatgtaa acaatccgga   2640
agcgaccaac gccttgattg acaaggatgg atggctacat tctggagaca tagcttactg   2700
ggacgaagac gaacacttct tcatagttga ccgcttgaag tctttaatta aatacaaagg   2760
atatcaggtg gcccccgctg aattggaatc gatattgtta caacaccca acatcttcga   2820 cgcgggcgtg gcaggtcttc ccgacgatga cgccggtgaa cttcccgccg ccgttgttgt   2880
tttggagcac ggaaagacga tgacggaaaa agagatcgtg gattacgtcg ccagtcaagt   2940
aacaaccgcg aaaaagttgc gcggaggagt tgtgtttgtg gacgaagtac cgaaaggtct   3000
taccggaaaa ctcgacgcaa gaaaaatcag agagatcctc ataaaggcca agaagggcgg   3060
aaagtccaaa ttgtaataat tataggataa ttgaataaaa acagtataga gagcagataa   3120
atactgctct ctattttact aataaggagg atttaaattg ctaaaaaata caaacttagc   3180
taattataaa aaagtgaata cacggtttgg aaatcttagt tttgacgaca aaggtatttc   3240
taatgactta acggaagaac agcaaaaaga attaggtaag cttcgaggat tcgaatatat   3300
taagacagaa cagaaaacaa aagaagaacc taagaaagaa gaacctaaga aagaagaacc   3360
taagaaagaa gaacctaaga aagaagaacc taagaaagaa gaacctaaga aagaaagtac   3420
```

-continued

```
agaaaatgaa ttagacagct tcttagctaa agagccttca atcaaagaat taaaagaatt   3480
tgcgagtaaa aaaggcatta aaattgaaaa aactaagaaa aatgatataa ttgaagaact   3540
aaagagaggg taatgtataa tgtatggagg ttatgaagga caagattctt acgaataccc   3600
ttactcacat gggaacccta agcatgtaga gccagaaaaa gttgacgaat atgttctttc   3660
tgattatggt tggactgcgg aaacaattaa agcatacatg tatggtgttc gtgtagtaga   3720
ccctgaaaca ggagaggaaa tgggagacac cttctacaat catattatag aggttgccgt   3780
tgataaggc                                                           3789
```

<210> SEQ ID NO 25
<211> LENGTH: 3789
<212> TYPE: DNA
<213> ORGANISM: Artificial
<220> FEATURE:
<223> OTHER INFORMATION: Recombinant Phage

<400> SEQUENCE: 25

```
atgccaaaaa ataacaaaga agaagaagtt aaagaagtaa accttaattc agtacaagag     60
gacgcgttaa agtcctttac aactggttat ggtatcacac ctgatacaca aacagatgca    120
ggagcattaa gacgtgagtt cctagacgac caaatctcaa tgcttacttg gacagagaat    180
gatttaacat tctataaaga catcgctaaa aaaccagcta catctacagt agcaaaatac    240
gatgtataca tgcaacatgg taaggtaggt catactagat ttactcgtga gattggggta    300
gcaccagtaa gtgaccctaa catccgtcaa aaaacagtaa acatgaaatt tgcttccgat    360
actaaaaaca tcagtatcgc agcaggtcta gtaaacaaca ttcaagaccc aatgcaaatt    420
ttgactgacg atgctatcgt aaatattgct aaaacaattg agtgggcttc attctttgga    480
gattctgact tatcagatag cccagaacca caagcaggac tagaatttga cggcttggct    540
aaacttatta accaagataa cgttcatgat gctcgtggag ctagcttgac tgaaagcttg    600
ttaaaccaag cagcagtaat gattagtaaa ggttatggta cacctacaga tgcttacatg    660
ccagtagggg ttcaagcaga cttttgttaac caacaacttt ctaaacaaac acaacttgtt    720
cgcgataacg aaacaacgt aagcgttggt ttcaacatcc aaggtttcca ttcagctcgt    780
ggatttatca acttcacgg ttctacagta atggaaaacg aacaaatctt agatgaacgt    840
attcttgctt taccaacagc tccacaacca gctaaggtaa ctgcaacaca agaagcaggt    900
aaaaaaggac aatttagagc agaagattta gcagcacatg aatataaagt tgttgtaagt    960
tctgacgatg cagagtctat tgcaagtgaa gtggctacag ctacagttac tgcaaaagat   1020
gacggcgtta aactagaaat cgaattagct ccaatgtata gctctcgtcc acaattcgtt   1080
tcaatctata gaaaggtgc agaaacaggt ttattctacc taatcgctcg tgtacctgct   1140
agcaaagcag agaacaacgt aatcactttc tacgacttaa acgactctat tcctgaaaca   1200
gtagacgtat tcgttggtga atgtcggct aacgtagtac acttgtttga attactacca   1260
atgatgagat tacctctagc tcaaattaac gcatctgtta catttgcagt tttatggtat   1320
ggcgcattag ctctaagagc acctaagaaa tgggtacgta ttagaaacgt taaatatatt   1380
cctgtaaaaa acgttcatag caactaagag gaggtaaata tatatggaag acgccaaaaa   1440
cataaagaaa ggcccggcgc cattctatcc tctagaggat ggaaccgctg gagagcaact   1500
gcataaggct atgaagagat acgccctggt tcctggaaca attgctttta cagatgcaca   1560
tatcgaggtg aacatcacgt acgcggaata cttcgaaatg tccgttcggt tggcagaagc   1620
tatgaaacga tatgggctga atacaaatca cagaatcgtc gtatgcagtg aaaactctct   1680
```

```
tcaattcttt atgccggtgt tgggcgcgtt atttatcgga gttgcagttg cgcccgcgaa      1740
cgacatttat aatgaacgtg aattgctcaa cagtatgaac atttcgcagc ctaccgtagt      1800
gtttgtttcc aaaaggggt tgcaaaaaat tttgaacgtg caaaaaaaat taccaataat      1860
ccagaaaatt attatcatgg attctaaaac ggattaccag ggatttcagt cgatgtacac      1920
gttcgtcaca tctcatctac ctcccggttt taatgaatac gattttgtac cagagtcctt      1980
tgatcgtgac aaaacaattg cactgataat gaattcctct ggatctactg ggttacctaa      2040
gggtgtggcc cttccgcata gaactgcctg cgtcagattc tcgcatgcca gagatcctat      2100
ttttggcaat caaatcattc cggatactgc gatttttaagt gttgttccat tccatcacgg      2160
ttttggaatg tttactacac tcggatattt gatatgtgga tttcgagtcg tcttaatgta      2220
tagatttgaa gaagagctgt ttttacgatc ccttccaggat tacaaaattc aaagtgcgtt      2280
gctagtacca accctatttt cattcttcgc caaaagcact ctgattgaca aatacgattt      2340 atctaatta cacgaaattg cttctggggg cgcacctctt tcgaaagaag tcggggaagc      2400
ggttgcaaaa cgcttccatc ttccagggat acgacaagga tatgggctca ctgagactac      2460
atcagctatt ctgattacac ccgaggggga tgataaaccg ggcgcggtcg gtaaagttgt      2520
tccatttttt gaagcgaagg ttgtggatct ggataccggg aaaacgctgg gcgttaatca      2580
gagaggcgaa ttatgtgtca gaggacctat gattatgtcc ggttatgtaa caatccgga       2640 agcgaccaac gccttgattg acaaggatgg atggctacat tctggagaca tagcttactg      2700
ggacgaagac gaacacttct tcatagttga ccgcttgaag tctttaatta aatacaaagg      2760
atatcaggtg ccccgctg aattggaatc gatattgtta caacaccca acatcttcga        2820 cgcgggcgtg gcaggtcttc ccgacgatga cgccggtgaa cttcccgccg ccgttgttgt      2880
tttggagcac ggaaagacga tgacggaaaa agagatcgtg gattacgtcg ccagtcaagt      2940
aacaaccgcg aaaagttgc gcggaggagt tgtgtttgtg gacgaagtac cgaaaggtct       3000
taccggaaaa ctcgacgcaa gaaaaatcag agagatcctc ataaaggcca gaagggcgg      3060 aaagtccaaa ttgtaataat tataggataa ttgaataaaa acagtataga gagcagataa      3120
atactgctct ctattttact aataaggagg atttaaattg ctaaaaaata caaacttagc      3180
taattataaa aaagtgaata cacggtttgg aaatcttagt tttgacgaca aaggtatttc      3240
taatgactta acgaagaac agcaaaaaga attaggtaag cttcgaggat tcgaatatat      3300
taagacagaa cagaaaacaa agaagaacc taagaaagaa gaacctaaga agaagaacc       3360 taagaaagaa gaacctaaga agaagaacc taagaaagaa gaacctaaga agaaagtac       3420 agaaaatgaa ttagacagct tcttagctaa agagccttca atcaaagaat taaaagaatt      3480
tgcgagtaaa aaaggcatta aaattgaaaa aactaagaaa aatgatataa ttgaagaact      3540
aaagagaggg taatgtataa tgtatggagg ttatgaagga caagattctt acgaatacc       3600 ttactcacat gggaacccta agcatgtaga gccagaaaaa gttgacgaat atgttctttc      3660
tgattatggt tggactgcgg aaacaattaa agcatacatg tatggtgttc gtgtagtaga      3720
ccctgaaaca ggagaggaaa tgggagacac cttctacaat catattatag aggttgccgt      3780
tgataaggc                                                             3789
```

<210> SEQ ID NO 26
<211> LENGTH: 3789
<212> TYPE: DNA
<213> ORGANISM: Artificial
<220> FEATURE:

<223> OTHER INFORMATION: Recombinant Phage

<400> SEQUENCE: 26

| | |
|---|---|
| atgccaaaaa ataacaaaga agaagaagtt aaagaagtaa accttaattc agtacaagag | 60 |
| gacgcgttaa agtcctttac aactggttat ggtatcacac ctgatacaca aacagatgca | 120 |
| ggagcattaa gacgtgagtt cctagacgac caaatctcaa tgcttacttg gacagagaat | 180 |
| gatttaacat tctataaaga catcgctaaa aaaccagcta catctacagt agcaaaatac | 240 |
| gatgtataca tgcaacatgg taaggtaggt catactagat ttactcgtga gattggggta | 300 |
| gcaccagtaa gtgaccctaa catccgtcaa aaaacagtaa acatgaaatt tgcttccgat | 360 |
| actaaaaaca tcagtatcgc agcaggtcta gtaaacaaca ttcaagaccc aatgcaaatt | 420 |
| ttgactgacg atgctatcgt aaatattgct aaaacaattg agtgggcttc attctttgga | 480 |
| gattctgact tatcagatag cccagaacca caagcaggac tagaatttga cggcttggct | 540 |
| aaacttatta accaagataa cgttcatgat gctcgtggag ctagcttgac tgaaagcttg | 600 |
| ttaaaccaag cagcagtaat gattagtaaa ggttatggta cacctacaga tgcttacatg | 660 |
| ccagtagggg ttcaagcaga cttttgttaac caacaacttt ctaaacaaac acaacttgtt | 720 |
| cgcgataacg gaaacaacgt aagcgttggt ttcaacatcc aaggtttcca ttcagctcgt | 780 |
| ggatttatca aacttcacgg ttctacagta atggaaaacg aacaaatctt agatgaacgt | 840 |
| attcttgctt taccaacagc tccacaacca gctaaggtaa ctgcaacaca agaagcaggt | 900 |
| aaaaaaggac aatttagagc agaagattta gcagcacatg aatataaagt tgttgtaagt | 960 |
| tctgacgatg cagagtctat tgcaagtgaa gtggctacag ctacagttac tgcaaaagat | 1020 |
| gacggcgtta aactagaaat cgaattagct ccaatgtata gctctcgtcc acaattcgtt | 1080 |
| tcaatctata gaaaggtgc agaaacaggt ttattctacc taatcgctcg tgtacctgct | 1140 |
| agcaaagcag agaacaacgt aatcactttc tacgacttaa acgactctat tcctgaaaca | 1200 |
| gtagacgtat tcgttggtga aatgtcggct aacgtagtac acttgtttga attactacca | 1260 |
| atgatgagat tacctctagc tcaaattaac gcatctgtta catttgcagt tttatggtat | 1320 |
| ggcgcattag ctctaagagc acctaagaaa tgggtacgta ttagaaacgt taaatatatt | 1380 |
| cctgtaaaaa acgttcatag caactaagag gaggtaaata tatatggaag acgccaaaaa | 1440 |
| cataaagaaa ggcccggcgc cattctatcc tctagaggat ggaaccgctg gagagcaact | 1500 |
| gcataaggct atgaagagat acgccctggt tcctggaaca attgctttta cagatgcaca | 1560 |
| tatcgaggtg aacatcacgt acgcggaata cttcgaaatg tccgttcggt tggcagaagc | 1620 |
| tatgaaacga tatgggctga atacaaatca cagaatcgtc gtatgcagtg aaaactctct | 1680 |
| tcaattcttt atgccggtgt tgggcgcgtt atttatcgga gttgcagttg cgcccgcgaa | 1740 |
| cgacatttat aatgaacgtg aattgctcaa cagtatgaac atttcgcagc ctaccgtagt | 1800 |
| gtttgtttcc aaaaggggt tgcaaaaaat tttgaacgtg caaaaaaaat taccaataat | 1860 |
| ccagaaaatt attatcatgg attctaaaac ggattaccag ggatttcagt cgatgtacac | 1920 |
| gttcgtcaca tctcatctac ctcccggttt taatgaatac gattttgtac cagagtcctt | 1980 |
| tgatcgtgac aaaacaattg cactgataat gaattcctct ggatctactg ggttacctaa | 2040 |
| gggtgtggcc cttccgcata gaactgcctg cgtcagattc tcgcatgcca gagatcctat | 2100 |
| ttttggcaat caaatcattc cggatactgc gattttaagt gttgttccat tccatcacgg | 2160 |
| ttttggaatg tttactacac tcggatattt gatatgtgga tttcgagtcg tcttaatgta | 2220 |
| tagatttgaa gaagagctgt ttttacgatc ccttcaggat tacaaaattc aaagtgcgtt | 2280 |

-continued

```
gctagtacca accctatttt cattcttcgc caaaagcact ctgattgaca aatacgattt   2340
atctaattta cacgaaattg cttctggggg cgcacctctt tcgaaagaag tcggggaagc   2400
ggttgcaaaa cgcttccatc ttccagggat acgacaagga tatgggctca ctgagactac   2460
atcagctatt ctgattacac ccgaggggga tgataaaccg ggcgcggtcg gtaaagttgt   2520
tccattttt gaagcgaagg ttgtggatct ggataccggg aaaacgctgg gcgttaatca   2580
gagaggcgaa ttatgtgtca gaggacctat gattatgtcc ggttatgtaa acaatccgga   2640
agcgaccaac gccttgattg acaaggatgg atggctacat tctggagaca tagcttactg   2700
ggacgaagac gaacacttct tcatagttga ccgcttgaag tctttaatta aatacaaagg   2760
atatcaggtg gcccccgctg aattggaatc gatattgtta caacacccca acatcttcga   2820
cgcgggcgtg gcaggtcttc ccgacgatga cgccggtgaa cttcccgccg ccgttgttgt   2880
tttggagcac ggaaagacga tgacggaaaa agagatcgtg gattacgtcg ccagtcaagt   2940
aacaaccgcg aaaagttgc gcggaggagt tgtgtttgtg gacgaagtac cgaaaggtct   3000
taccggaaaa ctcgacgcaa gaaaaatcag agagatcctc ataaaggcca gaagggcgg    3060
aaagtccaaa ttgtaataat tataggataa ttgaataaaa acagtataga gagcagataa   3120
atactgctct ctattttact aataaggagg atttaaattg ctaaaaata caaacttagc    3180
taattataaa aaagtgaata cacggtttgg aaatcttagt tttgacgaca aaggtatttc   3240
taatgactta acgaagaac agcaaaaaga attaggtaag cttcgaggat tcgaatatat   3300
taagacagaa cagaaaacaa aagaagaacc taagaaagaa gaacctaaga aagaagaacc   3360
taagaaagaa gaacctaaga aagaagaacc taagaaagaa gaacctaaga agaaagtac    3420
agaaaatgaa ttagacagct tcttagctaa agagccttca atcaaagaat taaaagaatt   3480
tgcgagtaaa aaaggcatta aaattgaaaa aactaagaaa aatgatataa ttgaagaact   3540
aaagagaggg taatgtataa tgtatggagg ttatgaagga caagattctt acgaataccc   3600
ttactcacat gggaacccta agcatgtaga gccagaaaaa gttgacgaat atgttctttc   3660
tgattatggt tggactgcgg aaacaattaa agcatacatg tatggtgttc gtgtagtaga   3720
ccctgaaaca ggagaggaaa tgggagacac cttctacaat catattatag aggttgccgt   3780
tgataaggc                                                           3789
```

<210> SEQ ID NO 27
<211> LENGTH: 3729
<212> TYPE: DNA
<213> ORGANISM: Artificial
<220> FEATURE:
<223> OTHER INFORMATION: Recombinant Phage

<400> SEQUENCE: 27

```
atgccaaaaa ataacaaaga agaagaagtt aaagaagtaa accttaattc agtacaagag    60
gacgcgttaa agtcctttac aactggttat ggtatcacac ctgatacaca aacagatgca   120
ggagcattaa gacgtgagtt cctagacgac caaatctcaa tgcttacttg gacagagaat   180
gatttaacat tctataaaga catcgctaaa aaaccagcta catctacagt agcaaaatac   240
gatgtataca tgcaacatgg taaggtaggt catactagat ttactcgtga gattggggta   300
gcaccagtaa gtgaccctaa catccgtcaa aaaacagtaa acatgaaatt tgcttccgat   360
actaaaaaca tcagtatcgc agcaggtcta gtaacaacaa ttcaagaccc aatgcaaatt   420
ttgactgacg atgctatcgt aaatattgct aaaacaattg agtgggcttc attctttgga   480
```

```
gattctgact tatcagatag cccagaacca caagcaggac tagaatttga cggcttggct      540
aaacttatta accaagataa cgttcatgat gctcgtggag ctagcttgac tgaaagcttg      600
ttaaaccaag cagcagtaat gattagtaaa ggttatggta cacctacaga tgcttacatg      660
ccagtagggg ttcaagcaga ctttgttaac caacaacttt ctaaacaaac acaacttgtt      720
cgtgataacg gaaacaacgt aagcgttggt ttcaacatcc aaggtttcca ttcagctcgt      780
ggatttatca aacttcacgg ttctacagta atggaaaacg aacaaatctt agatgaacgt      840
attcttgctt taccaacagc tccacaacca gctaaggtaa ctgcaacaca agaagcaggt      900
aaaaaaggac aatttagagc agaagattta gcagcacatg aatataaagt tgttgtaagt      960
tctgacgatg cagagtctat tgcaagtgaa gtggctacag ctacagttac tgcaaaagat     1020
gacggcgtta aactagaaat cgaattagct ccaatgtata gctctcgtcc acaattcgtt     1080
tcaatctata gaaaaggtgc agaaacaggt ttattctacc taatcgctcg tgtacctgct     1140
agcaaagcag agaacaacgt aatcactttc tacgacttaa acgactctat tcctgaaaca     1200
gtagacgtat tcgttggtga aatgtcggct aacgtagtac acttgtttga attactacca     1260
atgatgagat tacctctagc tcaaattaac gcatctgtta catttgcagt tttatggtat     1320
ggcgcattag ctctaagagc acctaagaaa tgggtacgta ttagaaacgt taaatatatt     1380
cctgtaaaaa acgttcatag caactaagag gaggtaaaata tatatggaag acgccaaaaa     1440
cataaagaaa ggcccggcgc cattctatcc tctagaggat ggaaccgctg gagagcaact     1500
gcataaggct atgaagagat acgccctggt tcctggaaca attgcttttta cagatgcaca     1560 tatcgaggtg aacatcacgt acgcggaata cttcgaaatg tccgttcggt tggcagaagc     1620
tatgaaacga tatgggctga atacaaatca cagaatcgtc gtatgcagtg aaaactctct     1680
tcaattcttt atgccggtgt tgggcgcgtt atttatcgga gttgcagttg cgcccgcgaa     1740
cgacatttat aatgaacgtg aattgctcaa cagtatgaac atttcgcagc ctaccgtagt     1800
gtttgtttcc aaaaaggggt tgcaaaaaat tttgaacgtg caaaaaaaat taccaataat     1860
ccagaaaatt attatcatgg attctaaaac ggattaccag ggatttcagt cgatgtacac     1920
gttcgtcaca tctcatctac ctcccggttt taatgaatac gattttgtac cagagtcctt     1980
tgatcgtgac aaaacaattg cactgataat gaattcctct ggatctactg ggttacctaa     2040
gggtgtggcc cttccgcata gaactgcctg cgtcagattc tcgcatgcca gagatcctat     2100
ttttggcaat caaatcattc cggatactgc gattttaagt gttgttccat tccatcacgg     2160
ttttggaatg tttactacac tcggatattt gatatgtgga tttcgagtcg tcttaatgta     2220
tagatttgaa gaagagctgt ttttacgatc ccttcaggat tacaaaattc aaagtgcgtt     2280
gctagtacca acccctattt cattcttcgc caaaagcact ctgattgaca atacgatttt     2340
atctaattta cacgaaattg cttctggggg cgcacctctt tcgaaagaag tcggggaagc     2400
ggttgcaaaa cgcttccatc ttccagggat acgacaagga tatgggctca ctgagactac     2460
atcagctatt ctgattacac ccgaggggga tgataaaccg ggcgcggtcg gtaaagttgt     2520 tccattttttt gaagcgaagg ttgtggatct ggataccggg aaaacgctgg gcgttaatca     2580
gagaggcgaa ttatgtgtca gaggacctat gattatgtcc ggttatgtaa acaatccgga     2640
agcgaccaac gccttgattg acaaggatgg atggctacat tctggagaca tagcttactg     2700
ggacgaagac gaacacttct tcatagttga ccgcttgaag tctttaatta aatacaaagg     2760
atatcaggtg gccccgctg aattggaatc gatattgtta caacacccca acatcttcga     2820
cgcgggcgtg gcaggtcttc ccgacgatga cgccggtgaa cttccagccg ccgttgttgt     2880
```

-continued

| | |
|---|---|
| tttggagcac ggaaagacga tgacggaaaa agagatcgtg gattacgtcg ccagtcaagt | 2940 |
| aacaaccgcg aaaagttgc gcggaggagt tgtgtttgtg gacgaagtac cgaaaggtct | 3000 |
| taccggaaaa ctcgacgcaa gaaaaatcag agagatcctc ataaaggcca agaagggcgg | 3060 |
| aaagtccaaa ttgtaataat tataggataa ttgaataaaa acagtataga gagcagataa | 3120 |
| atactgctct ctattttact aataaggagg atttaaattg ctaaaaaata caaacttagc | 3180 |
| taattataaa aaagtgaata cacggtttgg aaatcttagt tttgacgaca aaggtatttc | 3240 |
| taatgactta acggaagaac agcaaaaaga attaggtaag cttcgaggat tcgaatatat | 3300 |
| taagacagaa cagaaaacaa aagaagaacc taagaaagaa gaacctaaga aagaaagtac | 3360 |
| agaaaatgaa ttagacagct tcttagctaa agagccttca atcaaagaat taaagaatt | 3420 |
| tgcgagtaaa aaaggcatta aaattgaaaa aactaagaaa aatgatataa ttgaagaact | 3480 |
| aaagagaggg taatgtataa tgtatggagg ttatgaagga caagattctt acgaataccc | 3540 |
| ttactcacat gggaacccta agcatgtaga gccagaaaaa gttgacgaat atgttctttc | 3600 |
| tgattatggt tggactgcgg aaacaattaa agcatacatg tatggtgttc gtgtagtaga | 3660 |
| ccctgaaaca ggagaggaaa tgggagacac cttctacaat catattatag aggttgccgt | 3720 |
| tgataaggc | 3729 |

<210> SEQ ID NO 28
<211> LENGTH: 3786
<212> TYPE: DNA
<213> ORGANISM: Artificial
<220> FEATURE:
<223> OTHER INFORMATION: Recombinant Phage

<400> SEQUENCE: 28

| | |
|---|---|
| atgccaaaaa ataacaaaga agaagttaaa gaagtaaacc ttaattcagt acaagaggat | 60 |
| gcgttaaagt cctttacgac tggttatggt atcacacctg atacaaaac agatgcagga | 120 |
| gcattaagac gtgagttcct agacgaccaa atctcaatgc ttacttggac agagaatgat | 180 |
| ttaacattct ataaagacat cgctaaaaaa ccagctacat ctacagtagc aaaatacgat | 240 |
| gtatacatgc aacatggtaa ggtaggtcat actagattta ctcgtgagat tggggtagca | 300 |
| ccagtaagtg accctaacat ccgtcaaaaa acagtaaata tgaaatttgc ttccgatact | 360 |
| aaaaacatca gtatcgcagc aggtctagta acaacattc aagacccaat gcaaattttg | 420 |
| actgacgatg ctatcgtaaa tattgctaaa acaattgagt gggcttcatt ctttggagat | 480 |
| tctgacttat cagatagccc agaaccacaa gcaggactag aatttgacgg cttggctaaa | 540 |
| cttattaacc aagataacgt tcatgatgct cgtggagcta gcttgactga aagcttgtta | 600 |
| aaccaagcag cagtaatgat tagtaaaggt tatggtacac ctacagatgc ttacatgcca | 660 |
| gtaggggttc aagcagactt tgttaaccaa caactttcta acaaacaca acttgttcgc | 720 |
| gataacggaa acaacgtaag cgttggtttc aacatccaag gtttccattc agctcgtgga | 780 |
| tttatcaaac ttcacggttc tacagtaatg gaaaacgaac aaatcttaga tgaacgtatt | 840 |
| cttgctttac caacagctcc acaaccagct aaggtaactg caacacaaga agcaggtaaa | 900 |
| aaaggacaat ttagagcaga agatttagca gcacatgaat ataaagttgt tgtaagttct | 960 |
| gacgatgcag agtctattgc aagtgaagtg gctacagcta cagttactgc aaaagatgac | 1020 |
| ggcgttaaac tagaaatcga attagctcca atgtatagct ctcgtccaca attcgtttca | 1080 |
| atctatagaa aaggtgcaga aacaggttta ttctacctaa tcgctcgtgt acctgctagc | 1140 |

-continued

```
aaagcagaga acaacgtaat cactttctac gacttaaacg actctattcc tgaaacagta    1200
gacgtattcg ttggtgaaat gtcggctaac gtagtacact tgtttgaatt actaccaatg    1260
atgagattac ctctagctca aattaacgca tctgttacat ttgcagtttt atggtatggc    1320
gcattagctc taagagcacc taagaaatgg gtacgtatta gaaacgttaa atatattcct    1380
gtaaaaaacg ttcatagcaa ctaagaggag gtaaatatat atggaagacg ccaaaaacat    1440
aaagaaaggc ccggcgccat tctatcctct agaggatgga accgctggag agcaactgca    1500
taaggctatg aagagatacg ccctggttcc tggaacaatt gcttttacag atgcacatat    1560
cgaggtgaac atcacgtacg cggaatactt cgaaatgtcc gttcggttgg cagaagctat    1620
gaaacgatat gggctgaata caaatcacag aatcgtcgta tgcagtgaaa actctcttca    1680
attctttatg ccggtgttgg gcgcgttatt tatcggagtt gcagttgcgc ccgcgaacga    1740
catttataat gaacgtgaat tgctcaacag tatgaacatt tcgcagccta ccgtagtgtt    1800
tgtttccaaa aaggggttgc aaaaaatttt gaacgtgcaa aaaaaattac caataatcca    1860
gaaaattatt atcatggatt ctaaaacgga ttaccaggga tttcagtcga tgtacacgtt    1920
cgtcacatct catctacctc ccggttttaa tgaatacgat tttgtaccag agtcctttga    1980
tcgtgacaaa acaattgcac tgataatgaa ttcctctgga tctactgggt tacctaaggg    2040
tgtggcccct tccgcataga actgcctgcgt cagattctcg catgccagag atcctatttt    2100
tggcaatcaa atcattccgg atactgcgat tttaagtgtt gttccattcc atcacggttt    2160
tggaatgttt actacactcg gatatttgat atgtggattt cgagtcgtct taatgtatag    2220
atttgaagaa gagctgtttt tacgatccct tcaggattac aaaattcaaa gtgcgttgct    2280
agtaccaacc ctattttcat tcttcgccaa aagcactctg attgacaaat acgatttatc    2340
taatttacac gaaattgctt ctgggggcgc acctctttcg aaagaagtcg gggaagcggt    2400
tgcaaaacgc ttccatcttc cagggatacg acaaggatat gggctcactg agactacatc    2460
agctattctg attacacccg aggggatgat aaaccgggc gcggtcggta agttgttcc    2520
attttttgaa gcgaaggttg tggatctgga taccgggaaa acgctgggcg ttaatcagag    2580
aggcgaatta tgtgtcagag gacctatgat tatgtccggt tatgtaaaca atccggaagc    2640
gaccaacgcc ttgattgaca aggatggatg gctacattct ggagacatag cttactggga    2700
cgaagacgaa cacttcttca gttgaccg cttgaagtct ttaattaaat acaaaggata    2760
tcaggtggcc cccgctgaat tggaatcgat attgttacaa cacccccaaca tcttcgacgc    2820
gggcgtggca ggtcttcccg acgatgacgc cggtgaactt cccgccgccg ttgttgtttt    2880
ggagcacgga aagacgatga cggaaaaaga gatcgtggat tacgtcgcca gtcaagtaac    2940
aaccgcgaaa aagttgcgcg gaggagttgt gtttgtggac gaagtaccga aggtcttac    3000
cggaaaactc gacgcaagaa aaatcagaga gatcctcata aaggccaaga agggcggaaa    3060
gtccaaattg taataattat aggataattg aataaaaaca gtatagagag cagataaata    3120
ctgctctcta ttttactaat aaggaggatt taaattgcta aaaatacaa acttagctaa    3180
ttataaaaaa gtgaatacac ggtttggaaa tcttagtttt gacgacaaag gtatttctaa    3240
tgacttaacg gaagaacagc aaaaagaatt aggtaagctt cgaggattcg aatatattaa    3300
gacagaacag aaaacaaaag aagaacctaa gaaagaagaa cctaagaaag aagaacctaa    3360
gaaagaagaa cctaagaaag aagaacctaa gaaagaagaa cctaagaaag aagtacaga    3420
aaatgaatta gacagcttct tagctaaaga gccttcaatc aaagaattaa agaatttgc    3480
gagtaaaaaa ggcattaaaa ttgaaaaaac taagaaaaat gatataattg aagaactaaa    3540
```

-continued

| | |
|---|---|
| gagagggtaa tgtataatgt atggaggtta tgaaggacaa gattcttacg aatacccttaa | 3600 |
| ctcacatggg aaccctaagc atgtagagcc agaaaaagtt gacgaatatg ttctttctga | 3660 |
| ttatggttgg actgcggaaa caattaaagc atacatgtat ggtgttcgtg tagtagaccc | 3720 |
| tgaaacagga gaggaaatgg gagacaccct ctacaatcat attatagagg ttgccgttga | 3780 |
| taaggc | 3786 |

<210> SEQ ID NO 29
<211> LENGTH: 3786
<212> TYPE: DNA
<213> ORGANISM: Artificial
<220> FEATURE:
<223> OTHER INFORMATION: Recombinant Phage

<400> SEQUENCE: 29

| | |
|---|---|
| atgccaaaaa ataacaaaga agaagttaaa gaagtaaacc ttaattcagt acaagaggat | 60 |
| gcgttaaagt cctttacgac tggttatggt atcacacctg atacacaaac agatgcagga | 120 |
| gcattaagac gtgagttcct agacgaccaa atctcaatgc ttacttggac agagaatgat | 180 |
| ttaacattct ataagacat cgctaaaaaa ccagctacat ctacagtagc aaaatacgat | 240 |
| gtatacatgc aacatggtaa ggtaggtcat actagattta ctcgtgagat tggggtagca | 300 |
| ccagtaagtg accctaacat ccgtcaaaaa acagtaaata tgaaatttgc ttccgatact | 360 |
| aaaaacatca gtatcgcagc aggtctagta acaacattc aagacccaat gcaaattttg | 420 |
| actgacgatg ctatcgtaaa tattgctaaa acaattgagt gggcttcatt ctttggagat | 480 |
| tctgacttat cagatagccc agaaccacaa gcaggactag aatttgacgg cttggctaaa | 540 |
| cttattaacc aagataacgt tcatgatgct cgtggagcta gcttgactga agcttgtta | 600 |
| aaccaagcag cagtaatgat tagtaaaggt tatggtacac ctacagatgc ttacatgcca | 660 |
| gtaggggttc aagcagactt tgttaaccaa caactttcta acaaacaca acttgttcgc | 720 |
| gataacggaa acaacgtaag cgttggtttc aacatccaag gtttccattc agctcgtgga | 780 |
| tttatcaaac ttcacggttc tacagtaatg gaaaacgaac aaatcttaga tgaacgtatt | 840 |
| cttgctttac caacagctcc acaaccagct aaggtaactg caacacaaga agcaggtaaa | 900 |
| aaaggacaat ttagagcaga agatttagca gcacatgaat ataaagttgt tgtaagttct | 960 |
| gacgatgcag agtctattgc aagtgaagtg gctacagcta cagttactgc aaaagatgac | 1020 |
| ggcgttaaac tagaaatcga attagctcca atgtatagct ctcgtccaca attcgtttca | 1080 |
| atctatagaa aaggtgcaga aacaggttta ttctacctaa tcgctcgtgt acctgctagc | 1140 |
| aaagcagaga caacgtaat cactttctac gacttaaacg actctattcc tgaaacagta | 1200 |
| gacgtattcg ttggtgaaat gtcggctaac gtagtacact tgtttgaatt actaccaatg | 1260 |
| atgagattac ctctagctca aattaacgca tctgttacat ttgcagtttt atggtatggc | 1320 |
| gcattagctc taagagcacc taagaaatgg gtacgtatta gaaacgttaa atatattcct | 1380 |
| gtaaaaaacg ttcatagcaa ctaagaggag gtaaatatat atggaagacg ccaaaaacat | 1440 |
| aaagaaaggc ccggcgccat tctatcctct agaggatgga accgctggag agcaactgca | 1500 |
| taaggctatg aagagatacg ccctggttcc tggaacaatt gcttttacag atgcacatat | 1560 |
| cgaggtgaac atcacgtacg cggaatactt cgaaatgtcc gttcggttgg cagaagctat | 1620 |
| gaaacgatat gggctgaata caaatcacag aatcgtcgta tgcagtgaaa actctcttca | 1680 |
| attctttatg ccggtgttgg gcgcgttatt tatcggagtt gcagttgcgc ccgcgaacga | 1740 |

```
catttataat gaacgtgaat tgctcaacag tatgaacatt tcgcagccta ccgtagtgtt   1800
tgtttccaaa aagggttgc aaaaatttt gaacgtgcaa aaaaattac caataatcca      1860
gaaaattatt atcatggatt ctaaaacgga ttaccaggga tttcagtcga tgtacacgtt   1920
cgtcacatct catctacctc ccggttttaa tgaatacgat tttgtaccag agtcctttga   1980
tcgtgacaaa acaattgcac tgataatgaa ttcctctgga tctactgggt tacctaaggg   2040
tgtggccctt ccgcatagaa ctgcctgcgt cagattctcg catgccagag atcctatttt   2100
tggcaatcaa atcattccgg atactgcgat tttaagtgtt gttccattcc atcacggttt   2160
tggaatgttt actacactcg gatatttgat atgtggattt cgagtcgtct taatgtatag   2220
atttgaagaa gagctgtttt tacgatccct tcaggattac aaaattcaaa gtgcgttgct   2280
agtaccaacc ctattttcat tcttcgccaa aagcactctg attgacaaat acgatttatc   2340
taatttacac gaaattgctt ctgggggcgc acctctttcg aaagaagtcg gggaagcggt   2400
tgcaaaacgc ttccatcttc cagggatacg acaaggatat gggctcactg agactacatc   2460
agctattctg attacacccg aggggatga taaaccgggc gcggtcggta aagttgttcc   2520
attttttgaa gcgaaggttg tggatctgga taccggaaa acgctgggcg ttaatcagag   2580
aggcgaatta tgtgtcagag gacctatgat tatgtccggt tatgtaaaca atccggaagc   2640
gaccaacgcc ttgattgaca aggatggatg gctacattct ggagacatag cttactggga   2700
cgaagacgaa cacttcttca tagttgaccg cttgaagtct ttaattaaat acaaggata    2760
tcaggtggcc cccgctgaat tggaatcgat attgttacaa caccccaaca tcttcgacgc   2820
gggcgtggca ggtcttcccg acgatgacgc cggtgaactt cccgccgccg ttgttgtttt   2880
ggagcacgga aagacgatga cggaaaaaga gatcgtggat tacgtcgcca gtcaagtaac   2940
aaccgcgaaa aagttgcgcg gaggagttgt gtttgtggac gaagtaccga aaggtcttac   3000
cggaaaactc gacgcaagaa aaatcagaga gatcctcata aaggccaaga agggcggaaa   3060
gtccaaattg taataattat aggataattg aataaaaaca gtatagagag cagataaata   3120
ctgctctcta ttttactaat aaggaggatt taaattgcta aaaatacaa acttagctaa    3180
ttataaaaaa gtgaatacac ggtttggaaa tcttagtttt gacgacaaag gtatttctaa   3240
tgacttaacg gaagaacagc aaaaagaatt aggtaagctt cgaggattcg aatatattaa   3300
gacagaacag aaaacaaaag aagaacctaa gaaagaagaa cctaagaaag aagaacctaa   3360
gaaagaagaa cctaagaaag aagaacctaa gaaagaagaa cctaagaaag aaagtacaga   3420
aaatgaatta gacagcttct tagctaaaga gccttcaatc aaagaattaa aagaatttgc   3480
gagtaaaaaa ggcattaaaa ttgaaaaaac taagaaaaat gatataattg aagaactaaa   3540
gagagggtaa tgtataatgt atggaggtta tgaaggacaa gattcttacg aatacccta    3600
ctcacatggg aaccctaagc atgtagagcc agaaaaagtt gacgaatatg ttctttctga   3660
ttatggttgg actgcggaaa caattaaagc atacatgtat ggtgttcgtg tagtagaccc   3720
tgaaacagga gaggaaatgg gagacacctt ctacaatcat attatagagg ttgccgttga   3780
taaggc                                                              3786
```

<210> SEQ ID NO 30
<211> LENGTH: 3729
<212> TYPE: DNA
<213> ORGANISM: Artificial
<220> FEATURE:
<223> OTHER INFORMATION: Recombinant Phage

<400> SEQUENCE: 30

```
atgccaaaaa ataacaaaga agaagaagtt aaagaagtaa accttaattc agtacaagag     60
gacgcgttaa agtcctttac aactggttat ggtatcacac ctgatacaca aacagatgca    120
ggagcattaa gacgtgagtt cctagacgac caaatctcaa tgcttacttg gacagagaat    180
gatttaacat tctataaaga catcgctaaa aaaccagcta catctacagt agcaaaatac    240
gatgtataca tgcaacatgg taaggtaggt catactagat ttactcgtga gattggggta    300
gcaccagtaa gtgaccctaa catccgtcaa aaaacagtaa atatgaaatt tgcttccgat    360
actaaaaaca tcagtatcgc agcaggtcta gtaaacaaca ttcaagaccc aatgcaaatt    420
ttgactgacg atgctatcgt aaatattgct aaaacaattg agtgggcttc attctttgga    480
gattctgact tatcagatag cccagaacca caagcaggac tagaatttga cggcttggct    540
aaacttatta accaagataa cgttcatgat gctcgtggag ctagcttgac tgaaagcttg    600
ttaaaccaag cagcagtaat gattagtaaa ggttatggta cacctacaga tgcttacatg    660
ccagtagggg ttcaagcaga ctttgttaac caacaacttt ctaaacaaac acagcttgtt    720
cgtgataacg gaaacaacgt aagcgttggt ttcaacatcc aaggtttcca ttcagctcgt    780
ggatttatca aacttcacgg ttctacagta atggaaaacg aacaaatctt agatgaacgt    840
attcttgctt taccaacagc tccacaacca gctaaggtaa ctgcaacaca agaagcaggt    900
aaaaaaggac aatttagagc agaagactta gcagcacacg aatacaaagt tgttgtaagt    960
tctgacgatg cagagtctat tgcaagtgaa gtggctacag ctacagttac tgcaaaagat   1020
gacggcgtta aactagaaat cgagttagct ccaatgtaca gctcccgtcc acaattcgtt   1080
tcaatctata gaaaaggtgc agaaacaggt ttattctacc taatcgctcg tgtacctgct   1140
agcaaagcag agaacaacgt aatcactttc tatgacttaa acgactctat tcctgaaaca   1200
gtagacgtat tcgttggtga aatgtctgct aacgtagtac acttgtttga attactacca   1260
atgatgagat tacctctagc tcaaattaac gcatctgtta catttgcagt tttatggtat   1320
ggagcattag ctctaagagc acctaagaaa tgggtacgta ttagaaacgt taaatatatt   1380
cctgtaaaaa acgttcatag caactaagag gaggtaaata tatatggaag acgccaaaaa   1440
cataaagaaa ggcccggcgc cattctatcc tctagaggat ggaaccgctg gagagcaact   1500
gcataaggct atgaagagat acgccctggt tcctggaaca attgctttta cagatgcaca   1560
tatcgaggtg aacatcacgt acgcggaata cttcgaaatg tccgttcggt tggcagaagc   1620
tatgaaacga tatgggctga atacaaatca cagaatcgtc gtatgcagtg aaaactctct   1680
tcaattcttt atgccggtgt tgggcgcgtt atttatcgga gttgcagttg cgcccgcgaa   1740
cgacatttat aatgaacgtg aattgctcaa cagtatgaac atttcgcagc ctaccgtagt   1800
gtttgtttcc aaaaaggggt tgcaaaaaat tttgaacgtg caaaaaaaat taccaataat   1860
ccagaaaatt attatcatgg attctaaaac ggattaccag ggatttcagt cgatgtacac   1920
gttcgtcaca tctcatctac ctcccggttt taatgaatac gattttgtac cagagtcctt   1980
tgatcgtgac aaaacaattg cactgataat gaattcctct ggatctactg ggttacctaa   2040
gggtgtggcc cttccgcata gaactgcctg cgtcagattc tcgcatgcca gagatcctat   2100
ttttggcaat caaatcattc cggatactgc gattttaagt gttgttccat tccatcacgg   2160
ttttggaatg tttactacac tcggatattt gatatgtgga tttcgagtcg tcttaatgta   2220
tagatttgaa gaagagctgt ttttacgatc ccttcaggat tacaaaattc aaagtgcgtt   2280
gctagtacca accctatttt cattcttcgc caaaagcact ctgattgaca aatacgattt   2340
```

```
atctaattta cacgaaattg cttctggggg cgcacctctt tcgaaagaag tcggggaagc      2400
ggttgcaaaa cgcttccatc ttccaggat acgacaagga tatgggctca ctgagactac      2460
```

```
atctaattta cacgaaattg cttctggggg cgcacctctt tcgaaagaag tcggggaagc     2400
ggttgcaaaa cgcttccatc ttccaggat  acgacaagga tatgggctca ctgagactac     2460
atcagctatt ctgattacac ccgaggggga tgataaaccg ggcgcggtcg gtaaagttgt     2520
tccattttt  gaagcgaagg ttgtggatct ggataccggg aaaacgctgg gcgttaatca     2580
gagaggcgaa ttatgtgtca gaggacctat gattatgtcc ggttatgtaa acaatccgga     2640
agcgaccaac gccttgattg acaaggatgg atggctacat tctggagaca tagcttactg     2700
ggacgaagac gaacacttct tcatagttga ccgcttgaag tctttaatta aatacaaagg     2760
atatcaggtg gccccccgctg aattggaatc gatattgtta caacaccccca acatcttcga   2820
cgcgggcgtg gcaggtcttc ccgacgatga cgccggtgaa cttcccgccg ccgttgttgt     2880
tttggagcac ggaaagacga tgacggaaaa agagatcgtg gattacgtcg ccagtcaagt     2940
aacaaccgcg aaaaagttgc gcggaggagt tgtgtttgtg gacgaagtac cgaaaggtct     3000
taccggaaaa ctcgacgcaa gaaaaatcag agagatcctc ataaaggcca gaagggcgg      3060
aaagtccaaa ttgtaataat tataggataa ttgaataaaa acagtataga gagcagataa     3120
atactgctct ctattttact aataaggagg atttaaattg ctaaaaaata caaacttagc     3180
taattataaa aaagtgaata cacgatttgg aaatcttagt tttgatgata aaggtatttc     3240
taatgaccta acggaagagc agcaaaaaga attaggtaag cttagaggat tcgaatatat     3300
taagacagaa cagaaaacga aagaagaacc taagaaagaa gaacctaaga aagaaagtac     3360
agaaaatgaa ttagacagct tcttagctaa agaaccttca atcaaagaat taaagaatt      3420
tgcgagtaaa aaaggcatta aaattgaaaa aactaagaaa aatgatataa ttgaagaact     3480
aaagagaggg taatgtacaa tgtatggagg ttatgaagga caagattctt acgaatacc      3540
ttactcacac gggaacccta agcatgtaga gccagaaaaa gttgacgaat atgttctttc     3600
tgattatggc tggactgcgg aaacaattaa agcatacatg tatggtgttc gtgtagtaga     3660
cccctgaaaca ggagaggaaa tgggagacac cttctacaat catattatag aggttgccgt    3720
tgataaggc                                                              3729
```

<210> SEQ ID NO 31
<211> LENGTH: 2658
<212> TYPE: DNA
<213> ORGANISM: Artificial
<220> FEATURE:
<223> OTHER INFORMATION: Recombinant Phage

<400> SEQUENCE: 31

```
atgccaaaaa ataacaaaga agaagaagtt aaagaagtaa accttaattc agtacaagag      60
gacgcgttaa agtcctttac aactggttat ggtatcacac ctgatacaca aacagatgca     120
ggagcattaa gacgtgagtt cctagacgac caaatctcaa tgcttacttg gacagagaat     180
gatttaacat tctataaaga catcgctaaa aaaccagcta catctacagt agcaaaatac     240
gatgtataca tgcaacatgg taaggtaggt catactagat ttactcgtga gattgggta     300
gcaccagtaa gtgaccctaa catccgtcaa aaaacagtaa acatgaaatt tgcttccgat     360
actaaaaaca tcagtatcgc agcaggtcta gtaaacaaca ttcaagaccc aatgcaaatt     420
ttgactgacg atgctatcgt aaatattgct aaaacaattg agtgggcttc attctttgga     480
gattctgact tatcagatag cccagaacca caagcaggac tagaatttga cggcttggct     540
aaacttatta accaagataa cgttcatgat gctcgtggag ctagcttgac tgaaagcttg     600
ttaaaccaag cagcagtaat gattagtaaa ggttatggta cacctacaga tgcttacatg     660
```

```
ccagtagggg ttcaagcaga ctttgttaac caacaacttt ctaaacaaac acaacttgtt    720
cgcgataacg gaaacaacgt aagcgttggt ttcaacatcc aaggtttcca ttcagctcgt    780
ggatttatca aacttcacgg ttctacagta atggaaaacg aacaaatctt agatgaacgt    840
attcttgctt taccaacagc tccacaacca gctaaggtaa ctgcaacaca agaagcaggt    900
aaaaaaggac aatttagagc agaagattta gcagcacatg aatataaagt tgttgtaagt    960
tctgacgatg cagagtctat tgcaagtgaa gtggctacag ctacagttac tgcaaaagat   1020
gacggcgtta aactagaaat cgaattagct ccaatgtata gctctcgtcc acaattcgtt   1080
tcaatctata gaaaggtgc agaaacaggt ttattctacc taatcgctcg tgtacctgct    1140
agcaaagcag agaacaacgt aatcactttc tacgacttaa acgactctat tcctgaaaca   1200
gtagacgtat tcgttggtga aatgtcggct aacgtagtac acttgtttga attactacca   1260
atgatgagat tacctctagc tcaaattaac gcatctgtta catttgcagt tttatggtat   1320
ggcgcattag ctctaagagc acctaagaaa tgggtacgta ttagaaacgt taaatatatt   1380
cctgtaaaaa acgttcatag caactaataa taagaggagg taaatatata tggtcttcac   1440
actcgaagat ttcgttgggg actggcgaca gacagccggc tacaacctgg accaagtcct   1500
tgaacaggga ggtgtgtcca gtttgtttca gaatctcggg gtgtccgtaa ctccgatcca   1560
aaggattgtc ctgagcggtg aaaatgggct gaagatcgac atccatgtca tcatcccgta   1620
tgaaggtctg agcggcgacc aaatgggcca gatcgaaaaa atttttaagg tggtgtaccc   1680
tgtggatgat catcacttta aggtgatcct gcactatggc acactggtaa tcgacggggt   1740
tacgccgaac atgatcgact atttcggacg gccgtatgaa ggcatcgccg tgttcgacgg   1800
caaaaagatc actgtaacag ggaccctgtg aacggcaac aaaattatcg acgagcgcct    1860
gatcaacccc gacggctccc tgctgttccg agtaaccatc aacggagtga ccggctggcg   1920
gctgtgcgaa cgcattctgg cgtaataatt ataggataat tgaataaaaa cagtatagag   1980
agcagataaa tactgctctc tattttacta ataaggagga tttaaattgc taaaaaatac   2040
aaacttagct aattataaaa aagtgaatac acggtttgga atcttagtt ttgacgacaa    2100 aggtatttct aatgacttaa cggaagaaca gcaaaaagaa ttaggtaagc ttcgaggatt   2160
cgaatatatt aagacagaac agaaaacaaa agaagaacct aagaaagaag aacctaagaa   2220
agaagaacct aagaaagaag aacctaagaa agaagaacct aagaaagaag aacctaagaa   2280
agaaagtaca gaaaatgaat tagacagctt cttagctaaa gagccttcaa tcaaagaatt   2340
aaaagaattt gcgagtaaaa aaggcattaa aattgaaaaa actaagaaaa atgatataat   2400
tgaagaacta agagagggt aatgtataat gtatggaggt tatgaaggac aagattctta    2460
cgaataccct tactcacatg ggaaccctaa gcatgtagag ccagaaaaag ttgacgaata   2520
tgttctttct gattatggtt ggactgcgga acaattaaa gcatacatgt atggtgttcg    2580
tgtagtagac cctgaaacag gagaggaaat gggagacacc ttctacaatc atattataga   2640
ggttgccgtt gataaggc                                                 2658
```

<210> SEQ ID NO 32
<211> LENGTH: 2598
<212> TYPE: DNA
<213> ORGANISM: Artificial
<220> FEATURE:
<223> OTHER INFORMATION: Recombinant Phage

<400> SEQUENCE: 32

```
atgccaaaaa ataacaaaga agaagaagtt aaagaagtaa accttaattc agtacaagag    60
gacgcgttaa agtcctttac aactggttat ggtatcacac ctgatacaca aacagatgca   120
ggagcattaa gacgtgagtt cctagacgac caaatctcaa tgcttacttg gacagagaat   180
gatttaacat tctataaaga catcgctaaa aaaccagcta catctacagt agcaaaatac   240
gatgtataca tgcaacatgg taaggtaggt catactagat ttactcgtga gattggggta   300
gcaccagtaa gtgaccctaa catccgtcaa aaaacagtaa acatgaaatt tgcttccgat   360
actaaaaaca tcagtatcgc agcaggtcta gtaaacaaca ttcaagaccc aatgcaaatt   420
ttgactgacg atgctatcgt aaatattgct aaaacaattg agtgggcttc attctttgga   480
gattctgact tatcagatag cccagaacca caagcaggac tagaatttga cggcttggct   540
aaacttatta accaagataa cgttcatgat gctcgtggag ctagcttgac tgaaagcttg   600
ttaaaccaag cagcagtaat gattagtaaa ggttatggta cacctacaga tgcttacatg   660
ccagtagggg ttcaagcaga ctttgttaac caacaacttt ctaaacaaac acaacttgtt   720
cgtgataacg gaaacaacgt aagcgttggt ttcaacatcc aaggtttcca ttcagctcgt   780
ggatttatca aacttcacgg ttctacagta atggaaaacg aacaaatctt agatgaacgt   840
attcttgctt taccaacagc tccacaacca gctaaggtaa ctgcaacaca agaagcaggt   900
aaaaaaggac aatttagagc agaagattta gcagcacatg aatataaagt tgttgtaagt   960
tctgacgatg cagagtctat tgcaagtgaa gtggctacag ctacagttac tgcaaaagat  1020
gacggcgtta aactagaaat cgaattagct ccaatgtata gctctcgtcc acaattcgtt  1080
tcaatctata gaaaaggtgc agaaacaggt ttattctacc taatcgctcg tgtacctgct  1140
agcaaagcag agaacaacgt aatcactttc tacgacttaa cgactctatt cctgaaaca   1200
gtagacgtat cgttggtga atgtcggct aacgtagtac acttgtttga attactacca  1260
atgatgagat tacctctagc tcaaattaac gcatctgtta catttgcagt tttatggtat  1320
ggcgcattag ctctaagagc acctaagaaa tgggtacgta ttagaaacgt taaatatatt  1380
cctgtaaaaa acgttcatag caactaataa taagaggagg taaatatata tggtcttcac  1440
actcgaagat ttcgttgggg actggcgaca gacagccggc tacaacctgg accaagtcct  1500
tgaacaggga ggtgtgtcca gtttgtttca gaatctcggg gtgtccgtaa ctccgatcca  1560
aaggattgtc ctgagcggtg aaaatgggct gaagatcgac atccatgtca tcatcccgta  1620
tgaaggtctg agcggcgacc aaatgggcca gatcgaaaaa attttttaagg tggtgtaccc  1680
tgtggatgat catcacttta aggtgatcct gcactatggc acactggtaa tcgacggggt  1740
tacgccgaac atgatcgact atttcggacg gccgtatgaa ggcatcgccg tgttcgacgg  1800
caaaaagatc actgtaacag ggaccctgtg aacggcaac aaaattatcg acgagcgcct  1860
gatcaaccc gacggctccc tgctgttccg agtaaccatc aacggagtga ccggctggcg  1920
gctgtgcgaa cgcattctgg cgtaataatt ataggataat tgaataaaaa cagtatagag  1980
agcagataaa tactgctctc tattttacta ataaggagga tttaaattgc taaaaaatac  2040
aaacttagct aattataaaa aagtgaatac acggtttgga aatcttagtt ttgacgacaa  2100
aggtatttct aatgacttaa cggaagaaca gcaaaaagaa ttaggtaagc ttcgaggatt  2160
cgaatatatt aagacagaac agaaaacaaa agaagaacct aagaaagaag aacctaagaa  2220
agaaagtaca gaaaatgaat tagacagctt cttagctaaa gagccttcaa tcaaagaatt  2280
aaaagaattt gcgagtaaaa aaggcattaa aattgaaaaa actaagaaaa atgatataat  2340
tgaagaacta aagagagggt aatgtataat gtatggaggt tatgaaggac aagattctta  2400
```

-continued

| | |
|---|---|
| cgaataccct tactcacatg ggaaccctaa gcatgtagag ccagaaaaag ttgacgaata | 2460 |
| tgttctttct gattatggtt ggactgcgga acaattaaa gcatacatgt atggtgttcg | 2520 |
| tgtagtagac cctgaaacag gagaggaaat gggagacacc ttctacaatc atattataga | 2580 |
| ggttgccgtt gataaggc | 2598 |

<210> SEQ ID NO 33
<211> LENGTH: 2649
<212> TYPE: DNA
<213> ORGANISM: Artificial
<220> FEATURE:
<223> OTHER INFORMATION: Recombinant Phage

<400> SEQUENCE: 33

| | |
|---|---|
| atgccaaaaa ataacaaaga agaagttaaa gaagtaaacc ttaattcagt acaagaggat | 60 |
| gcgttaaagt cctttacgac tggttatggt atcacacctg atacacaaac agatgcagga | 120 |
| gcattaagac gtgagttcct agacgaccaa atctcaatgc ttacttggac agagaatgat | 180 |
| ttaacattct ataaagacat cgctaaaaaa ccagctacat ctacagtagc aaaatacgat | 240 |
| gtatacatgc aacatggtaa ggtaggtcat actagattta ctcgtgagat tgggggtagca | 300 |
| ccagtaagtg accctaacat ccgtcaaaaa acagtaaata tgaaatttgc ttccgatact | 360 |
| aaaaacatca gtatcgcagc aggtctagta acaacattc aagacccaat gcaaattttg | 420 |
| actgacgatg ctatcgtaaa tattgctaaa acaattgagt gggcttcatt ctttggagat | 480 |
| tctgacttat cagatagccc agaaccacaa gcaggactag aatttgacgg cttggctaaa | 540 |
| cttattaacc aagataacgt tcatgatgct cgtggagcta gcttgactga aagcttgtta | 600 |
| aaccaagcag cagtaatgat tagtaaaggt tatggtacac ctacagatgc ttacatgcca | 660 |
| gtaggggttc aagcagactt tgttaaccaa caactttcta acaaacaca acttgttcgc | 720 |
| gataacggaa acaacgtaag cgttggtttc aacatccaag gtttccattc agctcgtgga | 780 |
| tttatcaaac ttcacggttc tacagtaatg gaaaacgaac aaatcttaga tgaacgtatt | 840 |
| cttgctttac caacagctcc acaaccagct aaggtaactg caacacaaga agcaggtaaa | 900 |
| aaaggacaat ttagagcaga gatttagca gcacatgaat ataaagttgt tgtaagttct | 960 |
| gacgatgcag agtctattgc aagtgaagtg gctacagcta cagttactgc aaaagatgac | 1020 |
| ggcgttaaac tagaaatcga attagctcca atgtatagct ctcgtccaca attcgtttca | 1080 |
| atctatagaa aggtgcagaa acaggttta ttctacctaa tcgctcgtgt acctgctagc | 1140 |
| aaagcagaga caacgtaat cactttctac gacttaaacg actctattcc tgaaacagta | 1200 |
| gacgtattcg ttggtgaaat gtcggctaac gtagtacact tgtttgaatt actaccaatg | 1260 |
| atgagattac ctctagctca aattaacgca tctgttacat ttgcagtttt atggtatggc | 1320 |
| gcattagctc taagagcacc taagaaatgg gtacgtatta gaaacgttaa atatattcct | 1380 |
| gtaaaaaacg ttcatagcaa ctaagaggag gtaaatatat atggtcttca cactcgaaga | 1440 |
| tttcgttggg gactggcgac agacagccgg ctacaacctg gaccaagtcc ttgaacaggg | 1500 |
| aggtgtgtcc agtttgtttc agaatctcgg ggtgtccgta actccgatcc aaaggattgt | 1560 |
| cctgagcggt gaaatgggc tgaagatcga catccatgta atcatcccgt atgaaggtct | 1620 |
| gagcggcgac caaatgggcc agatcgaaaa aatttttaag gtggtgtacc ctgtggatga | 1680 |
| tcatcacttt aaggtgatcc tgcactatgg cacactggta atcgacgggg ttacgccgaa | 1740 |
| catgatcgac tatttcggac ggccgtatga aggcatcgcc gtgttcgacg gcaaaaagat | 1800 |

-continued

| | |
|---|---|
| cactgtaaca gggaccctgt ggaacggcaa caaaattatc gacgagcgcc tgatcaaccc | 1860 |
| cgacggctcc ctgctgttcc gagtaaccat caacggagtg accggctggc ggctgtgcga | 1920 |
| acgcattctg gcgtaataat tataggataa ttgaataaaa acagtataga gagcagataa | 1980 |
| atactgctct ctattttact aataaggagg atttaaattg ctaaaaaata caaacttagc | 2040 |
| taattataaa aaagtgaata cacggtttgg aaatcttagt tttgacgaca aaggtatttc | 2100 |
| taatgactta acggaagaac agcaaaaaga attaggtaag cttcgaggat tcgaatatat | 2160 |
| taagacagaa cagaaaacaa agaagaacc taagaaagaa gaacctaaga aagaagaacc | 2220 |
| taagaaagaa gaacctaaga aagaagaacc taagaaagaa gaacctaaga aagaagtac | 2280 |
| agaaaatgaa ttagacagct tcttagctaa agagccttca atcaaagaat taaaagaatt | 2340 |
| tgcgagtaaa aaaggcatta aaattgaaaa aactaagaaa aatgatataa ttgaagaact | 2400 |
| aaagagaggg taatgtataa tgtatggagg ttatgaagga caagattctt acgaataccc | 2460 |
| ttactcacat gggaacccta agcatgtaga gccagaaaaa gttgacgaat atgttctttc | 2520 |
| tgattatggt tggactgcgg aaacaattaa agcatacatg tatggtgttc gtgtagtaga | 2580 |
| ccctgaaaca ggagaggaaa tgggagacac cttctacaat catattatag aggttgccgt | 2640 |
| tgataaggc | 2649 |

<210> SEQ ID NO 34
<211> LENGTH: 2592
<212> TYPE: DNA
<213> ORGANISM: Artificial
<220> FEATURE:
<223> OTHER INFORMATION: Recombinant Phage

<400> SEQUENCE: 34

| | |
|---|---|
| atgccaaaaa ataacaaaga agaagaagtt aaagaagtaa accttaattc agtacaagag | 60 |
| gacgcgttaa agtcctttac aactggttat ggtatcacac ctgatacaca aacagatgca | 120 |
| ggagcattaa gacgtgagtt cctagacgac caaatctcaa tgcttacttg gacagagaat | 180 |
| gatttaacat tctataaaga catcgctaaa aaaccagcta catctacagt agcaaaatac | 240 |
| gatgtataca tgcaacatgg taaggtaggt catactagat ttactcgtga gattggggta | 300 |
| gcaccagtaa gtgaccctaa catccgtcaa aaaacagtaa atatgaaatt tgcttccgat | 360 |
| actaaaaaca tcagtatcgc agcaggtcta gtaaacaaca ttcaagaccc aatgcaaatt | 420 |
| ttgactgacg atgctatcgt aaatattgct aaaacaattg agtgggcttc attctttgga | 480 |
| gattctgact tatcagatag cccagaacca caagcaggac tagaatttga cggcttggct | 540 |
| aaacttatta accaagataa cgttcatgat gctcgtggag ctagcttgac tgaaagcttg | 600 |
| ttaaaccaag cagcagtaat gattagtaaa ggttatggta cacctacaga tgcttacatg | 660 |
| ccagtagggg ttcaagcaga ctttgttaac caacaacttt ctaaacaaac acagcttgtt | 720 |
| cgtgataacg gaaacaacgt aagcgttggt ttcaacatcc aaggtttcca ttcagctcgt | 780 |
| ggatttatca aacttcacgg ttctacagta atggaaaacg aacaaatctt agatgaacgt | 840 |
| attcttgctt taccaacagc tccacaacca gctaaggtaa ctgcaacaca gaagcaggt | 900 |
| aaaaaaggac aatttagagc agaagactta gcagcacacg aatacaaagt tgttgtaagt | 960 |
| tctgacgatg cagagtctat tgcaagtgaa gtggctacag ctacagttac tgcaaaagat | 1020 |
| gacggcgtta aactagaaat cgagttagct ccaatgtaca gctcccgtcc acaattcgtt | 1080 |
| tcaatctata gaaaggtgc agaaacaggt ttattctacc taatcgctcg tgtacctgct | 1140 |
| agcaaagcag agaacaacgt aatcactttc tatgacttaa acgactctat tcctgaaaca | 1200 |

```
gtagacgtat tcgttggtga aatgtctgct aacgtagtac acttgtttga attactacca   1260
atgatgagat tacctctagc tcaaattaac gcatctgtta catttgcagt tttatggtat   1320
ggagcattag ctctaagagc acctaagaaa tgggtacgta ttagaaacgt taaatatatt   1380
cctgtaaaaa acgttcatag caactaagag gaggtaaata tatatggtct tcacactcga   1440
agatttcgtt ggggactggc gacagacagc cggctacaac ctggaccaag tccttgaaca   1500
gggaggtgtg tccagtttgt ttcagaatct cggggtgtcc gtaactccga tccaaaggat   1560
tgtcctgagc ggtgaaaatg gctgaagat cgacatccat gtcatcatcc cgtatgaagg   1620
tctgagcggc gaccaaatgg gccagatcga aaaaattttt aaggtggtgt accctgtgga   1680
tgatcatcac tttaaggtga tcctgcacta tggcacactg gtaatcgacg gggttacgcc   1740
gaacatgatc gactatttcg gacggccgta tgaaggcatc gccgtgttcg acggcaaaaa   1800
gatcactgta acagggaccc tgtggaacgg caacaaaatt atcgacgagc gcctgatcaa   1860
ccccgacggc tccctgctgt tccgagtaac catcaacgga gtgaccggct ggcggctgtg   1920
cgaacgcatt ctggcgtaat aattatagga taattgaata aaaacagtat agagagcaga   1980
taaatactgc tctctatttt actaataagg aggatttaaa ttgctaaaaa atacaaactt   2040
agctaattat aaaaaagtga atacacgatt tggaaatctt agttttgatg ataaaggtat   2100
ttctaatgac ctaacggaag agcagcaaaa agaattaggt aagcttagag gattcgaata   2160
tattaagaca gaacagaaaa cgaaagaaga acctaagaaa gaagaaccta agaaagaaag   2220
tacagaaaat gaattagaca gcttcttagc taaagaacct tcaatcaaag aattaaaaga   2280
atttgcgagt aaaaaaggca ttaaaattga aaaaactaag aaaaatgata taattgaaga   2340
actaaagaga gggtaatgta caatgtatgg aggttatgaa ggacaagatt cttacgaata   2400
cccttactca cacgggaacc ctaagcatgt agagccagaa aaagttgacg aatatgttct   2460
ttctgattat ggctggactg cggaaacaat taaagcatac atgtatggtg ttcgtgtagt   2520
agaccctgaa acaggagagg aaatgggaga caccttctac aatcatatta tagaggttgc   2580
cgttgataag gc                                                       2592
```

<210> SEQ ID NO 35
<211> LENGTH: 2613
<212> TYPE: DNA
<213> ORGANISM: Artificial
<220> FEATURE:
<223> OTHER INFORMATION: Recombinant Phage

<400> SEQUENCE: 35

```
atgccaaaaa ataacaaaga agaagaagtt aaagaagtaa accttaattc agtacaagag    60
gatgcgttaa agtcctttac aactggttat ggtatcacac tgatacaca aacagatgca   120 ggggcactaa gacgtgagtt cctagacgac caaatctcaa tgcttacttg gacagaaaat   180
gatttaacat tctacaaaga catcgctaaa aaaccagcta catctacagt agcaaaatac   240
gatgtgtaca tgcaacacgg taaagtaggt catactagat ttactcgtga gattggggta   300
gcaccagtaa gtgaccctaa catccgtcaa aaaacagtaa acatgaaatt tgcttctgat   360
actaaaaata ttagtatcgc agcaggtcta gtaacaaca ttcaagaccc tatgcaaatt   420
ttgactgatg atgctatcgt aaatatcgct aaaacaattg agtgggcttc attctttgga   480
gattctgact tatcagatag cccagaacca caagcaggat tagaatttga tggcttggct   540
aaacttatta accaagataa cgttcatgat gctcgtggag ctagcttgac tgaaagcttg   600
```

-continued

```
ttaaaccaag cagcagtaat gattagtaaa ggttatggta cacctacaga tgcttacatg    660
ccagtagggg ttcaagcaga ctttgttaac caacaacttt ctaaacaaac acaacttgtt    720
cgcgataacg gaaacaacgt aagcgttggt ttcaacatcc aaggtttcca ttcagctcgt    780
ggatttatca aacttcacgg ttctacagta atggaaaacg aacaaatctt agatgaacgt    840
attcttgctt taccaacagc tccacaacca gctaaggtaa ctgcaacaca agaagcaggt    900
aaaaaaggac aatttagagc agaagattta gcagcacatg aatataaagt tgttgtaagt    960
tctgacgatg cagagtctat tgcaagtgaa gtggctacag ctacagttac tgcaaaagat   1020
gacggcgtta aactagaaat cgaattagct ccaatgtata gctctcgtcc acaattcgtt   1080
tcaatctata gaaaaggtgc agaaacaggt ttattctacc taatcgctcg tgtacctgct   1140
agcaaagcag agaacaacgt aatcactttc tacgacttaa acgactctat tcctgaaaca   1200
gtagacgtat tcgttggtga aatgtcggct aacgtagtac acttgtttga attactacca   1260
atgatgagat tacctctagc tcaaattaac gcatctgtta catttgcagt tttatggtat   1320
ggcgcattag ctctaagagc acctaagaaa tgggtacgta ttagaaacgt taaatatatt   1380
cctgtaaaaa acgttcatag caactaataa taagaggagg taaatatata tggtcttcac   1440
actcgaagat ttcgttgggg actggcgaca gacagccggc tacaacctgg accaagtcct   1500
tgaacaggga ggtgtgtcca gtttgtttca gaatctcggg gtgtccgtaa ctccgatcca   1560
aaggattgtc ctgagcggtg aaaatgggct gaagatcgac atccatgtca tcatcccgta   1620
tgaaggtctg agcggcgacc aaatgggcca gatcgaaaaa atttttaagg tggtgtaccc   1680
tgtggatgat catcacttta aggtgatcct gcactatggc acactggtaa tcgacggggt   1740
tacgccgaac atgatcgact atttcggacg gccgtatgaa ggcatcgccg tgttcgacgg   1800
caaaaagatc actgtaacag ggaccctgtg gaacggcaac aaaattatcg acgagcgcct   1860
gatcaacccc gacggctccc tgctgttccg agtaaccatc aacggagtga ccggctggcg   1920
gctgtgcgaa cgcattctgg cgtaataatt ataggataat tgaataaaaa cagtatagag   1980
agcagataaa tactgctctc tatttactata ataaggagga tttaaattgc taaaaaatac   2040
aaacttagct aattataaaa aagtgaatac acggtttgga aatcttagtt ttgacgacaa   2100
aggtatttct aatgacttaa cggaagaaca gcaaaaagaa ttaggtaagc ttcgaggatt   2160
cgaatatatt aagacagaac agaaaacaaa agaagaacct aagaaagaag aacctaagaa   2220
agaagaacct aagaaagaaa gtacagaaaa tgaattagac agcttcttag ctaaagagcc   2280
ttcaatcaaa gaattaaaag aatttgcgag taaaaaaggc attaaaattg aaaaaactaa   2340
gaaaaacgat ataattgaag aactaaagag agggtaatgt ataatgtatg gaggttatga   2400
aggacaagat tcttacgaat acccttactc acatgggaac cctaagcatg tagagccaga   2460
aaaagttgac gaatatgttc tttctgatta tggttggact gcggaaacaa ttaaagcata   2520
catgtatggt gttcgtgtag tagaccctga aacaggagag gaaatgggag acaccttcta   2580
caatcatatt atagaggttg ccgttgataa ggc                                 2613
```